US007261890B2

(12) United States Patent
Krah, III et al.

(10) Patent No.: US 7,261,890 B2
(45) Date of Patent: Aug. 28, 2007

(54) METHODS FOR USING CANINE IMMUNOGLOBULIN VARIABLE DOMAINS AND CANINIZED ANTIBODIES

(75) Inventors: Eugene Regis Krah, III, Freeport, ME (US); Hongliang Guo, Scarborough, ME (US); Ashok Aiyappa, Falmouth, ME (US); Robert Lawton, Gorham, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 393 days.

(21) Appl. No.: 10/327,598

(22) Filed: Dec. 20, 2002

(65) Prior Publication Data

US 2004/0181039 A1 Sep. 16, 2004

Related U.S. Application Data

(60) Provisional application No. 60/344,874, filed on Dec. 21, 2001.

(51) Int. Cl.
*A61K 39/395* (2006.01)
*C07K 16/00* (2006.01)
*C12P 21/04* (2006.01)
*C12P 21/08* (2006.01)

(52) U.S. Cl. .................. 424/130.1; 424/133.1; 424/141.1; 424/145.1; 530/387.1; 530/387.3; 530/388.1; 435/69.6

(58) Field of Classification Search ............. 424/130.1, 424/133.1, 141.1, 145.1, 171.1; 530/387.1, 530/387.3, 388.1; 435/69.1
See application file for complete search history.

(56) References Cited

U.S. PATENT DOCUMENTS

| 5,595,861 | A | 1/1997 | Garza |
| 5,622,842 | A | 4/1997 | Hollis et al. |
| 5,693,762 | A | 12/1997 | Queen et al. |
| 5,852,183 | A | 12/1998 | Maeda et al. |

FOREIGN PATENT DOCUMENTS

| JP | 1991083579 A1 | 4/1991 |
| JP | 1991123489 A1 | 5/1991 |
| JP | 1992040894 A1 | 2/1992 |
| JP | 1997169795 A3 | 6/1997 |
| WO | WO/01/77332 A2 | 10/2001 |

OTHER PUBLICATIONS

William E. Paul. Fundamental Immunology, 3rd Edition, 1993, pp. 292-295.*
Rudikoff et al. Proc. Natl. Acad. Sci., USA, 79:1979-1983, 1982.*
Tang et al., "Cloning and characterization of cDNAs encoding four different anine immunoglobulin γ Chains" Veterinary Immunology and Immunopathology, 80 (2001) 259-270.
McCumber and Capra, "The Complete Amino-Acid Sequence of a Canine Mu Chain", Molecular Immunology, vol. 16, pp. 565-570 (1979).
Wasserman and Capra, "Primary Structure of the Variable Regions of Two Canine Immunoglobulin Heavy Chains", Biochemistry, vol. 16, No. 14 (1977).
Wasserman and Capra, "The Amino Acid Sequence of the Light Chain Variable Region of a Canine Myeloma Immunoglobulin: Evidence that the VK Subgroups Predated Mammalian Speciation", Immunochemistry, vol. 15, pp. 303-305 (1978).
Patel et al, "Sequence of the dog Immunoglobulin Alpha and Epilson Constant Region Genes" Immunogenetics 1995, 41(5), 282-6.
Wasserman et al., "Amino Acid Sequence of the Fc Region of a Canine Immunoglobulin M: Interspecies Homology for the IgM Class", Science 200 (4346) 1159-1161 (1978).
Wasserman et al., "Primary Structure of the Variable Regions of Two Canine Immunoglobulin Heavy Chains", Biochemistry 16 (14) 3160-3168 (1977).
Gebhard D. et al., "Canine IgE Monoclonal Antibody Specific for a Filiarial Antigen: Production by a Canine×Murine Heterohybridoma using B cells from a clinically affected lymph node" Immunology, 1995, vol. 85, pp. 429-434.

* cited by examiner

*Primary Examiner*—Sheela J. Huff
*Assistant Examiner*—David J. Blanchard
(74) *Attorney, Agent, or Firm*—McDonnell Boehnen Hulbert & Berghoff LLP

(57) ABSTRACT

The present invention provides canine heavy chain and light chain (both λ and κ) variable domain nucleic acids and polypeptides. The present invention also provides caninized antibodies comprised of the presently disclosed canine variable domain framework sequences and CDRs specific for an antigen obtained from antibodies from other than canines (preferably mouse). The invention also provides methods of making caninized antibodies and using them. This disclosure specifically describes caninized antibodies that are useful in the treatment of canine allergy. The general process of caninization permits the development of useful therapeutics, which includes but is not limited to allergy, osteosarcomma's and lymphomma's.

3 Claims, 9 Drawing Sheets

```
              10         20         30         40         50
LAMB305   1 TDSQTVVTQE PSLSVSPGGT VTLTCGLSSG SVTASHFPGW YQQTQGRAPR
            || |       || ||    |       || |   |  ||||  |  | ||| ||
15A2      1 AISQAVVTQE SALTTSPGET VTLTCRSSTG AVTTSNYANW VQEKPDHLFT 60         70         80         90       100
LAMB305  51 TIIYNTYNRL SGVPSRFSGS ISGNKATLTI TGARPEDEAD YHCSVYTDDH
            ||  ||||    |   |    |       || |  |     ||     |   | ||||||
15A2     51 GLIGGPNNRA PGVPARFSGS LIGDKAALTI TGAQTEDEAI YFCALWYSNH

110
LAMB305 101 TPVFGGGTHL TVLGQ
            || 
15A2    101 W-VFGGGTKL TVLGQ
```

Fig. 2

```
              10         20         30         40         50
15A2   EVQLQQSGPE LVKPGASVKI SCKASGYSFT DYFMNWVMQS HGKSLEWIGR
        | ||  ||         |          |  | | || | ||
H74    EVQLVQSAAE VKKPGASVKV SCKTSGYTFT DYYMHWVQQA PGAGLDWMGW 60         70         80         90        100
15A2   INPFNGDPFY NQKFKGKATL TVDKSSSTAH MELRSLASED SAVYYCARFY
       |  |||  |   || |||   | | |  |     | ||  |         ||
H74    IDPEDGTTSY AQKFQGRVTL TADTSTSTAY MELSSLRAED AAVYYCASLY 110
15A2   YGRYYAM-DY WGQ
       ||| | |  |
H74    IYGYAAYLDL WGQ
```

Fig. 3

SCHEMATIC DIAGRAM (A)
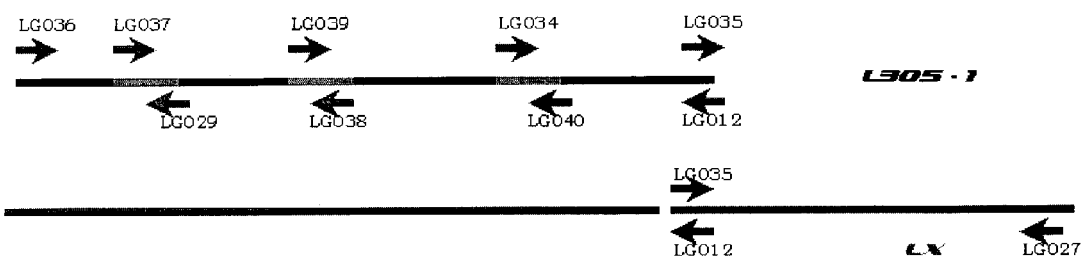
SCHEMATIC DIAGRAM (B)
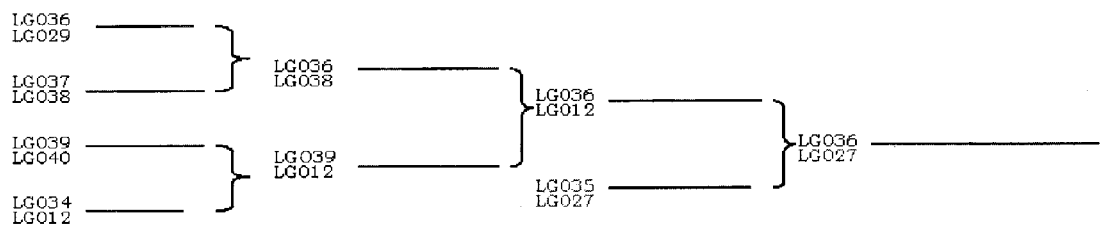
Fig. 4

Light Chain

```
15A2/1NGQ      QAVVTQESALTTSPGETVTLTCRSSTGAVTTSNYANWVQEKPDHLFTGLI
15A2/1FBI      SQAVVTQESALTTSPGETVTLTCRSSTGAVTTSNYANWVQEKPDHLFTGLI
15A2/2VIR      QAVVTQESALTTSPGETVTLTCRSSTGAVTTSNYANWVQEKPDHLFTGLI
                 ||   || ||    |             | |||||||||||
LAMB305-1      QTVVTQEPSLSVSPGGTVTLTCRSSTGAVTTSNYANWYQQTQGRAPRTII

15A2/1NGQ      GGPNNRAPGVPARFSGSLIGDKAALTITGAQTEDEAIYFCALWYSNHWVF
15A2/1FBI      GGPNNRAPGVPARFSGSLIGDKAALTITGAQTEDEAIYFCALWYSNHWVF
15A2/2VIR      GGPNNRAPGVPARFSGSLIGDKAALTITGAQTEDEAIYFCALWYSNHWVF
                        |  || |      ||   ||   |  |
LAMB305-1      YGPNNRAPGVPSRFSGSISGNKATLTITGARPEDEADYHCALWYSNHWVF

15A2/1NGQ      GGGTKLTVL
15A2/1FBI      GGGTKLTVL
15A2/2VIR      GGGTKLTVL
                   |
LAMB305-1      GGGTHLTVL
```

Heavy Chain

```
15A2/1NGQ          EVQLQQSGPELVKPGASVKISCKASGYSFTDYFMNWVMQSHGKSLEWIG
15A2/1FBI          EVQLQQSGPELVKPGASVKISCKASGYSFTDYFMNWVMQSHGKSLEWIG
15A2/2VIR          EVQLQQSGPELVKPGASVKISCKASGYSFTDYFMNWVMQSHGKSLEWIG
                      |  ||  ||        |   |           |  || || |
H74-1              EVQLVQSAAEVKKPGASVKVSCKTSGYSFTDYFMNWVQQAPGAGLDWMG

15A2/1NGQ    153   RINPFNGDPFYNQKFKGKATLTVDKSSSTAHMELRSLASEDSAVYYCAR
15A2/1FBI    152   RINPFNGDPFYNQKFKGKATLTVDKSSSTAHMELRSLASEDSAVYYCAR
15A2/2VIR    153   RINPFNGDPFYNQKFKGKATLTVDKSSSTAHMELRSLASEDSAVYYCAR
                                  ||   |||   |      |   ||    |
H74-1              RINPFNGDPFYNQKFKGRVTLTADTSTSTAYMELSSLRAEDAAVYYCAR

15A2/1NGQ    203   FYYGRYYAMDYWGQGTSVTVSS
15A2/1FBI    202   FYYGRYYAMDYWGQGTSVTVSS
15A2/2VIR    203   FYYGRYYAMDYWGQGTSVTVSS

H74-1              FYYGRYYAMDYWGQ
```

Fig. 5

SEQUENCE LISTING

<160> NUMBER OF SEQ ID NOS: 1139

<210> SEQ ID NO 1
<211> LENGTH: 14
<212> TYPE: PRT
<213> ORGANISM: Canis familiaris
<220> FEATURE:
<221> NAME/KEY: unsure
<222> LOCATION: (2)..(2)
<223> OTHER INFORMATION: X is absent or G
<220> FEATURE:
<221> NAME/KEY: unsure
<222> LOCATION: (3)..(3)

-continued

```
<223> OTHER INFORMATION: X is absent, G, S, or P
<220> FEATURE:
<221> NAME/KEY: unsure
<222> LOCATION: (4)..(4)
<223> OTHER INFORMATION: X is absent or G
<220> FEATURE:
<221> NAME/KEY: unsure
<222> LOCATION: (5)..(5)
<223> OTHER INFORMATION: X is absent, T, or A
<220> FEATURE:
<221> NAME/KEY: unsure
<222> LOCATION: (6)..(6)
<223> OTHER INFORMATION: X is absent, H, Q, L, Y, or R
<220> FEATURE:
<221> NAME/KEY: unsure
<222> LOCATION: (7)..(7)
<223> OTHER INFORMATION: X is absent or L
<220> FEATURE:
<221> NAME/KEY: unsure
<222> LOCATION: (8)..(8)
<223> OTHER INFORMATION: X is absent, T or A
<220> FEATURE:
<221> NAME/KEY: unsure
<222> LOCATION: (9)..(9)
<223> OTHER INFORMATION: X is absent or V
<220> FEATURE:
<221> NAME/KEY: unsure
<222> LOCATION: (10)..(10)
<223> OTHER INFORMATION: X is absent or L
<220> FEATURE:
<221> NAME/KEY: unsure
<222> LOCATION: (11)..(11)
<223> OTHER INFORMATION: X is absent, G, or S
<220> FEATURE:
<221> NAME/KEY: unsure
<222> LOCATION: (12)..(12)
<223> OTHER INFORMATION: X is absent or Q
<220> FEATURE:
<221> NAME/KEY: unsure
<222> LOCATION: (14)..(14)
<223> OTHER INFORMATION: X is K or R

<400> SEQUENCE: 1

Phe Xaa Xaa Xaa Xaa Xaa Xaa Xaa Xaa Xaa Xaa Xaa Pro Xaa
1               5                   10

<210> SEQ ID NO 2
<211> LENGTH: 25
<212> TYPE: PRT
<213> ORGANISM: canis familiaris;
<220> FEATURE:
<221> NAME/KEY: UNSURE
<222> LOCATION: (3)..(3)
<223> OTHER INFORMATION: X is Q or H
<220> FEATURE:
<221> NAME/KEY: unsure
<222> LOCATION: (5)..(5)
<223> OTHER INFORMATION: X is V or M
<220> FEATURE:
<221> NAME/KEY: unsure
<222> LOCATION: (6)..(6)
<223> OTHER INFORMATION: X is E or Q
<220> FEATURE:
<221> NAME/KEY: unsure
<222> LOCATION: (10)..(10)
<223> OTHER INFORMATION: X is D or N
<220> FEATURE:
<221> NAME/KEY: unsure
<222> LOCATION: (13)..(13)
<223> OTHER INFORMATION: X is K or R
<220> FEATURE:
<221> NAME/KEY: unsure
<222> LOCATION: (15)..(15)
<223> OTHER INFORMATION: X is G, A, S, or E
<220> FEATURE:
<221> NAME/KEY: unsure
<222> LOCATION: (24)..(24)
```

-continued

```
<223> OTHER INFORMATION: X is A, T, V, or G

<400> SEQUENCE: 2

Glu Val Xaa Leu Xaa Xaa Ser Gly Gly Xaa Leu Val Xaa Pro Xaa Gly
1               5                   10                  15

Ser Leu Arg Leu Ser Cys Val Xaa Ser
            20                  25

<210> SEQ ID NO 3
<211> LENGTH: 14
<212> TYPE: PRT
<213> ORGANISM: canis familiaris;
<220> FEATURE:
<221> NAME/KEY: UNSURE
<222> LOCATION: (4)..(4)
<223> OTHER INFORMATION: X is Q, H, R, or E
<220> FEATURE:
<221> NAME/KEY: UNSURE
<222> LOCATION: (5)..(5)
<223> OTHER INFORMATION: X is A, T, P, C, or S
<220> FEATURE:
<221> NAME/KEY: UNSURE
<222> LOCATION: (7)..(7)
<223> OTHER INFORMATION: X is G or E
<220> FEATURE:
<221> NAME/KEY: UNSURE
<222> LOCATION: (11)..(11)
<223> OTHER INFORMATION: X is Q, E, or K
<220> FEATURE:
<221> NAME/KEY: UNSURE
<222> LOCATION: (12)..(12)
<223> OTHER INFORMATION: X is W, L, or Y
<220> FEATURE:
<221> NAME/KEY: UNSURE
<222> LOCATION: (13)..(13)
<223> OTHER INFORMATION: X is V or I
<220> FEATURE:
<221> NAME/KEY: UNSURE
<222> LOCATION: (14)..(14)
<223> OTHER INFORMATION: X is A, G, V, or T

<400> SEQUENCE: 3

Trp Val Arg Xaa Xaa Pro Xaa Lys Gly Leu Xaa Xaa Xaa Xaa
1               5                   10

<210> SEQ ID NO 4
<211> LENGTH: 32
<212> TYPE: PRT
<213> ORGANISM: canis familiaris;
<220> FEATURE:
<221> NAME/KEY: UNSURE
<222> LOCATION: (3)..(3)
<223> OTHER INFORMATION: X is T or I
<220> FEATURE:
<221> NAME/KEY: UNSURE
<222> LOCATION: (4)..(4)
<223> OTHER INFORMATION: X is I or V
<220> FEATURE:
<221> NAME/KEY: UNSURE
<222> LOCATION: (8)..(8)
<223> OTHER INFORMATION: X is N, L, S, or D
<220> FEATURE:
<221> NAME/KEY: UNSURE
<222> LOCATION: (10)..(10)
<223> OTHER INFORMATION: X is K, R, or E
<220> FEATURE:
<221> NAME/KEY: UNSURE
<222> LOCATION: (11)..(11)
<223> OTHER INFORMATION: X is N or S
<220> FEATURE:
<221> NAME/KEY: UNSURE
<222> LOCATION: (13)..(13)
<223> OTHER INFORMATION: X is L, V, or F
<220> FEATURE:
```

```
<221> NAME/KEY: UNSURE
<222> LOCATION: (14)..(14)
<223> OTHER INFORMATION: X is Y, F, or S
<220> FEATURE:
<221> NAME/KEY: UNSURE
<222> LOCATION: (16)..(16)
<223> OTHER INFORMATION: X is Q, H, or E
<220> FEATURE:
<221> NAME/KEY: UNSURE
<222> LOCATION: (17)..(17)
<223> OTHER INFORMATION: X is M or L
<220> FEATURE:
<221> NAME/KEY: UNSURE
<222> LOCATION: (18)..(18)
<223> OTHER INFORMATION: X is N, D, or E
<220> FEATURE:
<221> NAME/KEY: UNSURE
<222> LOCATION: (19)..(19)
<223> OTHER INFORMATION: X is S or N
<220> FEATURE:
<221> NAME/KEY: UNSURE
<222> LOCATION: (21)..(21)
<223> OTHER INFORMATION: X is R or T
<220> FEATURE:
<221> NAME/KEY: UNSURE
<222> LOCATION: (22)..(22)
<223> OTHER INFORMATION: X is A, V, D, P, G, or T
<220> FEATURE:
<221> NAME/KEY: UNSURE
<222> LOCATION: (23)..(23)
<223> OTHER INFORMATION: X is E or D
<220> FEATURE:
<221> NAME/KEY: UNSURE
<222> LOCATION: (26)..(26)
<223> OTHER INFORMATION: X is V, I, T, R, or M
<220> FEATURE:
<221> NAME/KEY: UNSURE
<222> LOCATION: (28)..(28)
<223> OTHER INFORMATION: X is Y or F
<220> FEATURE:
<221> NAME/KEY: UNSURE
<222> LOCATION: (30)..(30)
<223> OTHER INFORMATION: X is A, G, T, or V
<220> FEATURE:
<221> NAME/KEY: UNSURE
<222> LOCATION: (32)..(32)
<223> OTHER INFORMATION: X is R, T, G, S, A, P, or K

<400> SEQUENCE: 4

Arg Phe Xaa Xaa Ser Arg Asp Xaa Ala Xaa Xaa Thr Xaa Xaa Leu Xaa
1               5                   10                  15

Xaa Xaa Xaa Leu Xaa Xaa Xaa Asp Thr Xaa Ala Xaa Tyr Xaa Cys Xaa
            20                  25                  30

<210> SEQ ID NO 5
<211> LENGTH: 10
<212> TYPE: PRT
<213> ORGANISM: canis familiaris;
<220> FEATURE:
<221> NAME/KEY: UNSURE
<222> LOCATION: (1)..(1)
<223> OTHER INFORMATION: X is Y, S, H, or L
<220> FEATURE:
<221> NAME/KEY: UNSURE
<222> LOCATION: (4)..(4)
<223> OTHER INFORMATION: X is Q or R
<220> FEATURE:
<221> NAME/KEY: UNSURE
<222> LOCATION: (6)..(6)
<223> OTHER INFORMATION: X is T, N, or A
<220> FEATURE:
<221> NAME/KEY: UNSURE
<222> LOCATION: (7)..(7)
<223> OTHER INFORMATION: X is L or P
<220> FEATURE:
<221> NAME/KEY: UNSURE
```

```
<222> LOCATION: (9)..(9)
<223> OTHER INFORMATION: X is T or absent
<220> FEATURE:
<221> NAME/KEY: UNSURE
<222> LOCATION: (10)..(10)
<223> OTHER INFORMATION: X is V or absent

<400> SEQUENCE: 5

Xaa Trp Gly Xaa Gly Xaa Xaa Val Xaa Xaa
1               5                   10

<210> SEQ ID NO 6
<211> LENGTH: 25
<212> TYPE: PRT
<213> ORGANISM: canis familiaris;

<400> SEQUENCE: 6

Glu Val Gln Leu Val Glu Ser Gly Gly Asp Leu Val Lys Pro Ala Gly
1               5                   10                  15

Ser Leu Arg Leu Ser Cys Val Thr Ser
            20                  25

<210> SEQ ID NO 7
<211> LENGTH: 25
<212> TYPE: PRT
<213> ORGANISM: canis familiaris;

<400> SEQUENCE: 7

Glu Val Gln Leu Met Glu Ser Gly Gly Asp Leu Val Lys Pro Gly Gly
1               5                   10                  15

Ser Leu Arg Leu Ser Cys Val Ala Ser
            20                  25

<210> SEQ ID NO 8
<211> LENGTH: 25
<212> TYPE: PRT
<213> ORGANISM: canis familiaris;

<400> SEQUENCE: 8

Glu Val Gln Leu Val Glu Ser Gly Gly Asp Leu Val Lys Pro Glu Gly
1               5                   10                  15

Ser Leu Arg Leu Ser Cys Val Val Ser
            20                  25

<210> SEQ ID NO 9
<211> LENGTH: 25
<212> TYPE: PRT
<213> ORGANISM: canis familiaris;

<400> SEQUENCE: 9

Glu Val Gln Leu Val Glu Ser Gly Gly Asp Leu Val Lys Pro Ala Gly
1               5                   10                  15

Ser Leu Arg Leu Ser Cys Val Ala Ser
            20                  25

<210> SEQ ID NO 10
<211> LENGTH: 25
<212> TYPE: PRT
<213> ORGANISM: canis familiaris;

<400> SEQUENCE: 10

Glu Val Gln Leu Val Glu Ser Gly Gly Asp Leu Val Arg Pro Gly Gly
1               5                   10                  15
```

```
Ser Leu Arg Leu Ser Cys Val Ala Ser
            20                  25

<210> SEQ ID NO 11
<211> LENGTH: 25
<212> TYPE: PRT
<213> ORGANISM: canis familiaris;
<220> FEATURE:
<221> NAME/KEY: UNSURE
<222> LOCATION: (10)..(10)
<223> OTHER INFORMATION: X is D, X, or N
<220> FEATURE:
<221> NAME/KEY: UNSURE
<222> LOCATION: (19)..(19)
<223> OTHER INFORMATION: X is any amino acid

<400> SEQUENCE: 11

Glu Val Gln Leu Val Glu Ser Gly Gly Xaa Leu Val Lys Phe Gly Gly
1               5                   10                  15

Ser Leu Xaa Leu Ser Cys Val Ala Ser
            20                  25

<210> SEQ ID NO 12
<211> LENGTH: 25
<212> TYPE: PRT
<213> ORGANISM: canis familiaris;

<400> SEQUENCE: 12

Glu Val His Leu Val Glu Ser Gly Gly Asp Leu Val Lys Pro Gly Gly
1               5                   10                  15

Ser Leu Arg Leu Ser Cys Val Ala Ser
            20                  25

<210> SEQ ID NO 13
<211> LENGTH: 25
<212> TYPE: PRT
<213> ORGANISM: canis familiaris;

<400> SEQUENCE: 13

Glu Val Gln Leu Val Glu Ser Gly Gly Asp Leu Val Lys Pro Gly Gly
1               5                   10                  15

Ser Leu Arg Leu Ser Cys Val Ala Ser
            20                  25

<210> SEQ ID NO 14
<211> LENGTH: 25
<212> TYPE: PRT
<213> ORGANISM: canis familiaris;

<400> SEQUENCE: 14

Glu Val Gln Leu Val Glu Ser Gly Gly Asp Leu Val Lys Pro Gly Gly
1               5                   10                  15

Ser Leu Arg Leu Ser Cys Val Gly Ser
            20                  25

<210> SEQ ID NO 15
<211> LENGTH: 25
<212> TYPE: PRT
<213> ORGANISM: canis familiaris;

<400> SEQUENCE: 15

Glu Val Gln Leu Val Glu Ser Gly Gly Asp Leu Val Lys Pro Gly Gly
1               5                   10                  15

Ser Leu Arg Leu Ser Cys Val Thr Ser
```

20                  25

<210> SEQ ID NO 16
<211> LENGTH: 25
<212> TYPE: PRT
<213> ORGANISM: canis familiaris;

<400> SEQUENCE: 16

Glu Val Gln Leu Val Gln Ser Gly Gly Asp Leu Val Lys Pro Ser Gly
1               5                   10                  15

Ser Leu Arg Leu Ser Cys Val Ala Ser
            20                  25

<210> SEQ ID NO 17
<211> LENGTH: 25
<212> TYPE: PRT
<213> ORGANISM: canis familiaris;

<400> SEQUENCE: 17

Glu Val Gln Leu Val Glu Ser Gly Gly Asn Leu Val Lys Pro Gly Gly
1               5                   10                  15

Ser Leu Arg Leu Ser Cys Val Ala Ser
            20                  25

<210> SEQ ID NO 18
<211> LENGTH: 14
<212> TYPE: PRT
<213> ORGANISM: canis familiaris;

<400> SEQUENCE: 18

Trp Val Arg Gln Ala Pro Gly Lys Gly Leu Gln Trp Val Ala
1               5                   10

<210> SEQ ID NO 19
<211> LENGTH: 14
<212> TYPE: PRT
<213> ORGANISM: canis familiaris;

<400> SEQUENCE: 19

Trp Val Arg Gln Ala Pro Gly Lys Gly Leu Gln Leu Val Ala
1               5                   10

<210> SEQ ID NO 20
<211> LENGTH: 14
<212> TYPE: PRT
<213> ORGANISM: canis familiaris;

<400> SEQUENCE: 20

Trp Val Arg Gln Ser Pro Gly Lys Gly Leu Gln Trp Val Ala
1               5                   10

<210> SEQ ID NO 21
<211> LENGTH: 14
<212> TYPE: PRT
<213> ORGANISM: canis familiaris;

<400> SEQUENCE: 21

Trp Val Arg Gln Ala Pro Glu Lys Gly Leu Gln Leu Val Ala
1               5                   10

<210> SEQ ID NO 22
<211> LENGTH: 14
<212> TYPE: PRT
<213> ORGANISM: canis familiaris;

```
<400> SEQUENCE: 22

Trp Val Arg Glu Ala Pro Gly Lys Gly Leu Gln Trp Val Ala
1               5                   10

<210> SEQ ID NO 23
<211> LENGTH: 14
<212> TYPE: PRT
<213> ORGANISM: canis familiaris;

<400> SEQUENCE: 23

Trp Val Arg Arg Ala Pro Gly Lys Gly Leu Gln Trp Ile Ala
1               5                   10

<210> SEQ ID NO 24
<211> LENGTH: 14
<212> TYPE: PRT
<213> ORGANISM: canis familiaris;

<400> SEQUENCE: 24

Trp Val Arg His Ser Pro Gly Lys Gly Leu Gln Trp Val Ala
1               5                   10

<210> SEQ ID NO 25
<211> LENGTH: 14
<212> TYPE: PRT
<213> ORGANISM: canis familiaris;

<400> SEQUENCE: 25

Trp Val Arg Gln Cys Pro Gly Lys Gly Leu Gln Trp Val Thr
1               5                   10

<210> SEQ ID NO 26
<211> LENGTH: 14
<212> TYPE: PRT
<213> ORGANISM: canis familiaris;

<400> SEQUENCE: 26

Trp Val Arg Gln Pro Pro Gly Lys Gly Leu Gln Trp Ile Val
1               5                   10

<210> SEQ ID NO 27
<211> LENGTH: 14
<212> TYPE: PRT
<213> ORGANISM: canis familiaris;

<400> SEQUENCE: 27

Trp Val Arg Gln Pro Pro Gly Lys Gly Pro Gln Trp Val Ala
1               5                   10

<210> SEQ ID NO 28
<211> LENGTH: 14
<212> TYPE: PRT
<213> ORGANISM: canis familiaris;

<400> SEQUENCE: 28

Trp Val Arg Gln Ala Pro Gly Lys Gly Leu Gln Tyr Val Ala
1               5                   10

<210> SEQ ID NO 29
<211> LENGTH: 14
<212> TYPE: PRT
<213> ORGANISM: canis familiaris;

<400> SEQUENCE: 29
```

-continued

Trp Val Arg Gln Ala Pro Gly Lys Gly Leu Lys Trp Val Ala
1               5                   10

<210> SEQ ID NO 30
<211> LENGTH: 14
<212> TYPE: PRT
<213> ORGANISM: canis familiaris;

<400> SEQUENCE: 30

Trp Val Arg Gln Ala Pro Gly Glu Gly Leu Gln Trp Ile Gly
1               5                   10

<210> SEQ ID NO 31
<211> LENGTH: 14
<212> TYPE: PRT
<213> ORGANISM: canis familiaris;

<400> SEQUENCE: 31

Trp Val Arg Gln Thr Pro Glu Arg Gly Leu Glu Leu Val Ala
1               5                   10

<210> SEQ ID NO 32
<211> LENGTH: 32
<212> TYPE: PRT
<213> ORGANISM: canis familiaris;

<400> SEQUENCE: 32

Arg Phe Thr Ile Ser Arg Asp Asn Ala Lys Asn Thr Val Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 33
<211> LENGTH: 32
<212> TYPE: PRT
<213> ORGANISM: canis familiaris;

<400> SEQUENCE: 33

Arg Phe Thr Ile Ser Arg Asp Asn Ala Lys Asn Thr Phe Tyr Leu Gln
1               5                   10                  15

Met Asn Ser Leu Arg Ala Glu Asp Ser Ala Met Tyr Tyr Cys Ala Ala
            20                  25                  30

<210> SEQ ID NO 34
<211> LENGTH: 32
<212> TYPE: PRT
<213> ORGANISM: canis familiaris;

<400> SEQUENCE: 34

Arg Phe Thr Ile Ser Arg Asp Asn Ala Lys Asn Thr Leu Tyr Leu Gln
1               5                   10                  15

Met Asn Ser Leu Arg Thr Glu Asp Thr Ala Val Tyr Tyr Cys Ala Arg
            20                  25                  30

<210> SEQ ID NO 35
<211> LENGTH: 32
<212> TYPE: PRT
<213> ORGANISM: canis familiaris;

<400> SEQUENCE: 35

Arg Phe Thr Ile Ser Arg Asp Asn Ala Lys Asn Thr Val Tyr Leu Gln
1               5                   10                  15

```
Met Asn Ser Leu Arg Ala Glu Asp Thr Ala Met Tyr Tyr Cys Ala Pro
            20                  25                  30
```

<210> SEQ ID NO 36
<211> LENGTH: 32
<212> TYPE: PRT
<213> ORGANISM: canis familiaris;

<400> SEQUENCE: 36

```
Arg Phe Thr Ile Ser Arg Asp Asn Ala Lys Asn Thr Val Tyr Leu Gln
1               5                   10                  15
Met Asn Ser Leu Arg Gly Glu Asp Thr Ala Met Tyr Tyr Cys Ala Lys
            20                  25                  30
```

<210> SEQ ID NO 37
<211> LENGTH: 32
<212> TYPE: PRT
<213> ORGANISM: canis familiaris;

<400> SEQUENCE: 37

```
Arg Phe Thr Ile Ser Arg Asp Asn Ala Lys Asn Thr Leu Tyr Leu Gln
1               5                   10                  15
Met Asn Ser Leu Arg Ala Glu Asp Thr Ala Val Tyr Tyr Cys Ala Lys
            20                  25                  30
```

<210> SEQ ID NO 38
<211> LENGTH: 32
<212> TYPE: PRT
<213> ORGANISM: canis familiaris;

<400> SEQUENCE: 38

```
Arg Phe Thr Ile Ser Arg Asp Asn Ala Lys Asn Thr Leu Tyr Leu Gln
1               5                   10                  15
Leu Asn Ser Leu Arg Val Glu Asp Thr Ala Val Tyr Tyr Cys Ala Arg
            20                  25                  30
```

<210> SEQ ID NO 39
<211> LENGTH: 32
<212> TYPE: PRT
<213> ORGANISM: canis familiaris;

<400> SEQUENCE: 39

```
Arg Phe Thr Ile Ser Arg Asp Asn Ala Glu Asn Thr Leu Tyr Leu Gln
1               5                   10                  15
Met Asn Ser Leu Arg Pro Glu Asp Thr Ala Val Tyr Tyr Cys Ala Ser
            20                  25                  30
```

<210> SEQ ID NO 40
<211> LENGTH: 32
<212> TYPE: PRT
<213> ORGANISM: canis familiaris;
<220> FEATURE:
<221> NAME/KEY: UNSURE
<222> LOCATION: (24)..(24)
<223> OTHER INFORMATION: X is D

<400> SEQUENCE: 40

```
Arg Phe Thr Ile Ser Arg Asp Asn Ala Lys Ser Thr Leu Tyr Leu Glu
1               5                   10                  15
Met Asn Arg Leu Arg Pro Asp Xaa Thr Ala Met Tyr Tyr Cys Val Thr
            20                  25                  30
```

<210> SEQ ID NO 41

```
<211> LENGTH: 32
<212> TYPE: PRT
<213> ORGANISM: canis familiaris;

<400> SEQUENCE: 41

Arg Phe Thr Ile Ser Arg Asp Asp Ala Asn Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 42
<211> LENGTH: 32
<212> TYPE: PRT
<213> ORGANISM: canis familiaris;

<400> SEQUENCE: 42

Arg Phe Thr Ile Ser Arg Asp Asn Ala Lys Asn Thr Leu Tyr Leu Gln
1               5                   10                  15

Leu Asn Ser Leu Arg Ala Glu Asp Thr Ala Val Tyr Tyr Cys Ala Lys
            20                  25                  30

<210> SEQ ID NO 43
<211> LENGTH: 32
<212> TYPE: PRT
<213> ORGANISM: canis familiaris;

<400> SEQUENCE: 43

Arg Phe Thr Ile Ser Arg Asp Asn Ala Lys Asn Thr Leu Ser Leu Glu
1               5                   10                  15

Met Asn Ser Leu Arg Asp Glu Asp Thr Ala Met Tyr Tyr Cys Ala Arg
            20                  25                  30

<210> SEQ ID NO 44
<211> LENGTH: 32
<212> TYPE: PRT
<213> ORGANISM: canis familiaris;

<400> SEQUENCE: 44

Arg Phe Thr Ile Ser Arg Asp Ser Ala Lys Asn Thr Leu Tyr Leu Gln
1               5                   10                  15

Leu Asn Ser Leu Thr Ala Glu Asp Thr Ala Arg Tyr Tyr Cys Ala Gly
            20                  25                  30

<210> SEQ ID NO 45
<211> LENGTH: 32
<212> TYPE: PRT
<213> ORGANISM: canis familiaris;
<220> FEATURE:
<221> NAME/KEY: UNSURE
<222> LOCATION: (16)..(16)
<223> OTHER INFORMATION: X is Q, H, or E

<400> SEQUENCE: 45

Arg Phe Thr Ile Ser Arg Asp Asn Ala Lys Asn Thr Leu Tyr Leu Xaa
1               5                   10                  15

Met Asn Ser Leu Arg Ala Glu Asp Thr Ala Val Tyr Tyr Cys Gly Lys
            20                  25                  30

<210> SEQ ID NO 46
<211> LENGTH: 32
<212> TYPE: PRT
<213> ORGANISM: canis familiaris;
<220> FEATURE:
<221> NAME/KEY: UNSURE
```

<222> LOCATION: (23)..(23)
<223> OTHER INFORMATION: X is E or D

<400> SEQUENCE: 46

Arg Phe Thr Ile Ser Arg Asp Asn Ala Lys Asn Thr Leu Tyr Leu Gln
1               5                   10                  15

Met Asn Ser Leu Arg Ala Xaa Asp Thr Ala Val Tyr Tyr Cys Ala Arg
            20                  25                  30

<210> SEQ ID NO 47
<211> LENGTH: 32
<212> TYPE: PRT
<213> ORGANISM: canis familiaris;

<400> SEQUENCE: 47

Arg Phe Thr Ile Ser Arg Asp Asn Ala Arg Asn Thr Val Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 48
<211> LENGTH: 32
<212> TYPE: PRT
<213> ORGANISM: canis familiaris;

<400> SEQUENCE: 48

Arg Phe Thr Ile Ser Arg Asp Asn Ala Lys Asn Thr Leu Ser Leu His
1               5                   10                  15

Met Asn Ser Leu Arg Val Glu Asp Thr Ala Val Tyr Phe Cys Thr Arg
            20                  25                  30

<210> SEQ ID NO 49
<211> LENGTH: 32
<212> TYPE: PRT
<213> ORGANISM: canis familiaris;

<400> SEQUENCE: 49

Arg Phe Thr Ile Ser Arg Asp Asn Ala Arg Asn Thr Leu Tyr Leu Gln
1               5                   10                  15

Met Asn Ser Leu Arg Ala Glu Asp Thr Ala Val Tyr Phe Cys Ala Lys
            20                  25                  30

<210> SEQ ID NO 50
<211> LENGTH: 32
<212> TYPE: PRT
<213> ORGANISM: canis familiaris;

<400> SEQUENCE: 50

Arg Phe Thr Val Ser Arg Asp Asn Ala Lys Ser Thr Leu Tyr Leu Gln
1               5                   10                  15

Met Glu Asn Leu Arg Ala Glu Asp Thr Ala Val Tyr Tyr Cys Ala Thr
            20                  25                  30

<210> SEQ ID NO 51
<211> LENGTH: 32
<212> TYPE: PRT
<213> ORGANISM: canis familiaris;

<400> SEQUENCE: 51

Arg Phe Thr Ile Ser Arg Asp Asn Ala Lys Asn Thr Leu Phe Leu Gln
1               5                   10                  15

Met His Ser Leu Arg Ala Glu Asp Thr Ala Ile Tyr Tyr Cys Ala Arg

-continued

<210> SEQ ID NO 52
<211> LENGTH: 32
<212> TYPE: PRT
<213> ORGANISM: canis familiaris;

<400> SEQUENCE: 52

Arg Phe Ile Ile Ser Arg Asp Leu Ala Lys Ser Thr Val Tyr Leu Gln
1               5                   10                  15

Met Asp Asn Leu Arg Ala Asp Thr Ala Thr Tyr Tyr Cys Ala Arg
            20                  25                  30

<210> SEQ ID NO 53
<211> LENGTH: 32
<212> TYPE: PRT
<213> ORGANISM: canis familiaris;

<400> SEQUENCE: 53

Arg Phe Thr Ile Ser Arg Asp Asn Ala Arg Asn Thr Val Tyr Leu Gln
1               5                   10                  15

Leu Asn Ser Leu Arg Ala Glu Asp Thr Ala Val Tyr Tyr Cys Gly Lys
            20                  25                  30

<210> SEQ ID NO 54
<211> LENGTH: 10
<212> TYPE: PRT
<213> ORGANISM: canis familiaris;

<400> SEQUENCE: 54

His Trp Gly Gln Gly Thr Leu Val Thr Val
1               5                   10

<210> SEQ ID NO 55
<211> LENGTH: 10
<212> TYPE: PRT
<213> ORGANISM: canis familiaris;

<400> SEQUENCE: 55

Leu Trp Gly Pro Gly Thr Leu Val Thr Val
1               5                   10

<210> SEQ ID NO 56
<211> LENGTH: 10
<212> TYPE: PRT
<213> ORGANISM: canis familiaris;

<400> SEQUENCE: 56

Tyr Trp Gly Gln Gly Thr Leu Val Thr Val
1               5                   10

<210> SEQ ID NO 57
<211> LENGTH: 10
<212> TYPE: PRT
<213> ORGANISM: canis familiaris;

<400> SEQUENCE: 57

Ser Trp Gly Gln Gly Thr Leu Val Thr Val
1               5                   10

<210> SEQ ID NO 58
<211> LENGTH: 9
<212> TYPE: PRT
<213> ORGANISM: canis familiaris;

```
<400> SEQUENCE: 58

Tyr Trp Gly Gln Gly Thr Leu Val Thr
1               5

<210> SEQ ID NO 59
<211> LENGTH: 9
<212> TYPE: PRT
<213> ORGANISM: canis familiaris;

<400> SEQUENCE: 59

Leu Trp Gly Gln Gly Thr Leu Val Thr
1               5

<210> SEQ ID NO 60
<211> LENGTH: 9
<212> TYPE: PRT
<213> ORGANISM: canis familiaris;

<400> SEQUENCE: 60

Leu Trp Gly Gln Gly Thr Leu Thr Val
1               5

<210> SEQ ID NO 61
<211> LENGTH: 9
<212> TYPE: PRT
<213> ORGANISM: canis familiaris;

<400> SEQUENCE: 61

His Trp Gly Gln Gly Thr Leu Val Thr
1               5

<210> SEQ ID NO 62
<211> LENGTH: 8
<212> TYPE: PRT
<213> ORGANISM: canis familiaris;

<400> SEQUENCE: 62

Tyr Trp Gly Gln Gly Thr Leu Val
1               5

<210> SEQ ID NO 63
<211> LENGTH: 10
<212> TYPE: PRT
<213> ORGANISM: canis familiaris;

<400> SEQUENCE: 63

Tyr Trp Gly Gln Gly Thr Pro Val Thr Val
1               5                   10

<210> SEQ ID NO 64
<211> LENGTH: 10
<212> TYPE: PRT
<213> ORGANISM: canis familiaris;

<400> SEQUENCE: 64

Gly Trp Gly Gln Gly Thr Leu Val Thr Val
1               5                   10

<210> SEQ ID NO 65
<211> LENGTH: 8
<212> TYPE: PRT
<213> ORGANISM: canis familiaris;

<400> SEQUENCE: 65
```

```
His Trp Gly Gln Gly Thr Leu Val
1               5

<210> SEQ ID NO 66
<211> LENGTH: 10
<212> TYPE: PRT
<213> ORGANISM: canis familiaris;

<400> SEQUENCE: 66

Tyr Trp Gly Pro Gly Thr Leu Val Thr Val
1               5                   10

<210> SEQ ID NO 67
<211> LENGTH: 10
<212> TYPE: PRT
<213> ORGANISM: canis familiaris;

<400> SEQUENCE: 67

Tyr Trp Gly Gln Gly Asn Leu Val Thr Val
1               5                   10

<210> SEQ ID NO 68
<211> LENGTH: 10
<212> TYPE: PRT
<213> ORGANISM: canis familiaris;

<400> SEQUENCE: 68

Ser Trp Gly Arg Gly Ala Leu Val Thr Val
1               5                   10

<210> SEQ ID NO 69
<211> LENGTH: 25
<212> TYPE: PRT
<213> ORGANISM: canis familiaris;
<220> FEATURE:
<221> NAME/KEY: UNSURE
<222> LOCATION: (3)..(3)
<223> OTHER INFORMATION: X is Q or H

<400> SEQUENCE: 69

Glu Val Xaa Leu Val Gln Ser Ala Ala Trp Val Lys Lys Pro Gly Ala
1               5                   10                  15

Ser Val Lys Val Ser Cys Lys Thr Ser
            20                  25

<210> SEQ ID NO 70
<211> LENGTH: 15
<212> TYPE: PRT
<213> ORGANISM: canis familiaris;
<220> FEATURE:
<221> NAME/KEY: UNSURE
<222> LOCATION: (11)..(11)
<223> OTHER INFORMATION: X is D or E

<400> SEQUENCE: 70

Trp Val Gln Gln Ala Pro Gly Ala Gly Leu Xaa Trp Met Gly Trp
1               5                   10                  15

<210> SEQ ID NO 71
<211> LENGTH: 31
<212> TYPE: PRT
<213> ORGANISM: canis familiaris;
<220> FEATURE:
<221> NAME/KEY: unsure
<222> LOCATION: (11)..(11)
<223> OTHER INFORMATION: X is S or N
```

```
<220> FEATURE:
<221> NAME/KEY: unsure
<222> LOCATION: (22)..(22)
<223> OTHER INFORMATION: X is A or T
<220> FEATURE:
<221> NAME/KEY: unsure
<222> LOCATION: (19)..(19)
<223> OTHER INFORMATION: X is S or N
<220> FEATURE:
<221> NAME/KEY: unsure
<222> LOCATION: (24)..(24)
<223> OTHER INFORMATION: X is T or A
<220> FEATURE:
<221> NAME/KEY: unsure
<222> LOCATION: (31)..(31)
<223> OTHER INFORMATION: X is R or S

<400> SEQUENCE: 71

Arg Val Thr Leu Thr Ala Asp Thr Ser Thr Xaa Val Thr Tyr Met Glu
 1               5                  10                  15

Leu Ser Xaa Leu Arg Xaa Glu Xaa Ala Val Tyr Tyr Cys Ala Xaa
            20                  25                  30

<210> SEQ ID NO 72
<211> LENGTH: 10
<212> TYPE: PRT
<213> ORGANISM: canis familiaris;
<220> FEATURE:
<221> NAME/KEY: unsure
<222> LOCATION: (1)..(1)
<223> OTHER INFORMATION: X is Y or L

<400> SEQUENCE: 72

Xaa Trp Gly Gln Gly Thr Leu Val Thr Val
 1               5                  10

<210> SEQ ID NO 73
<211> LENGTH: 25
<212> TYPE: PRT
<213> ORGANISM: canis familiaris;

<400> SEQUENCE: 73

Glu Val Gln Leu Val Gln Ser Ala Ala Glu Val Lys Lys Pro Gly Ala
 1               5                  10                  15

Ser Val Lys Val Ser Cys Lys Thr Ser
            20                  25

<210> SEQ ID NO 74
<211> LENGTH: 15
<212> TYPE: PRT
<213> ORGANISM: canis familiaris;

<400> SEQUENCE: 74

Trp Val Gln Gln Ala Pro Gly Ala Gly Leu Asp Trp Met Gly Trp
 1               5                  10                  15

<210> SEQ ID NO 75
<211> LENGTH: 15
<212> TYPE: PRT
<213> ORGANISM: canis familiaris;

<400> SEQUENCE: 75

Trp Val Gln Gln Ala Pro Gly Ala Gly Leu Glu Trp Met Gly Trp
 1               5                  10                  15

<210> SEQ ID NO 76
<211> LENGTH: 32
```

```
<212> TYPE: PRT
<213> ORGANISM: canis familiaris;

<400> SEQUENCE: 76

Arg Val Thr Leu Thr Ala Asp Thr Ser Thr Ser Thr Ala Tyr Met Glu
1               5                   10                  15

Leu Ser Ser Leu Arg Ala Glu Asp Thr Ala Val Tyr Tyr Cys Ala Ser
            20                  25                  30

<210> SEQ ID NO 77
<211> LENGTH: 32
<212> TYPE: PRT
<213> ORGANISM: canis familiaris;

<400> SEQUENCE: 77

Arg Val Thr Leu Thr Ala Asp Thr Ser Thr Asn Thr Val Tyr Met Glu
1               5                   10                  15

Leu Ser Asn Leu Arg Thr Glu Asp Thr Ala Val Tyr Tyr Cys Ala Arg
            20                  25                  30

<210> SEQ ID NO 78
<211> LENGTH: 32
<212> TYPE: PRT
<213> ORGANISM: canis familiaris;

<400> SEQUENCE: 78

Arg Val Thr Leu Thr Ala Asp Thr Ser Thr Ser Thr Ala Tyr Met Glu
1               5                   10                  15

Leu Ser Ser Leu Arg Ala Glu Asp Ala Ala Val Tyr Tyr Cys Ala Ser
            20                  25                  30

<210> SEQ ID NO 79
<211> LENGTH: 10
<212> TYPE: PRT
<213> ORGANISM: canis familiaris;

<400> SEQUENCE: 79

Leu Trp Gly Gln Gly Thr Leu Val Thr Val
1               5                   10

<210> SEQ ID NO 80
<211> LENGTH: 32
<212> TYPE: PRT
<213> ORGANISM: canis familiaris;

<400> SEQUENCE: 80

Arg Val Thr Leu Thr Ala Asp Thr Ser Thr Ser Thr Ala Tyr Met Glu
1               5                   10                  15

Leu Ser Ser Leu Arg Ala Glu Asp Thr Ala Val Tyr Tyr Cys Ala Arg
            20                  25                  30

<210> SEQ ID NO 81
<211> LENGTH: 25
<212> TYPE: PRT
<213> ORGANISM: canis familiaris;
<220> FEATURE:
<221> NAME/KEY: unsure
<222> LOCATION: (2)..(2)
<223> OTHER INFORMATION: X is V or L
<220> FEATURE:
<221> NAME/KEY: unsure
<222> LOCATION: (3)..(3)
<223> OTHER INFORMATION: X is I or T
<220> FEATURE:
<221> NAME/KEY: unsure
```

```
<222> LOCATION: (7)..(7)
<223> OTHER INFORMATION: X is S or A
<220> FEATURE:
<221> NAME/KEY: unsure
<222> LOCATION: (16)..(16)
<223> OTHER INFORMATION: X is Q or E
<220> FEATURE:
<221> NAME/KEY: unsure
<222> LOCATION: (23)..(23)
<223> OTHER INFORMATION: X is T or L
<220> FEATURE:
<221> NAME/KEY: unsure
<222> LOCATION: (24)..(24)
<223> OTHER INFORMATION: X is X or V

<400> SEQUENCE: 81

Glu Xaa Xaa Leu Gln Glu Xaa Gly Pro Gly Leu Val Lys Pro Ser Xaa
1               5                   10                  15

Thr Leu Ser Leu Thr Cys Xaa Xaa Ser
            20                  25

<210> SEQ ID NO 82
<211> LENGTH: 14
<212> TYPE: PRT
<213> ORGANISM: canis familiaris;
<220> FEATURE:
<221> NAME/KEY: unsure
<222> LOCATION: (4)..(4)
<223> OTHER INFORMATION: X is Q or R
<220> FEATURE:
<221> NAME/KEY: unsure
<222> LOCATION: (7)..(7)
<223> OTHER INFORMATION: X is D or G
<220> FEATURE:
<221> NAME/KEY: unsure
<222> LOCATION: (8)..(8)
<223> OTHER INFORMATION: X is R or G
<220> FEATURE:
<221> NAME/KEY: unsure
<222> LOCATION: (9)..(9)
<223> OTHER INFORMATION: X is G or E

<400> SEQUENCE: 82

Trp Ile Arg Xaa Arg Pro Xaa Xaa Xaa Leu Glu Trp Met Gly
1               5                   10

<210> SEQ ID NO 83
<211> LENGTH: 30
<212> TYPE: PRT
<213> ORGANISM: canis familiaris;
<220> FEATURE:
<221> NAME/KEY: unsure
<222> LOCATION: (4)..(4)
<223> OTHER INFORMATION: X is A or T
<220> FEATURE:
<221> NAME/KEY: unsure
<222> LOCATION: (6)..(6)
<223> OTHER INFORMATION: X is G or T
<220> FEATURE:
<221> NAME/KEY: unsure
<222> LOCATION: (7)..(7)
<223> OTHER INFORMATION: X is T or A
<220> FEATURE:
<221> NAME/KEY: unsure
<222> LOCATION: (8)..(8)
<223> OTHER INFORMATION: X is K or T
<220> FEATURE:
<221> NAME/KEY: unsure
<222> LOCATION: (10)..(10)
<223> OTHER INFORMATION: X is H or Q
<220> FEATURE:
<221> NAME/KEY: unsure
<222> LOCATION: (11)..(11)
<223> OTHER INFORMATION: X is S or F
```

```
<220> FEATURE:
<221> NAME/KEY: unsure
<222> LOCATION: (12)..(12)
<223> OTHER INFORMATION: X is S or F
<220> FEATURE:
<221> NAME/KEY: unsure
<222> LOCATION: (18)..(18)
<223> OTHER INFORMATION: X is T or V
<220> FEATURE:
<221> NAME/KEY: unsure
<222> LOCATION: (27)..(27)
<223> OTHER INFORMATION: X is Y or F
<220> FEATURE:
<221> NAME/KEY: unsure
<222> LOCATION: (29)..(29)
<223> OTHER INFORMATION: X is T or I

<400> SEQUENCE: 83

Ser Ile Thr Xaa Asp Xaa Xaa Xaa Asn Xaa Xaa Xaa Leu Gln Leu Thr
1               5                   10                  15

Ser Xaa Thr Thr Glu Asp Thr Ala Val Tyr Xaa Cys Xaa Arg
            20                  25                  30

<210> SEQ ID NO 84
<211> LENGTH: 10
<212> TYPE: PRT
<213> ORGANISM: canis familiaris;
<220> FEATURE:
<221> NAME/KEY: unsure
<222> LOCATION: (1)..(1)
<223> OTHER INFORMATION: X is V or F

<400> SEQUENCE: 84

Xaa Trp Gly Gln Gly Thr Leu Val Thr Val
1               5                   10

<210> SEQ ID NO 85
<211> LENGTH: 25
<212> TYPE: PRT
<213> ORGANISM: canis familiaris;
<220> FEATURE:
<221> NAME/KEY: UNSURE
<222> LOCATION: (24)..(24)
<223> OTHER INFORMATION: X is X or V

<400> SEQUENCE: 85

Glu Val Ile Leu Gln Glu Ser Gly Pro Gly Leu Val Lys Pro Ser Gln
1               5                   10                  15

Thr Leu Ser Leu Thr Cys Thr Xaa Ser
            20                  25

<210> SEQ ID NO 86
<211> LENGTH: 25
<212> TYPE: PRT
<213> ORGANISM: canis familiaris;

<400> SEQUENCE: 86

Glu Leu Thr Leu Gln Glu Ala Gly Pro Gly Leu Val Lys Pro Ser Glu
1               5                   10                  15

Thr Leu Ser Leu Thr Cys Leu Val Ser
            20                  25

<210> SEQ ID NO 87
<211> LENGTH: 14
<212> TYPE: PRT
<213> ORGANISM: canis familiaris;

<400> SEQUENCE: 87
```

```
Trp Ile Arg Gln Arg Pro Asp Arg Gly Leu Glu Trp Met Gly
1               5                   10
```

<210> SEQ ID NO 88
<211> LENGTH: 14
<212> TYPE: PRT
<213> ORGANISM: canis familiaris;

<400> SEQUENCE: 88

```
Trp Ile Arg Arg Arg Pro Gly Gly Glu Leu Glu Trp Met Gly
1               5                   10
```

<210> SEQ ID NO 89
<211> LENGTH: 29
<212> TYPE: PRT
<213> ORGANISM: canis familiaris;

<400> SEQUENCE: 89

```
Ile Thr Ala Asp Gly Thr Lys Asn His Leu Ser Leu Gln Leu Thr Ser
1               5                   10                  15
Thr Thr Thr Glu Asp Thr Ala Val Tyr Tyr Cys Thr Arg
            20                  25
```

<210> SEQ ID NO 90
<211> LENGTH: 30
<212> TYPE: PRT
<213> ORGANISM: canis familiaris;

<400> SEQUENCE: 90

```
Ser Ile Thr Thr Asp Thr Ala Thr Asn Gln Phe Phe Leu Gln Leu Thr
1               5                   10                  15
Ser Val Thr Thr Glu Asp Thr Ala Val Tyr Phe Cys Ile Arg
            20                  25                  30
```

<210> SEQ ID NO 91
<211> LENGTH: 10
<212> TYPE: PRT
<213> ORGANISM: canis familiaris;

<400> SEQUENCE: 91

```
Val Trp Gly Gln Gly Thr Leu Val Thr Val
1               5                   10
```

<210> SEQ ID NO 92
<211> LENGTH: 10
<212> TYPE: PRT
<213> ORGANISM: canis familiaris;

<400> SEQUENCE: 92

```
Phe Trp Gly Gln Gly Thr Leu Val Thr Val
1               5                   10
```

<210> SEQ ID NO 93
<211> LENGTH: 25
<212> TYPE: PRT
<213> ORGANISM: canis familiaris;

<400> SEQUENCE: 93

```
Ser Trp Ala Gln Ser Leu Leu Thr Gln Pro Ala Ser Val Ser Gly Ser
1               5                   10                  15
Leu Gly Gln Arg Val Thr Leu Ser Cys
            20                  25
```

<210> SEQ ID NO 94
<211> LENGTH: 25
<212> TYPE: PRT
<213> ORGANISM: canis familiaris;

<400> SEQUENCE: 94

Ser Trp Ala Gln Ser Val Leu Thr Gln Pro Ala Ser Val Ser Gly Ser
1               5                   10                  15

Leu Gly Gln Thr Val Thr Ile Ser Cys
            20                  25

<210> SEQ ID NO 95
<211> LENGTH: 20
<212> TYPE: PRT
<213> ORGANISM: canis familiaris;

<400> SEQUENCE: 95

Cys Leu Thr Gln Pro Ala Ser Val Ser Gly Ser Leu Gly Gln Arg Val
1               5                   10                  15

Thr Ile Ser Cys
            20

<210> SEQ ID NO 96
<211> LENGTH: 25
<212> TYPE: PRT
<213> ORGANISM: canis familiaris;

<400> SEQUENCE: 96

Ser Trp Ala Gln Ser Val Leu Thr Gln Pro Ala Ser Val Ser Gly Ser
1               5                   10                  15

Leu Gly Gln Arg Ile Thr Ile Ser Cys
            20                  25

<210> SEQ ID NO 97
<211> LENGTH: 25
<212> TYPE: PRT
<213> ORGANISM: canis familiaris;

<400> SEQUENCE: 97

Ser Trp Ala Gln Ser Ala Leu Thr Gln Pro Ala Ser Val Thr Gly Ser
1               5                   10                  15

Leu Gly Gln Arg Val Thr Ile Ser Cys
            20                  25

<210> SEQ ID NO 98
<211> LENGTH: 25
<212> TYPE: PRT
<213> ORGANISM: canis familiaris;

<400> SEQUENCE: 98

Ser Trp Ala Gln Ser Val Leu Thr Gln Pro Ala Ser Val Ser Gly Ser
1               5                   10                  15

Leu Gly Gln Arg Val Thr Ile Ser Cys
            20                  25

<210> SEQ ID NO 99
<211> LENGTH: 25
<212> TYPE: PRT
<213> ORGANISM: canis familiaris;

<400> SEQUENCE: 99

Ser Trp Ala Gln Ser Leu Leu Thr Gln Pro Ala Ser Val Ser Gly Ser

```
                1               5                  10                 15
Leu Gly Gln Arg Val Thr Ile Ser Cys
            20                  25

<210> SEQ ID NO 100
<211> LENGTH: 25
<212> TYPE: PRT
<213> ORGANISM: canis familiaris;

<400> SEQUENCE: 100

Ser Trp Ala Gln Ser Val Leu Thr Gln Pro Ala Ser Val Ser Gly Ser
1               5                  10                 15
Leu Gly Gln Lys Val Thr Ile Ser Cys
            20                  25

<210> SEQ ID NO 101
<211> LENGTH: 25
<212> TYPE: PRT
<213> ORGANISM: canis familiaris;

<400> SEQUENCE: 101

Ser Trp Ala Gln Ser Val Leu Thr Gln Pro Ala Ser Val Thr Gly Ser
1               5                  10                 15
Leu Gly Gln Arg Val Thr Ile Ser Cys
            20                  25

<210> SEQ ID NO 102
<211> LENGTH: 25
<212> TYPE: PRT
<213> ORGANISM: canis familiaris;

<400> SEQUENCE: 102

Ser Trp Ala Gln Ala Val Leu Asn Gln Pro Ala Ser Val Ser Gly Ala
1               5                  10                 15
Leu Gly Gln Lys Val Thr Ile Ser Cys
            20                  25

<210> SEQ ID NO 103
<211> LENGTH: 25
<212> TYPE: PRT
<213> ORGANISM: canis familiaris;

<400> SEQUENCE: 103

Ser Trp Ala Gln Ser Ile Leu Thr Gln Pro Ala Ser Val Ser Gly Ser
1               5                  10                 15
Leu Gly Gln Lys Val Thr Ile Ser Cys
            20                  25

<210> SEQ ID NO 104
<211> LENGTH: 25
<212> TYPE: PRT
<213> ORGANISM: canis familiaris;

<400> SEQUENCE: 104

Ser Trp Ala Gln Ser Val Leu Thr Gln Pro Ala Ser Met Ser Gly Ser
1               5                  10                 15
Leu Gly Gln Lys Val Thr Ile Ser Cys
            20                  25

<210> SEQ ID NO 105
<211> LENGTH: 25
<212> TYPE: PRT
```

<213> ORGANISM: canis familiaris;

<400> SEQUENCE: 105

Ser Trp Ala Gln Ser Ala Leu Thr Gln Pro Thr Ser Val Ser Gly Ser
1               5                   10                  15

Leu Gly Gln Arg Val Ser Ile Ser Cys
            20                  25

<210> SEQ ID NO 106
<211> LENGTH: 25
<212> TYPE: PRT
<213> ORGANISM: canis familiaris;

<400> SEQUENCE: 106

Ser Trp Ala Gln Ser Val Leu Thr Gln Pro Ala Ser Val Ser Gly Phe
1               5                   10                  15

Leu Gly Gln Arg Val Thr Ile Ser Cys
            20                  25

<210> SEQ ID NO 107
<211> LENGTH: 25
<212> TYPE: PRT
<213> ORGANISM: canis familiaris;

<400> SEQUENCE: 107

Ser Trp Ala Gln Ser Val Leu Thr Gln Pro Ala Ser Val Ser Gly Ser
1               5                   10                  15

Leu Gly Gln Arg Val Thr Val Ser Cys
            20                  25

<210> SEQ ID NO 108
<211> LENGTH: 25
<212> TYPE: PRT
<213> ORGANISM: canis familiaris;

<400> SEQUENCE: 108

Ser Trp Ala Gln Ser Leu Leu Thr Gln Pro Ala Ser Val Ser Gly Ser
1               5                   10                  15

Leu Gly Gln Lys Val Thr Ile Ser Cys
            20                  25

<210> SEQ ID NO 109
<211> LENGTH: 25
<212> TYPE: PRT
<213> ORGANISM: canis familiaris;

<400> SEQUENCE: 109

Ser Trp Ala Gln Ser Met Leu Thr Gln Pro Ala Ser Val Ser Gly Ser
1               5                   10                  15

Leu Gly Gln Thr Val Thr Ile Ser Cys
            20                  25

<210> SEQ ID NO 110
<211> LENGTH: 25
<212> TYPE: PRT
<213> ORGANISM: canis familiaris;

<400> SEQUENCE: 110

Ser Trp Ala Gln Ser Val Leu Thr Gln Pro Thr Ser Val Ser Gly Ser
1               5                   10                  15

Leu Gly Gln Arg Val Thr Ile Ser Cys
            20                  25

<210> SEQ ID NO 111
<211> LENGTH: 25
<212> TYPE: PRT
<213> ORGANISM: canis familiaris;

<400> SEQUENCE: 111

Ser Trp Ala Gln Ser Val Leu Thr Gln Pro Ala Ser Val Ser Gly Pro
1               5                   10                  15

Leu Gly Gln Lys Val Thr Ile Ser Cys
            20                  25

<210> SEQ ID NO 112
<211> LENGTH: 25
<212> TYPE: PRT
<213> ORGANISM: canis familiaris;

<400> SEQUENCE: 112

Ser Trp Ala Gln Ser Met Leu Thr Gln Pro Ala Ser Val Ser Gly Ser
1               5                   10                  15

Leu Gly Gln Lys Val Thr Ile Ser Cys
            20                  25

<210> SEQ ID NO 113
<211> LENGTH: 25
<212> TYPE: PRT
<213> ORGANISM: canis familiaris;
<220> FEATURE:
<221> NAME/KEY: UNSURE
<222> LOCATION: (7)..(7)
<223> OTHER INFORMATION: X is L, V, or absent

<400> SEQUENCE: 113

Ser Trp Ala Gln Ser Val Xaa Thr Gln Pro Ala Ser Val Ser Gly Ser
1               5                   10                  15

Leu Gly Gln Arg Val Thr Thr Ser Cys
            20                  25

<210> SEQ ID NO 114
<211> LENGTH: 25
<212> TYPE: PRT
<213> ORGANISM: canis familiaris;

<400> SEQUENCE: 114

Ser Trp Ala Gln Ser Val Leu Thr Gln Pro Ala Ser Val Ser Gly Ser
1               5                   10                  15

Leu Gly Gln Arg Ile Thr Val Ser Cys
            20                  25

<210> SEQ ID NO 115
<211> LENGTH: 25
<212> TYPE: PRT
<213> ORGANISM: canis familiaris;

<400> SEQUENCE: 115

Ser Trp Ala Gln Ser Val Leu Thr Gln Pro Ala Ser Val Ser Gly Ser
1               5                   10                  15

Leu Gly Gln Ser Val Thr Ile Ser Cys
            20                  25

<210> SEQ ID NO 116
<211> LENGTH: 25
<212> TYPE: PRT

<213> ORGANISM: canis familiaris;

<400> SEQUENCE: 116

Ser Trp Ala Gln Ser Val Leu Thr Gln Pro Ala Ser Val Ser Gly Pro
1               5                   10                  15

Leu Gly Gln Arg Val Thr Ile Ser Cys
            20                  25

<210> SEQ ID NO 117
<211> LENGTH: 10
<212> TYPE: PRT
<213> ORGANISM: canis familiaris;

<400> SEQUENCE: 117

Ser Leu Gly Gln Arg Val Thr Ile Ser Cys
1               5                   10

<210> SEQ ID NO 118
<211> LENGTH: 5
<212> TYPE: PRT
<213> ORGANISM: canis familiaris;

<400> SEQUENCE: 118

Val Thr Ile Ser Cys
1               5

<210> SEQ ID NO 119
<211> LENGTH: 25
<212> TYPE: PRT
<213> ORGANISM: canis familiaris;

<400> SEQUENCE: 119

Ser Trp Ala Gln Ser Glu Leu Thr Gln Ser Ala Ala Val Ser Gly Ser
1               5                   10                  15

Leu Gly Gln Glu Val Thr Ile Ser Cys
            20                  25

<210> SEQ ID NO 120
<211> LENGTH: 25
<212> TYPE: PRT
<213> ORGANISM: canis familiaris;

<400> SEQUENCE: 120

Ser Trp Ala Gln Ser Ile Val Thr Gln Ala Ala Ser Val Ser Gly Ser
1               5                   10                  15

Leu Gly Gln Arg Ile Thr Ile Ser Cys
            20                  25

<210> SEQ ID NO 121
<211> LENGTH: 25
<212> TYPE: PRT
<213> ORGANISM: canis familiaris;

<400> SEQUENCE: 121

Ser Trp Ala Gln Ser Ile Leu Thr Gln Pro Ser Ser Val Ser Gly Ser
1               5                   10                  15

Leu Gly Gln Arg Val Thr Ile Ser Cys
            20                  25

<210> SEQ ID NO 122
<211> LENGTH: 15
<212> TYPE: PRT
<213> ORGANISM: canis familiaris;

```
<400> SEQUENCE: 122

Trp Tyr Gln His Leu Pro Gly Thr Gly Pro Arg Thr Leu Ile Tyr
1               5                   10                  15

<210> SEQ ID NO 123
<211> LENGTH: 15
<212> TYPE: PRT
<213> ORGANISM: canis familiaris;

<400> SEQUENCE: 123

Trp Tyr Gln Gln Ile Pro Gly Thr Gly Pro Arg Thr Val Ile Tyr
1               5                   10                  15

<210> SEQ ID NO 124
<211> LENGTH: 15
<212> TYPE: PRT
<213> ORGANISM: canis familiaris;

<400> SEQUENCE: 124

Trp Tyr Gln Gln Phe Pro Gly Ala Gly Pro Arg Thr Leu Ile Tyr
1               5                   10                  15

<210> SEQ ID NO 125
<211> LENGTH: 15
<212> TYPE: PRT
<213> ORGANISM: canis familiaris;

<400> SEQUENCE: 125

Trp Tyr Gln Gln Leu Pro Gly Arg Ser Pro Lys Leu Leu Val Tyr
1               5                   10                  15

<210> SEQ ID NO 126
<211> LENGTH: 15
<212> TYPE: PRT
<213> ORGANISM: canis familiaris;

<400> SEQUENCE: 126

Trp Tyr Gln Gln Leu Pro Gly Arg Gly Pro Arg Thr Val Ile Tyr
1               5                   10                  15

<210> SEQ ID NO 127
<211> LENGTH: 15
<212> TYPE: PRT
<213> ORGANISM: canis familiaris;

<400> SEQUENCE: 127

Trp Phe Gln Gln Val Pro Gly Thr Gly Pro Arg Thr Val Ile Tyr
1               5                   10                  15

<210> SEQ ID NO 128
<211> LENGTH: 15
<212> TYPE: PRT
<213> ORGANISM: canis familiaris;

<400> SEQUENCE: 128

Trp Tyr Gln Gln Leu Pro Gly Thr Arg Pro Arg Thr Leu Ile Tyr
1               5                   10                  15

<210> SEQ ID NO 129
<211> LENGTH: 15
<212> TYPE: PRT
<213> ORGANISM: canis familiaris;

<400> SEQUENCE: 129
```

-continued

Trp Phe Gln Gln Leu Pro Gly Lys Gly Pro Arg Thr Val Ile Tyr
1               5                   10                  15

<210> SEQ ID NO 130
<211> LENGTH: 15
<212> TYPE: PRT
<213> ORGANISM: canis familiaris;

<400> SEQUENCE: 130

Trp Phe Gln Glu Leu Pro Gly Thr Gly Pro Lys Ile Leu Ile Tyr
1               5                   10                  15

<210> SEQ ID NO 131
<211> LENGTH: 15
<212> TYPE: PRT
<213> ORGANISM: canis familiaris;

<400> SEQUENCE: 131

Trp Tyr Gln Gln Leu Pro Gly Thr Gly Pro Arg Thr Leu Ile Tyr
1               5                   10                  15

<210> SEQ ID NO 132
<211> LENGTH: 15
<212> TYPE: PRT
<213> ORGANISM: canis familiaris;

<400> SEQUENCE: 132

Trp Phe Gln Gln Phe Pro Gly Lys Gly Pro Lys Thr Val Ile Tyr
1               5                   10                  15

<210> SEQ ID NO 133
<211> LENGTH: 15
<212> TYPE: PRT
<213> ORGANISM: canis familiaris;

<400> SEQUENCE: 133

Trp Tyr Gln Gln Leu Pro Gly Thr Gly Pro Lys Thr Leu Ile Tyr
1               5                   10                  15

<210> SEQ ID NO 134
<211> LENGTH: 15
<212> TYPE: PRT
<213> ORGANISM: canis familiaris;

<400> SEQUENCE: 134

Trp Tyr Gln Gln Leu Pro Gly Lys Ala Pro Lys Leu Leu Val Asp
1               5                   10                  15

<210> SEQ ID NO 135
<211> LENGTH: 15
<212> TYPE: PRT
<213> ORGANISM: canis familiaris;

<400> SEQUENCE: 135

Trp Tyr Gln Gln Leu Pro Gly Ile Gly Pro Lys Thr Val Ile Tyr
1               5                   10                  15

<210> SEQ ID NO 136
<211> LENGTH: 15
<212> TYPE: PRT
<213> ORGANISM: canis familiaris;

<400> SEQUENCE: 136

Trp Phe Gln Gln Phe Pro Gly Glu Gly Pro Arg Thr Val Ile Tyr

```
                1               5                  10                  15

<210> SEQ ID NO 137
<211> LENGTH: 15
<212> TYPE: PRT
<213> ORGANISM: canis familiaris;

<400> SEQUENCE: 137

Trp Tyr Arg Gln Leu Pro Gly Thr Gly Pro Thr Thr Leu Ile Tyr
1               5                  10                  15

<210> SEQ ID NO 138
<211> LENGTH: 15
<212> TYPE: PRT
<213> ORGANISM: canis familiaris;

<400> SEQUENCE: 138

Trp Tyr Gln Gln Phe Pro Gly Thr Gly Pro Arg Ile Leu Ile Tyr
1               5                  10                  15

<210> SEQ ID NO 139
<211> LENGTH: 15
<212> TYPE: PRT
<213> ORGANISM: canis familiaris;

<400> SEQUENCE: 139

Trp Tyr Gln Gln Leu Pro Gly Lys Ala Pro Lys Leu Leu Leu Asn
1               5                  10                  15

<210> SEQ ID NO 140
<211> LENGTH: 15
<212> TYPE: PRT
<213> ORGANISM: canis familiaris;

<400> SEQUENCE: 140

Trp Leu Gln Gln Leu Pro Gly Thr Gly Pro Lys Thr Val Ile Tyr
1               5                  10                  15

<210> SEQ ID NO 141
<211> LENGTH: 15
<212> TYPE: PRT
<213> ORGANISM: canis familiaris;

<400> SEQUENCE: 141

Trp Phe Gln Gln Leu Pro Gly Thr Gly Pro Arg Thr Val Ile Tyr
1               5                  10                  15

<210> SEQ ID NO 142
<211> LENGTH: 15
<212> TYPE: PRT
<213> ORGANISM: canis familiaris;

<400> SEQUENCE: 142

Trp His Gln Gln Val Pro Glu Thr Gly Pro Arg Asn Ile Ile Tyr
1               5                  10                  15

<210> SEQ ID NO 143
<211> LENGTH: 15
<212> TYPE: PRT
<213> ORGANISM: canis familiaris;

<400> SEQUENCE: 143

Trp Tyr Gln Gln Leu Pro Gly Arg Gly Pro Thr Thr Leu Leu Tyr
1               5                  10                  15
```

```
<210> SEQ ID NO 144
<211> LENGTH: 15
<212> TYPE: PRT
<213> ORGANISM: canis familiaris;

<400> SEQUENCE: 144

Trp Tyr Gln Gln Leu Pro Gly Ile Gly Pro Arg Thr Val Ile Tyr
1               5                   10                  15

<210> SEQ ID NO 145
<211> LENGTH: 15
<212> TYPE: PRT
<213> ORGANISM: canis familiaris;

<400> SEQUENCE: 145

Trp Tyr Gln Gln Val Pro Gly Thr Arg Pro Arg Thr Leu Ile Tyr
1               5                   10                  15

<210> SEQ ID NO 146
<211> LENGTH: 15
<212> TYPE: PRT
<213> ORGANISM: canis familiaris;

<400> SEQUENCE: 146

Trp Tyr Gln Gln Phe Pro Gly Arg Gly Pro Arg Ser Val Ile Tyr
1               5                   10                  15

<210> SEQ ID NO 147
<211> LENGTH: 15
<212> TYPE: PRT
<213> ORGANISM: canis familiaris;

<400> SEQUENCE: 147

Trp Tyr Gln Gln Leu Pro Gly Lys Ala Pro Lys Leu Leu Val Tyr
1               5                   10                  15

<210> SEQ ID NO 148
<211> LENGTH: 15
<212> TYPE: PRT
<213> ORGANISM: canis familiaris;

<400> SEQUENCE: 148

Trp Tyr Gln Asn Leu Pro Gly Lys Gly Pro Lys Thr Val Ile Phe
1               5                   10                  15

<210> SEQ ID NO 149
<211> LENGTH: 15
<212> TYPE: PRT
<213> ORGANISM: canis familiaris;

<400> SEQUENCE: 149

Trp Tyr Gln Gln Ile Pro Gly Thr Gly Pro Arg Thr Leu Ile Tyr
1               5                   10                  15

<210> SEQ ID NO 150
<211> LENGTH: 15
<212> TYPE: PRT
<213> ORGANISM: canis familiaris;

<400> SEQUENCE: 150

Trp Tyr Gln Gln Tyr Pro Gly Thr Gly Pro Lys Thr Leu Ile Tyr
1               5                   10                  15

<210> SEQ ID NO 151
```

```
<211> LENGTH: 15
<212> TYPE: PRT
<213> ORGANISM: canis familiaris;

<400> SEQUENCE: 151

Trp Tyr Gln Gln Val Pro Gly Thr Gly Pro Arg Thr Leu Ile His
1               5                   10                  15

<210> SEQ ID NO 152
<211> LENGTH: 15
<212> TYPE: PRT
<213> ORGANISM: canis familiaris;

<400> SEQUENCE: 152

Trp Tyr Arg Gln Phe Pro Gly Lys Ala Pro Glu Leu Leu Ile Tyr
1               5                   10                  15

<210> SEQ ID NO 153
<211> LENGTH: 15
<212> TYPE: PRT
<213> ORGANISM: canis familiaris;

<400> SEQUENCE: 153

Trp Tyr Gln Gln Leu Pro Gly Ile Gly Pro Arg Thr Val Ile Ser
1               5                   10                  15

<210> SEQ ID NO 154
<211> LENGTH: 15
<212> TYPE: PRT
<213> ORGANISM: canis familiaris;

<400> SEQUENCE: 154

Trp Phe Gln Gln Phe Pro Gly Thr Gly Pro Arg Thr Val Ile Tyr
1               5                   10                  15

<210> SEQ ID NO 155
<211> LENGTH: 15
<212> TYPE: PRT
<213> ORGANISM: canis familiaris;

<400> SEQUENCE: 155

Trp His Gln Gln Leu Pro Gly Thr Gly Pro Arg Thr Leu Ile Tyr
1               5                   10                  15

<210> SEQ ID NO 156
<211> LENGTH: 15
<212> TYPE: PRT
<213> ORGANISM: canis familiaris;

<400> SEQUENCE: 156

Trp Tyr Gln Gln Leu Pro Glu Thr Gly Pro Arg Thr Leu Ile Tyr
1               5                   10                  15

<210> SEQ ID NO 157
<211> LENGTH: 15
<212> TYPE: PRT
<213> ORGANISM: canis familiaris;

<400> SEQUENCE: 157

Trp Tyr Gln Gln Val Pro Gly Thr Gly Pro Arg Thr Leu Ile Tyr
1               5                   10                  15

<210> SEQ ID NO 158
<211> LENGTH: 15
<212> TYPE: PRT
```

<213> ORGANISM: canis familiaris;

<400> SEQUENCE: 158

Trp Tyr Gln Gln Val Pro Gly Ile Gly Pro Arg Thr Val Met Tyr
1               5                   10                  15

<210> SEQ ID NO 159
<211> LENGTH: 15
<212> TYPE: PRT
<213> ORGANISM: canis familiaris;

<400> SEQUENCE: 159

Trp Phe Gln His Leu Pro Gly Thr Arg Pro Lys Ser Leu Ile Tyr
1               5                   10                  15

<210> SEQ ID NO 160
<211> LENGTH: 15
<212> TYPE: PRT
<213> ORGANISM: canis familiaris;

<400> SEQUENCE: 160

Trp Phe Gln Gln Leu Pro Gly Thr Gly Pro Arg Thr Val Ile Cys
1               5                   10                  15

<210> SEQ ID NO 161
<211> LENGTH: 15
<212> TYPE: PRT
<213> ORGANISM: canis familiaris;

<400> SEQUENCE: 161

Trp Tyr Gln Leu Val Pro Gly Thr Gly Pro Arg Thr Leu Ile Tyr
1               5                   10                  15

<210> SEQ ID NO 162
<211> LENGTH: 15
<212> TYPE: PRT
<213> ORGANISM: canis familiaris;

<400> SEQUENCE: 162

Trp Tyr Gln Gln Leu Pro Gly Arg Gly Pro Arg Thr Val Ile His
1               5                   10                  15

<210> SEQ ID NO 163
<211> LENGTH: 15
<212> TYPE: PRT
<213> ORGANISM: canis familiaris;

<400> SEQUENCE: 163

Trp Cys Gln Gln Leu Pro Gly Lys Ala Pro Lys Leu Leu Val Asp
1               5                   10                  15

<210> SEQ ID NO 164
<211> LENGTH: 15
<212> TYPE: PRT
<213> ORGANISM: canis familiaris;

<400> SEQUENCE: 164

Trp Tyr Gln Gln Phe Pro Gly Thr Gly Pro Arg Thr Leu Ile Tyr
1               5                   10                  15

<210> SEQ ID NO 165
<211> LENGTH: 15
<212> TYPE: PRT
<213> ORGANISM: canis familiaris;

```
<400> SEQUENCE: 165

Trp Tyr Arg Gln Leu Pro Gly Glu Ala Pro Lys Leu Leu Leu Tyr
1               5                   10                  15

<210> SEQ ID NO 166
<211> LENGTH: 32
<212> TYPE: PRT
<213> ORGANISM: canis familiaris;

<400> SEQUENCE: 166

Gly Val Pro Asp Arg Phe Ser Gly Ser Arg Gly Ile Thr Ala Thr
1               5                   10                  15

Leu Thr Ile Ser Gly Leu Gln Ala Glu Asp Glu Ala Asp Tyr Tyr Cys
            20                  25                  30

<210> SEQ ID NO 167
<211> LENGTH: 32
<212> TYPE: PRT
<213> ORGANISM: canis familiaris;

<400> SEQUENCE: 167

Gly Val Pro Glu Arg Phe Ser Gly Pro Arg Ser Gly Ile Thr Ser Thr
1               5                   10                  15

Leu Thr Ile Ser Gly Leu Arg Ala Glu Asp Glu Gly Asp Tyr Tyr Cys
            20                  25                  30

<210> SEQ ID NO 168
<211> LENGTH: 32
<212> TYPE: PRT
<213> ORGANISM: canis familiaris;

<400> SEQUENCE: 168

Gly Val Pro Asp Arg Phe Ser Gly Ser Thr Ser Gly Ser Thr Ala Thr
1               5                   10                  15

Leu Thr Ile Ser Gly Leu Arg Ala Glu Asp Glu Ala Asp Tyr Tyr Cys
            20                  25                  30

<210> SEQ ID NO 169
<211> LENGTH: 32
<212> TYPE: PRT
<213> ORGANISM: canis familiaris;

<400> SEQUENCE: 169

Gly Val Pro Asp Arg Phe Ser Gly Ser Lys Ser Asp Asn Ser Ala Thr
1               5                   10                  15
Leu Thr Phe Thr Gly Leu Gln Ala Glu Asp Glu Ala Asp Tyr Tyr Cys
            20                  25                  30

<210> SEQ ID NO 170
<211> LENGTH: 32
<212> TYPE: PRT
<213> ORGANISM: canis familiaris;

<400> SEQUENCE: 170

Gly Val Pro Asp Arg Phe Ser Gly Ser Lys Ser Gly Ser Thr Ala Thr
1               5                   10                  15

Leu Thr Ile Ser Gly Leu Gln Ala Glu Asp Glu Ala Asp Tyr Tyr Cys
            20                  25                  30

<210> SEQ ID NO 171
<211> LENGTH: 32
<212> TYPE: PRT
<213> ORGANISM: canis familiaris;
```

-continued

```
<400> SEQUENCE: 171

Gly Val Pro Asp Arg Phe Ser Gly Ser Arg Ser Gly Ser Thr Ala Thr
1               5                   10                  15

Leu Thr Ile Ser Gly Leu Gln Ala Glu Asp Glu Ala Glu Tyr Tyr Cys
            20                  25                  30

<210> SEQ ID NO 172
<211> LENGTH: 32
<212> TYPE: PRT
<213> ORGANISM: canis familiaris;
<220> FEATURE:
<221> NAME/KEY: UNSURE
<222> LOCATION: (20)..(20)
<223> OTHER INFORMATION: X is S, T, or A
<220> FEATURE:
<221> NAME/KEY: UNSURE
<222> LOCATION: (31)..(31)
<223> OTHER INFORMATION: X is Y, F, or H

<400> SEQUENCE: 172

Gly Val Pro Asp Arg Phe Ser Gly Ser Lys Ser Arg Ser Thr Ala Thr
1               5                   10                  15

Leu Thr Ile Xaa Gly Leu Gln Ala Glu Asp Glu Ala Asp Tyr Xaa Cys
            20                  25                  30

<210> SEQ ID NO 173
<211> LENGTH: 32
<212> TYPE: PRT
<213> ORGANISM: canis familiaris;

<400> SEQUENCE: 173

Gly Val Pro Asp Arg Phe Ser Gly Ser Thr Ser Gly Asn Thr Ala Thr
1               5                   10                  15

Leu Thr Ile Ser Gly Leu Gln Pro Glu Asp Glu Thr Asp Tyr Tyr Cys
            20                  25                  30

<210> SEQ ID NO 174
<211> LENGTH: 32
<212> TYPE: PRT
<213> ORGANISM: canis familiaris;

<400> SEQUENCE: 174

Gly Val Pro Asp Arg Phe Ser Gly Ser Thr Ser Gly Ser Thr Ala Thr
1               5                   10                  15

Leu Thr Ile Ser Gly Leu Gln Ala Glu Asp Glu Ala Asp Tyr Tyr Cys
            20                  25                  30

<210> SEQ ID NO 175
<211> LENGTH: 32
<212> TYPE: PRT
<213> ORGANISM: canis familiaris;

<400> SEQUENCE: 175

Gly Val Pro Asp Arg Phe Ser Gly Ser Arg Ser Gly Thr Thr Ala Thr
1               5                   10                  15

Leu Thr Ile Ser Gly Leu Gln Ala Glu Asp Glu Ala Asp Tyr Tyr Cys
            20                  25                  30

<210> SEQ ID NO 176
<211> LENGTH: 32
<212> TYPE: PRT
<213> ORGANISM: canis familiaris;
```

-continued

<400> SEQUENCE: 176

Gly Val Pro Asp Arg Phe Ser Gly Ser Arg Ser Gly Ser Thr Ala Thr
1               5                   10                  15

Leu Thr Ile Ser Gly Leu Gln Pro Glu Asp Glu Ala Asp Tyr Tyr Cys
            20                  25                  30

<210> SEQ ID NO 177
<211> LENGTH: 32
<212> TYPE: PRT
<213> ORGANISM: canis familiaris;

<400> SEQUENCE: 177

Gly Val Pro Asp Arg Phe Ser Gly Ser Ser Gly Asn Ser Gly Thr
1               5                   10                  15

Leu Thr Ile Thr Gly Leu Gln Ala Glu Asp Glu Ala Asp Tyr Tyr Cys
            20                  25                  30

<210> SEQ ID NO 178
<211> LENGTH: 32
<212> TYPE: PRT
<213> ORGANISM: canis familiaris;

<400> SEQUENCE: 178

Gly Val Pro Asp Arg Phe Ser Gly Ser Lys Ser Gly Asn Ser Ala Thr
1               5                   10                  15

Leu Thr Ile Ser Gly Leu Gln Pro Glu Asp Glu Ala Glu Tyr Tyr Cys
            20                  25                  30

<210> SEQ ID NO 179
<211> LENGTH: 32
<212> TYPE: PRT
<213> ORGANISM: canis familiaris;

<400> SEQUENCE: 179

Gly Val Pro Asp Arg Phe Ser Gly Ser Lys Ser Gly Ser Thr Ala Thr
1               5                   10                  15

Leu Thr Ile Ser Glu Leu Gln Ala Glu Asp Glu Ala Asp Tyr Tyr Cys
            20                  25                  30

<210> SEQ ID NO 180
<211> LENGTH: 32
<212> TYPE: PRT
<213> ORGANISM: canis familiaris;

<400> SEQUENCE: 180

Gly Val Pro Asn Arg Phe Ser Gly Ser Arg Ser Gly Ser Thr Ala Thr
1               5                   10                  15

Leu Thr Ile Ser Gly Leu Gln Ala Asp Asp Glu Ala Asp Tyr Tyr Cys
            20                  25                  30

<210> SEQ ID NO 181
<211> LENGTH: 32
<212> TYPE: PRT
<213> ORGANISM: canis familiaris;

<400> SEQUENCE: 181

Gly Val Pro Asp Arg Phe Ser Gly Ser Arg Ser Gly Tyr Thr Ala Ala
1               5                   10                  15

Leu Thr Ile Ser Gly Leu Gln Ala Glu Asp Glu Ala Asp Tyr Tyr Cys
            20                  25                  30

<210> SEQ ID NO 182
<211> LENGTH: 32
<212> TYPE: PRT
<213> ORGANISM: canis familiaris;

<400> SEQUENCE: 182

Gly Val Pro Asp Arg Phe Ser Gly Ser Asn Ser Gly Ala Ser Ala Thr
1               5                   10                  15

Leu Thr Ile Thr Gly Leu Gln Ala Glu Asp Glu Ala Asp Tyr Tyr Cys
            20                  25                  30

<210> SEQ ID NO 183
<211> LENGTH: 32
<212> TYPE: PRT
<213> ORGANISM: canis familiaris;

<400> SEQUENCE: 183

Gly Val Pro Asp Arg Phe Ser Gly Ser Arg Ser Gly Thr Ala Thr
1               5                   10                  15

Leu Thr Ile Ser Gly Leu Gln Ala Glu Asp Glu Ala Asp Tyr Tyr Cys
            20                  25                  30

<210> SEQ ID NO 184
<211> LENGTH: 32
<212> TYPE: PRT
<213> ORGANISM: canis familiaris;

<400> SEQUENCE: 184

Gly Val Pro Asp Arg Phe Ser Gly Ser Arg Ser Gly Thr Ala Thr
1               5                   10                  15

Leu Thr Ile Ser Gly Leu Leu Ala Glu Asp Asp Ala Asp Tyr Tyr Cys
            20                  25                  30

<210> SEQ ID NO 185
<211> LENGTH: 32
<212> TYPE: PRT
<213> ORGANISM: canis familiaris;

<400> SEQUENCE: 185

Gly Val Pro Asp Arg Phe Ser Gly Ser Lys Ser Gly Ser Thr Ala Thr
1               5                   10                  15

Leu Thr Ile Ser Val Leu Gln Ala Glu Asp Glu Ala Asp Tyr Tyr Cys
            20                  25                  30

<210> SEQ ID NO 186
<211> LENGTH: 32
<212> TYPE: PRT
<213> ORGANISM: canis familiaris;

<400> SEQUENCE: 186

Gly Val Pro Asp Arg Phe Ser Gly Ser Arg Ser Gly Arg Thr Ala Thr
1               5                   10                  15

Leu Thr Ile Ser Gly Leu Gln Ala Glu Asp Glu Ala Asp Tyr Tyr Cys
            20                  25                  30

<210> SEQ ID NO 187
<211> LENGTH: 32
<212> TYPE: PRT
<213> ORGANISM: canis familiaris;

<400> SEQUENCE: 187

Gly Ile Ser Asp Arg Phe Ser Gly Ser Lys Ser Gly Asn Ser Ala Ser
1               5                   10                  15

Leu Thr Ile Ser Gly Leu Gln Ala Glu Asp Glu Ala Asp Tyr Phe Cys
            20                  25                  30

<210> SEQ ID NO 188
<211> LENGTH: 32
<212> TYPE: PRT
<213> ORGANISM: canis familiaris;

<400> SEQUENCE: 188

Gly Val Pro Asp Arg Phe Ser Val Ser Lys Ser Gly Ser Ser Ala Thr
1               5                   10                  15

Leu Thr Ile Ser Gly Leu Gln Ala Glu Asp Glu Ala Glu Tyr Tyr Cys
            20                  25                  30

<210> SEQ ID NO 189
<211> LENGTH: 32
<212> TYPE: PRT
<213> ORGANISM: canis familiaris;

<400> SEQUENCE: 189

Gly Val Pro Asp Arg Phe Ser Gly Ser Asn Ser Gly Asn Ser Ala Thr
1               5                   10                  15

Leu Thr Ile Thr Gly Leu Gln Ala Glu Asp Glu Ala Asp Tyr Tyr Cys
            20                  25                  30

<210> SEQ ID NO 190
<211> LENGTH: 32
<212> TYPE: PRT
<213> ORGANISM: canis familiaris;

<400> SEQUENCE: 190

Gly Val Pro Asp Arg Phe Ser Gly Ser Arg Ser Gly Ser Ser Ala Thr
1               5                   10                  15

Leu Thr Ile Ser Gly Leu Gln Ala Glu Asp Glu Ala Asp Tyr Tyr Cys
            20                  25                  30

<210> SEQ ID NO 191
<211> LENGTH: 32
<212> TYPE: PRT
<213> ORGANISM: canis familiaris;

<400> SEQUENCE: 191

Gly Val Pro Asp Arg Phe Ser Ala Ser Arg Ser Gly Asn Ser Ala Thr
1               5                   10                  15

Leu Thr Ile Ser Gly Leu Gln Ala Glu Asp Glu Ala Asp Tyr Tyr Cys
            20                  25                  30

<210> SEQ ID NO 192
<211> LENGTH: 32
<212> TYPE: PRT
<213> ORGANISM: canis familiaris;

<400> SEQUENCE: 192

Gly Val Pro Asp Arg Phe Ser Ala Ser Ala Ser Gly Ser Thr Ala Thr
1               5                   10                  15

Leu Thr Ile Ser Gly Leu Gln Ala Glu Asp Glu Ala Asp Tyr Tyr Cys
            20                  25                  30

<210> SEQ ID NO 193
<211> LENGTH: 32
<212> TYPE: PRT
<213> ORGANISM: canis familiaris;

```
<400> SEQUENCE: 193

Gly Val Pro Gly Arg Phe Ser Gly Ser Ile Ser Gly Asn Ser Ala Thr
1               5                   10                  15

Leu Thr Ile Thr Gly Leu Gln Ala Glu Asp Glu Ala Asp Tyr His Cys
            20                  25                  30

<210> SEQ ID NO 194
<211> LENGTH: 32
<212> TYPE: PRT
<213> ORGANISM: canis familiaris;

<400> SEQUENCE: 194

Gly Val Pro Asp Arg Phe Ser Gly Ser Lys Ser Gly Ser Ser Ala Thr
1               5                   10                  15

Leu Thr Ile Ser Gly Leu Gln Ala Glu Asp Glu Ala Glu Tyr Tyr Cys
            20                  25                  30

<210> SEQ ID NO 195
<211> LENGTH: 32
<212> TYPE: PRT
<213> ORGANISM: canis familiaris;

<400> SEQUENCE: 195

Gly Val Pro Asp Arg Phe Ser Gly Ser Arg Ser Gly Thr Ala Ile
1               5                   10                  15

Leu Thr Ile Ser Gly Leu Gln Ala Glu Asp Glu Ala Glu Tyr Tyr Cys
            20                  25                  30

<210> SEQ ID NO 196
<211> LENGTH: 32
<212> TYPE: PRT
<213> ORGANISM: canis familiaris;

<400> SEQUENCE: 196

Gly Val Pro Asp Arg Phe Ser Gly Ser Lys Ser Gly Ser Ala Ala Thr
1               5                   10                  15

Leu Thr Ile Ser Gly Leu Gln Ala Glu Asp Glu Ala Asp Tyr Tyr Cys
            20                  25                  30

<210> SEQ ID NO 197
<211> LENGTH: 32
<212> TYPE: PRT
<213> ORGANISM: canis familiaris;

<400> SEQUENCE: 197

Gly Val Pro Asp Arg Phe Ser Gly Ser Arg Ser Gly Thr Ala Thr
1               5                   10                  15

Leu Thr Ile Ser Gly Leu Gln Ala Asp Asp Glu Ala Asp Tyr Tyr Cys
            20                  25                  30

<210> SEQ ID NO 198
<211> LENGTH: 32
<212> TYPE: PRT
<213> ORGANISM: canis familiaris;

<400> SEQUENCE: 198

Gly Val Pro Glu Arg Phe Ser Gly Ser Lys Ser Gly Ser Thr Ala Ala
1               5                   10                  15

Leu Thr Ile Ser Gly Leu Gln Ala Glu Asp Glu Ala Asp Tyr Tyr Cys
            20                  25                  30
```

```
<210> SEQ ID NO 199
<211> LENGTH: 32
<212> TYPE: PRT
<213> ORGANISM: canis familiaris;

<400> SEQUENCE: 199

Gly Ala Pro Asp Arg Phe Ser Gly Ser Arg Ser Gly Ser Thr Ala Thr
1               5                   10                  15

Leu Thr Ile Ser Gly Leu Gln Ala Glu Asp Glu Ala Glu Tyr Tyr Cys
            20                  25                  30

<210> SEQ ID NO 200
<211> LENGTH: 32
<212> TYPE: PRT
<213> ORGANISM: canis familiaris;

<400> SEQUENCE: 200

Gly Val Pro Asp Arg Phe Ser Ser Ser Arg Ser Gly Ser Ala Thr
1               5                   10                  15

Leu Thr Ile Ala Gly Leu Gln Ala Glu Asp Glu Ala Ala Tyr Tyr Cys
            20                  25                  30

<210> SEQ ID NO 201
<211> LENGTH: 32
<212> TYPE: PRT
<213> ORGANISM: canis familiaris;

<400> SEQUENCE: 201

Gly Val Pro Asp Arg Phe Ser Gly Ser Lys Ser Gly Ser Thr Ala Thr
1               5                   10                  15

Leu Thr Ile Ser Gly Leu Gln Ala Glu Asp Glu Ala Ile Tyr Tyr Cys
            20                  25                  30

<210> SEQ ID NO 202
<211> LENGTH: 32
<212> TYPE: PRT
<213> ORGANISM: canis familiaris;

<400> SEQUENCE: 202

Arg Val Pro Asp Arg Phe Ser Gly Ser Glu Ser Gly Asn Ser Ala Thr
1               5                   10                  15

Leu Thr Ile Thr Gly Leu Gln Ala Glu Asp Glu Ala Asp Tyr Tyr Cys
            20                  25                  30

<210> SEQ ID NO 203
<211> LENGTH: 32
<212> TYPE: PRT
<213> ORGANISM: canis familiaris;

<400> SEQUENCE: 203

Gly Val Pro Asp Arg Phe Ser Gly Ser Arg Ser Gly Arg Thr Ala Thr
1               5                   10                  15

Leu Thr Ile Ser Gly Leu Gln Ala Glu Asp Glu Ala Glu Tyr Tyr Cys
            20                  25                  30

<210> SEQ ID NO 204
<211> LENGTH: 32
<212> TYPE: PRT
<213> ORGANISM: canis familiaris;

<400> SEQUENCE: 204

Gly Val Pro Glu Arg Phe Ser Gly Ser Arg Ser Gly Ser Thr Ala Thr
```

-continued

```
                 1               5                  10                 15
Leu Thr Ile Ser Gly Leu Gln Ala Glu Asp Glu Ala Glu Tyr Tyr Cys
                20                  25                  30

<210> SEQ ID NO 205
<211> LENGTH: 32
<212> TYPE: PRT
<213> ORGANISM: canis familiaris;

<400> SEQUENCE: 205

Gly Val Pro Asp Arg Phe Ser Gly Ser Lys Ser Gly Thr Thr Ala Ile
1               5                   10                  15
Leu Thr Ile Ser Gly Leu Gln Ala Asp Asp Glu Ala Asp Tyr Phe Cys
                20                  25                  30

<210> SEQ ID NO 206
<211> LENGTH: 32
<212> TYPE: PRT
<213> ORGANISM: canis familiaris;

<400> SEQUENCE: 206

Gly Val Pro Asp Arg Phe Ser Gly Ser Lys Ser Gly Ser Thr Ala Thr
1               5                   10                  15
Leu Thr Ile Ser Gly Leu Gln Ala Asp Asp Glu Ala Asp Tyr Tyr Cys
                20                  25                  30

<210> SEQ ID NO 207
<211> LENGTH: 32
<212> TYPE: PRT
<213> ORGANISM: canis familiaris;

<400> SEQUENCE: 207

Gly Ile Pro Asp Arg Phe Ser Gly Ser Arg Ser Asp Asn Ser Gly Ile
1               5                   10                  15
Leu Thr Ile Ser Gly Leu Gln Ala Glu Asp Glu Ala Asp Tyr His Cys
                20                  25                  30

<210> SEQ ID NO 208
<211> LENGTH: 32
<212> TYPE: PRT
<213> ORGANISM: canis familiaris;

<400> SEQUENCE: 208

Gly Val Pro Ala Arg Phe Ser Gly Ser Arg Ser Gly Asn Thr Ala Thr
1               5                   10                  15
Leu Thr Ile Ser Gly Leu Leu Ala Glu Asp Glu Ala Asp Tyr Tyr Cys
                20                  25                  30

<210> SEQ ID NO 209
<211> LENGTH: 32
<212> TYPE: PRT
<213> ORGANISM: canis familiaris;
<220> FEATURE:
<221> NAME/KEY: UNSURE
<222> LOCATION: (23)..(23)
<223> OTHER INFORMATION: X is Q, R, or L

<400> SEQUENCE: 209

Glu Val Ser Asp Arg Phe Ser Gly Ser Arg Ser Gly Asn Thr Ala Thr
1               5                   10                  15
Leu Thr Ile Ser Gly Leu Xaa Ala Glu Asp Glu Ala Asp Tyr Tyr Cys
                20                  25                  30
```

```
<210> SEQ ID NO 210
<211> LENGTH: 32
<212> TYPE: PRT
<213> ORGANISM: canis familiaris;

<400> SEQUENCE: 210

Gly Val Pro Asp Arg Phe Ser Gly Ser Asn Ser Gly Phe Ser Ala Thr
1               5                   10                  15

Leu Thr Ile Thr Gly Leu Gln Ala Asp Asp Glu Ala Asp Tyr Tyr Cys
            20                  25                  30

<210> SEQ ID NO 211
<211> LENGTH: 32
<212> TYPE: PRT
<213> ORGANISM: canis familiaris;

<400> SEQUENCE: 211

Gly Val Pro Asp Arg Phe Ser Gly Ser Arg Ser Gly Thr Thr Gly Thr
1               5                   10                  15

Leu Thr Ile Ser Gly Leu Gln Ala Glu Asp Glu Ala Asp Tyr Tyr Cys
            20                  25                  30

<210> SEQ ID NO 212
<211> LENGTH: 14
<212> TYPE: PRT
<213> ORGANISM: canis familiaris;

<400> SEQUENCE: 212

Phe Gly Gly Gly Thr His Leu Thr Val Leu Gly Gln Pro Lys
1               5                   10

<210> SEQ ID NO 213
<211> LENGTH: 14
<212> TYPE: PRT
<213> ORGANISM: canis familiaris;

<400> SEQUENCE: 213

Phe Gly Gly Gly Thr His Leu Ala Val Leu Gly Gln Pro Lys
1               5                   10

<210> SEQ ID NO 214
<211> LENGTH: 14
<212> TYPE: PRT
<213> ORGANISM: canis familiaris;

<400> SEQUENCE: 214

Phe Gly Ser Gly Thr Gln Leu Thr Val Leu Gly Gln Pro Lys
1               5                   10

<210> SEQ ID NO 215
<211> LENGTH: 14
<212> TYPE: PRT
<213> ORGANISM: canis familiaris;

<400> SEQUENCE: 215

Phe Gly Gly Gly Thr His Leu Thr Val Leu Ser Gln Pro Lys
1               5                   10

<210> SEQ ID NO 216
<211> LENGTH: 14
<212> TYPE: PRT
<213> ORGANISM: canis familiaris;

<400> SEQUENCE: 216
```

-continued

Phe Gly Gly Gly Thr Leu Leu Thr Val Leu Gly Gln Pro Lys
1               5                   10

<210> SEQ ID NO 217
<211> LENGTH: 15
<212> TYPE: PRT
<213> ORGANISM: canis familiaris;

<400> SEQUENCE: 217

Phe Gly Gly Gly Thr Gln Leu Thr Val Leu Gly Gln Pro Lys Ala
1               5                   10                  15

<210> SEQ ID NO 218
<211> LENGTH: 6
<212> TYPE: PRT
<213> ORGANISM: canis familiaris;

<400> SEQUENCE: 218

Phe Gly Gly Gly Thr His
1               5

<210> SEQ ID NO 219
<211> LENGTH: 13
<212> TYPE: PRT
<213> ORGANISM: canis familiaris;

<400> SEQUENCE: 219

Phe Gly Gly Gly Thr His Leu Thr Val Leu Gly Gln Pro
1               5                   10

<210> SEQ ID NO 220
<211> LENGTH: 14
<212> TYPE: PRT
<213> ORGANISM: canis familiaris;

<400> SEQUENCE: 220

Phe Gly Gly Gly Thr His Leu Thr Val Leu Gly Gln Pro Glu
1               5                   10

<210> SEQ ID NO 221
<211> LENGTH: 13
<212> TYPE: PRT
<213> ORGANISM: canis familiaris;

<400> SEQUENCE: 221

Phe Gly Ser Gly Thr Gln Leu Thr Val Leu Gly Gln Pro
1               5                   10

<210> SEQ ID NO 222
<211> LENGTH: 7
<212> TYPE: PRT
<213> ORGANISM: canis familiaris;

<400> SEQUENCE: 222

Phe Gly Gly Gly Thr His Leu
1               5

<210> SEQ ID NO 223
<211> LENGTH: 15
<212> TYPE: PRT
<213> ORGANISM: canis familiaris;

<400> SEQUENCE: 223

Phe Gly Ser Gly Thr Gln Leu Thr Val Leu Ser Gln Pro Lys Ala

```
1               5                  10                 15
```

<210> SEQ ID NO 224
<211> LENGTH: 15
<212> TYPE: PRT
<213> ORGANISM: canis familiaris;

<400> SEQUENCE: 224

```
Phe Gly Gly Gly Thr Tyr Leu Thr Val Val Gly Gln Pro Lys Ala
1               5                  10                 15
```

<210> SEQ ID NO 225
<211> LENGTH: 12
<212> TYPE: PRT
<213> ORGANISM: canis familiaris;

<400> SEQUENCE: 225

```
Phe Gly Gly Gly Thr His Leu Thr Val Leu Gly Gln
1               5                  10
```

<210> SEQ ID NO 226
<211> LENGTH: 15
<212> TYPE: PRT
<213> ORGANISM: canis familiaris;

<400> SEQUENCE: 226

```
Phe Gly Gly Gly Thr His Leu Thr Val Leu Gly Gln Pro Arg Ala
1               5                  10                 15
```

<210> SEQ ID NO 227
<211> LENGTH: 15
<212> TYPE: PRT
<213> ORGANISM: canis familiaris;

<400> SEQUENCE: 227

```
Phe Gly Ser Gly Thr His Leu Thr Ala Leu Gly Gln Pro Lys Ala
1               5                  10                 15
```

<210> SEQ ID NO 228
<211> LENGTH: 15
<212> TYPE: PRT
<213> ORGANISM: canis familiaris;

<400> SEQUENCE: 228

```
Phe Gly Ser Gly Thr Gln Leu Thr Val Leu Gly Gln Pro Lys Ala
1               5                  10                 15
```

<210> SEQ ID NO 229
<211> LENGTH: 15
<212> TYPE: PRT
<213> ORGANISM: canis familiaris;

<400> SEQUENCE: 229

```
Phe Gly Gly Gly Thr His Leu Thr Val Leu Gly Gln Pro Lys Ala
1               5                  10                 15
```

<210> SEQ ID NO 230
<211> LENGTH: 15
<212> TYPE: PRT
<213> ORGANISM: canis familiaris;

<400> SEQUENCE: 230

```
Phe Gly Gly Gly Thr His Leu Thr Val Leu Ser Gln Pro Lys Ala
1               5                  10                 15
```

```
<210> SEQ ID NO 231
<211> LENGTH: 15
<212> TYPE: PRT
<213> ORGANISM: canis familiaris;

<400> SEQUENCE: 231

Phe Gly Gly Gly Ala His Leu Thr Val Leu Gly Gln Pro Lys Ala
1               5                   10                  15

<210> SEQ ID NO 232
<211> LENGTH: 15
<212> TYPE: PRT
<213> ORGANISM: canis familiaris;

<400> SEQUENCE: 232

Phe Gly Pro Gly Thr Gln Leu Thr Val Leu Gly Gln Pro Lys Ala
1               5                   10                  15

<210> SEQ ID NO 233
<211> LENGTH: 15
<212> TYPE: PRT
<213> ORGANISM: canis familiaris;

<400> SEQUENCE: 233

Phe Gly Gly Gly Thr Arg Leu Thr Val Leu Gly Gln Pro Lys Ala
1               5                   10                  15

<210> SEQ ID NO 234
<211> LENGTH: 25
<212> TYPE: PRT
<213> ORGANISM: canis familiaris;
<220> FEATURE:
<221> NAME/KEY: UNSURE
<222> LOCATION: (1)..(1)
<223> OTHER INFORMATION: X is A, T, or absent
<220> FEATURE:
<221> NAME/KEY: UNSURE
<222> LOCATION: (2)..(2)
<223> OTHER INFORMATION: X is D or absent
<220> FEATURE:
<221> NAME/KEY: UNSURE
<222> LOCATION: (3)..(3)
<223> OTHER INFORMATION: X is S or absent
<220> FEATURE:
<221> NAME/KEY: UNSURE
<222> LOCATION: (4)..(4)
<223> OTHER INFORMATION: X is Q or absent
<220> FEATURE:
<221> NAME/KEY: UNSURE
<222> LOCATION: (5)..(5)
<223> OTHER INFORMATION: X is T or absent
<220> FEATURE:
<221> NAME/KEY: UNSURE
<222> LOCATION: (6)..(6)
<223> OTHER INFORMATION: X is V or absent
<220> FEATURE:
<221> NAME/KEY: UNSURE
<222> LOCATION: (7)..(7)
<223> OTHER INFORMATION: X is V or absent
<220> FEATURE:
<221> NAME/KEY: UNSURE
<222> LOCATION: (8)..(8)
<223> OTHER INFORMATION: X is T or absent
<220> FEATURE:
<221> NAME/KEY: UNSURE
<222> LOCATION: (9)..(9)
<223> OTHER INFORMATION: X is Q or absent
<220> FEATURE:
<221> NAME/KEY: UNSURE
<222> LOCATION: (10)..(10)
<223> OTHER INFORMATION: X is E or absent
<220> FEATURE:
```

-continued

```
<221> NAME/KEY: UNSURE
<222> LOCATION: (11)..(11)
<223> OTHER INFORMATION: X is P, A, or absent
<220> FEATURE:
<221> NAME/KEY: UNSURE
<222> LOCATION: (12)..(12)
<223> OTHER INFORMATION: X is S, F, or absent
<220> FEATURE:
<221> NAME/KEY: UNSURE
<222> LOCATION: (13)..(13)
<223> OTHER INFORMATION: X is L, V, or absent
<220> FEATURE:
<221> NAME/KEY: UNSURE
<222> LOCATION: (14)..(14)
<223> OTHER INFORMATION: X is S or absent
<220> FEATURE:
<221> NAME/KEY: UNSURE
<222> LOCATION: (15)..(15)
<223> OTHER INFORMATION: X is V or absent
<220> FEATURE:
<221> NAME/KEY: UNSURE
<222> LOCATION: (16)..(16)
<223> OTHER INFORMATION: X is S or absent
<220> FEATURE:
<221> NAME/KEY: UNSURE
<222> LOCATION: (17)..(17)
<223> OTHER INFORMATION: X is P, L, or absent
<220> FEATURE:
<221> NAME/KEY: UNSURE
<222> LOCATION: (18)..(18)
<223> OTHER INFORMATION: X is G or absent
<220> FEATURE:
<221> NAME/KEY: UNSURE
<222> LOCATION: (19)..(19)
<223> OTHER INFORMATION: X is G or absent
<220> FEATURE:
<221> NAME/KEY: UNSURE
<222> LOCATION: (20)..(20)
<223> OTHER INFORMATION: X is T or absent
<220> FEATURE:
<221> NAME/KEY: UNSURE
<222> LOCATION: (21)..(21)
<223> OTHER INFORMATION: X is V, I, or absent
<220> FEATURE:
<221> NAME/KEY: UNSURE
<222> LOCATION: (22)..(22)
<223> OTHER INFORMATION: X is T or absent
<220> FEATURE:
<221> NAME/KEY: UNSURE
<222> LOCATION: (23)..(23)
<223> OTHER INFORMATION: X is L or absent
<220> FEATURE:
<221> NAME/KEY: UNSURE
<222> LOCATION: (24)..(24)
<223> OTHER INFORMATION: X is T or absent
<220> FEATURE:
<221> NAME/KEY: UNSURE
<222> LOCATION: (25)..(25)
<223> OTHER INFORMATION: X is C or absent

<400> SEQUENCE: 234

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 235
<211> LENGTH: 15
<212> TYPE: PRT
<213> ORGANISM: canis familiaris;
<220> FEATURE:
<221> NAME/KEY: UNSURE
<222> LOCATION: (2)..(2)
<223> OTHER INFORMATION: X is Y or S
<220> FEATURE:
<221> NAME/KEY: UNSURE
```

```
<222> LOCATION: (4)..(4)
<223> OTHER INFORMATION: X is Q or H
<220> FEATURE:
<221> NAME/KEY: UNSURE
<222> LOCATION: (6)..(6)
<223> OTHER INFORMATION: X is L, Q, or P
<220> FEATURE:
<221> NAME/KEY: UNSURE
<222> LOCATION: (8)..(8)
<223> OTHER INFORMATION: X is R or Q
<220> FEATURE:
<221> NAME/KEY: UNSURE
<222> LOCATION: (12)..(12)
<223> OTHER INFORMATION: X is T or P
<220> FEATURE:
<221> NAME/KEY: UNSURE
<222> LOCATION: (14)..(14)
<223> OTHER INFORMATION: X is I or L
<220> FEATURE:
<221> NAME/KEY: UNSURE
<222> LOCATION: (15)..(15)
<223> OTHER INFORMATION: X is Y or S

<400> SEQUENCE: 235

Trp Xaa Gln Xaa Thr Xaa Gly Xaa Ala Pro Arg Xaa Ile Xaa Xaa
1               5                   10                  15

<210> SEQ ID NO 236
<211> LENGTH: 32
<212> TYPE: PRT
<213> ORGANISM: canis familiaris;
<220> FEATURE:
<221> NAME/KEY: UNSURE
<222> LOCATION: (4)..(4)
<223> OTHER INFORMATION: X is N, S, D, or R
<220> FEATURE:
<221> NAME/KEY: UNSURE
<222> LOCATION: (7)..(7)
<223> OTHER INFORMATION: X is S or T
<220> FEATURE:
<221> NAME/KEY: UNSURE
<222> LOCATION: (8)..(8)
<223> OTHER INFORMATION: X is G or A
<220> FEATURE:
<221> NAME/KEY: UNSURE
<222> LOCATION: (10)..(10)
<223> OTHER INFORMATION: X is I or V
<220> FEATURE:
<221> NAME/KEY: UNSURE
<222> LOCATION: (12)..(12)
<223> OTHER INFORMATION: X is G or D
<220> FEATURE:
<221> NAME/KEY: UNSURE
<222> LOCATION: (14)..(14)
<223> OTHER INFORMATION: X is K or R
<220> FEATURE:
<221> NAME/KEY: UNSURE
<222> LOCATION: (16)..(16)
<223> OTHER INFORMATION: X is A or T
<220> FEATURE:
<221> NAME/KEY: UNSURE
<222> LOCATION: (22)..(22)
<223> OTHER INFORMATION: X is A or V
<220> FEATURE:
<221> NAME/KEY: UNSURE
<222> LOCATION: (23)..(23)
<223> OTHER INFORMATION: X is Q or R
<220> FEATURE:
<221> NAME/KEY: UNSURE
<222> LOCATION: (28)..(28)
<223> OTHER INFORMATION: X is A, T, or G
<220> FEATURE:
<221> NAME/KEY: UNSURE
<222> LOCATION: (31)..(31)
<223> OTHER INFORMATION: X is Y or H

<400> SEQUENCE: 236
```

-continued

```
Gly Val Pro Xaa Arg Phe Xaa Xaa Ser Xaa Ser Xaa Asn Xaa Ala Xaa
1               5                   10                  15

Leu Thr Ile Thr Gly Xaa Xaa Pro Glu Asp Glu Xaa Asp Tyr Xaa Cys
            20                  25                  30

<210> SEQ ID NO 237
<211> LENGTH: 14
<212> TYPE: PRT
<213> ORGANISM: canis familiaris;
<220> FEATURE:
<221> NAME/KEY: UNSURE
<222> LOCATION: (1)..(1)
<223> OTHER INFORMATION: X is F or V
<220> FEATURE:
<221> NAME/KEY: UNSURE
<222> LOCATION: (3)..(3)
<223> OTHER INFORMATION: X is G or S
<220> FEATURE:
<221> NAME/KEY: UNSURE
<222> LOCATION: (6)..(6)
<223> OTHER INFORMATION: X is H or Q

<400> SEQUENCE: 237

Xaa Gly Xaa Gly Thr Xaa Leu Thr Leu Gly Gln Pro Lys Ala
1               5                   10

<210> SEQ ID NO 238
<211> LENGTH: 25
<212> TYPE: PRT
<213> ORGANISM: canis familiaris;

<400> SEQUENCE: 238

Ala Asp Ser Gln Thr Val Val Thr Gln Glu Pro Ser Leu Ser Val Ser
1               5                   10                  15

Pro Gly Gly Thr Val Thr Leu Thr Cys
            20                  25

<210> SEQ ID NO 239
<211> LENGTH: 5
<212> TYPE: PRT
<213> ORGANISM: canis familiaris;

<400> SEQUENCE: 239

Ile Thr Leu Thr Cys
1               5

<210> SEQ ID NO 240
<211> LENGTH: 7
<212> TYPE: PRT
<213> ORGANISM: canis familiaris;

<400> SEQUENCE: 240

Gly Thr Val Thr Leu Thr Cys
1               5

<210> SEQ ID NO 241
<211> LENGTH: 25
<212> TYPE: PRT
<213> ORGANISM: canis familiaris;

<400> SEQUENCE: 241

Thr Asp Ser Gln Thr Val Val Thr Gln Glu Pro Ser Leu Ser Val Ser
1               5                   10                  15

Pro Gly Gly Thr Val Thr Leu Thr Cys
            20                  25
```

```
<210> SEQ ID NO 242
<211> LENGTH: 25
<212> TYPE: PRT
<213> ORGANISM: canis familiaris;

<400> SEQUENCE: 242

Ala Asp Ser Gln Thr Val Val Thr Gln Glu Pro Ser Leu Ser Val Ser
1               5                   10                  15

Leu Gly Gly Thr Val Thr Leu Thr Cys
            20                  25

<210> SEQ ID NO 243
<211> LENGTH: 25
<212> TYPE: PRT
<213> ORGANISM: canis familiaris;

<400> SEQUENCE: 243

Ala Asp Ser Gln Thr Val Val Thr Gln Glu Ala Ser Val Ser Val Ser
1               5                   10                  15

Pro Gly Gly Thr Val Thr Leu Thr Cys
            20                  25

<210> SEQ ID NO 244
<211> LENGTH: 25
<212> TYPE: PRT
<213> ORGANISM: canis familiaris;

<400> SEQUENCE: 244

Ala Asp Ser Gln Thr Val Val Ile Gln Glu Pro Phe Leu Ser Val Ser
1               5                   10                  15

Pro Gly Gly Thr Val Thr Leu Thr Cys
            20                  25

<210> SEQ ID NO 245
<211> LENGTH: 15
<212> TYPE: PRT
<213> ORGANISM: canis familiaris;

<400> SEQUENCE: 245

Trp Tyr Gln Gln Thr Leu Gly Arg Ala Pro Arg Thr Ile Ile Tyr
1               5                   10                  15

<210> SEQ ID NO 246
<211> LENGTH: 15
<212> TYPE: PRT
<213> ORGANISM: canis familiaris;

<400> SEQUENCE: 246

Trp Tyr Gln Gln Thr Gln Gly Arg Ala Pro Arg Thr Ile Ile Tyr
1               5                   10                  15

<210> SEQ ID NO 247
<211> LENGTH: 15
<212> TYPE: PRT
<213> ORGANISM: canis familiaris;

<400> SEQUENCE: 247

Trp Ser Gln Gln Thr Pro Gly Gln Ala Pro Arg Thr Ile Ile Tyr
1               5                   10                  15

<210> SEQ ID NO 248
<211> LENGTH: 15
```

```
<212> TYPE: PRT
<213> ORGANISM: canis familiaris;

<400> SEQUENCE: 248

Trp Tyr Gln Gln Thr Leu Gly Arg Pro Pro Arg Thr Ile Ile Ser
1               5                   10                  15

<210> SEQ ID NO 249
<211> LENGTH: 15
<212> TYPE: PRT
<213> ORGANISM: canis familiaris;

<400> SEQUENCE: 249

Trp Tyr Gln Gln Thr Leu Gly Arg Pro Pro Arg Pro Ile Ile Tyr
1               5                   10                  15

<210> SEQ ID NO 250
<211> LENGTH: 15
<212> TYPE: PRT
<213> ORGANISM: canis familiaris;

<400> SEQUENCE: 250

Trp Ser Gln Gln Thr Pro Gly Gln Ala Pro Arg Thr Ile Leu Tyr
1               5                   10                  15

<210> SEQ ID NO 251
<211> LENGTH: 15
<212> TYPE: PRT
<213> ORGANISM: canis familiaris;

<400> SEQUENCE: 251

Trp Tyr Gln His Thr Gln Gly Arg Ala Pro Arg Thr Ile Ile Tyr
1               5                   10                  15

<210> SEQ ID NO 252
<211> LENGTH: 32
<212> TYPE: PRT
<213> ORGANISM: canis familiaris;

<400> SEQUENCE: 252

Gly Val Pro Asn Arg Phe Ser Gly Ser Ile Ser Gly Asn Lys Ala Ala
1               5                   10                  15

Leu Thr Ile Thr Gly Ala Gln Pro Glu Asp Glu Ala Asp Tyr Tyr Cys
                20                  25                  30

<210> SEQ ID NO 253
<211> LENGTH: 32
<212> TYPE: PRT
<213> ORGANISM: canis familiaris;

<400> SEQUENCE: 253

Gly Val Pro Asn Arg Phe Ser Gly Ser Ile Ser Gly Asn Lys Ala Ala
1               5                   10                  15

Leu Thr Ile Ile Gly Val Gln Pro Glu Asp Glu Ala Asp Tyr Tyr Cys
                20                  25                  30

<210> SEQ ID NO 254
<211> LENGTH: 32
<212> TYPE: PRT
<213> ORGANISM: canis familiaris;

<400> SEQUENCE: 254

Gly Val Pro Asn Arg Phe Ser Gly Ser Ile Ser Asp Asn Lys Ala Ala
1               5                   10                  15
```

-continued

Leu Thr Ile Thr Gly Val Gln Pro Glu Asp Glu Ala Asp Tyr Tyr Cys
            20                  25                  30

<210> SEQ ID NO 255
<211> LENGTH: 32
<212> TYPE: PRT
<213> ORGANISM: canis familiaris;

<400> SEQUENCE: 255

Gly Val Pro Ser Arg Phe Ser Gly Ser Ile Ser Gly Asn Lys Ala Thr
1               5                   10                  15

Leu Thr Ile Thr Gly Ala Arg Pro Glu Asp Glu Ala Asp Tyr His Cys
            20                  25                  30

<210> SEQ ID NO 256
<211> LENGTH: 32
<212> TYPE: PRT
<213> ORGANISM: canis familiaris;

<400> SEQUENCE: 256

Gly Val Pro Ser Arg Phe Thr Gly Ser Ile Ser Gly Asn Arg Ala Ala
1               5                   10                  15

Leu Thr Ile Thr Gly Ala Arg Pro Glu Asp Glu Ala Asp Tyr Tyr Cys
            20                  25                  30

<210> SEQ ID NO 257
<211> LENGTH: 32
<212> TYPE: PRT
<213> ORGANISM: canis familiaris;

<400> SEQUENCE: 257

Gly Val Pro Asp Arg Phe Ser Gly Ser Ile Ser Gly Asn Lys Ala Ala
1               5                   10                  15

Leu Thr Ile Thr Gly Ala Gln Pro Glu Asp Glu Gly Asp Tyr Tyr Cys
            20                  25                  30

<210> SEQ ID NO 258
<211> LENGTH: 32
<212> TYPE: PRT
<213> ORGANISM: canis familiaris;

<400> SEQUENCE: 258

Gly Val Pro Asn Arg Phe Thr Gly Ser Ile Ser Gly Asn Lys Ala Ala
1               5                   10                  15

Leu Thr Ile Thr Gly Ala Gln Pro Glu Asp Glu Ala Asp Tyr Tyr Cys
            20                  25                  30

<210> SEQ ID NO 259
<211> LENGTH: 32
<212> TYPE: PRT
<213> ORGANISM: canis familiaris;

<400> SEQUENCE: 259

Gly Val Pro Arg Arg Phe Ser Ala Ser Val Ser Gly Asn Lys Ala Thr
1               5                   10                  15

Leu Thr Ile Thr Gly Ala Gln Pro Glu Asp Glu Ala Asp Tyr Tyr Cys
            20                  25                  30

<210> SEQ ID NO 260
<211> LENGTH: 32
<212> TYPE: PRT
<213> ORGANISM: canis familiaris;

```
<400> SEQUENCE: 260

Gly Val Pro Asn Arg Phe Thr Ala Ser Ile Ser Gly Asn Lys Ala Ala
1               5                   10                  15

Leu Thr Ile Thr Gly Ala Gln Pro Glu Asp Glu Ala Asp Tyr Tyr Cys
            20                  25                  30

<210> SEQ ID NO 261
<211> LENGTH: 32
<212> TYPE: PRT
<213> ORGANISM: canis familiaris;

<400> SEQUENCE: 261

Gly Val Pro Asn Arg Phe Ser Gly Ser Ile Ser Gly Asn Lys Ala Ala
1               5                   10                  15

Leu Thr Ile Thr Gly Ala Gln Pro Glu Asp Glu Thr Asp Tyr Tyr Cys
            20                  25                  30

<210> SEQ ID NO 262
<211> LENGTH: 15
<212> TYPE: PRT
<213> ORGANISM: canis familiaris;

<400> SEQUENCE: 262

Val Gly Gly Gly Thr His Leu Thr Val Leu Gly Gln Pro Lys Ala
1               5                   10                  15

<210> SEQ ID NO 263
<211> LENGTH: 12
<212> TYPE: PRT
<213> ORGANISM: canis familiaris;

<400> SEQUENCE: 263

Phe Gly Ser Gly Thr Gln Leu Thr Val Leu Gly Gln
1               5                   10

<210> SEQ ID NO 264
<211> LENGTH: 25
<212> TYPE: PRT
<213> ORGANISM: canis familiaris;
<220> FEATURE:
<221> NAME/KEY: unsure
<222> LOCATION: (1)..(1)
<223> OTHER INFORMATION: X is S, P, or absent
<220> FEATURE:
<221> NAME/KEY: unsure
<222> LOCATION: (2)..(2)
<223> OTHER INFORMATION: X is W, A, or absent
<220> FEATURE:
<221> NAME/KEY: unsure
<222> LOCATION: (3)..(3)
<223> OTHER INFORMATION: X is  A or absent
<220> FEATURE:
<221> NAME/KEY: unsure
<222> LOCATION: (4)..(4)
<223> OTHER INFORMATION: X is Q or absent
<220> FEATURE:
<221> NAME/KEY: unsure
<222> LOCATION: (5)..(5)
<223> OTHER INFORMATION: X is A, S, T, or absent
<220> FEATURE:
<221> NAME/KEY: unsure
<222> LOCATION: (6)..(6)
<223> OTHER INFORMATION: X is V, M, or absent
<220> FEATURE:
<221> NAME/KEY: unsure
<222> LOCATION: (7)..(7)
<223> OTHER INFORMATION: X is L or absent
<220> FEATURE:
```

```
<221> NAME/KEY: unsure
<222> LOCATION: (8)..(8)
<223> OTHER INFORMATION: X is T or absent
<220> FEATURE:
<221> NAME/KEY: unsure
<222> LOCATION: (9)..(9)
<223> OTHER INFORMATION: X is Q or absent
<220> FEATURE:
<221> NAME/KEY: unsure
<222> LOCATION: (10)..(10)
<223> OTHER INFORMATION: X is P or absent
<220> FEATURE:
<221> NAME/KEY: unsure
<222> LOCATION: (11)..(11)
<223> OTHER INFORMATION: X is A, P, S, or absent
<220> FEATURE:
<221> NAME/KEY: unsure
<222> LOCATION: (12)..(12)
<223> OTHER INFORMATION: X is P, S, or absent
<220> FEATURE:
<221> NAME/KEY: unsure
<222> LOCATION: (13)..(13)
<223> OTHER INFORMATION: X is V, M, or absent
<220> FEATURE:
<221> NAME/KEY: unsure
<222> LOCATION: (14)..(14)
<223> OTHER INFORMATION: X is S or absent
<220> FEATURE:
<221> NAME/KEY: unsure
<222> LOCATION: (15)..(15)
<223> OTHER INFORMATION: X is G, A, T, or absent
<220> FEATURE:
<221> NAME/KEY: unsure
<222> LOCATION: (16)..(16)
<223> OTHER INFORMATION: X is S, A, T, or absent
<220> FEATURE:
<221> NAME/KEY: unsure
<222> LOCATION: (17)..(17)
<223> OTHER INFORMATION: X is L, P, or absent
<220> FEATURE:
<221> NAME/KEY: unsure
<222> LOCATION: (18)..(18)
<223> OTHER INFORMATION: X is G or absent
<220> FEATURE:
<221> NAME/KEY: unsure
<222> LOCATION: (19)..(19)
<223> OTHER INFORMATION: X is Q or absent
<220> FEATURE:
<221> NAME/KEY: unsure
<222> LOCATION: (20)..(20)
<223> OTHER INFORMATION: X is R, T, or absent
<220> FEATURE:
<221> NAME/KEY: unsure
<222> LOCATION: (21)..(21)
<223> OTHER INFORMATION: X is V or absent
<220> FEATURE:
<221> NAME/KEY: unsure
<222> LOCATION: (22)..(22)
<223> OTHER INFORMATION: X is T or absent

<400> SEQUENCE: 264

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Ile Ser Cys
            20                  25

<210> SEQ ID NO 265
<211> LENGTH: 17
<212> TYPE: PRT
<213> ORGANISM: canis familiaris;
<220> FEATURE:
<221> NAME/KEY: unsure
<222> LOCATION: (2)..(2)
<223> OTHER INFORMATION: X is Y or F
<220> FEATURE:
<221> NAME/KEY: unsure
```

```
<222> LOCATION: (3)..(3)
<223> OTHER INFORMATION: X is Q or R
<220> FEATURE:
<221> NAME/KEY: unsure
<222> LOCATION: (4)..(4)
<223> OTHER INFORMATION: X is Q or H
<220> FEATURE:
<221> NAME/KEY: unsure
<222> LOCATION: (5)..(5)
<223> OTHER INFORMATION: X is L, F, or V
<220> FEATURE:
<221> NAME/KEY: unsure
<222> LOCATION: (6)..(6)
<223> OTHER INFORMATION: X is P or L
<220> FEATURE:
<221> NAME/KEY: unsure
<222> LOCATION: (9)..(9)
<223> OTHER INFORMATION: X is T or K
<220> FEATURE:
<221> NAME/KEY: unsure
<222> LOCATION: (10)..(10)
<223> OTHER INFORMATION: X is G, S, or A
<220> FEATURE:
<221> NAME/KEY: unsure
<222> LOCATION: (13)..(13)
<223> OTHER INFORMATION: X is R, K, or S
<220> FEATURE:
<221> NAME/KEY: unsure
<222> LOCATION: (14)..(14)
<223> OTHER INFORMATION: X is T, L, or S
<220> FEATURE:
<221> NAME/KEY: unsure
<222> LOCATION: (15)..(15)
<223> OTHER INFORMATION: X is L, V, I, or F
<220> FEATURE:
<221> NAME/KEY: unsure
<222> LOCATION: (16)..(16)
<223> OTHER INFORMATION: X is I or A
<220> FEATURE:
<221> NAME/KEY: unsure
<222> LOCATION: (17)..(17)
<223> OTHER INFORMATION: X is Y, F, or H

<400> SEQUENCE: 265

Trp Xaa Xaa Xaa Xaa Xaa Tyr Gly Xaa Xaa Tyr Pro Xaa Xaa Xaa Xaa
1               5                   10                  15

Xaa

<210> SEQ ID NO 266
<211> LENGTH: 32
<212> TYPE: PRT
<213> ORGANISM: canis familiaris;
<220> FEATURE:
<221> NAME/KEY: unsure
<222> LOCATION: (2)..(2)
<223> OTHER INFORMATION: X is V or I
<220> FEATURE:
<221> NAME/KEY: unsure
<222> LOCATION: (4)..(4)
<223> OTHER INFORMATION: X is D, A, V, or E
<220> FEATURE:
<221> NAME/KEY: unsure
<222> LOCATION: (8)..(8)
<223> OTHER INFORMATION: X is G or A
<220> FEATURE:
<221> NAME/KEY: unsure
<222> LOCATION: (9)..(9)
<223> OTHER INFORMATION: X is S or P
<220> FEATURE:
<221> NAME/KEY: unsure
<222> LOCATION: (10)..(10)
<223> OTHER INFORMATION: X is R, K, S, or A
<220> FEATURE:
<221> NAME/KEY: unsure
<222> LOCATION: (13)..(13)
<223> OTHER INFORMATION: X is S or N
```

```
<220> FEATURE:
<221> NAME/KEY: unsure
<222> LOCATION: (14)..(14)
<223> OTHER INFORMATION: X is T or S
<220> FEATURE:
<221> NAME/KEY: unsure
<222> LOCATION: (15)..(15)
<223> OTHER INFORMATION: X is S or A
<220> FEATURE:
<221> NAME/KEY: unsure
<222> LOCATION: (16)..(16)
<223> OTHER INFORMATION: X is S, T, or A
<220> FEATURE:
<221> NAME/KEY: unsure
<222> LOCATION: (20)..(20)
<223> OTHER INFORMATION: X is S, T, or A
<220> FEATURE:
<221> NAME/KEY: unsure
<222> LOCATION: (21)..(21)
<223> OTHER INFORMATION: X is G or V
<220> FEATURE:
<221> NAME/KEY: unsure
<222> LOCATION: (22)..(22)
<223> OTHER INFORMATION: X is L or I
<220> FEATURE:
<221> NAME/KEY: unsure
<222> LOCATION: (24)..(24)
<223> OTHER INFORMATION: X is A or T
<220> FEATURE:
<221> NAME/KEY: unsure
<222> LOCATION: (28)..(28)
<223> OTHER INFORMATION: X is A, T, or G
<220> FEATURE:
<221> NAME/KEY: unsure
<222> LOCATION: (29)..(29)
<223> OTHER INFORMATION: X is D, E, or N
<220> FEATURE:
<221> NAME/KEY: unsure
<222> LOCATION: (31)..(31)
<223> OTHER INFORMATION: X is Y or F

<400> SEQUENCE: 266

Gly Xaa Pro Xaa Arg Phe Ser Xaa Xaa Xaa Ser Gly Xaa Xaa Xaa Xaa
1               5                   10                  15

Leu Thr Ile Xaa Xaa Xaa Gln Xaa Glu Asp Glu Xaa Xaa Tyr Xaa Cys
            20                  25                  30

<210> SEQ ID NO 267
<211> LENGTH: 14
<212> TYPE: PRT
<213> ORGANISM: canis familiaris;
<220> FEATURE:
<221> NAME/KEY: unsure
<222> LOCATION: (2)..(2)
<223> OTHER INFORMATION: X is G, S, or E
<220> FEATURE:
<221> NAME/KEY: unsure
<222> LOCATION: (5)..(5)
<223> OTHER INFORMATION: X is T or Q
<220> FEATURE:
<221> NAME/KEY: unsure
<222> LOCATION: (8)..(8)
<223> OTHER INFORMATION: X is T or absent
<220> FEATURE:
<221> NAME/KEY: unsure
<222> LOCATION: (9)..(9)
<223> OTHER INFORMATION: X is V, F, or absent
<220> FEATURE:
<221> NAME/KEY: unsure
<222> LOCATION: (10)..(10)
<223> OTHER INFORMATION: X is L or absent
<220> FEATURE:
<221> NAME/KEY: unsure
<222> LOCATION: (11)..(11)
<223> OTHER INFORMATION: X is G or absent
<220> FEATURE:
```

```
<221> NAME/KEY: unsure
<222> LOCATION: (12)..(12)
<223> OTHER INFORMATION: X is Q, H, N, or absent
<220> FEATURE:
<221> NAME/KEY: unsure
<222> LOCATION: (13)..(13)
<223> OTHER INFORMATION: X is P or E
<220> FEATURE:
<221> NAME/KEY: unsure
<222> LOCATION: (14)..(14)
<223> OTHER INFORMATION: X is K or absent

<400> SEQUENCE: 267

Phe Xaa Gly Gly Xaa His Leu Xaa Xaa Xaa Xaa Xaa Xaa Xaa
1               5                   10

<210> SEQ ID NO 268
<211> LENGTH: 25
<212> TYPE: PRT
<213> ORGANISM: canis familiaris;

<400> SEQUENCE: 268

Ser Trp Ala Gln Ala Val Leu Thr Gln Pro Pro Ser Val Ser Ala Ala
1               5                   10                  15

Leu Gly Gln Arg Val Thr Ile Ser Cys
            20                  25

<210> SEQ ID NO 269
<211> LENGTH: 25
<212> TYPE: PRT
<213> ORGANISM: canis familiaris;

<400> SEQUENCE: 269

Ser Trp Ala Gln Ser Ala Leu Thr Gln Pro Ser Ser Val Ser Gly Thr
1               5                   10                  15

Leu Gly Gln Thr Val Thr Ile Ser Cys
            20                  25

<210> SEQ ID NO 270
<211> LENGTH: 25
<212> TYPE: PRT
<213> ORGANISM: canis familiaris;
<220> FEATURE:
<221> NAME/KEY: UNSURE
<222> LOCATION: (14)..(14)
<223> OTHER INFORMATION: X is S or absent
<220> FEATURE:
<221> NAME/KEY: UNSURE
<222> LOCATION: (17)..(17)
<223> OTHER INFORMATION: X is L, P, or absent

<400> SEQUENCE: 270

Pro Trp Ala Gln Ser Val Leu Thr Gln Pro Ala Ser Val Xaa Gly Ser
1               5                   10                  15

Xaa Gly Gln Arg Val Thr Ile Ser Cys
            20                  25

<210> SEQ ID NO 271
<211> LENGTH: 25
<212> TYPE: PRT
<213> ORGANISM: canis familiaris;
<220> FEATURE:
<221> NAME/KEY: UNSURE
<222> LOCATION: (14)..(14)
<223> OTHER INFORMATION: X is S or absent

<400> SEQUENCE: 271
```

Ser Trp Ala Gln Ser Val Leu Thr Gln Pro Ala Ser Val Xaa Gly Ser
1               5                   10                  15

Leu Gly Gln Arg Val Thr Ile Ser Cys
            20                  25

<210> SEQ ID NO 272
<211> LENGTH: 25
<212> TYPE: PRT
<213> ORGANISM: canis familiaris;

<400> SEQUENCE: 272

Ser Trp Ala Gln Ala Val Leu Thr Gln Pro Pro Ser Met Ser Thr Ala
1               5                   10                  15

Leu Gly Gln Arg Val Thr Ile Thr Cys
            20                  25

<210> SEQ ID NO 273
<211> LENGTH: 25
<212> TYPE: PRT
<213> ORGANISM: canis familiaris;

<400> SEQUENCE: 273

Ser Trp Ala Gln Thr Val Leu Thr Gln Pro Ala Ser Val Ser Gly Ser
1               5                   10                  15

Leu Gly Gln Thr Val Thr Ile Ser Cys
            20                  25

<210> SEQ ID NO 274
<211> LENGTH: 10
<212> TYPE: PRT
<213> ORGANISM: canis familiaris;

<400> SEQUENCE: 274

Ser Leu Gly Gln Thr Val Thr Ile Ser Cys
1               5                   10

<210> SEQ ID NO 275
<211> LENGTH: 14
<212> TYPE: PRT
<213> ORGANISM: canis familiaris;

<400> SEQUENCE: 275

Pro Val Ser Ala Ala Pro Gly Gln Arg Val Thr Ile Ser Cys
1               5                   10

<210> SEQ ID NO 276
<211> LENGTH: 11
<212> TYPE: PRT
<213> ORGANISM: canis familiaris;

<400> SEQUENCE: 276

Gly Ser Leu Gly Gln Thr Val Thr Ile Ser Cys
1               5                   10

<210> SEQ ID NO 277
<211> LENGTH: 25
<212> TYPE: PRT
<213> ORGANISM: canis familiaris;

<400> SEQUENCE: 277

Ser Trp Ala Gln Ala Val Leu Thr Gln Pro Ala Ser Val Ser Gly Ser
1               5                   10                  15

Leu Gly Gln Arg Val Thr Ile Ser Cys

```
              20                  25

<210> SEQ ID NO 278
<211> LENGTH: 25
<212> TYPE: PRT
<213> ORGANISM: canis familiaris;
<220> FEATURE:
<221> NAME/KEY: UNSURE
<222> LOCATION: (17)..(17)
<223> OTHER INFORMATION: X is L, P, or absent

<400> SEQUENCE: 278

Ser Trp Ala Gln Ser Val Leu Thr Gln Pro Ala Ser Val Ser Gly Ser
1               5                   10                  15

Xaa Gly Gln Arg Val Thr Ile Ser Cys
            20                  25

<210> SEQ ID NO 279
<211> LENGTH: 6
<212> TYPE: PRT
<213> ORGANISM: canis familiaris;

<400> SEQUENCE: 279

Arg Val Thr Ile Ser Cys
1               5

<210> SEQ ID NO 280
<211> LENGTH: 15
<212> TYPE: PRT
<213> ORGANISM: canis familiaris;

<400> SEQUENCE: 280

Trp Tyr Gln Gln Val Pro Gly Lys Ser Pro Lys Thr Phe Ile Tyr
1               5                   10                  15

<210> SEQ ID NO 281
<211> LENGTH: 15
<212> TYPE: PRT
<213> ORGANISM: canis familiaris;

<400> SEQUENCE: 281

Trp Tyr Gln Gln Leu Pro Gly Thr Ser Pro Arg Thr Leu Ile Tyr
1               5                   10                  15

<210> SEQ ID NO 282
<211> LENGTH: 15
<212> TYPE: PRT
<213> ORGANISM: canis familiaris;

<400> SEQUENCE: 282

Trp Phe Gln His Phe Pro Gly Thr Ser Pro Lys Leu Leu Ile Tyr
1               5                   10                  15

<210> SEQ ID NO 283
<211> LENGTH: 15
<212> TYPE: PRT
<213> ORGANISM: canis familiaris;

<400> SEQUENCE: 283

Trp Tyr Gln Gln Val Pro Gly Thr Ser Pro Arg Thr Leu Ile Tyr
1               5                   10                  15

<210> SEQ ID NO 284
<211> LENGTH: 15
<212> TYPE: PRT
```

<213> ORGANISM: canis familiaris;

<400> SEQUENCE: 284

Trp Tyr Gln Gln Leu Pro Gly Thr Ser Pro Lys Thr Leu Ile Tyr
1               5                   10                  15

<210> SEQ ID NO 285
<211> LENGTH: 15
<212> TYPE: PRT
<213> ORGANISM: canis familiaris;

<400> SEQUENCE: 285

Trp Tyr Gln Gln Phe Pro Gly Thr Gly Pro Arg Thr Ile Ile Tyr
1               5                   10                  15

<210> SEQ ID NO 286
<211> LENGTH: 15
<212> TYPE: PRT
<213> ORGANISM: canis familiaris;

<400> SEQUENCE: 286

Trp Tyr Gln Gln Leu Pro Gly Lys Ser Pro Lys Ser Ile Ile Phe
1               5                   10                  15

<210> SEQ ID NO 287
<211> LENGTH: 15
<212> TYPE: PRT
<213> ORGANISM: canis familiaris;

<400> SEQUENCE: 287

Trp Tyr Arg Gln Phe Pro Gly Thr Gly Pro Arg Thr Val Ala Tyr
1               5                   10                  15

<210> SEQ ID NO 288
<211> LENGTH: 15
<212> TYPE: PRT
<213> ORGANISM: canis familiaris;

<400> SEQUENCE: 288

Trp Tyr Gln Gln Leu Pro Gly Lys Ser Pro Lys Thr Ile Ile Tyr
1               5                   10                  15

<210> SEQ ID NO 289
<211> LENGTH: 15
<212> TYPE: PRT
<213> ORGANISM: canis familiaris;

<400> SEQUENCE: 289

Trp Tyr Gln Gln Leu Pro Gly Thr Ser Pro Arg Thr Leu Ile His
1               5                   10                  15

<210> SEQ ID NO 290
<211> LENGTH: 15
<212> TYPE: PRT
<213> ORGANISM: canis familiaris;

<400> SEQUENCE: 290

Trp Tyr Gln Gln Phe Leu Gly Thr Gly Pro Arg Thr Ile Ile Tyr
1               5                   10                  15

<210> SEQ ID NO 291
<211> LENGTH: 15
<212> TYPE: PRT
<213> ORGANISM: canis familiaris;

-continued

```
<400> SEQUENCE: 291

Trp Tyr Gln Gln Leu Pro Gly Lys Ala Pro Ser Leu Leu Ile Tyr
1               5                   10                  15

<210> SEQ ID NO 292
<211> LENGTH: 15
<212> TYPE: PRT
<213> ORGANISM: canis familiaris;

<400> SEQUENCE: 292

Trp Tyr Gln Gln Leu Pro Gly Lys Gly Pro Arg Thr Val Ile Tyr
1               5                   10                  15

<210> SEQ ID NO 293
<211> LENGTH: 32
<212> TYPE: PRT
<213> ORGANISM: canis familiaris;

<400> SEQUENCE: 293

Gly Val Pro Val Arg Phe Ser Gly Ser Lys Ser Gly Ser Thr Ala Thr
1               5                   10                  15

Leu Thr Ile Thr Gly Ile Gln Ala Glu Asp Glu Thr Asp Tyr Tyr Cys
            20                  25                  30

<210> SEQ ID NO 294
<211> LENGTH: 32
<212> TYPE: PRT
<213> ORGANISM: canis familiaris;

<400> SEQUENCE: 294

Gly Val Pro Asp Arg Phe Ser Gly Ser Arg Ser Gly Ser Thr Ala Thr
1               5                   10                  15

Leu Thr Ile Ser Gly Leu Gln Thr Glu Asp Glu Ala Asp Tyr Tyr Cys
            20                  25                  30

<210> SEQ ID NO 295
<211> LENGTH: 32
<212> TYPE: PRT
<213> ORGANISM: canis familiaris;

<400> SEQUENCE: 295

Gly Val Pro Asp Arg Phe Ser Gly Ser Arg Ser Gly Asn Thr Ala Thr
1               5                   10                  15

Leu Thr Ile Ser Gly Leu Gln Ala Glu Asp Glu Ala Asp Tyr Tyr Cys
            20                  25                  30

<210> SEQ ID NO 296
<211> LENGTH: 32
<212> TYPE: PRT
<213> ORGANISM: canis familiaris;

<400> SEQUENCE: 296

Gly Ile Pro Ala Arg Phe Ser Gly Ser Arg Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 297
<211> LENGTH: 32
<212> TYPE: PRT
<213> ORGANISM: canis familiaris;
<220> FEATURE:
<221> NAME/KEY: UNSURE
```

<222> LOCATION: (19)..(19)
<223> OTHER INFORMATION: X is I

<400> SEQUENCE: 297

Gly Val Pro Asp Arg Phe Ser Gly Ser Lys Ser Gly Ser Thr Ala Thr
1               5                   10                  15

Leu Thr Xaa Ser Gly Leu Gln Ala Glu Asp Glu Ala Asp Tyr Tyr Cys
            20                  25                  30

<210> SEQ ID NO 298
<211> LENGTH: 32
<212> TYPE: PRT
<213> ORGANISM: canis familiaris;

<400> SEQUENCE: 298

Gly Val Pro Ala Arg Phe Ser Gly Ser Lys Ser Gly Asn Thr Ala Thr
1               5                   10                  15

Leu Thr Ile Thr Gly Ile Gln Ala Glu Asp Glu Ala Asp Tyr Tyr Cys
            20                  25                  30

<210> SEQ ID NO 299
<211> LENGTH: 32
<212> TYPE: PRT
<213> ORGANISM: canis familiaris;

<400> SEQUENCE: 299

Gly Val Pro Asp Arg Phe Ser Ala Ser Ser Gly Ser Thr Ser Thr
1               5                   10                  15

Leu Thr Ile Ala Gly Leu Gln Ala Glu Asp Glu Gly Asp Tyr Tyr Cys
            20                  25                  30

<210> SEQ ID NO 300
<211> LENGTH: 32
<212> TYPE: PRT
<213> ORGANISM: canis familiaris;

<400> SEQUENCE: 300

Gly Ile Pro Asp Arg Phe Ser Gly Ser Arg Ser Gly Ser Thr Ala Thr
1               5                   10                  15

Leu Thr Ile Ser Gly Leu Gln Ala Glu Asp Glu Ala Asp Tyr Tyr Cys
            20                  25                  30

<210> SEQ ID NO 301
<211> LENGTH: 32
<212> TYPE: PRT
<213> ORGANISM: canis familiaris;

<400> SEQUENCE: 301

Gly Val Pro Asp Arg Phe Ser Gly Ser Ser Ser Gly Ser Ser Ala Thr
1               5                   10                  15

Leu Thr Ile Ser Gly Leu Gln Ala Glu Asp Glu Ala Asp Tyr Tyr Cys
            20                  25                  30

<210> SEQ ID NO 302
<211> LENGTH: 32
<212> TYPE: PRT
<213> ORGANISM: canis familiaris;
<220> FEATURE:
<221> NAME/KEY: UNSURE
<222> LOCATION: (3)..(3)
<223> OTHER INFORMATION: X is P

<400> SEQUENCE: 302

```
Gly Val Xaa Asp Arg Phe Ser Gly Ser Arg Gly Ser Thr Ala Thr
1               5                   10                  15

Leu Thr Ile Ser Gly Leu Gln Ala Glu Asp Glu Ala Asp Tyr Tyr Cys
                20                  25                  30
```

<210> SEQ ID NO 303
<211> LENGTH: 32
<212> TYPE: PRT
<213> ORGANISM: canis familiaris;

<400> SEQUENCE: 303

```
Gly Val Pro Asp Arg Phe Ser Gly Ser Arg Gly Ser Thr Ala Ala
1               5                   10                  15

Leu Thr Ile Ser Gly Leu Gln Ala Glu Asp Glu Ala Asp Tyr Tyr Cys
                20                  25                  30
```

<210> SEQ ID NO 304
<211> LENGTH: 32
<212> TYPE: PRT
<213> ORGANISM: canis familiaris;

<400> SEQUENCE: 304

```
Gly Val Pro Asp Arg Phe Ser Gly Ser Arg Gly Ser Thr Ala Thr
1               5                   10                  15

Leu Thr Ile Ser Gly Leu Gln Ala Glu Asp Glu Ala Asp Tyr Phe Cys
                20                  25                  30
```

<210> SEQ ID NO 305
<211> LENGTH: 32
<212> TYPE: PRT
<213> ORGANISM: canis familiaris;

<400> SEQUENCE: 305

```
Gly Val Pro Glu Arg Phe Ser Gly Ser Lys Ser Gly Ser Ala Thr
1               5                   10                  15

Leu Thr Ile Thr Gly Leu Gln Ala Glu Asp Glu Ala Asn Tyr Tyr Cys
                20                  25                  30
```

<210> SEQ ID NO 306
<211> LENGTH: 32
<212> TYPE: PRT
<213> ORGANISM: canis familiaris;

<400> SEQUENCE: 306

```
Gly Val Pro Asp Arg Phe Ser Gly Ser Arg Gly Asn Thr Ala Thr
1               5                   10                  15

Leu Thr Thr Ser Gly Leu Gln Ala Glu Asp Glu Ala Asp Tyr Phe Cys
                20                  25                  30
```

<210> SEQ ID NO 307
<211> LENGTH: 32
<212> TYPE: PRT
<213> ORGANISM: canis familiaris;

<400> SEQUENCE: 307

```
Gly Val Pro Asp Arg Phe Ser Gly Ser Ala Ser Gly Ser Ser Ala Thr
1               5                   10                  15

Leu Thr Ile Ser Gly Leu Gln Ala Glu Asp Glu Ala Glu Tyr Tyr Cys
                20                  25                  30
```

<210> SEQ ID NO 308
<211> LENGTH: 14

```
<212> TYPE: PRT
<213> ORGANISM: canis familiaris;

<400> SEQUENCE: 308

Phe Gly Ser Gly Thr Gln Leu Thr Val Leu Gly Gln Asn Glu
1               5                   10

<210> SEQ ID NO 309
<211> LENGTH: 14
<212> TYPE: PRT
<213> ORGANISM: canis familiaris;

<400> SEQUENCE: 309

Phe Gly Gly Gly Thr His Leu Thr Val Leu Gly Gln His Glu
1               5                   10

<210> SEQ ID NO 310
<211> LENGTH: 15
<212> TYPE: PRT
<213> ORGANISM: canis familiaris;

<400> SEQUENCE: 310

Phe Gly Glu Gly Thr His Leu Thr Val Leu Gly Gln Pro Lys Ala
1               5                   10                  15

<210> SEQ ID NO 311
<211> LENGTH: 15
<212> TYPE: PRT
<213> ORGANISM: canis familiaris;

<400> SEQUENCE: 311

Phe Gly Gly Gly Thr His Leu Thr Val Phe Gly Gln Pro Lys Ala
1               5                   10                  15

<210> SEQ ID NO 312
<211> LENGTH: 23
<212> TYPE: PRT
<213> ORGANISM: canis familiaris;
<220> FEATURE:
<221> NAME/KEY: unsure
<222> LOCATION: (1)..(1)
<223> OTHER INFORMATION: X is D, E, A, or absent
<220> FEATURE:
<221> NAME/KEY: unsure
<222> LOCATION: (2)..(2)
<223> OTHER INFORMATION: X is I, L, V, or absent
<220> FEATURE:
<221> NAME/KEY: unsure
<222> LOCATION: (3)..(3)
<223> OTHER INFORMATION: X is V or absent
<220> FEATURE:
<221> NAME/KEY: unsure
<222> LOCATION: (4)..(4)
<223> OTHER INFORMATION: X is M, L, or absent
<220> FEATURE:
<221> NAME/KEY: unsure
<222> LOCATION: (5)..(5)
<223> OTHER INFORMATION: X is T or absent
<220> FEATURE:
<221> NAME/KEY: unsure
<222> LOCATION: (6)..(6)
<223> OTHER INFORMATION: X is Q, E, or absent
<220> FEATURE:
<221> NAME/KEY: unsure
<222> LOCATION: (7)..(7)
<223> OTHER INFORMATION: X is T, A, or absent
<220> FEATURE:
<221> NAME/KEY: unsure
<222> LOCATION: (8)..(8)
<223> OTHER INFORMATION: X is P or absent
<220> FEATURE:
```

```
<221> NAME/KEY: unsure
<222> LOCATION: (9)..(9)
<223> OTHER INFORMATION: X is P, L, R, S, or absent
<220> FEATURE:
<221> NAME/KEY: unsure
<222> LOCATION: (10)..(10)
<223> OTHER INFORMATION: X is P, S, or absent
<220> FEATURE:
<221> NAME/KEY: unsure
<222> LOCATION: (11)..(11)
<223> OTHER INFORMATION: X is L or absent
<220> FEATURE:
<221> NAME/KEY: unsure
<222> LOCATION: (12)..(12)
<223> OTHER INFORMATION: X is S or absent
<220> FEATURE:
<221> NAME/KEY: unsure
<222> LOCATION: (13)..(13)
<223> OTHER INFORMATION: X is V, A, or absent
<220> FEATURE:
<221> NAME/KEY: unsure
<222> LOCATION: (14)..(14)
<223> OTHER INFORMATION: X is S or absent
<220> FEATURE:
<221> NAME/KEY: unsure
<222> LOCATION: (15)..(15)
<223> OTHER INFORMATION: X is P or absent
<220> FEATURE:
<221> NAME/KEY: unsure
<222> LOCATION: (16)..(16)
<223> OTHER INFORMATION: X is G, R, or absent
<220> FEATURE:
<221> NAME/KEY: unsure
<222> LOCATION: (17)..(17)
<223> OTHER INFORMATION: X is E or absent
<220> FEATURE:
<221> NAME/KEY: unsure
<222> LOCATION: (18)..(18)
<223> OTHER INFORMATION: X is P, T, S, or absent
<220> FEATURE:
<221> NAME/KEY: unsure
<222> LOCATION: (19)..(19)
<223> OTHER INFORMATION: X is A or absent
<220> FEATURE:
<221> NAME/KEY: unsure
<222> LOCATION: (20)..(20)
<223> OTHER INFORMATION: X is S, F, or absent
<220> FEATURE:
<221> NAME/KEY: unsure
<222> LOCATION: (21)..(21)
<223> OTHER INFORMATION: X is I or absent
<220> FEATURE:
<221> NAME/KEY: unsure
<222> LOCATION: (22)..(22)
<223> OTHER INFORMATION: X is S or absent
<220> FEATURE:
<221> NAME/KEY: unsure
<222> LOCATION: (23)..(23)
<223> OTHER INFORMATION: X is C, Y, or absent

<400> SEQUENCE: 312

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 313
<211> LENGTH: 15
<212> TYPE: PRT
<213> ORGANISM: canis familiaris;
<220> FEATURE:
<221> NAME/KEY: unsure
<222> LOCATION: (1)..(1)
<223> OTHER INFORMATION: X is W or absent
<220> FEATURE:
<221> NAME/KEY: unsure
```

```
<222> LOCATION: (2)..(2)
<223> OTHER INFORMATION: X is F, Y, S, L, or absent
<220> FEATURE:
<221> NAME/KEY: unsure
<222> LOCATION: (3)..(3)
<223> OTHER INFORMATION: X is R, L, Q, M, or absent
<220> FEATURE:
<221> NAME/KEY: unsure
<222> LOCATION: (4)..(4)
<223> OTHER INFORMATION: X is Q, H, or absent
<220> FEATURE:
<221> NAME/KEY: unsure
<222> LOCATION: (5)..(5)
<223> OTHER INFORMATION: X is K, R, or absent
<220> FEATURE:
<221> NAME/KEY: unsure
<222> LOCATION: (6)..(6)
<223> OTHER INFORMATION: X is P, S, or absent
<220> FEATURE:
<221> NAME/KEY: unsure
<222> LOCATION: (7)..(7)
<223> OTHER INFORMATION: X is G or absent
<220> FEATURE:
<221> NAME/KEY: unsure
<222> LOCATION: (8)..(8)
<223> OTHER INFORMATION: X is Q, H, or absent
<220> FEATURE:
<221> NAME/KEY: unsure
<222> LOCATION: (9)..(9)
<223> OTHER INFORMATION: X is S, A, or absent
<220> FEATURE:
<221> NAME/KEY: unsure
<222> LOCATION: (10)..(10)
<223> OTHER INFORMATION: X is P or absent
<220> FEATURE:
<221> NAME/KEY: unsure
<222> LOCATION: (11)..(11)
<223> OTHER INFORMATION: X is Q, E, R, or absent
<220> FEATURE:
<221> NAME/KEY: unsure
<222> LOCATION: (12)..(12)
<223> OTHER INFORMATION: X is R, G, D, L, T, I, A, or absent
<220> FEATURE:
<221> NAME/KEY: unsure
<222> LOCATION: (13)..(13)
<223> OTHER INFORMATION: X is R, L, or absent
<220> FEATURE:
<221> NAME/KEY: unsure
<222> LOCATION: (14)..(14)
<223> OTHER INFORMATION: X is T or absent
<220> FEATURE:
<221> NAME/KEY: unsure
<222> LOCATION: (15)..(15)
<223> OTHER INFORMATION: X is Y, H, S, W, F, or absent

<400> SEQUENCE: 313

Xaa Xaa Xaa Xaa Xaa Xaa Xaa Xaa Xaa Xaa Xaa Xaa Xaa Xaa Xaa
1               5                   10                  15

<210> SEQ ID NO 314
<211> LENGTH: 32
<212> TYPE: PRT
<213> ORGANISM: canis familiaris;
<220> FEATURE:
<221> NAME/KEY: unsure
<222> LOCATION: (3)..(3)
<223> OTHER INFORMATION: X is S or P
<220> FEATURE:
<221> NAME/KEY: unsure
<222> LOCATION: (4)..(4)
<223> OTHER INFORMATION: X is D or E
<220> FEATURE:
<221> NAME/KEY: unsure
<222> LOCATION: (5)..(5)
<223> OTHER INFORMATION: X is R or G
<220> FEATURE:
<221> NAME/KEY: unsure
```

```
<222> LOCATION: (6)..(6)
<223> OTHER INFORMATION: X is F or I
<220> FEATURE:
<221> NAME/KEY: unsure
<222> LOCATION: (7)..(7)
<223> OTHER INFORMATION: X is S or A
<220> FEATURE:
<221> NAME/KEY: unsure
<222> LOCATION: (9)..(9)
<223> OTHER INFORMATION: X is S or R
<220> FEATURE:
<221> NAME/KEY: unsure
<222> LOCATION: (12)..(12)
<223> OTHER INFORMATION: X is G or V
<220> FEATURE:
<221> NAME/KEY: unsure
<222> LOCATION: (13)..(13)
<223> OTHER INFORMATION: X is T or A
<220> FEATURE:
<221> NAME/KEY: unsure
<222> LOCATION: (15)..(15)
<223> OTHER INFORMATION: X is F or C
<220> FEATURE:
<221> NAME/KEY: unsure
<222> LOCATION: (18)..(18)
<223> OTHER INFORMATION: X is R, K, T, or E
<220> FEATURE:
<221> NAME/KEY: unsure
<222> LOCATION: (20)..(20)
<223> OTHER INFORMATION: X is S, T, or G
<220> FEATURE:
<221> NAME/KEY: unsure
<222> LOCATION: (21)..(21)
<223> OTHER INFORMATION: X is R or G
<220> FEATURE:
<221> NAME/KEY: unsure
<222> LOCATION: (22)..(22)
<223> OTHER INFORMATION: X is V or A
<220> FEATURE:
<221> NAME/KEY: unsure
<222> LOCATION: (23)..(23)
<223> OTHER INFORMATION: X is E, V, or G
<220> FEATURE:
<221> NAME/KEY: unsure
<222> LOCATION: (24)..(24)
<223> OTHER INFORMATION: X is A or D
<220> FEATURE:
<221> NAME/KEY: unsure
<222> LOCATION: (25)..(25)
<223> OTHER INFORMATION: X is D, N, A, E, or G
<220> FEATURE:
<221> NAME/KEY: unsure
<222> LOCATION: (26)..(26)
<223> OTHER INFORMATION: X is D or G
<220> FEATURE:
<221> NAME/KEY: unsure
<222> LOCATION: (27)..(27)
<223> OTHER INFORMATION: X is A, T, S, V, or G
<220> FEATURE:
<221> NAME/KEY: unsure
<222> LOCATION: (28)..(28)
<223> OTHER INFORMATION: X is A or G
<220> FEATURE:
<221> NAME/KEY: unsure
<222> LOCATION: (29)..(29)
<223> OTHER INFORMATION: X is V, L, or I
<220> FEATURE:
<221> NAME/KEY: unsure
<222> LOCATION: (31)..(31)
<223> OTHER INFORMATION: X is Y, H, F, or C

<400> SEQUENCE: 314

Gly Val Xaa Xaa Xaa Xaa Xaa Gly Xaa Gly Ser Xaa Xaa Asp Xaa Thr
1               5                   10                  15

Leu Xaa Ile Xaa Xaa Xaa Xaa Xaa Xaa Xaa Xaa Xaa Xaa Tyr Xaa Cys
            20                  25                  30
```

```
<210> SEQ ID NO 315
<211> LENGTH: 18
<212> TYPE: PRT
<213> ORGANISM: canis familiaris;
<220> FEATURE:
<221> NAME/KEY: unsure
<222> LOCATION: (1)..(1)
<223> OTHER INFORMATION: X is F, L, or S
<220> FEATURE:
<221> NAME/KEY: unsure
<222> LOCATION: (2)..(2)
<223> OTHER INFORMATION: X is S or G
<220> FEATURE:
<221> NAME/KEY: unsure
<222> LOCATION: (3)..(3)
<223> OTHER INFORMATION: X is Q, A, K, P, or T
<220> FEATURE:
<221> NAME/KEY: unsure
<222> LOCATION: (5)..(5)
<223> OTHER INFORMATION: X is T or A
<220> FEATURE:
<221> NAME/KEY: unsure
<222> LOCATION: (6)..(6)
<223> OTHER INFORMATION: X is K, N, or H
<220> FEATURE:
<221> NAME/KEY: unsure
<222> LOCATION: (7)..(7)
<223> OTHER INFORMATION: X is L or V
<220> FEATURE:
<221> NAME/KEY: unsure
<222> LOCATION: (8)..(8)
<223> OTHER INFORMATION: X is E, D, V, or G
<220> FEATURE:
<221> NAME/KEY: unsure
<222> LOCATION: (9)..(9)
<223> OTHER INFORMATION: X is I, M, or L
<220> FEATURE:
<221> NAME/KEY: unsure
<222> LOCATION: (10)..(10)
<223> OTHER INFORMATION: X is K or R

<400> SEQUENCE: 315

Xaa Xaa Xaa Gly Xaa Xaa Xaa Xaa Xaa Xaa Arg Asn Asp Ala Gln Pro
1               5                   10                  15

Ala Val

<210> SEQ ID NO 316
<211> LENGTH: 23
<212> TYPE: PRT
<213> ORGANISM: canis familiaris;

<400> SEQUENCE: 316

Asp Thr Val Leu Thr Gln Thr Pro Pro Ser Leu Ser Val Ser Pro Gly
1               5                   10                  15

Glu Pro Ala Ser Ile Ser Cys
            20

<210> SEQ ID NO 317
<211> LENGTH: 23
<212> TYPE: PRT
<213> ORGANISM: canis familiaris;

<400> SEQUENCE: 317

Asp Ile Val Met Thr Gln Ala Pro Pro Ser Leu Ser Val Ser Pro Gly
1               5                   10                  15

Glu Pro Ala Ser Ile Ser Cys
            20

<210> SEQ ID NO 318
```

<211> LENGTH: 23
<212> TYPE: PRT
<213> ORGANISM: canis familiaris;

<400> SEQUENCE: 318

Asp Leu Val Leu Thr Gln Thr Pro Arg Ser Leu Ser Val Ser Pro Gly
1               5                   10                  15

Glu Thr Ala Ser Ile Ser Cys
            20

<210> SEQ ID NO 319
<211> LENGTH: 23
<212> TYPE: PRT
<213> ORGANISM: canis familiaris;

<400> SEQUENCE: 319

Asp Ile Val Met Thr Gln Thr Pro Leu Ser Leu Ser Val Ser Pro Gly
1               5                   10                  15

Glu Pro Ala Ser Ile Ser Cys
            20

<210> SEQ ID NO 320
<211> LENGTH: 23
<212> TYPE: PRT
<213> ORGANISM: canis familiaris;

<400> SEQUENCE: 320

Asp Ile Val Met Thr Gln Ala Pro Pro Leu Ser Val Ser Pro Gly
1               5                   10                  15

Glu Pro Ala Ser Ile Ser Cys
            20

<210> SEQ ID NO 321
<211> LENGTH: 23
<212> TYPE: PRT
<213> ORGANISM: canis familiaris;

<400> SEQUENCE: 321

Asp Ile Val Met Thr Gln Thr Pro Pro Ser Leu Ser Val Ser Pro Arg
1               5                   10                  15

Glu Pro Ala Ser Ile Ser Cys
            20

<210> SEQ ID NO 322
<211> LENGTH: 5
<212> TYPE: PRT
<213> ORGANISM: canis familiaris;

<400> SEQUENCE: 322

Ala Ser Ile Ser Cys
1               5

<210> SEQ ID NO 323
<211> LENGTH: 14
<212> TYPE: PRT
<213> ORGANISM: canis familiaris;

<400> SEQUENCE: 323

Ser Leu Ser Val Ser Pro Gly Glu Pro Ala Phe Ile Ser Cys
1               5                   10

<210> SEQ ID NO 324
<211> LENGTH: 21

```
<212> TYPE: PRT
<213> ORGANISM: canis familiaris;

<400> SEQUENCE: 324

Val Met Thr Gln Thr Pro Leu Ser Leu Ser Val Ser Pro Gly Glu Pro
1               5                   10                  15

Ala Ser Ile Ser Cys
            20

<210> SEQ ID NO 325
<211> LENGTH: 22
<212> TYPE: PRT
<213> ORGANISM: canis familiaris;

<400> SEQUENCE: 325

Ile Val Met Thr Gln Thr Pro Leu Ser Leu Ser Val Ser Pro Gly Glu
1               5                   10                  15

Pro Ala Ser Ile Ser Cys
            20

<210> SEQ ID NO 326
<211> LENGTH: 23
<212> TYPE: PRT
<213> ORGANISM: canis familiaris;
<220> FEATURE:
<221> NAME/KEY: UNSURE
<222> LOCATION: (11)..(11)
<223> OTHER INFORMATION: X is L or absent

<400> SEQUENCE: 326

Asp Ile Val Met Thr Gln Ala Pro Pro Ser Xaa Ser Val Ser Pro Gly
        1               5                   10                  15

Glu Pro Ala Ser Ile Ser Cys
            20

<210> SEQ ID NO 327
<211> LENGTH: 23
<212> TYPE: PRT
<213> ORGANISM: canis familiaris;

<400> SEQUENCE: 327

Asp Val Val Met Thr Gln Ala Pro Pro Ser Leu Ser Val Ser Pro Arg
1               5                   10                  15

Glu Pro Ala Ser Ile Ser Cys
            20

<210> SEQ ID NO 328
<211> LENGTH: 23
<212> TYPE: PRT
<213> ORGANISM: canis familiaris;

<400> SEQUENCE: 328

Asp Val Val Met Thr Gln Ala Pro Pro Ser Leu Ser Val Ser Pro Gly
1               5                   10                  15

Glu Pro Ala Ser Ile Ser Cys
            20

<210> SEQ ID NO 329
<211> LENGTH: 22
<212> TYPE: PRT
<213> ORGANISM: canis familiaris;
<220> FEATURE:
<221> NAME/KEY: UNSURE
<222> LOCATION: (14)..(14)
```

-continued

```
<223> OTHER INFORMATION: X is S or absent
<220> FEATURE:
<221> NAME/KEY: UNSURE
<222> LOCATION: (15)..(15)
<223> OTHER INFORMATION: X is P or absent

<400> SEQUENCE: 329

Ile Val Met Thr Gln Thr Pro Leu Ser Leu Ser Val Ser Xaa Xaa Glu
1               5                   10                  15

Pro Ala Ser Ile Ser Cys
            20

<210> SEQ ID NO 330
<211> LENGTH: 23
<212> TYPE: PRT
<213> ORGANISM: canis familiaris;

<400> SEQUENCE: 330

Asp Val Val Met Thr Gln Thr Pro Pro Ser Leu Ser Val Ser Pro Arg
1               5                   10                  15

Glu Pro Ala Ser Ile Ser Cys
            20

<210> SEQ ID NO 331
<211> LENGTH: 23
<212> TYPE: PRT
<213> ORGANISM: canis familiaris;

<400> SEQUENCE: 331

Glu Ile Val Met Thr Gln Thr Pro Leu Ser Leu Ser Val Ser Pro Gly
1               5                   10                  15

Glu Thr Ala Ser Ile Ser Tyr
            20

<210> SEQ ID NO 332
<211> LENGTH: 23
<212> TYPE: PRT
<213> ORGANISM: canis familiaris;

<400> SEQUENCE: 332

Asp Ile Val Met Thr Gln Thr Pro Leu Ser Leu Ser Ala Ser Pro Gly
1               5                   10                  15

Glu Thr Ala Ser Ile Ser Cys
            20

<210> SEQ ID NO 333
<211> LENGTH: 23
<212> TYPE: PRT
<213> ORGANISM: canis familiaris;

<400> SEQUENCE: 333

Asp Ile Val Met Thr Glu Ala Pro Pro Ser Leu Ser Val Ser Pro Gly
1               5                   10                  15

Glu Ser Ala Ser Ile Ser Cys
            20

<210> SEQ ID NO 334
<211> LENGTH: 23
<212> TYPE: PRT
<213> ORGANISM: canis familiaris;

<400> SEQUENCE: 334

Asp Ile Val Met Thr Gln Ile Pro Leu Ser Leu Ser Val Ser Pro Gly
```

```
                1               5                  10                  15

Glu Pro Ala Ser Ile Ser Cys
            20

<210> SEQ ID NO 335
<211> LENGTH: 23
<212> TYPE: PRT
<213> ORGANISM: canis familiaris;

<400> SEQUENCE: 335

Asp Ile Val Met Thr Gln Thr Pro Leu Ser Leu Ser Val Ser Pro Gly
1               5                  10                  15

Glu Thr Ala Ser Ile Ser Cys
            20

<210> SEQ ID NO 336
<211> LENGTH: 23
<212> TYPE: PRT
<213> ORGANISM: canis familiaris;

<400> SEQUENCE: 336

Asp Ile Val Met Thr Gln Thr Pro Pro Ser Leu Ser Val Ser Pro Gly
1               5                  10                  15

Glu Pro Ala Ser Ile Ser Cys
            20

<210> SEQ ID NO 337
<211> LENGTH: 23
<212> TYPE: PRT
<213> ORGANISM: canis familiaris;

<400> SEQUENCE: 337

Ile Ile Val Met Thr Gln Thr Pro Leu Ser Leu Ser Ala Ser Pro Gly
1               5                  10                  15

Glu Ser Ala Ser Ile Ser Cys
            20

<210> SEQ ID NO 338
<211> LENGTH: 23
<212> TYPE: PRT
<213> ORGANISM: canis familiaris;

<400> SEQUENCE: 338

Ala Ile Val Met Thr Gln Ala Pro Pro Ser Leu Ser Val Ser Pro Gly
1               5                  10                  15

Glu Pro Ala Ser Ile Ser Cys
            20

<210> SEQ ID NO 339
<211> LENGTH: 23
<212> TYPE: PRT
<213> ORGANISM: canis familiaris;

<400> SEQUENCE: 339

Asp Ile Val Met Thr Gln Thr Pro Pro Ser Leu Ser Val Ser Pro Gly
1               5                  10                  15

Glu Thr Ala Ser Ile Ser Cys
            20

<210> SEQ ID NO 340
<211> LENGTH: 20
<212> TYPE: PRT
```

<213> ORGANISM: canis familiaris;

<400> SEQUENCE: 340

Met Thr Gln Ala Pro Pro Ser Leu Ser Val Ser Pro Gly Glu Pro Ala
1               5                   10                  15

Ser Ile Ser Cys
            20

<210> SEQ ID NO 341
<211> LENGTH: 15
<212> TYPE: PRT
<213> ORGANISM: canis familiaris;

<400> SEQUENCE: 341

Pro Ser Leu Ser Val Ser Pro Arg Glu Pro Ala Ser Ile Ser Cys
1               5                   10                  15

<210> SEQ ID NO 342
<211> LENGTH: 19
<212> TYPE: PRT
<213> ORGANISM: canis familiaris;

<400> SEQUENCE: 342

Thr Gln Ala Pro Ser Ser Leu Ser Val Ser Pro Gly Glu Pro Ala Ser
1               5                   10                  15

Ile Ser Cys

<210> SEQ ID NO 343
<211> LENGTH: 23
<212> TYPE: PRT
<213> ORGANISM: canis familiaris;
<220> FEATURE:
<221> NAME/KEY: UNSURE
<222> LOCATION: (16)..(16)
<223> OTHER INFORMATION: X is G, R, or absent

<400> SEQUENCE: 343

Asp Ile Val Met Thr Gln Thr Pro Pro Ser Leu Ser Val Ser Pro Xaa
1               5                   10                  15

Glu Pro Ala Ser Ile Ser Cys
            20

<210> SEQ ID NO 344
<211> LENGTH: 15
<212> TYPE: PRT
<213> ORGANISM: canis familiaris;

<400> SEQUENCE: 344

Trp Tyr Leu Gln Lys Pro Gly Gln Ser Pro Gln Leu Leu Ile Tyr
1               5                   10                  15

<210> SEQ ID NO 345
<211> LENGTH: 15
<212> TYPE: PRT
<213> ORGANISM: canis familiaris;

<400> SEQUENCE: 345

Trp Tyr Arg Gln Lys Pro Gly Gln Ser Pro Glu Asp Leu Ile Tyr
1               5                   10                  15

<210> SEQ ID NO 346
<211> LENGTH: 15
<212> TYPE: PRT
<213> ORGANISM: canis familiaris;

-continued

```
<400> SEQUENCE: 346

Trp Phe Arg Gln Lys Pro Gly Gln Ser Pro Gln Arg Leu Ile Tyr
1               5                   10                  15

<210> SEQ ID NO 347
<211> LENGTH: 15
<212> TYPE: PRT
<213> ORGANISM: canis familiaris;

<400> SEQUENCE: 347

Trp Phe Arg Gln Lys Pro Gly Gln Ser Pro Glu Gly Leu Ile Tyr
1               5                   10                  15

<210> SEQ ID NO 348
<211> LENGTH: 15
<212> TYPE: PRT
<213> ORGANISM: canis familiaris;

<400> SEQUENCE: 348

Trp Phe Gln Gln Lys Pro Gly Gln Ser Pro Glu Gly Leu Ile Tyr
1               5                   10                  15

<210> SEQ ID NO 349
<211> LENGTH: 15
<212> TYPE: PRT
<213> ORGANISM: canis familiaris;

<400> SEQUENCE: 349

Trp Phe Arg Gln Lys Pro Gly Gln Ser Pro Glu Gly Leu Ile His
1               5                   10                  15

<210> SEQ ID NO 350
<211> LENGTH: 15
<212> TYPE: PRT
<213> ORGANISM: canis familiaris;

<400> SEQUENCE: 350

Trp Phe Arg Gln Lys Pro Gly Gln Ser Pro Gln Arg Leu Ile Ser
1               5                   10                  15

<210> SEQ ID NO 351
<211> LENGTH: 15
<212> TYPE: PRT
<213> ORGANISM: canis familiaris;

<400> SEQUENCE: 351

Trp Phe Gln Gln Lys Pro Gly Gln Ser Pro Gln Arg Leu Ile Trp
1               5                   10                  15

<210> SEQ ID NO 352
<211> LENGTH: 15
<212> TYPE: PRT
<213> ORGANISM: canis familiaris;

<400> SEQUENCE: 352

Trp Phe Arg Gln Lys Pro Gly Gln Ser Pro Glu Asp Leu Ile Tyr
1               5                   10                  15

<210> SEQ ID NO 353
<211> LENGTH: 15
<212> TYPE: PRT
<213> ORGANISM: canis familiaris;

<400> SEQUENCE: 353
```

Trp Phe Gln Gln Lys Pro Gly Gln Ser Pro Gln Gly Leu Ile Tyr
1               5                   10                  15

<210> SEQ ID NO 354
<211> LENGTH: 15
<212> TYPE: PRT
<213> ORGANISM: canis familiaris;

<400> SEQUENCE: 354

Trp Phe Arg His Lys Pro Gly Gln Ser Pro Gln Thr Leu Ile Tyr
1               5                   10                  15

<210> SEQ ID NO 355
<211> LENGTH: 15
<212> TYPE: PRT
<213> ORGANISM: canis familiaris;

<400> SEQUENCE: 355

Trp Phe Gln Gln Lys Pro Gly His Ser Pro Arg Gly Leu Ile Tyr
1               5                   10                  15

<210> SEQ ID NO 356
<211> LENGTH: 15
<212> TYPE: PRT
<213> ORGANISM: canis familiaris;

<400> SEQUENCE: 356

Trp Tyr Met Gln Lys Pro Gly Gln Ser Pro Gln Gly Arg Ile Tyr
1               5                   10                  15

<210> SEQ ID NO 357
<211> LENGTH: 15
<212> TYPE: PRT
<213> ORGANISM: canis familiaris;

<400> SEQUENCE: 357

Trp Phe Arg Gln Arg Pro Gly Gln Ser Pro Gln Arg Leu Ile Tyr
1               5                   10                  15

<210> SEQ ID NO 358
<211> LENGTH: 15
<212> TYPE: PRT
<213> ORGANISM: canis familiaris;

<400> SEQUENCE: 358

Trp Leu Arg Gln Lys Pro Gly Gln Ser Pro Glu Gly Leu Ile Tyr
1               5                   10                  15

<210> SEQ ID NO 359
<211> LENGTH: 15
<212> TYPE: PRT
<213> ORGANISM: canis familiaris;

<400> SEQUENCE: 359

Trp Ser Arg Gln Arg Pro Gly Gln Ser Pro Glu Gly Leu Ile Tyr
1               5                   10                  15

<210> SEQ ID NO 360
<211> LENGTH: 15
<212> TYPE: PRT
<213> ORGANISM: canis familiaris;

<400> SEQUENCE: 360

Trp Tyr Leu Gln Lys Pro Gly Gln Ser Pro Gln Ile Leu Ile Tyr

-continued

```
1               5                   10                  15

<210> SEQ ID NO 361
<211> LENGTH: 15
<212> TYPE: PRT
<213> ORGANISM: canis familiaris;

<400> SEQUENCE: 361

Trp Phe Arg Gln Lys Pro Gly Gln Ala Pro Gln Arg Leu Ile Tyr
1               5                   10                  15

<210> SEQ ID NO 362
<211> LENGTH: 15
<212> TYPE: PRT
<213> ORGANISM: canis familiaris;

<400> SEQUENCE: 362

Trp Phe Arg Gln Lys Pro Gly Gln Ser Pro Gln Arg Leu Ile Phe
1               5                   10                  15

<210> SEQ ID NO 363
<211> LENGTH: 15
<212> TYPE: PRT
<213> ORGANISM: canis familiaris;

<400> SEQUENCE: 363

Trp Phe Gln Gln Lys Pro Gly Gln Ser Pro Gln Arg Leu Ile Tyr
1               5                   10                  15

<210> SEQ ID NO 364
<211> LENGTH: 15
<212> TYPE: PRT
<213> ORGANISM: canis familiaris;

<400> SEQUENCE: 364

Trp Tyr Leu Gln Lys Pro Gly Gln Ser Pro Gln Arg Leu Ile Tyr
1               5                   10                  15

<210> SEQ ID NO 365
<211> LENGTH: 15
<212> TYPE: PRT
<213> ORGANISM: canis familiaris;

<400> SEQUENCE: 365

Trp Ile Arg Gln Lys Pro Gly Gln Ser Pro Glu Gly Leu Ile Tyr
1               5                   10                  15

<210> SEQ ID NO 366
<211> LENGTH: 15
<212> TYPE: PRT
<213> ORGANISM: canis familiaris;

<400> SEQUENCE: 366

Trp Phe Arg Gln Arg Pro Gly Gln Ser Pro Glu Ala Leu Ile Tyr
1               5                   10                  15

<210> SEQ ID NO 367
<211> LENGTH: 15
<212> TYPE: PRT
<213> ORGANISM: canis familiaris;

<400> SEQUENCE: 367

Trp Phe Arg Gln Lys Ser Gly Gln Ser Pro Gln Arg Leu Ile Tyr
1               5                   10                  15
```

<210> SEQ ID NO 368
<211> LENGTH: 32
<212> TYPE: PRT
<213> ORGANISM: canis familiaris;

<400> SEQUENCE: 368

Gly Val Ser Asp Arg Phe Ser Gly Ser Gly Ser Gly Thr Asp Phe Thr
1               5                   10                  15

Leu Arg Ile Ser Arg Val Glu Pro Asn Asp Thr Gly Ile Tyr Tyr Cys
            20                  25                  30

<210> SEQ ID NO 369
<211> LENGTH: 32
<212> TYPE: PRT
<213> ORGANISM: canis familiaris;

<400> SEQUENCE: 369

Gly Val Ser Asp Arg Phe Ser Gly Ser Gly Ser Gly Thr Asp Phe Thr
1               5                   10                  15

Leu Arg Ile Ser Arg Val Glu Ala Asp Asp Ala Gly Ile Tyr Tyr Cys
            20                  25                  30

<210> SEQ ID NO 370
<211> LENGTH: 32
<212> TYPE: PRT
<213> ORGANISM: canis familiaris;

<400> SEQUENCE: 370

Gly Val Pro Asp Arg Phe Ser Gly Ser Gly Ser Gly Thr Asp Phe Thr
1               5                   10                  15

Leu Arg Ile Ser Arg Val Glu Ala Asp Asp Thr Gly Leu Tyr Tyr Cys
            20                  25                  30

<210> SEQ ID NO 371
<211> LENGTH: 32
<212> TYPE: PRT
<213> ORGANISM: canis familiaris;

<400> SEQUENCE: 371

Gly Val Ser Asp Arg Phe Ser Gly Ser Gly Ser Gly Thr Asp Phe Thr
1               5                   10                  15

Leu Thr Ile Ser Arg Val Glu Ala Asp Asp Ala Gly Val Tyr Tyr Cys
            20                  25                  30

<210> SEQ ID NO 372
<211> LENGTH: 32
<212> TYPE: PRT
<213> ORGANISM: canis familiaris;

<400> SEQUENCE: 372

Gly Val Ser Asp Arg Phe Ser Gly Ser Gly Ser Gly Thr Asp Phe Thr
1               5                   10                  15

Leu Arg Ile Ser Arg Val Glu Ala Asp Asp Ala Gly Val Tyr Tyr Cys
            20                  25                  30

<210> SEQ ID NO 373
<211> LENGTH: 32
<212> TYPE: PRT
<213> ORGANISM: canis familiaris;

<400> SEQUENCE: 373

Gly Val Ser Asp Arg Phe Ser Gly Ser Gly Ser Gly Thr Asp Phe Thr

```
                1               5              10              15

Leu Arg Ile Ser Arg Val Glu Ala Asp Asp Ala Gly Leu Tyr Tyr Cys
                20              25              30

<210> SEQ ID NO 374
<211> LENGTH: 32
<212> TYPE: PRT
<213> ORGANISM: canis familiaris;

<400> SEQUENCE: 374

Gly Val Ser Asp Arg Phe Ser Gly Ser Gly Ser Gly Thr Asp Phe Thr
1               5              10              15

Leu Arg Ile Ser Arg Val Glu Ala Asp Asp Thr Gly Val Tyr Tyr Cys
                20              25              30

<210> SEQ ID NO 375
<211> LENGTH: 32
<212> TYPE: PRT
<213> ORGANISM: canis familiaris;

<400> SEQUENCE: 375

Gly Val Pro Asp Arg Phe Ser Gly Ser Gly Ser Gly Thr Asp Phe Thr
1               5              10              15

Leu Arg Ile Gly Arg Val Glu Ala Asp Asp Thr Gly Val Tyr Tyr Cys
                20              25              30

<210> SEQ ID NO 376
<211> LENGTH: 32
<212> TYPE: PRT
<213> ORGANISM: canis familiaris;

<400> SEQUENCE: 376

Gly Val Pro Asp Arg Phe Ser Gly Ser Gly Ser Gly Thr Asp Phe Thr
1               5              10              15

Leu Arg Ile Ser Arg Val Glu Ala Asp Asp Ala Gly Ile Tyr Tyr Cys
                20              25              30

<210> SEQ ID NO 377
<211> LENGTH: 32
<212> TYPE: PRT
<213> ORGANISM: canis familiaris;

<400> SEQUENCE: 377

Gly Val Pro Asp Arg Phe Ser Gly Ser Gly Ser Gly Thr Asp Cys Thr
1               5              10              15

Leu Thr Ile Ser Arg Val Glu Ala Asp Asp Ala Gly Val Tyr Tyr Cys
                20              25              30

<210> SEQ ID NO 378
<211> LENGTH: 32
<212> TYPE: PRT
<213> ORGANISM: canis familiaris;

<400> SEQUENCE: 378

Gly Val Ser Asp Arg Phe Ser Gly Ser Gly Ser Gly Thr Asp Phe Thr
1               5              10              15

Leu Arg Ile Ser Arg Val Glu Ala Asp Asp Ala Ala Val Tyr Tyr Cys
                20              25              30

<210> SEQ ID NO 379
<211> LENGTH: 32
<212> TYPE: PRT
```

-continued

<213> ORGANISM: canis familiaris;

<400> SEQUENCE: 379

Gly Val Pro Asp Arg Phe Ser Gly Ser Gly Ser Gly Thr Asp Phe Thr
1               5                   10                  15

Leu Arg Ile Ser Arg Val Glu Ala Asp Asp Ala Gly Val Tyr Tyr Cys
            20                  25                  30

<210> SEQ ID NO 380
<211> LENGTH: 32
<212> TYPE: PRT
<213> ORGANISM: canis familiaris;

<400> SEQUENCE: 380

Gly Val Pro Asp Arg Phe Arg Gly Ser Gly Ser Gly Thr Asp Phe Thr
1               5                   10                  15

Leu Arg Ile Ser Arg Ala Glu Ala Asp Asp Ala Gly Ile Tyr Tyr Cys
            20                  25                  30

<210> SEQ ID NO 381
<211> LENGTH: 32
<212> TYPE: PRT
<213> ORGANISM: canis familiaris;

<400> SEQUENCE: 381

Gly Val Ser Asp Arg Phe Ser Gly Ser Gly Ser Gly Thr Asp Phe Thr
1               5                   10                  15

Leu Arg Ile Ser Arg Val Glu Ala Asp Asp Ala Gly Val Tyr His Cys
            20                  25                  30

<210> SEQ ID NO 382
<211> LENGTH: 32
<212> TYPE: PRT
<213> ORGANISM: canis familiaris;

<400> SEQUENCE: 382

Gly Val Pro Asp Arg Phe Ser Gly Ser Gly Ser Gly Thr Asp Phe Thr
1               5                   10                  15

Leu Arg Ile Ser Arg Val Glu Ala Asn Asp Thr Gly Val Tyr Tyr Cys
            20                  25                  30

<210> SEQ ID NO 383
<211> LENGTH: 32
<212> TYPE: PRT
<213> ORGANISM: canis familiaris;
<220> FEATURE:
<221> NAME/KEY: UNSURE
<222> LOCATION: (17)..(17)
<223> OTHER INFORMATION: X is L

<400> SEQUENCE: 383

Gly Ala Ser Asp Arg Phe Ser Gly Ser Gly Ser Gly Ala Asp Phe Thr
1               5                   10                  15

Xaa Arg Ile Ser Arg Val Glu Ala Asp Asp Ala Gly Val Tyr Tyr Cys
            20                  25                  30

<210> SEQ ID NO 384
<211> LENGTH: 32
<212> TYPE: PRT
<213> ORGANISM: canis familiaris;

<400> SEQUENCE: 384

Gly Val Pro Asp Gly Phe Ser Gly Ser Gly Ser Gly Thr Asp Phe Thr

```
                1               5                  10                 15
Leu Arg Ile Ser Arg Val Glu Ala Asp Asp Ala Gly Val Tyr Tyr Cys
                20                  25                 30

<210> SEQ ID NO 385
<211> LENGTH: 32
<212> TYPE: PRT
<213> ORGANISM: canis familiaris;
<220> FEATURE:
<221> NAME/KEY: UNSURE
<222> LOCATION: (31)..(31)
<223> OTHER INFORMATION: X is Y, H, F, or C

<400> SEQUENCE: 385

Gly Val Ser Asp Arg Phe Ser Gly Ser Gly Ser Gly Thr Asp Phe Thr
1               5                  10                 15

Leu Lys Ile Ser Arg Val Glu Ala Asp Asp Thr Gly Val Tyr Xaa Cys
                20                  25                 30

<210> SEQ ID NO 386
<211> LENGTH: 32
<212> TYPE: PRT
<213> ORGANISM: canis familiaris;

<400> SEQUENCE: 386

Gly Val Pro Asp Arg Phe Ser Gly Ser Gly Ser Gly Thr Asp Phe Thr
1               5                  10                 15

Leu Arg Ile Ser Arg Val Glu Ala Asp Asp Ser Gly Val Tyr Tyr Cys
                20                  25                 30

<210> SEQ ID NO 387
<211> LENGTH: 32
<212> TYPE: PRT
<213> ORGANISM: canis familiaris;

<400> SEQUENCE: 387

Gly Val Pro Asp Arg Phe Ser Gly Ser Gly Ser Gly Thr Asp Phe Thr
1               5                  10                 15

Leu Arg Ile Ser Arg Val Glu Ala Asp Asp Thr Gly Val Tyr Tyr Cys
                20                  25                 30

<210> SEQ ID NO 388
<211> LENGTH: 32
<212> TYPE: PRT
<213> ORGANISM: canis familiaris;

<400> SEQUENCE: 388

Gly Val Ser Asp Arg Phe Ser Gly Arg Gly Ser Gly Thr Asp Phe Thr
1               5                  10                 15

Leu Arg Ile Ser Arg Val Glu Ala Gly Asp Ala Gly Val Tyr Tyr Cys
                20                  25                 30

<210> SEQ ID NO 389
<211> LENGTH: 32
<212> TYPE: PRT
<213> ORGANISM: canis familiaris;

<400> SEQUENCE: 389

Gly Val Ser Asp Arg Phe Ser Gly Ser Gly Ser Gly Thr Asp Phe Thr
1               5                  10                 15

Leu Lys Ile Ser Arg Val Glu Ala Asp Asp Ala Gly Val Tyr Phe Cys
                20                  25                 30
```

```
<210> SEQ ID NO 390
<211> LENGTH: 32
<212> TYPE: PRT
<213> ORGANISM: canis familiaris;

<400> SEQUENCE: 390

Gly Val Pro Asp Arg Phe Ser Gly Ser Gly Ser Gly Thr Asp Phe Thr
1               5                   10                  15

Leu Arg Ile Ser Arg Val Val Ala Asp Asp Ala Gly Val Tyr Tyr Cys
            20                  25                  30

<210> SEQ ID NO 391
<211> LENGTH: 32
<212> TYPE: PRT
<213> ORGANISM: canis familiaris;

<400> SEQUENCE: 391

Gly Val Pro Asp Arg Phe Ser Gly Ser Gly Ser Gly Thr Asp Phe Thr
1               5                   10                  15

Leu Arg Ile Ser Arg Val Glu Asp Glu Asp Ala Gly Leu Tyr Tyr Cys
            20                  25                  30

<210> SEQ ID NO 392
<211> LENGTH: 32
<212> TYPE: PRT
<213> ORGANISM: canis familiaris;

<400> SEQUENCE: 392

Gly Val Ser Asp Arg Phe Ser Gly Ser Gly Ser Gly Thr Asp Phe Thr
1               5                   10                  15

Leu Arg Ile Ser Arg Val Glu Ala Asp Asp Ser Gly Val Tyr Tyr Cys
            20                  25                  30

<210> SEQ ID NO 393
<211> LENGTH: 32
<212> TYPE: PRT
<213> ORGANISM: canis familiaris;

<400> SEQUENCE: 393

Gly Val Pro Asp Arg Phe Ser Gly Ser Gly Ser Gly Thr Asp Phe Thr
1               5                   10                  15

Leu Arg Ile Ser Arg Val Glu Ala Asp Asp Gly Gly Val Tyr His Cys
            20                  25                  30

<210> SEQ ID NO 394
<211> LENGTH: 32
<212> TYPE: PRT
<213> ORGANISM: canis familiaris;

<400> SEQUENCE: 394

Gly Ile Pro Asp Arg Phe Ser Gly Ser Gly Ser Gly Thr Asp Phe Thr
1               5                   10                  15

Leu Arg Ile Ser Gly Val Glu Ala Ala Asp Thr Gly Val Tyr Tyr Cys
            20                  25                  30

<210> SEQ ID NO 395
<211> LENGTH: 32
<212> TYPE: PRT
<213> ORGANISM: canis familiaris;

<400> SEQUENCE: 395

Gly Val Ser Asp Arg Phe Ser Gly Ser Gly Ser Gly Thr Asp Phe Thr
```

```
                1               5                  10                 15
Leu Arg Ile Ser Arg Val Glu Ala Asn Asp Thr Gly Val Tyr Tyr Cys
                20                  25                  30

<210> SEQ ID NO 396
<211> LENGTH: 32
<212> TYPE: PRT
<213> ORGANISM: canis familiaris;
<220> FEATURE:
<221> NAME/KEY: UNSURE
<222> LOCATION: (27)..(27)
<223> OTHER INFORMATION: X is A, T, S, V, or G

<400> SEQUENCE: 396

Gly Val Ser Asp Arg Phe Ser Gly Ser Gly Ser Gly Thr Asp Phe Thr
1               5                   10                  15

Leu Arg Ile Ser Arg Val Glu Ala Asp Asp Xaa Gly Val Tyr Tyr Cys
                20                  25                  30

<210> SEQ ID NO 397
<211> LENGTH: 32
<212> TYPE: PRT
<213> ORGANISM: canis familiaris;

<400> SEQUENCE: 397

Gly Val Pro Asp Arg Phe Ser Gly Ser Gly Ser Gly Thr Asp Phe Thr
1               5                   10                  15

Leu Arg Ile Ser Arg Val Glu Ala Asp Asp Thr Gly Val Tyr Phe Cys
                20                  25                  30

<210> SEQ ID NO 398
<211> LENGTH: 32
<212> TYPE: PRT
<213> ORGANISM: canis familiaris;

<400> SEQUENCE: 398

Gly Val Pro Asp Arg Phe Ala Gly Ser Gly Ser Gly Thr Asp Phe Thr
1               5                   10                  15

Leu Arg Ile Ser Arg Val Glu Ala Asp Asp Thr Gly Ile Tyr Tyr Cys
                20                  25                  30

<210> SEQ ID NO 399
<211> LENGTH: 32
<212> TYPE: PRT
<213> ORGANISM: canis familiaris;

<400> SEQUENCE: 399

Gly Val Pro Asp Arg Phe Ser Gly Ser Gly Ser Gly Thr Asp Cys Thr
1               5                   10                  15

Leu Thr Ile Ser Arg Val Glu Ala Asp Gly Ala Gly Val Tyr Tyr Cys
                20                  25                  30

<210> SEQ ID NO 400
<211> LENGTH: 32
<212> TYPE: PRT
<213> ORGANISM: canis familiaris;

<400> SEQUENCE: 400

Gly Val Pro Asp Arg Phe Ser Gly Ser Gly Ser Gly Thr Asp Cys Thr
1               5                   10                  15

Leu Thr Ile Ser Arg Val Glu Ala Asp Asp Ala Gly Val Tyr Cys Cys
                20                  25                  30
```

-continued

<210> SEQ ID NO 401
<211> LENGTH: 32
<212> TYPE: PRT
<213> ORGANISM: canis familiaris;

<400> SEQUENCE: 401

Gly Val Ser Glu Arg Phe Ser Gly Ser Gly Ser Gly Thr Asp Phe Thr
1               5                   10                  15

Leu Glu Ile Ser Arg Val Glu Ala Asp Asp Val Gly Val Tyr Tyr Cys
            20                  25                  30

<210> SEQ ID NO 402
<211> LENGTH: 32
<212> TYPE: PRT
<213> ORGANISM: canis familiaris;

<400> SEQUENCE: 402

Gly Val Ser Asp Arg Phe Ser Gly Ser Gly Ser Gly Thr Asp Phe Thr
1               5                   10                  15

Leu Arg Ile Thr Arg Val Glu Ala Asp Asp Ala Gly Val Tyr Tyr Cys
            20                  25                  30

<210> SEQ ID NO 403
<211> LENGTH: 32
<212> TYPE: PRT
<213> ORGANISM: canis familiaris;

<400> SEQUENCE: 403

Gly Val Ser Glu Arg Phe Ser Gly Ser Gly Ser Gly Thr Asp Phe Thr
1               5                   10                  15

Leu Glu Ile Ser Arg Val Gly Ala Asp Asp Val Gly Val Tyr Tyr Cys
            20                  25                  30

<210> SEQ ID NO 404
<211> LENGTH: 32
<212> TYPE: PRT
<213> ORGANISM: canis familiaris;

<400> SEQUENCE: 404

Gly Val Ser Asp Arg Phe Ser Gly Ser Gly Ser Gly Thr Asp Phe Thr
1               5                   10                  15

Leu Arg Ile Ser Arg Val Glu Ala Asp Asp Thr Gly Leu Tyr Tyr Cys
            20                  25                  30

<210> SEQ ID NO 405
<211> LENGTH: 32
<212> TYPE: PRT
<213> ORGANISM: canis familiaris;

<400> SEQUENCE: 405

Gly Val Pro Asp Arg Phe Ser Gly Ser Gly Ser Gly Thr Asp Phe Thr
1               5                   10                  15

Leu Thr Ile Ser Arg Val Glu Ala Asp Asp Ala Gly Val Tyr Tyr Cys
            20                  25                  30

<210> SEQ ID NO 406
<211> LENGTH: 32
<212> TYPE: PRT
<213> ORGANISM: canis familiaris;

<400> SEQUENCE: 406

Gly Val Ser Asp Arg Phe Ser Gly Ser Gly Ser Gly Ser Val Thr Asp Phe Thr

```
                     1               5                  10                 15
Leu Arg Ile Ser Arg Val Glu Ala Asp Asp Ala Gly Ile Tyr Tyr Cys
                20                  25                 30
```

<210> SEQ ID NO 407
<211> LENGTH: 32
<212> TYPE: PRT
<213> ORGANISM: canis familiaris;

<400> SEQUENCE: 407

```
Gly Val Ser Glu Arg Ile Ser Gly Ser Gly Ser Gly Thr Asp Phe Thr
1               5                   10                  15

Leu Arg Ile Ser Arg Val Glu Ala Asp Asp Ala Gly Ile Tyr Tyr Cys
                20                  25                  30
```

<210> SEQ ID NO 408
<211> LENGTH: 19
<212> TYPE: PRT
<213> ORGANISM: canis familiaris;

<400> SEQUENCE: 408

```
Phe Gly Ala Gly Thr Lys Val Glu Leu Lys Arg Asn Asp Ala Gln Pro
1               5                   10                  15

Ala Val Tyr
```

<210> SEQ ID NO 409
<211> LENGTH: 19
<212> TYPE: PRT
<213> ORGANISM: canis familiaris;

<400> SEQUENCE: 409

```
Phe Gly Lys Gly Thr His Leu Glu Ile Lys Arg Asn Asp Ala Gln Pro
1               5                   10                  15

Ala Val Tyr
```

<210> SEQ ID NO 410
<211> LENGTH: 19
<212> TYPE: PRT
<213> ORGANISM: canis familiaris;

<400> SEQUENCE: 410

```
Phe Ser Gln Gly Thr Asn Leu Glu Met Lys Arg Asn Asp Ala Gln Pro
1               5                   10                  15

Ala Val Tyr
```

<210> SEQ ID NO 411
<211> LENGTH: 19
<212> TYPE: PRT
<213> ORGANISM: canis familiaris;

<400> SEQUENCE: 411

```
Phe Gly Thr Gly Thr Lys Val Glu Leu Lys Arg Asn Asp Ala Gln Pro
1               5                   10                  15

Ala Val Tyr
```

<210> SEQ ID NO 412
<211> LENGTH: 19
<212> TYPE: PRT
<213> ORGANISM: canis familiaris;

<400> SEQUENCE: 412

Phe Ser Gln Gly Thr Lys Leu Glu Ile Lys Arg Asn Asp Ala Gln Pro
1               5                   10                  15

Ala Val Tyr

<210> SEQ ID NO 413
<211> LENGTH: 19
<212> TYPE: PRT
<213> ORGANISM: canis familiaris;

<400> SEQUENCE: 413

Phe Gly Gln Gly Thr Lys Val Glu Ile Lys Arg Asn Asp Ala Gln Pro
1               5                   10                  15

Ala Val Tyr

<210> SEQ ID NO 414
<211> LENGTH: 19
<212> TYPE: PRT
<213> ORGANISM: canis familiaris;

<400> SEQUENCE: 414

Phe Ser Gln Gly Thr Pro Leu Glu Ile Lys Arg Asn Gly Ala Gln Pro
1               5                   10                  15

Ala Val Tyr

<210> SEQ ID NO 415
<211> LENGTH: 19
<212> TYPE: PRT
<213> ORGANISM: canis familiaris;

<400> SEQUENCE: 415

Phe Gly Gln Gly Thr Lys Val Asp Ile Lys Arg Asn Asp Ala Gln Pro
1               5                   10                  15

Ala Val Tyr

<210> SEQ ID NO 416
<211> LENGTH: 19
<212> TYPE: PRT
<213> ORGANISM: canis familiaris;

<400> SEQUENCE: 416

Phe Gly Gln Gly Thr Lys Leu Glu Ile Lys Arg Asn Asp Ala Gln Pro
1               5                   10                  15

Ala Val Tyr

<210> SEQ ID NO 417
<211> LENGTH: 19
<212> TYPE: PRT
<213> ORGANISM: canis familiaris;

<400> SEQUENCE: 417

Phe Ser Gln Gly Thr Lys Leu Glu Ile Asn Arg Asn Asp Ala Gln Pro
1               5                   10                  15

Ala Val Tyr

<210> SEQ ID NO 418
<211> LENGTH: 17
<212> TYPE: PRT
<213> ORGANISM: canis familiaris;

<400> SEQUENCE: 418

Phe Gly Lys Gly Thr His Leu Glu Ile Lys Arg Asn Asp Ala Gln Pro

-continued

```
                1               5                  10                  15
Ala

<210> SEQ ID NO 419
<211> LENGTH: 12
<212> TYPE: PRT
<213> ORGANISM: canis familiaris;
<220> FEATURE:
<221> NAME/KEY: UNSURE
<222> LOCATION: (5)..(5)
<223> OTHER INFORMATION: X is T or A

<400> SEQUENCE: 419

Phe Ser Gln Gly Xaa Lys Leu Glu Ile Lys Arg Ala
1               5                  10

<210> SEQ ID NO 420
<211> LENGTH: 13
<212> TYPE: PRT
<213> ORGANISM: canis familiaris;

<400> SEQUENCE: 420

Phe Ser Gln Gly Thr Lys Leu Glu Ile Lys Arg Asn Asp
1               5                  10

<210> SEQ ID NO 421
<211> LENGTH: 18
<212> TYPE: PRT
<213> ORGANISM: canis familiaris;

<400> SEQUENCE: 421

Phe Gly Gln Gly Thr Lys Leu Glu Ile Lys Arg Asn Asp Ala Gln Pro
1               5                  10                  15
Ala Val

<210> SEQ ID NO 422
<211> LENGTH: 19
<212> TYPE: PRT
<213> ORGANISM: canis familiaris;

<400> SEQUENCE: 422

Phe Gly Ala Gly Thr Lys Leu Glu Ile Lys Arg Asn Asp Ala Gln Pro
1               5                  10                  15
Ala Val Tyr

<210> SEQ ID NO 423
<211> LENGTH: 19
<212> TYPE: PRT
<213> ORGANISM: canis familiaris;

<400> SEQUENCE: 423

Phe Gly Gln Gly Thr Lys Leu Glu Ile Arg Arg Asn Asp Ala Gln Pro
1               5                  10                  15
Ala Val Tyr

<210> SEQ ID NO 424
<211> LENGTH: 18
<212> TYPE: PRT
<213> ORGANISM: canis familiaris;

<400> SEQUENCE: 424

Phe Ser Gln Gly Thr Lys Leu Glu Ile Lys Arg Asn Asp Ala Gln Pro
1               5                  10                  15
```

Ala Val

<210> SEQ ID NO 425
<211> LENGTH: 18
<212> TYPE: PRT
<213> ORGANISM: canis familiaris;

<400> SEQUENCE: 425

Phe Gly Ala Gly Thr Lys Val Glu Leu Lys Arg Asn Asp Ala Gln Pro
1               5                   10                  15

Ala Val

<210> SEQ ID NO 426
<211> LENGTH: 18
<212> TYPE: PRT
<213> ORGANISM: canis familiaris;

<400> SEQUENCE: 426

Phe Gly Gln Gly Thr Lys Val Glu Ile Lys Arg Asn Asp Ala Gln Pro
1               5                   10                  15

Ala Val

<210> SEQ ID NO 427
<211> LENGTH: 18
<212> TYPE: PRT
<213> ORGANISM: canis familiaris;

<400> SEQUENCE: 427

Leu Ser Gln Gly Ala Lys Leu Asp Ile Lys Arg Asn Asp Ala Gln Pro
1               5                   10                  15

Ala Val

<210> SEQ ID NO 428
<211> LENGTH: 18
<212> TYPE: PRT
<213> ORGANISM: canis familiaris;

<400> SEQUENCE: 428

Ser Ser Gln Gly Thr Lys Leu Glu Ile Lys Arg Asn Asp Ala Gln Pro
1               5                   10                  15

Ala Val

<210> SEQ ID NO 429
<211> LENGTH: 18
<212> TYPE: PRT
<213> ORGANISM: canis familiaris;

<400> SEQUENCE: 429

Phe Gly Gln Gly Thr Asn Leu Glu Ile Lys Arg Asn Asp Ala Gln Pro
1               5                   10                  15

Ala Val

<210> SEQ ID NO 430
<211> LENGTH: 18
<212> TYPE: PRT
<213> ORGANISM: canis familiaris;

<400> SEQUENCE: 430

Phe Gly Lys Gly Thr His Leu Glu Ile Lys Arg Asn Asp Ala Gln Pro
1               5                   10                  15

Ala Val

<210> SEQ ID NO 431
<211> LENGTH: 18
<212> TYPE: PRT
<213> ORGANISM: canis familiaris;

<400> SEQUENCE: 431

Phe Ser Gln Gly Thr Asn Leu Glu Met Lys Arg Asn Asp Ala Gln Pro
1               5                   10                  15

Ala Val

<210> SEQ ID NO 432
<211> LENGTH: 18
<212> TYPE: PRT
<213> ORGANISM: canis familiaris;

<400> SEQUENCE: 432

Phe Ser Gln Gly Thr Arg Leu Glu Ile Lys Arg Asn Asp Ala Gln Pro
1               5                   10                  15

Ala Val

<210> SEQ ID NO 433
<211> LENGTH: 18
<212> TYPE: PRT
<213> ORGANISM: canis familiaris;

<400> SEQUENCE: 433

Phe Ser Gln Gly Thr Asn Leu Glu Ile Lys Arg Asn Asp Ala Gln Pro
1               5                   10                  15

Ala Val

<210> SEQ ID NO 434
<211> LENGTH: 18
<212> TYPE: PRT
<213> ORGANISM: canis familiaris;

<400> SEQUENCE: 434

Phe Gly Pro Gly Ala Lys Val Glu Leu Lys Arg Asn Asp Ala Gln Pro
1               5                   10                  15

Ala Val

<210> SEQ ID NO 435
<211> LENGTH: 18
<212> TYPE: PRT
<213> ORGANISM: canis familiaris;

<400> SEQUENCE: 435

Phe Ser Gln Gly Thr Lys Leu Val Ile Lys Arg Asn Asp Ala Gln Pro
1               5                   10                  15

Ala Val

<210> SEQ ID NO 436
<211> LENGTH: 18
<212> TYPE: PRT
<213> ORGANISM: canis familiaris;
<220> FEATURE:
<221> NAME/KEY: UNSURE
<222> LOCATION: (6)..(6)
<223> OTHER INFORMATION: X is K, N or H

<400> SEQUENCE: 436

-continued

Phe Gly Gln Gly Thr Xaa Leu Glu Ile Lys Arg Asn Asp Ala Gln Pro
1               5                   10                  15
Ala Val

<210> SEQ ID NO 437
<211> LENGTH: 18
<212> TYPE: PRT
<213> ORGANISM: canis familiaris;

<400> SEQUENCE: 437

Phe Ser Gln Gly Thr Asn Leu Gly Met Lys Arg Asn Asp Ala Gln Pro
1               5                   10                  15
Ala Val

<210> SEQ ID NO 438
<211> LENGTH: 18
<212> TYPE: PRT
<213> ORGANISM: canis familiaris;

<400> SEQUENCE: 438

Leu Ser Gln Gly Thr Lys Leu Glu Ile Glu Arg Asn Asp Ala Gln Pro
1               5                   10                  15
Ala Val

<210> SEQ ID NO 439
<211> LENGTH: 18
<212> TYPE: PRT
<213> ORGANISM: canis familiaris;

<400> SEQUENCE: 439

Phe Ser Gln Gly Thr Lys Leu Glu Ile Arg Arg Asn Asp Ala Gln Pro
1               5                   10                  15
Ala Val

<210> SEQ ID NO 440
<211> LENGTH: 10
<212> TYPE: PRT
<213> ORGANISM: canis familiaris;
<220> FEATURE:
<221> NAME/KEY: unsure
<222> LOCATION: (2)..(2)
<223> OTHER INFORMATION: X is F or L
<220> FEATURE:
<221> NAME/KEY: unsure
<222> LOCATION: (3)..(3)
<223> OTHER INFORMATION: X is T, S, or N
<220> FEATURE:
<221> NAME/KEY: unsure
<222> LOCATION: (5)..(5)
<223> OTHER INFORMATION: X is S, G, N, or R
<220> FEATURE:
<221> NAME/KEY: unsure
<222> LOCATION: (6)..(6)
<223> OTHER INFORMATION: X is S, D, G, N, Y, D, R, H, T, or Y
<220> FEATURE:
<221> NAME/KEY: unsure
<222> LOCATION: (7)..(7)
<223> OTHER INFORMATION: X is Y, F, N, or C
<220> FEATURE:
<221> NAME/KEY: unsure
<222> LOCATION: (8)..(8)
<223> OTHER INFORMATION: X is G, D, H, W, S, L, A, or V
<220> FEATURE:
<221> NAME/KEY: unsure
<222> LOCATION: (10)..(10)
<223> OTHER INFORMATION: X is S, N, G, Y, I, or L

<400> SEQUENCE: 440

```
Gly Xaa Xaa Phe Xaa Xaa Xaa Xaa Met Xaa
1               5                   10

<210> SEQ ID NO 441
<211> LENGTH: 10
<212> TYPE: PRT
<213> ORGANISM: canis familiaris;

<400> SEQUENCE: 441

Gly Phe Thr Phe Ser Ile Tyr Gly Met Asn
1               5                   10

<210> SEQ ID NO 442
<211> LENGTH: 10
<212> TYPE: PRT
<213> ORGANISM: canis familiaris;

<400> SEQUENCE: 442

Gly Phe Thr Phe Ser Asp Tyr Gly Met Asn
1               5                   10

<210> SEQ ID NO 443
<211> LENGTH: 10
<212> TYPE: PRT
<213> ORGANISM: canis familiaris;

<400> SEQUENCE: 443

Gly Phe Thr Phe Ser Ser Tyr Asp Met Ser
1               5                   10

<210> SEQ ID NO 444
<211> LENGTH: 10
<212> TYPE: PRT
<213> ORGANISM: canis familiaris;

<400> SEQUENCE: 444

Gly Phe Thr Phe Ser Ser Tyr Ser Met Ser
1               5                   10

<210> SEQ ID NO 445
<211> LENGTH: 10
<212> TYPE: PRT
<213> ORGANISM: canis familiaris;

<400> SEQUENCE: 445

Gly Phe Thr Phe Ser Asp Tyr Gly Met Ser
1               5                   10

<210> SEQ ID NO 446
<211> LENGTH: 10
<212> TYPE: PRT
<213> ORGANISM: canis familiaris;

<400> SEQUENCE: 446

Gly Phe Thr Phe Ser Ser Tyr Gly Met Ser
1               5                   10

<210> SEQ ID NO 447
<211> LENGTH: 10
<212> TYPE: PRT
<213> ORGANISM: canis familiaris;

<400> SEQUENCE: 447

Gly Phe Asn Phe Gly Ser Tyr His Met Gly
```

-continued

<210> SEQ ID NO 448
<211> LENGTH: 10
<212> TYPE: PRT
<213> ORGANISM: canis familiaris;

<400> SEQUENCE: 448

Gly Phe Thr Phe Ser Tyr Tyr Leu Met Ser
1               5                   10

<210> SEQ ID NO 449
<211> LENGTH: 10
<212> TYPE: PRT
<213> ORGANISM: canis familiaris;

<400> SEQUENCE: 449

Gly Phe Thr Phe Arg Thr Tyr Gly Met Ser
1               5                   10

<210> SEQ ID NO 450
<211> LENGTH: 10
<212> TYPE: PRT
<213> ORGANISM: canis familiaris;

<400> SEQUENCE: 450

Gly Phe Thr Phe Ser Gly Tyr Trp Met Ser
1               5                   10

<210> SEQ ID NO 451
<211> LENGTH: 10
<212> TYPE: PRT
<213> ORGANISM: canis familiaris;

<400> SEQUENCE: 451

Gly Leu Ser Phe Gly Asp Phe Ala Met Asn
1               5                   10

<210> SEQ ID NO 452
<211> LENGTH: 10
<212> TYPE: PRT
<213> ORGANISM: canis familiaris;

<400> SEQUENCE: 452

Gly Phe Thr Phe Ser Asp Tyr Tyr Met Tyr
1               5                   10

<210> SEQ ID NO 453
<211> LENGTH: 10
<212> TYPE: PRT
<213> ORGANISM: canis familiaris;

<400> SEQUENCE: 453

Gly Phe Thr Phe Ser Gly Cys Ala Met Ile
1               5                   10

<210> SEQ ID NO 454
<211> LENGTH: 10
<212> TYPE: PRT
<213> ORGANISM: canis familiaris;

<400> SEQUENCE: 454

Gly Phe Thr Phe Ser Asn Tyr Asp Met Ser
1               5                   10

```
<210> SEQ ID NO 455
<211> LENGTH: 10
<212> TYPE: PRT
<213> ORGANISM: canis familiaris;

<400> SEQUENCE: 455

Gly Phe Thr Phe Ser Ala Tyr Asp Met Leu
1               5                   10

<210> SEQ ID NO 456
<211> LENGTH: 10
<212> TYPE: PRT
<213> ORGANISM: canis familiaris;

<400> SEQUENCE: 456

Gly Phe Ser Phe Ser His Asn Asp Met Ser
1               5                   10

<210> SEQ ID NO 457
<211> LENGTH: 10
<212> TYPE: PRT
<213> ORGANISM: canis familiaris;

<400> SEQUENCE: 457

Gly Phe Thr Phe Ser Arg Tyr Trp Met Ser
1               5                   10

<210> SEQ ID NO 458
<211> LENGTH: 10
<212> TYPE: PRT
<213> ORGANISM: canis familiaris;

<400> SEQUENCE: 458

Gly Phe Thr Phe Asn Ser Tyr Trp Met Ser
1               5                   10

<210> SEQ ID NO 459
<211> LENGTH: 10
<212> TYPE: PRT
<213> ORGANISM: canis familiaris;

<400> SEQUENCE: 459

Gly Phe Ile Phe Ser Ser Phe His Met Ser
1               5                   10

<210> SEQ ID NO 460
<211> LENGTH: 10
<212> TYPE: PRT
<213> ORGANISM: canis familiaris;
<220> FEATURE:
<221> NAME/KEY: unsure
<222> LOCATION: (3)..(3)
<223> OTHER INFORMATION: X is T or I
<220> FEATURE:
<221> NAME/KEY: unsure
<222> LOCATION: (5)..(5)
<223> OTHER INFORMATION: X is T or I
<220> FEATURE:
<221> NAME/KEY: unsure
<222> LOCATION: (7)..(7)
<223> OTHER INFORMATION: X is Y or Q

<400> SEQUENCE: 460

Gly Tyr Xaa Phe Xaa Asp Xaa Tyr Met His
1               5                   10
```

```
<210> SEQ ID NO 461
<211> LENGTH: 10
<212> TYPE: PRT
<213> ORGANISM: canis familiaris;

<400> SEQUENCE: 461

Gly Tyr Thr Phe Thr Asp Tyr Tyr Met His
1               5                   10

<210> SEQ ID NO 462
<211> LENGTH: 10
<212> TYPE: PRT
<213> ORGANISM: canis familiaris;

<400> SEQUENCE: 462

Gly Tyr Ile Phe Ile Asp Gln Tyr Met His
1               5                   10

<210> SEQ ID NO 463
<211> LENGTH: 10
<212> TYPE: PRT
<213> ORGANISM: canis familiaris;
<220> FEATURE:
<221> NAME/KEY: unsure
<222> LOCATION: (4)..(4)
<223> OTHER INFORMATION: X is T or N
<220> FEATURE:
<221> NAME/KEY: unsure
<222> LOCATION: (5)..(5)
<223> OTHER INFORMATION: X is D or S
<220> FEATURE:
<221> NAME/KEY: unsure
<222> LOCATION: (6)..(6)
<223> OTHER INFORMATION: X is I or G
<220> FEATURE:
<221> NAME/KEY: unsure
<222> LOCATION: (7)..(7)
<223> OTHER INFORMATION: X is Y or H

<400> SEQUENCE: 463

Gly Ser Val Xaa Xaa Xaa Xaa Tyr Trp Ser
1               5                   10

<210> SEQ ID NO 464
<211> LENGTH: 10
<212> TYPE: PRT
<213> ORGANISM: canis familiaris;

<400> SEQUENCE: 464

Gly Ser Val Thr Asp Ile His Tyr Trp Ser
1               5                   10

<210> SEQ ID NO 465
<211> LENGTH: 10
<212> TYPE: PRT
<213> ORGANISM: canis familiaris;

<400> SEQUENCE: 465

Gly Ser Val Asn Ser Gly Tyr Tyr Trp Ser
1               5                   10

<210> SEQ ID NO 466
<211> LENGTH: 11
<212> TYPE: PRT
<213> ORGANISM: canis familiaris;

<400> SEQUENCE: 466

Ser Gly Tyr Ser Phe Thr Asp Tyr Phe Met Asn
```

-continued

```
1               5                   10

<210> SEQ ID NO 467
<211> LENGTH: 17
<212> TYPE: PRT
<213> ORGANISM: canis familiaris;
<220> FEATURE:
<221> NAME/KEY: unsure
<222> LOCATION: (1)..(1)
<223> OTHER INFORMATION: X is Y, G, V, Q, D, E, S, T, A, R, or W
<220> FEATURE:
<221> NAME/KEY: unsure
<222> LOCATION: (3)..(3)
<223> OTHER INFORMATION: X is S, N, H, W, or R
<220> FEATURE:
<221> NAME/KEY: unsure
<222> LOCATION: (4)..(4)
<223> OTHER INFORMATION: X is S, Y, T, N, D, G, R, or D
<220> FEATURE:
<221> NAME/KEY: unsure
<222> LOCATION: (5)..(5)
<223> OTHER INFORMATION: X is G, D, S, or A
<220> FEATURE:
<221> NAME/KEY: unsure
<222> LOCATION: (6)..(6)
<223> OTHER INFORMATION: X is G, E, or A
<220> FEATURE:
<221> NAME/KEY: unsure
<222> LOCATION: (7)..(7)
<223> OTHER INFORMATION: X is S, D, G, T, R, Y, or E
<220> FEATURE:
<221> NAME/KEY: unsure
<222> LOCATION: (8)..(8)
<223> OTHER INFORMATION: X is T, S, Y, N, I, or G
<220> FEATURE:
<221> NAME/KEY: unsure
<222> LOCATION: (9)..(9)
<223> OTHER INFORMATION: X is T, G, L, F, Y, I, E, or R
<220> FEATURE:
<221> NAME/KEY: unsure
<222> LOCATION: (10)..(10)
<223> OTHER INFORMATION: X is Y, S, F, T, D, H, or absent
<220> FEATURE:
<221> NAME/KEY: unsure
<222> LOCATION: (11)..(11)
<223> OTHER INFORMATION: X is Y, F, or H
<220> FEATURE:
<221> NAME/KEY: unsure
<222> LOCATION: (12)..(12)
<223> OTHER INFORMATION: X is A, T, or S
<220> FEATURE:
<221> NAME/KEY: unsure
<222> LOCATION: (13)..(13)
<223> OTHER INFORMATION: X is D or G
<220> FEATURE:
<221> NAME/KEY: unsure
<222> LOCATION: (14)..(14)
<223> OTHER INFORMATION: X is A or T
<220> FEATURE:
<221> NAME/KEY: unsure
<222> LOCATION: (16)..(16)
<223> OTHER INFORMATION: X is K or R

<400> SEQUENCE: 467

Xaa Ile Xaa Xaa Xaa Xaa Xaa Xaa Xaa Xaa Xaa Xaa Xaa Xaa Val Xaa
1               5                   10                  15

Gly

<210> SEQ ID NO 468
<211> LENGTH: 16
<212> TYPE: PRT
<213> ORGANISM: canis familiaris;

<400> SEQUENCE: 468
```

-continued

Val Ile Asn Ser Ala Gly Asp Thr Gly Tyr Ala Gly Ala Val Lys Gly
1               5                   10                  15

<210> SEQ ID NO 469
<211> LENGTH: 17
<212> TYPE: PRT
<213> ORGANISM: canis familiaris;

<400> SEQUENCE: 469

Tyr Ile Ser Thr Gly Gly Thr Thr Ser Phe Ala Asp Ala Val Lys
1               5                   10                  15

Gly

<210> SEQ ID NO 470
<211> LENGTH: 17
<212> TYPE: PRT
<213> ORGANISM: canis familiaris;

<400> SEQUENCE: 470

Tyr Ile Ser Ser Asp Gly Arg Ser Thr Ser Tyr Thr Asp Ala Val Lys
1               5                   10                  15

Gly

<210> SEQ ID NO 471
<211> LENGTH: 17
<212> TYPE: PRT
<213> ORGANISM: canis familiaris;

<400> SEQUENCE: 471

Gly Ile Asn Ser Gly Gly Ser Ser Thr Tyr Tyr Thr Asp Ala Val Lys
1               5                   10                  15

Gly

<210> SEQ ID NO 472
<211> LENGTH: 17
<212> TYPE: PRT
<213> ORGANISM: canis familiaris;

<400> SEQUENCE: 472

Gly Ile Asn Ser Gly Gly Ser Thr Thr Tyr Tyr Thr Asp Ala Val Lys
1               5                   10                  15

Gly

<210> SEQ ID NO 473
<211> LENGTH: 17
<212> TYPE: PRT
<213> ORGANISM: canis familiaris;

<400> SEQUENCE: 473

Trp Ile Arg Tyr Asp Gly Ser Ser Thr Tyr Tyr Ala Asp Ala Val Lys
1               5                   10                  15

Gly

<210> SEQ ID NO 474
<211> LENGTH: 17
<212> TYPE: PRT
<213> ORGANISM: canis familiaris;

<400> SEQUENCE: 474

Tyr Ile His Asn Asp Gly Gly Thr Arg Thr Tyr Ser Asp Thr Val Lys
1               5                   10                  15

Gly

<210> SEQ ID NO 475
<211> LENGTH: 17
<212> TYPE: PRT
<213> ORGANISM: canis familiaris;

<400> SEQUENCE: 475

Glu Ile Ser Asp Ser Gly Asp Tyr Leu Asp Tyr Thr Asp Ala Val Lys
1               5                   10                  15
Gly

<210> SEQ ID NO 476
<211> LENGTH: 17
<212> TYPE: PRT
<213> ORGANISM: canis familiaris;

<400> SEQUENCE: 476

Trp Ile Trp Tyr Gly Gly Ser Ser Thr Tyr Tyr Ala Asp Ala Val Lys
1               5                   10                  15
Gly

<210> SEQ ID NO 477
<211> LENGTH: 16
<212> TYPE: PRT
<213> ORGANISM: canis familiaris;

<400> SEQUENCE: 477

Ser Ile Ser Ser Ser Gly Gly Thr Phe Tyr Ala Asp Ala Val Lys Gly
1               5                   10                  15

<210> SEQ ID NO 478
<211> LENGTH: 17
<212> TYPE: PRT
<213> ORGANISM: canis familiaris;

<400> SEQUENCE: 478

Glu Ile Ser Gly Ser Gly Thr Thr Thr His Tyr Glu Asp Thr Val Arg
1               5                   10                  15
Gly

<210> SEQ ID NO 479
<211> LENGTH: 16
<212> TYPE: PRT
<213> ORGANISM: canis familiaris;

<400> SEQUENCE: 479

Thr Ile Asn Arg Ser Gly Thr Thr Tyr Tyr Ala Asp Thr Val Lys Gly
1               5                   10                  15

<210> SEQ ID NO 480
<211> LENGTH: 17
<212> TYPE: PRT
<213> ORGANISM: canis familiaris;

<400> SEQUENCE: 480

Arg Ile Arg Gly Asp Gly Thr Asn Ile Tyr Tyr Ala Asp Ala Val Lys
1               5                   10                  15
Gly

<210> SEQ ID NO 481
<211> LENGTH: 17

```
<212> TYPE: PRT
<213> ORGANISM: canis familiaris;

<400> SEQUENCE: 481

Tyr Ile Asn Ser Asp Gly Ser Thr Thr Tyr Tyr Ala Asp Ala Val Lys
1               5                   10                  15
Gly

<210> SEQ ID NO 482
<211> LENGTH: 17
<212> TYPE: PRT
<213> ORGANISM: canis familiaris;

<400> SEQUENCE: 482

Ala Ile Ser Tyr Asp Gly Ser Ser Thr Tyr Tyr Thr Asp Ala Val Lys
1               5                   10                  15
Gly

<210> SEQ ID NO 483
<211> LENGTH: 17
<212> TYPE: PRT
<213> ORGANISM: canis familiaris;

<400> SEQUENCE: 483

Tyr Ile Asn Ser Gly Gly Gly Ile Ile Phe Tyr Ala Asp Ala Val Lys
1               5                   10                  15
Gly

<210> SEQ ID NO 484
<211> LENGTH: 17
<212> TYPE: PRT
<213> ORGANISM: canis familiaris;

<400> SEQUENCE: 484

Ser Ile Arg Tyr Asp Glu Thr Gly Thr Ser Tyr Thr Asp Ala Val Lys
1               5                   10                  15
Gly

<210> SEQ ID NO 485
<211> LENGTH: 17
<212> TYPE: PRT
<213> ORGANISM: canis familiaris;

<400> SEQUENCE: 485

Asp Ile Ser Asp Ser Ala Tyr Ser Thr Tyr Tyr Thr Asp Ala Val Lys
1               5                   10                  15
Gly

<210> SEQ ID NO 486
<211> LENGTH: 16
<212> TYPE: PRT
<213> ORGANISM: canis familiaris;

<400> SEQUENCE: 486

Gln Ile Ser Val Gly Gly Glu Ile Glu Tyr Ala Asp Ala Val Lys Gly
1               5                   10                  15

<210> SEQ ID NO 487
<211> LENGTH: 17
<212> TYPE: PRT
<213> ORGANISM: canis familiaris;
```

-continued

```
<400> SEQUENCE: 487

Gly Ile Asn Gly Gly Thr Thr Arg Phe Tyr Ser Asp Ala Val Arg
1               5                   10                  15
Gly

<210> SEQ ID NO 488
<211> LENGTH: 17
<212> TYPE: PRT
<213> ORGANISM: canis familiaris;

<400> SEQUENCE: 488

Thr Ile Ser Tyr Asp Gly Ser Ser Thr Phe His Thr Asp Ala Val Lys
1               5                   10                  15
Gly

<210> SEQ ID NO 489
<211> LENGTH: 16
<212> TYPE: PRT
<213> ORGANISM: canis familiaris;
<220> FEATURE:
<221> NAME/KEY: unsure
<222> LOCATION: (6)..(6)
<223> OTHER INFORMATION: X is G or D
<220> FEATURE:
<221> NAME/KEY: unsure
<222> LOCATION: (9)..(9)
<223> OTHER INFORMATION: X is S or G

<400> SEQUENCE: 489

Ile Asp Pro Glu Asp Xaa Thr Thr Xaa Tyr Ala Gln Lys Phe Gln Gly
1               5                   10                  15

<210> SEQ ID NO 490
<211> LENGTH: 16
<212> TYPE: PRT
<213> ORGANISM: canis familiaris;

<400> SEQUENCE: 490

Ile Asp Pro Glu Asp Gly Thr Thr Ser Tyr Ala Gln Lys Phe Gln Gly
1               5                   10                  15

<210> SEQ ID NO 491
<211> LENGTH: 16
<212> TYPE: PRT
<213> ORGANISM: canis familiaris;

<400> SEQUENCE: 491

Ile Asp Pro Glu Asp Asp Thr Thr Gly Tyr Ala Gln Lys Phe Gln Gly
1               5                   10                  15

<210> SEQ ID NO 492
<211> LENGTH: 16
<212> TYPE: PRT
<213> ORGANISM: canis familiaris;
<220> FEATURE:
<221> NAME/KEY: unsure
<222> LOCATION: (3)..(3)
<223> OTHER INFORMATION: X is R or S
<220> FEATURE:
<221> NAME/KEY: unsure
<222> LOCATION: (5)..(5)
<223> OTHER INFORMATION: X is G or T
<220> FEATURE:
<221> NAME/KEY: unsure
<222> LOCATION: (7)..(7)
<223> OTHER INFORMATION: X is N or H
<220> FEATURE:
```

```
<221> NAME/KEY: unsure
<222> LOCATION: (8)..(8)
<223> OTHER INFORMATION: X is Y or H
<220> FEATURE:
<221> NAME/KEY: unsure
<222> LOCATION: (11)..(11)
<223> OTHER INFORMATION: X is A or T
<220> FEATURE:
<221> NAME/KEY: unsure
<222> LOCATION: (14)..(14)
<223> OTHER INFORMATION: X is E or G

<400> SEQUENCE: 492

Tyr Trp Xaa Gly Xaa Thr Xaa Xaa Asn Pro Xaa Phe Gln Xaa Arg Ile
1               5                   10                  15

<210> SEQ ID NO 493
<211> LENGTH: 16
<212> TYPE: PRT
<213> ORGANISM: canis familiaris;

<400> SEQUENCE: 493

Tyr Trp Arg Gly Gly Thr Asn His Asn Pro Ala Phe Gln Glu Arg Ile
1               5                   10                  15

<210> SEQ ID NO 494
<211> LENGTH: 16
<212> TYPE: PRT
<213> ORGANISM: canis familiaris;

<400> SEQUENCE: 494

Tyr Trp Ser Gly Thr Thr His Tyr Asn Pro Thr Phe Gln Gly Arg Ile
1               5                   10                  15

<210> SEQ ID NO 495
<211> LENGTH: 17
<212> TYPE: PRT
<213> ORGANISM: canis familiaris;

<400> SEQUENCE: 495

Arg Ile Asn Pro Phe Asn Gly Asp Pro Phe Tyr Asn Gln Lys Phe Lys
1               5                   10                  15

Gly

<210> SEQ ID NO 496
<211> LENGTH: 20
<212> TYPE: PRT
<213> ORGANISM: canis familiaris;
<220> FEATURE:
<221> NAME/KEY: unsure
<222> LOCATION: (1)..(1)
<223> OTHER INFORMATION: X is D, L, Y, T, G, X, E, A, V, W, I, or Q
<220> FEATURE:
<221> NAME/KEY: unsure
<222> LOCATION: (2)..(2)
<223> OTHER INFORMATION: X is G, R, I, H, T, P, S, Y, F, D, or W
<220> FEATURE:
<221> NAME/KEY: unsure
<222> LOCATION: (3)..(3)
<223> OTHER INFORMATION: X is D, E, Y, V, W, G, S, A, M, I, T, L, P,
     or R
<220> FEATURE:
<221> NAME/KEY: unsure
<222> LOCATION: (4)..(4)
<223> OTHER INFORMATION: X is G, S, I, A, Y, L, T, Q, D, I, N, L, or R
<220> FEATURE:
<221> NAME/KEY: unsure
<222> LOCATION: (5)..(5)
<223> OTHER INFORMATION: X is T, Y, S, F, L, C, W, X, G, or E
<220> FEATURE:
```

```
<221> NAME/KEY: unsure
<222> LOCATION: (6)..(6)
<223> OTHER INFORMATION: X is S, T, V, Y, M, H, C, G, F, P, K, W,
      or absent
<220> FEATURE:
<221> NAME/KEY: unsure
<222> LOCATION: (7)..(7)
<223> OTHER INFORMATION: X is V, E, W, S, T, D, L, G, Y, K, or absent
<220> FEATURE:
<221> NAME/KEY: unsure
<222> LOCATION: (8)..(8)
<223> OTHER INFORMATION: X is A, G, R, Y, E, D, W, M, S, or absent
<220> FEATURE:
<221> NAME/KEY: unsure
<222> LOCATION: (9)..(9)
<223> OTHER INFORMATION: X is E, P, V, D, G, Y, W, F, K, or absent
<220> FEATURE:
<221> NAME/KEY: unsure
<222> LOCATION: (10)..(10)
<223> OTHER INFORMATION: X is L, G, W, Y, A, N, S, F, C, D, T, P,
      or absent
<220> FEATURE:
<221> NAME/KEY: unsure
<222> LOCATION: (11)..(11)
<223> OTHER INFORMATION: X is D, S, F, N, Y, C, A, R, or absent
<220> FEATURE:
<221> NAME/KEY: unsure
<222> LOCATION: (12)..(12)
<223> OTHER INFORMATION: X is Y, F, G, L, D, P, or absent
<220> FEATURE:
<221> NAME/KEY: unsure
<222> LOCATION: (13)..(13)
<223> OTHER INFORMATION: X is F, D, G, N, H, R, or absent
<220> FEATURE:
<221> NAME/KEY: unsure
<222> LOCATION: (14)..(14)
<223> OTHER INFORMATION: X is D, V, I, W, F, or absent
<220> FEATURE:
<221> NAME/KEY: unsure
<222> LOCATION: (15)..(15)
<223> OTHER INFORMATION: X is V, D, G, or absent
<220> FEATURE:
<221> NAME/KEY: unsure
<222> LOCATION: (16)..(16)
<223> OTHER INFORMATION: X is H, F, or absent
<220> FEATURE:
<221> NAME/KEY: unsure
<222> LOCATION: (17)..(17)
<223> OTHER INFORMATION: X is D or absent
<220> FEATURE:
<221> NAME/KEY: unsure
<222> LOCATION: (18)..(18)
<223> OTHER INFORMATION: X is Y or absent
<220> FEATURE:
<221> NAME/KEY: unsure
<222> LOCATION: (19)..(19)
<223> OTHER INFORMATION: X is L or absent
<220> FEATURE:
<221> NAME/KEY: unsure
<222> LOCATION: (20)..(20)
<223> OTHER INFORMATION: X is N or absent

<400> SEQUENCE: 496

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 497
<211> LENGTH: 11
<212> TYPE: PRT
<213> ORGANISM: canis familiaris;

<400> SEQUENCE: 497

Asp Arg Glu Ile Thr Thr Val Ala Glu Leu Asp
```

```
<210> SEQ ID NO 498
<211> LENGTH: 14
<212> TYPE: PRT
<213> ORGANISM: canis familiaris;

<400> SEQUENCE: 498

Leu Ile Tyr Gly Tyr Val Glu Gly Pro Gly Ser Tyr Phe Asp
1               5                   10

<210> SEQ ID NO 499
<211> LENGTH: 12
<212> TYPE: PRT
<213> ORGANISM: canis familiaris;

<400> SEQUENCE: 499

Tyr His Asp Gly Ser Tyr Val Arg Val Trp Phe Tyr
1               5                   10

<210> SEQ ID NO 500
<211> LENGTH: 7
<212> TYPE: PRT
<213> ORGANISM: canis familiaris;

<400> SEQUENCE: 500

Thr Thr Val Ala Thr Met Glu
1               5

<210> SEQ ID NO 501
<211> LENGTH: 13
<212> TYPE: PRT
<213> ORGANISM: canis familiaris;

<400> SEQUENCE: 501

Gly Gly Asp Ser Ser His Trp Tyr Pro Tyr Asn Phe Asp
1               5                   10

<210> SEQ ID NO 502
<211> LENGTH: 12
<212> TYPE: PRT
<213> ORGANISM: canis familiaris;

<400> SEQUENCE: 502

Asp Pro Trp Ser Ser Ser Trp Tyr Asp Ala Phe Gly
1               5                   10

<210> SEQ ID NO 503
<211> LENGTH: 13
<212> TYPE: PRT
<213> ORGANISM: canis familiaris;
<220> FEATURE:
<221> NAME/KEY: UNSURE
<222> LOCATION: (1)..(1)
<223> OTHER INFORMATION: X is D, L, Y, T, G, X, E, A, V, W, I, or Q

<400> SEQUENCE: 503

Xaa Thr Tyr Gly Thr Ser Ser Glu Gly Asn Tyr Leu Gly
1               5                   10

<210> SEQ ID NO 504
<211> LENGTH: 20
<212> TYPE: PRT
<213> ORGANISM: canis familiaris;

<400> SEQUENCE: 504
```

```
Leu Ser Gly Tyr Tyr Cys Thr Asp Asp Ser Cys Phe Asn Val Val His
1               5                   10                  15

Asp Tyr Leu Asn
            20

<210> SEQ ID NO 505
<211> LENGTH: 6
<212> TYPE: PRT
<213> ORGANISM: canis familiaris;

<400> SEQUENCE: 505

Gly Gly Asp Leu Phe Gly
1               5

<210> SEQ ID NO 506
<211> LENGTH: 7
<212> TYPE: PRT
<213> ORGANISM: canis familiaris;

<400> SEQUENCE: 506

Glu Tyr Ser Ser Ser Phe Asp
1               5

<210> SEQ ID NO 507
<211> LENGTH: 11
<212> TYPE: PRT
<213> ORGANISM: canis familiaris;

<400> SEQUENCE: 507

Asp Pro Ala Thr Leu Pro Thr Gly Glu Phe Asp
1               5                   10

<210> SEQ ID NO 508
<211> LENGTH: 15
<212> TYPE: PRT
<213> ORGANISM: canis familiaris;

<400> SEQUENCE: 508

Asp Arg Gly Gln Cys Thr Val Asp Tyr Cys Ala Asp His Ile Asp
1               5                   10                  15

<210> SEQ ID NO 509
<211> LENGTH: 9
<212> TYPE: PRT
<213> ORGANISM: canis familiaris;

<400> SEQUENCE: 509

Ala Ser Met Asp Thr Lys Thr Phe Asp
1               5

<210> SEQ ID NO 510
<211> LENGTH: 7
<212> TYPE: PRT
<213> ORGANISM: canis familiaris;

<400> SEQUENCE: 510

Asp Phe Gly Asp Trp Val Leu
1               5

<210> SEQ ID NO 511
<211> LENGTH: 6
<212> TYPE: PRT
<213> ORGANISM: canis familiaris;
<220> FEATURE:
```

```
<221> NAME/KEY: UNSURE
<222> LOCATION: (5)..(5)
<223> OTHER INFORMATION: X is T, Y, S, F, L, C, W, X, G, or E

<400> SEQUENCE: 511

Gly Asp Ser Ser Xaa Trp
1               5

<210> SEQ ID NO 512
<211> LENGTH: 14
<212> TYPE: PRT
<213> ORGANISM: canis familiaris;

<400> SEQUENCE: 512

Val Ser Ile Ile Ser Ser Ser Trp Trp Gly Arg Tyr Phe Asp
1               5                   10

<210> SEQ ID NO 513
<211> LENGTH: 5
<212> TYPE: PRT
<213> ORGANISM: canis familiaris;

<400> SEQUENCE: 513

Trp Asp Thr Asn Gly
1               5

<210> SEQ ID NO 514
<211> LENGTH: 5
<212> TYPE: PRT
<213> ORGANISM: canis familiaris;

<400> SEQUENCE: 514

Glu Tyr Leu Gly Glu
1               5

<210> SEQ ID NO 515
<211> LENGTH: 10
<212> TYPE: PRT
<213> ORGANISM: canis familiaris;

<400> SEQUENCE: 515

Ile Thr Pro Leu Gly Pro Gly Asp Phe Asp
1               5                   10

<210> SEQ ID NO 516
<211> LENGTH: 13
<212> TYPE: PRT
<213> ORGANISM: canis familiaris;

<400> SEQUENCE: 516

Asp Gly Gly Ile Thr Ser Tyr Met Lys Thr Asn Leu Asp
1               5                   10

<210> SEQ ID NO 517
<211> LENGTH: 17
<212> TYPE: PRT
<213> ORGANISM: canis familiaris;

<400> SEQUENCE: 517

Ala Arg Glu Arg Tyr Cys Lys Asp Asp Tyr Cys Phe Arg Trp Gly Phe
1               5                   10                  15
Asp

<210> SEQ ID NO 518
```

```
<211> LENGTH: 15
<212> TYPE: PRT
<213> ORGANISM: canis familiaris;

<400> SEQUENCE: 518

Gln Trp Arg Asn Thr Trp Tyr Ser Phe Pro Asp Pro Gly Phe Asp
1               5                   10                  15

<210> SEQ ID NO 519
<211> LENGTH: 10
<212> TYPE: PRT
<213> ORGANISM: canis familiaris;

<400> SEQUENCE: 519

Gly Gly Ser Arg Pro Phe Asn Ala Phe Gly
1               5                   10

<210> SEQ ID NO 520
<211> LENGTH: 9
<212> TYPE: PRT
<213> ORGANISM: canis familiaris;

<400> SEQUENCE: 520

Lys Trp Arg Tyr Tyr Gly Ser Gln Asp
1               5

<210> SEQ ID NO 521
<211> LENGTH: 6
<212> TYPE: PRT
<213> ORGANISM: canis familiaris;

<400> SEQUENCE: 521

Asp Ile Trp Asp Phe Asp
1               5

<210> SEQ ID NO 522
<211> LENGTH: 10
<212> TYPE: PRT
<213> ORGANISM: canis familiaris;

<400> SEQUENCE: 522

Tyr Ile Tyr Gly Tyr Ala Ala Tyr Leu Asp
1               5                   10

<210> SEQ ID NO 523
<211> LENGTH: 9
<212> TYPE: PRT
<213> ORGANISM: canis familiaris;

<400> SEQUENCE: 523

Leu Tyr Arg Ser Asn Tyr Leu Leu Asp
1               5

<210> SEQ ID NO 524
<211> LENGTH: 11
<212> TYPE: PRT
<213> ORGANISM: canis familiaris;

<400> SEQUENCE: 524

Phe Tyr Tyr Gly Arg Tyr Tyr Ala Met Asp Tyr
1               5                   10

<210> SEQ ID NO 525
<211> LENGTH: 14
<212> TYPE: PRT
```

<213> ORGANISM: canis familiaris;
<220> FEATURE:
<221> NAME/KEY: unsure
<222> LOCATION: (1)..(1)
<223> OTHER INFORMATION: X is G or absent
<220> FEATURE:
<221> NAME/KEY: unsure
<222> LOCATION: (2)..(2)
<223> OTHER INFORMATION: X is L or absent
<220> FEATURE:
<221> NAME/KEY: unsure
<222> LOCATION: (3)..(3)
<223> OTHER INFORMATION: X is S, N, P, or absent
<220> FEATURE:
<221> NAME/KEY: unsure
<222> LOCATION: (4)..(4)
<223> OTHER INFORMATION: X is S, P, or absent
<220> FEATURE:
<221> NAME/KEY: unsure
<222> LOCATION: (5)..(5)
<223> OTHER INFORMATION: X is G or absent
<220> FEATURE:
<221> NAME/KEY: unsure
<222> LOCATION: (6)..(6)
<223> OTHER INFORMATION: X is S or absent
<220> FEATURE:
<221> NAME/KEY: unsure
<222> LOCATION: (7)..(7)
<223> OTHER INFORMATION: X is V or absent
<220> FEATURE:
<221> NAME/KEY: unsure
<222> LOCATION: (8)..(8)
<223> OTHER INFORMATION: X is S, T, or absent
<220> FEATURE:
<221> NAME/KEY: unsure
<222> LOCATION: (9)..(9)
<223> OTHER INFORMATION: X is T, A, G, P, or absent
<220> FEATURE:
<221> NAME/KEY: unsure
<222> LOCATION: (10)..(10)
<223> OTHER INFORMATION: X is S, Q, G, N, or absent
<220> FEATURE:
<221> NAME/KEY: unsure
<222> LOCATION: (11)..(11)
<223> OTHER INFORMATION: X is N, H, D, or absent
<220> FEATURE:
<221> NAME/KEY: unsure
<222> LOCATION: (12)..(12)
<223> OTHER INFORMATION: X is Y, F, or absent
<220> FEATURE:
<221> NAME/KEY: unsure
<222> LOCATION: (13)..(13)
<223> OTHER INFORMATION: X is P or absent
<220> FEATURE:
<221> NAME/KEY: unsure
<222> LOCATION: (14)..(14)
<223> OTHER INFORMATION: X is G, N, A, S, or absent

<400> SEQUENCE: 525

Xaa Xaa Xaa Xaa Xaa Xaa Xaa Xaa Xaa Xaa Xaa Xaa Xaa Xaa
1               5                   10

<210> SEQ ID NO 526
<211> LENGTH: 4
<212> TYPE: PRT
<213> ORGANISM: canis familiaris;

<400> SEQUENCE: 526

Asn Tyr Pro Gly
1

<210> SEQ ID NO 527
<211> LENGTH: 14
<212> TYPE: PRT
<213> ORGANISM: canis familiaris;

```
<400> SEQUENCE: 527

Gly Leu Ser Ser Gly Ser Val Ser Thr Ser Asn Tyr Pro Gly
1               5                   10

<210> SEQ ID NO 528
<211> LENGTH: 14
<212> TYPE: PRT
<213> ORGANISM: canis familiaris;

<400> SEQUENCE: 528

Gly Leu Asn Ser Gly Ser Val Ser Thr Ser Asn Tyr Pro Ala
1               5                   10

<210> SEQ ID NO 529
<211> LENGTH: 14
<212> TYPE: PRT
<213> ORGANISM: canis familiaris;

<400> SEQUENCE: 529

Gly Leu Ser Pro Gly Ser Val Ser Thr Ser Asn Tyr Pro Asn
1               5                   10

<210> SEQ ID NO 530
<211> LENGTH: 14
<212> TYPE: PRT
<213> ORGANISM: canis familiaris;

<400> SEQUENCE: 530

Gly Leu Ser Ser Gly Ser Val Ser Thr Ser Asn Tyr Pro Ala
1               5                   10

<210> SEQ ID NO 531
<211> LENGTH: 14
<212> TYPE: PRT
<213> ORGANISM: canis familiaris;

<400> SEQUENCE: 531

Gly Leu Ser Ser Gly Ser Val Thr Ala Ser His Phe Pro Gly
1               5                   10

<210> SEQ ID NO 532
<211> LENGTH: 14
<212> TYPE: PRT
<213> ORGANISM: canis familiaris;

<400> SEQUENCE: 532

Gly Leu Ser Ser Gly Ser Val Ser Gly Ser Asn Tyr Pro Gly
1               5                   10

<210> SEQ ID NO 533
<211> LENGTH: 14
<212> TYPE: PRT
<213> ORGANISM: canis familiaris;

<400> SEQUENCE: 533

Gly Leu Pro Ser Gly Ser Val Ser Thr Gln Asn Phe Pro Asn
1               5                   10

<210> SEQ ID NO 534
<211> LENGTH: 14
<212> TYPE: PRT
<213> ORGANISM: canis familiaris;

<400> SEQUENCE: 534
```

```
Gly Leu Ser Ser Gly Ser Val Ser Thr Gly Asp Phe Pro Gly
1               5                   10
```

<210> SEQ ID NO 535
<211> LENGTH: 14
<212> TYPE: PRT
<213> ORGANISM: canis familiaris;

<400> SEQUENCE: 535

```
Gly Leu Ser Ser Gly Ser Val Ser Thr Ser Asn Tyr Pro Asn
1               5                   10
```

<210> SEQ ID NO 536
<211> LENGTH: 14
<212> TYPE: PRT
<213> ORGANISM: canis familiaris;

<400> SEQUENCE: 536

```
Gly Leu Ser Ser Gly Ser Val Ser Pro Ser His Tyr Pro Gly
1               5                   10
```

<210> SEQ ID NO 537
<211> LENGTH: 14
<212> TYPE: PRT
<213> ORGANISM: canis familiaris;

<400> SEQUENCE: 537

```
Gly Leu Ser Ser Gly Ser Val Ser Thr Ser Asn Tyr Pro Ser
1               5                   10
```

<210> SEQ ID NO 538
<211> LENGTH: 14
<212> TYPE: PRT
<213> ORGANISM: canis familiaris;

<400> SEQUENCE: 538

```
Gly Leu Ser Ser Gly Ser Val Ser Thr Asn Asn Tyr Pro Gly
1               5                   10
```

<210> SEQ ID NO 539
<211> LENGTH: 13
<212> TYPE: PRT
<213> ORGANISM: canis familiaris;
<220> FEATURE:
<221> NAME/KEY: unsure
<222> LOCATION: (1)..(1)
<223> OTHER INFORMATION: X is T, S, A, or absent
<220> FEATURE:
<221> NAME/KEY: unsure
<222> LOCATION: (2)..(2)
<223> OTHER INFORMATION: X is G, R, or absent
<220> FEATURE:
<221> NAME/KEY: unsure
<222> LOCATION: (3)..(3)
<223> OTHER INFORMATION: X is S, T, R, D,  A or abent
<220> FEATURE:
<221> NAME/KEY: unsure
<222> LOCATION: (4)..(4)
<223> OTHER INFORMATION: X is S, G, E, N, T, P, V, Y,  M, or absent
<220> FEATURE:
<221> NAME/KEY: unsure
<222> LOCATION: (5)..(5)
<223> OTHER INFORMATION: X is S, N, D, A, Y, or K
<220> FEATURE:
<221> NAME/KEY: unsure
<222> LOCATION: (6)..(6)
<223> OTHER INFORMATION: X is N, D, or Y
<220> FEATURE:
<221> NAME/KEY: unsure

```
<222> LOCATION: (7)..(7)
<223> OTHER INFORMATION: X is I, V, or L
<220> FEATURE:
<221> NAME/KEY: unsure
<222> LOCATION: (8)..(8)
<223> OTHER INFORMATION: X is G, D, A, or N
<220> FEATURE:
<221> NAME/KEY: unsure
<222> LOCATION: (9)..(9)
<223> OTHER INFORMATION: X is R, Y, G, I, K, S, D, or V
<220> FEATURE:
<221> NAME/KEY: unsure
<222> LOCATION: (10)..(10)
<223> OTHER INFORMATION: X is G, R, V, Y, A, S, F, D, or N
<220> FEATURE:
<221> NAME/KEY: unsure
<222> LOCATION: (11)..(11)
<223> OTHER INFORMATION: X is Y, N, G, D, F, S, or H, V, or Q
<220> FEATURE:
<221> NAME/KEY: unsure
<222> LOCATION: (12)..(12)
<223> OTHER INFORMATION: X is V, A, or absent
<220> FEATURE:
<221> NAME/KEY: unsure
<222> LOCATION: (13)..(13)
<223> OTHER INFORMATION: X is G, H, S, N, A, D, T, or absent

<400> SEQUENCE: 539

Xaa Xaa Xaa Xaa Xaa Xaa Xaa Xaa Xaa Xaa Xaa Xaa Xaa
1               5                   10

<210> SEQ ID NO 540
<211> LENGTH: 13
<212> TYPE: PRT
<213> ORGANISM: canis familiaris;

<400> SEQUENCE: 540

Thr Gly Ser Gly Ser Asn Ile Gly Arg Gly Tyr Val Gly
1               5                   10

<210> SEQ ID NO 541
<211> LENGTH: 13
<212> TYPE: PRT
<213> ORGANISM: canis familiaris;

<400> SEQUENCE: 541

Thr Gly Ser Glu Ser Asn Ile Gly Arg Gly Phe Val Gly
1               5                   10

<210> SEQ ID NO 542
<211> LENGTH: 13
<212> TYPE: PRT
<213> ORGANISM: canis familiaris;

<400> SEQUENCE: 542

Thr Gly Ser Ser Ser Asn Val Gly Arg Gly Tyr Val Gly
1               5                   10

<210> SEQ ID NO 543
<211> LENGTH: 8
<212> TYPE: PRT
<213> ORGANISM: canis familiaris;

<400> SEQUENCE: 543

Asn Ile Gly Ser Val Gly Ala Thr
1               5

<210> SEQ ID NO 544
<211> LENGTH: 13
```

-continued

<212> TYPE: PRT
<213> ORGANISM: canis familiaris;

<400> SEQUENCE: 544

Thr Gly Ser Gly Ser Asn Ile Gly Gly Asn Asn Val Gly
1               5                   10

<210> SEQ ID NO 545
<211> LENGTH: 13
<212> TYPE: PRT
<213> ORGANISM: canis familiaris;

<400> SEQUENCE: 545

Thr Gly Ser Ser Ser Asn Ile Gly Gly Tyr Asn Val Gly
1               5                   10

<210> SEQ ID NO 546
<211> LENGTH: 13
<212> TYPE: PRT
<213> ORGANISM: canis familiaris;

<400> SEQUENCE: 546

Thr Gly Ser Ser Ser Asn Ile Gly Arg Asp Tyr Val Gly
1               5                   10

<210> SEQ ID NO 547
<211> LENGTH: 13
<212> TYPE: PRT
<213> ORGANISM: canis familiaris;

<400> SEQUENCE: 547

Thr Gly Ser Ser Ser Asn Leu Gly Arg Tyr Gly Val Ala
1               5                   10

<210> SEQ ID NO 548
<211> LENGTH: 13
<212> TYPE: PRT
<213> ORGANISM: canis familiaris;

<400> SEQUENCE: 548

Thr Gly Thr Thr Ser Asn Ile Gly Arg Gly Phe Val Gly
1               5                   10

<210> SEQ ID NO 549
<211> LENGTH: 13
<212> TYPE: PRT
<213> ORGANISM: canis familiaris;

<400> SEQUENCE: 549

Thr Gly Ser Ser Ser Asn Ile Gly Ser Gly Tyr Val Gly
1               5                   10

<210> SEQ ID NO 550
<211> LENGTH: 13
<212> TYPE: PRT
<213> ORGANISM: canis familiaris;

<400> SEQUENCE: 550

Thr Gly Ser Ser Ser Asn Ile Gly Gly Tyr Asn Val Asn
1               5                   10

<210> SEQ ID NO 551
<211> LENGTH: 13
<212> TYPE: PRT
<213> ORGANISM: canis familiaris;

```
<400> SEQUENCE: 551

Thr Gly Ser Ser Ser Asn Ile Gly Gly Gly Tyr Val Gly
1               5                   10

<210> SEQ ID NO 552
<211> LENGTH: 13
<212> TYPE: PRT
<213> ORGANISM: canis familiaris;

<400> SEQUENCE: 552

Ser Gly Ser Thr Asn Asp Ile Asp Ile Phe Gly Val Ser
1               5                   10

<210> SEQ ID NO 553
<211> LENGTH: 13
<212> TYPE: PRT
<213> ORGANISM: canis familiaris;

<400> SEQUENCE: 553

Ser Gly Asp Ser Ser Asn Ile Gly Asp Asn Phe Val Ala
1               5                   10

<210> SEQ ID NO 554
<211> LENGTH: 13
<212> TYPE: PRT
<213> ORGANISM: canis familiaris;

<400> SEQUENCE: 554

Thr Gly Ser Ser Ser Asn Ile Gly Lys Tyr Val Val Gly
1               5                   10

<210> SEQ ID NO 555
<211> LENGTH: 13
<212> TYPE: PRT
<213> ORGANISM: canis familiaris;

<400> SEQUENCE: 555

Thr Gly Ser Ser Ser Asn Ile Gly Arg Gly Tyr Val Gly
1               5                   10

<210> SEQ ID NO 556
<211> LENGTH: 13
<212> TYPE: PRT
<213> ORGANISM: canis familiaris;

<400> SEQUENCE: 556

Thr Gly Ser Ser Ser Asn Ile Gly Arg Asp Tyr Val Ala
1               5                   10

<210> SEQ ID NO 557
<211> LENGTH: 13
<212> TYPE: PRT
<213> ORGANISM: canis familiaris;

<400> SEQUENCE: 557

Ser Gly Ser Thr Ser Asn Ile Gly Ile Val Gly Ala Ser
1               5                   10

<210> SEQ ID NO 558
<211> LENGTH: 13
<212> TYPE: PRT
<213> ORGANISM: canis familiaris;

<400> SEQUENCE: 558
```

Thr Gly Ser Pro Ser Asn Ile Gly Gly Tyr Asp Val Ala
1               5                   10

<210> SEQ ID NO 559
<211> LENGTH: 13
<212> TYPE: PRT
<213> ORGANISM: canis familiaris;

<400> SEQUENCE: 559

Thr Gly Ser Ser Ser Asn Ile Gly Gly Tyr Ser Val Ala
1               5                   10

<210> SEQ ID NO 560
<211> LENGTH: 13
<212> TYPE: PRT
<213> ORGANISM: canis familiaris;

<400> SEQUENCE: 560

Thr Gly Ser Ser Ser Asn Ile Gly Gly Asn Tyr Val Ser
1               5                   10

<210> SEQ ID NO 561
<211> LENGTH: 13
<212> TYPE: PRT
<213> ORGANISM: canis familiaris;

<400> SEQUENCE: 561

Thr Gly Ser Asn Ser Asn Ile Gly Arg Gly Tyr Val Asp
1               5                   10

<210> SEQ ID NO 562
<211> LENGTH: 13
<212> TYPE: PRT
<213> ORGANISM: canis familiaris;

<400> SEQUENCE: 562

Thr Gly Ser Asn Ser Asn Ile Gly Gly Asn Asp Val Ala
1               5                   10

<210> SEQ ID NO 563
<211> LENGTH: 13
<212> TYPE: PRT
<213> ORGANISM: canis familiaris;

<400> SEQUENCE: 563

Thr Gly Ser Val Ser Asn Ile Gly Ile Phe Asp Val Gly
1               5                   10

<210> SEQ ID NO 564
<211> LENGTH: 13
<212> TYPE: PRT
<213> ORGANISM: canis familiaris;

<400> SEQUENCE: 564

Thr Gly Ser Gly Ser Asn Ile Gly Arg Asp Ser Val Gly
1               5                   10

<210> SEQ ID NO 565
<211> LENGTH: 13
<212> TYPE: PRT
<213> ORGANISM: canis familiaris;

<400> SEQUENCE: 565

Thr Gly Ser Ser Ser Asn Ile Gly Gly Asn Gln Val Gly

```
1               5                  10
```

<210> SEQ ID NO 566
<211> LENGTH: 13
<212> TYPE: PRT
<213> ORGANISM: canis familiaris;

<400> SEQUENCE: 566

```
Ser Gly Ser Thr Asn Asp Ile Ala Ile Val Gly Ala Ser
1               5                  10
```

<210> SEQ ID NO 567
<211> LENGTH: 13
<212> TYPE: PRT
<213> ORGANISM: canis familiaris;

<400> SEQUENCE: 567

```
Thr Gly Ser Ser Ser Asn Ile Gly Gly Asn Tyr Val Gly
1               5                  10
```

<210> SEQ ID NO 568
<211> LENGTH: 13
<212> TYPE: PRT
<213> ORGANISM: canis familiaris;

<400> SEQUENCE: 568

```
Thr Arg Ser Ser Ser Asn Ile Ala Gly Gly Tyr Val Ala
1               5                  10
```

<210> SEQ ID NO 569
<211> LENGTH: 13
<212> TYPE: PRT
<213> ORGANISM: canis familiaris;

<400> SEQUENCE: 569

```
Thr Gly Ser Ser Ala Tyr Ile Gly Ser Gly Tyr Val Gly
1               5                  10
```

<210> SEQ ID NO 570
<211> LENGTH: 13
<212> TYPE: PRT
<213> ORGANISM: canis familiaris;

<400> SEQUENCE: 570

```
Ser Gly Ser Thr Lys Asn Ile Gly Ile Phe Gly Ala His
1               5                  10
```

<210> SEQ ID NO 571
<211> LENGTH: 13
<212> TYPE: PRT
<213> ORGANISM: canis familiaris;

<400> SEQUENCE: 571

```
Thr Gly Ser Ser Ser Asn Ile Gly Gly Ser Ser Val Gly
1               5                  10
```

<210> SEQ ID NO 572
<211> LENGTH: 13
<212> TYPE: PRT
<213> ORGANISM: canis familiaris;

<400> SEQUENCE: 572

```
Thr Gly Ser Ser Ser Asn Ile Gly Arg Gly Phe Val Ala
1               5                  10
```

<210> SEQ ID NO 573
<211> LENGTH: 13
<212> TYPE: PRT
<213> ORGANISM: canis familiaris;

<400> SEQUENCE: 573

Thr Gly Ala Tyr Ser Asn Ile Gly Thr Asn Val Gly
1               5                   10

<210> SEQ ID NO 574
<211> LENGTH: 13
<212> TYPE: PRT
<213> ORGANISM: canis familiaris;

<400> SEQUENCE: 574

Thr Gly Ser Gly Ser Asn Ile Gly Arg Gly Tyr Val Ala
1               5                   10

<210> SEQ ID NO 575
<211> LENGTH: 11
<212> TYPE: PRT
<213> ORGANISM: canis familiaris;

<400> SEQUENCE: 575

Thr Gly Ser Ser Ile Asn Tyr Arg Tyr Val Gly
1               5                   10

<210> SEQ ID NO 576
<211> LENGTH: 13
<212> TYPE: PRT
<213> ORGANISM: canis familiaris;

<400> SEQUENCE: 576

Ser Gly Arg Thr Asp Asn Ile Gly Val Ala Gly Ala Ala
1               5                   10

<210> SEQ ID NO 577
<211> LENGTH: 11
<212> TYPE: PRT
<213> ORGANISM: canis familiaris;

<400> SEQUENCE: 577

Thr Gly Ser Gly Ser Asp Ile Gly Gly Phe Gly
1               5                   10

<210> SEQ ID NO 578
<211> LENGTH: 12
<212> TYPE: PRT
<213> ORGANISM: canis familiaris;

<400> SEQUENCE: 578

Thr Gly Ser Ser Ser Asn Ile Gly Tyr Asn Val Gly
1               5                   10

<210> SEQ ID NO 579
<211> LENGTH: 13
<212> TYPE: PRT
<213> ORGANISM: canis familiaris;

<400> SEQUENCE: 579

Thr Gly Ser Ser Ser Asn Val Gly Gly Gly Phe Val Gly
1               5                   10

<210> SEQ ID NO 580

```
<211> LENGTH: 13
<212> TYPE: PRT
<213> ORGANISM: canis familiaris;

<400> SEQUENCE: 580

Ala Gly Thr Asn Ser Asp Ile Gly Thr Asn His Val Ala
1               5                   10

<210> SEQ ID NO 581
<211> LENGTH: 13
<212> TYPE: PRT
<213> ORGANISM: canis familiaris;

<400> SEQUENCE: 581

Ser Gly Ser Thr Asn Asp Ile Gly Arg Phe Gly Val Asn
1               5                   10

<210> SEQ ID NO 582
<211> LENGTH: 13
<212> TYPE: PRT
<213> ORGANISM: canis familiaris;

<400> SEQUENCE: 582

Thr Gly Ser Thr Ala Asn Ile Gly Ser Gly Tyr Val Asn
1               5                   10

<210> SEQ ID NO 583
<211> LENGTH: 13
<212> TYPE: PRT
<213> ORGANISM: canis familiaris;

<400> SEQUENCE: 583

Thr Gly Ser Ser Ser Asn Ile Gly Arg Asn Asn Val Gly
1               5                   10

<210> SEQ ID NO 584
<211> LENGTH: 13
<212> TYPE: PRT
<213> ORGANISM: canis familiaris;

<400> SEQUENCE: 584

Ser Gly Ser Met Tyr Asn Leu Gly Val Val Gly Ala Thr
1               5                   10

<210> SEQ ID NO 585
<211> LENGTH: 13
<212> TYPE: PRT
<213> ORGANISM: canis familiaris;

<400> SEQUENCE: 585

Thr Gly Ser Asn Ser Asn Ile Gly Arg Gly Tyr Val Gly
1               5                   10

<210> SEQ ID NO 586
<211> LENGTH: 14
<212> TYPE: PRT
<213> ORGANISM: canis familiaris;
<220> FEATURE:
<221> NAME/KEY: unsure
<222> LOCATION: (1)..(1)
<223> OTHER INFORMATION: X is T or D
<220> FEATURE:
<221> NAME/KEY: unsure
<222> LOCATION: (3)..(3)
<223> OTHER INFORMATION: X is S, T, I, N, R, or absent
<220> FEATURE:
<221> NAME/KEY: unsure
```

```
<222> LOCATION: (4)..(4)
<223> OTHER INFORMATION: X is S, N, T, K, D, or G
<220> FEATURE:
<221> NAME/KEY: unsure
<222> LOCATION: (5)..(5)
<223> OTHER INFORMATION: X is S, T, D, or N
<220> FEATURE:
<221> NAME/KEY: unsure
<222> LOCATION: (6)..(6)
<223> OTHER INFORMATION: X is N, D, or absent
<220> FEATURE:
<221> NAME/KEY: unsure
<222> LOCATION: (7)..(7)
<223> OTHER INFORMATION: X is V, I, or L
<220> FEATURE:
<221> NAME/KEY: unsure
<222> LOCATION: (8)..(8)
<223> OTHER INFORMATION: X is G or D
<220> FEATURE:
<221> NAME/KEY: unsure
<222> LOCATION: (9)..(9)
<223> OTHER INFORMATION: X is Y, N, F, S, D, or G
<220> FEATURE:
<221> NAME/KEY: unsure
<222> LOCATION: (10)..(10)
<223> OTHER INFORMATION: X is G, D, T, or E
<220> FEATURE:
<221> NAME/KEY: unsure
<222> LOCATION: (11)..(11)
<223> OTHER INFORMATION: X is N, D, Y, or S
<220> FEATURE:
<221> NAME/KEY: unsure
<222> LOCATION: (12)..(12)
<223> OTHER INFORMATION: X is Y, D, I, S, T, or H
<220> FEATURE:
<221> NAME/KEY: unsure
<222> LOCATION: (13)..(13)
<223> OTHER INFORMATION: X is V, A, or I
<220> FEATURE:
<221> NAME/KEY: unsure
<222> LOCATION: (14)..(14)
<223> OTHER INFORMATION: X is G, Q, H, or A

<400> SEQUENCE: 586

Xaa Gly Xaa Xaa Xaa Xaa Xaa Xaa Xaa Xaa Xaa Xaa Xaa Xaa
1               5                   10

<210> SEQ ID NO 587
<211> LENGTH: 14
<212> TYPE: PRT
<213> ORGANISM: canis familiaris;

<400> SEQUENCE: 587

Thr Gly Thr Asn Thr Asn Ile Gly Asn Gly Tyr Asp Val His
1               5                   10

<210> SEQ ID NO 588
<211> LENGTH: 14
<212> TYPE: PRT
<213> ORGANISM: canis familiaris;

<400> SEQUENCE: 588

Thr Gly Ser Ser Ser Asn Val Gly Tyr Gly Asp Tyr Val Gly
1               5                   10

<210> SEQ ID NO 589
<211> LENGTH: 14
<212> TYPE: PRT
<213> ORGANISM: canis familiaris;

<400> SEQUENCE: 589

Thr Gly Ser Ser Ser Asn Val Gly Tyr Ala Asn His Val Gly
```

```
1               5                    10
```

<210> SEQ ID NO 590
<211> LENGTH: 14
<212> TYPE: PRT
<213> ORGANISM: canis familiaris;

<400> SEQUENCE: 590

```
Thr Gly Ser Ser Ser Asn Val Gly Tyr Gly Asn Tyr Val Gly
1               5                   10
```

<210> SEQ ID NO 591
<211> LENGTH: 14
<212> TYPE: PRT
<213> ORGANISM: canis familiaris;

<400> SEQUENCE: 591

```
Asp Gly Ile Asn Ser Asn Ile Asp Asn Ser Asn Tyr Ile Glu
1               5                   10
```

<210> SEQ ID NO 592
<211> LENGTH: 14
<212> TYPE: PRT
<213> ORGANISM: canis familiaris;

<400> SEQUENCE: 592

```
Thr Gly Ser Ser Ser Asp Val Gly Tyr Ala Asp Tyr Val Gly
1               5                   10
```

<210> SEQ ID NO 593
<211> LENGTH: 14
<212> TYPE: PRT
<213> ORGANISM: canis familiaris;

<400> SEQUENCE: 593

```
Thr Gly Ser Ser Ser Asn Val Gly Phe Gly Asn Tyr Val Gly
1               5                   10
```

<210> SEQ ID NO 594
<211> LENGTH: 14
<212> TYPE: PRT
<213> ORGANISM: canis familiaris;
<220> FEATURE:
<221> NAME/KEY: UNSURE
<222> LOCATION: (1)..(1)
<223> OTHER INFORMATION: X is T or D

<400> SEQUENCE: 594

```
Xaa Gly Ser Ser Ser Asn Val Gly Ser Gly Ser Thr Val Gly
1               5                   10
```

<210> SEQ ID NO 595
<211> LENGTH: 14
<212> TYPE: PRT
<213> ORGANISM: canis familiaris;

<400> SEQUENCE: 595

```
Thr Gly Ser Lys Thr Asn Ile Gly Ser Gly Tyr Asp Val Gln
1               5                   10
```

<210> SEQ ID NO 596
<211> LENGTH: 14
<212> TYPE: PRT
<213> ORGANISM: canis familiaris;

<400> SEQUENCE: 596

Thr Gly Ser Lys Asp Asn Ile Gly Tyr Gly Asn Tyr Val Gly
1               5                   10

<210> SEQ ID NO 597
<211> LENGTH: 14
<212> TYPE: PRT
<213> ORGANISM: canis familiaris;

<400> SEQUENCE: 597

Thr Gly Ser Asn Thr Asn Ile Gly Ser Asp Tyr Asp Val Gln
1               5                   10

<210> SEQ ID NO 598
<211> LENGTH: 14
<212> TYPE: PRT
<213> ORGANISM: canis familiaris;

<400> SEQUENCE: 598

Thr Gly Ser Ser Ser Asn Val Gly Tyr Gly Asp Tyr Ala Gly
1               5                   10

<210> SEQ ID NO 599
<211> LENGTH: 14
<212> TYPE: PRT
<213> ORGANISM: canis familiaris;

<400> SEQUENCE: 599

Thr Gly Ser Thr Ser Asn Val Gly Tyr Gly Asn Tyr Val Gly
1               5                   10

<210> SEQ ID NO 600
<211> LENGTH: 14
<212> TYPE: PRT
<213> ORGANISM: canis familiaris;

<400> SEQUENCE: 600

Thr Gly Ser Asn Ser Asn Val Gly Tyr Ala Asn Tyr Val Gly
1               5                   10

<210> SEQ ID NO 601
<211> LENGTH: 14
<212> TYPE: PRT
<213> ORGANISM: canis familiaris;
<220> FEATURE:
<221> NAME/KEY: UNSURE
<222> LOCATION: (12)..(12)
<223> OTHER INFORMATION: X is Y, D, I, S, T, or H

<400> SEQUENCE: 601

Thr Gly Ser Ser Ser Asn Val Gly Tyr Gly Asp Xaa Val Gly
1               5                   10

<210> SEQ ID NO 602
<211> LENGTH: 14
<212> TYPE: PRT
<213> ORGANISM: canis familiaris;

<400> SEQUENCE: 602

Thr Gly Asn Ser Ser Asn Val Gly Tyr Gly Asn Tyr Val Gly
1               5                   10

<210> SEQ ID NO 603
<211> LENGTH: 14
<212> TYPE: PRT
<213> ORGANISM: canis familiaris;

<400> SEQUENCE: 603

Thr Gly Ser Ser Ser Asn Val Gly Asp Thr Ser Ser Val Gly
1               5                   10

<210> SEQ ID NO 604
<211> LENGTH: 14
<212> TYPE: PRT
<213> ORGANISM: canis familiaris;

<400> SEQUENCE: 604

Thr Gly Ser Asp Ser Asn Val Gly Tyr Gly Asn Tyr Val Gly
1               5                   10

<210> SEQ ID NO 605
<211> LENGTH: 14
<212> TYPE: PRT
<213> ORGANISM: canis familiaris;

<400> SEQUENCE: 605

Thr Gly Ser Ser Ser Asn Val Gly Tyr Gly Asp Tyr Val Ala
1               5                   10

<210> SEQ ID NO 606
<211> LENGTH: 14
<212> TYPE: PRT
<213> ORGANISM: canis familiaris;

<400> SEQUENCE: 606

Thr Gly Ser Thr Ser Asn Leu Gly Tyr Ser Ser Ile Val Gly
1               5                   10

<210> SEQ ID NO 607
<211> LENGTH: 14
<212> TYPE: PRT
<213> ORGANISM: canis familiaris;

<400> SEQUENCE: 607

Thr Gly Ser Thr Asn Asp Ile Gly Ser Glu Asn Tyr Val His
1               5                   10

<210> SEQ ID NO 608
<211> LENGTH: 14
<212> TYPE: PRT
<213> ORGANISM: canis familiaris;

<400> SEQUENCE: 608

Thr Gly Ser Gly Ser Asn Val Gly Tyr Gly Asn Tyr Val Gly
1               5                   10

<210> SEQ ID NO 609
<211> LENGTH: 14
<212> TYPE: PRT
<213> ORGANISM: canis familiaris;

<400> SEQUENCE: 609

Thr Gly Thr Ser Ser Asn Val Gly Phe Gly Asp Tyr Val Gly
1               5                   10

<210> SEQ ID NO 610
<211> LENGTH: 14
<212> TYPE: PRT
<213> ORGANISM: canis familiaris;

<400> SEQUENCE: 610

Thr Gly Arg Ser Ser Asn Ile Gly Gly Gly Asn Tyr Val Gly
1               5                   10

<210> SEQ ID NO 611
<211> LENGTH: 7
<212> TYPE: PRT
<213> ORGANISM: canis familiaris;
<220> FEATURE:
<221> NAME/KEY: unsure
<222> LOCATION: (1)..(1)
<223> OTHER INFORMATION: X is N, R, G, T, S, or H
<220> FEATURE:
<221> NAME/KEY: unsure
<222> LOCATION: (2)..(2)
<223> OTHER INFORMATION: X is T or A
<220> FEATURE:
<221> NAME/KEY: unsure
<222> LOCATION: (3)..(3)
<223> OTHER INFORMATION: X is N, S, Y, G, or D
<220> FEATURE:
<221> NAME/KEY: unsure
<222> LOCATION: (4)..(4)
<223> OTHER INFORMATION: X is S, R, N, or T
<220> FEATURE:
<221> NAME/KEY: unsure
<222> LOCATION: (6)..(6)
<223> OTHER INFORMATION: X is P or L
<220> FEATURE:
<221> NAME/KEY: unsure
<222> LOCATION: (7)..(7)
<223> OTHER INFORMATION: X is S or L

<400> SEQUENCE: 611

Xaa Xaa Xaa Xaa Arg Xaa Xaa
1               5

<210> SEQ ID NO 612
<211> LENGTH: 7
<212> TYPE: PRT
<213> ORGANISM: canis familiaris;

<400> SEQUENCE: 612

Arg Thr Ser Ser Arg Pro Ser
1               5

<210> SEQ ID NO 613
<211> LENGTH: 7
<212> TYPE: PRT
<213> ORGANISM: canis familiaris;

<400> SEQUENCE: 613

Asn Thr Asn Ser Arg Pro Ser
1               5

<210> SEQ ID NO 614
<211> LENGTH: 7
<212> TYPE: PRT
<213> ORGANISM: canis familiaris;

<400> SEQUENCE: 614

Gly Ala Asn Ser Arg Pro Ser
1               5

<210> SEQ ID NO 615
<211> LENGTH: 7
<212> TYPE: PRT
<213> ORGANISM: canis familiaris;

<400> SEQUENCE: 615

Asn Thr Gly Ser Arg Pro Ser
1               5

<210> SEQ ID NO 616
<211> LENGTH: 7
<212> TYPE: PRT
<213> ORGANISM: canis familiaris;

<400> SEQUENCE: 616

Asn Thr Tyr Asn Arg Leu Ser
1               5

<210> SEQ ID NO 617
<211> LENGTH: 7
<212> TYPE: PRT
<213> ORGANISM: canis familiaris;

<400> SEQUENCE: 617

Asn Thr Asn Thr Arg Pro Leu
1               5

<210> SEQ ID NO 618
<211> LENGTH: 7
<212> TYPE: PRT
<213> ORGANISM: canis familiaris;

<400> SEQUENCE: 618

Arg Thr Asn Arg Arg Pro Ser
1               5

<210> SEQ ID NO 619
<211> LENGTH: 7
<212> TYPE: PRT
<213> ORGANISM: canis familiaris;

<400> SEQUENCE: 619

Arg Thr Asp Ser Arg Pro Ser
1               5

<210> SEQ ID NO 620
<211> LENGTH: 7
<212> TYPE: PRT
<213> ORGANISM: canis familiaris;

<400> SEQUENCE: 620

Thr Thr Ser Ser Arg Pro Ser
1               5

<210> SEQ ID NO 621
<211> LENGTH: 7
<212> TYPE: PRT
<213> ORGANISM: canis familiaris;

<400> SEQUENCE: 621

Ser Thr Ser Ser Arg Pro Ser
1               5

<210> SEQ ID NO 622
<211> LENGTH: 7
<212> TYPE: PRT
<213> ORGANISM: canis familiaris;

<400> SEQUENCE: 622

His Thr Ser Ser Arg Pro Ser

```
<210> SEQ ID NO 623
<211> LENGTH: 7
<212> TYPE: PRT
<213> ORGANISM: canis familiaris;
<220> FEATURE:
<221> NAME/KEY: unsure
<222> LOCATION: (1)..(1)
<223> OTHER INFORMATION: X is G, D, S, R, A, T, N, or absent
<220> FEATURE:
<221> NAME/KEY: unsure
<222> LOCATION: (2)..(2)
<223> OTHER INFORMATION: X is T, D, H, N, R, I, S, F, or K
<220> FEATURE:
<221> NAME/KEY: unsure
<222> LOCATION: (3)..(3)
<223> OTHER INFORMATION: X is T, F, H, Y, K, D, S, R, E, or V
<220> FEATURE:
<221> NAME/KEY: unsure
<222> LOCATION: (4)..(4)
<223> OTHER INFORMATION: X is N, S, H, D, Y, K, R, F, V, or E
<220> FEATURE:
<221> NAME/KEY: unsure
<222> LOCATION: (6)..(6)
<223> OTHER INFORMATION: X is P, L, or A
<220> FEATURE:
<221> NAME/KEY: unsure
<222> LOCATION: (7)..(7)
<223> OTHER INFORMATION: X is S orP

<400> SEQUENCE: 623

Xaa Xaa Xaa Xaa Arg Xaa Xaa
1               5

<210> SEQ ID NO 624
<211> LENGTH: 7
<212> TYPE: PRT
<213> ORGANISM: canis familiaris;

<400> SEQUENCE: 624

Gly Asp Ile Asn Arg Pro Ser
1               5

<210> SEQ ID NO 625
<211> LENGTH: 7
<212> TYPE: PRT
<213> ORGANISM: canis familiaris;

<400> SEQUENCE: 625

Gly His Asn His Arg Pro Ser
1               5

<210> SEQ ID NO 626
<211> LENGTH: 7
<212> TYPE: PRT
<213> ORGANISM: canis familiaris;

<400> SEQUENCE: 626

Gly Asn Asn Asn Arg Pro Ser
1               5

<210> SEQ ID NO 627
<211> LENGTH: 7
<212> TYPE: PRT
<213> ORGANISM: canis familiaris;

<400> SEQUENCE: 627

Ser Asp Gly His Arg Pro Ser
```

<210> SEQ ID NO 628
<211> LENGTH: 7
<212> TYPE: PRT
<213> ORGANISM: canis familiaris;

<400> SEQUENCE: 628

Asp Thr Tyr Ser Arg Leu Ser
1               5

<210> SEQ ID NO 629
<211> LENGTH: 7
<212> TYPE: PRT
<213> ORGANISM: canis familiaris;

<400> SEQUENCE: 629

Ser Arg Ser Asn Arg Pro Ser
1               5

<210> SEQ ID NO 630
<211> LENGTH: 7
<212> TYPE: PRT
<213> ORGANISM: canis familiaris;

<400> SEQUENCE: 630

Gly Asn Ser Asn Arg Pro Ser
1               5

<210> SEQ ID NO 631
<211> LENGTH: 7
<212> TYPE: PRT
<213> ORGANISM: canis familiaris;

<400> SEQUENCE: 631

Ser Ile Asp Asn Arg Pro Ser
1               5

<210> SEQ ID NO 632
<211> LENGTH: 7
<212> TYPE: PRT
<213> ORGANISM: canis familiaris;

<400> SEQUENCE: 632

Gly Asn Gly Asn Arg Pro Ser
1               5

<210> SEQ ID NO 633
<211> LENGTH: 7
<212> TYPE: PRT
<213> ORGANISM: canis familiaris;

<400> SEQUENCE: 633

Ser Ser Ser Asn Arg Pro Ser
1               5

<210> SEQ ID NO 634
<211> LENGTH: 7
<212> TYPE: PRT
<213> ORGANISM: canis familiaris;

<400> SEQUENCE: 634

Ser Ser Thr Asp Arg Pro Ser
1               5

```
<210> SEQ ID NO 635
<211> LENGTH: 7
<212> TYPE: PRT
<213> ORGANISM: canis familiaris;

<400> SEQUENCE: 635

Gly Asp Ser Asn Arg Pro Ser
1               5

<210> SEQ ID NO 636
<211> LENGTH: 7
<212> TYPE: PRT
<213> ORGANISM: canis familiaris;

<400> SEQUENCE: 636

Ser Asp Gly Asp Arg Pro Ser
1               5

<210> SEQ ID NO 637
<211> LENGTH: 7
<212> TYPE: PRT
<213> ORGANISM: canis familiaris;

<400> SEQUENCE: 637

Gly Thr Ile Tyr Arg Pro Ser
1               5

<210> SEQ ID NO 638
<211> LENGTH: 7
<212> TYPE: PRT
<213> ORGANISM: canis familiaris;

<400> SEQUENCE: 638

Ser Thr Ser Tyr Arg Pro Ser
1               5

<210> SEQ ID NO 639
<211> LENGTH: 7
<212> TYPE: PRT
<213> ORGANISM: canis familiaris;

<400> SEQUENCE: 639

Asp Asp Ser Ser Arg Pro Ser
1               5

<210> SEQ ID NO 640
<211> LENGTH: 7
<212> TYPE: PRT
<213> ORGANISM: canis familiaris;

<400> SEQUENCE: 640

Asp Thr Arg Ser Arg Pro Ser
1               5

<210> SEQ ID NO 641
<211> LENGTH: 7
<212> TYPE: PRT
<213> ORGANISM: canis familiaris;

<400> SEQUENCE: 641

Ser Asp Gly Ser Arg Pro Ser
1               5

<210> SEQ ID NO 642
```

<211> LENGTH: 7
<212> TYPE: PRT
<213> ORGANISM: canis familiaris;

<400> SEQUENCE: 642

Ser Ser Thr Asn Arg Pro Ser
1               5

<210> SEQ ID NO 643
<211> LENGTH: 7
<212> TYPE: PRT
<213> ORGANISM: canis familiaris;

<400> SEQUENCE: 643

Ser Asn Thr Lys Arg Pro Ser
1               5

<210> SEQ ID NO 644
<211> LENGTH: 7
<212> TYPE: PRT
<213> ORGANISM: canis familiaris;

<400> SEQUENCE: 644

Ala Asp Asn Tyr Arg Ala Ser
1               5

<210> SEQ ID NO 645
<211> LENGTH: 7
<212> TYPE: PRT
<213> ORGANISM: canis familiaris;

<400> SEQUENCE: 645

Gly Thr Ala Asn Arg Pro Ser
1               5

<210> SEQ ID NO 646
<211> LENGTH: 7
<212> TYPE: PRT
<213> ORGANISM: canis familiaris;

<400> SEQUENCE: 646

Gly Lys Asn Asn Arg Pro Ser
1               5

<210> SEQ ID NO 647
<211> LENGTH: 7
<212> TYPE: PRT
<213> ORGANISM: canis familiaris;

<400> SEQUENCE: 647

Ser Thr Asn Ser Arg Pro Ser
1               5

<210> SEQ ID NO 648
<211> LENGTH: 7
<212> TYPE: PRT
<213> ORGANISM: canis familiaris;

<400> SEQUENCE: 648

Gly Thr Thr Asn Arg Pro Ser
1               5

<210> SEQ ID NO 649
<211> LENGTH: 7
<212> TYPE: PRT

<213> ORGANISM: canis familiaris;

<400> SEQUENCE: 649

Gly Asp Asn His Arg Pro Ser
1               5

<210> SEQ ID NO 650
<211> LENGTH: 7
<212> TYPE: PRT
<213> ORGANISM: canis familiaris;

<400> SEQUENCE: 650

Thr Phe Gly Asp Arg Pro Ser
1               5

<210> SEQ ID NO 651
<211> LENGTH: 7
<212> TYPE: PRT
<213> ORGANISM: canis familiaris;

<400> SEQUENCE: 651

Ala Asp Asp His Arg Pro Ser
1               5

<210> SEQ ID NO 652
<211> LENGTH: 7
<212> TYPE: PRT
<213> ORGANISM: canis familiaris;

<400> SEQUENCE: 652

Ser Thr Thr Val Arg Pro Ser
1               5

<210> SEQ ID NO 653
<211> LENGTH: 7
<212> TYPE: PRT
<213> ORGANISM: canis familiaris;

<400> SEQUENCE: 653

Gly Asp Ser Ser Arg Pro Ser
1               5

<210> SEQ ID NO 654
<211> LENGTH: 7
<212> TYPE: PRT
<213> ORGANISM: canis familiaris;

<400> SEQUENCE: 654

Ser Thr Ser Asn Arg Pro Pro
1               5

<210> SEQ ID NO 655
<211> LENGTH: 7
<212> TYPE: PRT
<213> ORGANISM: canis familiaris;

<400> SEQUENCE: 655

Asn Ser Arg Glu Arg Pro Ser
1               5

<210> SEQ ID NO 656
<211> LENGTH: 7
<212> TYPE: PRT
<213> ORGANISM: canis familiaris;

```
<400> SEQUENCE: 656

Gly Asn Asn Tyr Arg Pro Ser
1               5

<210> SEQ ID NO 657
<211> LENGTH: 7
<212> TYPE: PRT
<213> ORGANISM: canis familiaris;

<400> SEQUENCE: 657

Ser Ile Ser Ser Arg Pro Ser
1               5

<210> SEQ ID NO 658
<211> LENGTH: 7
<212> TYPE: PRT
<213> ORGANISM: canis familiaris;

<400> SEQUENCE: 658

Arg Ser Glu Arg Arg Pro Ser
1               5

<210> SEQ ID NO 659
<211> LENGTH: 7
<212> TYPE: PRT
<213> ORGANISM: canis familiaris;

<400> SEQUENCE: 659

Ser Thr Asp Ser Arg Pro Ser
1               5

<210> SEQ ID NO 660
<211> LENGTH: 7
<212> TYPE: PRT
<213> ORGANISM: canis familiaris;

<400> SEQUENCE: 660

Asp Thr Ser Arg Arg Pro Ser
1               5

<210> SEQ ID NO 661
<211> LENGTH: 7
<212> TYPE: PRT
<213> ORGANISM: canis familiaris;

<400> SEQUENCE: 661

Asp Asn Gly Lys Arg Pro Ser
1               5

<210> SEQ ID NO 662
<211> LENGTH: 7
<212> TYPE: PRT
<213> ORGANISM: canis familiaris;

<400> SEQUENCE: 662

Gly Asp Asn Asn Arg Pro Ser
1               5

<210> SEQ ID NO 663
<211> LENGTH: 7
<212> TYPE: PRT
<213> ORGANISM: canis familiaris;

<400> SEQUENCE: 663
```

```
Gly Asn Ser Lys Arg Pro Ser
1               5
```

<210> SEQ ID NO 664
<211> LENGTH: 7
<212> TYPE: PRT
<213> ORGANISM: canis familiaris;

<400> SEQUENCE: 664

```
Asn Asp Gly His Arg Pro Ser
1               5
```

<210> SEQ ID NO 665
<211> LENGTH: 7
<212> TYPE: PRT
<213> ORGANISM: canis familiaris;

<400> SEQUENCE: 665

```
Gly Asp Ser Asp Arg Pro Ser
1               5
```

<210> SEQ ID NO 666
<211> LENGTH: 7
<212> TYPE: PRT
<213> ORGANISM: canis familiaris;

<400> SEQUENCE: 666

```
Ser Thr Asp Arg Arg Pro Ser
1               5
```

<210> SEQ ID NO 667
<211> LENGTH: 7
<212> TYPE: PRT
<213> ORGANISM: canis familiaris;

<400> SEQUENCE: 667

```
Gly Asn Ser Asp Arg Pro Ser
1               5
```

<210> SEQ ID NO 668
<211> LENGTH: 7
<212> TYPE: PRT
<213> ORGANISM: canis familiaris;

<400> SEQUENCE: 668

```
Thr Thr Asn Ser Arg Pro Ser
1               5
```

<210> SEQ ID NO 669
<211> LENGTH: 7
<212> TYPE: PRT
<213> ORGANISM: canis familiaris;

<400> SEQUENCE: 669

```
Thr Ser Thr Asn Arg Pro Ser
1               5
```

<210> SEQ ID NO 670
<211> LENGTH: 7
<212> TYPE: PRT
<213> ORGANISM: canis familiaris;

<400> SEQUENCE: 670

```
Ser Thr Tyr Ser Arg Pro Ser
1               5
```

```
<210> SEQ ID NO 671
<211> LENGTH: 7
<212> TYPE: PRT
<213> ORGANISM: canis familiaris;

<400> SEQUENCE: 671

Ser Asn Gly Ser Arg Pro Ser
1               5

<210> SEQ ID NO 672
<211> LENGTH: 6
<212> TYPE: PRT
<213> ORGANISM: canis familiaris;

<400> SEQUENCE: 672

Ser Ser Asn Arg Pro Ser
1               5

<210> SEQ ID NO 673
<211> LENGTH: 7
<212> TYPE: PRT
<213> ORGANISM: canis familiaris;

<400> SEQUENCE: 673

Asp Thr Thr Phe Arg Pro Ser
1               5

<210> SEQ ID NO 674
<211> LENGTH: 7
<212> TYPE: PRT
<213> ORGANISM: canis familiaris;
<220> FEATURE:
<221> NAME/KEY: unsure
<222> LOCATION: (1)..(1)
<223> OTHER INFORMATION: X is D, G, R, H, Y, A, or F
<220> FEATURE:
<221> NAME/KEY: unsure
<222> LOCATION: (2)..(2)
<223> OTHER INFORMATION: X is S, T, N, D, H, or K
<220> FEATURE:
<221> NAME/KEY: unsure
<222> LOCATION: (3)..(3)
<223> OTHER INFORMATION: X is S, G, N, D, R, or T
<220> FEATURE:
<221> NAME/KEY: unsure
<222> LOCATION: (4)..(4)
<223> OTHER INFORMATION: X is S, R, N, D, A, F, K, Y, or V
<220> FEATURE:
<221> NAME/KEY: unsure
<222> LOCATION: (6)..(6)
<223> OTHER INFORMATION: X is P, A, or E
<220> FEATURE:
<221> NAME/KEY: unsure
<222> LOCATION: (7)..(7)
<223> OTHER INFORMATION: X is S or A

<400> SEQUENCE: 674

Xaa Xaa Xaa Xaa Arg Xaa Xaa
1               5

<210> SEQ ID NO 675
<211> LENGTH: 7
<212> TYPE: PRT
<213> ORGANISM: canis familiaris;

<400> SEQUENCE: 675

Arg Thr Gly Asn Arg Pro Ser
1               5
```

<210> SEQ ID NO 676
<211> LENGTH: 7
<212> TYPE: PRT
<213> ORGANISM: canis familiaris;

<400> SEQUENCE: 676

His Ser Ser Asp Arg Pro Ser
1               5

<210> SEQ ID NO 677
<211> LENGTH: 7
<212> TYPE: PRT
<213> ORGANISM: canis familiaris;

<400> SEQUENCE: 677

Asp Ser Ser Ser Arg Pro Ser
1               5

<210> SEQ ID NO 678
<211> LENGTH: 7
<212> TYPE: PRT
<213> ORGANISM: canis familiaris;

<400> SEQUENCE: 678

Tyr Thr Asn Asn Arg Pro Ser
1               5

<210> SEQ ID NO 679
<211> LENGTH: 7
<212> TYPE: PRT
<213> ORGANISM: canis familiaris;

<400> SEQUENCE: 679

Asp Thr Ser Lys Arg Pro Ser
1               5

<210> SEQ ID NO 680
<211> LENGTH: 7
<212> TYPE: PRT
<213> ORGANISM: canis familiaris;

<400> SEQUENCE: 680

Asp Ser Ser Arg Arg Pro Ser
1               5

<210> SEQ ID NO 681
<211> LENGTH: 7
<212> TYPE: PRT
<213> ORGANISM: canis familiaris;

<400> SEQUENCE: 681

Tyr Asp Gly Ser Arg Pro Ser
1               5

<210> SEQ ID NO 682
<211> LENGTH: 7
<212> TYPE: PRT
<213> ORGANISM: canis familiaris;

<400> SEQUENCE: 682

Ala Asn Asp Ala Arg Pro Ser
1               5

```
<210> SEQ ID NO 683
<211> LENGTH: 7
<212> TYPE: PRT
<213> ORGANISM: canis familiaris;

<400> SEQUENCE: 683

Gly His Gly Phe Arg Pro Ser
1               5

<210> SEQ ID NO 684
<211> LENGTH: 7
<212> TYPE: PRT
<213> ORGANISM: canis familiaris;

<400> SEQUENCE: 684

Asp Thr Arg Arg Arg Pro Ser
1               5

<210> SEQ ID NO 685
<211> LENGTH: 7
<212> TYPE: PRT
<213> ORGANISM: canis familiaris;

<400> SEQUENCE: 685

Ala Lys Ser Asn Arg Pro Ser
1               5

<210> SEQ ID NO 686
<211> LENGTH: 7
<212> TYPE: PRT
<213> ORGANISM: canis familiaris;

<400> SEQUENCE: 686

Gly Ser Ser Tyr Arg Pro Ser
1               5

<210> SEQ ID NO 687
<211> LENGTH: 7
<212> TYPE: PRT
<213> ORGANISM: canis familiaris;
<220> FEATURE:
<221> NAME/KEY: UNSURE
<222> LOCATION: (1)..(1)
<223> OTHER INFORMATION: X is D, G, R, H, Y, A, or F
<220> FEATURE:
<221> NAME/KEY: UNSURE
<222> LOCATION: (3)..(3)
<223> OTHER INFORMATION: X is S, G, N, D, R, or T
<220> FEATURE:
<221> NAME/KEY: UNSURE
<222> LOCATION: (5)..(5)
<223> OTHER INFORMATION: X is R

<400> SEQUENCE: 687

Xaa Ser Xaa Ser Xaa Pro Ser
1               5

<210> SEQ ID NO 688
<211> LENGTH: 7
<212> TYPE: PRT
<213> ORGANISM: canis familiaris;

<400> SEQUENCE: 688

Tyr Ser Ser Ser Arg Pro Ser
1               5

<210> SEQ ID NO 689
```

```
<211> LENGTH: 7
<212> TYPE: PRT
<213> ORGANISM: canis familiaris;

<400> SEQUENCE: 689

Phe Ile Gly Ser Arg Pro Ser
1               5

<210> SEQ ID NO 690
<211> LENGTH: 7
<212> TYPE: PRT
<213> ORGANISM: canis familiaris;

<400> SEQUENCE: 690

Arg Ser Ser Asn Arg Ala Ser
1               5

<210> SEQ ID NO 691
<211> LENGTH: 7
<212> TYPE: PRT
<213> ORGANISM: canis familiaris;

<400> SEQUENCE: 691

Tyr Asn Thr Gly Arg Pro Ser
1               5

<210> SEQ ID NO 692
<211> LENGTH: 7
<212> TYPE: PRT
<213> ORGANISM: canis familiaris;

<400> SEQUENCE: 692

His Ser Ser Ser Arg Pro Ser
1               5

<210> SEQ ID NO 693
<211> LENGTH: 7
<212> TYPE: PRT
<213> ORGANISM: canis familiaris;

<400> SEQUENCE: 693

Tyr Asp Ser Ser Arg Pro Ser
1               5

<210> SEQ ID NO 694
<211> LENGTH: 7
<212> TYPE: PRT
<213> ORGANISM: canis familiaris;

<400> SEQUENCE: 694

Gly Asp Asp Asn Arg Glu Ser
1               5

<210> SEQ ID NO 695
<211> LENGTH: 7
<212> TYPE: PRT
<213> ORGANISM: canis familiaris;

<400> SEQUENCE: 695

Ala Thr Ser Ser Arg Pro Ser
1               5

<210> SEQ ID NO 696
<211> LENGTH: 7
<212> TYPE: PRT
```

```
<213> ORGANISM: canis familiaris;

<400> SEQUENCE: 696

Asp Thr Ser Ser Arg Pro Ser
1               5

<210> SEQ ID NO 697
<211> LENGTH: 7
<212> TYPE: PRT
<213> ORGANISM: canis familiaris;

<400> SEQUENCE: 697

Asp His Asn Val Arg Pro Ala
1               5

<210> SEQ ID NO 698
<211> LENGTH: 7
<212> TYPE: PRT
<213> ORGANISM: canis familiaris;

<400> SEQUENCE: 698

Gly Asn Asn Arg Arg Pro Ser
1               5

<210> SEQ ID NO 699
<211> LENGTH: 12
<212> TYPE: PRT
<213> ORGANISM: canis familiaris;
<220> FEATURE:
<221> NAME/KEY: unsure
<222> LOCATION: (1)..(1)
<223> OTHER INFORMATION: X is S or A
<220> FEATURE:
<221> NAME/KEY: unsure
<222> LOCATION: (2)..(2)
<223> OTHER INFORMATION: X is L, F, or V
<220> FEATURE:
<221> NAME/KEY: unsure
<222> LOCATION: (3)..(3)
<223> OTHER INFORMATION: X is G or absent
<220> FEATURE:
<221> NAME/KEY: unsure
<222> LOCATION: (4)..(4)
<223> OTHER INFORMATION: X is Y, F, L, or R
<220> FEATURE:
<221> NAME/KEY: unsure
<222> LOCATION: (5)..(5)
<223> OTHER INFORMATION: X is T, S, or M
<220> FEATURE:
<221> NAME/KEY: unsure
<222> LOCATION: (6)..(6)
<223> OTHER INFORMATION: X is G, D, S, or V
<220> FEATURE:
<221> NAME/KEY: unsure
<222> LOCATION: (7)..(7)
<223> OTHER INFORMATION: X is S, G, D, Y, T, R, or I
<220> FEATURE:
<221> NAME/KEY: unsure
<222> LOCATION: (8)..(8)
<223> OTHER INFORMATION: X is Y, Q, V, H, D, P, or S
<220> FEATURE:
<221> NAME/KEY: unsure
<222> LOCATION: (9)..(9)
<223> OTHER INFORMATION: X is S, N, or absent
<220> FEATURE:
<221> NAME/KEY: unsure
<222> LOCATION: (10)..(10)
<223> OTHER INFORMATION: X is T, S, V, I, Y, or absent
<220> FEATURE:
<221> NAME/KEY: unsure
<222> LOCATION: (11)..(11)
<223> OTHER INFORMATION: X is A, D, V, N, P, Y, G, or absent
<220> FEATURE:
```

<221> NAME/KEY: unsure
<222> LOCATION: (12)..(12)
<223> OTHER INFORMATION: X is V, M, L, or absent

<400> SEQUENCE: 699

Xaa Xaa Xaa Xaa Xaa Xaa Xaa Xaa Xaa Xaa Xaa Xaa
1               5                   10

<210> SEQ ID NO 700
<211> LENGTH: 10
<212> TYPE: PRT
<213> ORGANISM: canis familiaris;

<400> SEQUENCE: 700

Ser Val Tyr Met Gly Thr Tyr Thr Val Val
1               5                   10

<210> SEQ ID NO 701
<211> LENGTH: 10
<212> TYPE: PRT
<213> ORGANISM: canis familiaris;

<400> SEQUENCE: 701

Ser Leu Arg Thr Gly Tyr Gln Asn Thr Met
1               5                   10

<210> SEQ ID NO 702
<211> LENGTH: 10
<212> TYPE: PRT
<213> ORGANISM: canis familiaris;

<400> SEQUENCE: 702

Ser Leu Tyr Met Gly Ser Tyr Thr Asp Met
1               5                   10

<210> SEQ ID NO 703
<211> LENGTH: 10
<212> TYPE: PRT
<213> ORGANISM: canis familiaris;

<400> SEQUENCE: 703

Ser Leu Tyr Met Gly Gly Tyr Ser Asp Val
1               5                   10

<210> SEQ ID NO 704
<211> LENGTH: 10
<212> TYPE: PRT
<213> ORGANISM: canis familiaris;

<400> SEQUENCE: 704

Ser Leu Tyr Thr Gly Ser Tyr Thr Ala Val
1               5                   10

<210> SEQ ID NO 705
<211> LENGTH: 10
<212> TYPE: PRT
<213> ORGANISM: canis familiaris;

<400> SEQUENCE: 705

Ser Phe Phe Thr Asp Ile Val Val Asn Val
1               5                   10

<210> SEQ ID NO 706
<211> LENGTH: 10
<212> TYPE: PRT

<213> ORGANISM: canis familiaris;

<400> SEQUENCE: 706

Ser Val Tyr Thr Asp Asp His Thr Pro Val
1               5                   10

<210> SEQ ID NO 707
<211> LENGTH: 10
<212> TYPE: PRT
<213> ORGANISM: canis familiaris;

<400> SEQUENCE: 707

Ser Phe Tyr Thr Gly Asp Tyr Thr Ala Val
1               5                   10

<210> SEQ ID NO 708
<211> LENGTH: 10
<212> TYPE: PRT
<213> ORGANISM: canis familiaris;

<400> SEQUENCE: 708

Ser Leu Tyr Met Val Gly Tyr Thr Ala Val
1               5                   10

<210> SEQ ID NO 709
<211> LENGTH: 11
<212> TYPE: PRT
<213> ORGANISM: canis familiaris;

<400> SEQUENCE: 709

Ala Leu Gly Phe Ser Gly Gly Asp Tyr Val Val
1               5                   10

<210> SEQ ID NO 710
<211> LENGTH: 10
<212> TYPE: PRT
<213> ORGANISM: canis familiaris;

<400> SEQUENCE: 710

Ser Leu Tyr Met Gly Ser Tyr Thr Gly Leu
1               5                   10

<210> SEQ ID NO 711
<211> LENGTH: 11
<212> TYPE: PRT
<213> ORGANISM: canis familiaris;

<400> SEQUENCE: 711

Ala Leu Gly Phe Ser Ser Ser Ser Ser Tyr Val
1               5                   10

<210> SEQ ID NO 712
<211> LENGTH: 10
<212> TYPE: PRT
<213> ORGANISM: canis familiaris;

<400> SEQUENCE: 712

Ser Leu Tyr Met Asp Ile Tyr Thr Gly Val
1               5                   10

<210> SEQ ID NO 713
<211> LENGTH: 11
<212> TYPE: PRT
<213> ORGANISM: canis familiaris;

-continued

```
<400> SEQUENCE: 713

Ala Leu Gly Leu Ser Gly Ile Ser Ser Ile Val
1               5                   10

<210> SEQ ID NO 714
<211> LENGTH: 8
<212> TYPE: PRT
<213> ORGANISM: canis familiaris;

<400> SEQUENCE: 714

Ser Leu Tyr Thr Gly Arg Pro Val
1               5

<210> SEQ ID NO 715
<211> LENGTH: 10
<212> TYPE: PRT
<213> ORGANISM: canis familiaris;

<400> SEQUENCE: 715

Ser Leu Tyr Thr Gly Ser Ser Thr Asp Val
1               5                   10

<210> SEQ ID NO 716
<211> LENGTH: 7
<212> TYPE: PRT
<213> ORGANISM: canis familiaris;

<400> SEQUENCE: 716

Ser Phe Tyr Thr Ser Ser Tyr
1               5

<210> SEQ ID NO 717
<211> LENGTH: 12
<212> TYPE: PRT
<213> ORGANISM: canis familiaris;
<220> FEATURE:
<221> NAME/KEY: unsure
<222> LOCATION: (1)..(1)
<223> OTHER INFORMATION: X is S, Q, or A
<220> FEATURE:
<221> NAME/KEY: unsure
<222> LOCATION: (2)..(2)
<223> OTHER INFORMATION: X is S, T, A, G, or absent
<220> FEATURE:
<221> NAME/KEY: unsure
<222> LOCATION: (3)..(3)
<223> OTHER INFORMATION: X is W, S, L, Y, F, V, or absent
<220> FEATURE:
<221> NAME/KEY: unsure
<222> LOCATION: (4)..(4)
<223> OTHER INFORMATION: X is D, Q, or absent
<220> FEATURE:
<221> NAME/KEY: unsure
<222> LOCATION: (5)..(5)
<223> OTHER INFORMATION: X is S, N, Y, P, A, D, T, E, R, H, I, or absent
<220> FEATURE:
<221> NAME/KEY: unsure
<222> LOCATION: (6)..(6)
<223> OTHER INFORMATION: X is S, N, R, T, G, A, D, Y, or absent
<220> FEATURE:
<221> NAME/KEY: unsure
<222> LOCATION: (7)..(7)
<223> OTHER INFORMATION: X is L, V, R, P, F, or absent
<220> FEATURE:
<221> NAME/KEY: unsure
<222> LOCATION: (8)..(8)
<223> OTHER INFORMATION: X is S, R, G, K, T, I, N, Q, P, A, or absent
<220> FEATURE:
<221> NAME/KEY: unsure
<222> LOCATION: (9)..(9)
<223> OTHER INFORMATION: X is G, T, S, V, A, K, D, L, I, E, Y, or absent
```

```
<220> FEATURE:
<221> NAME/KEY: unsure
<222> LOCATION: (10)..(10)
<223> OTHER INFORMATION: X is V, Y, T, P, S, G, L, Q, A, D, N, or absent
<220> FEATURE:
<221> NAME/KEY: unsure
<222> LOCATION: (11)..(11)
<223> OTHER INFORMATION: X is S, P, Y, A, D, I, T, or absent
<220> FEATURE:
<221> NAME/KEY: unsure
<222> LOCATION: (12)..(12)
<223> OTHER INFORMATION: X is V, I, L, or absent

<400> SEQUENCE: 717

Xaa Xaa Xaa Xaa Xaa Xaa Xaa Xaa Xaa Xaa Xaa Xaa
1               5                   10

<210> SEQ ID NO 718
<211> LENGTH: 11
<212> TYPE: PRT
<213> ORGANISM: canis familiaris;

<400> SEQUENCE: 718

Ser Ser Trp Asp Tyr Ser Leu Ser Ser Thr Leu
1               5                   10

<210> SEQ ID NO 719
<211> LENGTH: 11
<212> TYPE: PRT
<213> ORGANISM: canis familiaris;
<220> FEATURE:
<221> NAME/KEY: UNSURE
<222> LOCATION: (3)..(3)
<223> OTHER INFORMATION: X is W, S, L, Y, F, V, or absent
<220> FEATURE:
<221> NAME/KEY: UNSURE
<222> LOCATION: (5)..(5)
<223> OTHER INFORMATION: X is S, N, Y, P, A, D, T, E, R, H, I, or absent

<400> SEQUENCE: 719

Ser Ser Xaa Asp Xaa Ser Leu Ser Val Val Leu
1               5                   10

<210> SEQ ID NO 720
<211> LENGTH: 11
<212> TYPE: PRT
<213> ORGANISM: canis familiaris;

<400> SEQUENCE: 720

Ser Ser Trp Asp Ala Ser Arg Ser Val Thr Val
1               5                   10

<210> SEQ ID NO 721
<211> LENGTH: 10
<212> TYPE: PRT
<213> ORGANISM: canis familiaris;

<400> SEQUENCE: 721

Gln Ser Leu Asp Ser Asn Leu Gly Pro Val
1               5                   10

<210> SEQ ID NO 722
<211> LENGTH: 11
<212> TYPE: PRT
<213> ORGANISM: canis familiaris;

<400> SEQUENCE: 722

Ser Thr Trp Asp Asp Ser Leu Arg Ala Tyr Leu
```

-continued 1               5               10

<210> SEQ ID NO 723
<211> LENGTH: 11
<212> TYPE: PRT
<213> ORGANISM: canis familiaris;

<400> SEQUENCE: 723

Ser Thr Trp Asp Ser Ser Leu Lys Ala Pro Val
1               5               10

<210> SEQ ID NO 724
<211> LENGTH: 11
<212> TYPE: PRT
<213> ORGANISM: canis familiaris;

<400> SEQUENCE: 724

Ser Thr Trp Asp Asn Ser Leu Thr Val Pro Val
1               5               10

<210> SEQ ID NO 725
<211> LENGTH: 11
<212> TYPE: PRT
<213> ORGANISM: canis familiaris;

<400> SEQUENCE: 725

Ser Thr Tyr Asp Thr Arg Leu Gly Thr Ser Val
1               5               10

<210> SEQ ID NO 726
<211> LENGTH: 11
<212> TYPE: PRT
<213> ORGANISM: canis familiaris;

<400> SEQUENCE: 726

Ser Ser Trp Asp Asn Asn Leu Ile Lys Ile Leu
1               5               10

<210> SEQ ID NO 727
<211> LENGTH: 11
<212> TYPE: PRT
<213> ORGANISM: canis familiaris;

<400> SEQUENCE: 727

Ser Thr Tyr Asp Ser Thr Leu Asn Ala Val Val
1               5               10

<210> SEQ ID NO 728
<211> LENGTH: 11
<212> TYPE: PRT
<213> ORGANISM: canis familiaris;

<400> SEQUENCE: 728

Ser Ala Trp Asp Asn Ser Leu Lys Leu Pro Leu
1               5               10

<210> SEQ ID NO 729
<211> LENGTH: 11
<212> TYPE: PRT
<213> ORGANISM: canis familiaris;

<400> SEQUENCE: 729

Ser Ser Trp Asp Thr Gly Leu Ser Ala Leu Val
1               5               10

```
<210> SEQ ID NO 730
<211> LENGTH: 11
<212> TYPE: PRT
<213> ORGANISM: canis familiaris;

<400> SEQUENCE: 730

Gln Ser Val Asp Ser Thr Leu Gly Ala Ile Val
1               5                   10

<210> SEQ ID NO 731
<211> LENGTH: 11
<212> TYPE: PRT
<213> ORGANISM: canis familiaris;
<220> FEATURE:
<221> NAME/KEY: UNSURE
<222> LOCATION: (8)..(8)
<223> OTHER INFORMATION: X is S, R, G, K, T, I, N, Q, P, A, or absent

<400> SEQUENCE: 731

Ser Ser Trp Asp Asp Ser Leu Xaa Gly Ile Val
1               5                   10

<210> SEQ ID NO 732
<211> LENGTH: 11
<212> TYPE: PRT
<213> ORGANISM: canis familiaris;

<400> SEQUENCE: 732

Ser Thr Tyr Asp Ser Ser Leu Gly Gly Ser Val
1               5                   10

<210> SEQ ID NO 733
<211> LENGTH: 11
<212> TYPE: PRT
<213> ORGANISM: canis familiaris;

<400> SEQUENCE: 733

Ser Ala Tyr Asp Ser Thr Leu Thr Gly Thr Val
1               5                   10

<210> SEQ ID NO 734
<211> LENGTH: 11
<212> TYPE: PRT
<213> ORGANISM: canis familiaris;

<400> SEQUENCE: 734

Ser Thr Tyr Asp Ser Ser Leu Ser Gly Pro Leu
1               5                   10

<210> SEQ ID NO 735
<211> LENGTH: 12
<212> TYPE: PRT
<213> ORGANISM: canis familiaris;

<400> SEQUENCE: 735

Gln Ser Phe Asp Pro Thr Pro Asp His Tyr Val
1               5                   10

<210> SEQ ID NO 736
<211> LENGTH: 11
<212> TYPE: PRT
<213> ORGANISM: canis familiaris;

<400> SEQUENCE: 736

Ser Ala Trp Asp Ser Thr Leu Arg Ala Gly Val
```

-continued

```
<210> SEQ ID NO 737
<211> LENGTH: 11
<212> TYPE: PRT
<213> ORGANISM: canis familiaris;

<400> SEQUENCE: 737

Ser Thr Trp Asp Ser Ser Leu Lys Ala Leu Leu
1               5                   10

<210> SEQ ID NO 738
<211> LENGTH: 10
<212> TYPE: PRT
<213> ORGANISM: canis familiaris;

<400> SEQUENCE: 738

Gln Ser Phe Asp Thr Ala Leu Gly Thr Val
1               5                   10

<210> SEQ ID NO 739
<211> LENGTH: 11
<212> TYPE: PRT
<213> ORGANISM: canis familiaris;

<400> SEQUENCE: 739

Ser Ser Trp Asp Asp Gly Leu Arg Ala Leu Val
1               5                   10

<210> SEQ ID NO 740
<211> LENGTH: 11
<212> TYPE: PRT
<213> ORGANISM: canis familiaris;

<400> SEQUENCE: 740

Ser Ser Trp Asp Asp Ser Leu Lys Gly His Val
1               5                   10

<210> SEQ ID NO 741
<211> LENGTH: 11
<212> TYPE: PRT
<213> ORGANISM: canis familiaris;

<400> SEQUENCE: 741

Ser Thr Trp Asp Glu Asn Leu Ser Val Pro Val
1               5                   10

<210> SEQ ID NO 742
<211> LENGTH: 10
<212> TYPE: PRT
<213> ORGANISM: canis familiaris;

<400> SEQUENCE: 742

Ser Thr Trp Asp Asn Ser Val Thr Val Leu
1               5                   10

<210> SEQ ID NO 743
<211> LENGTH: 10
<212> TYPE: PRT
<213> ORGANISM: canis familiaris;

<400> SEQUENCE: 743

Ser Ser Trp Asp Asn Asp Phe Gly His Val
1               5                   10
```

```
<210> SEQ ID NO 744
<211> LENGTH: 11
<212> TYPE: PRT
<213> ORGANISM: canis familiaris;

<400> SEQUENCE: 744

Gln Ser Phe Asp Thr Thr Leu Gly Ala Tyr Val
1               5                   10

<210> SEQ ID NO 745
<211> LENGTH: 11
<212> TYPE: PRT
<213> ORGANISM: canis familiaris;

<400> SEQUENCE: 745

Ser Ser Trp Asp Arg Ser Leu Arg Gly Gln Val
1               5                   10

<210> SEQ ID NO 746
<211> LENGTH: 11
<212> TYPE: PRT
<213> ORGANISM: canis familiaris;

<400> SEQUENCE: 746

Ser Gly Tyr Asp Thr Thr Val Asn Gly Val Val
1               5                   10

<210> SEQ ID NO 747
<211> LENGTH: 10
<212> TYPE: PRT
<213> ORGANISM: canis familiaris;

<400> SEQUENCE: 747

Ser Ser Trp Asp Thr Ser Leu Arg Thr Ile
1               5                   10

<210> SEQ ID NO 748
<211> LENGTH: 10
<212> TYPE: PRT
<213> ORGANISM: canis familiaris;

<400> SEQUENCE: 748

Ser Ala Ser Asp Ser Ser Leu Ser Val Val
1               5                   10

<210> SEQ ID NO 749
<211> LENGTH: 13
<212> TYPE: PRT
<213> ORGANISM: canis familiaris;

<400> SEQUENCE: 749

Gln Ser Phe Asp Thr Thr Leu Gly Asp Gly Asp Val Leu
1               5                   10

<210> SEQ ID NO 750
<211> LENGTH: 11
<212> TYPE: PRT
<213> ORGANISM: canis familiaris;

<400> SEQUENCE: 750

Ser Ser Trp Asp Asp Ser Leu Arg Ile Ser Val
1               5                   10

<210> SEQ ID NO 751
```

```
<211> LENGTH: 11
<212> TYPE: PRT
<213> ORGANISM: canis familiaris;

<400> SEQUENCE: 751

Ser Ala Trp Asp Ser Ser Leu Lys Glu Ala Val
1               5                   10

<210> SEQ ID NO 752
<211> LENGTH: 10
<212> TYPE: PRT
<213> ORGANISM: canis familiaris;

<400> SEQUENCE: 752

Ser Thr Trp Asp Asp Ser Val Thr Val Leu
1               5                   10

<210> SEQ ID NO 753
<211> LENGTH: 11
<212> TYPE: PRT
<213> ORGANISM: canis familiaris;

<400> SEQUENCE: 753

Ser Ala His Asp Asn Ser Val Ser Gly Val Val
1               5                   10

<210> SEQ ID NO 754
<211> LENGTH: 11
<212> TYPE: PRT
<213> ORGANISM: canis familiaris;

<400> SEQUENCE: 754

Ser Ala Trp Asp Asp Ser Leu Thr Ala Tyr Val
1               5                   10

<210> SEQ ID NO 755
<211> LENGTH: 11
<212> TYPE: PRT
<213> ORGANISM: canis familiaris;

<400> SEQUENCE: 755

Ser Thr Tyr Asp Ile Thr Ile Thr Gly Gly Val
1               5                   10

<210> SEQ ID NO 756
<211> LENGTH: 10
<212> TYPE: PRT
<213> ORGANISM: canis familiaris;

<400> SEQUENCE: 756

Ser Ser Tyr Asp Ser Ser Phe Thr Ala Asp
1               5                   10

<210> SEQ ID NO 757
<211> LENGTH: 11
<212> TYPE: PRT
<213> ORGANISM: canis familiaris;

<400> SEQUENCE: 757

Ser Thr Trp Asp Ser Ser Leu Lys Ala Ile Val
1               5                   10

<210> SEQ ID NO 758
<211> LENGTH: 11
<212> TYPE: PRT
```

<213> ORGANISM: canis familiaris;

<400> SEQUENCE: 758

Ser Ser Trp Asp Asp Ser Leu Arg Gly His Val
1               5                   10

<210> SEQ ID NO 759
<211> LENGTH: 10
<212> TYPE: PRT
<213> ORGANISM: canis familiaris;

<400> SEQUENCE: 759

Ser Thr Trp Asp Asn Ser Leu Thr Tyr Val
1               5                   10

<210> SEQ ID NO 760
<211> LENGTH: 11
<212> TYPE: PRT
<213> ORGANISM: canis familiaris;

<400> SEQUENCE: 760

Gln Ser Phe Gln Thr Thr Leu Asn Ile Tyr Val
1               5                   10

<210> SEQ ID NO 761
<211> LENGTH: 11
<212> TYPE: PRT
<213> ORGANISM: canis familiaris;

<400> SEQUENCE: 761

Ser Thr Trp Asp Ala Ser Leu Arg Val Gly Val
1               5                   10

<210> SEQ ID NO 762
<211> LENGTH: 11
<212> TYPE: PRT
<213> ORGANISM: canis familiaris;

<400> SEQUENCE: 762

Ser Thr Trp Asp Ser Ser Leu Lys Ala Val Val
1               5                   10

<210> SEQ ID NO 763
<211> LENGTH: 11
<212> TYPE: PRT
<213> ORGANISM: canis familiaris;

<400> SEQUENCE: 763

Ser Thr Trp Asp Asp Ser Leu Ser Glu Pro Val
1               5                   10

<210> SEQ ID NO 764
<211> LENGTH: 11
<212> TYPE: PRT
<213> ORGANISM: canis familiaris;

<400> SEQUENCE: 764

Ser Thr Tyr Asp Thr Arg Leu Asn Asp Val Ile
1               5                   10

<210> SEQ ID NO 765
<211> LENGTH: 11
<212> TYPE: PRT
<213> ORGANISM: canis familiaris;

-continued

```
<400> SEQUENCE: 765

Ser Ala Trp Asp Asp Arg Leu Thr Glu Pro Val
1               5                   10

<210> SEQ ID NO 766
<211> LENGTH: 11
<212> TYPE: PRT
<213> ORGANISM: canis familiaris;

<400> SEQUENCE: 766

Gln Ser Val Asp His Thr Leu Ala Ala Ala Val
1               5                   10

<210> SEQ ID NO 767
<211> LENGTH: 11
<212> TYPE: PRT
<213> ORGANISM: canis familiaris;

<400> SEQUENCE: 767

Ala Ala Tyr Asp Ser Ser Leu Ser Ile Gly Val
1               5                   10

<210> SEQ ID NO 768
<211> LENGTH: 11
<212> TYPE: PRT
<213> ORGANISM: canis familiaris;

<400> SEQUENCE: 768

Ser Thr Trp Asp Asp Tyr Leu Gln Ile Tyr Val
1               5                   10

<210> SEQ ID NO 769
<211> LENGTH: 12
<212> TYPE: PRT
<213> ORGANISM: canis familiaris;

<400> SEQUENCE: 769

Gln Ser Leu Asp Ser Thr Arg Gly Tyr His Ile Val
1               5                   10

<210> SEQ ID NO 770
<211> LENGTH: 11
<212> TYPE: PRT
<213> ORGANISM: canis familiaris;

<400> SEQUENCE: 770

Ser Thr Trp Asp Asn Ser Leu Asn Thr Gly Val
1               5                   10

<210> SEQ ID NO 771
<211> LENGTH: 11
<212> TYPE: PRT
<213> ORGANISM: canis familiaris;

<400> SEQUENCE: 771

Ser Ala Tyr Asp Thr Ser Leu Ser Ser Asn Phe
1               5                   10

<210> SEQ ID NO 772
<211> LENGTH: 12
<212> TYPE: PRT
<213> ORGANISM: canis familiaris;

<400> SEQUENCE: 772
```

```
Ser Ser Trp Asp Ser Ser Leu Ser Gly Val Ser Val
1               5                   10
```

<210> SEQ ID NO 773
<211> LENGTH: 12
<212> TYPE: PRT
<213> ORGANISM: canis familiaris;
<220> FEATURE:
<221> NAME/KEY: unsure
<222> LOCATION: (1)..(1)
<223> OTHER INFORMATION: X is S, Q, or A
<220> FEATURE:
<221> NAME/KEY: unsure
<222> LOCATION: (2)..(2)
<223> OTHER INFORMATION: X is A, T, or V
<220> FEATURE:
<221> NAME/KEY: unsure
<222> LOCATION: (3)..(3)
<223> OTHER INFORMATION: X is Y, F, W, or G
<220> FEATURE:
<221> NAME/KEY: unsure
<222> LOCATION: (4)..(4)
<223> OTHER INFORMATION: X is D, H, E, or absent
<220> FEATURE:
<221> NAME/KEY: unsure
<222> LOCATION: (5)..(5)
<223> OTHER INFORMATION: X is S, D, N, R, Y, or T
<220> FEATURE:
<221> NAME/KEY: unsure
<222> LOCATION: (6)..(6)
<223> OTHER INFORMATION: X is S, T, N, or G
<220> FEATURE:
<221> NAME/KEY: unsure
<222> LOCATION: (7)..(7)
<223> OTHER INFORMATION: X is L, I, V, T, P, or absent
<220> FEATURE:
<221> NAME/KEY: unsure
<222> LOCATION: (8)..(8)
<223> OTHER INFORMATION: X is S, G, R, K, D, N, A, Q, H, or absent
<220> FEATURE:
<221> NAME/KEY: unsure
<222> LOCATION: (9)..(9)
<223> OTHER INFORMATION: X is G, T, S, H, A, V, or absent
<220> FEATURE:
<221> NAME/KEY: unsure
<222> LOCATION: (10)..(10)
<223> OTHER INFORMATION: X is G, I, V, R, P, L, Y, S, or absent
<220> FEATURE:
<221> NAME/KEY: unsure
<222> LOCATION: (11)..(11)
<223> OTHER INFORMATION: X is A or absent
<220> FEATURE:
<221> NAME/KEY: unsure
<222> LOCATION: (12)..(12)
<223> OTHER INFORMATION: X is V or L

<400> SEQUENCE: 773

```
Xaa Xaa Xaa Xaa Xaa Xaa Xaa Xaa Xaa Xaa Xaa Xaa
1               5                   10
```

<210> SEQ ID NO 774
<211> LENGTH: 11
<212> TYPE: PRT
<213> ORGANISM: canis familiaris;

<400> SEQUENCE: 774

```
Gln Ser Tyr Asp Asp Asn Leu Asp Gly Tyr Val
1               5                   10
```

<210> SEQ ID NO 775
<211> LENGTH: 10
<212> TYPE: PRT
<213> ORGANISM: canis familiaris;

<400> SEQUENCE: 775

Ser Ser Phe Asp Arg Ser Val Ser Ala Val
1               5                   10

<210> SEQ ID NO 776
<211> LENGTH: 10
<212> TYPE: PRT
<213> ORGANISM: canis familiaris;

<400> SEQUENCE: 776

Ser Ala Tyr Asp Thr Thr Leu Asn Ala Val
1               5                   10

<210> SEQ ID NO 777
<211> LENGTH: 11
<212> TYPE: PRT
<213> ORGANISM: canis familiaris;

<400> SEQUENCE: 777

Ser Ser Tyr Asp Ser Ser Leu Ser Gly Gly Val
1               5                   10

<210> SEQ ID NO 778
<211> LENGTH: 10
<212> TYPE: PRT
<213> ORGANISM: canis familiaris;

<400> SEQUENCE: 778

Ser Ala Tyr Ser Gly Thr Asp Thr Tyr Val
1               5                   10

<210> SEQ ID NO 779
<211> LENGTH: 11
<212> TYPE: PRT
<213> ORGANISM: canis familiaris;

<400> SEQUENCE: 779

Ser Ser Tyr His Ser Ser Pro His Gly Val Val
1               5                   10

<210> SEQ ID NO 780
<211> LENGTH: 10
<212> TYPE: PRT
<213> ORGANISM: canis familiaris;

<400> SEQUENCE: 780

Ser Ser Tyr Asp Ser Glu Val Arg Val Val
1               5                   10

<210> SEQ ID NO 781
<211> LENGTH: 10
<212> TYPE: PRT
<213> ORGANISM: canis familiaris;

<400> SEQUENCE: 781

Ser Ser Trp Asp Asn Ser Gln Gly Ser Val
1               5                   10

<210> SEQ ID NO 782
<211> LENGTH: 11
<212> TYPE: PRT
<213> ORGANISM: canis familiaris;

<400> SEQUENCE: 782

```
Gln Ser Tyr Asp Asp Asn Leu Ala Gly Leu Val
1               5                   10

<210> SEQ ID NO 783
<211> LENGTH: 10
<212> TYPE: PRT
<213> ORGANISM: canis familiaris;

<400> SEQUENCE: 783

Ser Thr Tyr Asp Asn Ser Leu Ser Val Val
1               5                   10

<210> SEQ ID NO 784
<211> LENGTH: 12
<212> TYPE: PRT
<213> ORGANISM: canis familiaris;

<400> SEQUENCE: 784

Ala Ser Tyr Asp Arg Thr Ile Gly Gly Gly Ala Val
1               5                   10

<210> SEQ ID NO 785
<211> LENGTH: 11
<212> TYPE: PRT
<213> ORGANISM: canis familiaris;

<400> SEQUENCE: 785

Ser Val Gly Asp Asp Ser Leu Lys Ala Pro Val
1               5                   10

<210> SEQ ID NO 786
<211> LENGTH: 11
<212> TYPE: PRT
<213> ORGANISM: canis familiaris;

<400> SEQUENCE: 786

Ser Ser Tyr Asp Ser Ser Leu Ser Gly Ile Val
1               5                   10

<210> SEQ ID NO 787
<211> LENGTH: 11
<212> TYPE: PRT
<213> ORGANISM: canis familiaris;

<400> SEQUENCE: 787

Ser Ser Tyr Asp Ser Ser Leu Asp Gly Ala Val
1               5                   10

<210> SEQ ID NO 788
<211> LENGTH: 11
<212> TYPE: PRT
<213> ORGANISM: canis familiaris;

<400> SEQUENCE: 788

Ser Ser Tyr Glu Ser Ser Leu Arg Gly Val Val
1               5                   10

<210> SEQ ID NO 789
<211> LENGTH: 11
<212> TYPE: PRT
<213> ORGANISM: canis familiaris;

<400> SEQUENCE: 789

Ser Ser Trp Asp Asn Ser Leu Lys Thr Arg Val
1               5                   10
```

<210> SEQ ID NO 790
<211> LENGTH: 11
<212> TYPE: PRT
<213> ORGANISM: canis familiaris;

<400> SEQUENCE: 790

Ser Ser Tyr Asp Ser Gly Leu Ser His Ile Val
1               5                   10

<210> SEQ ID NO 791
<211> LENGTH: 11
<212> TYPE: PRT
<213> ORGANISM: canis familiaris;

<400> SEQUENCE: 791

Ser Ala Tyr Asp Tyr Ser Leu Ser Ser Gly Val
1               5                   10

<210> SEQ ID NO 792
<211> LENGTH: 11
<212> TYPE: PRT
<213> ORGANISM: canis familiaris;

<400> SEQUENCE: 792

Ser Ser Tyr Asp Asn Ser Leu Ser Gly Gly Val
1               5                   10

<210> SEQ ID NO 793
<211> LENGTH: 11
<212> TYPE: PRT
<213> ORGANISM: canis familiaris;

<400> SEQUENCE: 793

Ser Ser Trp Asp Asn Ser Leu Lys Gly Ile Val
1               5                   10

<210> SEQ ID NO 794
<211> LENGTH: 11
<212> TYPE: PRT
<213> ORGANISM: canis familiaris;

<400> SEQUENCE: 794

Gln Ser Tyr Asp Asp Ser Leu Asn Thr Tyr Val
1               5                   10

<210> SEQ ID NO 795
<211> LENGTH: 11
<212> TYPE: PRT
<213> ORGANISM: canis familiaris;

<400> SEQUENCE: 795

Ser Ser Tyr Asp Thr Ser Leu Ser Gly Gly Val
1               5                   10

<210> SEQ ID NO 796
<211> LENGTH: 11
<212> TYPE: PRT
<213> ORGANISM: canis familiaris;

<400> SEQUENCE: 796

Ser Ser Tyr Asp Ser Ser Leu Ser Gly Ala Val
1               5                   10

```
<210> SEQ ID NO 797
<211> LENGTH: 10
<212> TYPE: PRT
<213> ORGANISM: canis familiaris;

<400> SEQUENCE: 797

Ser Ser Tyr Asp Ser Ser Leu Ser Ile Val
1               5                   10

<210> SEQ ID NO 798
<211> LENGTH: 11
<212> TYPE: PRT
<213> ORGANISM: canis familiaris;

<400> SEQUENCE: 798

Ser Ser Trp Asp Asp Ser Leu Arg Gly Ala Leu
1               5                   10

<210> SEQ ID NO 799
<211> LENGTH: 12
<212> TYPE: PRT
<213> ORGANISM: canis familiaris;

<400> SEQUENCE: 799

Ser Ala Tyr Asp Ser Ser Leu Ser Gly Gly Ala Val
1               5                   10

<210> SEQ ID NO 800
<211> LENGTH: 231
<212> TYPE: PRT
<213> ORGANISM: canis familiaris;

<400> SEQUENCE: 800

Glu Val Lys Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Asn
            20                  25                  30

Gly Met Ser Trp Val Arg Gln Asp Pro Gly Glu Gly Leu Gln Trp Val
        35                  40                  45

Ala Asp Ile Ser Ser Ser Gly Gln Thr Tyr Tyr Ala Asp Ala Val Lys
    50                  55                  60

Gly Arg Phe Ser Ile Ser Arg Asp Asn Ala Lys Asn Thr Leu Tyr Leu
65                  70                  75                  80

Gln Met Glu Asp Leu Arg Val Glu Asp Thr Ala Val Tyr Tyr Cys Ala
                85                  90                  95

Thr Glu Gly Asp Ile Glu Ile Pro Arg Tyr Phe Gly Gln Gly Thr Ile
            100                 105                 110

Val Thr Val Ser Ser Glu Val Gln Leu Val Glu Ser Gly Gly Asp Leu
        115                 120                 125

Val Lys Pro Gly Gly Ser Leu Arg Leu Ser Cys Val Ala Ser Gly Ile
    130                 135                 140

Thr Phe Ser Gly Tyr Asp Met Gln Trp Val Arg Gln Ala Pro Gly Lys
145                 150                 155                 160

Gly Leu Gln Lys Val Ala Tyr Phe Asn Asp Ala Leu Ser Ala Gln Gly
                165                 170                 175

Tyr Ala Asp Ala Val Lys Gly Arg Phe Thr Ile Ser Lys Asp Asn Ala
            180                 185                 190

Lys Asp Ser Leu Tyr Leu Gln Met Asn Ser Leu Arg Ala Glu Asp Thr
        195                 200                 205
```

Ala Val Tyr Tyr Cys Ala Pro Trp Gln Phe Glu Tyr Trp Gly Gln Gly
    210             215                 220

Thr Leu Val Thr Val Ser Ser
225             230

<210> SEQ ID NO 801
<211> LENGTH: 108
<212> TYPE: PRT
<213> ORGANISM: canis familiaris;

<400> SEQUENCE: 801

Asp Ile Val Met Thr Gln Thr Pro Leu Ser Leu Ser Val Ser Pro Gly
1               5                   10                  15

Glu Pro Ala Ser Ile Ser Cys Arg Ser Ser Gln Ser Asn Leu Asp Tyr
            20                  25                  30

Leu Asn Trp Tyr Leu Gln Lys Ala Gly Gln Ser Pro Arg Leu Leu Pro
        35                  40                  45

Glu Gln Asp Ser Gln Arg Ala Ser Gly Val Pro Asp Arg Phe Ser Gly
    50                  55                  60

Ser Gly Ser Gly Thr Asp Phe Thr Leu Arg Ile Gly Arg Val Glu Ala
65                  70                  75                  80

Glu Asp Ala Gly Ile Tyr Tyr Cys Met Gln Arg Ser Phe Tyr Pro Tyr
                85                  90                  95

Thr Phe Gly Gln Gly Thr Arg Leu Glu Val Arg Arg
            100                 105

<210> SEQ ID NO 802
<211> LENGTH: 118
<212> TYPE: PRT
<213> ORGANISM: canis familiaris;

<400> SEQUENCE: 802

Glu Val Gln Leu Val Gln Ser Ala Ala Glu Val Lys Lys Pro Gly Ala
1               5                   10                  15

Ser Val Lys Val Ser Cys Lys Thr Ser Gly Tyr Ser Phe Thr Asp Tyr
            20                  25                  30

Phe Met Asn Trp Val Gln Gln Ala Pro Gly Ala Gly Leu Asp Trp Met
        35                  40                  45

Gly Arg Ile Asn Pro Phe Asn Gly Asp Pro Phe Tyr Asn Gln Lys Phe
    50                  55                  60

Lys Gly Arg Val Thr Leu Thr Ala Asp Thr Ser Thr Ser Thr Ala Tyr
65                  70                  75                  80

Met Glu Leu Ser Ser Leu Arg Ala Glu Asp Ala Ala Val Tyr Tyr Cys
                85                  90                  95

Ala Arg Phe Tyr Tyr Gly Arg Tyr Tyr Ala Met Asp Tyr Trp Gly Gln
            100                 105                 110

Gly Thr Leu Val Thr Val
        115

<210> SEQ ID NO 803
<211> LENGTH: 118
<212> TYPE: PRT
<213> ORGANISM: canis familiaris;

<400> SEQUENCE: 803

Glu Val Gln Leu Val Gln Ser Ala Ala Glu Val Lys Lys Pro Gly Ala
1               5                   10                  15

Ser Val Lys Val Ser Cys Lys Thr Ser Gly Tyr Ser Phe Thr Asp Tyr

-continued

```
                    20                  25                  30
Phe Met Asn Trp Val Gln Gln Ala Pro Gly Lys Gly Leu Asp Trp Met
         35                  40                  45
Gly Arg Ile Asn Pro Phe Asn Gly Asp Pro Phe Tyr Asn Gln Lys Phe
     50                  55                  60
Lys Gly Arg Val Thr Leu Thr Ala Asp Thr Ser Thr Ser Thr Ala Tyr
 65                  70                  75                  80
Met Glu Leu Ser Ser Leu Arg Ala Glu Asp Ala Ala Val Tyr Tyr Cys
                 85                  90                  95
Ala Arg Phe Tyr Tyr Gly Arg Tyr Tyr Ala Met Asp Tyr Trp Gly Gln
            100                 105                 110
Gly Thr Leu Val Thr Val
            115

<210> SEQ ID NO 804
<211> LENGTH: 118
<212> TYPE: PRT
<213> ORGANISM: canis familiaris;

<400> SEQUENCE: 804

Glu Val Gln Leu Val Gln Ser Ala Ala Glu Val Lys Lys Pro Gly Ala
 1               5                  10                  15
Ser Val Lys Val Ser Cys Lys Thr Ser Gly Tyr Ser Phe Thr Asp Tyr
                 20                  25                  30
Phe Met Asn Trp Val Gln Gln Ala Pro Gly Ala Gly Leu Asp Trp Met
             35                  40                  45
Gly Arg Ile Asn Pro Phe Asn Gly Asp Pro Phe Tyr Asn Gln Lys Phe
     50                  55                  60
Lys Gly Arg Val Thr Leu Thr Val Asp Thr Ser Thr Ser Thr Ala Tyr
 65                  70                  75                  80
Met Glu Leu Ser Ser Leu Arg Ala Glu Asp Ala Ala Val Tyr Tyr Cys
                 85                  90                  95
Ala Arg Phe Tyr Tyr Gly Arg Tyr Tyr Ala Met Asp Tyr Trp Gly Gln
            100                 105                 110
Gly Thr Leu Val Thr Val
            115

<210> SEQ ID NO 805
<211> LENGTH: 118
<212> TYPE: PRT
<213> ORGANISM: canis familiaris;

<400> SEQUENCE: 805

Glu Val Gln Leu Val Gln Ser Ala Ala Glu Val Lys Lys Pro Gly Ala
 1               5                  10                  15
Ser Val Lys Val Ser Cys Lys Thr Ser Gly Tyr Ser Phe Thr Asp Tyr
                 20                  25                  30
Phe Met Asn Trp Val Gln Gln Ala Pro Gly Lys Gly Leu Asp Trp Met
             35                  40                  45
Gly Arg Ile Asn Pro Phe Asn Gly Asp Pro Phe Tyr Asn Gln Lys Phe
     50                  55                  60
Lys Gly Arg Val Thr Leu Thr Val Asp Thr Ser Thr Ser Thr Ala Tyr
 65                  70                  75                  80
Met Glu Leu Ser Ser Leu Arg Ala Glu Asp Ala Ala Val Tyr Tyr Cys
                 85                  90                  95
Ala Arg Phe Tyr Tyr Gly Arg Tyr Tyr Ala Met Asp Tyr Trp Gly Gln
```

100                 105                 110
Gly Thr Leu Val Thr Val
        115

<210> SEQ ID NO 806
<211> LENGTH: 118
<212> TYPE: PRT
<213> ORGANISM: canis familiaris;

<400> SEQUENCE: 806

Glu Val Gln Leu Val Gln Ser Ala Ala Glu Val Lys Lys Pro Gly Ala
1               5                   10                  15

Ser Val Lys Val Ser Cys Lys Thr Ser Gly Tyr Ser Phe Thr Asp Tyr
                20                  25                  30

Phe Met Asn Trp Val Gln Gln Ala Pro Gly Ala Gly Leu Asp Trp Met
            35                  40                  45

Gly Arg Ile Asn Pro Phe Asn Gly Asp Pro Phe Tyr Asn Gln Lys Phe
        50                  55                  60

Lys Gly Arg Val Thr Leu Thr Val Asp Lys Ser Thr Ser Thr Ala Tyr
65                  70                  75                  80

Met Glu Leu Ser Ser Leu Arg Ala Glu Asp Ala Ala Val Tyr Tyr Cys
                85                  90                  95

Ala Arg Phe Tyr Tyr Gly Arg Tyr Tyr Ala Met Asp Tyr Trp Gly Gln
                100                 105                 110

Gly Thr Leu Val Thr Val
        115

<210> SEQ ID NO 807
<211> LENGTH: 118
<212> TYPE: PRT
<213> ORGANISM: canis familiaris;

<400> SEQUENCE: 807

Glu Val Gln Leu Val Gln Ser Ala Ala Glu Val Lys Lys Pro Gly Ala
1               5                   10                  15

Ser Val Lys Val Ser Cys Lys Thr Ser Gly Tyr Ser Phe Thr Asp Tyr
                20                  25                  30

Phe Met Asn Trp Val Gln Gln Ala Pro Gly Lys Gly Leu Asp Trp Met
            35                  40                  45

Gly Arg Ile Asn Pro Phe Asn Gly Asp Pro Phe Tyr Asn Gln Lys Phe
        50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Ala Ala Val Tyr Tyr Cys
                85                  90                  95

Ala Arg Phe Tyr Tyr Gly Arg Tyr Tyr Ala Met Asp Tyr Trp Gly Gln
                100                 105                 110

Gly Thr Leu Val Thr Val
        115

<210> SEQ ID NO 808
<211> LENGTH: 118
<212> TYPE: PRT
<213> ORGANISM: canis familiaris;

<400> SEQUENCE: 808

Glu Val Gln Leu Val Gln Ser Ala Ala Glu Val Lys Lys Pro Gly Ala
1               5                   10                  15

Ser Val Lys Val Ser Cys Lys Thr Ser Gly Tyr Ser Phe Thr Asp Tyr
            20                  25                  30

Phe Met Asn Trp Val Gln Gln Ala Pro Gly Lys Gly Leu Asp Trp Met
        35                  40                  45

Gly Arg Ile Asn Pro Phe Asn Gly Asp Pro Tyr Asn Gln Lys Phe
    50                  55                  60

Lys Gly Arg Val Thr Leu Thr Val Asp Thr Ser Thr Ser Thr Ala Tyr
65                  70                  75                  80

Met Glu Leu Arg Ser Leu Arg Ala Glu Asp Ala Ala Val Tyr Tyr Cys
                85                  90                  95

Ala Arg Phe Tyr Tyr Gly Arg Tyr Tyr Ala Met Asp Tyr Trp Gly Gln
            100                 105                 110

Gly Thr Leu Val Thr Val
            115

<210> SEQ ID NO 809
<211> LENGTH: 112
<212> TYPE: PRT
<213> ORGANISM: canis familiaris;

<400> SEQUENCE: 809

Thr Asp Ser Gln Thr Val Val Thr Gln Glu Pro Ser Leu Ser Val Ser
1               5                   10                  15

Pro Gly Gly Thr Val Thr Leu Thr Cys Arg Ser Ser Thr Gly Ala Val
            20                  25                  30

Thr Thr Ser Asn Tyr Ala Asn Trp Val Gln Gln Thr Gln Gly Arg Ala
        35                  40                  45

Pro Arg Gly Ile Ile Gly Gly Pro Asn Asn Arg Ala Pro Gly Val Pro
    50                  55                  60

Ser Arg Phe Ser Gly Ser Ile Ser Gly Asn Lys Ala Thr Leu Thr Ile
65                  70                  75                  80

Thr Gly Ala Arg Pro Glu Asp Glu Ala Asp Tyr Phe Cys Ala Leu Trp
                85                  90                  95

Tyr Ser Asn His Trp Val Phe Gly Gly Thr His Leu Thr Val Leu
            100                 105                 110

<210> SEQ ID NO 810
<211> LENGTH: 18
<212> TYPE: DNA
<213> ORGANISM: Artificial Sequence
<220> FEATURE:
<223> OTHER INFORMATION: :

<400> SEQUENCE: 810
gtcaggctca ggtagctg                                                   18

<210> SEQ ID NO 811
<211> LENGTH: 19
<212> TYPE: DNA
<213> ORGANISM: Artificial sequence
<220> FEATURE:
<223> OTHER INFORMATION: :

<400> SEQUENCE: 811
ggccgcgtac ttgttgttg                                                  19

<210> SEQ ID NO 812
<211> LENGTH: 19
<212> TYPE: DNA

```
<213> ORGANISM: Artificial sequence
<220> FEATURE:
<223> OTHER INFORMATION: :

<400> SEQUENCE: 812
gtcgctgatg aggcacacc                                                    19

<210> SEQ ID NO 813
<211> LENGTH: 20
<212> TYPE: DNA
<213> ORGANISM: Artificial sequence
<220> FEATURE:
<223> OTHER INFORMATION: :

<400> SEQUENCE: 813
gctcttgtga gtgatctcac                                                   20

<210> SEQ ID NO 814
<211> LENGTH: 19
<212> TYPE: DNA
<213> ORGANISM: Artificial sequence
<220> FEATURE:
<223> OTHER INFORMATION: :

<400> SEQUENCE: 814
gtgctgctga ggctgtagg                                                    19

<210> SEQ ID NO 815
<211> LENGTH: 20
<212> TYPE: DNA
<213> ORGANISM: Artificial sequence
<220> FEATURE:
<223> OTHER INFORMATION: :

<400> SEQUENCE: 815
ccatccactt tccacttgac                                                   20

<210> SEQ ID NO 816
<211> LENGTH: 21
<212> TYPE: DNA
<213> ORGANISM: Artificial sequence
<220> FEATURE:
<223> OTHER INFORMATION: :

<400> SEQUENCE: 816
ggcttgtcta ctttagtttt g                                                 21

<210> SEQ ID NO 817
<211> LENGTH: 24
<212> TYPE: DNA
<213> ORGANISM: Artificial sequence
<220> FEATURE:
<223> OTHER INFORMATION: :

<400> SEQUENCE: 817
actttagtgt tggtggccgg gtgg                                              24

<210> SEQ ID NO 818
<211> LENGTH: 24
<212> TYPE: DNA
<213> ORGANISM: Artificial sequence
<220> FEATURE:
<223> OTHER INFORMATION: :

<400> SEQUENCE: 818
actttagttt tgctggccgg gtgg                                              24
```

```
<210> SEQ ID NO 819
<211> LENGTH: 27
<212> TYPE: DNA
<213> ORGANISM: Artificial sequence
<220> FEATURE:
<223> OTHER INFORMATION: :

<400> SEQUENCE: 819
ctcgcattct tgaccactg gcttgtc                                          27

<210> SEQ ID NO 820
<211> LENGTH: 27
<212> TYPE: DNA
<213> ORGANISM: Artificial sequence
<220> FEATURE:
<223> OTHER INFORMATION: :

<400> SEQUENCE: 820
tctgcattca ttgaacactg gcttgtc                                         27

<210> SEQ ID NO 821
<211> LENGTH: 16
<212> TYPE: DNA
<213> ORGANISM: Artificial sequence
<220> FEATURE:
<223> OTHER INFORMATION: :

<400> SEQUENCE: 821
gagctcctca gaggag                                                     16

<210> SEQ ID NO 822
<211> LENGTH: 26
<212> TYPE: DNA
<213> ORGANISM: Artificial sequence
<220> FEATURE:
<223> OTHER INFORMATION: :

<400> SEQUENCE: 822
cagaggcact tcctgtgtgt aactgg                                          26

<210> SEQ ID NO 823
<211> LENGTH: 19
<212> TYPE: DNA
<213> ORGANISM: Artificial sequence
<220> FEATURE:
<223> OTHER INFORMATION: :

<400> SEQUENCE: 823
accgctggtc aaggagccg                                                  19

<210> SEQ ID NO 824
<211> LENGTH: 21
<212> TYPE: DNA
<213> ORGANISM: Artificial sequence
<220> FEATURE:
<223> OTHER INFORMATION: :

<400> SEQUENCE: 824
tggaccacgt tgcaggtgaa g                                               21

<210> SEQ ID NO 825
<211> LENGTH: 19
<212> TYPE: DNA
<213> ORGANISM: Artificial sequence
<220> FEATURE:
```

<223> OTHER INFORMATION: :

<400> SEQUENCE: 825
tacaggctcg gggaagtag                                    19

<210> SEQ ID NO 826
<211> LENGTH: 18
<212> TYPE: DNA
<213> ORGANISM: Artificial sequence
<220> FEATURE:
<223> OTHER INFORMATION: :

<400> SEQUENCE: 826
ggggtccagt gggaaaac                                     18

<210> SEQ ID NO 827
<211> LENGTH: 23
<212> TYPE: DNA
<213> ORGANISM: Artificial sequence
<220> FEATURE:
<223> OTHER INFORMATION: :

<400> SEQUENCE: 827
gtctcgctgg accacctgct gga                               23

<210> SEQ ID NO 828
<211> LENGTH: 21
<212> TYPE: PRT
<213> ORGANISM: Canis familiaris

<400> SEQUENCE: 828

Met Asp Trp Thr Trp Arg Val Phe Phe Leu Ala Leu Leu Ala Leu Ala
1               5                   10                  15

Thr Gly Val His Ser
            20

<210> SEQ ID NO 829
<211> LENGTH: 31
<212> TYPE: DNA
<213> ORGANISM: Artificial sequence
<220> FEATURE:
<223> OTHER INFORMATION: :

<400> SEQUENCE: 829
ggatccgcca ccatgaactt gtggctaaac t                      31

<210> SEQ ID NO 830
<211> LENGTH: 33
<212> TYPE: DNA
<213> ORGANISM: Artificial sequence
<220> FEATURE:
<223> OTHER INFORMATION: :

<400> SEQUENCE: 830
ggatccgcca ccatggactg gacctggagg gtc                    33

<210> SEQ ID NO 831
<211> LENGTH: 20
<212> TYPE: DNA
<213> ORGANISM: Artificial sequence
<220> FEATURE:
<223> OTHER INFORMATION: :

<400> SEQUENCE: 831
accgagggcg ccgtggtgga                                   20

<210> SEQ ID NO 832
<211> LENGTH: 20
<212> TYPE: DNA
<213> ORGANISM: Artificial sequence
<220> FEATURE:
<223> OTHER INFORMATION: :

<400> SEQUENCE: 832
tccaccacgg cgccctcggt                                          20

<210> SEQ ID NO 833
<211> LENGTH: 33
<212> TYPE: DNA
<213> ORGANISM: Artificial sequence
<220> FEATURE:
<223> OTHER INFORMATION: :

<400> SEQUENCE: 833
gggtctagag cccttcatt tacccggaga atg                            33

<210> SEQ ID NO 834
<211> LENGTH: 19
<212> TYPE: DNA
<213> ORGANISM: Artificial
<220> FEATURE:
<223> OTHER INFORMATION: primer LG036

<400> SEQUENCE: 834
ctacgatctc tgagagtcc                                           19

<210> SEQ ID NO 835
<211> LENGTH: 18
<212> TYPE: DNA
<213> ORGANISM: Artificial sequence
<220> FEATURE:
<223> OTHER INFORMATION: :

<400> SEQUENCE: 835
ccgccctcct ctgaggag                                            18

<210> SEQ ID NO 836
<211> LENGTH: 18
<212> TYPE: DNA
<213> ORGANISM: Artificial sequence
<220> FEATURE:
<223> OTHER INFORMATION: :

<400> SEQUENCE: 836
ctaagagcac tctgcggg                                            18

<210> SEQ ID NO 837
<211> LENGTH: 44
<212> TYPE: DNA
<213> ORGANISM: Artificial sequence
<220> FEATURE:
<223> OTHER INFORMATION: :

<400> SEQUENCE: 837
cgtcaccgca cccgtgctgc tgcgacatgt gagtgtgact gtcc               44

<210> SEQ ID NO 838
<211> LENGTH: 62
<212> TYPE: DNA
<213> ORGANISM: Artificial sequence
<220> FEATURE:

<223> OTHER INFORMATION: :

<400> SEQUENCE: 838
cgcagcagca cgggtgcggt gacgacgagc aactacgcca actggtatca gcagacccaa    60
gg    62

<210> SEQ ID NO 839
<211> LENGTH: 39
<212> TYPE: DNA
<213> ORGANISM: Artificial sequence
<220> FEATURE:
<223> OTHER INFORMATION: :

<400> SEQUENCE: 839
cggcgctctg ttgttagggc cgtagataat cgtgcgagg    39

<210> SEQ ID NO 840
<211> LENGTH: 44
<212> TYPE: DNA
<213> ORGANISM: Artificial sequence
<220> FEATURE:
<223> OTHER INFORMATION: :

<400> SEQUENCE: 840
ggccctaaca acagagcgcc gggcgtccct agtcgcttct ctgg    44

<210> SEQ ID NO 841
<211> LENGTH: 40
<212> TYPE: DNA
<213> ORGANISM: Artificial sequence
<220> FEATURE:
<223> OTHER INFORMATION: :

<400> SEQUENCE: 841
tggtacagca accattgggt gttcggcgga ggcacccacc    40

<210> SEQ ID NO 842
<211> LENGTH: 49
<212> TYPE: DNA
<213> ORGANISM: Artificial sequence
<220> FEATURE:
<223> OTHER INFORMATION: :

<400> SEQUENCE: 842
cacccaatgg ttgctgtacc acaacgcaca gtgatagtca gcctcatcc    49

<210> SEQ ID NO 843
<211> LENGTH: 31
<212> TYPE: DNA
<213> ORGANISM: Artificial sequence
<220> FEATURE:
<223> OTHER INFORMATION: :

<400> SEQUENCE: 843
tcatttactg actactttat gaactgggta c    31

<210> SEQ ID NO 844
<211> LENGTH: 27
<212> TYPE: DNA
<213> ORGANISM: Artificial sequence
<220> FEATURE:
<223> OTHER INFORMATION: :

<400> SEQUENCE: 844
aaagtagtca gtaaatgagt aaccaga    27

<210> SEQ ID NO 845
<211> LENGTH: 39
<212> TYPE: DNA
<213> ORGANISM: Artificial sequence
<220> FEATURE:
<223> OTHER INFORMATION: :

<400> SEQUENCE: 845
ggtgatcctt tctacaacca gaagttcaag ggcagagtc                                  39

<210> SEQ ID NO 846
<211> LENGTH: 45
<212> TYPE: DNA
<213> ORGANISM: Artificial sequence
<220> FEATURE:
<223> OTHER INFORMATION: :

<400> SEQUENCE: 846
gttgtagaaa ggatcaccat tgaaaggatt aatacgtccc atcca                           45

<210> SEQ ID NO 847
<211> LENGTH: 24
<212> TYPE: DNA
<213> ORGANISM: Artificial sequence
<220> FEATURE:
<223> OTHER INFORMATION: :

<400> SEQUENCE: 847
gtgtactact gcgcaagatt ctac                                                  24

<210> SEQ ID NO 848
<211> LENGTH: 24
<212> TYPE: DNA
<213> ORGANISM: Artificial sequence
<220> FEATURE:
<223> OTHER INFORMATION: :

<400> SEQUENCE: 848
gtagaatctt gcgcagtagt acac                                                  24

<210> SEQ ID NO 849
<211> LENGTH: 411
<212> TYPE: DNA
<213> ORGANISM: canis familiaris;

<400> SEQUENCE: 849
atggagtggg ggctcaactt gattttcctt gtcgctattt tacaaggtgt ccagggtgag           60
gtgcagctgg tggagtctgg gggagacctg gtgaagcctg cggggtccct gagactgtcc          120
tgtgtgacct ctggattcac cttcagtatc tacggcatga actgggtccg ccaggctcct          180
gggaaggggc tgcagtgggt cgcagttatt aatagcgctg gagacacagg ctacgcaggc          240
gctgtgaagg gccgattcac catctccaga gacaacgcca gaacacagt gtatctgcag           300 atgaacagcc tgagagccga ggacacggcc gtgtattact gtgcgaagga tcgggaaatc          360
actacggtag ctgagcttga ccactgggc cagggaaccc tggtcaccgt c                   411

<210> SEQ ID NO 850
<211> LENGTH: 423
<212> TYPE: DNA
<213> ORGANISM: canis familiaris;

<400> SEQUENCE: 850

```
atgaagttgt ggttaagctt ggttttcctt gtcgcttttt taaaaggtgt ccagactgag    60
gtgcaactga tggagtctgg gggagacctg gtgaagcctg ggggatccct gagactctcc   120
tgtgtggcct ctggattcac cttcagtgac tatggcatga actgggtccg ccaggctcca   180
gggaagggac ttcaatgggt cgcttacatt agcactggtg gaggtaccac atcctttgca   240
gatgctgtga agggccggtt caccatctcc agagacaacg ccaagaacac gttctatctt   300
cagatgaaca gcctgagagc cgaggactcg gccatgtatt actgtgcggc cttgatatat   360
ggatacgttg agggcccggg gtcatacttt gacctctggg gcccgggcac cctggtcacc   420
gtc                                                                 423

<210> SEQ ID NO 851
<211> LENGTH: 405
<212> TYPE: DNA
<213> ORGANISM: canis familiaris;

<400> SEQUENCE: 851
atgaagttgg ggctaagctg ggttttcctt gtcgctattc taaaaggtgt ccagggtgag    60
gtgcaactgg tggagtctgg gggagacctg gtgaagcctg ggggtccctt gagactgtca   120
tgtgtggcct cgggactctc cttcggtgac tttgccatga actgggtccg tcagcctcca   180
gggaaggggc cgcagtgggt cgcgactatt aacaggagtg gaaccacata ctacgcagac   240
actgtgaagg gccgattcac catctccaga cagcgccaga gaacacgct atatctgcag    300 ttgaacagcc tgacagccga ggacacggcc cggtattact gtgcggggc cagtatggat   360 actaagactt ttgactactg gggccaggga acccttgtca ccgtc                   405

<210> SEQ ID NO 852
<211> LENGTH: 417
<212> TYPE: DNA
<213> ORGANISM: canis familiaris;

<400> SEQUENCE: 852
atgaagttcg ggctaaactg ggttttcctt gtcgctattt taaaaggtgt ccagggtgag    60
gtgcagctgg tggagtctgg gggagaccta gtgaggcctg ggggtccctt aagactctcc   120
tgtgtggcct ctggattcac cttcagtagc tatggcatga gttgggtccg tcagtctcca   180 gggaagggc tgcagtgggt cgcatggatt aggtatgatg aagtagcac atactacgca    240 gacgctgtga agggccgatt caccatctcc agagacaatg ccaagaacac actgtatctt   300
cagatgaaca gcctgagagc cgaggacacg gccgtgtatt actgtgcgaa ggatccctgg   360
agtagcagtt ggtacgatgc ttttggttat tggggccagg gcaccctggt cactgtc     417

<210> SEQ ID NO 853
<211> LENGTH: 396
<212> TYPE: DNA
<213> ORGANISM: canis familiaris;

<400> SEQUENCE: 853
atggagttgt ggctaaactg ggttttcctt gtcgctattc tacaaggtgt ccagggtgag    60
gttcaactgg tggagtctgg gggagacctg gtgaagcctg ggggtccct gagactctcc    120 tgtgtagcct ctggattcag cttcagtcac aacgacatga gttgggtccg ccaggctcct   180
gggaagggtc tgcagtgggt cgcatctatt agatatgatg agactggcac atcctacact   240
gacgctgtga agggccgatt caccatctcc agagacaacg ccaggaacac actgtatctg   300
cagatgaaca gcctgagagc cgaggacacg gctgtatatt tctgtgcgaa ggaatattta   360
```

```
ggggagtatt ggggcccggg aaccctggtc accgtc                                396
```

<210> SEQ ID NO 854
<211> LENGTH: 450
<212> TYPE: DNA
<213> ORGANISM: canis familiaris;

<400> SEQUENCE: 854

```
atggatatct gcagaattcg cccttgggaa ttcatggagt ttgggctgag ctggctttct     60
cttgtcgcta ttttacaagg tgtccagggt gaggtcagc tggtggagtc tgggggagac    120
ctggtgaagc ctgcagggtc cctgagactg tcctgtgtgg cctctggatt caccttcagt   180
gactacggca tgagctgggt ccgccaggct cctgggaagg gctgcagtt ggtcgcaggt    240
attaacagcg gtggaagtac tacatactac acagacgcag tgaagggccg attcaccatt   300
tccagagaca cgccaagaa cacagtgtat ctgcagatga acagcctgag aggcgaagac   360
acggccatgt attactgtgc aaggggggg gacagtagtc actggtaccc gtacaatttt    420
gactactggg gccagggaac cctggtcacc                                    450
```

<210> SEQ ID NO 855
<211> LENGTH: 417
<212> TYPE: DNA
<213> ORGANISM: canis familiaris;

<400> SEQUENCE: 855

```
atggacttct ggctaagctg ggttttccta gtcactattt taaaaggtgt ccagtgtgag    60
gtgcagctgg tggagtctgg gggagacctt gtgaaacctg aggggtccct gagactctcc   120
tgtgtggtct ctggcttcac cttcagtagc tacgacatga gctgggtccg ccaggctcca   180
gggaagggc tgcagtgggt cgcatacatt agcagtgatg gaggagcac aagttacaca    240
gacgctgtga agggccgatt caccatctcc agagacaatg ccaagaatac gctgtatctg   300
cagatgaaca gcctgagaac tgaggacaca gccgtgtatt actgtgcgag gtatcacgac   360
ggtagctacg tacgtgtctg gttctactac tggggccaag ggaccctggt cactgtg      417
```

<210> SEQ ID NO 856
<211> LENGTH: 438
<212> TYPE: DNA
<213> ORGANISM: canis familiaris;

<400> SEQUENCE: 856

```
atggagcttg ggctgagctg gctttctctt gtcgctattt tacaaggtgt ccagggtgag    60
gtgcagctgg tggagtctgg gggagacctg gtgaagcctg cagggtccct gagactgtcc   120
tgtgtggcct ctggattcac cttcagtagc tacagcatga gctgggtccg ccaggctcct   180
gggaagggc tgcagttggt cgcaggtatt aacagcggtg aagtagcac atactacaca    240
gacgcagtga agggccgatt caccatctcc agagacaacg ccaagaacac agtgtatctg   300
cagatgaaca gcctgagagc cgaggacacg gccatgtatt actgtgcaaa ggccgagctg   360
acgtactact gtactgatga ttactgttcc cgaacctcaa attttgacta ctggggccag   420
ggaaccctgg tcaccgtc                                                  438
```

<210> SEQ ID NO 857
<211> LENGTH: 432
<212> TYPE: DNA
<213> ORGANISM: canis familiaris;

-continued

```
<400> SEQUENCE: 857
atgaacttgg ggttaagctt ggttttcctt gtcgctattt tacaaggtgt ccagggtgag      60
gtgcaactgg tgcagtctgg gggagaccta gtaaagcctt cggggtccct gagactgtcc     120
tgtgtggcct ctggattcat cttcagtagc ttccacatga gttgggtccg ccagacccct     180
gagaggggac tggagttggt cgcaggtatt aatggcggtg gaaccaccag attctactca     240
gacgctgtga ggggccgttt catcatttcc agagacctcg ccaagagtac agtctatctg     300
cagatggaca acctgcgagc cgacgacacg gccacttact actgtgcaag ggcccgggag     360
agatactgta aagatgatta ttgtttcagg tggggttttg attcctgggg ccggggagcc     420
ctggtcaccg tc                                                         432

<210> SEQ ID NO 858
<211> LENGTH: 414
<212> TYPE: DNA
<213> ORGANISM: canis familiaris;

<400> SEQUENCE: 858
atgaacttgt ggctaaactg gattttcctt gtcgctattt taaaaggtgt ccagggtgag      60
gtacaactgg tggagtctgg gggagacctg gtgaagcctg ggggtccttt aagactctcc     120
tgtgtggcct ctggattcac cttcagtagt tccggcatga gctgggtccg tcagtctcca     180
gggaaggggc tgcagtgggt cgcatggatt aagtctgatg aagtagtaca atattatgta     240
gacgctgtga agggccgatt caccatcgcc agagacaacg ccaagaacac cctgtatctg     300
cagatgaaca gcctgagagc cgacgacacg gccgtgtatt attgtgcgaa gctttgggac     360
agttggggcg cgtacaattt tgactactgg ggccagggaa ccctggtcac cgtc           414

<210> SEQ ID NO 859
<211> LENGTH: 402
<212> TYPE: DNA
<213> ORGANISM: canis familiaris;

<400> SEQUENCE: 859
atggagtttg ggctgacctg gctttctctt gtcgctattt tacaaggtgt ccagggtgag      60
gtgcagctgg tggagtctgg gggagacctg gtgaagcctg cagggtccct gagactgtcc     120
tgtgtggcct ctggattcac cttcagtagc tacagcatga gctgggtccg ccaggctcct     180 gggaagggc tgcagttggt cgcaggtatt aacagcggtg gaagtagcac atactacaca     240
gacgcagtga agggccgatt caccatctcc agagacaacg ccaagaacac agtgtatctg     300
cagatgaaca gcctgagagc cgaggacacg gccatgtatt actgtgcccc tactacggta     360
gctactatgg agtcctgggg ccagggaacc ctggtcaccg tc                        402

<210> SEQ ID NO 860
<211> LENGTH: 399
<212> TYPE: DNA
<213> ORGANISM: canis familiaris;
<220> FEATURE:
<221> NAME/KEY: UNSURE
<222> LOCATION: (324)..(324)
<223> OTHER INFORMATION: n is a, c, t, or g
<220> FEATURE:
<221> NAME/KEY: UNSURE
<222> LOCATION: (365)..(365)
<223> OTHER INFORMATION: n is a, c, t, or g

<400> SEQUENCE: 860
atggagtctg tgctctgctg ggttttcctt gtcgctattt taaaaggtgt ccagggtgag      60
```

```
gtgcagctgg tggagtctgg gggagacctg gtgaagcctg gggggtccct gagactctcc    120
tgtgtgactt ctggattcac cttcagtggc tgtgccatga tctgggtccg ccaggctcca    180
gggaaggggc tgcagtgggt cgcatacatt aacagtgatg gaagtaccac atactacgca    240
gacgctgtga agggacgatt caccatctcc agagacaacg ccaagaacac gctctatctg    300
cagatgaaca gcctgagagc tgangacacg gccgtgtatt actgtgcgag gggtgattct    360
agtanttggg gctggggcca aggaaccctg gtcatcgtc                            399
```

<210> SEQ ID NO 861
<211> LENGTH: 426
<212> TYPE: DNA
<213> ORGANISM: canis familiaris;
<220> FEATURE:
<221> NAME/KEY: UNSURE
<222> LOCATION: (423)..(423)
<223> OTHER INFORMATION: n is a, c, t, or g

<400> SEQUENCE: 861

```
atggaatctg tgctcggatg gatttctt gccactattt taaaaggtgt ccagggtgag     60
gtgcagttgg tggagtctgg gggagacctg gtgaagcctg gggggtccct aagactctcc   120
tgtgtgggct ctggattcac cttcagtggt tactggatga gttgggtccg ccaacctcca   180
gggaaggggc tacagtggat tgtggagatc agcggtagtg gaaccaccac acactatgaa   240
gacactgtga ggggccgatt taccatttcc agagacaatg ccaagaacac gctgtctctg   300
gagatgaata gtctgagaga cgaggacacg gccatgtatt attgtgcaag ggatcggggg   360
caatgtactg ttgattactg cgccgatcat attgactact ggggccaggg aaccctggtc   420 atngtc                                                              426
```

<210> SEQ ID NO 862
<211> LENGTH: 429
<212> TYPE: DNA
<213> ORGANISM: canis familiaris;
<220> FEATURE:
<221> NAME/KEY: UNSURE
<222> LOCATION: (85)..(85)
<223> OTHER INFORMATION: n is a, c, t, or g
<220> FEATURE:
<221> NAME/KEY: UNSURE
<222> LOCATION: (113)..(113)
<223> OTHER INFORMATION: n is a, c, t, or g
<220> FEATURE:
<221> NAME/KEY: UNSURE
<222> LOCATION: (348)..(348)
<223> OTHER INFORMATION: n is a, c, t, or g
<220> FEATURE:
<221> NAME/KEY: UNSURE
<222> LOCATION: (354)..(354)
<223> OTHER INFORMATION: n is a, c, t, or g
<220> FEATURE:
<221> NAME/KEY: UNSURE
<222> LOCATION: (393)..(393)
<223> OTHER INFORMATION: n is a, c, t, or g
<220> FEATURE:
<221> NAME/KEY: UNSURE
<222> LOCATION: (429)..(429)
<223> OTHER INFORMATION: n is a, c, t, or g

<400> SEQUENCE: 862

```
atggagtctg tgctctgctg gttttccctt gtcgctattt taaaaggtgt ccagggtgag     60
gtgcagctgg tggagtctgg gggnacctg gtgaagtttg gggggtcctt ganactgtcc    120
tgtgtggcct ctggattcac cttcagtagc tacagcatga gttgggtccg ccaggctcct   180
```

```
gaaaagggc  tgcagttggt  cgcaggtatt  aacagcggtg  gaagtagcac  atactacaca      240
gacgctgtga  agggccgatt  caccatctcc  agagacaacg  ccaagaacac  gctatatcta      300
cagttgaaca  gcctgagagt  cgaagacacg  gccgtgtatt  actgtgcnag  gcanacctat      360
ggtacctcct  ctgaggggaa  ttacttaggt  ctntggggcc  agggcaccct  ggtcaccctg      420 gtcaccgtn                                                                   429

<210> SEQ ID NO 863
<211> LENGTH: 399
<212> TYPE: DNA
<213> ORGANISM: canis familiaris;
<220> FEATURE:
<221> NAME/KEY: UNSURE
<222> LOCATION: (325)..(325)
<223> OTHER INFORMATION: n is a, c, t, or g

<400> SEQUENCE: 863
atggaatctg  tgctcggatg  gatttccctt  gccactattt  taaaggtgt   ccagggtgag      60 gtgcagttgg  tggagtctgg  gggagacctg  gtgaagcctg  gggggtccct  gagactctcc     120
tgtgtggcct  ctggattcac  cttcagttac  tacttaatga  gctgggtccg  ccgggctcca     180
gggaaggggt  tacagtggat  tgcagaaatt  tccgatagtg  gagattatct  ggactataca     240
gacgctgtga  agggccgatt  caccatctcc  agagacaatg  ccaagagcac  gctgtatctg     300
gagatgaaca  ggctgaggcc  cgacnacacg  gccatgtatt  actgtgttac  cggcggggac     360
ctctttggtc  actggggcca  aggcaccctg  gtcactgtc                              399

<210> SEQ ID NO 864
<211> LENGTH: 441
<212> TYPE: DNA
<213> ORGANISM: canis familiaris;

<400> SEQUENCE: 864
atggagtctg  cgctcagctg  ggtgttcctt  gtcactattt  taaaaggtgt  ccagggtgag      60
gtgcatctgg  tggagtctgg  gggagacctg  gtgaagcctg  gagggtccct  gagactttcc     120
tgtgtggcct  ctggattcaa  cttcggcagc  taccacatgg  gctgggtccg  cgaggctcca     180
gggaagggcc  ttcagtgggt  cgcatacatt  cacaatgatg  gaggtaccag  gacctattca     240
gacactgtga  agggccgatt  caccatctcc  agagacaacg  ccgagaacac  gctgtatctt     300
cagatgaaca  gcctgaggcc  cgaggacacg  gccgtgtatt  attgtgcgag  cctatccggg     360
tattattgta  ctgatgattc  ctgtttcaac  gttgtacatg  attacttaaa  cctctggggc     420
caaggcaccc  tggcaaccgt  t                                                  441

<210> SEQ ID NO 865
<211> LENGTH: 402
<212> TYPE: DNA
<213> ORGANISM: canis familiaris;
<220> FEATURE:
<221> NAME/KEY: UNSURE
<222> LOCATION: (303)..(303)
<223> OTHER INFORMATION: n is a, c, t, or g

<400> SEQUENCE: 865
atggagtctg  tgttctgctg  ggttttcctt  gtcgctattt  taaaaggtgt  ccagggcgag      60
gtgcagctgg  tggagtctgg  gggagacctg  gtgaagcctg  gggggtccct  gagactgtcc     120
tgtgtggcct  ctggattcac  cttcagtgac  tactacatgt  actgggtccg  ccaggctcca     180
gggaaggggc  ttcagtacgt  cgcacggatt  agggtgatg   gaactaacat  atactacgca     240
```

-continued

```
gacgctgtga agggccgatt caccatctcc agagacaatg ccaagaacac gctgtatctg        300
canatgaaca gcctgagagc cgaggacacg gctgtgtatt attgtggaaa ggatttcggg        360
gactgggttc tatcctgggg ccagggaacc ctggtcaccg tt                          402
```

<210> SEQ ID NO 866
<211> LENGTH: 417
<212> TYPE: DNA
<213> ORGANISM: canis familiaris;

<400> SEQUENCE: 866

```
atggaatctg tgctcggatg dattttcctt gccactattt taaaaggtgt ccagggtgag        60
gtgcagttgg tggaatctgg gggagacctg gtgaagcctg gggggtccct gagactctcc       120
tgtgtgggct ctggattcac cttcaatagt tactggatga gctgggtccg ccaggctcca       180
ggggaggggc tacaatggat tggacagata agtgttggtg gtgaaataga gtatgcagac       240
gctgtgaagg gccgattcac catctccaga gacaatgcca gaacacgct gtttctgcag        300 atgcacagtc tgagagccga ggacacggcc atatattact gtgcaagaga cgggggtatt       360
acctcataca tgaaaacgaa tcttgactac tggggccagg gaaacctggt caccgtc         417
```

<210> SEQ ID NO 867
<211> LENGTH: 390
<212> TYPE: DNA
<213> ORGANISM: canis familiaris;

<400> SEQUENCE: 867

```
atggagtctg tgctctgctg ggttttcctt gtcgctattt taaaaggtgt ccagggtgag        60
gtgcaactgg tggagtctgg gggagacctg gtgaagcctg gggggtccct gagactctcc       120
tgtgttggct ctggattcac cttcagtgcc tatgacatgc tatgggtccg tcaggctcca       180
gggaaggggc tgcagtgggt cgcatacatt aacagcggtg gagggatcat attctacgca       240
gacgctgtga agggccgatt caccatctcc agagacaacg ccaagaacac actctctctg       300
catatgaaca gcctgagagt cgaggacacg gccgtgtatt tctgtacaag atgggatact       360
aacggacact ggggccaggg caccctggtc                                        390
```

<210> SEQ ID NO 868
<211> LENGTH: 411
<212> TYPE: DNA
<213> ORGANISM: canis familiaris;

<400> SEQUENCE: 868

```
atggagtctg tgctctgctg ggttttcctt gtcgccattc taaatggtgt ccagggtgag        60
gtgcagctgg tagagtctgg gggagacctg gtgaagcctg ggggggtcctt aagactgtcc      120 tgtgtggcct ctggattcac cttcaggacc tatggcatga gctgggtccg tcagtgtcca       180
gggaagggac tgcagtgggt cacaagtatc agcagcagcg gaggcacgtt ctacgcagac       240
gctgtgaagg gccgattcac catctccaga gacaacgcca gaacacgct gtatctgcag        300 ttgaacagcc tgagagccga ggacacggcc gtgtattatt gtgcgaagga tccggctacg       360
ctacctacgg gggaatttga ctactggggc cagggcaccc cggtcaccgt c                411
```

<210> SEQ ID NO 869
<211> LENGTH: 411
<212> TYPE: DNA
<213> ORGANISM: canis familiaris;

```
<400> SEQUENCE: 869
atggactgca gctggagaat cttcttcctg ctggcactgg ccacaggtgt gcactctgag      60
gtccagctgg tgcagtctgc agctgaggtt aaaaagccag gggcatctgt gaaggtctcc     120
tgcaagacat ctggatacac cttcactgac tactatatgc actgggtaca acaggctcca     180
ggagcagggc ttgattggat gggatggatt gatcctgaag atggtaccac aagttatgca     240
cagaagttcc agggcagagt caccctgacg gcagacacat ccacaagcac agcctacatg     300
gagctgagca gtctgagagc tgaggacaca gctgtgtact actgtgcaag cggagggagt     360
cggcccttca atgcttttgg ttactggggc cagggcaccc tggtcactgt t              411

<210> SEQ ID NO 870
<211> LENGTH: 414
<212> TYPE: DNA
<213> ORGANISM: canis familiaris;

<400> SEQUENCE: 870
atggactgga cctggagggt cttcttcctg ctggcactgg ccacaggtgt gcactctgag      60
gtccagctgg tgcagtctgc agctgaggtt aagaagccag gggcatctgt gaaggtctcc     120
tgcaagacat ctggatacac cttcactgac tactatatgc actgggtaca acaggctcca     180
ggagcagggc ttgattggat gggatggatt gatcctgaag atggtaccac aagttatgca     240
cagaagttcc agggcagagt caccctgacg gcagacacat ccacaagcac agcctacatg     300
gagctgagca gtctgagagc tgaggacgca gctgtgtact actgtgcaag cttatatata     360
tatggatacg ctgcttactt agacctctgg ggccagggca ccctggtcac cgtc           414

<210> SEQ ID NO 871
<211> LENGTH: 408
<212> TYPE: DNA
<213> ORGANISM: canis familiaris;

<400> SEQUENCE: 871
atggactgga cctggaggat cctcttcctg ctggcactgg ccacaggtgt gcactctgag      60
gtccagctgg tacagtctgc agctgaggtt aagaagccag gggcatctgt gaaggtctcc     120
tgcaagacat ctggatacac cttcactgac tactatatgc actgggtaca acaggctcca     180
ggagcagggc ttgattggat gggatggatt gatcctgaag atgataccac aggttatgca     240
cagaagttcc agggcagagt caccctgacg gcagacacat ccacaagcac agcctacatg     300
gagctgagca gtctgagagc tgaggacaca gctgtgtact actgtgcaag aaagtggagg     360
tactacggta gccaagatta ctggggccag ggaaccctgg tcaccgtc                  408

<210> SEQ ID NO 872
<211> LENGTH: 399
<212> TYPE: DNA
<213> ORGANISM: canis familiaris;

<400> SEQUENCE: 872
atggactgca gctggagaat cttcttcctg ctggcactgg ccacaggtgt gcactctgag      60
gtccagctgg tgcagtctgc agctgaggtt aagaagccag gggcatctgt gaaggtctcc     120
tgcaagacat ctggatacat cttcattgac cagtatatgc actgggtaca gcaggctcca     180
ggagcagggc ttgaatggat gggatggatt gatcctgagg atggtaccac aagttatgca     240
cagaagttcc agggcagagt caccctgacg gcagacacat ccacaaacac agtctatatg     300
gagctgagca atctgagaac tgaggacaca gctgtgtact actgtgcaag ggatatatgg     360
```

```
gattttgact actggggcca gggaaccctg gtcaccgtc                     399
```

<210> SEQ ID NO 873
<211> LENGTH: 426
<212> TYPE: DNA
<213> ORGANISM: canis familiaris;

<400> SEQUENCE: 873

```
atgaagttgg ggttaagctg gattttctt gtcgctattt tacaaggtgt ccagggtgag     60
gtgcagctgg tggagtctgg gggaaacctg gtgaagccgg ggggtccct gagactctcc    120
tgtgtagcct ctggattcac cttcagtaat tacgacatga gttgggtccg ccaggctcct   180
gggaaggggc tgcagtgggt cgcgactatt agttatgatg gaagtagtac atttcatact   240
gacgctgtga agggccgatt caccatctcc agagacaacg ccaggaacac agtgtatcta   300
cagctgaaca gcctgagagc cgaggacacg gctgtttatt attgtgggaa gcagtggaga   360
aacacctggt attcttttcc cgatcccggt tttgactatt ggggtcaggg aaccctggtc   420
accgtc                                                              426
```

<210> SEQ ID NO 874
<211> LENGTH: 142
<212> TYPE: PRT
<213> ORGANISM: canis familiaris;

<400> SEQUENCE: 874

```
Met Lys Leu Gly Leu Ser Trp Ile Phe Leu Val Ala Ile Leu Gln Gly
1               5                   10                  15
Val Gln Gly Glu Val Gln Leu Val Glu Ser Gly Gly Asn Leu Val Lys
            20                  25                  30
Pro Gly Gly Ser Leu Arg Leu Ser Cys Val Ala Ser Gly Phe Thr Phe
        35                  40                  45
Ser Asn Tyr Asp Met Ser Trp Val Arg Gln Ala Pro Gly Lys Gly Leu
    50                  55                  60
Gln Trp Val Ala Thr Ile Ser Tyr Asp Gly Ser Ser Thr Phe His Thr
65                  70                  75                  80
Asp Ala Val Lys Gly Arg Phe Thr Ile Ser Arg Asp Asn Ala Arg Asn
                85                  90                  95
Thr Val Tyr Leu Gln Leu Asn Ser Leu Arg Ala Glu Asp Thr Ala Val
            100                 105                 110
Tyr Tyr Cys Gly Lys Gln Trp Arg Asn Thr Trp Tyr Ser Phe Pro Asp
        115                 120                 125
Pro Gly Phe Asp Tyr Trp Gly Gln Gly Thr Leu Val Thr Val
    130                 135                 140
```

<210> SEQ ID NO 875
<211> LENGTH: 405
<212> TYPE: DNA
<213> ORGANISM: canis familiaris;

<400> SEQUENCE: 875

```
atggagttcg ggttcaactt gattttcctt gkgactattt taaaaggtgc ccagggtgag    60
gtgcagctkg tggaatctgg gggagacctg atgaagcctg ggggtccct gagactctcc   120
tgtgtggcct ctggattcac tttcagtagc cactacatga actgggtccg ccaggctcca   180
gggaaggggc tgcagtgggt cggatacatt aacagtgatg acatagcac gagctacgca   240
gacgctgtga agggccgatt caccatctcc agagacaatg ccaagaacac gctgtatctg   300
```

```
cagatgaaca gcctgagaac cgaggacacc ggccgtgtat tactgtgtga agggatggca    360
ggtagtactt ataggtgggg tggtatggac tactggggcc atggc                   405
```

<210> SEQ ID NO 876
<211> LENGTH: 135
<212> TYPE: PRT
<213> ORGANISM: canis familiaris;
<220> FEATURE:
<221> NAME/KEY: UNSURE
<222> LOCATION: (11)..(11)
<223> OTHER INFORMATION: X is any amino acid
<220> FEATURE:
<221> NAME/KEY: UNSURE
<222> LOCATION: (23)..(23)
<223> OTHER INFORMATION: X is any amino acid

<400> SEQUENCE: 876

```
Met Glu Phe Gly Phe Asn Leu Ile Phe Leu Xaa Thr Ile Leu Lys Gly
1               5                   10                  15

Ala Gln Gly Glu Val Gln Xaa Val Glu Ser Gly Gly Asp Leu Met Lys
            20                  25                  30

Pro Gly Gly Ser Leu Arg Leu Ser Cys Val Ala Ser Gly Phe Thr Phe
        35                  40                  45

Ser Ser His Tyr Met Asn Trp Val Arg Gln Ala Pro Gly Lys Gly Leu
    50                  55                  60

Gln Trp Val Gly Tyr Ile Asn Ser Asp Gly His Ser Thr Ser Tyr Ala
65                  70                  75                  80

Asp Ala Val Lys Gly Arg Phe Thr Ile Ser Arg Asp Asn Ala Lys Asn
                85                  90                  95

Thr Leu Tyr Leu Gln Met Asn Ser Leu Arg Thr Glu Asp Thr Gly Arg
            100                 105                 110

Val Leu Leu Cys Glu Gly Met Ala Gly Ser Thr Tyr Arg Trp Gly Gly
        115                 120                 125

Met Asp Tyr Trp Gly His Gly
        130                 135
```

<210> SEQ ID NO 877
<211> LENGTH: 405
<212> TYPE: DNA
<213> ORGANISM: canis familiaris;

<400> SEQUENCE: 877

```
atggagttct ggttcaactg gattttcctt gtcgstactt taaaaggtgt ccagggtgag    60
gtgcaactgg tgragtctkg gggagacatg gtgaagcctg ggggtccct gagactytyc    120 tstgtggsct ctggatttac cttcagtagt cactacatgt attgggtccg ccaggctcca    180 gggaagggc ttcagtgggt ctcacacatt aacgcagatg gaggtaccac aaggtatgcg    240
gacgctgtga agggccgatt caccatctcc agagacaacg caaagaatac gctgtatctc    300
cagatgaaca gcctgagagc cgaggacaca gcggtatatt actgtacaaa ggactcccat    360
actacggcta gttttgacta ctggggccag ggaaccctgg tcacc                    405
```

<210> SEQ ID NO 878
<211> LENGTH: 135
<212> TYPE: PRT
<213> ORGANISM: canis familiaris;
<220> FEATURE:
<221> NAME/KEY: UNSURE
<222> LOCATION: (12)..(12)
<223> OTHER INFORMATION: X is any amino acid

```
<220> FEATURE:
<221> NAME/KEY: UNSURE
<222> LOCATION: (25)..(25)
<223> OTHER INFORMATION: X is any amino acid
<220> FEATURE:
<221> NAME/KEY: UNSURE
<222> LOCATION: (27)..(27)
<223> OTHER INFORMATION: X is any amino acid
<220> FEATURE:
<221> NAME/KEY: UNSURE
<222> LOCATION: (39)..(41)
<223> OTHER INFORMATION: X is any amino acid
<220> FEATURE:
<221> NAME/KEY: UNSURE
<222> LOCATION: (43)..(43)
<223> OTHER INFORMATION: X is any amino acid

<400> SEQUENCE: 878

Met Glu Phe Trp Phe Asn Trp Ile Phe Leu Val Xaa Thr Leu Lys Gly
1               5                   10                  15

Val Gln Gly Glu Val Gln Leu Val Xaa Ser Xaa Gly Asp Met Val Lys
            20                  25                  30

Pro Gly Gly Ser Leu Arg Xaa Xaa Xaa Val Xaa Ser Gly Phe Thr Phe
        35                  40                  45

Ser Ser His Tyr Met Tyr Trp Val Arg Gln Ala Pro Gly Lys Gly Leu
    50                  55                  60

Gln Trp Val Ser His Ile Asn Ala Asp Gly Thr Thr Arg Tyr Ala
65                  70                  75                  80

Asp Ala Val Lys Gly Arg Phe Thr Ile Ser Arg Asp Asn Ala Lys Asn
                85                  90                  95

Thr Leu Tyr Leu Gln Met Asn Ser Leu Arg Ala Glu Asp Thr Ala Val
            100                 105                 110

Tyr Tyr Cys Thr Lys Asp Ser His Thr Thr Ala Ser Phe Asp Tyr Trp
        115                 120                 125

Gly Gln Gly Thr Leu Val Thr
        130                 135

<210> SEQ ID NO 879
<211> LENGTH: 402
<212> TYPE: DNA
<213> ORGANISM: canis familiaris;

<400> SEQUENCE: 879
atgaagttct ggctcagctg ggttttcctt gtcgctactt tacaaggtgt ccagggtgag      60
gtgcagctgg tggagtctgg gggagacctg gtgaagcctg ggggtccct gagactctcc     120 tgtgttgcct ccggattcat cttcagtaac tacgacatga actgggtccg cctggctcct    180 gggaagggc tgcagtgggt cgcaagtatt agctatgatg gaagtcgcac atactacact    240
gacgctgtga agggccgatt caccatctcc agagacaacg ccacgaacac agtgtatctg    300
cagatgaatg gcctgagaac cgaggacacg gctgtgtatt cctgtgcggc agatatttgg    360
atccgggggg tggactactg gggccaggga accctggtca cc                       402

<210> SEQ ID NO 880
<211> LENGTH: 134
<212> TYPE: PRT
<213> ORGANISM: canis familiaris;

<400> SEQUENCE: 880

Met Lys Phe Trp Leu Ser Trp Val Phe Leu Val Ala Thr Leu Gln Gly
1               5                   10                  15
```

-continued

```
Val Gln Gly Glu Val Gln Leu Val Glu Ser Gly Gly Asp Leu Val Lys
            20                  25                  30

Pro Gly Gly Ser Leu Arg Leu Ser Cys Val Ala Ser Gly Phe Ile Phe
        35                  40                  45

Ser Asn Tyr Asp Met Asn Trp Val Arg Leu Ala Pro Gly Lys Gly Leu
    50                  55                  60

Gln Trp Val Ala Ser Ile Ser Tyr Asp Gly Ser Arg Thr Tyr Tyr Thr
65                  70                  75                  80

Asp Ala Val Lys Gly Arg Phe Thr Ile Ser Arg Asp Asn Ala Thr Asn
                85                  90                  95

Thr Val Tyr Leu Gln Met Asn Gly Leu Arg Thr Glu Asp Thr Ala Val
            100                 105                 110

Tyr Ser Cys Ala Ala Asp Ile Trp Ile Arg Gly Val Asp Tyr Trp Gly
        115                 120                 125

Gln Gly Thr Leu Val Thr
            130
```

<210> SEQ ID NO 881
<211> LENGTH: 402
<212> TYPE: DNA
<213> ORGANISM: canis familiaris;

<400> SEQUENCE: 881

```
atgcagatgc cgtggtccct cctctgcctg ctggcagctc ccctgggtgt cctgtctgaa      60
ctcacactcc aggaggcagg gccaggactg gtgaagccct cagagaccct ctctctcacc     120
tgtcttgtgt ccggaggctc cgtcaacagc ggttattact ggagttggat ccgtcgacgc     180
cctgggggag aattggaatg gatgggatac tggtcaggta cgaccccacta caacccgaca     240
ttccagggac gcatttccat tactactgat acggccacga accaattctt cctccagctg     300
acttccgtga ccaccgaaga cacggccgtt tatttctgta tacgactcta taggtctaac     360
tactttcttg actttggggg tcagggaacc ctggtcaccg tc                        402
```

<210> SEQ ID NO 882
<211> LENGTH: 134
<212> TYPE: PRT
<213> ORGANISM: canis familiaris;

<400> SEQUENCE: 882

```
Met Gln Met Pro Trp Ser Leu Leu Cys Leu Leu Ala Ala Pro Leu Gly
1               5                   10                  15

Val Leu Ser Glu Leu Thr Leu Gln Glu Ala Gly Pro Gly Leu Val Lys
            20                  25                  30

Pro Ser Glu Thr Leu Ser Leu Thr Cys Leu Val Ser Gly Gly Ser Val
        35                  40                  45

Asn Ser Gly Tyr Tyr Trp Ser Trp Ile Arg Arg Arg Pro Gly Gly Glu
    50                  55                  60

Leu Glu Trp Met Gly Tyr Trp Ser Gly Thr Thr His Tyr Asn Pro Thr
65                  70                  75                  80

Phe Gln Gly Arg Ile Ser Ile Thr Thr Asp Thr Ala Thr Asn Gln Phe
                85                  90                  95

Phe Leu Gln Leu Thr Ser Val Thr Thr Glu Asp Thr Ala Val Tyr Phe
            100                 105                 110

Cys Ile Arg Leu Tyr Arg Ser Asn Tyr Phe Leu Asp Phe Trp Gly Gln
        115                 120                 125

Gly Thr Leu Val Thr Val
            130
```

-continued

130

<210> SEQ ID NO 883
<211> LENGTH: 402
<212> TYPE: DNA
<213> ORGANISM: canis familiaris;

<400> SEQUENCE: 883

| | |
|---|---|
| atgcagatgc cgtggtccct cctctgcctg ctggcagctc ccctggggtgt cctgtctgaa | 60 |
| ctcacactcc aggaggcagg gccaggactg gtgaagccct caragaccct ctctctcacc | 120 |
| tgtcttgtgt ccggaggctc cgtcaacagc ggttattact ggagttggat ccgtcgacgc | 180 |
| cctgggggag aattggaatg gatgggatac tggtcaggta cgacccacta caacccgaca | 240 |
| ttccagggac gcatttccat tactactgat acggccacga accaattctt cctccagctg | 300 |
| acttccgtga ccaccgaaga cacggccgtt tatttctgta tacgactcta taggtctaac | 360 |
| tactttcttg acttttgggg tcagggaacc ctggtcaccg tc | 402 |

<210> SEQ ID NO 884
<211> LENGTH: 134
<212> TYPE: PRT
<213> ORGANISM: canis familiaris;
<220> FEATURE:
<221> NAME/KEY: UNSURE
<222> LOCATION: (35)..(35)
<223> OTHER INFORMATION: X is any amino acid

<400> SEQUENCE: 884

Met Gln Met Pro Trp Ser Leu Leu Cys Leu Leu Ala Ala Pro Leu Gly
1               5                   10                  15

Val Leu Ser Glu Leu Thr Leu Gln Glu Ala Gly Pro Gly Leu Val Lys
            20                  25                  30

Pro Ser Xaa Thr Leu Ser Leu Thr Cys Leu Val Ser Gly Gly Ser Val
        35                  40                  45

Asn Ser Gly Tyr Tyr Trp Ser Trp Ile Arg Arg Pro Gly Gly Glu
    50                  55                  60

Leu Glu Trp Met Gly Tyr Trp Ser Gly Thr Thr His Tyr Asn Pro Thr
65              70                  75                  80

Phe Gln Gly Arg Ile Ser Ile Thr Thr Asp Thr Ala Thr Asn Gln Phe
                85                  90                  95

Phe Leu Gln Leu Thr Ser Val Thr Thr Glu Asp Thr Ala Val Tyr Phe
            100                 105                 110

Cys Ile Arg Leu Tyr Arg Ser Asn Tyr Phe Leu Asp Phe Trp Gly Gln
        115                 120                 125

Gly Thr Leu Val Thr Val
        130

<210> SEQ ID NO 885
<211> LENGTH: 403
<212> TYPE: DNA
<213> ORGANISM: canis familiaris;

<400> SEQUENCE: 885

| | |
|---|---|
| atggagttgt ggttcaactg gattttcctt gtcgctattt taaaaggtgt ccagggtgag | 60 |
| gtgcagttgg tggagtctgg gggagacctg gtgaagcctg gggggtcctt aagactctcc | 120 |
| tgtgtggcct ctggattcac cttcagtgat tatggcatga actgggtccg tcactctcca | 180 |
| gggaaggggc tgcagtgggt cgcatggatt tggtatggcg ggagtagcac atactacgca | 240 |

| | | |
|---|---|---|
| gacgctgtga agggccgatt caccatctcc agagacgacg ccaacaacac actatatcta | 300 | |
| cagatgaaca gcctgagagc cgaggacacg gccgtctatt actgtgcgaa ggagtatagt | 360 | |
| agtagctttg actactgggg ccagggaacc ctggtcaccg tct | 403 | |

<210> SEQ ID NO 886
<211> LENGTH: 134
<212> TYPE: PRT
<213> ORGANISM: canis familiaris;

<400> SEQUENCE: 886

```
Met Glu Leu Trp Phe Asn Trp Ile Phe Leu Val Ala Ile Leu Lys Gly
1               5                   10                  15

Val Gln Gly Glu Val Gln Leu Val Glu Ser Gly Gly Asp Leu Val Lys
            20                  25                  30

Pro Gly Gly Ser Leu Arg Leu Ser Cys Val Ala Ser Gly Phe Thr Phe
        35                  40                  45

Ser Asp Tyr Gly Met Asn Trp Val Arg His Ser Pro Gly Lys Gly Leu
    50                  55                  60

Gln Trp Val Ala Trp Ile Trp Tyr Gly Gly Ser Ser Thr Tyr Tyr Ala
65                  70                  75                  80

Asp Ala Val Lys Gly Arg Phe Thr Ile Ser Arg Asp Asp Ala Asn Asn
                85                  90                  95

Thr Leu Tyr Leu Gln Met Asn Ser Leu Arg Ala Glu Asp Thr Ala Val
            100                 105                 110

Tyr Tyr Cys Ala Lys Glu Tyr Ser Ser Ser Phe Asp Tyr Trp Gly Gln
        115                 120                 125

Gly Thr Leu Val Thr Val
    130
```

<210> SEQ ID NO 887
<211> LENGTH: 402
<212> TYPE: DNA
<213> ORGANISM: canis familiaris;

<400> SEQUENCE: 887

| | |
|---|---|
| atgcagatgc cgtggtccct cctctgcctg ctggcagctc ccctgggtgt cctgtctgaa | 60 |
| ctcacactcc aggaggcagg gccaggactg gtgaagccct cagagaccct ctctctcacc | 120 |
| tgtcttgtgt ccggaggctc cgtcaacagc ggttattact ggagttggat ccgtcgacgc | 180 |
| cctgggggag aattggaatg gatgggatac tggtcaggta cgacccacta caacccgaca | 240 |
| ttccagggac gcatttccat tactactgat acggccacga accaattctt cctccagctg | 300 |
| acttccgtga ccaccgaaga cacggccgtt tatttctgta tacgactcta taggtctaac | 360 |
| taccttcttg acttttgggg tcagggaacc ctggtcaccg tc | 402 |

<210> SEQ ID NO 888
<211> LENGTH: 134
<212> TYPE: PRT
<213> ORGANISM: canis familiaris;

<400> SEQUENCE: 888

```
Met Gln Met Pro Trp Ser Leu Leu Cys Leu Leu Ala Ala Pro Leu Gly
1               5                   10                  15

Val Leu Ser Glu Leu Thr Leu Gln Glu Ala Gly Pro Gly Leu Val Lys
            20                  25                  30

Pro Ser Glu Thr Leu Ser Leu Thr Cys Leu Val Ser Gly Gly Ser Val
        35                  40                  45
```

```
Asn Ser Gly Tyr Tyr Trp Ser Trp Ile Arg Arg Pro Gly Gly Glu
        50                  55                  60

Leu Glu Trp Met Gly Tyr Trp Ser Gly Thr Thr His Tyr Asn Pro Thr
65                  70                  75                  80

Phe Gln Gly Arg Ile Ser Ile Thr Thr Asp Thr Ala Thr Asn Gln Phe
                85                  90                  95

Phe Leu Gln Leu Thr Ser Val Thr Thr Glu Asp Thr Ala Val Tyr Phe
            100                 105                 110

Cys Ile Arg Leu Tyr Arg Ser Asn Tyr Leu Leu Asp Phe Trp Gly Gln
        115                 120                 125

Gly Thr Leu Val Thr Val
        130

<210> SEQ ID NO 889
<211> LENGTH: 402
<212> TYPE: DNA
<213> ORGANISM: canis familiaris;

<400> SEQUENCE: 889
atgcagatgc cgtggtccct cctctgcctg ctggcagctc ccctgggtgt cctgtctgaa      60
ctcacactcc aggaggcagg gccaggactg gtgaagccct cagagaccct ctctctcacc     120
tgtcttgtgt ccggaggctc cgtcaacagc ggttattact ggagttggat ccgtcgacgc     180
cctgggggag aattggaatg gatgggatac tggtcaggta cgacccacta caacccgaca     240
ttccagggac gcatttccat tactactgat acggccacga accaattctt cctccagctg     300
acttccgtga ccaccgaaga cacggccgtt tatttctgta tacgactcta taggcctaac     360
tactttcttg acttttgggg tcagggaacc ctggtcaccg tc                        402

<210> SEQ ID NO 890
<211> LENGTH: 134
<212> TYPE: PRT
<213> ORGANISM: canis familiaris;

<400> SEQUENCE: 890

Met Gln Met Pro Trp Ser Leu Leu Cys Leu Leu Ala Ala Pro Leu Gly
1               5                   10                  15

Val Leu Ser Glu Leu Thr Leu Gln Glu Ala Gly Pro Gly Leu Val Lys
            20                  25                  30

Pro Ser Glu Thr Leu Ser Leu Thr Cys Leu Val Ser Gly Gly Ser Val
        35                  40                  45

Asn Ser Gly Tyr Tyr Trp Ser Trp Ile Arg Arg Pro Gly Gly Glu
    50                  55                  60

Leu Glu Trp Met Gly Tyr Trp Ser Gly Thr Thr His Tyr Asn Pro Thr
65                  70                  75                  80

Phe Gln Gly Arg Ile Ser Ile Thr Thr Asp Thr Ala Thr Asn Gln Phe
                85                  90                  95

Phe Leu Gln Leu Thr Ser Val Thr Thr Glu Asp Thr Ala Val Tyr Phe
            100                 105                 110

Cys Ile Arg Leu Tyr Arg Pro Asn Tyr Phe Leu Asp Phe Trp Gly Gln
        115                 120                 125

Gly Thr Leu Val Thr Val
        130

<210> SEQ ID NO 891
<211> LENGTH: 384
```

```
<212> TYPE: DNA
<213> ORGANISM: canis familiaris;
<220> FEATURE:
<221> NAME/KEY: UNSURE
<222> LOCATION: (128)..(128)
<223> OTHER INFORMATION: n is a, c, t, or g

<400> SEQUENCE: 891
atgcagatgc cgtggtccct cctctgcctg ctggcagctc ccctgggtgt cctgtctgaa      60
gtcatactgc aggagtccgg gccaggactg gtgaagccct cacagaccct ctctctcacc     120
tgtacggngt ccggaggctc cgtcaccgac attcactact ggagctggat ccgccagcgc     180
cctgacaggg gactggaatg gatgggatac tggagaggtg gcacaaatca acccggca      240 ttccaggaac gcatctccat cactgctgac gggaccaaaa accacctctc cctgcaattg     300
acctccacga ccaccgagga cacggccgtc tattactgta caagaaactc agacgtctgg     360
ggccagggca ccctggtcac cgtc                                            384

<210> SEQ ID NO 892
<211> LENGTH: 128
<212> TYPE: PRT
<213> ORGANISM: canis familiaris;
<220> FEATURE:
<221> NAME/KEY: UNSURE
<222> LOCATION: (43)..(43)
<223> OTHER INFORMATION: X is any amino acid

<400> SEQUENCE: 892

Met Gln Met Pro Trp Ser Leu Leu Cys Leu Leu Ala Ala Pro Leu Gly
 1               5                  10                  15

Val Leu Ser Glu Val Ile Leu Gln Glu Ser Gly Pro Gly Leu Val Lys
            20                  25                  30

Pro Ser Gln Thr Leu Ser Leu Thr Cys Thr Xaa Ser Gly Gly Ser Val
        35                  40                  45

Thr Asp Ile His Tyr Trp Ser Trp Ile Arg Gln Arg Pro Asp Arg Gly
    50                  55                  60

Leu Glu Trp Met Gly Tyr Trp Arg Gly Gly Thr Asn His Asn Pro Ala
65                  70                  75                  80

Phe Gln Glu Arg Ile Ser Ile Thr Ala Asp Gly Thr Lys Asn His Leu
                85                  90                  95

Ser Leu Gln Leu Thr Ser Thr Thr Thr Glu Asp Thr Ala Val Tyr Tyr
            100                 105                 110

Cys Thr Arg Asn Ser Asp Val Trp Gly Gln Gly Thr Leu Val Thr Val
        115                 120                 125

<210> SEQ ID NO 893
<211> LENGTH: 399
<212> TYPE: DNA
<213> ORGANISM: canis familiaris;

<400> SEQUENCE: 893
atggactgca gctggagaat cttcttcctg ctggcactgg ccacaggtgt gcactctgag      60
gtccagctgg tgcagtctgc agctgaggtt aagaagccag ggcatctgt gaaggtctcc      120 tgcaagacat ctggatacat cttcattgac cagtatatgc actgggtaca gcaggctcca     180
ggagcagggc ttgaatggat gggatggatt gatcctgagg atggtaccac aagttatgca     240
cagaagttcc agggcagagt caccctgacg gcagacacat ccacaaacac agtctatatg     300
gagctgagca atctgagaac tgaggacaca gctgtgtact actgtgcaag ggatatatgg     360
```

```
gattttgact actggggcca gggaaccctg gtcaccgtc                          399
```

<210> SEQ ID NO 894
<211> LENGTH: 133
<212> TYPE: PRT
<213> ORGANISM: canis familiaris;

<400> SEQUENCE: 894

```
Met Asp Cys Ser Trp Arg Ile Phe Phe Leu Leu Ala Leu Ala Thr Gly
1               5                   10                  15

Val His Ser Glu Val Gln Leu Val Gln Ser Ala Ala Glu Val Lys Lys
            20                  25                  30

Pro Gly Ala Ser Val Lys Val Ser Cys Lys Thr Ser Gly Tyr Ile Phe
        35                  40                  45

Ile Asp Gln Tyr Met His Trp Val Gln Gln Ala Pro Gly Ala Gly Leu
    50                  55                  60

Glu Trp Met Gly Trp Ile Asp Pro Glu Asp Gly Thr Thr Ser Tyr Ala
65                  70                  75                  80

Gln Lys Phe Gln Gly Arg Val Thr Leu Thr Ala Asp Thr Ser Thr Asn
                85                  90                  95

Thr Val Tyr Met Glu Leu Ser Asn Leu Arg Thr Glu Asp Thr Ala Val
            100                 105                 110

Tyr Tyr Cys Ala Arg Asp Ile Trp Asp Phe Asp Tyr Trp Gly Gln Gly
        115                 120                 125

Thr Leu Val Thr Val
    130
```

<210> SEQ ID NO 895
<211> LENGTH: 396
<212> TYPE: DNA
<213> ORGANISM: canis familiaris;

<400> SEQUENCE: 895

```
tggtcccctc tcctcctcac catcctcgct cactgcacag gtcctgggc ccagtctcta    60
ctgactcagc cggcctcagt gtccgggtcc ctgggccaga gggtcaccct ctcctgcact   120
ggaagcggct ccaacatcgg tagaggttat gtgggctggt accaacacct cccggggaca   180
ggcccagaa ccctcatcta tggtgatatt aaccgaccct caggggtccc cgatcggttc    240
tctggctcca ggtcaggcat cacagccacc ctgaccatct ctgggctcca ggctgaggat   300
gaggctgatt attactgttc atcgtgggac tacagtctca gtagtacttt gttcggcgga   360
ggcacccacc tgaccgtcct cggtcagccc aaggcc                             396
```

<210> SEQ ID NO 896
<211> LENGTH: 414
<212> TYPE: DNA
<213> ORGANISM: canis familiaris;
<220> FEATURE:
<221> NAME/KEY: UNSURE
<222> LOCATION: (343)..(344)
<223> OTHER INFORMATION: n is a, c, t, or g
<220> FEATURE:
<221> NAME/KEY: UNSURE
<222> LOCATION: (349)..(349)
<223> OTHER INFORMATION: n is a, c, t, or g

<400> SEQUENCE: 896

```
atgacctcca ccatgggctg gtcccctctc ctcctcacca tcctgctcca ctgcacaggg    60
tcctgggccc aatctgttct gactcagccg gcctcagtgt ccgggtccct gggccagacg   120
```

-continued

```
gtcaccatct cctgcactgg aagcgaatcc aacatcggta gaggttttgt tggctggtac    180
caacagatcc cgggaacagg ccccagaacc gtcatttacg gtcataatca ccgaccctca    240
ggggtccccg aacggttctc tggccccagg tccggcatca cctctaccct gaccatctct    300
ggactccggg ctgaggatga gggtgattat tattgttcat ccnnggacnc tagtctcagt    360
gtcgttctgt tcggcggagg cacccacctg accgtcctcg gtcagcccaa ggcc          414
```

<210> SEQ ID NO 897
<211> LENGTH: 345
<212> TYPE: DNA
<213> ORGANISM: canis familiaris;

<400> SEQUENCE: 897

```
agtctgtgct tgactcagcc ggcctcagtg tccgggtccc tgggccagag ggtcaccatc     60
tcctgcactg gaagcagctc aacgtcggt agaggttatg tgggctggta ccaacagttc    120 ccggagcgg gccccagaac cctcatctat ggtaataata tcggccctc aggggtcccc    180 gatcggttct ctggctccac gtcaggcagc acagccactc tgaccatctc tggcctccgg    240
gctgaggatg aggctgatta ttactgctca tcgtgggacg ccagtcgcag tgttactgtc    300
ttcggcggag gcacccacct ggccgtcctc ggtcagccca aggcc                   345
```

<210> SEQ ID NO 898
<211> LENGTH: 303
<212> TYPE: DNA
<213> ORGANISM: canis familiaris;

<400> SEQUENCE: 898

```
cttggccaga gggtcaccat ttcctgctct ggaagtacgt acaacatcgg tagtgttggt     60
gcgacctggt accaacagct cccagggagg tcccctaaac ttctcgtcta tagtgatggg    120
catcgcccgt caggggttcc tgaccggttc tccggctcca agtctgacaa ctctgccacc    180
ctgaccttca ctgggcttca ggctgaggac gaggctgatt attattgtca gtctcttgat    240
tccaacctcg ggcctgtgtt cggcggaggc acccacctga ccgtcctcgg tcagcccaag    300
gcc                                                                  303
```

<210> SEQ ID NO 899
<211> LENGTH: 414
<212> TYPE: DNA
<213> ORGANISM: canis familiaris;

<400> SEQUENCE: 899

```
atgacctcca ccatggcctg gttccctctc ctcctgaccc tccttgctca ctacacaggg     60
tcctgggccc agtctgtgct gactcagccg gcctcagtgt ctgggtccct gggccagagg    120
atcaccatct cctgcactgg aagcggttcc aacattggag gtaataatgt gggttggtac    180
cagcagctcc caggaagagg ccccagaact gtcatctatg atacttatag tcgactctcg    240
ggggtgcccg atcgattctc tggctccaag tctggcagca cagccaccct gaccatctct    300
gggctccagg ctgaggatga ggctgattat tactgctcaa cgtgggatga tagtctccgt    360
gcttacttgt tcgggtcagg aacccaactg accgttcttg gtcagcccaa ggcc          414
```

<210> SEQ ID NO 900
<211> LENGTH: 414
<212> TYPE: DNA
<213> ORGANISM: canis familiaris;

<400> SEQUENCE: 900

```
atgacctcca ccatgggctg gtccctctc ctccttaccc tcctcgctca ctgcacaggt    60
tcctgggccc agtctgcgct gactcagccg gcctcagtga ctgggtccct gggccagagg   120
gtcaccatct cctgcactgg aagcagctcc aacatcggtg gatataatgt tggctggttc   180
caacaggtcc cgggaacagg ccccagaacc gtcatctata gtcgtagtaa tcgaccctcg   240
ggggtcccgg atcgattctc tggctccagg tcaggcagca cagccaccct gaccatctct   300
ggcctccagg cagaagacga ggctgaatat tactgctcaa catgggacag cagtctcaaa   360
gctcctgtgt cggcggagg cacccacctg accgtcctcg gtcagcccaa ggcc          414
```

<210> SEQ ID NO 901
<211> LENGTH: 414
<212> TYPE: DNA
<213> ORGANISM: canis familiaris;

<400> SEQUENCE: 901

```
atgacctcca ccatggcctg gtcctctttc ctcctcaccc tcctcgctca cttcacaggt    60
tcctgggccc agtctgtgct gactcaacca gcctcagtgt ccgggtctct gggccagagg   120
gtcaccatct cctgcactgg aagcagctcc aacattggta gagattatgt gggctggtac   180
caacagctcc cgggaacacg ccccagaacc ctcatctatg gtaatagtaa ccgaccctcg   240
ggggtccccg atcgattctc tggctccaag tcaggcagca cagccaccct gaccatctct   300 ggctccagg ctgaggacga ggctgattat tactgctcta catgggacaa cagtctcact   360
gttcctgtgt cggcggagg cacccacctg accgtcctcg gtcagcccaa ggcc          414
```

<210> SEQ ID NO 902
<211> LENGTH: 374
<212> TYPE: DNA
<213> ORGANISM: canis familiaris;
<220> FEATURE:
<221> NAME/KEY: UNSURE
<222> LOCATION: (299)..(299)
<223> OTHER INFORMATION: n is a, c, t, or g
<220> FEATURE:
<221> NAME/KEY: UNSURE
<222> LOCATION: (333)..(333)
<223> OTHER INFORMATION: n is a, c, t, or g

<400> SEQUENCE: 902

```
atgacctcca ccatgggctg gtccctctc ctcctcaccc tcctcgctca ctgcacaggt    60
tcctgggccc agtctgtact gactcagccg gcctcagtgt ctgggtccct gggtcagagg   120
gtcaccatct cctgcactgg aagcagctcc aacctcggta gatatggtgt tgcctggttc   180
cagcagctcc cgggaaaagg ccccagaacc gtcatctata gtattgataa ccgaccctca   240
ggggtccctg atcgattctc tggctccaag tcccgcagta cagccaccct gaccatctnt   300 ggctccagg ctgaggacga ggctgattat ttntgctcaa catacgacac caggctcggt   360
actagtgtgt tcgt                                                    374
```

<210> SEQ ID NO 903
<211> LENGTH: 414
<212> TYPE: DNA
<213> ORGANISM: canis familiaris;

<400> SEQUENCE: 903

```
atgacctcca ccatgggctg gtccctctc ctcctcacca tcctcgctca ctgcacaggg    60
tcctgggccc aatctctact gacgcagccg gcctcagtgt ccgggtccct gggccagagg   120
```

```
gtcaccatct cctgcaccgg aaccacctcc aacattggta gaggttttgt gggctggttt    180
caagaactcc cgggaacagg ccccaaaatt ctcatctatg gcaatggtaa ccgaccctca    240
ggggtccccg atcgattctc tggctccacg tcaggcaaca cagccaccct gaccatctct    300
gggctccagc ctgaggatga gactgattat tactgttcat cgtgggacaa caatctcata    360
aaaattttgt tcggcggagg cactcatctg accgtcctcg gtcagcccaa ggcc          414
```

<210> SEQ ID NO 904
<211> LENGTH: 414
<212> TYPE: DNA
<213> ORGANISM: canis familiaris;
<220> FEATURE:
<221> NAME/KEY: UNSURE
<222> LOCATION: (28)..(28)
<223> OTHER INFORMATION: n is a, c, t, or g

<400> SEQUENCE: 904

```
atgacctcca ccatgggctg gttccctntg ctcctcaccc tcctggctca ctgcacaggt    60
tcctgggccc agtctgtgct gactcagccg gcctcagtgt ctgggtccct gggccagaag    120
gtcaccatct cctgcactgg gagcagctcc aacataggta gtggttatgt gggctggtac    180
cagcagctcc caggaacagg ccccagaacc ctcatctata gtagtagtaa ccgaccttcg    240
ggggtccccg atcgattctc tggctccacg tcaggcagca cggcaaccct gaccatctct    300
gggctccagg ctgaggacga ggctgattat tactgctcaa catatgacag cactctcaat    360
gctgttgtgt tcggcggagg cacccacctg accgtcctcg gtcagcccaa ggcc          414
```

<210> SEQ ID NO 905
<211> LENGTH: 414
<212> TYPE: DNA
<213> ORGANISM: canis familiaris;

<400> SEQUENCE: 905

```
atgacctcca ccatgggctg gtccctctc ctccttaccc tcctcgctca ctgcacaggt    60
tcctgggccc agtctgtgct gactcagccg gcctcagtga ctgggtccct gggccagagg    120
gtcaccatct cctgcactgg aagcagctcc aacatcggtg gatataatgt taattggttc    180
caacagttcc cgggaaaagg ccccaaaacc gtcatctata gtagtactga ccgaccctcg    240
ggggtcccgg atcgattctc cgggtccagg tcaggcacca cagccaccct gaccatctct    300
ggactccagg ctgaggacga ggctgactat tattgctcag catgggacaa cagtctcaaa    360
cttcctctgt tcggcggagg cacacacctg accgtcctcg gtcagcccaa ggcc          414
```

<210> SEQ ID NO 906
<211> LENGTH: 402
<212> TYPE: DNA
<213> ORGANISM: canis familiaris;

<400> SEQUENCE: 906

```
atgggctggt cccctctcct cctcaccatc ctcgctcact gcacagggtc ctgggcccag    60
tctgtgctga ctcagccggc tcagtgtcc gggtccctgg ccagagggt caccatctcc    120 tgcactggaa gcagctccaa catcggtgga ggttatgtgg ctggtacca acaactcccg    180 ggaacaggcc ccaaaaccct catctatggt gatagtaacc gaccctcagg ggtcccgat    240 cggttctctg gctccaggtc aggcagcaca gccaccctga ccatctctgg gctccagcct    300
gaggatgagg ctgattatta ctgctcatcg tgggacaccg gtctcagtgc tcttgtgttc    360
ggcggaggca cccacctgac cgtcctcagt cagcccaagg cc                      402
```

<210> SEQ ID NO 907
<211> LENGTH: 414
<212> TYPE: DNA
<213> ORGANISM: canis familiaris;

<400> SEQUENCE: 907

```
atgtcctccg acatggcctg gtcccctctc ctcttcacac tcctcgctca ctgcacaggg      60
tcctgggccc aggctgtgct gaatcagccg gcctcagtgt ctggggccct gggccagaag     120
gtcaccatct cctgctctgg aagcacaaat gacattgata tatttggtgt gagctggtac     180
caacagctcc caggaaaggc ccctaaactc ctcgtggaca gtgatgggga tcgaccctca     240
ggggtccctg acagattttc tggctccagc tctggcaact caggcaccct gaccatcact     300
ggctccagg ctgaggacga ggctgattat tactgtcagt ctgttgattc cacgcttggt     360
gctattgtgt tcggcggagg cacccatctg accgtcctcg gtcagcccaa ggcc          414
```

<210> SEQ ID NO 908
<211> LENGTH: 414
<212> TYPE: DNA
<213> ORGANISM: canis familiaris;
<220> FEATURE:
<221> NAME/KEY: UNSURE
<222> LOCATION: (359)..(359)
<223> OTHER INFORMATION: n is a, c, t, or g

<400> SEQUENCE: 908

```
atgatcttca ccatggcctg gtcccctctc ctcctcggcc tccttgctca ctgcacaggg      60
tcctgggccc agtctatact gactcagcca gcctcagtgt ctgggtccct gggccagaag     120
gtcaccatct cctgctctgg agacagttcc aacatcggtg ataattttgt ggcctggtac     180
caacaactcc caggaatagg cccaaaaacc gtcatctatg gtactattta ccgaccttca     240
ggggtccccg atcgattttc tggctccaag tcaggcaatt cagccaccct gaccatctct     300
ggctccagc ctgaggacga ggctgaatat tactgtcat catgggatga tagtctcana     360
ggtattgtgt tcggcggagg cacccttctg accgtcctcg gtcagcccaa ggcc          414
```

<210> SEQ ID NO 909
<211> LENGTH: 393
<212> TYPE: DNA
<213> ORGANISM: canis familiaris;

<400> SEQUENCE: 909

```
atgacctcca ccatgggctg gtcccctctc ctcctcaccc tcctcgctca ctgcacaggt      60
tcctgggccc agtctgtgct gactcagccg gcctcaatgt ctgggtccct gggccagaag     120
gtcaccatct cctgcactgg aagcagctcc aacatcggta aatatgttgt cggctggttc     180
cagcagtttc cgggagaagg ccccagaacc gtcatctata gtactagtta tcgaccctca     240
ggggtccctg atcgattctc tggctccaag tcaggcagca cagccaccct gaccatctct     300
gaactccagg ctgaggacga ggctgattat tactgtcaa catacgacag cagtctcggt     360
ggtagtgtgt tcggcggagg cacccatcat gac                                 393
```

<210> SEQ ID NO 910
<211> LENGTH: 408
<212> TYPE: DNA
<213> ORGANISM: canis familiaris;

<400> SEQUENCE: 910

```
atgacctcca ccatgggatg gttccctctg ctcctcaccc tcctggctca ctgcacaggt    60
tcctgggccc agtctgtgct gactcagccg gcctcagtgt ctgggtccct gggccagagg   120
gtcaccatct cctgcactgg aagcagctcc aacatcggta gaggttatgt gggctggtac   180
cggcagctcc caggaacagg ccccacaacc ctcatctatg atgatagtag ccgaccctcg   240
ggggtcccta tcgattctc tggctccagg tcaggcagca ctgcaaccct gaccatctcg   300
ggcctccagg ctgacgacga ggctgattat tactgctcag catatgacag cactctcact   360
ggtactgtat tcggcggagg cacccacctg accgtcctcg gtcagccc               408
```

<210> SEQ ID NO 911
<211> LENGTH: 414
<212> TYPE: DNA
<213> ORGANISM: canis familiaris;

<400> SEQUENCE: 911

```
atgacctcca ccatgggatg gttccctctg ctcctcaccc tcctggctca ctgcacaggt    60
tcctgggccc agtctgtgct gactcagccg gcctcagtgt ctgggtccct gggccagagg   120
gtcaccatct cctgcactgg aagcagctcc aacatcggta gagattatgt ggcctggtac   180
caacagttcc caggaacagg ccccagaatc ctcatctatg atactcgtag ccgaccctcg   240
ggggtccctg atcgattctc tggctccagg tcaggctaca cagctgccct gaccatctct   300
ggactccagg ctgaggacga ggctgactat tactgctcaa catatgacag cagtctcagt   360 ggtcctctt tcggcggagg cacccacctg accgtcctcg gtcagcccga ggcc          414
```

<210> SEQ ID NO 912
<211> LENGTH: 411
<212> TYPE: DNA
<213> ORGANISM: canis familiaris;
<220> FEATURE:
<221> NAME/KEY: UNSURE
<222> LOCATION: (18)..(18)
<223> OTHER INFORMATION: n is a, c, t, or g

<400> SEQUENCE: 912

```
atgacctcca acatggcntg gtcccctttc ctcctcacac tccttgctta ctgcacagga    60
tcctgggccc agtctgcgct gactcagccg acctcagtgt cggggtccct tggccagagg   120
gtctccattt cctgctctgg aagcacgagc aacatcggta ttgtcggtgc gagctggtac   180
caacaactcc caggaaaggc ccctaaactc ctcctgaaca gtgatgggag tcgaccgtca   240
ggggtccctg accggttttc cggctccaac tctggcgcct cagccaccct gaccatcact   300
gggcttcagg ctgaggacga ggctgattat tactgtcagt cttttgatcc cacgcctcct   360
gatcattacg tgttcggctc aggaacccaa ctgaccgtcc ttggtcagcc c             411
```

<210> SEQ ID NO 913
<211> LENGTH: 413
<212> TYPE: DNA
<213> ORGANISM: canis familiaris;

<400> SEQUENCE: 913

```
atgacctcca ccatgggctg gtcccctctc ctccttaccc tcctcgctca ctgcacaggt    60
tcctgggccc agtctgtact gactcagccg gcctcagtga gtgggtcctt gggccagagg   120
gtcaccatct cctgcactgg aagcccctcc aacatcggtg gatatgatgt tgcctggctc   180
cagcagctcc cggaacagg ccccaagacc gtcatctata gtagtactaa ccgaccctcg   240
ggggtcccgg atcgattctc cggctccagg tcaggcagca cagccaccct gaccatctct   300
```

```
gggctccagg ctgaggacga ggctgactat tactgttccg catgggacag cactctcaga    360
gctggtgtgt tcggcggagg cacccacctg accgtcctcg gtcagcccaa ggc           413

<210> SEQ ID NO 914
<211> LENGTH: 405
<212> TYPE: DNA
<213> ORGANISM: canis familiaris;

<400> SEQUENCE: 914
atgacctcca ccatgggctg gtcccctctc ctccttaccc tcctcgctca ctgcacaagt     60
tcctgggccc agtctgtgct gactcagccg cctcagtga ctgggtccct gggccagagg    120
gtcaccatct cctgcactgg aagcagctcc aacatcggtg gatatagtgt tgcctggttc    180
cagcagctcc cgggaacagg ccccagaacc gtcatctata gtaatactaa gcgaccctcg    240
ggggtcccgg atcgattctc tggctccagg tcaggcagca cagccaccct gaccatctct    300
gggctcctgg ctgaggacga cgctgattat tattgctcaa catgggacag cagtctcaaa    360
gctcttctgt tcggcggagg cacccatctg accgtcctcg gtcag                    405

<210> SEQ ID NO 915
<211> LENGTH: 351
<212> TYPE: DNA
<213> ORGANISM: canis familiaris;

<400> SEQUENCE: 915
tcctgggccc actctgtcct gactcagccg cctcagtgt ctgggtttct gggccagagg      60
gtcaccatct cctgcactgg aagcagctcc aacattggtg gaaattatgt gagctggcac    120
cagcaggtcc cagaaacagg ccccagaaac atcatctatg ctgataacta ccagcctcg     180 ggggtccctg atcgatttc tggctccaag tcaggcagca cagccaccct gaccatctct     240
gtgctccagg ctgaggatga ggctgattat tactgccagt cctttgatac cgctcttggt    300
actgtgttcg gcggaggcac ccacctgacc gtcctcggtc agcccagggc c             351

<210> SEQ ID NO 916
<211> LENGTH: 414
<212> TYPE: DNA
<213> ORGANISM: canis familiaris;

<400> SEQUENCE: 916
atgacctcca ccatggcctg gttccctctc ctcctgaccc tccttgctca ctacacaggg     60
tcctgggccc agtctgtgct gactcagccg cctcagtgt ccgggtccct gggccagagg    120
gtcaccgtct cctgcactgg aagcaactcc aacatcggtc gaggttatgt ggactggtac    180
caacaactcc cgggaagagg ccccacaacc ctcttgtatg gtactgctaa ccgcccctca    240
ggggtccccg atcggttctc tggctccagg tcaggacgca cagccaccct gaccatctct    300
gggctccagg ctgaggatga ggctgattat tactgctcat cgtgggacga cggtctcagg    360
gctctcgtgt tcggctcagg aacccacctg accgcccttg tcagcccaa ggcc           414

<210> SEQ ID NO 917
<211> LENGTH: 384
<212> TYPE: DNA
<213> ORGANISM: canis familiaris;

<400> SEQUENCE: 917
ctcctcacca tcctcgctca ctgcacaggg tcctgggccc agtctctact gactcagcca     60
```

```
gcctcagtgt ctgggtccct gggccagaag gtcaccatct cctgcactgg aagcaactcc      120
aacatcggtg gtaatgatgt ggcctggtat caacagctcc aggaataggg ccctagaacc      180
gtcatctatg gtaaaaataa ccgaccttca ggaatctccg atcgattctc tggctccaag      240
tcaggcaatt cagccagttt gaccatatct gggctccagg ctgaggacga ggctgattat      300
ttctgctcat catgggatga tagtctcaaa ggtcacgtgt tcggctcagg aacccaactg      360
accgtccttg gtcagcccaa ggcc                                             384

<210> SEQ ID NO 918
<211> LENGTH: 414
<212> TYPE: DNA
<213> ORGANISM: canis familiaris;

<400> SEQUENCE: 918
atgacctcca ccatggcctg gttccctctc ctcctgaccc tccttgctca ctacacaggg       60
tcctgggccc agtctgtgct gactcagccg gcctcagtgt ctgggtccct gggccagagg      120
atcaccatct cctgcactgg aagcgtctcc aacattggca ttttttgatgt gggttggtat      180 caacaactcc aggaagaggc cccagaact gtcatctatt ctacaaacag tcgcccctcg       240
ggggtgcccg atcgattttc tggctccaag tctggcagca cagccaccct gaccatctct      300
gggctccagg ctgaggatga ggctgattat tactgctcaa cgtgggatga gaatctcagt      360
gttcccgtgt tcggcggagg cacccacctg accgtcctcg gtcagcccaa ggcc            414

<210> SEQ ID NO 919
<211> LENGTH: 411
<212> TYPE: DNA
<213> ORGANISM: canis familiaris;

<400> SEQUENCE: 919
atgacctcca ccatggcctg gtcctctttc ctcctcaccc tcctgctcca cttcacaggt       60
tcctgggccc agtctgtact gactcaacca gcctcagtgt ccgggtctct gggccagagg      120
gtcaccatct cgtgcactgg aagcggctcc aacattggta gagattctgt gggctggtac      180
caacaggtcc cgggaacacg cccagaacc ctcatctatg gtactactaa ccgaccctcg       240
ggggtccccg atcgattctc tggctccaag tcaggcagca cagccaccct gaccatctct      300
ggcctccagg ctgaggacga ggctgattat tactgctcta catgggacaa cagtgtcact      360
gttctgttcg gcggaggcac ccatctgacc gtcctcagtc agcccaaggc c                411

<210> SEQ ID NO 920
<211> LENGTH: 411
<212> TYPE: DNA
<213> ORGANISM: canis familiaris;

<400> SEQUENCE: 920
atgatcttca ccatggcctg gtcccctctc ctcctcggcc tccttgctca ctgcacaggg       60
tcctgggccc agtctgtatgct gactcagcca gcctcagtgt ctgggtccct gggccagacg    120
gtcaccatct cctgcactgg aagtagctcc aacatcggtg gtaatcaagt gggctggtac      180
caacagttcc aggaagaggc cctagaagc gtcatctatg gtgataatca tcgaccctca       240
ggggtccccg atcgattctc tgtctccaag tcaggcagtt cagccaccct gaccatctct      300
ggactccagg ctgaggacga ggctgaatat tactgctcat catgggataa tgatttcggt      360
cacgtgttcg gctcaggaac ccaactgacc gtccttagtc agcccaaggc c                411
```

<210> SEQ ID NO 921
<211> LENGTH: 414
<212> TYPE: DNA
<213> ORGANISM: canis familiaris;

<400> SEQUENCE: 921

| | | | | | |
|---|---|---|---|---|---|
| atgacctcca | acatggcctg | gtcccctctc | ctcctcacac | tccttgctta | ctgcacaggg | 60 |
| tcctgggccc | agtctgtgct | gactcagccg | acctcagtgt | cggggtccct | tggccagagg | 120 |
| gtcaccatct | cctgctctgg | aagcacgaac | gacatcgcta | ttgttggtgc | gagctggtac | 180 |
| cagcagctcc | caggaaaggc | ccctaaactc | ctcgtgtaca | cttttgggga | tcggccgtca | 240 |
| ggggtccctg | accggttttc | cggctccaac | tctggcaact | cagccaccct | gaccatcact | 300 |
| ggcttcagg | ctgaggacga | ggctgattat | tactgccagt | cctttgatac | cacgcttggt | 360 |
| gcttacgtct | tcggctcagg | aacccaactg | accgtccttg | gtcagcccaa | ggcc | 414 |

<210> SEQ ID NO 922
<211> LENGTH: 407
<212> TYPE: DNA
<213> ORGANISM: canis familiaris;

<400> SEQUENCE: 922

| | | | | | |
|---|---|---|---|---|---|
| atgatcttca | ccatggcctg | gtcccctctc | ctcctcggcc | tccttgctca | ctgcacaggg | 60 |
| tcctgggccc | agtctatcct | gactcagcca | gcctcagtgt | ctgggtccct | gggccagaag | 120 |
| gtcaccatct | cctgcactgg | aagcagctcc | aatatcggtg | gtaattatgt | gggctggtac | 180 |
| caaaatctcc | caggaaaagg | ccctaaaacc | gtcatctttg | ctgatgatca | ccgaccttca | 240 |
| ggggtccccg | atcgattctc | tggctccagg | tcaggcagtt | cagccaccct | gaccatttct | 300 |
| gggctccagg | ctgaggacga | ggctgactat | tattgttcat | catgggatag | gagtctcaga | 360 |
| ggtcaggttt | tcggcggagg | cacccacctg | accgtcctcg | gtcagcc | 407 |

<210> SEQ ID NO 923
<211> LENGTH: 414
<212> TYPE: DNA
<213> ORGANISM: canis familiaris;

<400> SEQUENCE: 923

| | | | | | |
|---|---|---|---|---|---|
| atgacctcca | ccatgggctg | gttccctctg | ctcctcaccc | tcctggctca | ctgcacaggt | 60 |
| tcctgggccc | agtctgtgct | gactcagccg | gcctcagtgt | ctgggcccct | gggccagaag | 120 |
| gtcaccatct | cctgcactag | aagcagctcc | aacattgctg | gtggttatgt | ggcctggtac | 180 |
| cagcagatcc | caggaacagg | ccccagaacc | ctcatctata | gtactactgt | ccgaccttcg | 240 |
| ggggtccccg | atcgattctc | tggctccagg | tcaggcagca | cagcaaccct | gaccatctct | 300 |
| gggctccagg | ctgaggacga | ggctgattat | tattgctcag | gatatgacac | cactgtcaat | 360 |
| ggtgttgtct | tcggcggagg | cacccatctg | accgtcctcg | gtcagcccaa | ggcc | 414 |

<210> SEQ ID NO 924
<211> LENGTH: 411
<212> TYPE: DNA
<213> ORGANISM: canis familiaris;

<400> SEQUENCE: 924

| | | | | | |
|---|---|---|---|---|---|
| atgacctcca | ccatgggctg | gtcccctctc | ctcctcacca | tcctcgctca | ctgcacaggg | 60 |
| tcctgggccc | agtctgtgct | gactcagccg | gcctcagtgt | ccgggtccct | gggccagagg | 120 |
| gtcaccatct | catgcactgg | aagcgggtcc | aacatcggga | gaggttatgt | gggctggtac | 180 |

| | | |
|---|---|---|
| caacagtacc cgggaacagg ccccaaaacg ctaatctatg gtgatagtag tcgaccctca | 240 | |
| ggggtccccg atcggttctc tgcctccagg tcaggcaact cagccaccct gaccatctct | 300 | |
| ggctccagg ctgaggatga ggcggattat tactgttcat cgtgggacac cagtctcaga | 360 | |
| actatattcg gcggaggcac ctatctgacc gtcgtcggtc agcccaaggc c | 411 | |

<210> SEQ ID NO 925
<211> LENGTH: 411
<212> TYPE: DNA
<213> ORGANISM: canis familiaris;

<400> SEQUENCE: 925

| | |
|---|---|
| atgacctcca ccatgggctg gttccctctg ctcctcaccc tcctggctca ctgcacaggt | 60 |
| tcctgggccc agtctctgct gactcagccg gcctcagtgt ctgggtccct gggacagaag | 120 |
| gtcaccatct cctgcactgg aagcagtgcc tacattggta gtggctatgt gggctggtac | 180 |
| cagcaggtcc caggaacagg ccccagaacc ctcattcata gtaccagtaa ccgacccccg | 240 |
| ggggtccccg atcgattctc tgcctccgcg tcaggcagca cagcaaccct gaccatttct | 300 |
| gggctccagg ctgaggacga ggctgattat tactgctcag cctctgacag cagtctcagt | 360 |
| gttgtgttcg gcggaggcac ccacctgacc gtcctcggtc agcccaaggc c | 411 |

<210> SEQ ID NO 926
<211> LENGTH: 408
<212> TYPE: DNA
<213> ORGANISM: canis familiaris;

<400> SEQUENCE: 926

| | |
|---|---|
| atggcctggt cccctctcct cctcacactc cttgcgtact gcacagggtc ctgggcccag | 60 |
| tctgtactga ctcagccgac ctcagtgtcg ggtcccttg gccagagggt caccatttcc | 120 |
| tgctctggaa gcacgaagaa catcggaatt tttggtgcgc actggtaccg acaattcccg | 180 |
| ggaaaggccc ctgaactcct catttataat agtagagaac gaccgtcagg ggtccctggc | 240 |
| cggttttccg gctccatctc tggcaactca gccaccctga ccatcactgg gcttcaggct | 300 |
| gaggacgagg ctgattatca ctgccagtct tttgatacca cgcttggtga tggtgatgtt | 360 |
| ttgttcggcg gcggcacccca cctgaccgtc ctcggtcagc ccaaggcc | 408 |

<210> SEQ ID NO 927
<211> LENGTH: 419
<212> TYPE: DNA
<213> ORGANISM: canis familiaris;

<400> SEQUENCE: 927

| | |
|---|---|
| aggatcagtg atgatcttca ccatggcctg gtcccctctc ctcctcggcc tccttgctca | 60 |
| ctgcacaggg tcctgggccc agtctatgct gactcagcca gcctcagtgt ctgggtccct | 120 |
| gggccagaag gtcaccatct cctgcactgg aagcagctcc aacatcggtg gtaattatgt | 180 |
| gggctggtac caacagctcc caggaatagg ccctagaacc gtcatctctg gtaataatta | 240 |
| ccgaccttca ggggtccccg atcgattctc tggctccaag tcaggcagtt cagccaccct | 300 |
| gaccatctct gggctccagg ctgaggacga ggctgagtat tactgctcat catgggatga | 360 |
| tagtctcaga atttctgtgt ttggcggagg caccccacctg accgtcctcg gtcagccca | 419 |

<210> SEQ ID NO 928
<211> LENGTH: 414
<212> TYPE: DNA
<213> ORGANISM: canis familiaris;

<400> SEQUENCE: 928

| | |
|---|---|
| atgacctcca ccatgggctg gtcccctctc ctccttaccc tcctcgctca ctgcacaggt | 60 |
| tcctgggccc agtctgtcct gactcagccg gcctcagtga ctgggtccct gggccagagg | 120 |
| gtcaccatct cctgcactgg aagcagctcc aacatcggtg gatctagtgt tggttggttc | 180 |
| cagcagttcc cgggaacagg ccccagaacc gtcatctata gtattagtag ccgaccctcg | 240 |
| ggggtcccgg atcgattctc tggctccagg tcaggcagca cagccatcct gaccatctct | 300 |
| gggctccagg ctgaggacga ggctgagtat tactgctcag catgggacag cagtctcaaa | 360 |
| gaagctgtgt tcggcggagg cacccacctg accgtcctcg gtcagcccaa ggcc | 414 |

<210> SEQ ID NO 929
<211> LENGTH: 411
<212> TYPE: DNA
<213> ORGANISM: canis familiaris;

<400> SEQUENCE: 929

| | |
|---|---|
| atgacctcca ccatggcctg gtcctctttc ctcctcaccc tcctcgctca cttcacaggt | 60 |
| tcctgggccc agtctgtact gactcaacca gcctcagtgt ccgggtctct gggccagagg | 120 |
| gtcaccatct cgtgcactgg aagcggctcc aacattggta gagattctgt gggctggtac | 180 |
| caacaggtcc cgggaacacg ccccagaacc ctcatctatg gtactactaa ccgaccctcg | 240 |
| ggggtccccg atcgattctc tggctccaag tcaggcagca cagccaccct gaccatctct | 300 |
| ggcctccagg ctgaggacga ggctgattat tactgctcta catgggacaa cagtgtcact | 360 |
| gttctgttcg gcggaggcac ccatctgacc gtcctcagtc agcccaaggc c | 411 |

<210> SEQ ID NO 930
<211> LENGTH: 411
<212> TYPE: DNA
<213> ORGANISM: canis familiaris;

<400> SEQUENCE: 930

| | |
|---|---|
| atgacctcca ccatggcctg gtcctctttc ctcctcaccc tcctcgctca cttcacaggt | 60 |
| tcctgggccc agtctgtact gactcaacca gcctcagtgt ccgggtctct gggccagagg | 120 |
| gtcaccatct cgtgcactgg aagcggctcc aacattggta gagattctgt gggctggtac | 180 |
| caacaggtcc cgggaacacg ccccagaacc ctcatctatg gtactactaa ccgaccctcg | 240 |
| ggggtccccg atcgattctc tggctccaag tcaggcagca cagccaccct gaccatctct | 300 |
| ggcctccagg ctgaggacga ggctgattat tactgctcta catgggacga cagtgtcact | 360 |
| gttctgttcg gcggaggcac ccatctgacc gtcctcagtc agcccaaggc c | 411 |

<210> SEQ ID NO 931
<211> LENGTH: 410
<212> TYPE: DNA
<213> ORGANISM: canis familiaris;

<400> SEQUENCE: 931

| | |
|---|---|
| atgacctcca ccatggctgg tcctctttcc tcctcaccct cctcgctcac ttcacaggtt | 60 |
| cctgggccca gtctgtactg actcaaccag cctcagtgtc cgggtctctg gccagaggg | 120 |
| tcaccatctc gtgcactgga agcggctcca acattggtag agattctgtg ggctggtacc | 180 |
| aacaggtccc gggaacacgc cccagaaccc tcatctatgg tactactaac cgaccctcgg | 240 |
| ggtccccga tcgattctct ggctccaagt caggcagcgc agccaccctg accatctctg | 300 |

```
gcctccaggc tgaggacgag gctgattatt actgctctac atgggacaac agtgtcactg    360
ttctgttcgg cggaggcacc catctgaccg tcctcagtca gcccaaggcc               410
```

<210> SEQ ID NO 932
<211> LENGTH: 414
<212> TYPE: DNA
<213> ORGANISM: canis familiaris;
<220> FEATURE:
<221> NAME/KEY: UNSURE
<222> LOCATION: (26)..(26)
<223> OTHER INFORMATION: n is a, c, t, or g
<220> FEATURE:
<221> NAME/KEY: UNSURE
<222> LOCATION: (28)..(28)
<223> OTHER INFORMATION: n is a, c, t, or g
<220> FEATURE:
<221> NAME/KEY: UNSURE
<222> LOCATION: (63)..(63)
<223> OTHER INFORMATION: n is a, c, t, or g
<220> FEATURE:
<221> NAME/KEY: UNSURE
<222> LOCATION: (79)..(79)
<223> OTHER INFORMATION: n is a, c, t, or g

<400> SEQUENCE: 932

```
atgacctcca ccatgggatg gttccntntg ctcctcaccc tcctggctca ctgcacaggt     60
tcntgggccc agtctgtgnt gactcagccg gcctcagtgt ctgggtccct gggcagagg    120 gtcaccacct cctgcactgg aagcagctcc aacatcggta gaggttttgt ggcctggcac   180
cagcaactcc caggaacagg ccccagaaca ctcatatatc gttctgagag gcggccctcg   240
ggggtccctg atcgattctc cggctccagg tcaggcagca cagcaaccct gaccatctct   300
gggctccagc ctgaggacga ggctgattat tactgttcag cacatgacaa cagtgtcagt   360
ggtgttgtgt tcggcggagg cacccatctg accgtcctcg gtcagcccaa ggcc         414
```

<210> SEQ ID NO 933
<211> LENGTH: 414
<212> TYPE: DNA
<213> ORGANISM: canis familiaris;

<400> SEQUENCE: 933

```
atgacctcca ccatggcctg gttccctctc ctcctgaccc tccttgctca ctacacaggg     60
tcctgggccc agtctgtgct gactcagccg gcctcagtgt ctgggtccct gggcagagg    120 atcaccgtct cctgcactgg cgcctactcc aacattggaa ctaataatgt gggttggtac   180
caacaactcc caggaagagg ccccagaact gtcatctata gtacagatag tcgaccctcg   240
ggggtgcccg atcgattctc tggctccagg tctggcacca ctgccaccct gaccatctct   300
gggctccagg ctgaggatga ggctgattat tactgctcag catgggatga tagtctcact   360
gcttacgtgt tcggctcagg gacccaactg accgtccttg gtcagcccaa ggcc         414
```

<210> SEQ ID NO 934
<211> LENGTH: 414
<212> TYPE: DNA
<213> ORGANISM: canis familiaris;

<400> SEQUENCE: 934

```
atgacctcca ccatgggatg gttccctctg ctcctcaccc tcctggctca ctgcacaggt     60
tcctgggccc agtctgtgct gactcagccg gcctcagtgt ctgggtccct gggccagagg   120
gtcaccatct cctgcactgg aagcggctcc aacatcggtc gaggttatgt ggcctggtac   180
caacagctcc cagaaacagg ccccagaacc ctcatctatg atactagtcg tcgaccctcg   240
```

-continued

```
ggggtccctg atcgattctc tggctccagg tcaggcagca cagcgaccct gaccatctct    300
ggactccagg cagacgacga ggctgattat tactgttcaa catatgacat cactatcact    360
ggtggtgtgt tcggcggggg cacccacctg accgtcctcg gtcagcccaa ggcc          414
```

<210> SEQ ID NO 935
<211> LENGTH: 405
<212> TYPE: DNA
<213> ORGANISM: canis familiaris;

<400> SEQUENCE: 935

```
atgaccttca ccgtgggatg gtcccctctc ctcctcacct tccttgctca ctgcacaggg    60
tcttgggccc agtctgtcct gactcagccg gcctcagtgt ccgggtctct gggccagagc    120
gtcaccatct cctgcactgg ctccagcatc aattatagat acgttggctg gtaccagcag    180
gtcccgggaa caggcccag  aaccctcatc tatgataatg caaacgacc  ctcgggggtt    240 cccgagcgat tctctggctc caagtcaggc agcacagccg ccctaaccat ctctgggctc    300
caggctgagg acgaggctga ttattattgc tcttcatatg acagcagttt cactgctgac    360
ttcggcggag gcacccagtt gaccgtcctc ggtcagccca aggcc                    405
```

<210> SEQ ID NO 936
<211> LENGTH: 402
<212> TYPE: DNA
<213> ORGANISM: canis familiaris;
<220> FEATURE:
<221> NAME/KEY: UNSURE
<222> LOCATION: (6)..(6)
<223> OTHER INFORMATION: n is a, c, t, or g

<400> SEQUENCE: 936

```
atgggntggt ccctctcct ccttaccctc ctcgctcact gcacaggttc ctgggcccag     60
tctgtgctga ctcagccggc ctcagtgact gggtccctgg ccagagggt caccatctcc    120 tgcactggaa gcagctccaa catcggtgga tataatgttg ctggttcca  gcagctcccg    180 ggaacaggcc ccagaaccgt catctatagt agtagtaacc gaccctcggg ggccccggat    240
cgattctctg gctccaggtc aggcagcaca gccaccctga ccatctctgg ctccaggct    300 gaggacgagg ctgagtatta ctgctcaaca tgggacagca gtctcaaagc tattgtgttc    360
ggcggaggca cccatctgac cgtcctcggt cagcccaagg cc                      402
```

<210> SEQ ID NO 937
<211> LENGTH: 414
<212> TYPE: DNA
<213> ORGANISM: canis familiaris;

<400> SEQUENCE: 937

```
atgatcttca ccatggcttg gtcccctctc ctcctcggcc tcctgctca  ctgcacaggg    60 tcctgggccc agtctatgct gactcagcca gcctcagtgt ctgggtccct gggccagaag    120
gtcaccatct cctgcactgg aagcagttcc aacatcggtg gtaattatgt gggctggtac    180
caacaggtcc caggaatagg ccctagaacc gtcatgtatg gtgataataa ccgaccttca    240
ggggtccccg atcgattctc tagctccagg tcaggcagtt cagccaccct gaccatcgct    300
ggcctccagg cggaggacga ggctgcgtat tactgttcgt catgggatga tagtctcaga    360
ggtcatgtgt tcggcggagg cacccatctg accgtcctcg gtcagcccaa ggcc          414
```

<210> SEQ ID NO 938

```
<211> LENGTH: 399
<212> TYPE: DNA
<213> ORGANISM: canis familiaris;
<220> FEATURE:
<221> NAME/KEY: UNSURE
<222> LOCATION: (6)..(6)
<223> OTHER INFORMATION: n is a, c, t, or g

<400> SEQUENCE: 938
atggcntggt cctctttcct cctcaccctc ctcgctcact tcacaggttc ctgggcccag      60
tctgtgctga ctcaaccagc ctcagtgtcc gggcctctgg gccagagggt caccatctcc     120
tgcactggaa gcagctccaa cattggtaga gattatgtgg gctggttcca acacctcccg     180
ggaacacgcc ccaaaagcct catctatggt aatagtaagc gaccctcggg ggtccccgat     240
cgattctctg gctccaagtc aggcagcaca gccaccctga ccatctctgg ctccaggct      300 gaggacgagg ctatttatta ctgctctaca tgggacaaca gtctcactta cgtgttcggc     360
tcaggaaccc aactgaccgt ccttggtcag cccaaggcc                            399

<210> SEQ ID NO 939
<211> LENGTH: 296
<212> TYPE: DNA
<213> ORGANISM: canis familiaris;

<400> SEQUENCE: 939
gggtcaccat ctcgtgctct ggacgtacgg acaacatcgg tgtcgctggt gcggcttggt      60
accaacaact cccaggaaag gcccctaaac tcctcgtgga caatgatggc catcgaccgt     120
caagggtccc tgaccggttt tccggctccg agtctggcaa ctcagccact ctgaccatca     180
ctgggcttca ggctgaggac gaggctgatt actactgcca gtcctttcaa accacgctta     240
atatttacgt gttcggctca gggacccaac tgaccgtcct tggtcagccc aaggcc        296

<210> SEQ ID NO 940
<211> LENGTH: 408
<212> TYPE: DNA
<213> ORGANISM: canis familiaris;

<400> SEQUENCE: 940
atgacctcca ccatgggctg gtcccctctc ctccttaccc tcctgctcca ctgcacaggt      60
tcctgggccc agtctgtgct gactcagccg gcctcagtga ctgggtccct gggccagagg     120
gtcaccatct cctgcactgg aagcggctcc gacatcggtg gatttggctg gttccagcag     180
ctcccgggaa caggccccag aaccgtcatc tatggtgata gtgaccgacc ctcgggggtc     240
ccggatcgat tctctggctc caggtcaggc aggacagcca ccctgaccat ctctgggctc     300
caggctgagg acgaggctga gtattactgc tcaacatggg acgccagtct ccgggttggt     360
gtgttcggcg gaggcaccca cctgaccgtc ctcggtcagc ccaaggcc                  408

<210> SEQ ID NO 941
<211> LENGTH: 414
<212> TYPE: DNA
<213> ORGANISM: canis familiaris;

<400> SEQUENCE: 941
atgacctcca ccatgggctg gtcccctctc ctccttaccc tcctgctcca ctgcacaggt      60
tcctgggccc agtctgtgct gactcagccg gcctcagtga ctgggtccct gggccagagg     120
gtcaccatct cctgcactgg aagcagctcc aacatcggtg gatataatgt tggctggttc     180
cagcagctcc cgggaacagg ccccagaacc gtcatctgta gtagtagtaa ccgaccctcg     240
```

```
ggggtcccgg aacgattctc tggctccagg tcaggcagca cagccaccct gaccatctct     300 ggctccagg  ctgaagacga ggctgagtat tactgctcaa catgggacag cagtctcaaa     360
gctgttgtgt tcggcggagg cacccacctg accgtcctcg gtcagcccaa ggcc           414

<210> SEQ ID NO 942
<211> LENGTH: 233
<212> TYPE: DNA
<213> ORGANISM: canis familiaris;

<400> SEQUENCE: 942
agcagctccc aggaagaggc cccagaactg tcatctatag tacagatagg cgaccctcgg     60
gggtgcccga tcgattctct ggctccaagt ctggcagcac agccaccctg accatctctg     120
ggctccaggc tgaggatgag gctgattatt actgctcaac gtgggatgac agtctcagtg     180
aacctgtgtt cggcggaggc acccacctga ccgtcctcgg tcagcccaag gcc            233

<210> SEQ ID NO 943
<211> LENGTH: 284
<212> TYPE: DNA
<213> ORGANISM: canis familiaris;

<400> SEQUENCE: 943
cctgcactgg aagcagctcc aacgtcggtg gaggttttgt gggctggtac caactggtcc     60
cagggacagg tcccagaaca ctcatctatg gtaattctga ccgaccctcg ggggtccctg     120
atcggttctc tggctccaag tcaggcacca cagccattct gaccatctct ggactccagg     180
ctgacgacga ggctgattat ttttgctcga catacgacac cagactcaat gatgttattt     240
tcggcggcgg cacccacctg accgtcctcg gtcagcccaa ggcc                      284

<210> SEQ ID NO 944
<211> LENGTH: 414
<212> TYPE: DNA
<213> ORGANISM: canis familiaris;

<400> SEQUENCE: 944
atgacctcca ccatggcctg gttccctctc ctcctgaccc tccttgctca ctacacaggg     60
tcctgggccc agtctgtgct gactcagccg gcctcagtgt ctgggtccct gggcagagg     120 atcaccatct cttgcgctgg aaccaactcc gacattggaa ctaatcatgt ggcttggtac     180
cagcagctcc agggagagg ccccagaact gtcatcccata ctacaaatag tcggccctcg     240
ggggtgcccg atcgattctc tggttccaag tctggcagca cagccaccct gaccatctct     300 ggctccagg  ctgacgatga ggctgattat tactgttcag cgtgggatga tcgtctcact     360
gagcctgtat tcggcggagg cgcccacctg accgtcctcg gtcagcccaa ggcc           414

<210> SEQ ID NO 945
<211> LENGTH: 414
<212> TYPE: DNA
<213> ORGANISM: canis familiaris;

<400> SEQUENCE: 945
atgtcctccg acatggcctg gtccctctc ctcttcacac tcctcgctca ctgcacaggg      60
tcctgggccc aggctgtact gaatcagccg gcctcagtgt ctgggccct gggccagaag     120 gtcaccatct cctgctctgg tagcacaaat gacataggta gatttggtgt caactggtgc    180
caacaactcc caggaaaggc ccctaagctc ctcgtggaca gtgatgggga ccgaccctca    240
```

```
gggatccctg acagattttc aggctcccgc tctgacaact caggcatcct gaccatcagt    300
ggcctccagg ctgaggacga ggctgattat cactgtcagt ctgttgatca cacgcttgcc    360
gctgctgtgt tcggcggggg cacccacctg accgtcctcg gtcagcccaa ggcc          414

<210> SEQ ID NO 946
<211> LENGTH: 414
<212> TYPE: DNA
<213> ORGANISM: canis familiaris;

<400> SEQUENCE: 946
atgacctcca ccatgggctg gttccctctg ctcctcaccc tcctggctca ctgcacaggt    60
tcctgggccc agtctgaact gactcagtcg ccgccgtat ctgggtccct gggccaggaa     120
gtcaccatct cctgcactgg aagcaccgcc aacattggaa gtggttatgt gaattggtac    180
caacaattcc cagggacagg tcccagaacc ctcatctata cttctactaa ccgaccttcg    240
ggggtccccg ctcgattttc tgggtccagg tcaggcaaca cagcgaccct gaccatctct    300 ggctcctgg ctgaggacga ggctgattat tattgcgctg catatgacag tagtctcagt     360
attggtgtgt tcggcggagg cacccacctg accgtcctcg gtcagcccaa ggcc          414

<210> SEQ ID NO 947
<211> LENGTH: 211
<212> TYPE: DNA
<213> ORGANISM: canis familiaris;

<400> SEQUENCE: 947
cagaaccgtc atctatatga gtagtaaccg accctcgggg gtcccggatc gattctctgg    60
ctccaggtca ggcagcacag ccaccctgac catctctggg ctccaggctg aggacgaggc    120
tgagtattat tgctcaacat gggacaacag tctcaatact ggtgtgttcg gcggggcac    180 ccacctgacc gtcctcggtc agcccaaggc c                                  211

<210> SEQ ID NO 948
<211> LENGTH: 417
<212> TYPE: DNA
<213> ORGANISM: canis familiaris;
<220> FEATURE:
<221> NAME/KEY: UNSURE
<222> LOCATION: (18)..(18)
<223> OTHER INFORMATION: n is a, c, t, or g

<400> SEQUENCE: 948
atgacctcca acatggcntg gtccctctc ctcctccac tccttgctta ctgcacaggg      60
tcctgggccc agtctatact gactcagccg tcctcagtgt cggggtccct tggccagagg    120
gtcaccatct cctgttctgg aagcatgtac aacctcggtg ttgttggtgc gacctggtac    180
cgacaactcc caggggaggc ccctaaactc ctcctataca gtaatgggag tcgaccgtca    240
ggggtccctg accggttttc cggctccaac tctggcttct ctgccaccct gaccatcact    300 ggcttcagg ctgacgacga ggctgattat tactgccagt cccttgattc cacgcgtggt     360
tatcatattg tattcggcgg aggcacccac ctgaccgtcc tcggtcagcc caaggcc      417

<210> SEQ ID NO 949
<211> LENGTH: 414
<212> TYPE: DNA
<213> ORGANISM: canis familiaris;

<400> SEQUENCE: 949
atgacctcca ccatgggatg gttccctctg ctcctcaccc tcctggctca ctgcacaggt    60
```

-continued

```
tcctgggccc agtctgtgct gactcagccg gcctcagtgt ctgggtccct gggccagagg      120
gtcaccatct cctgcactgg aagcaactcc aacatcggta gaggttatgt gggctggtac      180
cagcagctcc caggaacagg ccccagaacc ctcatctatg atactacttt ccgaccctcg      240
ggggtccctg atcgattctc tggctcccgg tcaggcacca caggaaccct gaccatctct      300
gggctccagg ctgaggacga ggctgattat tactgctcag catatgacac cagtctcagt      360
agtaatttct cggcggagg cacccgcctg accgtcctcg gtcagcccaa ggcc            414
```

<210> SEQ ID NO 950
<211> LENGTH: 237
<212> TYPE: DNA
<213> ORGANISM: canis familiaris;

<400> SEQUENCE: 950

```
tggtaccagc agaccctagg ccgggctcct cgcacgatta tctacagaac aagcagccgc      60
ccctctgggg tccctaatcg cttctccgga tccatctctg gaacaaagc cgccctcacc      120 atcacaggag cccagcctga ggacgaggct gactattact gttccgtgta tatgggtact      180
tacactgttg tgttcggcgg aggcacccac ctgaccgtcc tcggtcagcc caaggcc       237
```

<210> SEQ ID NO 951
<211> LENGTH: 250
<212> TYPE: DNA
<213> ORGANISM: canis familiaris;
<220> FEATURE:
<221> NAME/KEY: UNSURE
<222> LOCATION: (13)..(13)
<223> OTHER INFORMATION: n is a, c, t, or g

<400> SEQUENCE: 951

```
taattaccct ggntggtacc agcagaccca aggccgggct cctcgcacga ttatctacaa      60
cacaaacagc cggccctctg gggtccctaa tcgcttctct ggatccatct ctggaaacaa      120
agccgccctc accatcacag gagcccagcc cgaggatgag gctgactatt attgttcctt      180
gcgcacgggt tatcaaaata ctatggtcgg cggaggcacc cacctgaccg tcctcggtca      240
gcccaaggcc                                                             250
```

<210> SEQ ID NO 952
<211> LENGTH: 401
<212> TYPE: DNA
<213> ORGANISM: canis familiaris;
<220> FEATURE:
<221> NAME/KEY: UNSURE
<222> LOCATION: (86)..(86)
<223> OTHER INFORMATION: n is a, c, t, or g

<400> SEQUENCE: 952

```
gcttggaacg ttgcttcttc tttgtgctcc ttgcctatgg ctcaggagca gattctcaga      60
ctgtggtaac ccaggagcca tcactntcag tgtctccagg agggacagtc acactcacat      120
gtggcctcag ctctgggtca gtctccacaa gtaattaccc tggctggtac cagcagaccc      180
taggccgggc tcctcgcacg attatctaca gaacaagcag ccgcccctct ggggtcccta      240
atcgcttctc tggatccatc tctgggaaca aagccgccct caccatcata ggagtccagc      300
ctgaggacga ggctgactat tactgttcct tatatatggg tagttacact gatatgttcg      360
gcggaggcac ccacctgacc gtcctcggtc agcccaaggc c                          401
```

<210> SEQ ID NO 953

```
<211> LENGTH: 296
<212> TYPE: DNA
<213> ORGANISM: canis familiaris;

<400> SEQUENCE: 953
ggatcacact cacatgtggc ctcaactctg ggtcagtctc tacaagtaat taccctgcct      60
ggtaccagca gacccctaggc cgggctcctc gcacgattat ctatggagca aacagccgcc    120 cctctgggt  ccctaatcgc ttctctggat ccatctctga caacaaagcc gccctcacca    180
tcacaggagt ccagcctgag gacgaggctg actattactg ttccttgtat atgggtggtt    240
atagtgacgt gttcggctca ggaacccaac tgaccgtcct tggtcagccc aaggcc        296

<210> SEQ ID NO 954
<211> LENGTH: 405
<212> TYPE: DNA
<213> ORGANISM: canis familiaris;

<400> SEQUENCE: 954
atggcctgga cactgattct ccttggactt cttgcttatg gctcaggagc agattctcag      60
actgtggtga cccaggagcc atcactctca gtgtctctgg agggacagt  caccctcaca    120 tgtggcctcc cctccgggtc agtctctaca caaaacttcc ccaactggtc ccagcagacc    180
ccagggcagg ctcctcgcac gattatttac aacacaaaca cccgcccctt aggggtccct    240
agtcgcttca cgggatccat ctctgggaac agggccgccc tcaccatcac aggagcccgg    300
cctgaggacg aggctgacta ctattgtgct ctgggcttca gtggtggtga ttatgtcgtg    360
ttcggcggag gcacccacct gaccgtcctc ggtcagccca aggcc                     405

<210> SEQ ID NO 955
<211> LENGTH: 402
<212> TYPE: DNA
<213> ORGANISM: canis familiaris;

<400> SEQUENCE: 955
atggcttgga cggtgcttct tcttgtgctc cttgcctatg gctcaggagc agattctcag      60
actgtggtaa cccaggagcc atcactctca gtgtctccag agggacagt  cacactcaca    120 tgtggcctca gctctgggtc agtctctaca ataattaccc tggctggta  ccagcagacc    180 caaggccggg ctcctcgcac gattatctac agcacaagca gccgcccctc tggggtccct    240
aatcgcttct ctggatccat ctctggaaac aaagccgccc tcaccatcac aggagcccag    300
cccgaggatg aaactgacta ttactgttcc ttatatacgg gtagttccac tgatgtgttc    360
ggcggaggca cccatctgac cgtcctcggt cagcccaagg cc                        402

<210> SEQ ID NO 956
<211> LENGTH: 402
<212> TYPE: DNA
<213> ORGANISM: canis familiaris;

<400> SEQUENCE: 956
atggcttgga cggtgcttct tcttgtgctc cttgcctatg gctcaggagc agattctcag      60
actgtggtaa cccaggagcc atccctctca gtgtctccag agggacagt  cacactcaca    120 tgtggcctca gctctgggtc agtctctaca agtaattacc ctggctggta ccagcagacc    180
caaggccggg ctcctcgcac gattatctac aacacaaaca gccgcccctc tggggtccct    240
aatcgcttct ctggatccat ctctggaaac aaagccgccc tcaccatcac aggagcccag    300
cccgaggatg aggctgacta ttactgttcc ttctatacgg gtgattacac tgctgtgttc    360
```

```
ggcggaggca cccacctgac cgtcctcggt cagcccaagg cc                402
```

<210> SEQ ID NO 957
<211> LENGTH: 402
<212> TYPE: DNA
<213> ORGANISM: canis familiaris;

<400> SEQUENCE: 957

```
atggcttgga cggtgcttct tcttgtgctc cttgcctatg ctcaggaac agattctcag    60
actgtggtca cccaggagcc atcactctca gtgtctccag agggacggt cacactcaca   120
tgtggcctca gctctgggtc agttactgcg agtcatttcc ctggctggta ccagcagacc   180
caaggccggg ctcctcgcac gattatctac aacacataca accgcctttc tggggtccct   240
agtcgcttct ctggatccat ctctggaaac aaagccaccc tcaccatcac aggggcccgg   300
cccgaggatg aggctgacta tcactgttct gtatatacgg atgatcacac tcctgtattc   360
ggcggaggca cccacctgac cgtcctcggt cagcacgagg cc                     402
```

<210> SEQ ID NO 958
<211> LENGTH: 294
<212> TYPE: DNA
<213> ORGANISM: canis familiaris;

<400> SEQUENCE: 958

```
gggacggtca cactcacatg tggcctcagc cctgggtcag tctctacgag taattaccct    60
aattggtacc agcagaccca aggccgggct ccccgcacga ttatctacaa cacaggtagc   120
cgcccctctg gggtcctaa tcgcttctct ggatccatct ctggaaacaa agccgccctc   180
accatcacag gagcccagcc cgaggatgag gctgactatt actgttcctt atatacgggt   240
agttatactg ctgtgttcgg cggaggcacc cacctgaccg tcctcggtca gccc         294
```

<210> SEQ ID NO 959
<211> LENGTH: 395
<212> TYPE: DNA
<213> ORGANISM: canis familiaris;

<400> SEQUENCE: 959

```
atggcttgga cggtgcttct tcttgtgctc cttgcctatg ctcaggagc agattctcag    60
actgtggtaa cccaggagcc atcactctca gtgtctccag agggacagt cacactcaca   120
tgtggcctca gctctgggtc ggtctctacg agtaattatc ctgcctggta ccagcagacc   180
caaggccggg ctcctcgcac gattatctac aacacaaaca gccgccccstc tggggtccct   240
aatcgcttct ctggatccat ctctggaaac aaagccgccc tcaccatcac aggagcccag   300
cccgaggatg aggctgacta ttattgttcc tttttttacag atattgtcgt taacgtgttc   360
ggctcaggaa ctcaattgac cgtccttggt cagcc                              395
```

<210> SEQ ID NO 960
<211> LENGTH: 402
<212> TYPE: DNA
<213> ORGANISM: canis familiaris;

<400> SEQUENCE: 960

```
atggcttgga cgttgcttct tcttgtgctc cttgcctatg ctcaggagc agattctcag    60
actgtggtaa cccaggagcc atcactctca gtgtctccag agggacagt cacactcaca   120
tgtggcctca gctctgggtc ggtctctgga agtaattacc ctggctggta ccagcagacc   180
```

```
ctaggccggg ctcctcgcac gattatctac agaacaagca gccgcccctc tggggtccct    240
aatcgcttct ctggatccat ctctggaaac aaagccgccc tcaccatcac aggagcccag    300
cctgaggacg aggctgacta ttactgttcc ttgtatatgg tcggttacac tgccgtgttc    360
ggctcaggga cccaactgac cgtccttggt cagcccaagg cc                       402

<210> SEQ ID NO 961
<211> LENGTH: 405
<212> TYPE: DNA
<213> ORGANISM: canis familiaris;

<400> SEQUENCE: 961
atggcctgga cactgattct ccttgggctt cttgcttatg ctcaggagc agattctcag      60 actgtggtga cccaggagcc atcactctca gtgtctctgg agggacagt caccctcaca    120 tgtggcctca gctccgggtc agtctctaca gtaactacc ccaactggtc ccagcagacc    180
ccagggcagg ctcctcgcac gattatctac aacacaaaca gccgcccctc tggggtccct    240
aatcgcttca ctggatccat ctctgggaac aaagccgccc tcaccatcac aggagcccag    300
cctgaggacg aggctgacta ctactgtgct ctgggattta gtagtagtag tagttacgtg    360
ttcggctcag gaacccaact gaccgtcctt ggtcagccca aggcc                    405

<210> SEQ ID NO 962
<211> LENGTH: 395
<212> TYPE: DNA
<213> ORGANISM: canis familiaris;

<400> SEQUENCE: 962
atggcttgga cgttgcttct tcttgtgctc cttgcctatg ctcaggagc agattctcag      60 actgtggtga cccaggaggc atcagtctcg gtgtctccag agggacagt cacactcaca    120 tgtggtctca gctctgggtc agtctctaca ggtgatttcc ctggctggta ccagcagacc    180
ctaggccggc ctcctcgcac gattatatcc agaacgaata gacgcccctc tggggtccct    240
gatcgcttct ctggatccat ctctgggaac aaagccgccc tcaccatcac aggagcccag    300
cctgaggacg agggtgacta ttattgttcc ttatatatgg gttcttacac tggtttgttc    360
ggcggaggca cccacctgac cgtcctcggt cagcc                               395

<210> SEQ ID NO 963
<211> LENGTH: 390
<212> TYPE: DNA
<213> ORGANISM: canis familiaris;

<400> SEQUENCE: 963
ttgcttcctc ttgtgctcct tgcctatggc tcaggagccg attctcagac tgtggtcatc     60
caggagccat tcctctcagt gtctccagga gggacggtca cactcacatg tggcctcagc    120
tctgggtcag tctctccaag tcattaccct ggctggtacc agcagaccct aggccggcct    180
cctcgcccga tcatctacag aacagacagc cgccctctg gggtccctcg tcgcttctct    240
gcatccgtct ctgggaacaa agccacccct caccattacag gagcccagcc tgaggacgag    300
gctgactatt actgttcctt atatatggac atttacactg tgtgttcgg cggaggcacc    360 cacctgaccg tcctcggtca gcccaaggcc                                     390

<210> SEQ ID NO 964
<211> LENGTH: 405
<212> TYPE: DNA
<213> ORGANISM: canis familiaris;
```

<400> SEQUENCE: 964

```
atggcttgga cactgattct ccttgggctt cttgcttatg gctcaggagc agattctcag      60
actgtggtga cccaggagcc atcactctca gtgtctctgg agggacagt caccctcaca     120
tgtggcctca gctccgggtc agtctctaca gtaactacc ccagctggtc ccagcagacc     180
ccagggcagg ctcctcgcac gattctctac aacacaaaca gccgcccctc tggggtccct    240
aatcgcttca ctgcatccat ctctgggaac aaagccgccc tcaccatcac aggagcccag    300
cctgaggacg aggctgacta ctactgtgct ctgggattaa gtgggattag cagtattgtg    360
ttcggcggag gcacccacct gaccgtcctc ggtcagccca aggcc                    405
```

<210> SEQ ID NO 965
<211> LENGTH: 387
<212> TYPE: DNA
<213> ORGANISM: canis familiaris;

<400> SEQUENCE: 965

```
gacggtgttc ttcttgtgct ccttgcctat ggctcaggag cagattctca gactgtggta     60
acccaggagc catcactctc agtgtctcca ggagggacag tcacactcac atgtggcctc    120
agctctgggt cagtctctac aagtaattac cctggctggt accagcacac ccaaggccgg    180
gctcctcgca cgattatcta caccacaagc agccgcccct ctgggtccc taatcgcttc     240
tctggatcca tctctggaaa caaagccgcc ctcaccatca caggagccca gcccgaggat    300
gaggctgact attactgttc cttgtatacg gtaggcctg tgttcggcgg aggcacccac     360
ctgaccgtcc tcggtcagcc caaggcc                                        387
```

<210> SEQ ID NO 966
<211> LENGTH: 406
<212> TYPE: DNA
<213> ORGANISM: canis familiaris;

<400> SEQUENCE: 966

```
atggcttgga tggtgcttct tcttgtgctc cttgcctatg gctcaggagc agattctcag     60
actgtggtaa cccaggagcc atcactctca gtgtctccag gagggacagt cacactcaca    120
tgtggcctca gctctgggtc agtctctaca gtaattaccc tggctggta ccagcagacc     180
caaggccggg ctcctcgcac gattatctac acacaagca gccgcccctc tggggtccct    240
aatcgcttct ctggatccat ctctggaaac aaagccgccc tcaccatcac aggagcccag    300
cccgaggatg aggctgacta ttactgttcc ttttatacga gtagttacat tgctgcctgg    360
tcacgcacga gggagcacc tgaccgtcct cggtcagccc aaggcc                    406
```

<210> SEQ ID NO 967
<211> LENGTH: 414
<212> TYPE: DNA
<213> ORGANISM: canis familiaris;

<400> SEQUENCE: 967

```
atgacctcca ccatgggctg gtcccctctc gtcctcaccc tcttcgctca ctgcgcaggg     60
tcctgggccc agtctgtgct gactcagccg gcctcagtgt ccgggtccct gggcagagg    120
gtcaccatct cctgcactgg aagcagttcc aatgttggtt atggcgatta tgtgggctgg    180
taccagcagt tcccaggaac aggccccaga accctcatct atcgtactgg taatcgaccc    240
tcgggggtcc ctgatcgatt ctctggctcc aggtcgggca gcacagcaac cctgaccatc    300
```

```
tctgggctcc agactgagga tgaagccgat tattactgct catcctttga cagaagtgtc    360
agtgctgtgt tcggcggagg cacccacctg accgtcctcg gtcagcccaa ggcc          414

<210> SEQ ID NO 968
<211> LENGTH: 414
<212> TYPE: DNA
<213> ORGANISM: canis familiaris;

<400> SEQUENCE: 968
atgacctcca ccatgggctg gtcccctctc gtcctcaccc tcttcgctca ctgcgcaggg    60
tcctgggccc agtctgtgct gactcagccg gcctcagtgt ccgggtccct gggccagagg    120
gtcaccatct cctgcactgg aagcagttcc aatgttggtt atggcgatta tgtgggctgg    180
taccagcagt tcccaggaac aggccccaga accctcatct atcgtactgg taatcgaccc    240 tcggggtcc ctgatcgatt ctctggctcc aggtcgggca gcacagcaac cctgaccatc    300
tctgggctcc agactgagga tgaagccgat tattactgct catcctttga cagaagtgtc    360
agtgctgtgt tcggcggagg cacccacctg accgtcctcg gtcagcccaa ggcc          414

<210> SEQ ID NO 969
<211> LENGTH: 402
<212> TYPE: DNA
<213> ORGANISM: canis familiaris;

<400> SEQUENCE: 969
atgggctggt cccctctcat cctcaccctc ttcgctcact gcgcagggtc ctgggcccag    60
tctgtgctga ctcagccggc tcagtgtct gggtccctgg ccagagggt caccatctcc    120 tgcactggaa gcagctccaa tgttggttat gccaatcatg tgggctggta ccagcagctc    180
ccaggaacag gccccagaac cctcatctat catagtagtg accgaccttc gggggtcccc    240
gatcgattct ctggctccag gtcaggcaac acagcaaccc tgaccatctc tggcctccag    300
gctgaggacg aggctgatta ttactgctca gcgtatgaca ccactctcaa tgctgtgttc    360
ggcggaggca cacctgac cgtcctcggt cagcccaagg cc                        402

<210> SEQ ID NO 970
<211> LENGTH: 420
<212> TYPE: DNA
<213> ORGANISM: canis familiaris;

<400> SEQUENCE: 970
atgatgacct ccaccatggg ctggttccct ctcatcctca ccctcctcgc tcactgcgca    60
gggtcctggg cccagtctgt gctgactcag ccggcctcag tgtctgggtc cctgggccag    120
agggtcacca tctcctgcac tggaagcagc tccaatgttg gttatggcaa ttatgtgggc    180
tggtaccagc agctcccagg aacaagcccc agaaccctca tctatgatag tagtagccga    240
ccctcggggg tccctgatcg attctctggc tccaggtcag gcagcacagc aaccctgacc    300
atctctgggc tccaggctga ggatgaagcc gattattact gctcatccta tgacagcagt    360
ctcagtggtg gcgtgttcgg ctcaggaacc caactgaccg tcctcggtca gcccaaggcc    420

<210> SEQ ID NO 971
<211> LENGTH: 402
<212> TYPE: DNA
<213> ORGANISM: canis familiaris;

<400> SEQUENCE: 971
atggcctgga ctctggtcct cctcaccttt ctctctcagg gcacagggtc ctgggcccag    60
```

-continued

```
tctgccctga ctcaaccttc ctcggtgtct gggactttgg gccagactgt caccatctcc    120
tgtgatggaa tcaacagtaa cattgacaat agtaattata tcgaatggtt ccaacatttc    180
ccaggcacct cccccaaact cctgatttac tataccaata atcggccatc aggaatccct    240
gctcgcttct ctggctccag gtctgggaac acggcctcct tgaccatctc tgggctccag    300
gctgaagatg aggcagatta ttactgtagc gcatatagtg gcactgatac ttacgtgttc    360
ggctcaggaa cccaactgac cgtccttggt cagaacgagg cc                       402
```

<210> SEQ ID NO 972
<211> LENGTH: 413
<212> TYPE: DNA
<213> ORGANISM: canis familiaris;

<400> SEQUENCE: 972

```
atgatgacct ccaccatggg ctggttccct ctcatcctca ccctcctcgc tcactgcgca    60
gggtcctggg cccagtctgt gctgactcag ccggcctcag tgtctgggtc cctgggccag    120
agggtcacca tctcctgcac tggaagcagc tccgatgttg gttatgccga ttatgtgggc    180
tggtaccagc aggtcccagg aacaagcccc agaacctaa tctatgatac tagtaagcga    240
ccctcggggg tccctgatcg attctctggg tccaggtcag gcagcacagc aaccctgacc    300
atctctgggc tccaggctga ggatgaagcc gattattact gttcatccta tcacagcagt    360
cctcatggtg ttgtcttcgg cggaggcacc cacctgaccg tcctcggtca gcc           413
```

<210> SEQ ID NO 973
<211> LENGTH: 416
<212> TYPE: DNA
<213> ORGANISM: canis familiaris;
<220> FEATURE:
<221> NAME/KEY: UNSURE
<222> LOCATION: (104)..(104)
<223> OTHER INFORMATION: n is a, c, t, or g
<220> FEATURE:
<221> NAME/KEY: UNSURE
<222> LOCATION: (112)..(112)
<223> OTHER INFORMATION: n is a, c, t, or g
<220> FEATURE:
<221> NAME/KEY: UNSURE
<222> LOCATION: (180)..(180)
<223> OTHER INFORMATION: n is a, c, t, or g

<400> SEQUENCE: 973

```
atgatgacct ccaccatggg ctggttccct ctcatcctca ccctcctcgc tcactgcgca    60
gggccctggg cccagtctgt gctgactcag ccggcctcag tgtntgggtc cntgggccag    120
agggtcacca tctcctgcac tggaagcagc tccaatgttg gttttggcaa ttatgtgggn    180
tggtaccagc agctcccagg aacaagcccc aaaaccctta tctatgatag tagtagacga    240
ccctcggggg tccctgatcg attctctggc tccaggtcag gcagcacagc aaccctgacc    300
atctctgggc tccaggctga ggatgaagcc gattattact gctcatcgta tgacagcgag    360
gtcagggttg tgttcggcgg aggcacccac ctgaccgtcc tcggtcagca cgaggc        416
```

<210> SEQ ID NO 974
<211> LENGTH: 416
<212> TYPE: DNA
<213> ORGANISM: canis familiaris;
<220> FEATURE:
<221> NAME/KEY: UNSURE
<222> LOCATION: (101)..(101)
<223> OTHER INFORMATION: n is a, c, t, or g
<220> FEATURE:

```
<221> NAME/KEY: UNSURE
<222> LOCATION: (132)..(132)
<223> OTHER INFORMATION: n is a, c, t, or g
<220> FEATURE:
<221> NAME/KEY: UNSURE
<222> LOCATION: (137)..(137)
<223> OTHER INFORMATION: n is a, c, t, or g
<220> FEATURE:
<221> NAME/KEY: UNSURE
<222> LOCATION: (298)..(299)
<223> OTHER INFORMATION: n is a, c, t, or g

<400> SEQUENCE: 974
atgacctcca ccatggcctg gtccctctc ctactcaccc tccttgctca tttcacaggg      60
tcctgggccc agtctgtgct gactcagcca gcctccgtgt ntgggtccct gggccagagg    120
gtcaccattt cntgcantgg gagcagctcc aacgttggtt ctggcagtac tgtgggctgg    180
taccagcagt tcccaggaac aggccccaga accatcatct attatgatgg tagccgaccc    240 tcggggtcc ccgatcgatt ctctggctcc aagtctggca gcacagccac cctgaccnnc    300
tctgggctcc aggctgagga tgaggctgat tattactgct catcttggga caacagtcaa    360
ggtagtgtgt tcggcggagg cacccatctt gaccgtcctc gggtcagccc aaggcc       416

<210> SEQ ID NO 975
<211> LENGTH: 417
<212> TYPE: DNA
<213> ORGANISM: canis familiaris;
<220> FEATURE:
<221> NAME/KEY: UNSURE
<222> LOCATION: (18)..(18)
<223> OTHER INFORMATION: n is a, c, t, or g

<400> SEQUENCE: 975
atgacctcca ccatggcntg gtccctctc ctcctcaccc tcctcgctca ttgcacagtg     60
tcctgggccc aggctgtgct gactcagcca ccctctatgt ctacagccct ggggcagagg   120
gtcaccataa cctgcactgg aagtaagacc aacatcggca gtggttatga tgtacaatgg   180
taccagcagc tcccaggaaa gtcccctaaa agtatcatct cgctaatga cgctcgaccc    240 tcggggtcc cggctcgatt ctctggctcc aagtcaggca acacagccac cctgaccatc    300
actgggatcc aggctgagga tgaggctgat tattactgcc agtcctatga tgacaacctc   360
gctggtcttg tgttcggcgg aggcacccag ttgaccgtcc tcggtcagcc caaggcc      417

<210> SEQ ID NO 976
<211> LENGTH: 411
<212> TYPE: DNA
<213> ORGANISM: canis familiaris;

<400> SEQUENCE: 976
atgacctcca ccatgggctg gttccctctc ctcctcacct tcctggctca ctgcacaggg    60
tcctgggccc agactgtatt gactcagccg gcctcagtgt ctgggtctct gggcagacg    120 gtcaccatct cctgcactgg aagcaaggac aatattggtt atggcaatta tgtgggctgg   180
tatcgacaat tcccaggaac aggccccaga accgtcgcct atggtcatgg atttcgaccc   240
tcggggggtt ctgaccgatt ctctgcctcc agttcaggca gcacatccac actgaccatc   300
gccgggctcc aggctgaaga tgaaggtgat tattactgct caacctatga caacagtctc   360
tctgttgtgt tcggcggagg cacccacctg accgtcctcg gtcagcccaa g            411

<210> SEQ ID NO 977
<211> LENGTH: 306
```

```
<212> TYPE: DNA
<213> ORGANISM: canis familiaris;

<400> SEQUENCE: 977
cagacggtca ccatctcctg cactggaagc agctccaatg ttggttatgg cgattatgtg    60
ggctggtacc aacaactccc agggacaggt cccaaaaccc tcatctatga tactcgtagg   120
cgaccctcgg ggattcctga tcgattctct ggtccaggt caggcagcac agcgaccctg    180
accatctctg gactccaggc tgaggatgag ccgattatt actgtgcatc ctatgaccgt    240
actatcggtg gtggtgctgt gttcggcgga ggcacccacc tgaccgtcct cggtcagccc   300
aaggcc                                                              306

<210> SEQ ID NO 978
<211> LENGTH: 309
<212> TYPE: DNA
<213> ORGANISM: canis familiaris;

<400> SEQUENCE: 978
ccggggcaga gggtcaccat ctcctgcact ggaagtaaca ccaacatcgg cagtgattat    60
gatgttcaat ggtaccagca actcccagga aagtcccctg aaactatcat ttacgctaag   120
agcaatcgac cctcgggggt ccctgatcga ttctctggct ccaagtcagg cagcacagcc   180
accctgacca tctctgtgct ccaggctgag gatgaggctg attattactg ctcagtgggg   240
gatgatagtc tcaaagcacc tgtgttcggc ggaggcaccc acctgaccgt cctcggtcag   300
cccaaggcc                                                           309

<210> SEQ ID NO 979
<211> LENGTH: 315
<212> TYPE: DNA
<213> ORGANISM: canis familiaris;

<400> SEQUENCE: 979
tccctgggcc agacggtcac catctcctgc actggaagca gctccaatgt tggttatggc    60
gattatgcgg ctggtaccaa caactcccag ggacaggtc ccaaaaccct catctatgat    120
actcgtaggc gaccctcggg gattcctgat cgattctctg gtccaggtc aggcagcaca   180
gcgaccctga ccatctctgg actccaggct gaggatgagg ccgattatta ctgtgcatcc   240
tatgaccgta ctatcggtgg tggtgctgtg ttcggcggag gcacccacct gaccgtcctc   300
ggtcagccca aggcc                                                    315

<210> SEQ ID NO 980
<211> LENGTH: 409
<212> TYPE: DNA
<213> ORGANISM: canis familiaris;

<400> SEQUENCE: 980
atgacctcca ccatgggctg gttccctctc ctcctcacct tcctggctca ctgcacaggg    60
tcctgggccc aggctgtgct gactcagccg gcctcagtgt ctgggtccct gggccagagg   120
gtcaccatct cctgcactgg aagcacctcc aatgttggtt atggcaatta tgtgggctgg   180
taccagcagc tcccaggaac aggccccaaa accctcatct atggtagtag ttaccgaccc   240
tcgggggtcc ctgatcgatt ctctggctcc agttcaggca gctcagccac actgaccatc   300
tctgggctcc aggctgagga tgaagctgat tattactgct catcctatga cagcagtctc   360
agtgggattg tgttcggcgg aggcacccat ctgaccgtcc tcggtcagc               409
```

<210> SEQ ID NO 981
<211> LENGTH: 417
<212> TYPE: DNA
<213> ORGANISM: canis familiaris;

<400> SEQUENCE: 981

```
atgacctcca ccatgggctg gtccctatc atcctcaccc tcctcgctca ctgcgcaggg      60
tcctgggccc agtctgtgct gactcagccg gcctcagtgt ctgggtccct gggccagagg     120
gtcaccatct cctgcactgg aagcaactcc aatgttggtt atgccaatta tgtgggctgg    180
taccagcagc tcccaggaac aggccccaga accctcatct atgatagtag tagccgaccc    240
tcggggtcc ctgatcgatt ctctggctcc aggtcaggca gcacagcaac cctgaccatc     300
tctgggctcc aggctgagga tgaagccgat tattactgct catcctatga cagcagtctc    360
gatggtgctg tgttcggcgg aggcacccac ctgaccgtcc tcggtcagcc caaggcc       417
```

<210> SEQ ID NO 982
<211> LENGTH: 417
<212> TYPE: DNA
<213> ORGANISM: canis familiaris;

<400> SEQUENCE: 982

```
atgacctcca ccatgggctg gttccctctc atcctcaccc tcttcgctca ctgcgcaggg    60
tcctgggccc agtctgtgct gactcagccg gcctcagtgt ctgggtccct gggccagagg    120
gtcaccatct cctgcactgg aaacagctcc aatgttggtt atgcaatta tgtgggctgg     180
taccagcagc tcccaggaac aagccccaga accctcatct attatagtag tagccgaccc    240
tcgggagtcc ccgatcgatt ctctggctcc aggtcaggca gcacagctgc cctaaccatc    300
tctgggctcc aggctgagga tgaagccgat tattactgct catcctatga cagcagtctc    360
agtggtggtg tattcggcgg aggcacccat ctgaccgtcc tcggtcagcc caaggcc       417
```

<210> SEQ ID NO 983
<211> LENGTH: 417
<212> TYPE: DNA
<213> ORGANISM: canis familiaris;

<400> SEQUENCE: 983

```
atgacctcca ccatggcctg gtcccctctc ctactcaccc tccttgctca tttcacaggg    60
tcctgggccc agtctgtgct gactcagcca gcctccgtgt ctgggtccct gggccagagg    120
gtcaccattt cctgcactgg aagcagctcc aacgttggtg acacaagtag tgtgggctgg    180
taccaacagt tcccaggaac aggccccaga accatcatct attttattgg tagccgaccc    240
tcggggtcc ccgatcgctt ctctggctcc aagtctggca gcacagccac cctgaccatc     300
tctgggctcc aggctgagga tgaggctgat tattactgct catcttggga caacagtctc    360
aaaactcggg tgttcggcga aggcacccat ctgaccgtcc tcggtcagcc caaggcc       417
```

<210> SEQ ID NO 984
<211> LENGTH: 292
<212> TYPE: DNA
<213> ORGANISM: canis familiaris;

<400> SEQUENCE: 984

```
catctcctgc actggaagca gctccaatgt tggttatggc aattatgtgg ctggtacca     60
acagctccca ggaacaggcc ccagaaccct catctatcgt agtagtaacc gagcctcggg    120
ggtccctgat cgattctctg ctccaggtc aggcagcaca gcaaccctga ccatctctgg    180
```

```
gctccaggct gaggatgagg ccgattattt ctgctcatcc tatgacagcg gtctcagtca      240
tattgtgttc ggcggaggca cccacctgac cgtcttcggt cagcccaagg cc             292

<210> SEQ ID NO 985
<211> LENGTH: 299
<212> TYPE: DNA
<213> ORGANISM: canis familiaris;

<400> SEQUENCE: 985
agggtcacca tctcctgcac tggaagcgac tccaatgttg gttatggcaa ttatgtgggc      60
tggtaccagc agctcccagg aacaagcccc agaaccctca tttattataa tactgggcga     120
ccctcgggag tccccgatcg cttttctggc tccaggtcag gcaatacagc aaccctgacc     180
atctctgggc tccaggctga ggatgaagcc gattattact gttcagccta tgactacagt     240
ctcagttctg gcgtcttcgg cggaggcacc cacctgaccg tcctcggtca gcccaaggc      299

<210> SEQ ID NO 986
<211> LENGTH: 417
<212> TYPE: DNA
<213> ORGANISM: canis familiaris;

<400> SEQUENCE: 986
atgacctcca ccatgggctg gttccctctc atcctcaccc ttttcgctca ctgcgcaggg      60
tcctgggccc agtctgtgct gactcagccg gcctcagtgt ctgggtccct gggccagagg     120
gtcaccatct cctgcactgg aagcagttcc aatgttggtt atggcgatta tgtgcctgg     180 taccagcagc tcccaggaac aagccccaga accctcatcc atcatagtag tagccgaccc     240
tcgggagtcc ccgatcgatt ctctggctcc aggtcaggca gcacagcaac cctgaccatc     300 tctggctcc aggctgagga tgaagccgat tattactgct catcctatga caacagtctc     360
agtggtggcg tgttcggcgg aggcacccac ctgaccgtcc tcggtcagcc caaggcc       417

<210> SEQ ID NO 987
<211> LENGTH: 417
<212> TYPE: DNA
<213> ORGANISM: canis familiaris;

<400> SEQUENCE: 987
atgacctcca ccatggcctg gtcccctctc ctactcaccc tccttgctca tttcacaggg      60
tcctgggccc agtctgtgct gactcagcca gcctccgtgt ctgggtccct gggccagagg     120
gtcaccattt cctgcactgg aagcacctcc aaccttggtt atagcagtat tgtgggctgg     180
taccagcagt tcctaggaac aggccccaga accatcatct attatgatag tagccgaccc     240 tcggggggtcc ccgatcgatt ctctggctcc aagtctggca gcagccac cctgaccatc     300 tctggctcc aggctgagga tgaggctgat tattattgtt catcttggga caacagtctc     360
aaaggtattg tgttcggcgg aggcacccat ctgaccgtcc tcggtcagcc caaggcc       417

<210> SEQ ID NO 988
<211> LENGTH: 417
<212> TYPE: DNA
<213> ORGANISM: canis familiaris;

<400> SEQUENCE: 988
atgacctcta ccatggcctg gttccctctc ctcctcaccc tcctgctca ctgcacaggg      60 tcctgggccc agtctgtgct gactcagcca gcctcagtgt ctggatccct gggccaaagg    120
```

```
gtcaccatct cctgcactgg aagcacaaac gacatcggta gtgagaatta tgtgcactgg       180
taccaacagc tcccaggaaa ggcacccagt ctcctcatct atggtgatga taacagagaa       240
tctggggtcc ctgaacgatt ctctggctcc aagtcaggca gctcagccac tctgaccatc       300
actgggctcc aggctgagga cgaggctaat tattattgcc agtcctatga tgacagtctc       360
aatacttacg tgttcggctc aggaacccaa ctgaccgtcc ttggtcagcc caaggcc         417
```

<210> SEQ ID NO 989
<211> LENGTH: 414
<212> TYPE: DNA
<213> ORGANISM: canis familiaris;

<400> SEQUENCE: 989

```
atgatcttca ccatggcctg gtcccctctc ctcctcggcc tccttgctca ctgcacaggg       60
tcctgggccc agtctatgct gactcagcca gcctcagtgt ctgggtccct gggccagaag      120
gtcaccatct cctgcactgg aagaagctcc aacatcggtg gtaattatgt gggctggtac      180
caacagctcc caggaaaagg ccctagaacc gtcatctatg gtaataatcg tcgaccttca      240
ggggtccccg atcgattctc tggctccgcg tcaggcagtt cagccaccct gaccatctct      300 ggctccagg ctgaggacga ggctgagtat tactgctcat catgggatga tagtctcaga      360
ggtgctttgt tcggcggagg cacccacctg accgtcctcg gtcagcccaa ggcc            414
```

<210> SEQ ID NO 990
<211> LENGTH: 420
<212> TYPE: DNA
<213> ORGANISM: canis familiaris;
<220> FEATURE:
<221> NAME/KEY: UNSURE
<222> LOCATION: (21)..(21)
<223> OTHER INFORMATION: n is a, c, t, or g

<400> SEQUENCE: 990

```
atgatgacct ccaccatggg ntggttccct ctcatcctca ccctcctcgc tcactgcgca       60
gggtcctggg cccaggctgt gctgactcag ccggcctcag tgtctgggtc cctgggccag      120 aggtcacca tctcctgcac tggaagcggc tccaatgttg gttatggcaa ttatgtgggc       180
tggtaccagc agctcccagg aacaagcccc agaaccctca tctatgctac tagtagccga      240
ccctcggggg tccctgatcg attctctggc tccaggtcag gcagcacagc aaccctgacc      300
atctctgggc tccaggctga ggatgaagcc gattattact gctcatccta tgacaccagt      360
ctcagtggtg gcgtgttcgg cggaggcacc cacctgaccg tcctcggtca gcccaaggcc      420
```

<210> SEQ ID NO 991
<211> LENGTH: 414
<212> TYPE: DNA
<213> ORGANISM: canis familiaris;

<400> SEQUENCE: 991

```
atgacctcca ccatgggctg gttccctctc atcctcaccc tcttgctcca ctgcgcaggg       60
tcctgggccc agtctgtgct gactcagccg gcctcagtgt ctgggtccct gggccagagg      120
gtcaccatct cctgcactgg aaccagttcc aatgttggtt ttggcgatta tgtgggctgg      180
taccagcagc tcccaggaac gagccccaaa accctcatct atgatcataa tgtccgaccc      240 gcggggtcc ccgatcgatt ctctggctcc aggtcaggca acacagcaac cctgaccacc      300
tctgggctcc aggctgagga tgaagccgac tatttctgtt catcctatga cagtagtctc      360
agtattgtgt tcggcggagg cacccatctg accgtcctcg gtcagcccaa ggcc            414
```

<210> SEQ ID NO 992
<211> LENGTH: 420
<212> TYPE: DNA
<213> ORGANISM: canis familiaris;
<220> FEATURE:
<221> NAME/KEY: UNSURE
<222> LOCATION: (31)..(31)
<223> OTHER INFORMATION: n is a, c, t, or g

<400> SEQUENCE: 992

| | | | | | |
|---|---|---|---|---|---|
| atgatgacct | ccaccatggg | ctggttccct | ntcatcctca | ccctcctcgc | tcactgcgca | 60 |
| gggtcctggg | cccagtctgt | gctgactcag | ccggcctcag | tgtctgggtc | cctgggccag | 120 |
| agggtcacca | tctcctgcac | tggaagcagc | tccaatgttg | gttatggcaa | ttatgtgggc | 180 |
| tggtaccagc | agctcccagg | aacaagcccc | agaaccctca | tctatgatac | tagtagccga | 240 |
| ccctcggggg | tccctgatcg | attctctggc | tccaggtcag | gcagcacagc | aaccctgacc | 300 |
| atctctgggc | tccaggctga | ggatgaagcc | gattattact | gctcatccta | tgacagcagt | 360 |
| ctcagtggtg | ctgtgttcgg | cggaggcacc | cacctgaccg | tcctcggtca | gcccaaggcc | 420 |

<210> SEQ ID NO 993
<211> LENGTH: 423
<212> TYPE: DNA
<213> ORGANISM: canis familiaris;

<400> SEQUENCE: 993

| | | | | | |
|---|---|---|---|---|---|
| atgaggttcc | cttctcagct | cctggggctg | ctgatgctct | ggatcccagg | atccggtggg | 60 |
| gatactgtcc | tgacacagac | cccaccgtcc | ctgtctgtca | gccctggaga | gccggcctcc | 120 |
| atctcctgca | aggccagtca | gagcctcctg | cacagtaatg | gaaacaccaa | tttatattgg | 180 |
| tacctgcaaa | agccaggcca | gtctccacaa | cttctgatct | acttggtttc | caaccgcttc | 240 |
| actggcgtgt | cagacaggtt | cagtggcagc | gggtcaggga | cagatttcac | cctcagaatc | 300 |
| agcagggtgg | agcctaacga | tactggaatt | tattactgcg | ggcaacagtc | acaacttcct | 360 |
| ccgacgttcg | gagcaggaac | caaggtggag | ctcaaacgga | atgatgccca | gccagccgtc | 420 |
| tat | | | | | | 423 |

<210> SEQ ID NO 994
<211> LENGTH: 402
<212> TYPE: DNA
<213> ORGANISM: canis familiaris;

<400> SEQUENCE: 994

| | | | | | |
|---|---|---|---|---|---|
| ctggggctgc | tgatgctctg | gatcccagga | tccagtgggg | atattgtcat | gacacaggcc | 60 |
| ccaccgtctc | tgtccgtcag | ccctggagag | ccggcctcca | tctcctgcac | ggccagtcag | 120 |
| agcctcctgc | acagtaatgg | aaacgcctat | ttaacctggt | accgacagaa | gccaggccag | 180 |
| tctccagagg | acctgatcta | tgaggtgtcc | aaccgcttct | ctggcgtgtc | agacaggttc | 240 |
| agtggcagcg | ggtcagggac | agatttcacc | ctgagaatca | gcagagtgga | ggctgacgat | 300 |
| gctggaattt | attactgcgg | gcagaatcta | cagtttccga | tcacctttgg | caaagggaca | 360 |
| catctggaga | ttaaacggaa | tgatgcccag | ccagccgtct | at | | 402 |

<210> SEQ ID NO 995
<211> LENGTH: 421
<212> TYPE: DNA
<213> ORGANISM: canis familiaris;

```
<400> SEQUENCE: 995
gaggttccca tctcagctcc tggggctgct gatgctctgg atcccaggat ccagtgagga      60
tcttgtcttg acacagaccc cacggtccct gtctgtcagc cctggagaga ctgcctccat     120
ctcctgcaag gccagtcaga gcctcctgtc tcctgatgga aacacatact tgaattggtt     180
ccgacagaag ccaggccagt ctcctcagcg tttgatctat aaggtctcca atagagacat     240
tggggtccca gacaggttca gtggcagcgg gtcaggggaca gatttcaccc tgagaatcag    300
cagagtggag gctgacgata ctggacttta ttactgtggg caagtcacat atcttcccat     360
tactttcagc cagggaacca acctggagat gaaacggaat gatgcccagc cagccgtcta    420
t                                                                     421

<210> SEQ ID NO 996
<211> LENGTH: 405
<212> TYPE: DNA
<213> ORGANISM: canis familiaris;

<400> SEQUENCE: 996
ctcctggggc tgctgatgct ctggatccca ggatccagtg ggatatcgt catgacacag       60 accccactgt ccctgtccgt ctccctgga gagccggcct ccatctcctg caaggccagt     120
cagagtctcc tgcacagtaa tgggaacacc tatttgtctt ggttccgaca gaagccaggc    180
cagtctccag agggcctgat ctatgaggtg tccaagcgct tcactggcgt gtcagacagg    240
ttcagtggca gcgggtcagg gacagatttc accctgacaa tcagtagagt ggaggctgac    300
gatgctggag tttattactg cgggcagggt ctacaatatc ctcggacgtt cggaacagga    360
accaaggtgg agctcaagcg gaatgatgcc cagccagccg tctat                    405

<210> SEQ ID NO 997
<211> LENGTH: 417
<212> TYPE: DNA
<213> ORGANISM: canis familiaris;

<400> SEQUENCE: 997
ttcccatctc agctcctggg gctgctgatg ctctggatcc caggatccag tgaggatctt      60
gtcttgacac agaccccacg gtccctgtct gtcagccctg gagagactgc ctccatctcc    120
tgcaaggcca gtcagagcct cctgtctcct gatggaaaca catacttgaa ttggttccga    180
cagaagccag gccagtctcc tcagcgtttg atctataagg tctccaatag agacattggg    240
gtcccagaca ggttcagtgg cagcgggtca gggacagatt tcaccctgag aatcagcaga    300
gtggaggctg acgatactgg actttattac tgtgggcaag tcacatatct tcccattact    360
ttcagccagg gaaccaacct ggagatgaaa cggaatgatg cccagccagc cgtctat       417

<210> SEQ ID NO 998
<211> LENGTH: 423
<212> TYPE: DNA
<213> ORGANISM: canis familiaris;

<400> SEQUENCE: 998
atgaggttcc catctcagct cctggggctg ctgatgctct ggatcccagg atccagtgag      60
gatcttgtct tgacacagac cccacggtcc ctgtctgtca gccctggaga gactgcctcc    120
atctcctgca aggccagtca gagcctcctg tctcctgatg gaaacacata cttgaattgg    180
ttccgacaga agccaggcca gtctcctcag cgtttgatct ataaggtctc caatagagac    240
attggggtcc cagacaggtt cagtggcagc gggtcaggga cagatttcac cctgagaatc    300
```

```
agcagagtgg aggctgacga tactggactt tattactgtg ggcaagtcac atatcttccc    360
attactttca gccagggaac caacctggag atgaaacgga atgatgccca gccagccgtc    420
tat                                                                  423

<210> SEQ ID NO 999
<211> LENGTH: 423
<212> TYPE: DNA
<213> ORGANISM: canis familiaris;

<400> SEQUENCE: 999
atgaggttcc cttctcagct cctggggctg ctgatgctct ggatcccagg atccagtggg     60
gatattgtca tgacacaggc cccaccgtct ctgtccgtca gccctggaga gccggcctcc    120
atctcctgca aggccagtca gagcctcctg cacagtaatg ggacaccta tttctcttgg     180 ttccaacaga agccaggcca gtctccagag ggcctgatct ataaggtgtc caatcgctac    240
actggcgtgt cagacaggtt cagtggcagc gggtcaggga cagatttcac cctgagaatc    300
agcagagtgg aggctgacga tgctggagtt tattactgcg ggcagatttc acagtttcct    360
tatactttca gccagggaac caagctggag ataaaacgga atgatgccca gccagccgtc    420
tat                                                                  423

<210> SEQ ID NO 1000
<211> LENGTH: 423
<212> TYPE: DNA
<213> ORGANISM: canis familiaris;

<400> SEQUENCE: 1000
atgaggttcc cttctcagct cctggggctg ctgatgctct ggatcccagg atccagtggg     60
gatattgtca tgacacaggc cccaccgcct ctgtccgtca gtcctggaga gccggcctcc    120
atctcctgca aggccagtca gaccctccta cacagtaatg gaacaccta tttgtattgg     180 ttccgacaga agccaggcca gtctccagag ggcctgatcc ataaggtgtc caaccgcttc    240
actggcgtgt cagacaggtt cagtggcagc gggtcaggga cagatttcac cctgagaatc    300
agcagagtgg aggctgacga tgctggactt tattactgcg ggcaaaattt acagtggcct    360
cttacgttcg gccaagggac caaggtggag atcaaacgga atgatgccca gccagccgtc    420
tat                                                                  423

<210> SEQ ID NO 1001
<211> LENGTH: 423
<212> TYPE: DNA
<213> ORGANISM: canis familiaris;

<400> SEQUENCE: 1001
atgaggttcc cttctcagct cctggggctg ctgatgctct ggatcccagg atccggtggg     60
gatattgtca tgacacagac gccaccgtcc ctgtctgtca gccctagaga gccggcctcc    120
atctcctgca gggccagtca gagcctcctg cacagtaacg gaacaccta tttgagttgg     180 tacctgcaaa agccaggcca gtctccacag cttctgatct acttggtttc caaccgcttc    240
actggcgtgt cagacaggtt cagtggcagc gggtcaggga cagatttcac cctgagaatc    300
agcagagtgg aggctgacga tactggagtt tattactgcg ggcaaggtac acagtttcct    360
ccgacgttcg gagcaggaac caaggtggag ctcaaacgga atgatgccca gccagccgtc    420
tat                                                                  423
```

<210> SEQ ID NO 1002
<211> LENGTH: 312
<212> TYPE: DNA
<213> ORGANISM: canis familiaris;

<400> SEQUENCE: 1002

| | | | | | |
|---|---|---|---|---|---|
| actgcctcca | tctcctgcaa | ggccagtcag | agtctcctgc | acagtgatgg | ctacacgtat | 60 |
| ttgagttggt | tccgacagaa | gccaggccag | tctccacagc | gtttgatctc | taaggtctcc | 120 |
| aacagagaca | ctgggtccc | agacaggttc | agtggcagcg | ggtcagggac | agatttcacc | 180 |
| ctgagaatcg | gcagagtgga | ggctgacgat | actggagttt | attactgtgg | gcaagttata | 240 |
| caagatcctt | atactttcag | ccagggaacc | ccgctggaga | taaaacggaa | tggtgcccag | 300 |
| ccagccgtct | at | | | | | 312 |

<210> SEQ ID NO 1003
<211> LENGTH: 298
<212> TYPE: DNA
<213> ORGANISM: canis familiaris;

<400> SEQUENCE: 1003

| | | | | | |
|---|---|---|---|---|---|
| tgcaaggccc | agtcagagtc | tcttgcacag | taatgggaac | acctatttgt | gttggttcca | 60 |
| acagaagcca | ggccagtctc | cacagcgttt | gatctggcgg | gtctccaaca | gagaccctgg | 120 |
| ggtcccagac | aggttcagtg | gcagcgggtc | agggacagat | tttaccctga | gaatcagcag | 180 |
| agtggaggct | gatgatgctg | gaatttatta | ctgcggacaa | ggtacacaat | atccttttac | 240 |
| gttcggccaa | gggaccaagg | tggacattaa | acggaatgat | gcccagccag | ccgtctat | 298 |

<210> SEQ ID NO 1004
<211> LENGTH: 423
<212> TYPE: DNA
<213> ORGANISM: canis familiaris;

<400> SEQUENCE: 1004

| | | | | | |
|---|---|---|---|---|---|
| atgaggttcc | cttctcagct | cctggggctg | ctgatgctct | ggatcccagg | atccagtggg | 60 |
| gatattgtca | tgacacaggc | cccaccgtct | ctgtccgtca | gccctggaga | gccggcctcc | 120 |
| atctcctgca | aggccagtca | gagcttcctg | cacagtgatg | gaacaccta | tttgtattgg | 180 |
| ttccgacaga | agccaggcca | gtctccagag | ggcctgatct | ataaggtgtc | caaccgcttc | 240 |
| actggcgtgt | cagacaggtt | cagtggcagc | ggtcaggga | cagatttcac | cctgagaatc | 300 |
| agcagagtgg | aggctgacga | tgctggagtt | tattactgcg | ggcagaattt | acattttcct | 360 |
| tatactttca | gccagggaac | caagctggag | ataaaacgga | atgatgccca | gccagccgtc | 420 |
| tat | | | | | | 423 |

<210> SEQ ID NO 1005
<211> LENGTH: 330
<212> TYPE: DNA
<213> ORGANISM: canis familiaris;

<400> SEQUENCE: 1005

| | | | | | |
|---|---|---|---|---|---|
| tccgtcagcc | ctgagagcc | ggccttcatc | tcctgcaagg | ccagtcagag | cctcctgcac | 60 |
| agtaatgggt | acagcttgtt | gtattggttc | cgacagaagc | caggccagtc | tcctcagcgt | 120 |
| ttgatctata | aggtctccaa | tagagacatt | ggggtcccag | acaggttcag | tggcagcggg | 180 |
| tcagggacag | attgcaccct | gacaattagc | agagtggagg | ctgatgatgc | tggagtttat | 240 |

| | |
|---|---|
| tactgcgggc aagtataca agatccgttc acttttggcc aagggaccaa actggagatc | 300 |
| aaacggaatg atgcccagcc agccgtctat | 330 |

<210> SEQ ID NO 1006
<211> LENGTH: 354
<212> TYPE: DNA
<213> ORGANISM: canis familiaris;

<400> SEQUENCE: 1006

| | |
|---|---|
| atgacacaga ccccactgtc cctgtccgtc agccctggag agccggcctc catctcctgc | 60 |
| aaggccagtc agagcctcct gcacagtaat gggtacagct tgttgtattg gttccgacag | 120 |
| aagccaggcc agtctccaga ggacctgatc tatgaggtgt ccaaccgctt ctctggcgtg | 180 |
| tcagacaggt tcagtggcag cgggtcaggg acagatttca ccctgagaat cagcagagtg | 240 |
| gaggctgacg atgctggaat ttattactgc gggcagaatc tacagtttcc gatcaccttt | 300 |
| ggcaaaggga cacatctgga gattaaacgg aatgatgccc agccagccgt ctat | 354 |

<210> SEQ ID NO 1007
<211> LENGTH: 357
<212> TYPE: DNA
<213> ORGANISM: canis familiaris;

<400> SEQUENCE: 1007

| | |
|---|---|
| gtcatgacac agaccccact gtccctgtcc gtcagccctg gagagccggc ctccatctcc | 60 |
| tgcaaggcca gtcagagcct cctgcacagt aatgggaaca cctattttaa ttggttccga | 120 |
| cagaagccag gccagtctcc agagggcctg atctatcagg tgtccaaccg cttcactggc | 180 |
| gtgtcagaca ggttcagtgg cagcgggtca gggacagatt tcaccctgag aatcagcaga | 240 |
| gtggaggctg acgatgctgc agtttattac tgcgggcaag atacacactt tccttatact | 300 |
| ttcagccagg gaaccaagct ggagataaat cggaatgatg cccagccagc cgtctat | 357 |

<210> SEQ ID NO 1008
<211> LENGTH: 363
<212> TYPE: DNA
<213> ORGANISM: canis familiaris;
<220> FEATURE:
<221> NAME/KEY: UNSURE
<222> LOCATION: (31)..(31)
<223> OTHER INFORMATION: n is a, c, t, or g
<220> FEATURE:
<221> NAME/KEY: UNSURE
<222> LOCATION: (117)..(117)
<223> OTHER INFORMATION: n is a, c, t, or g
<220> FEATURE:
<221> NAME/KEY: UNSURE
<222> LOCATION: (186)..(186)
<223> OTHER INFORMATION: n is a, c, t, or g

<400> SEQUENCE: 1008

| | |
|---|---|
| gatattgtca tgacacaggc cccaccgtct ntgtccgtca gccctggaga gccggcctcc | 60 |
| atctcctgca cggccggtca gagcctcctg cacagtaatg gaacaccta tttaacntgg | 120 |
| taccgacaga agccaggcca gtctccagag gacctgatct atgaggtgtc caaccgcttc | 180 |
| tctggngtgt cagacaggtt cagtggcagc gggtcaggga cagatttcac cctgagaatc | 240 |
| agcagagtgg aggctgacga tgctgcagtt tattactgcg ggcaagatac acactttcct | 300 |
| tatactttca gccagggaac caagctggaa ataaacgga atgatgccca gccagccgtc | 360 |
| tat | 363 |

<210> SEQ ID NO 1009
<211> LENGTH: 285
<212> TYPE: DNA
<213> ORGANISM: canis familiaris;

<400> SEQUENCE: 1009

| | | | | |
|---|---|---|---|---|
| ctccatctcc tgcacagtac cgggaacacc tatttgaatt ggttccaaca gaagccaggc | 60 |
| cagtctccac agggcctgat ctataaggtc tccaacagag accctggggt cccagacagg | 120 |
| ttcagtggca gcgggtcagg gacagatttc accctgagaa tcagcagagt ggaggctgac | 180 |
| gatgctggag tttattactg catgcaaggt gtacaaactc cgttcacttt tggccaaggg | 240 |
| accaaactgg agatcaaacg aatgatgcca cagccagccg tctat | 285 |

<210> SEQ ID NO 1010
<211> LENGTH: 285
<212> TYPE: DNA
<213> ORGANISM: canis familiaris;

<400> SEQUENCE: 1010

| | | | | |
|---|---|---|---|---|
| ctccatctcc tgcacagtac cgggaacacc tatttgaatt ggttccaaca gaagccaggc | 60 |
| cagtctccac agggcctgat ctataaggtc tccaacagag accctggggt cccagacagg | 120 |
| ttcagaggca gcgggtcagg gacagatttc accctgagaa tcagcagagc ggaggctgat | 180 |
| gatgctggaa tttattactg cgggcaaggt acacaagatc ctcccacctt tggcaaaggg | 240 |
| acacatctgg agattaaacg aatgatgcca cagccagccg tctat | 285 |

<210> SEQ ID NO 1011
<211> LENGTH: 423
<212> TYPE: DNA
<213> ORGANISM: canis familiaris;

<400> SEQUENCE: 1011

| | | | | |
|---|---|---|---|---|
| atgaggttcc cttctcagct cctggggctg ctgatgctct ggatcccagg atccagtggg | 60 |
| gatgttgtca tgacacaggc cccaccgtct ctgtccgtca gccctagaga gccggcctcc | 120 |
| atctcctgca aggccagtca gagcctcctg tatagtaatg gaacaccta tttgtattgg | 180 |
| ttccgccaga agccaggcca gtctccacag cgtttgatct ataaggtctc caatagagac | 240 |
| cctggggtcc cagacaggtt cagtggcagc gggtcaggga cagatttcac cctgagaatc | 300 |
| agcagagtgg aggctgacga tgctggagtt tattactgca tgcaaggtgt acaaactccg | 360 |
| ttcactttg gccagggaac caagctggag ataaaacgga atgatgccca gccagccgtc | 420 |
| tat | 423 |

<210> SEQ ID NO 1012
<211> LENGTH: 418
<212> TYPE: DNA
<213> ORGANISM: canis familiaris;

<400> SEQUENCE: 1012

| | | | | |
|---|---|---|---|---|
| atgaggttcc cttctcagct cctggggctg ctgatgctct ggatcccagg atccagtggg | 60 |
| gatattgtca tgacacagac cccactgtcc ctgtccgtca gccctggaga gccggcctcc | 120 |
| atctcctgca aggccagtca gagcctcctg tatagtaatg gaacaccta tttgtattgg | 180 |
| ttccgccaga agccaggcca gtctccacag cgtttgatct ataaggtctc caatagagac | 240 |
| cctggggtcc cagacaggtt cagtggcagc gggtcaggga cagatttcac cctgagaatc | 300 |
| agcagagtgg aggctgatga tgctggaatt tattactgcg ggcaaggtac acaagatcct | 360 |

-continued

| cccacctttg gcaaagggac acatctggag attaaacgga atgatgccca gccagccg | 418 |

<210> SEQ ID NO 1013
<211> LENGTH: 423
<212> TYPE: DNA
<213> ORGANISM: canis familiaris;

<400> SEQUENCE: 1013

| atgaggttcc cttctcagct cctggggctg ctgatgctct ggatcccagg atccagtggg | 60 |
| gatgttgtca tgacacagac cccaccgtct ctgtccgtca gccctagaga gccggcctcc | 120 |
| atctcctgca aggccagtca gagcctcctg aacagtaatg gcacaccta tttgtattgg | 180 |
| ttccgacaga aacccggcca gtctccagag ggcctgatct ataaggtgtc caaccgcttc | 240 |
| actggcgtgt cagacagatt cagtggcagc gggtcaggga cagatttcac cctgagaatc | 300 |
| agcagagtgg aggctgacga tgctggagtt tattactgcg ggcaaggtat acaggttcct | 360 |
| tatactttca gccagggaac caagctggag ataaaacgga atgatgccca gccagccgtc | 420 |
| tat | 423 |

<210> SEQ ID NO 1014
<211> LENGTH: 423
<212> TYPE: DNA
<213> ORGANISM: canis familiaris;

<400> SEQUENCE: 1014

| atgaggttcc cttctcagct cctggggctg ctgatgctct ggatcccagg atccagtggg | 60 |
| gatgttgtca tgacacaggc cccaccgtct ctgtccgtca gccctagaga gccggcctcc | 120 |
| atctcctgca aggccagtca gagcctcctg aacagtaatg gcacaccta tttgtattgg | 180 |
| ttccgacaga aacccggcca gtctccagag ggcctgatct ataaggtgtc caaccgcttc | 240 |
| actggcgtgt cagacagatt cagtggcagc gggtcaggga cagatttcac cctgagaatc | 300 |
| agcagagtgg aggctgacga tgctggagtt tatcactgcg ggcaaggtat acaggttcct | 360 |
| tatactttca gccagggaac caagctggag ataaaacgga atgatgccca gccagccgtc | 420 |
| tat | 423 |

<210> SEQ ID NO 1015
<211> LENGTH: 423
<212> TYPE: DNA
<213> ORGANISM: canis familiaris;

<400> SEQUENCE: 1015

| atgaggttcc cttctcagct cctggggctg ctgatgctct ggatcccagg atccagtggg | 60 |
| gatatagtca tgacacagac cccactgtcc ctgtccgtca gccctggaga gccggcctcc | 120 |
| atctcctgca aggccagtca gagtctcctg cgcagtaacg ggaacaccta tttgttttgg | 180 |
| tttcgacaca agccaggcca gtctccacag actttgatct atgaggtctc caacagagac | 240 |
| cctggggtcc cagacaggtt cagtggcagc gggtcaggga cagacttcac tctgagaatc | 300 |
| agcagagtgg aggctaacga tactggagtt tattactgcg gacaaggtac acagtttcct | 360 |
| tatactttca gccagggaac caagctggag ataaaacgga atgatgccca gccagccgtc | 420 |
| tat | 423 |

<210> SEQ ID NO 1016
<211> LENGTH: 423
<212> TYPE: DNA
<213> ORGANISM: canis familiaris;

<400> SEQUENCE: 1016

```
atgaggttcc cttctcagct cctggggctg ctgatgctct ggatcccagg atccagtggg    60
gatgttgtca tgacacaggc cccaccgtct ctgtccgtca gccctggaga gccggcctcc   120
atctcctgca aggccagtca gagcctcctg aacagtaatg gcacaccta tttgtattgg    180
ttccgacaga aacccggcca gtctccagag ggcctgatct ataaggtgtc caaccgcttc   240
actggcgtgt cagacagatt cagtggcagc gggtcaggga cagatttcac cctgagaatc   300
agcagagtgg aggctgacga tgctggagtt tatcactgcg ggcaaggtat acaggttcct   360
tatactttca gccagggaac caagctggag ataaaacgga atgatgccca gccagccgtc   420
tat                                                                 423
```

<210> SEQ ID NO 1017
<211> LENGTH: 410
<212> TYPE: DNA
<213> ORGANISM: canis familiaris;

<400> SEQUENCE: 1017

```
atgaggttcc cttctcagct cctggggctg ctgatgctct ggatcccagg atccagtggg    60
gatgttgtca tgacacaggc cccaccgtct ctgtccgtca gccctagaga gccggcctcc   120
atctcctgca aggccagtca gagcctcctg aacagtaatg gcacaccta tttgtattgg    180
ttccgacaga aacccggcca gtctccagag ggcctgatct ataaggtgtc caaccgcttc   240
actggcgtgt cagacagatt cagtggcagc gggtcaggga cagatttcac cctgaggatc   300
agcagagtgg aggctgacga tgctggagtt tattactgcg ggcaaggtat acaggttcct   360
tatactttca gccagggaac caagctggag ataaaacgga atgatgccca              410
```

<210> SEQ ID NO 1018
<211> LENGTH: 378
<212> TYPE: DNA
<213> ORGANISM: canis familiaris;
<220> FEATURE:
<221> NAME/KEY: UNSURE
<222> LOCATION: (11)..(11)
<223> OTHER INFORMATION: n is a, c, t, or g
<220> FEATURE:
<221> NAME/KEY: UNSURE
<222> LOCATION: (56)..(56)
<223> OTHER INFORMATION: n is a, c, t, or g
<220> FEATURE:
<221> NAME/KEY: UNSURE
<222> LOCATION: (58)..(58)
<223> OTHER INFORMATION: n is a, c, t, or g
<220> FEATURE:
<221> NAME/KEY: UNSURE
<222> LOCATION: (61)..(61)
<223> OTHER INFORMATION: n is a, c, t, or g
<220> FEATURE:
<221> NAME/KEY: UNSURE
<222> LOCATION: (104)..(104)
<223> OTHER INFORMATION: n is a, c, t, or g
<220> FEATURE:
<221> NAME/KEY: UNSURE
<222> LOCATION: (107)..(107)
<223> OTHER INFORMATION: n is a, c, t, or g
<220> FEATURE:
<221> NAME/KEY: UNSURE
<222> LOCATION: (292)..(292)
<223> OTHER INFORMATION: n is a, c, t, or g

<400> SEQUENCE: 1018

```
atgaggttcc nttctcagct cctggggctg ctgatgctct ggatcccagg atccantngg    60
```

```
natattgtca tgacacagac cccactgtcc ctgtccgtca gccntgnaga gccggcctcc      120
atctcctgca aggccagtca gagcctcctg tatagtaatg gaacaccta  tttgtattgg     180 ttccgccaga agccaggcca gtctcctcag cgtttgatct ataaggtgtc caaccgcttc     240
acaggcgcgt cagacagatt cagtggcagc gggtcagggg cagatttcac cntgagaatc    300
agcagagtgg aggctgacga tgctggagtt tattactgcg ggcaaggtat acaggttcct   360
tatactttca gccaggga                                                  378
```

```
<210> SEQ ID NO 1019
<211> LENGTH: 401
<212> TYPE: DNA
<213> ORGANISM: canis familiaris;
<220> FEATURE:
<221> NAME/KEY: UNSURE
<222> LOCATION: (39)..(39)
<223> OTHER INFORMATION: n is a, c, t, or g

<400> SEQUENCE: 1019
atgaggttcc cttctcagtt cctggggctg ctgatgctnt ggatcccagg atccagtggg      60
gatattgtca tgacacagac cccactgtcc ctgtccgtca gccctggaga gacggcctcc    120
atctcctgca cagaaccggg aacacctatt tgaattggtt ccaacagaag ccaggccact    180
ctccacgggg cctgatctat aaggtctcca cagagaccc  tggggtccca gacaggttca    240
gtggcagcgg gtcagggaca gatttcaccc tgagaatcag cagagtggag gctgacgatg   300
ctggagttta ttactgcatg caaggtgtac aaactccgtt cacttttggc caagggacca    360
aactggagat caaacggaat gatgcccagc cagccgtcta t                        401
```

```
<210> SEQ ID NO 1020
<211> LENGTH: 423
<212> TYPE: DNA
<213> ORGANISM: canis familiaris;

<400> SEQUENCE: 1020
atgaggttcc cttctcagct cctggggctg ctgatgctct ggatcccagg atccagtggg      60
gatgttgtca tgacacaggc cccaccgtct ctgtccgtca gccctagaga gccggcctcc    120
atctcctgca aggccagtca gagcctcctg aacagtaatg gcacaccta  tttgtattgg     180 ttccgacaga aacccggcca gtctccagag ggcctgatct ataaggtgtc caaccgcttc    240
actggcgtgt cagacagatt cagtggcagc gggtcaggga cagatttcac cctgagaatc   300
agcagagtgg aggctgacga tgctggagtt tattactgcg ggcaaggtat acaggttcct   360
tatactttca gccagggaac caagctggag ataaaacgga atgatgccca gccagccgtc   420
tat                                                                   423
```

```
<210> SEQ ID NO 1021
<211> LENGTH: 423
<212> TYPE: DNA
<213> ORGANISM: canis familiaris;

<400> SEQUENCE: 1021
atgaggttcc cttctcagcc cctggggctg ctgatgctct ggatcccagg atccagtggg      60
gatgttgtca tgacacaggc cccaccgtct ctgtccgtca gccctagaga gccggcctcc    120
atctcctgca aggccagtca gagcctcctg aacagtaatg gcacaccta  tttgtattgg     180 ttccgacaga aacccggcca gtctccagag ggcctgatct ataaggtgtc caaccgcttc    240
actggcgtgt cagacagatt cagtggcagc gggtcaggga cagatttcac cctgagaatc   300
```

```
agcagagtgg aggctgacga tgctggagtt tattactgcg ggcaaggtat acaggttcct    360
tatactttca gccagggaac caagctggag ataaaacgga atgatgccca gccagccgtc    420
tat                                                                  423

<210> SEQ ID NO 1022
<211> LENGTH: 420
<212> TYPE: DNA
<213> ORGANISM: canis familiaris;

<400> SEQUENCE: 1022
atgaggttcc cttctcagct cctggggctg ctgatgctct ggatcccagg atccagtggg     60
gatgttgtca tgacacagac cccaccgtct ctgtccgtca gccctagaga gccggcctcc    120
atctcctgca aggccagtca gagcctcctg aacagtaatg gcacaccta tttgtattgg    180 ttccgacaga aacccggcca gtctccgagg ggcctgatct ataaggtgtc caaccgcttc    240
actggcgtgt cagacagatt cagtggcagc gggtcaggga cagatttcac cctgagaatc    300
agcagagtgg aggctgacga tgctggagtt tattactgcg ggcaaggtat acaggttcct    360
tatactttca gccagggaac caagctggag ataaaacgga atgatgccca gccagccgtc    420

<210> SEQ ID NO 1023
<211> LENGTH: 400
<212> TYPE: DNA
<213> ORGANISM: canis familiaris;

<400> SEQUENCE: 1023
atgaggttcc cttctcagtt cctggggctg ctgatgctct ggatcccagg atccagtggg     60
gatattgtca tgacacagac cccactgtcc ctgtccgtca gccctggaga gacggcctcc    120
atctcctgca cagtaccggg aacacctatt tgaattggtt ccaacagaag ccaggccagt    180
ctccacaggg cctgatctat aaggtctcca acagagaccc tggggtccca gacgggttca    240
gtggcagcgg gtcagggaca gatttcaccc tgagaatcag cagagtggag gctgacgatg    300
ctggagttta ttactgcatg caaggtgtac aaactccgtt cacttttggc caagggacca    360
aactggagat caaacggaat gatgcccagc cagccgtcta                          400

<210> SEQ ID NO 1024
<211> LENGTH: 392
<212> TYPE: DNA
<213> ORGANISM: canis familiaris;
<220> FEATURE:
<221> NAME/KEY: UNSURE
<222> LOCATION: (335)..(335)
<223> OTHER INFORMATION: n is a, c, t, or g

<400> SEQUENCE: 1024
atgaggttcc cttctcagct cctggggctg ctgatgctct ggatcccagg gtccagtggg     60
gagatcgtca tgacacagac cccactgtcc ctgtccgtca gtcctggaga gacggcctcc    120
atctcctaca gggccaagca gagcctcctg tatagtgatg gaacacccta tttggattgg    180
tacatgcaga agccaggcca gtctccccag gccggatct atttggtgtc caatcacttc    240
acaggcgtgt cagacaggtt cagtggcagc gggtcaggga cagatttcac cctgaagatc    300
agcagagtgg aggctgacga tactggagtt tattnctgcg ggcaaggtac acactctcct    360
ccactttcag ccagggaacc aagctggaga ta                                  392

<210> SEQ ID NO 1025
```

```
<211> LENGTH: 291
<212> TYPE: DNA
<213> ORGANISM: canis familiaris;

<400> SEQUENCE: 1025
gccagtcaga gcctcctcca cagtaacggg atcacctatt tgttttggtt tcgacagagg    60
ccaggccagt ctccacagcg tctgatctat aaggcctcca acagagaccc tggggtccca   120
gacaggttca gtggcagcgg gtcagggaca gacttcaccc tgagaatcag cagagtggag   180
gctgacgata gtggagttta ttactgcggg caaggtctac aggttccgtg gacgttcgga   240
gcaggaacca agctggagat aaaacggaat gatgcccagc cagccgtcta t            291

<210> SEQ ID NO 1026
<211> LENGTH: 423
<212> TYPE: DNA
<213> ORGANISM: canis familiaris;

<400> SEQUENCE: 1026
atgaggttcc catctcagct cctggggctg ctgatgctct ggatcccagg atccagtggg    60
gatattgtca tgacacagac cccactgtcc ctgtctgcca gccctggaga gactgcctcc   120
atctcctgca aggccagaca gagcctcctg cacagttatg gaaacacgta tttgaattgg   180
ttccgacaga gccaggtcag tctccacag cgtttgatct ataaggtctc caacagagac   240
actggggtcc cggacaggtt cagtggcagc gggtcaggga cagatttcac cctgagaatc   300
agcagagtgg aggctgacga tactgggggtt tattactgcg ggcaaggtat acagtttcct   360 cgcactttg ccaagggac caaactggag atcagacgga atgatgccca gccagccgtc   420
tat                                                                  423

<210> SEQ ID NO 1027
<211> LENGTH: 423
<212> TYPE: DNA
<213> ORGANISM: canis familiaris;

<400> SEQUENCE: 1027
atgaggttcc cttctcagct cctggggctg ctgatgctct ggatcccagg atccagcgga    60
gatattgtca tgacagaggc ccaccgtct ctgtccgtca gccctggaga gtcggcctcc   120
atctcctgca aggccagtca gagcctcctg cacagtaatg ggaacaccta tttgttctgg   180
ctccgacaga gccaggcca gtctccagag ggcctgatct ataaggtgtc caaccgcttc   240
actggcgtgt cagacaggtt cagtggcaga gggtcaggga cagatttcac cctgcgaatc   300
agcagagtgg aggctggcga tgctggagtt tattactgcg ggcaaaattt acagtttcct   360
tatactttca gccagggaac caagctggag ataaaacgga atgatgccca gccagccgtc   420
tat                                                                  423

<210> SEQ ID NO 1028
<211> LENGTH: 421
<212> TYPE: DNA
<213> ORGANISM: canis familiaris;

<400> SEQUENCE: 1028
atgaggttcc cttctcagct cctggggctg ctgatgctct ggatcccagg atccagtggg    60
gatatcgtca tgacacagac cccactgtcc ctgtccgtca gccctggaga gccggcctcc   120
atttcctgca aggccagtca gagcctcctg cacagtaacg ggaacaccta tttgtattgg   180
tctcgacaga ggccaggcca gtctccggag ggcctgatct ataaggtgtc caaccgcttc   240
```

```
attggcgtgt cagacaggtt cagtggcagc gggtcaggga cagatttcac cctgaaaatc      300
agcagagtgg aggctgacga tgctggagtt tatttctgcg ggcaaaattt acagtttcct      360
tttactttca gccagggaac caagctggag ataaaacgga atgatgccca gccagccgtc      420
t                                                                      421
```

<210> SEQ ID NO 1029
<211> LENGTH: 422
<212> TYPE: DNA
<213> ORGANISM: canis familiaris;

<400> SEQUENCE: 1029

```
atgaggttcc cttctcagct cctggggctg ctgatgctct ggatcccagg atccagtggg       60
gatatcgtca tgacacagat cccactgtcc ctgtccgtca gtcctggaga gccggcctcc      120
atctcctgca aggccagtca gagcctcctg cacagtaacg tgtcaccta tttgttttgg      180 tttcgacaga gccaggcca gtctccacag cgtttgatct ataggggtctc caggagagac     240 cctggggtcc cagacaggtt cagtggcagc gggtcaggga cagatttcac cctgagaatc      300
agcagagtgg aggctgatga tgctggagtt tattactgcg ggcaagcttt acaaactcgt      360
cggacgttcg gagcaggaac caaggtggag ctcaaacgga atgatgccca gccagccgtc      420
ta                                                                     422
```

<210> SEQ ID NO 1030
<211> LENGTH: 420
<212> TYPE: DNA
<213> ORGANISM: canis familiaris;

<400> SEQUENCE: 1030

```
atgaggttcc cttctcagct cctggggctg ctgatgctct ggatccagga tccagtgggg       60
atattgtcat gacacaggcc ccaccgtctc tgtccgtcag ccctggagag ccggcctcca      120
tctcctgcag ggccagtcag agcctcccgc acagtgatgg aaacacctat tgtactggt      180 tccgccagaa gccaggccag tctccagagg gcctgatcta aaggtgtcc aaccgcttca      240 ctggcgtgtc agacaggttc agtggcagcg gtcagggac agatttcacc ctgagaatca      300
gcagagtgga ggctgacgat gctggagttt attactgcgg gcaaaattta cagtttcctc      360
ttacgttcgg ccaagggacc aaggtggaga tcaaacgaa tgatgcccag ccagccgtct      420
```

<210> SEQ ID NO 1031
<211> LENGTH: 422
<212> TYPE: DNA
<213> ORGANISM: canis familiaris;

<400> SEQUENCE: 1031

```
atgaggttcc cttctcagct cctggggctg ctgatgctct ggatcccagg atccagtggg       60
gatattgtca tgacacagac tccactgtcc ctgtctgtca gccctggaga gactgcctcc      120
atctcctgta aggccagtca gagcctcctg tacagtgatg aaactcgat tttgaattgg      180 ttccgacaga gccaggcca gtctccacag cgtttgatct ataaggtctc caacagagac      240
cctggggtcc cagacaggtt cagtggcagc gggtcaggga cagatttcac cctgagaatc      300
agtagagtgg tggctgatga tgctggagtt tattactgcg ggcaagctat acaagatccg      360
tggacgttcg gagcaggaac caaggtggag ctcaaacgga atgacgccca gccagccgtc      420
ta                                                                     422
```

<210> SEQ ID NO 1032
<211> LENGTH: 423
<212> TYPE: DNA
<213> ORGANISM: canis familiaris;

<400> SEQUENCE: 1032

| | | | | | | |
|---|---|---|---|---|---|---|
| atgaggttcc | catctcagct | cctggggctg | ctgatgctct | ggatcccagg | atccagtggg | 60 |
| attattgtca | tgacacagac | cccactgtcc | ctgtctgcca | gccctggaga | gtctgcctcc | 120 |
| atctcctgca | aggccagtca | gagcctcctc | acagtactg | aaacacgta | tttgaattgg | 180 |
| ttccgacaga | agccaggcca | gtctccacag | cgtttgatct | ataggtctc | caacagagac | 240 |
| acggggtcc | cagacaggtt | cagtggcagc | gggtcaggga | cagatttcac | cctgagaatc | 300 |
| agcagagtgg | aggatgagga | tgctggactt | tattactgcg | ggcaaggtat | acaatatccg | 360 |
| ttcactttg | gccaagggac | caaactggag | atcaaacgga | atgatgccca | gccagccgtc | 420 |
| tat | | | | | | 423 |

<210> SEQ ID NO 1033
<211> LENGTH: 285
<212> TYPE: DNA
<213> ORGANISM: canis familiaris;

<400> SEQUENCE: 1033

| | | | | | | |
|---|---|---|---|---|---|---|
| cagagcctcc | tgcacagtaa | cggaaacacc | tatttgaatt | ggtacctgca | aaagccaggc | 60 |
| cagtctcctc | agattctgat | ctacttggct | tcccaccgca | gcaatggcgt | gtcagacagg | 120 |
| ttcagtggca | gcgggtcagg | gacagacttc | accctgagaa | tcagcagagt | ggaggctgac | 180 |
| gatagtggag | tttattactg | cgggcaaggt | ctacaggttc | cgtggacgtt | cggagcagga | 240 |
| accaaggtgg | agctcaaacg | gaatgatgcc | cagccagccg | tctat | | 285 |

<210> SEQ ID NO 1034
<211> LENGTH: 139
<212> TYPE: DNA
<213> ORGANISM: canis familiaris;

<400> SEQUENCE: 1034

| | | | | | | |
|---|---|---|---|---|---|---|
| caagatcctc | atactttcag | ccagggaacc | aagctgggga | taaaacggaa | tgatgcccag | 60 |
| ccagccgtct | atttgttcca | accatctcca | gaccagttac | acacaggaag | tgcctctgtt | 120 |
| gtgtgtttgc | tgaatagct | | | | | 139 |

<210> SEQ ID NO 1035
<211> LENGTH: 396
<212> TYPE: DNA
<213> ORGANISM: canis familiaris;

<400> SEQUENCE: 1035

| | | | | | | |
|---|---|---|---|---|---|---|
| ctgctgatgc | tctggatccc | aggatccagt | ggggatattg | tcatgacaca | gaccccactg | 60 |
| tccctgtccg | tcagccctgg | agagccggcc | tccatctcct | gcaaggccag | tcagagcctc | 120 |
| ctgcacagtg | acgggaacac | ctacttgtat | tggttccgac | agaagccagg | ccaggctcca | 180 |
| cagcgcctga | tctacgtggg | tatcaagaga | gacgctgggg | tcccagacag | gttcagtggc | 240 |
| agcgggtcag | ggacagactt | caccctgaga | atcagcagag | tggaggctga | tgatggtgga | 300 |
| gtttatcact | gcgggcaagg | tacacagctt | ccttatactt | tcagccaggg | aaccaagctg | 360 |
| gagataaaac | ggaatgatgc | ccagccagcc | gtctat | | | 396 |

<210> SEQ ID NO 1036
<211> LENGTH: 285
<212> TYPE: DNA
<213> ORGANISM: canis familiaris;

<400> SEQUENCE: 1036

| | | | | | |
|---|---|---|---|---|---|
| cagagcctcc | tccacagtaa | cgggatcacc | tatttgtttt | ggtttcgaca | gaggccaggc | 60 |
| cagtctccac | agcgtctgat | ctataaggcc | tccaacagag | accctggggt | cccagacagg | 120 |
| ttcagtggca | gcgggtcagg | gacagacttc | accctgagaa | tcagcagagt | ggaggctgac | 180 |
| gatagtggag | tttattactg | cgggcaaaac | atagggtttc | ctaatacttc | cagccaggga | 240 |
| accaagctgg | agataaaacg | gaatgatgcc | cagccagccg | tctat | | 285 |

<210> SEQ ID NO 1037
<211> LENGTH: 423
<212> TYPE: DNA
<213> ORGANISM: canis familiaris;

<400> SEQUENCE: 1037

| | | | | | |
|---|---|---|---|---|---|
| atgaggttcc | cttctcagct | cctggggctg | ctgatgctct | ggatcccagg | atccagtggg | 60 |
| gccattgtca | tgacacaggc | cccaccgtct | ctgtccgtca | gccctggaga | gccggcctcc | 120 |
| atctcctgca | aggccagtca | gagcctcctg | cacggtgatg | ggaccaccta | tttgttttgg | 180 |
| ttccgacaga | agccaggcca | gtctccacag | cgtttgatct | ataaggcctc | caacagagac | 240 |
| cctggggtcc | cagacaggtt | cagtggcagc | gggtcaggga | cagacttcac | cctgagaatc | 300 |
| agcagagtgg | aggctgacga | tagtggagtt | tattactgcg | gcaaggtctc | acaggttccg | 360 |
| cggacgttcg | gagcaggaac | caaggtggag | ctcaaacgga | atgatgccca | gccagccgtc | 420 |
| tat | | | | | | 423 |

<210> SEQ ID NO 1038
<211> LENGTH: 399
<212> TYPE: DNA
<213> ORGANISM: canis familiaris;

<400> SEQUENCE: 1038

| | | | | | |
|---|---|---|---|---|---|
| gggctgctga | tgctctggat | cccaggatcc | agtggggata | ttgtcatgac | acagacgcca | 60 |
| ccgtccctgt | ctgtcagccc | tggggagact | gcctccatct | cctgcaaggc | cagtcagagc | 120 |
| ctcctgttca | gtaacgggaa | aacctatttg | ttttggtttc | gacagaagcc | aggccagtct | 180 |
| ccacaacgtt | tgatctatca | ggtctccaat | agagacctg | gtatcccaga | caggttcagt | 240 |
| ggcagcgggt | caggacagc | tttcaccctg | agaatcagcg | gagtggaggc | tgccgatact | 300 |
| ggagtttatt | actgcgtgca | aggtatacag | tttccttata | ctttcggcca | gggaaccaac | 360 |
| ctggagataa | aacggaatga | tgcccagcca | gccgtctat | | | 399 |

<210> SEQ ID NO 1039
<211> LENGTH: 408
<212> TYPE: DNA
<213> ORGANISM: canis familiaris;

<400> SEQUENCE: 1039

| | | | | | |
|---|---|---|---|---|---|
| atggaagccc | agctcgcct | tctctgcctt | ctgttactct | ggctcccaga | tatcaccgga | 60 |
| gaaatcctac | tgacacagtc | tccagactcc | ctctccttgt | ctcaggagac | agaagtcacc | 120 |
| atcacctgcc | gggccagtca | gtatgttagc | agggacttag | cctggtatca | acaaaaacct | 180 |
| gggcaggccc | ccaaactcct | catctatggt | gcctccaata | aggccactgg | tgtcccatcc | 240 |

| cgtttcagtc gcagtgggtc tgggacagac tttagcctca caatcagcag cctggagccc | 300 |
| gaagatgttg cagtttattt ctgtcaacag tatcatacgg gtccgctaac gttcggccaa | 360 |
| gggaccaagg tggagatcca gcggaatgat gcccagccag ccgtctat | 408 |

<210> SEQ ID NO 1040
<211> LENGTH: 408
<212> TYPE: DNA
<213> ORGANISM: canis familiaris;

<400> SEQUENCE: 1040

| atggaagccc cagctcgcct tctctgcctt ctgttactct ggctcccaga tatcaccgga | 60 |
| gaaatcctac tgacacagtc tccagactcc ctctccttgt ctcaggagac agaagtcacc | 120 |
| atcacctgcc gggccagtca gtatgttagc agggacttag cctggtatca acaaaaacct | 180 |
| gggcaggccc ccaaactcct catctatggt gcctccaata aggccactgg tgtcccatcc | 240 |
| cgtttcagtc gcagtgggtc tgggacagac tttagcctca taatcagcag cctggagccc | 300 |
| gaagatgttg cagtttattt ctgtcaacag tatcatacgg gtccgctaac gttcggccaa | 360 |
| gggaccaagg tggagatcca gcggaatgat gcccagccag ccgtctat | 408 |

<210> SEQ ID NO 1041
<211> LENGTH: 402
<212> TYPE: DNA
<213> ORGANISM: canis familiaris;

<400> SEQUENCE: 1041

| cctggggctg ctgatgtctg gatcccagga tccagtgggg atattgtcat gacacaggcc | 60 |
| ccaccgtctc tgtccgtcag ccctggagag ccggcctcca tctcctgcac ggccagtcag | 120 |
| agcctcctgc acagtaatgg gaacacctat ttaacctggt accgacagaa gccaggccag | 180 |
| tctccagagg acctgatcta tgaggtgtcc aaccgcttct ctggcgtgtc agacaggttc | 240 |
| agtggcagcg ggtcagggac agatttcacc ctgagaatca gcagagtgga ggctgacgat | 300 |
| gctggaattt attactgcgg gcagaatcta cagtttccga tcacctttgg caaagggaca | 360 |
| catctggaga ttaaacggaa tgatgcccag ccagccgtct at | 402 |

<210> SEQ ID NO 1042
<211> LENGTH: 384
<212> TYPE: DNA
<213> ORGANISM: canis familiaris;
<220> FEATURE:
<221> NAME/KEY: UNSURE
<222> LOCATION: (378)..(378)
<223> OTHER INFORMATION: n is a, c, t, or g

<400> SEQUENCE: 1042

| ggatcccagg atccaagtga ggatcttgtc ttgacacaga ccccacggtc cctgtctgtc | 60 |
| agccctggag agactgcctc catctcctgc aaggccagtc agagcctcct gtctcctgat | 120 |
| ggaaacacat acttgaattg gttccgacag aagccaggcc agtctcctca gcgtttgatc | 180 |
| tataaggtct ccaatagaga cattgggggtc ccagacaggt tcagtggcag cgggtcaggg | 240 |
| acagatttca ccctgagaat cagcagagtg gaggctgacg atactggact ttattactgt | 300 |
| gggcaagtca cacatcttcc cattactttc agcagggaa ccaacctgga gatgaaacgg | 360 |
| aatgatgccc agccagcngt ctat | 384 |

<210> SEQ ID NO 1043
<211> LENGTH: 423

```
<212> TYPE: DNA
<213> ORGANISM: canis familiaris;

<400> SEQUENCE: 1043
atgaggttcc cttctcagct cctggggctg ctgatgctct ggatcccagg atccagtgag      60
gatcttgtct tgacacagac cccacggtcc ctgtctgtca gccctggaga gactgcctcc     120
atctcctgca aggccagtca gagcctcctg cacagtaacg gaacaccta tttgttttgg      180 tttcgacaga gccaggcca gtctccacag cgtttgatct ataaggtctc caatagagac     240
attggggtcc cagacaggtt cagtggcagc gggtcaggga cagatttcac cctgagaatc     300
agcagagtgg aggctgacga tactggactt tattactgtg ggcaagtcac atatcttccc     360
attactttca gccaaggaac caacctggag atgaaacgga atgatgccca gccagccgtc     420
tat                                                                   423

<210> SEQ ID NO 1044
<211> LENGTH: 423
<212> TYPE: DNA
<213> ORGANISM: canis familiaris;

<400> SEQUENCE: 1044
atgaggttcc cttctcagct cctggggctg ctgatgctct ggatcccagg atccagtggg      60
gatatcgtca tgacacagac cccactgtcc ctgtccgtca gccctggaga gccggcctcc     120
atctcctgca aggccagtca gagcctcctg cacagtaatg gaaacaccaa tttatattgg      180
tacctgcaaa agccaggcca gtctccacaa cttctgatct acttggtttc caaccgcttc     240
actggcgtgt cagacaggtt cagtggcagc gggtcaggga cagatttcac cctgagaatc     300
agcagagtgg aggctaacga tactggagtt tattactgcg gacaaggtat atattttccg     360
ttcgcttttg gccaagggac caaactggag atcaaacgga atgatgccca gccagccgtc     420
tat                                                                   423

<210> SEQ ID NO 1045
<211> LENGTH: 342
<212> TYPE: DNA
<213> ORGANISM: canis familiaris;
<220> FEATURE:
<221> NAME/KEY: UNSURE
<222> LOCATION: (242)..(242)
<223> OTHER INFORMATION: n is a, c, t, or g

<400> SEQUENCE: 1045
ccaccgtccc tgtctgtcag ccctagagag ccggcctcca tctcctgcag ggccagtcag      60
agcctcctgc acagtaacgg aacacctat tgaattggt acctgcaaaa gccaggccag      120
tctccacagc ttctgatcta cttggtttcc aaccgcttca ctggcgtgtc agacaggttc     180
agtggcagcg ggtcagggac agatttcacc ctgagaatca gcagagtgga ggctgacgat     240
antggagtct attactgcgg gcaaggtaca caggttcctt atactttcag ccagggaacc     300
aggctggaga taaaaaggaa tgatgcccag ccagccgtct at                        342

<210> SEQ ID NO 1046
<211> LENGTH: 423
<212> TYPE: DNA
<213> ORGANISM: canis familiaris;

<400> SEQUENCE: 1046
atgaggttcc catctcagct cctggggctg ctgatgctct ggatcccagg atccagtgag      60
```

-continued

| | |
|---|---|
| gatcttgtct tgacacagac cccacggtcc ctgtctgtca gccctggaga gactgcctcc | 120 |
| atctcctgca aggccagtca gagcctcctg tctcctgatg gaaacacata cttgaattgg | 180 |
| ttccgacaga agccaggcca gtctcctcag cgtttgatct ataaggtctc caatagagac | 240 |
| attggggtcc cagacaggtt cagtggcagc gggtcaggga cagatttcac cctgagaatc | 300 |
| agcagagtgg aggctgacga tactggactt tattactgtg ggcaagtcac atatcttccc | 360 |
| attactttca gccagggaac caacctggag atgaaacgga atgatgccca gccagccgtc | 420 |
| tat | 423 |

<210> SEQ ID NO 1047
<211> LENGTH: 423
<212> TYPE: DNA
<213> ORGANISM: canis familiaris;
<220> FEATURE:
<221> NAME/KEY: UNSURE
<222> LOCATION: (31)..(31)
<223> OTHER INFORMATION: n is a, c, t, or g

<400> SEQUENCE: 1047

| | |
|---|---|
| atgaggttcc catctcagct cctggggctg ntgatgctct ggatcccagg atccagtgag | 60 |
| gatcttgtct tgacacagac cccacggtcc ctgtctgtca gccctggaga gactgcctcc | 120 |
| atctcctgca aggccagtca gagcctcctg tctcctgatg gaaacacata cttgaattgg | 180 |
| ttccgacaga agccaggcca gtctcctcag cgtttgatct ataaggtctc caatagagac | 240 |
| attggggtcc cagacaggtt cagtggcagc gggtcaggga cagatttcac cctgagaatc | 300 |
| agcagagtgg aggctgacga tactggactt tattactgtg ggcaagtcac acatcttccc | 360 |
| attactttca gccagggaac caacctggag atgaaacgga atgatgccca gccagccgtc | 420 |
| tat | 423 |

<210> SEQ ID NO 1048
<211> LENGTH: 384
<212> TYPE: DNA
<213> ORGANISM: canis familiaris;

<400> SEQUENCE: 1048

| | |
|---|---|
| tggatcccag gatccagtga ggatcttgtc ttgacacaga ccccacggtc cctgtctgtc | 60 |
| agccctggag agactgcctc catctcctgc aaggccagtc agagcctcct gtctcctgat | 120 |
| ggaaacacat acttgaattg gttccgacag aagccaggcc agtctcctca gcgtttgatc | 180 |
| tataaggtct ccaatagaga cattggggtc ccagacaggt tcagtggcag cgggtcaggg | 240 |
| acagatttca ccctgagaat cagcagagtg gaggctgacg atactggact ttattactgt | 300 |
| gggcaagtca catatcttcc cattactttc agccagggaa ccaacctgga gatgaaacgg | 360 |
| aatgatgccc agccagccgt ctat | 384 |

<210> SEQ ID NO 1049
<211> LENGTH: 423
<212> TYPE: DNA
<213> ORGANISM: canis familiaris;

<400> SEQUENCE: 1049

| | |
|---|---|
| atgaggttcc cttctcagct cctggggctg ctgatgctct ggatcccagg atccagtggg | 60 |
| gatattgtca tgacacagac cccaccgtcc ctgtctgtca gccctggaga gccggcctcc | 120 |
| atctcctgca aggccagtca gagcctcctg taccctaatg gaaataccta tttgtattgg | 180 |
| tatttgcaaa agccaggcca gtctccacag cttctgatct acttggtttc caatcgcttc | 240 |

```
actggcgtgt cagacaggtt cagtggcagc gggtcaggga cagatttcac cctgcgaatt    300
agcagagtgg aggctaacga tactggagtt tattactgcg acaaggtac atattttccg     360 ttcgcttttg gccaagggac caaactggag atcaaacgga atgatgccca gccagccgtc    420
tat                                                                  423

<210> SEQ ID NO 1050
<211> LENGTH: 411
<212> TYPE: DNA
<213> ORGANISM: canis familiaris;

<400> SEQUENCE: 1050
tctcagctcc tggggctgct gatgctctgg atcccaggat ccagtgggga tattgtcatg     60
acacagaccc cactgtccct gtctgtcagc cctggagaga ctgcctccat ctcctgcaag    120
gccagtcaga gcctcctcta cagtaatgga aacacgtatt tgagttggtt ccgacagaag    180
ccaggccagt ctccacagcg tttgatctat aaggtctcca cagagaccc tggggtccca    240 gacagattca gtggcagcgg gtcagggaca gacttcaccc tgagaatcag cagagtggag    300
gctgacgata ctggagttta ttttgcggc caaggtatac agtctccttt tactttcagc    360
cagggaacca acctggagat aaaacggaat gatgcccagc cagccgtcta t            411

<210> SEQ ID NO 1051
<211> LENGTH: 423
<212> TYPE: DNA
<213> ORGANISM: canis familiaris;

<400> SEQUENCE: 1051
atgaggttcc catctcagct cctggggctg ctgatgctct ggatcccagg atccagtgag     60
gatcttgtct tgacacagac cccacggtcc ctgtctgtca gccctggaga gactgcctcc    120
atctcctgca aggccagtca gagcctcctg tctcctgatg aaacacata cttgaattgg    180 ttccgacaga agccaggcca gtctcctcag cgtttgatct ataaggtctc caatagagac    240
attggggtcc cagacaggtt cagtggcagc gggtcaggga cagatttcac cctgagaatc    300
agcagagtgg aggctgacga tactggactt tattactgtg ggcaagtcac atatcttccc    360
attactttca gccaggggac caacctggag atgaaacgga atgatgccca gccagccgtc    420
tat                                                                  423

<210> SEQ ID NO 1052
<211> LENGTH: 423
<212> TYPE: DNA
<213> ORGANISM: canis familiaris;

<400> SEQUENCE: 1052
atgaggttcc cttctcagct cctggggctg ctgatgctct ggatcccagg atccagtggg     60
gatatcgtca tgacacagac cccactgtcc ctgtctgtca gccctggaga gactgcctcc    120
atctcctgca aggccggtca gagcctcctc tacagtaatg gaaacacgta tttgagttgg    180
ttccgacaga agccaggcca gtctccacag cgtttgatct tgaggtctc caacagagac    240 actggggtcc cggacaggtt cgctggcagc gggtcaggga cagatttcac cctgagaatc    300
agcagagtgg aggctgacga tactggaatt tattactgcg ggcaaggtat acagtttcct    360
cggacgttcg gaccaggagc caaggtggaa ctcaaacgga atgatgccca gccagccgtc    420
tat                                                                  423
```

<210> SEQ ID NO 1053
<211> LENGTH: 411
<212> TYPE: DNA
<213> ORGANISM: canis familiaris;

<400> SEQUENCE: 1053

| | | | | | | |
|---|---|---|---|---|---|---|
| ctcagctcct | gggggctgct | tgatgtctgg | atcccaggat | ccagtgggga | tatcgtcatg | 60 |
| acacagaccc | cactgtccct | gtccgtcagc | cctggagagc | cggcctccat | ctcctgcaag | 120 |
| gccagtcaga | gcctcctgca | cagtaacggg | aacacctatt | tgttttggtt | tcgacagaag | 180 |
| ccaggccagt | ctccacagcg | tttgatctat | aaggtctcca | acagagaccc | tggggtccca | 240 |
| gacaggttca | gtggcagcgg | gtcagggaca | gatttcaccc | tgagaatcag | cagagtggag | 300 |
| gctgacgata | ctggagttta | ctactgcggg | caaggtatac | agtttcctca | tactttcagc | 360 |
| cagggaacca | agctggtgat | aaaacggaat | gatgcccagc | cagccgtcta | t | 411 |

<210> SEQ ID NO 1054
<211> LENGTH: 381
<212> TYPE: DNA
<213> ORGANISM: canis familiaris;

<400> SEQUENCE: 1054

| | | | | | | |
|---|---|---|---|---|---|---|
| ttccctggat | ccagtgggga | tatcgtcatg | acgcagaccc | cactgtccct | gtctgtcagc | 60 |
| cctggagagc | cggcctccat | ctcctgcagg | gccagtcaga | gcctcctgca | cagtaatggg | 120 |
| aacacctatt | tcgcttggtt | ccaacagaag | ccaggccagt | ctccacagcg | tttgatctat | 180 |
| cacgtctcca | agagagaccc | tggggttcca | gacaggttca | gtggcagcgg | gtcagggaca | 240 |
| gattgcaccc | tgacaattag | cagagtggag | gctgatggtg | ctggagttta | ttactgcggg | 300 |
| caaggtatac | aagatccgtt | cacttttggc | caagggacca | aactggagat | caaacggaat | 360 |
| gatgcccagc | cagccgtcta | t | | | | 381 |

<210> SEQ ID NO 1055
<211> LENGTH: 423
<212> TYPE: DNA
<213> ORGANISM: canis familiaris;

<400> SEQUENCE: 1055

| | | | | | | |
|---|---|---|---|---|---|---|
| atgaggttcc | cttctcagct | cctggggctg | ctgatgctct | ggatcccagg | atccggtggg | 60 |
| gatattgtca | tgacacagac | cccaccgtcc | ctgtctgtca | gccctggaga | gccggcctcc | 120 |
| atctcctgca | aggccagtca | gagcctcctg | taccctaatg | gaaataccta | tttgtattgg | 180 |
| tatttgcaaa | agccaggcca | gtctcctcag | cgtttgatct | ataaggtctc | caatagagac | 240 |
| attggggtcc | cagacaggtt | cagtggcagc | gggtcaggga | cagatttcac | cctgagaatc | 300 |
| agcagagtgg | aggctgacga | tactggactt | tattactgtg | ggcaagtcac | atatcttccc | 360 |
| attactttca | gccagggaac | caacctggag | atgaaacgga | atgatgccca | gccagccgtc | 420 |
| tat | | | | | | 423 |

<210> SEQ ID NO 1056
<211> LENGTH: 405
<212> TYPE: DNA
<213> ORGANISM: canis familiaris;
<220> FEATURE:
<221> NAME/KEY: UNSURE
<222> LOCATION: (364)..(364)
<223> OTHER INFORMATION: n is a, c, t, or g

<400> SEQUENCE: 1056

```
gctcctgggg ctgctgatgc tctggatccc aggatccggt ggggatattg tcatgacaca      60
gaccccaccg tccctgtctg tcagccctgg agagccggcc tccatctcct gcaagccagt     120
cagagcctcc tgcacagtaa tgggaacacc tatttcgctt ggttccaaca aagccaggc     180 cagtctccac agcgtttgat ctatcacgtc tccaagagac accctggggt tccagacagg    240
ttcagtggca gcgggtcagg gacagattgc accctgacaa ttagcagagt ggaggctgat    300
gatgctggag tttattgctg cgggcaaggt atacaagatc cgttcacttt tggccaaggg    360
accnaactgg agatcaaacg gaatgatgcc cagccagccg tctat                    405

<210> SEQ ID NO 1057
<211> LENGTH: 423
<212> TYPE: DNA
<213> ORGANISM: canis familiaris;

<400> SEQUENCE: 1057
atgaggttcc cttctcagct cctggggctg ctgatgctct ggatcccagg atccggtggg    60
gatattgtca tgacacagac cccaccgtcc ctgtctgtca gccctggaga gccggcctcc   120
atctcctgca aggccagtca gagcctcctg taccctaatg gaaataccta tttgtattgg   180
tatttgcaaa agccaggcca gtctccacag cttctgatct acttggtttc caatcgcttc   240
actggcgtgt cagacaggtt cagtggcagc gggtcaggga cagatttcac cctgcgaatt   300
agcagagtgg aggctaacga tactggagtt tattactgcg acaaggttc atattttccg    360 ttcgcttttg gccaagggac caaactggag atcaaacgga tgatgccca gctagccgtc    420 tat                                                                 423

<210> SEQ ID NO 1058
<211> LENGTH: 423
<212> TYPE: DNA
<213> ORGANISM: canis familiaris;

<400> SEQUENCE: 1058
atgaggttcc catctcagct cctggggctg ctgatgctct ggatcccagg atccagtgag    60
gatcttgtct tgacacagac cccacggtcc ctgtctgtca gccctggaga gactgcctcc   120
atctcctgca aggccagtca gagcctcctg tctcctgatg aaacacata cttgaattgg    180 ttccgacaga agccaggcca gtctcctcag cgtttgatct ataaggtctc caatagagac    240
attggggtcc cagacaggtt cagtggcagc gggtcaggga cagatttcac cctgagaatc    300
agcagagtgg aggctgacga tactggactt tattactgtg ggcaagtcac atatcttccc    360
attactttca gccagggaac caacctgggg atgaaacgga tgatgccca gccagccgtc    420 tat                                                                 423

<210> SEQ ID NO 1059
<211> LENGTH: 423
<212> TYPE: DNA
<213> ORGANISM: canis familiaris;

<400> SEQUENCE: 1059
atgaggttcc cttctcagct cctggggctg ctgatgctct ggatcccagg atccagtggg    60
gatattgtca tgacacaggc cccaccgtct ctgtccgtca gccctggaga gccggcctcc   120
atctcctgca aggccagtca gagcctcctg tacagtaatg gaacacgca tttgtattgg    180 ttccgacaga agccaggcca gtctccagag ggcctgatct ataggtgtc caagcgcttc    240
```

```
actggcgtgt cagaaaggtt cagtggcagc gggtcaggga cagatttcac cctggaaatc    300
agcagagtgg aggctgacga tgttggagtt tattactgcg gcaaaatttt acagcctcct    360
tatactttca gccagggaac caagctggaa ataaaacgga atgatgccca gccagccgtc    420
tat                                                                  423
```

```
<210> SEQ ID NO 1060
<211> LENGTH: 423
<212> TYPE: DNA
<213> ORGANISM: canis familiaris;

<400> SEQUENCE: 1060
atgaggttcc cttctcagct cctggggctg ctgatgctct ggatcccagg atccggtggg    60
gatattgtca tgacacagac cccaccgtcc ctgtctgtca gccctggaga gccggcctcc    120
atctcctgca aggccagtca gagcctcctg taccctaatg aaataccta  tttgtattgg    180 tatttgcaaa agccaggcca gtctccacag cttctgatct acttggtttc caatcgcttc    240
actggcgtgt cagacaggtt cagtggcagc gggtcaggga cagatttcac cctgcgaatt    300
agcagagtgg aggctaacga tactggagtt tattactgcg gacaaggtac atattttccg    360
ttcgcttttg gccaagggac caaactggag atcaaacgga atgatgccca gccagccgtc    420
tat                                                                  423
```

```
<210> SEQ ID NO 1061
<211> LENGTH: 339
<212> TYPE: DNA
<213> ORGANISM: canis familiaris;

<400> SEQUENCE: 1061
tcgtctctgt ccgtcagtcc tggagagccg gcctccatct cctgtaaggc cagtcagagc    60
ctcctgtcta gtaatgggaa cacctattta tattggatcc gacagaagcc aggccagtct    120
ccagagggcc tgatctacaa ggtgtccaac cgcttcactg gcgtgtcaga caggttcagt    180
ggcagcggat caggaacaga tttcaccctg agaatcacca gagtgaggc  tgacgatgct    240 ggagtttatt actgcgggca gaatttccgg tttccttata ctctcagcca gggaaccaaa    300
ctggagatag aacggaatga tgcccagcca gccgtctat                          339
```

```
<210> SEQ ID NO 1062
<211> LENGTH: 423
<212> TYPE: DNA
<213> ORGANISM: canis familiaris;

<400> SEQUENCE: 1062
atgaggttcc cttctcagct cctggggctg ctgatgctct ggatcccagg atccggtggg    60
gatattgtca tgacacagac cccaccgtcc ctgtctgtca gccctggaga gccggcctcc    120
atctcctgca aggccagtca gagcctcctg tacagtaatg gaacacgca  tttgtattgg    180 ttccgacaga agccaggcca gtctccagag ggcctgatct ataggtgtc  caagcgcttc    240 actggcgtgt cagaaaggtt cagtggcagc gggtcaggga cagatttcac cctggaaatc    300
agcagagtgg gggctgacga tgttggagtt tattactgcg gcaaaatttt acagcctcct    360
tatactttca gccagggaac caagctggaa ataaaacgga atgatgccca gccagccgtc    420
tat                                                                  423
```

```
<210> SEQ ID NO 1063
<211> LENGTH: 423
```

```
<212> TYPE: DNA
<213> ORGANISM: canis familiaris;

<400> SEQUENCE: 1063
atgaggttcc catctcagct cctggggctg ctgatgctct ggatcccagg atccagtgag      60
gatcttgtct tgacacagac cccacggtcc ctgtctgtca gccctggaga gactgcctcc     120
atctcctgca aggccagtca gagcctcctg tctcctgatg gaaacacata cttgaattgg     180
ttccgacaga agccaggcca gtctcctcag cgtttgatct ataaggtctc caatagagac     240
attggggtcc cagacaggtt cagtggcagc gggtcaggga cagatttcac cctgagaatc     300
agcagagtgg aggctgacga tactggactt tattactgtg ggcaagtcac atatcttccc     360
attactttca gccagggaac caacctggag atgaaacgga atgatgccca gccagccgtc     420
tat                                                                   423

<210> SEQ ID NO 1064
<211> LENGTH: 423
<212> TYPE: DNA
<213> ORGANISM: canis familiaris;
<220> FEATURE:
<221> NAME/KEY: UNSURE
<222> LOCATION: (107)..(107)
<223> OTHER INFORMATION: n is a, c, t, or g

<400> SEQUENCE: 1064
atgaggttcc cttctcagct cctggggctg ctgatgctct ggatcccagg atccggtggg      60
gatattgtca tgacacagac cccaccgtcc ctgtctgtca gccctgnaga gccggcctcc     120
atctcctgca aggccagtca gagcccctg tacccctaatg gaaataccta tttgtattgg     180
tatttgcaaa agccaggcca gtctccacag cttctgatct acttggtttc caatcgcttc     240
actggcgtgt cagacaggtt cagtggcagc gggtcaggga cagatttcac cctgcgaatt     300
agcagagtgg aggctaacga tactggagtt tattactgcg acaaggtac atattttccg      360
ttcgcttttg gccaagggac caaactggag atcaaacgga atgatgccca gccagccgtc     420
tat                                                                   423

<210> SEQ ID NO 1065
<211> LENGTH: 423
<212> TYPE: DNA
<213> ORGANISM: canis familiaris;

<400> SEQUENCE: 1065
atgaggttcc cttctcagct cctggggctg ctgatgctct ggatcccagg atccggtggg      60
gatattgtca tgacacagac cccaccgtcc ctgtctgtca gccctggaga gccggcctcc     120
atctcctgca aggccagtca gagcctcctg tacccctaatg gaaataccta tttgtattgg     180
tatttgcaaa agccaggcca gtctccacag cttctgatct acttggtttc caatcgcttc     240
actggcgtgt cagacaggtt cagtggcagc gggtcaggga cagatttcac cctgagaatc     300
agcagagtgg aggctgacga tactggactt tattactgtg ggcaagtcac atatcttccc     360
attactttca gccagggaac caacctggag atgaaacgga atgatgccca gccagccgtc     420
tat                                                                   423

<210> SEQ ID NO 1066
<211> LENGTH: 423
<212> TYPE: DNA
<213> ORGANISM: canis familiaris;
```

```
<400> SEQUENCE: 1066
atgaggttcc cttctcagct cctggggctg ctgatgctct ggatcccagg atccggtggg      60
gatattgtca tgacacagac cccaccgtcc ctgtctgtca gccctggaga gccggcctcc     120
atctcctgca aggccagtca gagcctcctg taccctaatg gaaataccta tttgtattgg    180
tatttgcaaa agccaggcca gtctccacag cttctgatct acttggtttc caatcgcttc    240
actggcgtgt cagacaggtt cagtggcagc gggtcaggga cagatttcac cctgcgaatt    300
agcagagtgg aggctaacga tactggagtt tattactgcg ggcaaggtat acaagatccg    360 ttcactttg gccaagggac caaactggag atcaaacgga atgatgccca gccagccgtc     420
tat                                                                   423

<210> SEQ ID NO 1067
<211> LENGTH: 423
<212> TYPE: DNA
<213> ORGANISM: canis familiaris;

<400> SEQUENCE: 1067
atgaggttcc cttctcagct cctggggctg ctgatgctct ggatcccagg atccggtggg      60
gatattgtca tgacacagac cccaccgtcc ctgtctgtca gccctggaga gccggcctcc     120
atctcctgca aggccagtca gagcctcctg taccctaatg gaaataccta tttgtattgg    180
tatttgcaaa agccaggcca gtctccacag cttctgatct acttggtttc caatcgcttc    240
actggcgtgt cagacaggtt cagtggcagc gggtcaggga cagatttcac cctgcgaatt    300
agcagagtgg aggctaacga tactggagtt tattactgcg gacaaggtac atattttccg    360
ttcgcttttg gccaagggac caaactggag atcaaacgga atgatgccca gccagccgtc    420
tat                                                                   423

<210> SEQ ID NO 1068
<211> LENGTH: 423
<212> TYPE: DNA
<213> ORGANISM: canis familiaris;

<400> SEQUENCE: 1068
atgaggttcc catctcagct cctggggctg ctgatgctct ggatcccagg atccagtgag      60
gatcttgtct tgacacagac cccacggtcc ctgtctgtca gccctggaga gactgcctcc     120
atctcctgca aggccagtca gagcctcctg tctcctgatg gaaacacata cttgaattgg    180
ttccgacaga gccaggcca gtctcctcag cgtttgatct ataaggtctc caatagagac    240
attggggtcc cagacaggtt cagtggcagc gggtcaggga cagatttcac cctgacaatc    300
agcagagtgg aggctgacga tgctggagtt tattactgtg ccaagttct acaggatcct    360 tatactttca gccagggaac caagctggag ataagacgga atgatgccca gccagccgtc    420
tat                                                                   423

<210> SEQ ID NO 1069
<211> LENGTH: 264
<212> TYPE: DNA
<213> ORGANISM: canis familiaris;

<400> SEQUENCE: 1069
gggaacacct atttgtattg gttccgacag aggccaggcc agtctccgga ggccctgatc      60
tatagggtgt ccagccgctt ccctggcgtg tcagacaggt tcagtggcag cgggtcagtg    120
acagatttca ccctgagaat cagcagagtg gaggctgacg atgctggaat ttattactgc    180
```

```
gggcagaatc tacagtttcc gatcacctttt ggcaaaggga cacatctgga gattaaacgg    240
aatgatgccc agccagccgt ctat                                            264

<210> SEQ ID NO 1070
<211> LENGTH: 282
<212> TYPE: DNA
<213> ORGANISM: canis familiaris;

<400> SEQUENCE: 1070
agcctcctgc acagtaacgg gaacacctat ttgtcttggt ttcgacagaa gtcaggccag     60
tctccacaac gtttgatcta tagggtctcc aacagagacc ctggggtccc agacaggttc    120
agtggcagcg ggtcagggac agatttcacc ctgagaatca gcagagtgga ggctgacgat    180
actggacttt attactgtgg gcaagtcaca tatcttccca ttactttcag ccagggaacc    240
aacctggaga tgaaacggaa tgatgcccag ccagccgtct at                       282

<210> SEQ ID NO 1071
<211> LENGTH: 201
<212> TYPE: DNA
<213> ORGANISM: canis familiaris;

<400> SEQUENCE: 1071
aaggtgtcca accgcttcag tggcgtgtca gaaaggatca gtggcagcgg gtcagggaca     60
gatttcaccc tgagaatcag cagagtggag gctgacgatg ctgggattta ttactgcggg    120
caaactacac actttcctta ctttcggc cagggaacca agctggaaat aaaacggaat     180
gatgcccagc cagccgtcta t                                              201

<210> SEQ ID NO 1072
<211> LENGTH: 282
<212> TYPE: DNA
<213> ORGANISM: canis familiaris;

<400> SEQUENCE: 1072
agcctcctgc acagtaatgg gaacacctat ttcgcttggt tccaacagaa gccaggccag     60
tctccacagc gtttgatcta tcacgtctcc aagagagacc ctggggttcc agacaggttc    120
agtggcagcg ggtcaggaac agattgcacc ctgacaatta gcagagtgga ggctgatgat    180
gctggagttt attactgcgg gcaaggtata caagatccgt tcacttttgg ccaagggacc    240
aaactggaga tcaaacggaa tgatgcccag ccagccgtct at                       282

<210> SEQ ID NO 1073
<211> LENGTH: 414
<212> TYPE: DNA
<213> ORGANISM: canis familiaris;

<400> SEQUENCE: 1073
atgacctcca acatggcctg gtcccctctc ctcctcacac tccttcctta ctacacaggg     60
tcctgggccc agtctgtgct gactcagccg acctcagtgt cggggtcccc tggccagagg    120
gtcaccatct cctgctctgg aagcacggac aacatcggtc ttgttggtgc gagttggtac    180
caacaactcc caggaagggc ccctaaactc ctcctgtata gtgatgggga tcgaccgtca    240
ggggtccctg accggttttc cggctccagg tctggcaact cagccaccct ggccatcact    300
gggcttcagg ctgaggacga ggctgactat tactgccagt cctttgattc cacgcttgat    360
ggtttcgtgt tcggctcagg aacccaactg accgtccttg gtcagcccaa ggcg          414
```

<210> SEQ ID NO 1074
<211> LENGTH: 138
<212> TYPE: PRT
<213> ORGANISM: canis familiaris;

<400> SEQUENCE: 1074

Met Thr Ser Asn Met Ala Trp Ser Pro Leu Leu Thr Leu Leu Pro
1               5                   10                  15

Tyr Tyr Thr Gly Ser Trp Ala Gln Ser Val Leu Thr Gln Pro Thr Ser
            20                  25                  30

Val Ser Gly Ser Pro Gly Gln Arg Val Thr Ile Ser Cys Ser Gly Ser
        35                  40                  45

Thr Asp Asn Ile Gly Leu Val Gly Ala Ser Trp Tyr Gln Gln Leu Pro
    50                  55                  60

Gly Arg Ala Pro Lys Leu Leu Tyr Ser Asp Gly Asp Arg Pro Ser
65                  70                  75                  80

Gly Val Pro Asp Arg Phe Ser Gly Ser Arg Ser Gly Asn Ser Ala Thr
                85                  90                  95

Leu Ala Ile Thr Gly Leu Gln Ala Glu Asp Glu Ala Asp Tyr Tyr Cys
            100                 105                 110

Gln Ser Phe Asp Ser Thr Leu Asp Gly Phe Val Phe Gly Ser Gly Thr
        115                 120                 125

Gln Leu Thr Val Leu Gly Gln Pro Lys Ala
    130                 135

<210> SEQ ID NO 1075
<211> LENGTH: 408
<212> TYPE: DNA
<213> ORGANISM: canis familiaris;

<400> SEQUENCE: 1075
atggactggg tcccctttta cctcctgccc ttcattttct ctacaggttt ctgtgctcct      60
cctgtgctga cccagcctcc aagtgcatct gcctccctgg aagcctcggt caagctcacc     120
tgcactctga gcagtgagca cagcagttac tttatttact ggtatcaaca acaaccacca    180
gagaaggccc ctcggtatct gatgagggtt aacagtgatg gaagccacag cagaggggac    240
gggatcccca gtcgcttctc aggctccagc tctggggctg accgctattt aaccatctcc    300
aacatccagt ctgaggatga ggcagattat tactgtttta cacctgatga tagcaatagt    360
gtgttcggcg aggcacccca tctgaccgtc ctcggtcagc ccaaggcc               408

<210> SEQ ID NO 1076
<211> LENGTH: 136
<212> TYPE: PRT
<213> ORGANISM: canis familiaris;

<400> SEQUENCE: 1076

Met Asp Trp Val Pro Phe Tyr Leu Leu Pro Phe Ile Phe Ser Thr Gly
1               5                   10                  15

Phe Cys Ala Pro Pro Val Leu Thr Gln Pro Pro Ser Ala Ser Ala Ser
            20                  25                  30

Leu Glu Ala Ser Val Lys Leu Thr Cys Thr Leu Ser Ser Glu His Ser
        35                  40                  45

Ser Tyr Phe Ile Tyr Trp Tyr Gln Gln Gln Pro Glu Lys Ala Pro
    50                  55                  60

Arg Tyr Leu Met Arg Val Asn Ser Asp Gly Ser His Ser Arg Gly Asp
65                  70                  75                  80

```
Gly Ile Pro Ser Arg Phe Ser Gly Ser Ser Gly Ala Asp Arg Tyr
                85                  90                  95

Leu Thr Ile Ser Asn Ile Gln Ser Glu Asp Glu Ala Asp Tyr Tyr Cys
            100                 105                 110

Phe Thr Pro Asp Asp Ser Asn Ser Val Phe Gly Gly Gly Thr His Leu
        115                 120                 125

Thr Val Leu Gly Gln Pro Lys Ala
    130                 135

<210> SEQ ID NO 1077
<211> LENGTH: 417
<212> TYPE: DNA
<213> ORGANISM: canis familiaris;

<400> SEQUENCE: 1077
atgacctcca ccatggcctg gtccctctc ctcctcaccc tcctcgctca ttgcacagtg      60
tcctgggccc aggctgtgct gactcagcca ccctctgtgt ctgcagccct ggggcagagg    120
gtcaccatct cctgcactgg aactaacacc aacatcggca atggttatga tgtacattgg    180
taccagcagg tcccaggaaa gtcccctaaa accttcatct atggtaataa caatcgaccc    240 tcggggtcc cggttcgatt ctctggctcc aagtcaggca gcacagccac cctgaccatc     300
actgggatcc aggctgagga tgagactgat tattactgcc agtcctatga tgacaacctc    360
gatggttacg tgttcggctc gggaacccaa ctgaccgtcc ttggtcagcc caaggcc       417

<210> SEQ ID NO 1078
<211> LENGTH: 139
<212> TYPE: PRT
<213> ORGANISM: canis familiaris;

<400> SEQUENCE: 1078

Met Thr Ser Thr Met Ala Trp Ser Pro Leu Leu Leu Thr Leu Leu Ala
1               5                   10                  15

His Cys Thr Val Ser Trp Ala Gln Ala Val Leu Thr Gln Pro Pro Ser
            20                  25                  30

Val Ser Ala Ala Leu Gly Gln Arg Val Thr Ile Ser Cys Thr Gly Thr
        35                  40                  45

Asn Thr Asn Ile Gly Asn Gly Tyr Asp Val His Trp Tyr Gln Gln Val
    50                  55                  60

Pro Gly Lys Ser Pro Lys Thr Phe Ile Tyr Gly Asn Asn Asn Arg Pro
65                  70                  75                  80

Ser Gly Val Pro Val Arg Phe Ser Gly Ser Lys Ser Gly Ser Thr Ala
                85                  90                  95

Thr Leu Thr Ile Thr Gly Ile Gln Ala Glu Asp Glu Thr Asp Tyr Tyr
            100                 105                 110

Cys Gln Ser Tyr Asp Asp Asn Leu Asp Gly Tyr Val Phe Gly Ser Gly
        115                 120                 125

Thr Gln Leu Thr Val Leu Gly Gln Pro Lys Ala
    130                 135

<210> SEQ ID NO 1079
<211> LENGTH: 408
<212> TYPE: DNA
<213> ORGANISM: canis familiaris;

<400> SEQUENCE: 1079
atggactggg tcccttttta cctcctgccc ttcattttct ctacaggttt ctgtgctcct     60
```

```
cctgtgctga cccagactcc aagtgcatct gcctccctgg aagactcggt caagctcacc    120
tgcactttga gcagggagca cagcacttac tatattacct ggtatcaaca acaacaacca    180
gggaaggccc ctcggtatct gatgaaggtt aacagtgatg gaagccacag caggggagac    240
gggatcccca gtcgcttctc aggctccagc tctggggctg accgctattt aaccatctcc    300
aacatccagt ctgaggatga ggcagattat tactgtttta cacccgctaa tagcaatagt    360
gtgttcggcg gaggcaccca tctgaccgtc ctcggtcagc ccaaggcc              408
```

<210> SEQ ID NO 1080
<211> LENGTH: 136
<212> TYPE: PRT
<213> ORGANISM: canis familiaris;

<400> SEQUENCE: 1080

Met Asp Trp Val Pro Phe Tyr Leu Leu Pro Phe Ile Phe Ser Thr Gly
1               5                   10                  15

Phe Cys Ala Pro Pro Val Leu Thr Gln Thr Pro Ser Ala Ser Ala Ser
            20                  25                  30

Leu Glu Asp Ser Val Lys Leu Thr Cys Thr Leu Ser Arg Glu His Ser
        35                  40                  45

Thr Tyr Tyr Ile Thr Trp Tyr Gln Gln Gln Pro Gly Lys Ala Pro
    50                  55                  60

Arg Tyr Leu Met Lys Val Asn Ser Asp Gly Ser His Ser Arg Gly Asp
65                  70                  75                  80

Gly Ile Pro Ser Arg Phe Ser Gly Ser Ser Ser Gly Ala Asp Arg Tyr
                85                  90                  95

Leu Thr Ile Ser Asn Ile Gln Ser Glu Asp Glu Ala Asp Tyr Tyr Cys
            100                 105                 110

Phe Thr Pro Ala Asn Ser Asn Ser Val Phe Gly Gly Gly Thr His Leu
        115                 120                 125

Thr Val Leu Gly Gln Pro Lys Ala
    130                 135

<210> SEQ ID NO 1081
<211> LENGTH: 342
<212> TYPE: DNA
<213> ORGANISM: canis familiaris;

<400> SEQUENCE: 1081

```
tcctgggccc agtctgtgct gactcagccg gcctctgtgt ctgggtccct gggccagagg    60
gtcgccatct cctgcactgg aagcagctcc aatgttggtt ttggccctta tttgggctgg    120
taccaacagg tcccaggagc aggcccccaga accctcatgt atcgtattag tcgccgcccc    180 tcggggtcc ctgatcgatt ctctggctcc aggtcaggca acacagcaac cctgaccatc    240
tctggcctcc agcctgatga tgagggcgat tattactgct catcctatga caccagtctc    300
agtgcgattg tgttcggcgg aggcacccac ctgaccgttg tc                     342
```

<210> SEQ ID NO 1082
<211> LENGTH: 114
<212> TYPE: PRT
<213> ORGANISM: canis familiaris;

<400> SEQUENCE: 1082

Ser Trp Ala Gln Ser Val Leu Thr Gln Pro Ala Ser Val Ser Gly Ser
1               5                   10                  15

-continued

Leu Gly Gln Arg Val Ala Ile Ser Cys Thr Gly Ser Ser Ser Asn Val
                20                  25                  30

Gly Phe Gly Pro Tyr Leu Gly Trp Tyr Gln Gln Val Pro Gly Ala Gly
            35                  40                  45

Pro Arg Thr Leu Met Tyr Arg Ile Ser Arg Arg Pro Ser Gly Val Pro
        50                  55                  60

Asp Arg Phe Ser Gly Ser Arg Ser Gly Asn Thr Ala Thr Leu Thr Ile
65                  70                  75                  80

Ser Gly Leu Gln Pro Asp Asp Glu Gly Asp Tyr Tyr Cys Ser Ser Tyr
                85                  90                  95

Asp Thr Ser Leu Ser Ala Ile Val Phe Gly Gly Thr His Leu Thr
                100                 105                 110

Val Val

<210> SEQ ID NO 1083
<211> LENGTH: 414
<212> TYPE: DNA
<213> ORGANISM: canis familiaris;
<220> FEATURE:
<221> NAME/KEY: UNSURE
<222> LOCATION: (206)..(206)
<223> OTHER INFORMATION: n is a, c, t, or g

<400> SEQUENCE: 1083
atgacctcca ccatgggctg gttccctctc ctcctcacca tcctcgctca ctgcacaggg     60
tcctgggccc agtctgtgct gagtcagccg gcctcagtgt ccgggtccct gggccagagg    120
gtcaccatct cctgcactgg aagcagctcc aacatcggta gaggttatgt gggctggtac    180
caacagctcc cgggaacagg cccanaacc ctcatctttg gtcctaataa gcgaccctca     240
ggggtccccg atcgcttctc tggctccagg tcggacagca caggcaccct gaccatctct    300
gggctccagg ctgaggatga gggtgattat tactgctcat cgtgggacac cactctcagt    360
gcttacgtgt tcggctcagg gacccaactg accgttcttg gtcagcccaa ggcc          414

<210> SEQ ID NO 1084
<211> LENGTH: 138
<212> TYPE: PRT
<213> ORGANISM: canis familiaris;
<220> FEATURE:
<221> NAME/KEY: UNSURE
<222> LOCATION: (69)..(69)
<223> OTHER INFORMATION: X is any amino acid

<400> SEQUENCE: 1084

Met Thr Ser Thr Met Gly Trp Phe Pro Leu Leu Leu Thr Ile Leu Ala
1               5                   10                  15

His Cys Thr Gly Ser Trp Ala Gln Ser Val Leu Ser Gln Pro Ala Ser
                20                  25                  30

Val Ser Gly Ser Leu Gly Gln Arg Val Thr Ile Ser Cys Thr Gly Ser
            35                  40                  45

Ser Ser Asn Ile Gly Arg Gly Tyr Val Gly Trp Tyr Gln Gln Leu Pro
        50                  55                  60

Gly Thr Gly Pro Xaa Thr Leu Ile Phe Gly Pro Asn Lys Arg Pro Ser
65                  70                  75                  80

Gly Val Pro Asp Arg Phe Ser Gly Ser Arg Ser Asp Ser Thr Gly Thr
                85                  90                  95

Leu Thr Ile Ser Gly Leu Gln Ala Glu Asp Glu Gly Asp Tyr Tyr Cys
                100                 105                 110

-continued

Ser Ser Trp Asp Thr Thr Leu Ser Ala Tyr Val Phe Gly Ser Gly Thr
            115                 120                 125

Gln Leu Thr Val Leu Gly Gln Pro Lys Ala
    130                 135

<210> SEQ ID NO 1085
<211> LENGTH: 378
<212> TYPE: DNA
<213> ORGANISM: canis familiaris;
<220> FEATURE:
<221> NAME/KEY: UNSURE
<222> LOCATION: (38)..(38)
<223> OTHER INFORMATION: n is a, c, t, or g
<220> FEATURE:
<221> NAME/KEY: UNSURE
<222> LOCATION: (93)..(93)
<223> OTHER INFORMATION: n is a, c, t, or g
<220> FEATURE:
<221> NAME/KEY: UNSURE
<222> LOCATION: (300)..(300)
<223> OTHER INFORMATION: n is a, c, t, or g
<220> FEATURE:
<221> NAME/KEY: UNSURE
<222> LOCATION: (326)..(326)
<223> OTHER INFORMATION: n is a, c, t, or g
<220> FEATURE:
<221> NAME/KEY: UNSURE
<222> LOCATION: (360)..(360)
<223> OTHER INFORMATION: n is a, c, t, or g

<400> SEQUENCE: 1085
accatcctcg ctcactgcac agggtcctgg gcccagtntc tactgactca gccggcctca      60
gtgtccgggt ccctgggcca gagggtcacc ctntcctgca ctggaagcgg ctccaacatc     120
ggtagaggtt atgtgggctg gtaccaacac ctcccgggga caggcccag aaccctcatc     180 tatggtgata ttaaccgacc ctcaggggtc cccgatcggt tctctggctc caggtcaggc     240
atcacagcca ccctgaccat ctctgggctc caggctgagg atgaggctga ttattactgn     300
tcatcgtggg actacagtct cagtantact ttgttcggcg aggcaccca cctgaccgtn     360 ctcggtcagc ccaaggcc                                                    378

<210> SEQ ID NO 1086
<211> LENGTH: 126
<212> TYPE: PRT
<213> ORGANISM: canis familiaris;
<220> FEATURE:
<221> NAME/KEY: UNSURE
<222> LOCATION: (13)..(13)
<223> OTHER INFORMATION: X is any amino acid
<220> FEATURE:
<221> NAME/KEY: UNSURE
<222> LOCATION: (100)..(100)
<223> OTHER INFORMATION: X is any amino acid
<220> FEATURE:
<221> NAME/KEY: UNSURE
<222> LOCATION: (109)..(109)
<223> OTHER INFORMATION: X is any amino acid

<400> SEQUENCE: 1086

Thr Ile Leu Ala His Cys Thr Gly Ser Trp Ala Gln Xaa Leu Leu Thr
1               5                   10                  15

Gln Pro Ala Ser Val Ser Gly Ser Leu Gly Gln Arg Val Thr Leu Ser
            20                  25                  30

Cys Thr Gly Ser Gly Ser Asn Ile Gly Arg Gly Tyr Val Gly Trp Tyr
        35                  40                  45

Gln His Leu Pro Gly Thr Gly Pro Arg Thr Leu Ile Tyr Gly Asp Ile
    50                  55                  60

```
Asn Arg Pro Ser Gly Val Pro Asp Arg Phe Ser Gly Ser Arg Ser Gly
 65                  70                  75                  80

Ile Thr Ala Thr Leu Thr Ile Ser Gly Leu Gln Ala Glu Asp Glu Ala
                 85                  90                  95

Asp Tyr Tyr Xaa Ser Ser Trp Asp Tyr Ser Leu Ser Xaa Thr Leu Phe
            100                 105                 110

Gly Gly Gly Thr His Leu Thr Val Leu Gly Gln Pro Lys Ala
            115                 120                 125
```

<210> SEQ ID NO 1087
<211> LENGTH: 93
<212> TYPE: DNA
<213> ORGANISM: canis familiaris;

<400> SEQUENCE: 1087

```
gctgattatt actgttcagc atatgacagc aatctcagtg gtgtcctgtt cggctcagga    60
acccaactga ccgtccttgg tcagcccaag gcc                                 93
```

<210> SEQ ID NO 1088
<211> LENGTH: 31
<212> TYPE: PRT
<213> ORGANISM: canis familiaris;

<400> SEQUENCE: 1088

```
Ala Asp Tyr Tyr Cys Ser Ala Tyr Asp Ser Asn Leu Ser Gly Val Leu
 1               5                  10                  15

Phe Gly Ser Gly Thr Gln Leu Thr Val Leu Gly Gln Pro Lys Ala
             20                  25                  30
```

<210> SEQ ID NO 1089
<211> LENGTH: 402
<212> TYPE: DNA
<213> ORGANISM: canis familiaris;
<220> FEATURE:
<221> NAME/KEY: UNSURE
<222> LOCATION: (58)..(58)
<223> OTHER INFORMATION: n is a, c, t, or g

<400> SEQUENCE: 1089

```
atggcctggt cccctctcct cctcacactc cttccttact gcacagggtc ctgggggnag    60
tctatactga ctcagccgac ctcactgtcg gggtcccctg gccaaagggt caccatttcc   120
tgctctggag gcacgagcaa cgtcgtcatt gtcggtgcga gttggtacca acaggtccca   180
ggaaaggccc ctaaacttct cgtttacagt aatggggatc gaccgtcagg ggtccctgac   240
cggttttccg gctccaagtc tggcaactca gccaccctga ccatcactgg acttcaggct   300
gaggacgagg ctgattatta ctgccagtcc tttgatacca cgcttcatgt tcatctgttc   360
ggcggaggca cctatctgac cgtcctcggt cagcccaagg cc                      402
```

<210> SEQ ID NO 1090
<211> LENGTH: 134
<212> TYPE: PRT
<213> ORGANISM: canis familiaris;
<220> FEATURE:
<221> NAME/KEY: UNSURE
<222> LOCATION: (20)..(20)
<223> OTHER INFORMATION: X is any amino acid

<400> SEQUENCE: 1090

```
Met Ala Trp Ser Pro Leu Leu Leu Thr Leu Leu Pro Tyr Cys Thr Gly
 1               5                  10                  15
```

```
Ser Trp Gly Xaa Ser Ile Leu Thr Gln Pro Thr Ser Leu Ser Gly Ser
            20                  25                  30

Pro Gly Gln Arg Val Thr Ile Ser Cys Ser Gly Gly Thr Ser Asn Val
        35                  40                  45

Val Ile Val Gly Ala Ser Trp Tyr Gln Gln Val Pro Gly Lys Ala Pro
    50                  55                  60

Lys Leu Leu Val Tyr Ser Asn Gly Asp Arg Pro Ser Gly Val Pro Asp
65                  70                  75                  80

Arg Phe Ser Gly Ser Lys Ser Gly Asn Ser Ala Thr Leu Thr Ile Thr
                85                  90                  95

Gly Leu Gln Ala Glu Asp Glu Ala Asp Tyr Tyr Cys Gln Ser Phe Asp
            100                 105                 110

Thr Thr Leu His Val His Leu Phe Gly Gly Gly Thr Tyr Leu Thr Val
        115                 120                 125

Leu Gly Gln Pro Lys Ala
        130

<210> SEQ ID NO 1091
<211> LENGTH: 410
<212> TYPE: DNA
<213> ORGANISM: canis familiaris;
<220> FEATURE:
<221> NAME/KEY: UNSURE
<222> LOCATION: (60)..(60)
<223> OTHER INFORMATION: n is a, c, t, or g

<400> SEQUENCE: 1091
atgacctcca ccatgggctg gtccctctc ctccttaccc tcctcgctca ctgcacaggn      60
tcctgggccc agtctgtgct gactcagccg gcctcagtga ctgggtccct gggccagagg    120
gtcaccatct cctgcactgg aagcagctcc aacatcggtg gatataatgt tggctggttc    180
cagcagctcc cggaatagg ccccagaacc gtcatctata gtagtagtaa gcgaccctcg    240
ggggtcccgg atcgattctc tggctccagg tcaggcagca cagccaccct gaccatctct    300
gggctccagg ctgaggacga ggctgagtat tactgctcaa catgggacac cagtctcaaa    360
ggtattgtgt tcggcggagg cacccatctg accgtcctcg gtcaagccca              410

<210> SEQ ID NO 1092
<211> LENGTH: 136
<212> TYPE: PRT
<213> ORGANISM: canis familiaris;

<400> SEQUENCE: 1092

Met Thr Ser Thr Met Gly Trp Ser Pro Leu Leu Leu Thr Leu Leu Ala
1               5                   10                  15

His Cys Thr Gly Ser Trp Ala Gln Ser Val Leu Thr Gln Pro Ala Ser
            20                  25                  30

Val Thr Gly Ser Leu Gly Gln Arg Val Thr Ile Ser Cys Thr Gly Ser
        35                  40                  45

Ser Ser Asn Ile Gly Gly Tyr Asn Val Gly Trp Phe Gln Gln Leu Pro
    50                  55                  60

Gly Ile Gly Pro Arg Thr Val Ile Tyr Ser Ser Ser Lys Arg Pro Ser
65                  70                  75                  80

Gly Val Pro Asp Arg Phe Ser Gly Ser Arg Ser Gly Ser Thr Ala Thr
                85                  90                  95

Leu Thr Ile Ser Gly Leu Gln Ala Glu Asp Glu Ala Glu Tyr Tyr Cys
            100                 105                 110
```

Ser Thr Trp Asp Thr Ser Leu Lys Gly Ile Val Phe Gly Gly Gly Thr
            115                 120                 125

His Leu Thr Val Leu Gly Gln Ala
    130                 135

<210> SEQ ID NO 1093
<211> LENGTH: 399
<212> TYPE: DNA
<213> ORGANISM: canis familiaris;
<220> FEATURE:
<221> NAME/KEY: UNSURE
<222> LOCATION: (105)..(105)
<223> OTHER INFORMATION: n is a, c, t, or g

<400> SEQUENCE: 1093
atggcctgga ctctggtcct cctcaccttt ctctctcagg gcacagggtc ctgggcccag      60
tccgccctga ctcaaccttc ctcggtgtct gggactttgg gccanactgt caccatctcc     120
tgtgatggga acaacaataa cattggcaat agtgattata tcgaatggta ccagcagttc     180
ccaggcacct cccccaaact cctgatttac tatgtcaata gcggccatc aggatccct       240 actcgcttct ctgcctccaa gtctgggaac acggcctcct tgaccatctc tgggctccag     300
gctgaagatg aggctgatta ttactgcaac tcttatattg gcgatgaggc tatgttcggc     360
ggaggcactc acctgaccgt cctcggtcag cccaaggcc                            399

<210> SEQ ID NO 1094
<211> LENGTH: 133
<212> TYPE: PRT
<213> ORGANISM: canis familiaris;
<220> FEATURE:
<221> NAME/KEY: UNSURE
<222> LOCATION: (35)..(35)
<223> OTHER INFORMATION: X is any amino acid

<400> SEQUENCE: 1094

Met Ala Trp Thr Leu Val Leu Leu Thr Phe Leu Ser Gln Gly Thr Gly
1               5                   10                  15

Ser Trp Ala Gln Ser Ala Leu Thr Gln Pro Ser Ser Val Ser Gly Thr
            20                  25                  30

Leu Gly Xaa Thr Val Thr Ile Ser Cys Asp Gly Asn Asn Asn Asn Ile
        35                  40                  45

Gly Asn Ser Asp Tyr Ile Glu Trp Tyr Gln Gln Phe Pro Gly Thr Ser
    50                  55                  60

Pro Lys Leu Leu Ile Tyr Tyr Val Asn Arg Arg Pro Ser Gly Ile Pro
65                  70                  75                  80

Thr Arg Phe Ser Ala Ser Lys Ser Gly Asn Thr Ala Ser Leu Thr Ile
                85                  90                  95

Ser Gly Leu Gln Ala Glu Asp Glu Ala Asp Tyr Tyr Cys Asn Ser Tyr
            100                 105                 110

Ile Gly Asp Glu Ala Met Phe Gly Gly Gly Thr His Leu Thr Val Leu
        115                 120                 125

Gly Gln Pro Lys Ala
    130

<210> SEQ ID NO 1095
<211> LENGTH: 416
<212> TYPE: DNA
<213> ORGANISM: canis familiaris;

<400> SEQUENCE: 1095

```
atgacctcca ccatggcctg gtccctctc ctcctcaccc tcctcgctca ttgcacagtg      60
tcctgggccc aggctgtgct gactcagtca ccctctgtgt ctgcagccct ggggcagagg    120
gtctccatct cctgcactgg aagtgacacc aacatcggcg gttatgatgt acaatggtac    180
cagcaggtcc caggagagtc ccctaaaact atcatccgtg ctaataccaa tcgaccctcg    240
ggggtcccgg ttcgattctc tggctccagg tcaggcacca cagccaccct gaccatcact    300
ggtatccagg ctgaggatga ggctgattat tactgtcagt cctatgatga caagtccgat    360
gctcttgtgt cggcggagg cacccatctg accgtcctcg gtcagcccaa ggccgg        416
```

<210> SEQ ID NO 1096
<211> LENGTH: 138
<212> TYPE: PRT
<213> ORGANISM: canis familiaris;

<400> SEQUENCE: 1096

```
Met Thr Ser Thr Met Ala Trp Ser Pro Leu Leu Thr Leu Leu Ala
1               5                   10                  15

His Cys Thr Val Ser Trp Ala Gln Ala Val Leu Thr Gln Ser Pro Ser
        20                  25                  30

Val Ser Ala Ala Leu Gly Gln Arg Val Ser Ile Ser Cys Thr Gly Ser
            35                  40                  45

Asp Thr Asn Ile Gly Gly Tyr Asp Val Gln Trp Tyr Gln Gln Val Pro
        50                  55                  60

Gly Glu Ser Pro Lys Thr Ile Ile Arg Ala Asn Thr Asn Arg Pro Ser
65                  70                  75                  80

Gly Val Pro Val Arg Phe Ser Gly Ser Arg Ser Gly Thr Thr Ala Thr
                85                  90                  95

Leu Thr Ile Thr Gly Ile Gln Ala Glu Asp Glu Ala Asp Tyr Tyr Cys
            100                 105                 110

Gln Ser Tyr Asp Asp Lys Ser Asp Ala Leu Val Phe Gly Gly Gly Thr
        115                 120                 125

His Leu Thr Val Leu Gly Gln Pro Lys Ala
    130                 135
```

<210> SEQ ID NO 1097
<211> LENGTH: 384
<212> TYPE: DNA
<213> ORGANISM: canis familiaris;
<220> FEATURE:
<221> NAME/KEY: UNSURE
<222> LOCATION: (8)..(8)
<223> OTHER INFORMATION: n is a, c, t, or g
<220> FEATURE:
<221> NAME/KEY: UNSURE
<222> LOCATION: (251)..(251)
<223> OTHER INFORMATION: n is a, c, t, or g
<220> FEATURE:
<221> NAME/KEY: UNSURE
<222> LOCATION: (261)..(261)
<223> OTHER INFORMATION: n is a, c, t, or g
<220> FEATURE:
<221> NAME/KEY: UNSURE
<222> LOCATION: (314)..(314)
<223> OTHER INFORMATION: n is a, c, t, or g
<220> FEATURE:
<221> NAME/KEY: UNSURE
<222> LOCATION: (334)..(334)
<223> OTHER INFORMATION: n is a, c, t, or g

<400> SEQUENCE: 1097

```
atggcttnga cgttgcttct tcttgtgctc cttgcctatg gctcaggggc agattctcag    60
```

```
actgtcgtga tccaggaccc atcagtctcg gtgtctccag gagggacagt cacactcaca      120
tgtggcctca actgtgggtc actctctaca aataatttcc ctggctggta ccagcagacc      180
ctaggccggg ctcctcgcac gattatcttc aaaacaaata gccgcccctc tggggtccct      240
gatcgcttct ntggagcctt ntctgacaac aaagctgtcc ttaccatcac aggagtccag      300
cctgaggacg aggntgacta tcactgttcc ttcnatttgg gtagttatac tatattcggc      360
ggaggcaccc acttgaccgt cctc                                             384
```

```
<210> SEQ ID NO 1098
<211> LENGTH: 128
<212> TYPE: PRT
<213> ORGANISM: canis familiaris;
<220> FEATURE:
<221> NAME/KEY: UNSURE
<222> LOCATION: (3)..(3)
<223> OTHER INFORMATION: X is any amino acid
<220> FEATURE:
<221> NAME/KEY: UNSURE
<222> LOCATION: (84)..(84)
<223> OTHER INFORMATION: X is any amino acid
<220> FEATURE:
<221> NAME/KEY: UNSURE
<222> LOCATION: (87)..(87)
<223> OTHER INFORMATION: X is any amino acid
<220> FEATURE:
<221> NAME/KEY: UNSURE
<222> LOCATION: (105)..(105)
<223> OTHER INFORMATION: X is any amino acid
<220> FEATURE:
<221> NAME/KEY: UNSURE
<222> LOCATION: (112)..(112)
<223> OTHER INFORMATION: X is any amino acid

<400> SEQUENCE: 1098
```

```
Met Ala Xaa Thr Leu Leu Leu Val Leu Leu Ala Tyr Gly Ser Gly
1               5                   10                  15

Ala Asp Ser Gln Thr Val Val Ile Gln Asp Pro Ser Val Ser Val
            20                  25                  30

Pro Gly Gly Thr Val Thr Leu Thr Cys Gly Leu Asn Cys Gly Ser Leu
        35                  40                  45

Ser Thr Asn Asn Phe Pro Gly Trp Tyr Gln Gln Thr Leu Gly Arg Ala
    50                  55                  60

Pro Arg Thr Ile Ile Phe Lys Thr Asn Ser Arg Pro Ser Gly Val Pro
65                  70                  75                  80

Asp Arg Phe Xaa Gly Ala Xaa Ser Asp Asn Lys Ala Val Leu Thr Ile
                85                  90                  95

Thr Gly Val Gln Pro Glu Asp Glu Xaa Asp Tyr His Cys Ser Phe Xaa
            100                 105                 110

Leu Gly Ser Tyr Thr Ile Phe Gly Gly Gly Thr His Leu Thr Val Leu
        115                 120                 125
```

```
<210> SEQ ID NO 1099
<211> LENGTH: 306
<212> TYPE: DNA
<213> ORGANISM: canis familiaris;

<400> SEQUENCE: 1099
cagacggtca ccatctcctg cactggaagc agctccaatg ttggttatgg cgattatgcg      60
ggctggtacc aacaactccc agggacaggt cccaaaaccc tcatctatga tactcgtagg     120
cgaccctcgg ggattcctga tcgattctct gggtccaggt caggcagcac agcgaccctg     180
```

```
accatctctg gactccaggc tgaggatgag gccgattatt actgtgcatc ctatgaccgt    240
actatcggtg gtggtgctgt gttcggcgga ggcacccacc tgaccgtcct cggtcagccc    300
aaggcc                                                               306
```

<210> SEQ ID NO 1100
<211> LENGTH: 102
<212> TYPE: PRT
<213> ORGANISM: canis familiaris;

<400> SEQUENCE: 1100

```
Gln Thr Val Thr Ile Ser Cys Thr Gly Ser Ser Asn Val Gly Tyr
1               5                   10                  15

Gly Asp Tyr Ala Gly Trp Tyr Gln Gln Leu Pro Gly Thr Gly Pro Lys
            20                  25                  30

Thr Leu Ile Tyr Asp Thr Arg Arg Arg Pro Ser Gly Ile Pro Asp Arg
        35                  40                  45

Phe Ser Gly Ser Arg Ser Gly Ser Thr Ala Thr Leu Thr Ile Ser Gly
    50                  55                  60

Leu Gln Ala Glu Asp Glu Ala Asp Tyr Tyr Cys Ala Ser Tyr Asp Arg
65                  70                  75                  80

Thr Ile Gly Gly Gly Ala Val Phe Gly Gly Gly Thr His Leu Thr Val
                85                  90                  95

Leu Gly Gln Pro Lys Ala
            100
```

<210> SEQ ID NO 1101
<211> LENGTH: 336
<212> TYPE: DNA
<213> ORGANISM: canis familiaris;

<400> SEQUENCE: 1101

```
gcctcctatg tgctgtctca gccgccatca gcgactgtga ccctgaggca gacggcccgc    60
ctcacctgtg ggggagacag cattggaagt aaaagtgctc aatggtacca gcagaagccg   120
ggccagcccc ccgtgctcat tatctatggt gatagcagca ggccgtcagg gatccctgag   180
cgattctctg gcgccaactc ggggaacacg gccaccctga ccatcagcgg ggccctggcc   240
gaggacgagg ctgactatta ctgccaggtg tgggaccgca gtgcttacgt gttcggctca   300
ggaacccaac tgaccgtcct tggtcagccc aaggcc                             336
```

<210> SEQ ID NO 1102
<211> LENGTH: 112
<212> TYPE: PRT
<213> ORGANISM: canis familiaris;

<400> SEQUENCE: 1102

```
Ala Ser Tyr Val Leu Ser Gln Pro Pro Ser Ala Thr Val Thr Leu Arg
1               5                   10                  15

Gln Thr Ala Arg Leu Thr Cys Gly Gly Asp Ser Ile Gly Ser Lys Ser
            20                  25                  30

Ala Gln Trp Tyr Gln Gln Lys Pro Gly Gln Pro Pro Val Leu Ile Ile
        35                  40                  45

Tyr Gly Asp Ser Ser Arg Pro Ser Gly Ile Pro Glu Arg Phe Ser Gly
    50                  55                  60

Ala Asn Ser Gly Asn Thr Ala Thr Leu Thr Ile Ser Gly Ala Leu Ala
65                  70                  75                  80

Glu Asp Glu Ala Asp Tyr Tyr Cys Gln Val Trp Asp Arg Ser Ala Tyr
```

```
                85                  90                  95
Val Phe Gly Ser Gly Thr Gln Leu Thr Val Leu Gly Gln Pro Lys Ala
            100                 105                 110
```

<210> SEQ ID NO 1103
<211> LENGTH: 240
<212> TYPE: DNA
<213> ORGANISM: canis familiaris;

<400> SEQUENCE: 1103

```
tggtaccagc agttcacagg aacaggcccc agaaccctca tctatgatac tagtagccga    60
ccctcggggg tccctgatcg aatctctggc tccaggtcag gcagcacagc aacactgacc   120
atttctgggc tccaggctga ggacgaggct gattattact gctcagcata tgacaacagt   180
ctcattgctg gtatgttcgg cggaggcacc cacctgaccg tcctcggtca gcccaaggcc   240
```

<210> SEQ ID NO 1104
<211> LENGTH: 80
<212> TYPE: PRT
<213> ORGANISM: canis familiaris;

<400> SEQUENCE: 1104

```
Trp Tyr Gln Gln Phe Thr Gly Thr Gly Pro Arg Thr Leu Ile Tyr Asp
1               5                   10                  15
Thr Ser Ser Arg Pro Ser Gly Val Pro Asp Arg Ile Ser Gly Ser Arg
            20                  25                  30
Ser Gly Ser Thr Ala Thr Leu Thr Ile Ser Gly Leu Gln Ala Glu Asp
        35                  40                  45
Glu Ala Asp Tyr Tyr Cys Ser Ala Tyr Asp Asn Ser Leu Ile Ala Gly
    50                  55                  60
Met Phe Gly Gly Gly Thr His Leu Thr Val Leu Gly Gln Pro Lys Ala
65                  70                  75                  80
```

<210> SEQ ID NO 1105
<211> LENGTH: 354
<212> TYPE: DNA
<213> ORGANISM: canis familiaris;

<400> SEQUENCE: 1105

```
gcggtttctc agactgtgct aacccaggag ccatcactct cagtgtctcc aggagggaca    60
gtcacactca catgtggcct cagttctggg tcagtctcta caagtaatta ccctggctgg   120
taccagcaga ccctgggccg gctcctcgc acgattatct acagaacaag cagccgcccc   180
tctgggtcc ctgatcgctt ctctggatcc atctctggga acacagccgc cctcaccatc   240
acaggagccc agcctgagga cgaggctgac tattactgtt ccttctatat gggtgattac   300
actactctgt tcggcggagg cacccacctg accgtcctcg gtcagcccaa ggcc         354
```

<210> SEQ ID NO 1106
<211> LENGTH: 118
<212> TYPE: PRT
<213> ORGANISM: canis familiaris;

<400> SEQUENCE: 1106

```
Ala Val Ser Gln Thr Val Leu Thr Gln Glu Pro Ser Leu Ser Val Ser
1               5                   10                  15
Pro Gly Gly Thr Val Thr Leu Thr Cys Gly Leu Ser Ser Gly Ser Val
            20                  25                  30
Ser Thr Ser Asn Tyr Pro Gly Trp Tyr Gln Gln Thr Leu Gly Arg Ala
```

```
            35                  40                  45
Pro Arg Thr Ile Ile Tyr Arg Thr Ser Ser Arg Pro Ser Gly Val Pro
     50                  55                  60

Asp Arg Phe Ser Gly Ser Ile Ser Gly Asn Thr Ala Ala Leu Thr Ile
 65                  70                  75                  80

Thr Gly Ala Gln Pro Glu Asp Glu Ala Asp Tyr Tyr Cys Ser Phe Tyr
                 85                  90                  95

Met Gly Asp Tyr Thr Thr Leu Phe Gly Gly Thr His Leu Thr Val
            100                 105                 110

Leu Gly Gln Pro Lys Ala
        115

<210> SEQ ID NO 1107
<211> LENGTH: 393
<212> TYPE: DNA
<213> ORGANISM: canis familiaris;

<400> SEQUENCE: 1107
atggcctgga cccatctcct gctccccgtg ctcactctct gcacaggctc cgtggcctcc     60
agtgtggtga ctcagcctcc ctcggtatca gtgtctctgg gacagacagc aaccatctcc    120
tgctctggag agagtctgag taaatattat gcacaatggt tccagcagaa ggcaggccaa    180
gcccctgtgt tggtcatata taaggacact gagcggccct ctgggatccc tgaccgattc    240
tctggctcca gttcagggaa cacacacacc ctgaccatca gcggggctcg ggccgaggac    300
gaggctgact attactgcga gtcagcagtc agtactgata ctgctgtgtt cggcggaggc    360
acccacctga ccgtcctcgg tcagcccaag gcc                                 393

<210> SEQ ID NO 1108
<211> LENGTH: 131
<212> TYPE: PRT
<213> ORGANISM: canis familiaris;

<400> SEQUENCE: 1108

Met Ala Trp Thr His Leu Leu Pro Val Leu Thr Leu Cys Thr Gly
 1               5                  10                  15

Ser Val Ala Ser Ser Val Val Thr Gln Pro Pro Ser Val Ser Val Ser
                20                  25                  30

Leu Gly Gln Thr Ala Thr Ile Ser Cys Ser Gly Glu Ser Leu Ser Lys
            35                  40                  45

Tyr Tyr Ala Gln Trp Phe Gln Gln Lys Ala Gly Gln Ala Pro Val Leu
     50                  55                  60

Val Ile Tyr Lys Asp Thr Glu Arg Pro Ser Gly Ile Pro Asp Arg Phe
 65                  70                  75                  80

Ser Gly Ser Ser Ser Gly Asn Thr His Thr Leu Thr Ile Ser Gly Ala
                 85                  90                  95

Arg Ala Glu Asp Glu Ala Asp Tyr Tyr Cys Glu Ser Ala Val Ser Thr
            100                 105                 110

Asp Thr Ala Val Phe Gly Gly Gly Thr His Leu Thr Val Leu Gly Gln
        115                 120                 125

Pro Lys Ala
    130

<210> SEQ ID NO 1109
<211> LENGTH: 315
<212> TYPE: DNA
<213> ORGANISM: canis familiaris;
```

```
<400> SEQUENCE: 1109
ctccctgcag cctcggtcaa cctcacctgc actttgagca gtgaacacat cagttacttt    60
attatttggt atcaacaaca acacccaggg agggcccctc gatatctgat gaagattaac   120
tttgatgggg agcacaccag gggagacggg atccctagtc gcttctcagg ctccagctct   180
gggtctgacc gctatttaac catctccaac atccagtctg aggatgaggc agattatttc   240
tgttttacac ccgctagtac caacagtgtt ttcggcggag gcacccatct gaccgtcctc   300
ggtcagccca aggcc                                                    315

<210> SEQ ID NO 1110
<211> LENGTH: 105
<212> TYPE: PRT
<213> ORGANISM: canis familiaris;

<400> SEQUENCE: 1110

Leu Pro Ala Ala Ser Val Asn Leu Thr Cys Thr Leu Ser Ser Glu His
 1               5                  10                  15

Ile Ser Tyr Phe Ile Ile Trp Tyr Gln Gln Gln His Pro Gly Arg Ala
            20                  25                  30

Pro Arg Tyr Leu Met Lys Ile Asn Phe Asp Gly Glu His Thr Arg Gly
        35                  40                  45

Asp Gly Ile Pro Ser Arg Phe Ser Gly Ser Ser Gly Ser Asp Arg
    50                  55                  60

Tyr Leu Thr Ile Ser Asn Ile Gln Ser Glu Asp Glu Ala Asp Tyr Phe
 65                  70                  75                  80

Cys Phe Thr Pro Ala Ser Thr Asn Ser Val Phe Gly Gly Gly Thr His
                85                  90                  95

Leu Thr Val Leu Gly Gln Pro Lys Ala
            100                 105

<210> SEQ ID NO 1111
<211> LENGTH: 393
<212> TYPE: DNA
<213> ORGANISM: canis familiaris;

<400> SEQUENCE: 1111
atggcctgga cccatctcct gctccccgtg ctcactctct gcacaggctc cgtggcctcc    60
agtgtgctga ctcagcctcc ctcggtatca gtgtctctgg acagacagc aaccatctcc   120 tgctctggag agagtctgag taaatattat gcacaatggt tccagcagaa ggcaggccaa   180 gccccctgtgt tggtcatata taaggacact gagcggccct ctgggatccc tgaccgattc   240
tccggctcca gttcagggaa cacacacacc ctgaccatca gcggggctcg ggccgaggac   300
gaggctgact attactgcga gtcagcagtc agtactgata ctgttgtgtt cggcggaggc   360
acccacctga ccgtcctcgg tcagcccaag gcc                                393

<210> SEQ ID NO 1112
<211> LENGTH: 131
<212> TYPE: PRT
<213> ORGANISM: canis familiaris;

<400> SEQUENCE: 1112

Met Ala Trp Thr His Leu Leu Pro Val Leu Thr Leu Cys Thr Gly
 1               5                  10                  15

Ser Val Ala Ser Ser Val Leu Thr Gln Pro Pro Ser Val Ser Val Ser
            20                  25                  30
```

-continued

```
Leu Gly Gln Thr Ala Thr Ile Ser Cys Ser Gly Glu Ser Leu Ser Lys
             35                  40                  45

Tyr Tyr Ala Gln Trp Phe Gln Gln Lys Ala Gly Gln Ala Pro Val Leu
 50                  55                  60

Val Ile Tyr Lys Asp Thr Glu Arg Pro Ser Gly Ile Pro Asp Arg Phe
 65                  70                  75                  80

Ser Gly Ser Ser Ser Gly Asn Thr His Thr Leu Thr Ile Ser Gly Ala
                 85                  90                  95

Arg Ala Glu Asp Glu Ala Asp Tyr Tyr Cys Glu Ser Ala Val Ser Thr
            100                 105                 110

Asp Thr Val Val Phe Gly Gly Gly Thr His Leu Thr Val Leu Gly Gln
        115                 120                 125

Pro Lys Ala
        130
```

<210> SEQ ID NO 1113
<211> LENGTH: 371
<212> TYPE: DNA
<213> ORGANISM: canis familiaris;

<400> SEQUENCE: 1113

| | | | | |
|---|---|---|---|---|
| tctctacagg | tttctgtgct | cctcctgttc | tgacccagac | tccaagtgct tctgcctccc | 60 |
| tggaagcctc | ggtcaagctc | acctgcactt | tgagcggtga | tcacagcagt cactatattt | 120 |
| cctggtatca | acaacatcaa | ccagggaagg | cccctcggta | tctgatgaag gttaacagtg | 180 |
| atggaagcca | cagcagggga | gacgggatcc | ctagtcgctt | ctcaggctcc agctctgggg | 240 |
| ctgaccgcta | tttaagcatc | tccaacatcc | agtctgacga | tgaggcagat tattattgtt | 300 |
| ttatagccac | tggtgacaat | agtgtattcg | gcggaggcac | ccatctgacc gtcctcggtc | 360 |
| agcccaaggc | c | | | | 371 |

<210> SEQ ID NO 1114
<211> LENGTH: 123
<212> TYPE: PRT
<213> ORGANISM: canis familiaris;

<400> SEQUENCE: 1114

```
Ser Thr Gly Phe Cys Ala Pro Pro Val Leu Thr Gln Thr Pro Ser Ala
 1               5                  10                  15

Ser Ala Ser Leu Glu Ala Ser Val Lys Leu Thr Cys Thr Leu Ser Gly
             20                  25                  30

Asp His Ser Ser His Tyr Ile Ser Trp Tyr Gln Gln His Gln Pro Gly
             35                  40                  45

Lys Ala Pro Arg Tyr Leu Met Lys Val Asn Ser Asp Gly Ser His Ser
 50                  55                  60

Arg Gly Asp Gly Ile Pro Ser Arg Phe Ser Gly Ser Ser Ser Gly Ala
 65                  70                  75                  80

Asp Arg Tyr Leu Ser Ile Ser Asn Ile Gln Ser Asp Asp Glu Ala Asp
                 85                  90                  95

Tyr Tyr Cys Phe Ile Ala Thr Gly Asp Asn Ser Val Phe Gly Gly Gly
            100                 105                 110

Thr His Leu Thr Val Leu Gly Gln Pro Lys Ala
        115                 120
```

<210> SEQ ID NO 1115
<211> LENGTH: 408

```
-continued
```

```
<212> TYPE: DNA
<213> ORGANISM: canis familiaris;

<400> SEQUENCE: 1115
atggactggg tcccctttta cctcctgccc ttcatttttct ctacaggttt ctgtgctcct    60
cctgtgctga cccagactcc aagtgcatct gcctccctgg aagcctcggt caagctcacc   120
tgcactttga gcagtgagca cagcagttac tatattacct ggtatcaaca acaacaacca   180
gggaaggccc ctcggtatct gatgaaggtt aacagtgatg gaagccacag caggggagac   240
gggatcccta gtcgcttctc aggctccagc tctggggctg accgctattt aaccatctcc   300
aacatccagt ctgaggatga ggcagattat tactgttttta cacccgctac tggcattagt   360
gtcttcggcg gaggcaccca tctgaccgtc ctcggtcagc ccaaggcc                 408

<210> SEQ ID NO 1116
<211> LENGTH: 136
<212> TYPE: PRT
<213> ORGANISM: canis familiaris;

<400> SEQUENCE: 1116

Met Asp Trp Val Pro Phe Tyr Leu Leu Pro Phe Ile Phe Ser Thr Gly
1               5                   10                  15

Phe Cys Ala Pro Pro Val Leu Thr Gln Thr Pro Ser Ala Ser Ala Ser
            20                  25                  30

Leu Glu Ala Ser Val Lys Leu Thr Cys Thr Leu Ser Ser Glu His Ser
        35                  40                  45

Ser Tyr Tyr Ile Thr Trp Tyr Gln Gln Gln Pro Gly Lys Ala Pro
    50                  55                  60

Arg Tyr Leu Met Lys Val Asn Ser Asp Gly Ser His Ser Arg Gly Asp
65                  70                  75                  80

Gly Ile Pro Ser Arg Phe Ser Gly Ser Ser Ser Gly Ala Asp Arg Tyr
                85                  90                  95

Leu Thr Ile Ser Asn Ile Gln Ser Glu Asp Glu Ala Asp Tyr Tyr Cys
            100                 105                 110

Phe Thr Pro Ala Thr Gly Ile Ser Val Phe Gly Gly Thr His Leu
        115                 120                 125

Thr Val Leu Gly Gln Pro Lys Ala
    130                 135

<210> SEQ ID NO 1117
<211> LENGTH: 273
<212> TYPE: DNA
<213> ORGANISM: canis familiaris;

<400> SEQUENCE: 1117
agcaactcca acatcggtag aggttatgtg ggctggtacc aacagctccc gggaacaggc    60
cccaggaccc tcttctatgg aactgggaac cgaccctcag ggtccccga tcggttctct   120 ggctccaggt caggcagcac agccaccctg accatctctg gctccaggc tgaggatgag   180 gctgattatt actgctcatc gtgggacacc agtctcagta tttacgtgtt cgcctcagga   240
acccaactga ccgtccttgg tcagcccaag gcc                                273

<210> SEQ ID NO 1118
<211> LENGTH: 91
<212> TYPE: PRT
<213> ORGANISM: canis familiaris;

<400> SEQUENCE: 1118
```

-continued

```
Ser Asn Ser Asn Ile Gly Arg Gly Tyr Val Gly Trp Tyr Gln Gln Leu
1               5                   10                  15

Pro Gly Thr Gly Pro Arg Thr Leu Phe Tyr Gly Thr Gly Asn Arg Pro
            20                  25                  30

Ser Gly Val Pro Asp Arg Phe Ser Gly Ser Arg Ser Gly Ser Thr Ala
        35                  40                  45

Thr Leu Thr Ile Ser Gly Leu Gln Ala Glu Asp Glu Ala Asp Tyr Tyr
    50                  55                  60

Cys Ser Ser Trp Asp Thr Ser Leu Ser Ile Tyr Val Phe Ala Ser Gly
65                  70                  75                  80

Thr Gln Leu Thr Val Leu Gly Gln Pro Lys Ala
                85                  90
```

<210> SEQ ID NO 1119
<211> LENGTH: 420
<212> TYPE: DNA
<213> ORGANISM: canis familiaris;

<400> SEQUENCE: 1119

```
atggactggg ttccctttta catcctgccc ttcattttct ctacaggtct ctgtgcattg    60
cccgtgctga cccagcctac aagtgcatct gcccccctgg aagagtcggt caagctgacc   120
tgcactttga gcagtgagca cagcaattac attgttcatt ggtatcaaca acaaccaggg   180
aaggcccctc ggtatctgat gtatgtcagg agtgatggag ctacaaaag gggggacggg   240
atccccagtc gcttctcagg ctccagctct ggggctgacc gctatttaac catctccaac   300
atcaagtctg aagatgagga tgactattat tactgtggtg cagactatac aatcagtggc   360
caatatggta acgtgttcgg ctcaggaacc cgactgaccg tccttggtca gcccaaggcc   420
```

<210> SEQ ID NO 1120
<211> LENGTH: 140
<212> TYPE: PRT
<213> ORGANISM: canis familiaris;

<400> SEQUENCE: 1120

```
Met Asp Trp Val Pro Phe Tyr Ile Leu Pro Phe Ile Phe Ser Thr Gly
1               5                   10                  15

Leu Cys Ala Leu Pro Val Leu Thr Gln Pro Thr Ser Ala Ser Ala Pro
            20                  25                  30

Leu Glu Glu Ser Val Lys Leu Thr Cys Thr Leu Ser Ser Glu His Ser
        35                  40                  45

Asn Tyr Ile Val His Trp Tyr Gln Gln Pro Gly Lys Ala Pro Arg
    50                  55                  60

Tyr Leu Met Tyr Val Arg Ser Asp Gly Gly Tyr Lys Arg Gly Asp Gly
65                  70                  75                  80

Ile Pro Ser Arg Phe Ser Gly Ser Ser Gly Ala Asp Arg Tyr Leu
                85                  90                  95

Thr Ile Ser Asn Ile Lys Ser Glu Asp Glu Asp Tyr Tyr Tyr Cys
            100                 105                 110

Gly Ala Asp Tyr Thr Ile Ser Gly Gln Tyr Gly Asn Val Phe Gly Ser
        115                 120                 125

Gly Thr Arg Leu Thr Val Leu Gly Gln Pro Lys Ala
    130                 135                 140
```

<210> SEQ ID NO 1121
<211> LENGTH: 405

-continued

```
<212> TYPE: DNA
<213> ORGANISM: canis familiaris;

<400> SEQUENCE: 1121
atggactggg tccccttta  cctcctgccc ttcattttct ctacaggttt ctgtgctcct       60
cctgtgctga cccagactcc aagtgcatct gcctccctgg aagcctcggt caagctcacc      120
tgcactttga gcagtgagca cagcagttac tatattacct ggtatcaaca acaacaacca      180
gggaaggccc ctcggtatct gatgagggtt aacagcgatg gaagccacag caggggagac      240
gggatcccta gtcgcttctc aggctccagc tctggggctg accgctattt aaccatctcc      300
aacatccagt ctgaggatga ggcagattat tactgtttta cccctctag tataagtgtg       360 ttcggcggag gcaccatct gaccgtcctc ggtcagccca aggcc                      405

<210> SEQ ID NO 1122
<211> LENGTH: 135
<212> TYPE: PRT
<213> ORGANISM: canis familiaris;

<400> SEQUENCE: 1122

Met Asp Trp Val Pro Phe Tyr Leu Leu Pro Phe Ile Phe Ser Thr Gly
1               5                  10                  15

Phe Cys Ala Pro Pro Val Leu Thr Gln Thr Pro Ser Ala Ser Ala Ser
            20                  25                  30

Leu Glu Ala Ser Val Lys Leu Thr Cys Thr Leu Ser Ser Glu His Ser
        35                  40                  45

Ser Tyr Tyr Ile Thr Trp Tyr Gln Gln Gln Pro Gly Lys Ala Pro
    50                  55                  60

Arg Tyr Leu Met Arg Val Asn Ser Asp Gly Ser His Ser Arg Gly Asp
65                  70                  75                  80

Gly Ile Pro Ser Arg Phe Ser Gly Ser Ser Ser Gly Ala Asp Arg Tyr
                85                  90                  95

Leu Thr Ile Ser Asn Ile Gln Ser Glu Asp Glu Ala Asp Tyr Tyr Cys
            100                 105                 110

Phe Thr Pro Ser Ser Ile Ser Val Phe Gly Gly Gly Thr His Leu Thr
        115                 120                 125

Val Leu Gly Gln Pro Lys Ala
    130                 135

<210> SEQ ID NO 1123
<211> LENGTH: 252
<212> TYPE: DNA
<213> ORGANISM: canis familiaris;

<400> SEQUENCE: 1123
tgtgggttgg taccaacaac tcccagaaga ggccccagaa ctgtcatcta gtacaagt        60 agtcgaccct cggggtgcc cgatcgattc tctggctcca gtctggcag cacagccacc       120 ctgaccatct ctgggctcca ggctgaggat gaggctgatt attactgctc gacgtgggat     180
gatagtctca gtggttacgt tttcggctca ggaacccaat gcaattgac cgtccttggt     240 cagcccaagg cc                                                          252

<210> SEQ ID NO 1124
<211> LENGTH: 84
<212> TYPE: PRT
<213> ORGANISM: canis familiaris;

<400> SEQUENCE: 1124
```

Cys Gly Leu Val Pro Thr Thr Pro Arg Arg Gly Pro Arg Thr Val Ile
1               5                   10                  15

Tyr Ser Thr Ser Ser Arg Pro Ser Gly Val Pro Asp Arg Phe Ser Gly
                20                  25                  30

Ser Lys Ser Gly Ser Thr Ala Thr Leu Thr Ile Ser Gly Leu Gln Ala
            35                  40                  45

Glu Asp Glu Ala Asp Tyr Tyr Cys Ser Thr Trp Asp Asp Ser Leu Ser
        50                  55                  60

Gly Tyr Val Phe Gly Ser Gly Thr Gln Leu Gln Leu Thr Val Leu Gly
65                  70                  75                  80

Gln Pro Lys Ala

<210> SEQ ID NO 1125
<211> LENGTH: 405
<212> TYPE: DNA
<213> ORGANISM: canis familiaris;

<400> SEQUENCE: 1125
atggactggg tccccttta cctcctgccc ttcattttct ctacaggttt ctgtgctcct      60
cctgtgctga cccagactcc aagtgcatct gcctccctgg aagcctcggt caagctcacc     120
tgcactttga gcagtgaaca cagcagttac tatattacct ggtatcaaca acaacaacca     180
gggaaggccc ctcggtatct gatgacggtt aacagtgatg gaagccacag caggggagac     240
gggatcccta gtcgcttctc aggctccagc tctggggctg accgctattt aaccatctcc     300
aacatccagt ctgaggatga ggcagattat tactgttttg cacccgctaa caatgctgta     360
ttcggcggag gcacccacct gaccgtcctc ggtcagccca aggcc                    405

<210> SEQ ID NO 1126
<211> LENGTH: 135
<212> TYPE: PRT
<213> ORGANISM: canis familiaris;

<400> SEQUENCE: 1126

Met Asp Trp Val Pro Phe Tyr Leu Leu Pro Phe Ile Phe Ser Thr Gly
1               5                   10                  15

Phe Cys Ala Pro Pro Val Leu Thr Gln Thr Pro Ser Ala Ser Ala Ser
                20                  25                  30

Leu Glu Ala Ser Val Lys Leu Thr Cys Thr Leu Ser Ser Glu His Ser
            35                  40                  45

Ser Tyr Tyr Ile Thr Trp Tyr Gln Gln Gln Pro Gly Lys Ala Pro
        50                  55                  60

Arg Tyr Leu Met Thr Val Asn Ser Asp Gly Ser His Ser Arg Gly Asp
65                  70                  75                  80

Gly Ile Pro Ser Arg Phe Ser Gly Ser Ser Ser Gly Ala Asp Arg Tyr
                85                  90                  95

Leu Thr Ile Ser Asn Ile Gln Ser Glu Asp Glu Ala Asp Tyr Tyr Cys
            100                 105                 110

Phe Ala Pro Ala Asn Asn Ala Val Phe Gly Gly Gly Thr His Leu Thr
        115                 120                 125

Val Leu Gly Gln Pro Lys Ala
            130                 135

<210> SEQ ID NO 1127
<211> LENGTH: 384
<212> TYPE: DNA

-continued

<213> ORGANISM: canis familiaris;

<400> SEQUENCE: 1127

| ctcctcacca | tcctcgctca | ctgcacaggg | tcctgggccc | agtctctact | gactcagccg | 60 |
| gcctcagtgt | ccgggtccct | gggccagagg | gtcaccctct | cctgcactgg | aagcggctcc | 120 |
| aacatcggta | gaggttatgt | gggctggtac | caacacctcc | cggggacagg | ccccagaacc | 180 |
| ctcatctatg | gtgatattaa | ccgaccctca | ggggtccccg | atcggttctc | tggctccagg | 240 |
| tcaggcatca | cagccaccct | gaccatctct | gggctccagg | ctgaggatga | ggctgattat | 300 |
| tactgttcat | cgtgggacta | cagtctcagt | agtactttgt | tcggcggagg | cacccacctg | 360 |
| accgtcctcg | gtcagcccaa | ggcc | | | | 384 |

<210> SEQ ID NO 1128
<211> LENGTH: 128
<212> TYPE: PRT
<213> ORGANISM: canis familiaris;

<400> SEQUENCE: 1128

Leu Leu Thr Ile Leu Ala His Cys Thr Gly Ser Trp Ala Gln Ser Leu
1               5                   10                  15

Leu Thr Gln Pro Ala Ser Val Ser Gly Ser Leu Gly Gln Arg Val Thr
            20                  25                  30

Leu Ser Cys Thr Gly Ser Gly Ser Asn Ile Gly Arg Gly Tyr Val Gly
        35                  40                  45

Trp Tyr Gln His Leu Pro Gly Thr Gly Pro Arg Thr Leu Ile Tyr Gly
    50                  55                  60

Asp Ile Asn Arg Pro Ser Gly Val Pro Asp Arg Phe Ser Gly Ser Arg
65                  70                  75                  80

Ser Gly Ile Thr Ala Thr Leu Thr Ile Ser Gly Leu Gln Ala Glu Asp
                85                  90                  95

Glu Ala Asp Tyr Tyr Cys Ser Ser Trp Asp Tyr Ser Leu Ser Ser Thr
            100                 105                 110

Leu Phe Gly Gly Gly Thr His Leu Thr Val Leu Gly Gln Pro Lys Ala
        115                 120                 125

<210> SEQ ID NO 1129
<211> LENGTH: 414
<212> TYPE: DNA
<213> ORGANISM: canis familiaris;

<400> SEQUENCE: 1129

| atgacctcca | ccatggcctg | gttccctctc | ctcctgaccc | tccttgctca | ctacacaggg | 60 |
| tcctgggccc | agtctgtact | gactcagccg | gcctcagtgt | ctgggtccct | gggccagagg | 120 |
| atcaccatct | cctgcactgg | aagcggttcc | aacattggag | gtaataatgt | gggttggtac | 180 |
| cagcagctcc | caggaagagg | ccccagaact | gtcatctatg | atacttatag | tcgactctcg | 240 |
| ggggtgcccg | atcgattctc | tggctccaag | tctggcagca | cagccaccct | gaccatctct | 300 |
| gggctccagg | ctgaggatga | ggctgattat | tactgctcaa | cgtgggatga | tagtctccgt | 360 |
| gcttacttgt | tcgggtcagg | aacccaactg | accgttcttg | gtcagcccaa | ggcc | 414 |

<210> SEQ ID NO 1130
<211> LENGTH: 138
<212> TYPE: PRT
<213> ORGANISM: canis familiaris;

<400> SEQUENCE: 1130

```
Met Thr Ser Thr Met Ala Trp Phe Pro Leu Leu Leu Thr Leu Leu Ala
1               5                   10                  15

His Tyr Thr Gly Ser Trp Ala Gln Ser Val Leu Thr Gln Pro Ala Ser
            20                  25                  30

Val Ser Gly Ser Leu Gly Gln Arg Ile Thr Ile Ser Cys Thr Gly Ser
        35                  40                  45

Gly Ser Asn Ile Gly Gly Asn Asn Val Gly Trp Tyr Gln Gln Leu Pro
    50                  55                  60

Gly Arg Gly Pro Arg Thr Val Ile Tyr Asp Thr Tyr Ser Arg Leu Ser
65              70                  75                  80

Gly Val Pro Asp Arg Phe Ser Gly Ser Lys Ser Gly Ser Thr Ala Thr
                85                  90                  95

Leu Thr Ile Ser Gly Leu Gln Ala Glu Asp Glu Ala Asp Tyr Tyr Cys
            100                 105                 110

Ser Thr Trp Asp Asp Ser Leu Arg Ala Tyr Leu Phe Gly Ser Gly Thr
            115                 120                 125

Gln Leu Thr Val Leu Gly Gln Pro Lys Ala
    130                 135
```

<210> SEQ ID NO 1131
<211> LENGTH: 414
<212> TYPE: DNA
<213> ORGANISM: canis familiaris;

<400> SEQUENCE: 1131

```
atgacctcca ccatggcctg gttccctctc ctcctgaccc tccttgctca ctacacaggg     60
tcctgggccc agtctgtgct gactcagccg gcctcagtgt ctgggtccct gggccagagg    120
atcaccatct cctgcactgg aagcggttcc aacattggag gtaataatgt gggttggtac    180
cagcagctcc caggaagagg ccccagaact gtcatctatg atacttatag tcgactctcg    240
ggggtgcccg atcgattctc tggctccaag tctggcagca cagccaccct gaccatctct    300
gggctccagg ctgaggatga ggctgattat tactgctcaa cgtgggatga tagtctccgt    360
gcttacttgt tcgggtcagg aacccaactg accgttcttg gtcagcccaa ggcc          414
```

<210> SEQ ID NO 1132
<211> LENGTH: 138
<212> TYPE: PRT
<213> ORGANISM: canis familiaris;

<400> SEQUENCE: 1132

```
Met Thr Ser Thr Met Ala Trp Phe Pro Leu Leu Leu Thr Leu Leu Ala
1               5                   10                  15

His Tyr Thr Gly Ser Trp Ala Gln Ser Val Leu Thr Gln Pro Ala Ser
            20                  25                  30

Val Ser Gly Ser Leu Gly Gln Arg Ile Thr Ile Ser Cys Thr Gly Ser
        35                  40                  45

Gly Ser Asn Ile Gly Gly Asn Asn Val Gly Trp Tyr Gln Gln Leu Pro
    50                  55                  60

Gly Arg Gly Pro Arg Thr Val Ile Tyr Asp Thr Tyr Ser Arg Leu Ser
65              70                  75                  80

Gly Val Pro Asp Arg Phe Ser Gly Ser Lys Ser Gly Ser Thr Ala Thr
                85                  90                  95

Leu Thr Ile Ser Gly Leu Gln Ala Glu Asp Glu Ala Asp Tyr Tyr Cys
            100                 105                 110
```

-continued

```
Ser Thr Trp Asp Asp Ser Leu Arg Ala Tyr Leu Phe Gly Ser Gly Thr
            115                 120                 125

Gln Leu Thr Val Leu Gly Gln Pro Lys Ala
    130                 135
```

<210> SEQ ID NO 1133
<211> LENGTH: 397
<212> TYPE: DNA
<213> ORGANISM: canis familiaris;

<400> SEQUENCE: 1133

```
atgacctcca acatggcctg gtccctctc ctcctcacac tccttgctta ctgcacagga      60
tcctgggccc agtctgcgct gactcagccg acctcagtgt cggggtccct tggccagagg    120
gtctccattt cctgctctgg aagcacgagc aacatcggta ttgtcggtgc gagctggtac    180
caacaactcc caggaaaggc ccctaaactc ctcctgaaca gtgatgggag tgaccgtca    240
ggggtccctg accggttttc cggctccaac tctggcgcct cagccaccct gaccatcact    300
gggcttcagg ctgaggacga ggctgattat tactgtcagt cttttgatcc cacgcctcct    360
gatcattacg tgttcggctc aggaacccaa ctgaccg                             397
```

<210> SEQ ID NO 1134
<211> LENGTH: 125
<212> TYPE: PRT
<213> ORGANISM: canis familiaris;

<400> SEQUENCE: 1134

```
Met Thr Ser Asn Met Ala Trp Ser Pro Leu Leu Thr Leu Leu Ala
1               5                   10                  15

Tyr Cys Thr Gly Ser Trp Ala Gln Ser Ala Leu Thr Gln Pro Thr Ser
                20                  25                  30

Val Ser Gly Ser Leu Gly Gln Arg Val Ser Ile Ser Cys Ser Gly Ser
            35                  40                  45

Thr Ser Asn Ile Gly Ile Val Gly Ala Ser Trp Tyr Gln Gln Leu Pro
    50                  55                  60

Gly Lys Ala Pro Lys Leu Leu Leu Asn Gly Val Pro Asp Arg Phe Ser
65                  70                  75                  80

Gly Ser Asn Ser Gly Ala Ser Ala Thr Leu Thr Ile Thr Gly Leu Gln
                85                  90                  95

Ala Glu Asp Glu Ala Asp Tyr Tyr Cys Gln Ser Phe Asp Pro Thr Pro
            100                 105                 110

Pro Asp His Tyr Val Phe Gly Ser Gly Thr Gln Leu Thr
        115                 120                 125
```

<210> SEQ ID NO 1135
<211> LENGTH: 14
<212> TYPE: PRT
<213> ORGANISM: canis familiaris;

<400> SEQUENCE: 1135

```
Trp Tyr Gln Gln Thr Leu Gly Arg Ala Pro Arg Thr Ile Tyr
1               5                   10
```

<210> SEQ ID NO 1136
<211> LENGTH: 25
<212> TYPE: PRT
<213> ORGANISM: canis familiaris;
<220> FEATURE:
<221> NAME/KEY: unsure
<222> LOCATION: (1)..(1)

```
<223> OTHER INFORMATION: X is absent or S
<220> FEATURE:
<221> NAME/KEY: unsure
<222> LOCATION: (2)..(2)
<223> OTHER INFORMATION: X is absent or W
<220> FEATURE:
<221> NAME/KEY: unsure
<222> LOCATION: (4)..(4)
<223> OTHER INFORMATION: X is absent or Q
<220> FEATURE:
<221> NAME/KEY: unsure
<222> LOCATION: (5)..(5)
<223> OTHER INFORMATION: X is absent, S, or A
<220> FEATURE:
<221> NAME/KEY: unsure
<222> LOCATION: (3)..(3)
<223> OTHER INFORMATION: X is absent or A
<220> FEATURE:
<221> NAME/KEY: unsure
<222> LOCATION: (6)..(6)
<223> OTHER INFORMATION: X is absent, V, L, A, N, C, or M
<220> FEATURE:
<221> NAME/KEY: unsure
<222> LOCATION: (7)..(7)
<223> OTHER INFORMATION: X is absent, V, or L
<220> FEATURE:
<221> NAME/KEY: unsure
<222> LOCATION: (8)..(8)
<223> OTHER INFORMATION: X is absent, T, or N
<220> FEATURE:
<221> NAME/KEY: unsure
<222> LOCATION: (9)..(9)
<223> OTHER INFORMATION: X is absent or Q
<220> FEATURE:
<221> NAME/KEY: unsure
<222> LOCATION: (10)..(10)
<223> OTHER INFORMATION: X is absent, P, A, or S
<220> FEATURE:
<221> NAME/KEY: unsure
<222> LOCATION: (11)..(11)
<223> OTHER INFORMATION: X is absent, A, P, T, or S
<220> FEATURE:
<221> NAME/KEY: unsure
<222> LOCATION: (12)..(12)
<223> OTHER INFORMATION: X is absent, S, or A
<220> FEATURE:
<221> NAME/KEY: unsure
<222> LOCATION: (13)..(13)
<223> OTHER INFORMATION: X is absent, V, or M
<220> FEATURE:
<221> NAME/KEY: unsure
<222> LOCATION: (14)..(14)
<223> OTHER INFORMATION: X is absent, S, or T
<220> FEATURE:
<221> NAME/KEY: unsure
<222> LOCATION: (15)..(15)
<223> OTHER INFORMATION: X is absent or G
<220> FEATURE:
<221> NAME/KEY: unsure
<222> LOCATION: (16)..(16)
<223> OTHER INFORMATION: X is absent, S, A, P, or F
<220> FEATURE:
<221> NAME/KEY: unsure
<222> LOCATION: (17)..(17)
<223> OTHER INFORMATION: X is absent or L
<220> FEATURE:
<221> NAME/KEY: unsure
<222> LOCATION: (18)..(18)
<223> OTHER INFORMATION: X is absent or G
<220> FEATURE:
<221> NAME/KEY: unsure
<222> LOCATION: (19)..(19)
<223> OTHER INFORMATION: X is absent or Q
<220> FEATURE:
<221> NAME/KEY: unsure
<222> LOCATION: (20)..(20)
<223> OTHER INFORMATION: X is absent, R, K, T, S, or E
<220> FEATURE:
<221> NAME/KEY: unsure
```

```
<222> LOCATION: (21)..(21)
<223> OTHER INFORMATION: X is absent, V, or I
<220> FEATURE:
<221> NAME/KEY: unsure
<222> LOCATION: (22)..(22)
<223> OTHER INFORMATION: X is absent, T, or S

<400> SEQUENCE: 1136

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 1137
<211> LENGTH: 15
<212> TYPE: PRT
<213> ORGANISM: canis familiaris;
<220> FEATURE:
<221> NAME/KEY: UNSURE
<222> LOCATION: (2)..(2)
<223> OTHER INFORMATION: X is Y, F, H, or C
<220> FEATURE:
<221> NAME/KEY: UNSURE
<222> LOCATION: (3)..(3)
<223> OTHER INFORMATION: X is Q or R
<220> FEATURE:
<221> NAME/KEY: UNSURE
<222> LOCATION: (4)..(4)
<223> OTHER INFORMATION: X is Q, E, N, L, or H
<220> FEATURE:
<221> NAME/KEY: UNSURE
<222> LOCATION: (5)..(5)
<223> OTHER INFORMATION: X is L, F, V, I, or Y
<220> FEATURE:
<221> NAME/KEY: UNSURE
<222> LOCATION: (7)..(7)
<223> OTHER INFORMATION: X is G or E
<220> FEATURE:
<221> NAME/KEY: UNSURE
<222> LOCATION: (8)..(8)
<223> OTHER INFORMATION: X is T, K, R, A, I, or E
<220> FEATURE:
<221> NAME/KEY: UNSURE
<222> LOCATION: (9)..(9)
<223> OTHER INFORMATION: X is G, S, A, or R
<220> FEATURE:
<221> NAME/KEY: UNSURE
<222> LOCATION: (11)..(11)
<223> OTHER INFORMATION: X is R, K, T, or E
<220> FEATURE:
<221> NAME/KEY: UNSURE
<222> LOCATION: (12)..(12)
<223> OTHER INFORMATION: X is T, L, S, N, or I
<220> FEATURE:
<221> NAME/KEY: UNSURE
<222> LOCATION: (13)..(13)
<223> OTHER INFORMATION: X is L, V, I, or F
<220> FEATURE:
<221> NAME/KEY: UNSURE
<222> LOCATION: (14)..(14)
<223> OTHER INFORMATION: X is I, L, V, or M
<220> FEATURE:
<221> NAME/KEY: UNSURE
<222> LOCATION: (15)..(15)
<223> OTHER INFORMATION: X is Y, F, N, D, H, or S

<400> SEQUENCE: 1137

Trp Xaa Xaa Xaa Xaa Pro Xaa Xaa Xaa Pro Xaa Xaa Xaa Xaa Xaa
1               5                   10                  15

<210> SEQ ID NO 1138
<211> LENGTH: 32
<212> TYPE: PRT
<213> ORGANISM: canis familiaris;
```

-continued

```
<220> FEATURE:
<221> NAME/KEY: UNSURE
<222> LOCATION: (1)..(1)
<223> OTHER INFORMATION: X is G, R, or E
<220> FEATURE:
<221> NAME/KEY: UNSURE
<222> LOCATION: (2)..(2)
<223> OTHER INFORMATION: X is V, I, or A
<220> FEATURE:
<221> NAME/KEY: UNSURE
<222> LOCATION: (3)..(3)
<223> OTHER INFORMATION: X is P or S
<220> FEATURE:
<221> NAME/KEY: UNSURE
<222> LOCATION: (4)..(4)
<223> OTHER INFORMATION: X is D, A, N, or E
<220> FEATURE:
<221> NAME/KEY: UNSURE
<222> LOCATION: (8)..(8)
<223> OTHER INFORMATION: X is G, A, or V
<220> FEATURE:
<221> NAME/KEY: UNSURE
<222> LOCATION: (10)..(10)
<223> OTHER INFORMATION: X is R, K, T, N, S, I, or E
<220> FEATURE:
<221> NAME/KEY: UNSURE
<222> LOCATION: (12)..(12)
<223> OTHER INFORMATION: X is G, D, or R
<220> FEATURE:
<221> NAME/KEY: UNSURE
<222> LOCATION: (13)..(13)
<223> OTHER INFORMATION: X is S, N, A, R, I, T, or F
<220> FEATURE:
<221> NAME/KEY: UNSURE
<222> LOCATION: (14)..(14)
<223> OTHER INFORMATION: X is T, S, or A
<220> FEATURE:
<221> NAME/KEY: UNSURE
<222> LOCATION: (15)..(15)
<223> OTHER INFORMATION: X is A, G, or S
<220> FEATURE:
<221> NAME/KEY: UNSURE
<222> LOCATION: (16)..(16)
<223> OTHER INFORMATION: X is T, S, A, or I
<220> FEATURE:
<221> NAME/KEY: UNSURE
<222> LOCATION: (20)..(20)
<223> OTHER INFORMATION: X is S, T, or A
<220> FEATURE:
<221> NAME/KEY: UNSURE
<222> LOCATION: (21)..(21)
<223> OTHER INFORMATION: X is G, V, or E
<220> FEATURE:
<221> NAME/KEY: UNSURE
<222> LOCATION: (23)..(23)
<223> OTHER INFORMATION: X is Q, R, or L
<220> FEATURE:
<221> NAME/KEY: UNSURE
<222> LOCATION: (24)..(24)
<223> OTHER INFORMATION: X is A or P
<220> FEATURE:
<221> NAME/KEY: UNSURE
<222> LOCATION: (25)..(25)
<223> OTHER INFORMATION: X is E or D
<220> FEATURE:
<221> NAME/KEY: UNSURE
<222> LOCATION: (28)..(28)
<223> OTHER INFORMATION: X is A or G
<220> FEATURE:
<221> NAME/KEY: UNSURE
<222> LOCATION: (29)..(29)
<223> OTHER INFORMATION: X is D, E, I, or A
<220> FEATURE:
<221> NAME/KEY: UNSURE
<222> LOCATION: (30)..(30)
<223> OTHER INFORMATION: X is Y or absent
<220> FEATURE:
<221> NAME/KEY: UNSURE
<222> LOCATION: (31)..(31)
```

-continued

<223> OTHER INFORMATION: X is Y, F, or H

<400> SEQUENCE: 1138

Xaa Xaa Xaa Xaa Arg Phe Ser Xaa Ser Xaa Ser Xaa Xaa Xaa Xaa
1               5                   10                  15

Leu Thr Ile Xaa Xaa Leu Xaa Xaa Xaa Asp Glu Xaa Xaa Xaa Cys
            20                  25                  30

<210> SEQ ID NO 1139
<211> LENGTH: 423
<212> TYPE: DNA
<213> ORGANISM: canis familiaris;

<400> SEQUENCE: 1139

```
atgaggttcc cttctcagct cctggggctg ctgatgctct ggatcccagg atccagtggg       60
gatattgtca tgacacaggc cccaccgtct ctgtccgtca gccctggaga gccggcctcc      120
atctcctgca aggccagtca gagcctcctg tacagtaatg gaatacccta tttgtattgg      180
ttccgacaga agccaggcca gtctccagag ggcctgatct ataaggtgtc caaccgcttc      240
actggcgtgt cagacaggtt cagtggcagc gggtcaggga cagatttcac cctgagaatc      300
agcagagtgg aggctgacga tgctggagtt tattactgcg ggcaaggtat acagtttcct      360
attactctca gccagggagc caagctggac ataaaacgga atgatgccca gccagccgtc      420
tat                                                                    423
```

METHODS FOR USING CANINE IMMUNOGLOBULIN VARIABLE DOMAINS AND CANINIZED ANTIBODIES

This application claims the benefit under 35 U.S.C. §119 (e) of U.S. Provisional Application No. 60/344,874 filed Dec. 21, 2001.

The sequence listing submitted on compact disc, in compliance with 37 C.F.R. §1.52(eX5), is incorporated by reference. Two dulpicate compact discs are submitted, each containing the file "01-799-A SeqList.txt" (24,203,264 bytes in size), each created on CD on Aug. 8, 2006.

BACKGROUND OF THE INVENTION

1. Field of the Invention

The present invention relates to the field of immunology. More specifically, the present invention relates to canine immunoglobulin light and heavy chain variable domains, caninized antibodies, and methods for making and using them.

2. Summary of the Related Art

The process of modifying a monoclonal antibody from an animal to render it less immunogenic for therapeutic administration to humans (humanization) has been aggressively pursued and has been described in a number of publications (e.g. Antibody Engineering: A practical Guide. Carl A. K. Borrebaeck ed. W.H. Freeman and Company, 1992). However, this process has not been applied for the development of therapeutic or diagnostics for canines. In fact, very little has been published with regard to canine variable domains at all.

Wasserman and Capra, *Biochem.* 16, 3160 (1977), determined the amino acid sequence of the variable regions of both a canine IgM and a canine IgA heavy chain.

Wasserman and Capra, *Immunochem.* 15, 303 (1978), determined the amino acid sequence of the κ light chain from a canine IgA.

McCumber and Capra, *Mol. Immunol.* 16, 565 (1979), disclose the complete amino-acid sequence of a canine mu chain.

Tang et al., *Vet. Immunology Immunopathology* 80, 259 (2001), discloses a single canine IgG-A γ chain cDNA and four canine IgG-A γ chain protein sequences. It describes PCR amplification of a canine spleen cDNA library with a degenerate oligonucleotide primer designed from the conserved regions of human, mouse, pig, and bovine IgGs.

The paucity of information available on canine antibodies prevents their development as therapeutics for the treatment canine disease.

All publications recited in this specification (e.g., patent publications and scientific journal articles) are hereby incorporated by reference in their entirety.

SUMMARY OF THE INVENTION

The present invention provides canine heavy chain and light chain (both λ and κ) domain nucleic acids and polypeptides The present invention also provides caninized antibodies comprised of the presently disclosed canine variable and CDRs specific for an antigen obtained from antibodies from other than canines (preferably mouse or canine).

The invention also provides methods of making caninized antibodies and using them. This disclosure specifically describes caninized antibodies that are useful in the treatment of canine allergy. The general process of caninization permits the development of useful therapeutics, which includes but is not limited to allergy, osteosarcoma and lymphoma.

BRIEF DESCRIPTION OF THE DRAWINGS

FIG. 2 displays light chain variable domain (SEQ ID NO: 1140) selected for caninization and its alignment to 15A2 (SEQ ID NO: 1141). Amino acid differences are indicated by vertical lines.

FIG. 3 displays the H74 heavy chain variable domain (SEQ ID NO: 1142) selected for caninization and its alignment to 15A2 (SEQ ID NO: 1143). Differences are indicated with vertical lines.

FIGS. 4A and 4B display schematic diagrams of CDR grafting of the 15A2 CDR's onto canine variable domains and the construction of full-length heavy and light chains.

FIG. 5 displays the interpretation of the molecular modeling of 15A2: light chain followed by heavy chain, including light chains 15A2/1NGQ (SEQ ID NO: 1144), 15A2/1FBI (SEQ ID NO: 1145), 15A2/2VIR (SEQ ID NO: 1146), and LAMB305-1 (SEQ ID NO: 1147); heavy chains 15A2/1NGQ (SEQ ID NO: 1148), 15A2/1FBI (SEQ ID NO: 1149), 15A2/2VIR (SEQ ID NO: 1150), and H74-1 (SEQ ID NO: 1151).

DETAILED DESCRIPTION OF THE INVENTION

Figure 1:
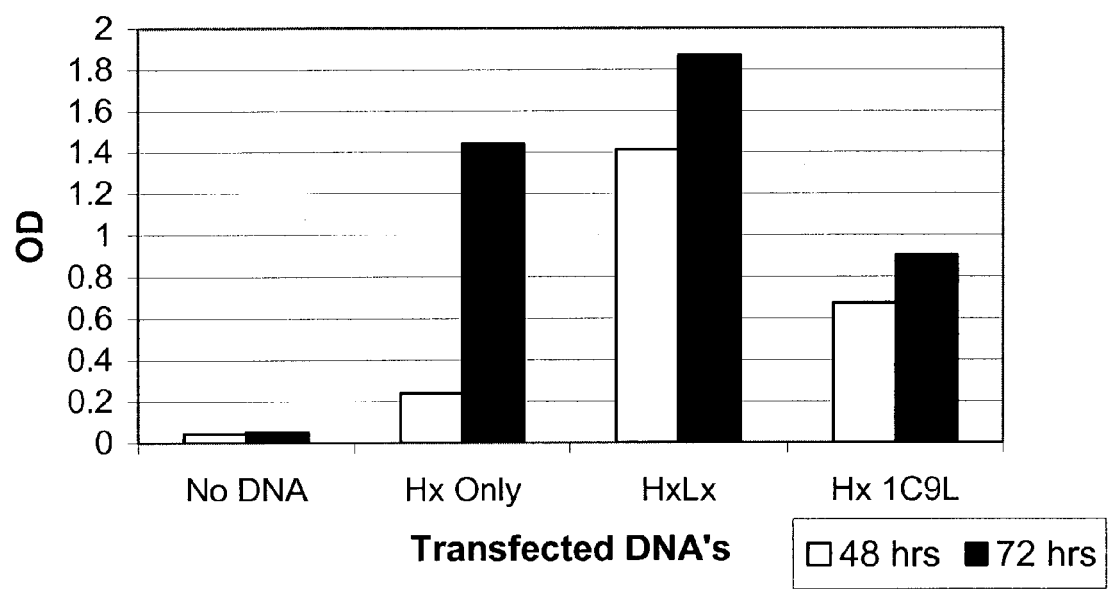
FIG. 1 displays the results for screening of functional heavy and light chain variable domains by measuring secretion of $IgG_H$ from COS cells.

IDEXX has engaged in the development of a therapeutic monoclonal antibody for the treatment of allergy in canines. The therapeutic antibody used in canine clinical trials was a chimeric recombinant molecule, consisting of canine antibody constant domains of the heavy and light chains attached to murine derived antibody variable domains of the mouse monoclonal antibody 15A2. Therapeutic administration of this antibody to dogs sensitized to rag weed alleviated the symptoms of allergy and was considered successful. However, repeated and extended administration of the chimeric molecule in canines caused the induction of a neutralizing humoral immune response to the therapeutic, rendering it ineffective. Analysis of the anti-chimeric response clearly demonstrated the response was to the murine component of the therapeutic molecule. Accordingly, we set forth to overcome this disadvantage by "caninization" of an antibody: taking a monoclonal antibody from another organism, usually a mouse, and substituting canine immunoglobulin sequences into the variable domain to render the molecule less immunogenic when administered to canines. In particular, this process focuses on the framework regions of the immunoglobulin variable domain, but could also include the compliment determinant regions (CDR's) of the variable domain. The enabling steps and reduction to practice for this process are described in this disclosure.

Polypeptide Compositions of Matter

In a first aspect, the present invention comprises chimeric canine variable domain polypeptides having one or more CDR's from a non-canine antibody.

1. H58 Family Genus

In one embodiment, the present invention provides chimeric canine heavy chain variable domain polypeptides having one or more CDR's from a non-canine antibody. The chimeric canine heavy chain variable domain polypeptides according to the invention are compounds comprising the sequence:

$$Fr^1\text{-}CDR^1\text{-}Fr^2\text{-}CDR^2\text{-}Fr^3\text{-}CDR^3\text{-}Fr^4$$

wherein $Fr^1$ is $X^1$ $X^2$ $X^3$ $X^4$ $X^5$ $X^6$ $X^7$ $X^8$ $X^9$ $X^{10}$ $X^{11}$ $X^{12}$ $X^{13}$ $X^{14}$ $X^{15}$ $X^{16}$ $X^{17}$ $X^{18}$ $X^{19}$ $X^{20}$ $X^{21}$ $X^{22}$ $X^{23}$ $X^{24}$ $X^{81}$ (SEQ ID NO: 2);

$Fr^2$ is $X^{25}$ $X^{26}$ $X^{27}$ $X^{28}$ $X^{29}$ $X^{30}$ $X^{31}$ $X^{32}$ $X^{33}$ $X^{34}$ $X^{35}$ $X^{36}$ $X^{37}$ $X^{38}$ (SEQ ID NO: 3);

$Fr^3$ is $X^{39}$ $X^{40}$ $X^{41}$ $X^{42}$ $X^{43}$ $X^{44}$ $X^{45}$ $X^{46}$ $X^{47}$ $X^{48}$ $X^{49}$ $X^{50}$ $X^{51}$ $X^{52}$ $X^{53}$ $X^{54}$ $X^{55}$ $X^{56}$ $X^{57}$ $X^{58}$ $X^{59}$ $X^{60}$ $X^{61}$ $X^{62}$ $X^{63}$ $X^{64}$ $X^{65}$ $X^{66}$ $X^{67}$ $X^{68}$ $X^{69}$ $X^{70}$ (SEQ ID NO: 4);

$Fr^4$ is $X^{71}$ $X^{72}$ $X^{73}$ $X^{74}$ $X^{75}$ $X^{76}$ $X^{77}$ $X^{78}$ $X^{79}$ $X^{80}$ (SEQ ID NO: 5);

$X^1$ is E, $X^2$ is V, $X^3$ is Q $X^4$ is L, $X^5$ is V or M; or H;

$X^6$ is E or Q; $X^7$ is S, $X^8$ is G, $X^9$ is G, $X^{10}$ is D, or N;

$X^{11}$ is L, $X^{12}$ is V, $X^{13}$ is K or R, $X^{14}$ is P, $X^{15}$ is G, A, S, or E $X^{16}$ is G, $X^{17}$ is S, $X^{18}$ is L, $X^{19}$ is R, $X^{20}$ is L

$X^{21}$ is S, $X^{22}$ is C, $X^{23}$ is V, $X^{24}$ is A, T, V, or G', $X^{25}$ is W, $X^{26}$ is V, $X^{27}$ is R, H, R, or E; $X^{28}$ is Q, T, P, C, or S; $X^{29}$ is A, $X^{30}$ is P, $X^{31}$ is G $X^{32}$ is K, $X^{33}$ is G, $X^{34}$ is L, $X^{35}$ is Q, E, or E;

$X^{36}$ is W, L, or Y; $X^{37}$ is V or I; $X^{38}$ is A, G, V or T; $X^{39}$ is R, $X^{40}$ is F, or K;

$X^{41}$ is T or I; $X^{42}$ is I or V; $X^{43}$ is S, $X^{44}$ is R, $X^{45}$ is D, $X^{46}$ is N, L, S, or D; $X^{47}$ is A, $X^{48}$ is K, R, or E; $X^{49}$ is N or S; $X^{50}$ is T, $X^{51}$ is L, V, or F; $X^{52}$ is Y, F, or S; $X^{53}$ is L, $X^{54}$ is Q, H, or E; $X^{55}$ is M or L;

$X^{56}$ is N, D, or E; $X^{57}$ is S or N; $X^{58}$ is L $X^{59}$ is R or T; $X^{60}$ is A, V, D, P, G, or T;

$X^{61}$ is E or D; $X^{62}$ is D, $X^{63}$ is T, $X^{63}$ is V, I, T, R, M; $X^{64}$ is A, $X^{65}$ is Y or F; $X^{66}$ is Y, G, T, G, or V; $X^{67}$ is A, $X^{68}$ is C $X^{70}$ is R, T, G, S, A, P, or K, $X^{71}$ is Y, S, H or L; $X^{72}$ is W, $X^{73}$ is G, $X^{74}$ is Q or R; $X^{75}$ is G, $X^{76}$ is T, N, or A; $X^{77}$ is L or P; $X^{78}$ is V, $X^{79}$ is T or –; $X^{80}$ is V or –; and $X^{81}$ is S.

provided that when $X^{79}$ is -, $X^{80}$ is - ("-" means no residue or residues are present at the respective position).

2. H58 Family Subgenus

Preferably, the canine heavy chain variable domain according to the invention is a compound comprising the sequence:

$$Fr^1\text{-}CDR^1\text{-}Fr^2\text{-}CDR^2\text{-}Fr^3\text{-}CDR^3\text{-}Fr^4$$

wherein $Fr^1$ is

```
EVQLVESGGDLVKPAGSLRLSCVTS    EVQLMESGGDLVKPGGSLRLSCVAS    EVQLVESGGDLVKPEGSLRLSCVVS
SEQ ID NO: 6                 SEQ ID NO: 7                 SEQ ID NO: 8

EVQLVESGGDLVKPAGSLRLSCVAS    EVQLVESGGDLVRPGGSLRLSCVAS    EVQLVESGGXLVKFGGSLXLSCVAS
SEQ ID NO: 9                 SEQ ID NO: 10                SEQ ID NO: 11
```

-continued

```
EVHLVESGGDLVKPGGSLRLSCVAS    EVQLVESGGDLVKPGGSLRLSCVAS    EVQLVESGGDLVKPGGSLRLSCVGS
SEQ ID NO: 12                SEQ ID NO: 13                SEQ ID NO: 14

EVQLVESGGDLVKPGGSLRLSCVTS    EVQLVQSGGDLVKPSGSLRLSCVAS or EVQLVESGGNLVKPGGSLRLSCVAS;
SEQ ID NO: 15                SEQ ID NO: 16                SEQ ID NO: 17
```

$Fr^2$ is

```
WVRQAPGKGLQWVA  WVRQAPGKGLQLVA  WVRQSPGKGLQWVA   WVRQAPEKGLQLVA
SEQ ID NO: 18   SEQ ID NO: 19   SEQ ID NO: 20    SEQ ID NO: 21

WVREAPGKGLQWVA  WVRRAPGKGLQWIA  WVRHSPGKGLQWVA   WVRQCPGKGLQWVT
SEQ ID NO: 22   SEQ ID NO: 23   SEQ ID NO: 24    SEQ ID NO: 25

WVRQPPGKGLQWIV  WVRQPPGKGPQWVA  WVRQAPGKGLQYVA   WVRQAPGKGLKWVA
SEQ ID NO: 26   SEQ ID NO: 27   SEQ ID NO: 28    SEQ ID NO: 29

WVRQAPGEGLQWIG or            WVRQTPERGLELVA;
SEQ ID NO: 30                SEQ ID NO: 31
```

$Fr^3$ is

```
RFTISRDNAKNTVYLQMNSLRAEDTAVYYCAK    RFTISRDNAKNTFYLQMNSLRAEDSAMYYCAA
SEQ ID NO: 32                       SEQ ID NO: 33

RFTISRDNAKNTLYLQMNSLRTEDTAVYYCAR    RFTISRDNAKNTVYLQMNSLRAEDTAMYYCAP
SEQ ID NO: 34                       SEQ ID NO: 35

RFTISRDNAKNTVYLQMNSLRGEDTAMYYCAK    RFTISRDNAKNTLYLQMNSLRAEDTAVYYCAK
SEQ ID NO: 36                       SEQ ID NO: 37

RFTISRDNAKNTLYLQLNSLRVEDTAVYYCAR    RFTISRDNAENTLYLQMNSLRPEDTAVYYCAS
SEQ ID NO: 38                       SEQ ID NO: 39

RFTISRDNAKSTLYLEMNRLRPDXTAMYYCVT    RFTISRDDANNTLYLQMNSLRAEDTAVYYCAK
SEQ ID NO: 40                       SEQ ID NO: 41

RFTISRDNAKNTLYLQLNSLRAEDTAVYYCAK    RFTISRDNAKNTLSLEMNSLRDEDTAMYYCAR
SEQ ID NO: 42                       SEQ ID NO: 43

RFTISRDSAKNTLYLQLNSLTAEDTARYYCAG    RFTISRDNAKNTLYLXMNSLRAEDTAVYYCGK
SEQ ID NO: 44                       SEQ ID NO: 45

RFTISRDNAKNTLYLQMNSLRAXDTAVYYCAR    RFTISRDNARNTVYLQMNSLRAEDTAVYYCAK
SEQ ID NO: 46                       SEQ ID NO: 47

RFTISRDNAKNTLSLHMNSLRVEDTAVYFCTR    RFTISRDNARNTLYLQMNSLRAEDTAVYFCAK
SEQ ID NO: 48                       SEQ ID NO: 49

RFTVSRDNAKSTLYLQMENLRAEDTAVYYCAT    RFTISRDNAKNTLFLQMHSLRAEDTAIYYCAR
SEQ ID NO: 50                       SEQ ID NO: 51

RFIISRDLAKSTVYLQMDNLRADDTATYYCAR or RFTISRDNARNTVYLQLNSLRAEDTAVYYCGK;
SEQ ID NO: 52                       SEQ ID NO: 53
``` and
$Fr^4$ is

```
HWGQGTLVTV   LWGPGTLVTV     YWGQGTLVTV   SWGQGTLVTV     YWGQGTLVT
SEQ ID NO:   SEQ ID NO: 55  SEQ ID NO:   SEQ ID NO: 57  SEQ ID NO:
54                          56                          58

LWGQGTLVT    LWGQGTLTV      HWGQGTLVT    YWGQGTLV       YWGQGTPVTV
SEQ ID NO:   SEQ ID NO: 60  SEQ ID NO:   SEQ ID NO: 62  SEQ ID NO:
59                          61                          63

GWGQGTLVTV   HWGQGTLV       YWGPGTLVTV   YWGQGNLVTV or  SWGRGALVTV.
SEQ ID NO:   SEQ ID NO: 65  SEQ ID NO:   SEQ ID NO: 67  SEQ ID NO:
64                          66                          68
```

3. H58 Family Species

In a more preferred embodiment, the chimeric heavy chain variable region according to the invention is a compound comprising the sequence:

$$Fr^1\text{-}CDR^1\text{-}Fr^2\text{-}CDR^2\text{-}Fr^3\text{-}CDR^3\text{-}Fr^4 \qquad 5$$

wherein $Fr^1$, $Fr^2$, $Fr^3$, and $Fr^4$ are selected from the following combinations:

| # | $Fr^1$ | $Fr^2$ | $Fr^3$ | $Fr^4$ |
|---|---|---|---|---|
| H3 | EVQLVESGGDLVKPAGSLRLSCVTS<br>SEQ ID NO: 6 | WVRQAPGKGLQWVA<br>SEQ ID NO: 18 | RFTISRDNAKNTVYLQMNSLRAEDTAVYYCAK<br>SEQ ID NO: 32 | HWGQGTLVTV;<br>SEQ ID NO: 54 |
| H4 | EVQLMESGGDLVKPGGSLRLSCVAS<br>SEQ ID NO: 7 | WVRQAPGKGLQWVA<br>SEQ ID NO: 18 | RFTISRDNAKNTFYLQMNSLRAEDSAMYYCAA<br>SEQ ID NO: 33 | LWGPGTLVTV;<br>SEQ ID NO: 55 |
| H53 | EVQLVESGGDLVKPEGSLRLSCVVS<br>SEQ ID NO: 8 | WVRQAPGKGLQWVA<br>SEQ ID NO: 18 | RFTISRDNAKNTLYLQMNSLRTEDTAVYYCAR<br>SEQ ID NO: 34 | YWGQGTLVTV;<br>SEQ ID NO: 56 |
| H67 | EVQLVESGGDLVKPAGSLRLSCVAS<br>SEQ ID NO: 9 | WVRQAPGKGLQLVA<br>SEQ ID NO: 19 | RFTISRDNAKNTVYLQMNSLRAEDTAMYYCAP<br>SEQ ID NO: 35 | SWGQGTLVTV;<br>SEQ ID NO: 57 |
| H51 | EVQLVESGGDLVKPAGSLRLSCVAS<br>SEQ ID NO: 9 | WVRQAPGKGLQLVA<br>SEQ ID NO: 19 | RFTISRDNAKNTVYLQMNSLRGEDTAMYYCAK<br>SEQ ID NO: 36 | YWGQGTLVT;<br>SEQ ID NO: 58 |
| H7 | EVQLVESGGDLVRPGGSLRLSCVAS<br>SEQ ID NO: 10 | WVRQSPGKGLQWVA<br>SEQ ID NO: 20 | RFTISRDNAKNTLYLQMNSLRAEDTAVYYCAK<br>SEQ ID NO: 37 | YWGQGTLVTV;<br>SEQ ID NO: 56 |
| H404 | EVQLVESGGXLVKFGGSLXLSCVAS<br>SEQ ID NO: 11 | WVRQAPEKGLQLVA<br>SEQ ID NO: 21 | RFTISRDNAKNTLYLQLNSLRVEDTAVYYCAR<br>SEQ ID NO: 38 | LWGQGTLVT;<br>SEQ ID NO: 59 |
| H445 | EVHLVESGGDLVKPGGSLRLSCVAS<br>SEQ ID NO: 12 | WVREAPGKGLQWVA<br>SEQ ID NO: 22 | RFTISRDNAENTLYLQMNSLRPEDTAVYYCAS<br>SEQ ID NO: 39 | LWGQGTLTV;<br>SEQ ID NO: 60 |
| H422 | EVQLVESGGDLVKPGGSLRLSCVAS<br>SEQ ID NO: 13 | WVRRAPGKGLQWIA<br>SEQ ID NO: 23 | RFTISRDNAKSTLYLEMNRLRPDXTAMYYCVT<br>SEQ ID NO: 40 | HWGQGTLVTV;<br>SEQ ID NO: 54 |
| H442 | EVQLVESGGDLVKPGGSLRLSCVAS<br>SEQ ID NO: 13 | WVRRAPGKGLQWIA<br>SEQ ID NO: 23 | RFTISRDNAKSTLYLEMNRLRPDXTAMYYCVT<br>SEQ ID NO: 40 | HWGQGTLVT;<br>SEQ ID NO: 61 |
| H2 | EVQLVESGGDLVKPGGSLRLSCVAS<br>SEQ ID NO: 13 | WVRHSPGKGLQWVA<br>SEQ ID NO: 24 | RFTISRDDANNTLYLQMNSLRAEDTAVYYCAK<br>SEQ ID NO: 41 | YWGQGTLV;<br>SEQ ID NO: 62 |
| H602 | EVQLVESGGDLVKPGGSLRLSCVAS<br>SEQ ID NO: 13 | WVRQCPGKGLQWVT<br>SEQ ID NO: 25 | RFTISRDNAKNTLYLQLNSLRAEDTAVYYCAK<br>SEQ ID NO: 42 | YWGQGTPVTV<br>SEQ ID NO: 63 |
| H396 | EVQLVESGGDLVKPGGSLRLSCVGS<br>SEQ ID NO: 14 | WVRQPPGKGLQWIV<br>SEQ ID NO: 26 | RFTISRDNAKNTLSLEMNSLRDEDTAMYYCAR<br>SEQ ID NO: 43 | YWGQGTLVT;<br>SEQ ID NO: 58 |
| H5 | EVQLVESGGDLVKPGGSLRLSCVAS<br>SEQ ID NO: 13 | WVRQPPGKGPQWVA<br>SEQ ID NO: 27 | RFTISRDSAKNTLYLQLNSLTAEDTARYYCAG<br>SEQ ID NO: 44 | YWGQGTLVTV;<br>SEQ ID NO: 56 |
| H574 | EVQLVESGGDLVKPGGSLRLSCVAS<br>SEQ ID NO: 13 | WVRQAPGKGLQYVA<br>SEQ ID NO: 28 | RFTISRDNAKNTLYLXMNSLRAEDTAVYYCGK<br>SEQ ID NO: 45 | SWGQGTLVTV;<br>SEQ ID NO: 57 |
| H378 | EVQLVESGGDLVKPGGSLRLSCVTS<br>SEQ ID NO: 15 | WVRQAPGKGLQWVA<br>SEQ ID NO: 18 | RFTISRDNAKNTLYLQMNSLRAXDTAVYYCAR<br>SEQ ID NO: 46 | GWGQGTLVTV;<br>SEQ ID NO: 64 |
| H8 | EVQLVESGGDLVKPGGSLRLSCVAS<br>SEQ ID NO: 13 | WVRQAPGKGLQWVA<br>SEQ ID NO: 18 | RFTISRDNARNTVYLQMNSLRAEDTAVYYCAK<br>SEQ ID NO: 47 | YWGQGTLVTV;<br>SEQ ID NO: 56 |

-continued

| # | Fr¹ | Fr² | Fr³ | Fr⁴ |
|---|---|---|---|---|
| H592 | EVQLVESGGDLVKPGGSLRLSCVGS SEQ ID NO: 14 | WVRQAPGKGLQWVA SEQ ID NO: 18 | RFTISRDNAKNTLSLHMNSLRVEDTAVYFCTR SEQ ID NO: 48 | HWGQGTLV; SEQ ID NO: 65 |
| H9 | EVQLVESGGDLVKPGGSLRLSCVAS SEQ ID NO: 13 | WVRQAPGKGLQWVA SEQ ID NO: 18 | RFTISRDNARNTLYLQMNSLRAEDTAVYFCAK SEQ ID NO: 49 | YWGPGTLVTV; SEQ ID NO: 66 |
| H55 | EVQLVESGGDLVKPGGSLRLSCVAS SEQ ID NO: 13 | WVRQAPGKGLKWVA SEQ ID NO: 29 | RFTVSRDNAKSTLYLQMENLRAEDTAVYYCAT SEQ ID NO: 50 | YWGQGTLVTV; SEQ ID NO: 56 |
| H585 | EVQLVESGGDLVKPGGSLRLSCVGS SEQ ID NO: 14 | WVRQAPGEGLQWIG SEQ ID NO: 30 | RFTISRDNAKNTLFLQMHSLRAEDTAIYYCAR SEQ ID NO: 51 | YWGQGNLVTV; SEQ ID NO: 67 |
| H56 | EVQLVQSGGDLVKPSGSLRLSCVAS SEQ ID NO: 16 | WVRQTPERGLELVA SEQ ID NO: 31 | RFIISRDLAKSTVYLQMDNLRADDTATYYCAR SEQ ID NO: 52 | SWGRGALVTV; SEQ ID NO: 68 |
| H58 | EVQLVESGGNLVKPGGSLRLSCVAS SEQ ID NO: 17 | WVRQAPGKGLQWVA SEQ ID NO: 18 | RFTISRDNARNTVYLQLNSLRAEDTAVYYCGK SEQ ID NO: 53 | YWGQGTLVTV. SEQ ID NO: 56 |

4. H74 Heavy Chain Variable Domain Genus

The canine group H74 heavy chain variable domain polypeptides according to the invention are compounds comprising the sequence:

Fr¹-CDR¹-Fr²-CDR²-Fr³-CDR³-Fr⁴ wherein
Fr¹ is $X^{'1} X^{'2} X^{'3} X^{'4} X^{'5} X^{'6} X^{'7} X^{'8} X^{'9} X^{'10} X^{'11} X^{'12} X^{'13} X^{'14} X^{'15} X^{'16} X^{'17} X^{'18} X^{'19} X^{'20} X^{'21} X^{'22} X^{'23} X^{'24} X^{'25}$ (SEQ ID NO: 69);
Fr² is $X^{'26} X^{'27} X^{'28} X^{'29} X^{'30} X^{'31} X^{'32} X^{'33} X^{'34} X^{'35} X^{'36} X^{'37} X^{'38} X^{'39} X^{'40}$ (SEQ ID NO: 70)
Fr³ is $X^{'41} X^{'42} X^{'43} X^{'44} X^{'45} X^{'46} X^{'47} X^{'48} X^{'49} X^{'50} X^{'51} X^{'11} X^{'52} X^{'54} X^{'55} X^{'56} X^{'57} X^{'58} X^{'59} X^{'60} X^{'61} X^{'62} X^{'63} X^{'64} X^{'65} X^{'66} X^{'67} X^{'68} X^{'69} X^{'70} X^{'71} X^{'72}$ (SEQ ID NO: 71), and
Fr⁴ is $X^{'73} X^{'74} X^{'75} X^{'76} X^{'77} X^{'78} X^{'79} X^{'80} X^{'81} X^{'82}$ (SEQ ID NO: 72), wherein $X^{'1}$ is E, $X^{'2}$ is V, $X^{'3}$ is Q or H; $X^{'4}$ is L, $X^{'5}$ is V, $X^{'6}$ is Q; $X^{'7}$ is S, $X^{'8}$ is A, $X^{'9}$ is A, $X^{'10}$ is W;

$X^{'11}$ is V, $X^{'12}$ is K, $X^{'13}$ is K, $X^{'14}$ is P, $X^{'15}$ is G, $X^{'16}$ is A, $X^{'17}$ is S, $X^{'18}$ is V, $X^{'19}$ is K, $X^{'20}$ is V, $X^{'21}$ is S, $X^{'22}$ is C, $X^{'23}$ is K, $X^{'24}$ is T, $X^{'25}$ is S, $X^{'26}$ is W, $X^{'27}$ is V, $X^{'28}$ is Q, $X^{'29}$ is Q, $X^{'30}$ is A, $X^{'31}$ is P; $X^{'32}$ is G, $X^{'33}$ is A, $X^{'34}$ is G, $X^{'35}$ is L, $X^{'36}$ is D or E, $X^{'37}$ is W, $X^{'38}$ is M, $X^{'39}$ is G, $X^{'40}$ is W, $X^{'41}$ is R, $X^{'42}$ is V, $X^{'43}$ is T, $X^{'44}$ is L, $X^{'45}$ is T, $X^{'46}$ is A, $X^{'47}$ is D, $X^{'48}$ is T, $X^{'49}$ is S, $X^{'50}$ is T, $X^{'51}$ is S $X^{'52}$ is $X^{'53}$ is Q $X^{'54}$ is $X^{'55}$ is or N, T, or V, Y, M, $X^{'56}$ is E, $X^{'57}$ is L, $X^{'58}$ is S $X^{'59}$ is S or N, $X^{'60}$ is L, $X^{'61}$ is R, $X^{'62}$ is A or T, $X^{'63}$ is E, $X^{'63}$ is D, $X^{'64}$ is T of A, $X^{'65}$ is A, $X^{'66}$ is V, $X^{'67}$ is Y, $X^{'68}$ is Y, $X^{'70}$ is C, $X^{'71}$ is A, $X^{'72}$ is R or S, $X^{'73}$ is Y or L, $X^{'74}$ is W; $X^{'75}$ is G, $X^{'76}$ is Q, $X^{'77}$ is G, $X^{'78}$ is T, $X^{'79}$ is L, $X^{'80}$ is V, $X^{'81}$ is T, and $X^{'82}$ is V.

5. H74 Heavy Chain Variable Domain Subgenus

Preferably, the canine heavy chain variable domain according to the invention is a compound comprising the sequence:

Fr¹-CDR¹-Fr²-CDR²-Fr³-CDR³-Fr⁴ wherein
Fr¹ is EVQLVQSAAEVKKPGASVKVSCKTS (SEQ ID NO: 73),
Fr² is WVQQAPGAGLDWMGW (SEQ ID NO: 74) or WVQQAPGAGLEWMGW (SEQ ID NO: 75),
Fr³ is RVTLTADTSTSTAYMELSSLRAEDTAVYYCAS (SEQ ID NO: 76), RVTLTADTSTNTVYMELSNLRTEDTAVYYCAR (SEQ ID NO: 77), or RVTLTADTSTSTAYMELSSLRAEDAAVYYCAS (SEQ ID NO: 78), and
Fr⁴ is YWGQGTLVTV (SEQ ID NO: 56) or LWGQGTLVTV (SEQ ID NO: 79).

6. H74 Heavy Chain Variable Domain Species

In a more preferred embodiment, the chimeric heavy chain variable region according to the invention is a compound comprising the sequence:

Fr¹-CDR¹-Fr²-CDR²-Fr³-CDR³-Fr⁴ wherein Fr¹, Fr², Fr³, and Fr⁴ are selected from the following combinations:

| # | Fr¹ | Fr² | Fr³ | Fr⁴ |
|---|---|---|---|---|
| H392 | EVQLVQSAAEVKKPGASVKVSCKTS SEQ ID NO: 73 | WVQQAPGAGLDWMGW SEQ ID NO: 74 | RVTLTADTSTSTAYMELSSLRAEDTAVYYCAS SEQ ID NO: 76 | YWGQGTLVTV SEQ ID NO: 56 |
| H76 | EVQLVQSAAEVKKPGASVKVSCKTS SEQ ID NO: 73 | WVQQAPGAGLDWMGW SEQ ID NO: 74 | RVTLTADTSTSTAYMELSSLRAEDTAVYYCAR SEQ ID NO: 80 | YWGQGTLVTV SEQ ID NO: 56 |
| H645 | EVQLVQSAAEVKKPGASVKVSCKTS SEQ ID NO: 73 | WVQQAPGAGLEWMGW SEQ ID NO: 75 | RVTLTADTSTNTVYMELSNLRTEDTAVYYCAR SEQ ID NO: 77 | YWGQGTLVTV or SEQ ID NO: 56 |
| H74 | EVQLVQSAAEVKKPGASVKVSCKTS SEQ ID NO: 73 | WVQQAPGAGLDWMGW SEQ ID NO: 74 | RVTLTADTSTSTAYMELSSLRAEDAAVYYCAS SEQ ID NO: 78 | LWGQGTLVTV SEQ ID NO: 79 |

7. H103 Heavy Chain Variable Domain Genus

A canine heavy chain variable domain polypeptide comprising the sequence:

Fr¹-CDR¹-Fr²-CDR²-Fr³-CDR³-Fr⁴ wherein

Fr¹ is $X^1 X^2 X^3 X^4 X^5 X^6 X^7 X^8 X^9 X^{10} X^{11} X^{12} X^{13} X^{14} X^{15} X^{16} X^{17} X^{18} X^{19} X^{20} X^{21} X^{22} X^{23} X^{24} X^{25}$ (SEQ ID NO: 81)

Fr² is $X^{26} X^{27} X^{28} X^{29} X^{30} X^{31} X^{32} X^{33} X^{34} X^{35} X^{36} X^{37} X^{38} X^{39}$ (SEQ ID NO: 82);

Fr³ is $X^{40} X^{41} X^{42} X^{43} X^{44} X^{45} X^{46} X^{47} X^{48} X^{49} X^{50} X^{51} X^{52} X^{53} X^{54} X^{55} X^{56} X^{57} X^{58} X^{59} X^{60} X^{61} X^{62} X^{63} X^{64} X^{65} X^{66} X^{67} X^{68} X^{69}$ (SEQ ID NO: 83);

Fr⁴ is $X^{70} X^{71} X^{72} X^{73} X^{74} X^{75} X^{76} X^{77} X^{78} X^{79}$ (SEQ ID NO: 84);

$X^1$ is E, $X^2$ is V or L, $X^3$ is I or T, $X^4$ is L, $X^5$ is Q, $X^6$ is E, $X^7$ is S or A, $X^8$ is G, $X^9$ is P, $X^{10}$ is G, $X^{11}$ is L, $X^{12}$ is V, $X^{13}$ is K, $X^{14}$ is P, $X^{15}$ is S, $X^{16}$ is Q or E, $X^{17}$ is T, $X^{18}$ is L, $X^{19}$ is S, $X^{20}$ is L

$X^{21}$ is T, $X^{22}$ is C, $X^{23}$ is T or L, $X^{24}$ is X or V, $X^{25}$ is S, $X^{26}$ is W, $X^{27}$ is I, $X^{28}$ is R, $X^{29}$ is Q or R, $X^{30}$ is R, $X^{31}$ is P or G, $X^{32}$ is D G, $X^{33}$ is R or E, $X^{34}$ is G, $X^{35}$ is L, $X^{36}$ is E, $X^{37}$ is W, $X^{38}$ is M, $X^{39}$ is G, $X^{40}$ is S, $X^{41}$ is I, $X^{42}$ is T, $X^{43}$ is A or T, $X^{44}$ is D, $X^{45}$ is G or T, $X^{46}$ is T or A, $X^{47}$ is K or T, $X^{48}$ is N, $X^{49}$ is H or Q, $X^{50}$ is L or F, $X^{51}$ is S, $X^{52}$ is L, $X^{53}$ is Q, $X^{54}$ is L, $X^{55}$ is T, or F, $X^{56}$ is S, $X^{57}$ is T, $X^{58}$ is T, $X^{59}$ is T, $X^{60}$ is E, or V, $X^{61}$ is D, $X^{62}$ is T, $X^{63}$ is A, $X^{64}$ is V, $X^{65}$ is Y, $X^{66}$ is Y or F, $X^{67}$ is C, $X^{68}$ is T or I, $X^{69}$ is R, $X^{70}$ is V or F, $X^{71}$ is W, $X^{72}$ is G, $X^{73}$ is Q, $X^{74}$ is G, $X^{75}$ is T, $X^{76}$ is L, $X^{77}$ is V, $X^{78}$ is T, $X^{79}$ is V, and

8. H103 Heavy Chain Variable Domain Sub-genus

In another embodiment, the invention comprises a canine heavy chain variable domain polypeptide according to paragraph [0028] comprising the sequence:

Fr¹-CDR¹-Fr²-CDR²-Fr³-CDR³-Fr⁴ wherein

Fr¹ is EVILQESGPGLVKPSQTLSLTCTXS (SEQ ID NO: 85) or ELTLQEAGPGLVKPSETLSLTCLVS (SEQ ID NO: 86);

Fr² is WIRQRPDRGLEWMG (SEQ ID NO: 87) or WIRRRPGGELEWMG (SEQ ID NO: 88);

Fr³ is SITADGTKNHLSLQLTSTTTEDTAVYYCTR (SEQ ID NO: 89) or SITTDTATNQFFLQLTSVTTEDTAVYFCIR (SEQ ID NO: 90); and Fr⁴ is VWGQGTLVTV (SEQ ID NO: 91) or FWGQGTLVTV (SEQ ID NO: 92).

9. H103 Heavy Chain Variable Domain Species

In another embodiment, the invention comprises a canine heavy chain variable domain polypeptide according to paragraph [0028] comprising the sequence:

Fr¹-CDR¹-Fr²-CDR²-Fr³-CDR³-Fr⁴ wherein

| # | Fr¹ | Fr² | Fr³ | Fr⁴ |
|---|---|---|---|---|
| H637 | EVILQESGPGLVKPSQTLSLTCTXS SEQ ID NO: 85 | WIRQRPDRGLEWMG SEQ ID NO: 87 | SITADGTKNHLSLQLTSTTTEDTAVYYCTR SEQ ID NO: 89 | VWGQGTLVTV SEQ ID NO: 91 |

-continued

| # | Fr¹ | Fr² | Fr³ | Fr⁴ |
|---|---|---|---|---|
| H103 | ELTLQEAGPGLVKPSETLSLTCLVS SEQ ID NO: 86 | WIRRRPGGELEWMG SEQ ID NO: 88 | SITTDTATNQFFLQLTSVTTEDTAVYFCIR SEQ ID NO: 90 | FWGQGTLVTV SEQ ID NO: 92 |

10. Other Heavy Chain Variable Domains

In another embodiment, the invention comprises the sequence:

Fr¹-CDR¹-Fr²-CDR²-Fr³-CDR³-Fr⁴ wherein Fr¹, Fr², Fr³, and Fr⁴ are framework regions selected from the framework regions of the heavy chain variable sequences displayed in Table $N_{Other\ H}$. The framework sequence of the polypeptides in Table $N_{Other\ H}$ are readily and routinely determinable by those of ordinary skill in the art as those sequences that align with corresponding framework sequences of any of the known human variable domain sequences using any of the many accepted and widely available sequence alignment programs.

11. Group 2 λ Light Chain Variable Domain Genus

The chimeric canine light chain variable domain polypeptides according to the invention are compounds comprising the sequence:

Fr¹- -CDR¹- -Fr²-CDR²- -Fr³-CDR³- -Fr⁴ wherein

Fr¹ is $Y^1\ Y^2\ Y^3\ Y^4\ Y^5\ Y^6\ Y^7\ Y^8\ Y^9\ Y^{10}\ Y^{11}\ Y^{12}\ Y^{13}\ Y^{14}\ Y^{15}\ Y^{16}\ Y^{17}\ Y^{18}\ Y^{19}\ Y^{20}\ Y^{21}\ Y^{22}\ Y^{23}\ Y^{24}\ Y^{25}$ (SEQ ID NO: 1136);

Fr² is $Y^{26}\ Y^{27}\ Y^{28}\ Y^{29}\ Y^{30}\ Y^{31}\ Y^{32}\ Y^{33}\ Y^{34}\ Y^{35}\ Y^{36}\ Y^{37}\ Y^{38}\ Y^{39}\ Y^{40}$ (SEQ ID NO: 1137);

Fr³ is $Y^{41}\ Y^{42}\ Y^{43}\ Y^{44}\ Y^{45}\ Y^{46}\ Y^{47}\ Y^{48}\ Y^{49}\ Y^{50}\ Y^{51}\ Y^{52}\ Y^{53}\ Y^{54}\ Y^{55}\ Y^{56}\ Y^{57}\ Y^{58}\ Y^{59}\ Y^{60}\ Y^{61}\ Y^{62}\ Y^{63}\ Y^{64}\ Y^{65}\ Y^{66}\ Y^{67}\ Y^{68}\ Y^{69}\ Y^{70}\ Y^{71}\ Y^{72}$ (SEQ ID NO: 1138);

Fr⁴ is $Y^{73}\ Y^{74}\ Y^{75}\ Y^{76}\ Y^{77}\ Y^{78}\ Y^{79}\ Y^{80}\ Y^{81}\ Y^{82}\ Y^{83}\ Y^{84}\ Y^{85}\ Y^{86}$ (SEQ ID NO: 1);

| | | | |
|---|---|---|---|
| $Y^1$ is S, or - | $Y^2$ is W or -, | $Y^3$ is A or -, | $Y^4$ is Q or -, |
| $Y^5$ is S A, or - | $Y^6$ is V, L, A, N, C, M, or - | $Y^7$ is L, V, or - | $Y^8$ is T, N, or - |
| $Y^9$ is Q or -, | $Y^{10}$ is P, A, S, or - | $Y^{11}$ is A, P, T, S, or - | $Y^{12}$ is S,A, or - |
| $Y^{13}$ is V, M, or - | $Y^{14}$ is S, T or - | $Y^{15}$ is G, or - | $Y^{16}$ is S, A, P, F, or - |
| $Y^{17}$ is L, or - | $Y^{18}$ is G or -, | $Y^{19}$ is Q or -, | $Y^{20}$ is R, K, T, S, E, or - |
| $Y^{21}$ is V, I, or - | $Y^{22}$ is T, S, or - | $Y^{23}$ is I, L, V, or - | $Y^{24}$ is S, or - |
| $Y^{25}$ is C, or -, | $Y^{26}$ is W, | $Y^{27}$ is Y, F, H, or C, | $Y^{28}$ is Q or R, |
| $Y^{29}$ is Q, E, N, L, or H, | $Y^{30}$ is L, F, V, I, or Y, | $Y^{31}$ is P, | $Y^{32}$ is G, or E, |
| $Y^{33}$ is T, K, R, A, I, or E, | $Y^{34}$ is G, S, A, or R, | $Y^{35}$ is P, | $Y^{36}$ is R, K, T, or E, |
| $Y^{37}$ is T, L, S, N, or I, | $Y^{38}$ is L, V, I, or F, | $Y^{39}$ is I, L, V, or M, | $Y^{40}$ is Y, F, N, D, H, or S |
| $Y^{41}$ is G, R, or E, | $Y^{42}$ is V, I, or A, | $Y^{43}$ is P or S, | $Y^{44}$ is D, A, N, or E, |
| $Y^{45}$ is R, | $Y^{46}$ is F, | $Y^{47}$ is S, | $Y^{48}$ is G, A, or V, |
| $Y^{49}$ is S, | $Y^{50}$ is R, K, T, N, S, I, or E, | $Y^{51}$ is S, | $Y^{52}$ is G, D, or R, |
| $Y^{53}$ is S, N, A, R, I, T, or F, | $Y^{54}$ is T, S, or A, | $Y^{55}$ is A, G, or S, | $Y^{56}$ is T, S, A, or I, |
| $Y^{57}$ is L, | $Y^{58}$ is T, | $Y^{59}$ is I, | $Y^{60}$ is S, T, or A, |
| $Y^{61}$ is G, V, or E, | $Y^{62}$ is L, | $Y^{63}$ is Q, R, or L, | $Y^{64}$ is A, or P, |
| $Y^{65}$ is E or D, | $Y^{66}$ is D, | $Y^{67}$ is E, | $Y^{68}$ is A or G, |
| $Y^{69}$ is D, E, I, or A, | $Y^{70}$ is Y or -, | $Y^{71}$ is Y, F, or H, | $Y^{72}$ is C |
| $Y^{73}$ is F | $Y^{74}$ is G or -, | $Y^{75}$ is G, S, P, or -, | $Y^{76}$ is G or -, |

$Y^{77}$ is T, A, or -, $\quad Y^{78}$ is H, Q, L, Y, R, or -, $\quad Y^{79}$ is L or -, $\quad Y^{80}$ is T, A, or -, $Y^{81}$ is V or -, $\quad Y^{82}$ is L or -, $\quad Y^{83}$ is G, S, or -, $\quad Y^{84}$ is Q or -, $Y^{85}$ is P, and $\quad Y^{86}$ is K, or R provided that when $Y^k$ for $k \leq 40$ is - -, $Y^l$ for l<k is - -, and when $Y^n$ for $n \geq 69$ is - -, $Y^m$ for m>n is - -.

12. Group 2 λ Light Chain Variable Domain Subgenus

Preferably, the canine λ light chain variable domain according to the invention is a compound comprising the sequence:

$$Fr^1\text{-}CDR^1\text{-}Fr^2\text{-}CDR^2\text{-}Fr^3\text{-}CDR^3\text{-}Fr^4$$

wherein $Fr^1$ is

| | | |
|---|---|---|
| SWAQSLLTQPASVSGSLGQRVTLSC SEQ ID NO: 93 | SWAQSVLTQPASVSGSLGQTVTISC SEQ ID NO: 94 | CLTQPASVSGSLGQRVTISC SEQ ID NO: 95 |
| SWAQSVLTQPASVSGSLGQRITISC SEQ ID NO: 96 | SWAQSALTQPASVTGSLGQRVTISC SEQ ID NO: 97 | SWAQSVLTQPASVSGSLGQRVTISC SEQ ID NO: 98 |
| SWAQSLLTQPASVSGSLGQRVTISC SEQ ID NO: 99 | SWAQSVLTQPASVSGSLGQKVTISC SEQ ID NO: 100 | SWAQSVLTQPASVTGSLGQRVTISC SEQ ID NO: 101 |
| SWAQAVLNQPASVSGALGQKVTISC SEQ ID NO: 102 | SWAQSILTQPASVSGSLGQKVTISC SEQ ID NO: 103 | SWAQSVLTQPASMSGSLGQKVTISC SEQ ID NO: 104 |
| SWAQSALTQPTSVSGSLGQRVSISC SEQ ID NO: 105 | SWAQSVLTQPASVSGFLGQRVTISC SEQ ID NO: 106 | SWAQSVLTQPASVSGSLGQRVTVSC SEQ ID NO: 107 |
| SWAQSLLTQPASVSGSLGQKVTISC SEQ ID NO: 108 | SWAQSMLTQPASVSGSLGQTVTISC SEQ ID NO: 109 | SWAQSVLTQPTSVSGSLGQRVTISC SEQ ID NO: 110 |
| SWAQSVLTQPASVSGPLGQKVTISC SEQ ID NO: 111 | SWAQSMLTQPASVSGSLGQKVTISC SEQ ID NO: 112 | SWAQSVXTQPASVSGSLGQRVTTSC SEQ ID NO: 113 |
| SWAQSVLTQPASVSGSLGQRITVSC SEQ ID NO: 114 | SWAQSVLTQPASVSGSLGQSVTISC SEQ ID NO: 115 | SWAQSVLTQPASVSGPLGQRVTISC SEQ ID NO: 116 |
| SLGQRVTISC SEQ ID NO: 117 | VTISC SEQ ID NO: 118 | SWAQSELTQSAAVSGSLGQEVTISC SEQ ID NO: 119 |
| SWAQSIVTQAASVSGSLGQRITISC SEQ ID NO: 120 | SWAQSILTQPSSVSGSLGQRVTISC SEQ ID NO: 121; | or- |

$Fr^2$ is

| | | | |
|---|---|---|---|
| WYQHLPGTGPRTLIY SEQ ID NO: 122 | WYQQIPGTGPRTVIY SEQ ID NO: 123 | WYQQFPGAGPRTLIY SEQ ID NO: 124 | WYQQLPGRSPKLLVY SEQ ID NO: 125 |
| WYQQLPGRGPRTVIY SEQ ID NO: 126 | WFQQVPGTGPRTVIY SEQ ID NO: 127 | WYQQLPGTRPRTLIY SEQ ID NO: 128 | WFQQLPGKGPRTVIY SEQ ID NO: 129 |
| WFQELPGTGPKILIY SEQ ID NO: 130 | WYQQLPGTGPRTLIY SEQ ID NO: 131 | WFQQFPGKGPKTVIY SEQ ID NO: 132 | WYQQLPGTGPKTLIY SEQ ID NO: 133 |
| WYQQLPGKAPKLLVD SEQ ID NO: 134 | WYQQLPGIGPKTVIY SEQ ID NO: 135 | WFQQFPGEGPRTVIY SEQ ID NO: 136 | WYRQLPGTGPTTLIY SEQ ID NO: 137 |
| WYQQFPGTGPRILIY SEQ ID NO: 138 | WYQQLPGKAPKLLLN SEQ ID NO: 139 | WLQQLPGTGPKTVIY SEQ ID NO: 140 | WFQQLPGTGPRTVIY SEQ ID NO: 141 |
| WHQQVPETGPRNIIY SEQ ID NO: 142 | WYQQLPGRGPTTLLY SEQ ID NO: 143 | WYQQLPGIGPRTVIY SEQ ID NO: 144 | WYQQVPGTRPRTLIY SEQ ID NO: 145 |
| WYQQFPGRGPRSVIY SEQ ID NO: 146 | WYQQLPGKAPKLLVY SEQ ID NO: 147 | WYQNLPGKGPKTVIF SEQ ID NO: 148 | WYQQIPGTGPRTLIY SEQ ID NO: 149 |
| WYQQYPGTGPKTLIY SEQ ID NO: 150 | WYQQVPGTGPRTLIH SEQ ID NO: 151 | WYRQFPGKAPELLIY SEQ ID NO: 152 | WYQQLPGIGPRTVIS SEQ ID NO: 153 |
| WFQQFPGTGPRTVIY SEQ ID NO: 154 | WHQQLPGTGPRTLIY SEQ ID NO: 155 | WYQQLPETGPRTLIY SEQ ID NO: 156 | WYQQVPGTGPRTLIY SEQ ID NO: 157 |

-continued

| | | | |
|---|---|---|---|
| WYQQVPGIGPRTVMY | WFQHLPGTRPKSLIY | WFQQLPGTGPRTVIC | WYQLVPGTGPRTLIY |
| SEQ ID NO: 158 | SEQ ID NO: 159 | SEQ ID NO: 160 | SEQ ID NO: 161 |
| | | | |
| WYQQLPGRGPRTVIH | WCQQLPGKAPKLLVD | WYQQFPGTGPRTLIY | or |
| SEQ ID NO: 162 | SEQ ID NO: 163 | SEQ ID NO: 164 | |

WYRQLPGEAPKLLLY
SEQ ID NO: 165;

Fr³ is

| | |
|---|---|
| GVPDRFSGSRSGITATLTISGLQAEDEADYYC | GVPERFSGPRSGITSTLTISGLRAEDEGDYYC |
| SEQ ID NO: 166 | SEQ ID NO: 167 |
| | |
| GVPDRFSGSTSGSTATLTISGLRAEDEADYYC | GVPDRFSGSKSDNSATLTFTGLQAEDEADYYC |
| SEQ ID NO: 168 | SEQ ID NO: 169 |
| | |
| GVPDRFSGSKSGSTATLTISGLQAEDEADYYC | GVPDRFSGSRSGSTATLTISGLQAEDEAEYYC |
| SEQ ID NO: 170 | SEQ ID NO: 171 |
| | |
| GVPDRFSGSKSRSTATLTIXGLQAEDEADYXC | GVPDRFSGSTSGNTATLTISGLQPEDETDYYC |
| SEQ ID NO: 172 | SEQ ID NO: 173 |
| | |
| GVPDRFSGSTSGSTATLTISGLQAEDEADYYC | GVPDRFSGSRSGTTATLTISGLQAEDEADYYC |
| SEQ ID NO: 174 | SEQ ID NO: 175 |
| | |
| GVPDRFSGSRSGSTATLTISGLQPEDEADYYC | GVPDRFSGSSSGNSGTLTITGLQAEDEADYYC |
| SEQ ID NO: 176 | SEQ ID NO: 177 |
| | |
| GVPDRFSGSKSGNSATLTISGLQPEDEAEYYC | GVPDRFSGSKSGSTATLTISELQAEDEADYYC |
| SEQ ID NO: 178 | SEQ ID NO: 179 |
| | |
| GVPNRFSGSRSGSTATLTISGLQADDEADYYC | GVPDRFSGSRSGYTAALTISGLQAEDEADYYC |
| SEQ ID NO: 180 | SEQ ID NO: 181 |
| | |
| GVPDRFSGSNSGASATLTITGLQAEDEADYYC | GVPDRFSGSRSGSTATLTISGLQAEDEADYYC |
| SEQ ID NO: 182 | SEQ ID NO: 183 |
| | |
| GVPDRFSGSRSGSTATLTISGLLAEDDADYYC | GVPDRFSGSKSGSTATLTISVLQAEDEADYYC |
| SEQ ID NO: 184 | SEQ ID NO: 185 |
| | |
| GVPDRFSGSRSGRTATLTISGLQAEDEADYYC | GISDRFSGSKSGNSASLTISGLQAEDEADYFC |
| SEQ ID NO: 186 | SEQ ID NO: 187 |
| | |
| GVPDRFSVSKSGSSATLTISGLQAEDEAEYYC | GVPDRFSGSNSGNSATLTITGLQAEDEADYYC |
| SEQ ID NO: 188 | SEQ ID NO: 189 |
| | |
| GVPDRFSGSRSGSSATLTISGLQAEDEADYYC | GVPDRFSASRSGNSATLTISGLQAEDEADYYC |
| SEQ ID NO: 190 | SEQ ID NO: 191 |
| | |
| GVPDRFSASASGSTATLTISGLQAEDEADYYC | GVPGRFSGSISGNSATLTITGLQAEDEADYHC |
| SEQ ID NO: 192 | SEQ ID NO: 193 |
| | |
| GVPDRESGSKSGSSATLTISGLQAEDEAEYYC | GVPDRFSGSRSGSTAILTISGLQAEDEAEYYC |
| SEQ ID NO: 194 | SEQ ID NO: 195 |
| | |
| GVPDRFSGSKSGSAATLTISGLQAEDEADYYC | GVPDRFSGSRSGSTATLTISGLQADDEADYYC |
| SEQ ID NO: 196 | SEQ ID NO: 197 |
| | |
| GVPERFSGSKSGSTAALTISGLQAEDEADYYC | GAPDRFSGSRSGSTATLTISGLQAEDEADYYC |
| SEQ ID NO: 198 | SEQ ID NO: 199 |

-continued

| | |
|---|---|
| GVPDRFSSSRSGSSATLTIAGLQAEDEAAYYC SEQ ID NO: 200 | GVPDRFSGSKSGSTATLTISGLQAEDEAIYYC SEQ ID NO: 201 |
| RVPDRFSGSESGNSATLTITGLQAEDEADYYC SEQ ID NO: 202 | GVPDRFSGSRSGRTATLTISGLQAEDEAEYYC SEQ ID NO: 203 |
| GVPERFSGSRSGSTATLTISGLQAEDEAEYYC SEQ ID NO: 204 | GVPDRFSGSKSGTTAILTISGLQADDEADYFC SEQ ID NO: 205 |
| GVPDRFSGSKSGSTATLTISGLQADDEADYYC SEQ ID NO: 206 | GIPDRFSGSRSDNSGILTISGLQAEDEADYHC SEQ ID NO: 207 |
| GVPARFSGSRSGNTATLTISGLLAEDEADYYC SEQ ID NO: 208 | EVSDRFSGSRSGNTATLTISGLXAEDEADYYC SEQ ID NO: 209 |
| GVPDRFSGSNSGFSATLTITGLQADDEADYYC SEQ ID NO: 210 | or GVPDRFSGSRSGTTGTLTISGLQAEDEADYYC SEQ ID NO: 211; |

$Fr^4$ is

| | | | |
|---|---|---|---|
| FGGGTHLTVLGQPK SEQ ID NO: 212 | FGGGTHLAVLGQPK SEQ ID NO: 213 | FGSGTQLTVLGQPK SEQ ID NO: 214 | F |
| FGGGTHLTVLSQPK SEQ ID NO: 215 | FGGGTLLTVLGQPK SEQ ID NO: 216 | FGGGTQLTVLGQPKA SEQ ID NO: 217 | FGGGTH SEQ ID NO: 218 |
| FGGGTHLTVLGQP SEQ ID NO: 219 | FGGGTHLTVLGQPE SEQ ID NO: 220 | FGSGTQLTVLGQP SEQ ID NO: 221 | FGGGTHL SEQ ID NO: 222 |
| FGSGTQLTVLSQPKA SEQ ID NO: 223 | FGGGTYLTVVGQPKA SEQ ID NO: 224 | FGGGTHLTVLGQ SEQ ID NO: 225 | FGGGTHLTVLGQPRA SEQ ID NO: 226 |
| FGSGTHLTALGQPKA SEQ ID NO: 227 | FGSGTQLTVLGQPKA SEQ ID NO: 228 | FGGGTHLTVLGQPKA SEQ ID NO: 229 | FGGGTHLTVLSQPKA SEQ ID NO: 230 |
| FGGGAHLTVLGQPKA SEQ ID NO: 231 | FGPGTQLTVLGQPKA SEQ ID NO: 232 | FGGGTRLTVLGQPKA SEQ ID NO: 233 | or FGGGTHLTVLGQPK SEQ ID NO: 212. |

13. Group 2 Light Chain Variable Domain Species

Preferably, the canine λ light chain variable domain according to the invention is a compound comprising the sequence:

$Fr^1$-$CDR^1$-$Fr^2$-$CDR^2$-$Fr^3$-$CDR^3$-$Fr^4$ wherein $Fr^1$, $Fr^2$, $Fr^3$, and $Fr^4$ are selected from the following combinations:

| # | $Fr^1$ | $Fr^2$ | $Fr^3$ | $Fr^4$ |
|---|---|---|---|---|
| λ101 | SWAQSLLTQPASVSGSLGQRVTLSC SEQ ID NO: 93 | WYQHLPGTGPRTLIY SEQ ID NO: 122 | GVPDRFSGSRSGITATLTISGLQAEDEADYYC SEQ ID NO: 166 | FGGGTHLTVLGQPK SEQ ID NO: 212 |
| λ109 | SWAQSVLTQPASVSGSLGQTVTISC SEQ ID NO: 94 | WYQQIPGTGPRTVIY SEQ ID NO: 123 | GVPERFSGPRSGITSTLTISGLRAEDEGDYYC SEQ ID NO: 167 | FGGGTHLTVLGQPK SEQ ID NO: 212 |
| λ111 | CLTQPASVSGSLGQRVTISC SEQ ID NO: 95 | WYQQFPGAGPRTLIY SEQ ID NO: 124 | GVPDRFSGSTSGSTATLTISGLRAEDEADYYC SEQ ID NO: 168 | FGGGTHLAVLGQPK SEQ ID NO: 213 |
| λ120 | — | WYQQLPGRSPKLLVY SEQ ID NO: 125 | GVPDRFSGSKSDNSATLTFTGLQAEDEADYYC SEQ ID NO: 169 | FGGGTHLTVLGQPK SEQ ID NO: 212 |
| λ127 | SWAQSVLTQPASVSGSLGQRITISC SEQ ID NO: 96 | WYQQLPGRGPRTVIY SEQ ID NO: 126 | GVPDRFSGSKSGSTATLTISGLQAEDEADYYC SEQ ID NO: 170 | FGSGTQLTVLGQPK SEQ ID NO: 214 |
| λ201 | SWAQSALTQPASVTGSLGQRVTISC SEQ ID NO: 97 | WFQQVPGTGPRTVIY SEQ ID NO: 127 | GVPDRFSGSRSGSTATLTISGLQAEDEAEYYC SEQ ID NO: 171 | FGGGTHLTVLGQPK SEQ ID NO: 212 |
| λ203 | SWAQSVLTQPASVSGSLGQRVTISC SEQ ID NO: 98 | WYQQLPGTRPRTLIY SEQ ID NO: 128 | GVPDRFSGSKSGSTATLTISGLQAEDEADYYC SEQ ID NO: 170 | FGGGTHLTVLGQPK SEQ ID NO: 212 |
| λ204 | SWAQSVLTQPASVSGSLGQRVTISC SEQ ID NO: 98 | WFQQLPGKGPRTVIY SEQ ID NO: 129 | GVPDRFSGSKSRSTATLTIXGLQAEDEADYXC SEQ ID NO: 172 | F |
| λ207 | SWAQSLLTQPASVSGSLGQRVTISC SEQ ID NO: 99 | WFQELPGTGPKILIY SEQ ID NO: 130 | GVPDRFSGSTSGNTATLTISGLQPEDETDYYC SEQ ID NO: 173 | FGGGTHLTVLGQPK SEQ ID NO: 212 |

-continued

| # | Fr¹ | Fr² | Fr³ | Fr⁴ |
|---|---|---|---|---|
| λ215 | SWAQSVLTQPASVSGSLGQKVTISC<br>SEQ ID NO:100 | WYQQLPGTGPRTLIY<br>SEQ ID NO: 131 | GVPDRFSGSTSGSTATLTISGLQAEDEADYYC<br>SEQ ID NO: 174 | FGGGTHLTVLGQPK<br>SEQ ID NO: 212 |
| λ220 | SWAQSVLTQPASVTGSLGQRVTISC<br>SEQ ID NO: 101 | WFQQFPGKGPKTVIY<br>SEQ ID NO: 132 | GVPDRFSGSRSGTTATLTISGLQAEDEADYYC<br>SEQ ID NO: 175 | FGGGTHLTVLGQPK<br>SEQ ID NO: 212 |
| λ225 | SWAQSVLTQPASVSGSLGQRVTISC<br>SEQ ID NO: 98 | WYQQLPGTGPKTLIY<br>SEQ ID NO: 133 | GVPDRFSGSRSGSTATLTISGLQPEDEADYYC<br>SEQ ID NO: 176 | FGGGTHLTVLSQPK<br>SEQ ID NO: 215 |
| λ227 | SWAQAVLNQPASVSGALGQKVTISC<br>SEQ ID NO: 102 | WYQQLPGKAPKLLVD<br>SEQ ID NO: 134 | GVPDRFSGSSSGNSGTLTITGLQAEDEADYYC<br>SEQ ID NO: 177 | FGGGTHLTVLGQPK<br>SEQ ID NO: 212 |
| λ228 | SWAQSILTQPASVSGSLGQKVTISC<br>SEQ ID NO: 103 | WYQQLPGIGPKTVIY<br>SEQ ID NO: 135 | GVPDRFSGSKSGNSATLTISGLQPEDEAEYYC<br>SEQ ID NO: 178 | FGGGTLLTVLGQPK<br>SEQ ID NO: 216 |
| λ302 | SWAQSVLTQPASMSGSLGQKVTISC<br>SEQ ID NO: 104 | WFQQFPGEGPRTVIY<br>SEQ ID NO: 136 | GVPDRFSGSKSGSTATLTISELQAEDEADYYC<br>SEQ ID NO: 179 | FGGGTH<br>SEQ ID NO: 218 |
| λ306 | SWAQSVLTQPASVSGSLGQRVTISC<br>SEQ ID NO: 98 | WYRQLPGTGPTTLIY<br>SEQ ID NO: 137 | GVPNRFSGSRSGSTATLTISGLQADDEADYYC<br>SEQ ID NO: 180 | FGGGTHLTVLGQP<br>SEQ ID NO: 219 |
| λ310 | SWAQSVLTQPASVSGSLGQRVTISC<br>SEQ ID NO: 98 | WYQQFPGTGPRILIY<br>SEQ ID NO: 138 | GVPDRFSGSRSGYTAALTISGLQAEDEADYYC<br>SEQ ID NO: 181 | FGGGTHLTVLGQPE<br>SEQ ID NO: 220 |
| λ320 | SWAQSALTQPTSVSGSLGQRVSISC<br>SEQ ID NO: 105 | WYQQLPGKAPKLLLN<br>SEQ ID NO: 139 | GVPDRFSGSNSGASATLTITGLQAEDEADYYC<br>SEQ ID NO: 182 | FGSGTQLTVLGQP<br>SEQ ID NO: 221 |
| λ325 | SWAQSVLTQPASVSGSLGQRVTISC<br>SEQ ID NO: 98 | WLQQLPGTGPKTVIY<br>SEQ ID NO: 140 | GVPDRFSGSRSGSTATLTISGLQAEDEADYYC<br>SEQ ID NO: 183 | FGGGTHLTVLGQPK<br>SEQ ID NO: 212 |
| λ326 | SWAQSVLTQPASVTGSLGQRVTISC<br>SEQ ID NO: 101 | WFQQLPGTGPRTVIY<br>SEQ ID NO: 141 | GVPDRFSGSRSGSTATLTISGLLAEDDADYYC<br>SEQ ID NO: 184 | FGGGTHLTVLGQ<br>SEQ IS NO: 225 |
| λ129 | SWAQSVLTQPASVSGFLGQRVTISC<br>SEQ ID NO: 106 | WHQQVPETGPRNIIY<br>SEQ ID NO: 142 | GVPDRFSGSKSGSTATLTISVLQAEDEADYYC<br>SEQ ID NO: 185 | FGGGTHLTVLGQPRA<br>SEQ ID NO: 226 |
| λ130 | SWAQSVLTQPASVSGSLGQRVTVSC<br>SEQ ID NO: 107 | WYQQLPGRGPTTLLY<br>SEQ ID NO: 143 | GVPDRFSGSRSGRTATLTISGLQAEDEADYYC<br>SEQ ID NO: 186 | FGSGTHLTALGQPKA<br>SEQ ID NO: 227 |
| λ134 | SWAQSLLTQPASVSGSLGQKVTISC<br>SEQ ID NO: 108 | WYQQLPGIGPRTVIY<br>SEQ ID NO: 144 | GISDRFSGSKSGNSASLTISGLQAEDEADYFC<br>SEQ ID NO: 187 | FGSGTQLTVLGQPKA<br>SEQ ID NO: 228 |
| λ213 | SWAQSVLTQPASVSGSLGQRITISC<br>SEQ ID NO: 96 | WYQQLPGRGPRTVIY<br>SEQ ID NO: 126 | GVPDRFSGSKSGSTATLTISGLQAEDEADYYC<br>SEQ ID NO: 170 | FGGGTHLTVLGQPKA<br>SEQ ID NO: 229 |
| λ214 | SWAQSVLTQPASVSGSLGQRVTISC<br>SEQ ID NO: 98 | WYQQVPGTRPRTLIY<br>SEQ ID NO: 145 | GVPDRFSGSKSGSTATLTISGLQAEDEADYYC<br>SEQ ID NO: 170 | FGGGTHLTVLSQPKA<br>SEQ ID NO: 230 |
| λ216A | SWAQSMLTQPASVSGSLGQTVTISC<br>SEQ ID NO: 109 | WYQQFPGRGPRSVIY<br>SEQ ID NO: 146 | GVPDRFSVSKSGSSATLTISGLQAEDEAEYYC<br>SEQ ID NO: 188 | FGSGTQLTVLSQPKA<br>SEQ ID NO: 223 |
| L204-79 | SWAQSVLTQPTSVSGSLGQRVTISC<br>SEQ ID NO: 110 | WYQQLPGKAPKLLVY<br>SEQ ID NO: 147 | GVPDRFSGSNSGNSATLTITGLQAEDEADYYC<br>SEQ ID NO: 189 | FGSGTQLTVLGQPKA<br>SEQ ID NO: 228 |
| L205-79 | SWAQSILTQPASVSGSLGQKVTISC<br>SEQ ID NO: 103 | WYQNLPGKGPKTVIF<br>SEQ ID NO: 148 | GVPDRFSGSRSGSSATLTISGLQAEDEADYYC<br>SEQ ID NO: 190 | FGGGTHLTVLGQ<br>SEQ ID NO: 225 |
| L206-79 | SWAQSVLTQPASVSGPLGQKVTISC<br>SEQ ID NO: 111 | WYQQIPGTGPRTLIY<br>SEQ ID NO: 149 | GVPDRFSGSRSGSTATLTISGLQAEDEADYYC<br>SEQ ID NO: 183 | FGGGTHLTVLGQPKA<br>SEQ ID NO: 229 |
| L207-79 | SWAQSVLTQPASVSGSLGQRVTISC<br>SEQ ID NO: 98 | WYQQYPGTGPKTLIY<br>SEQ ID NO: 150 | GVPDRFSASRSGNSATLTISGLQAEDEADYYC<br>SEQ ID NO: 191 | FGGGTYLTVVGQPKA<br>SEQ ID NO: 224 |
| L210-79 | SWAQSLLTQPASVSGSLGQRVTISC<br>SEQ ID NO: 108 | WYQQVPGTGPRTLIH<br>SEQ ID NO: 151 | GVPDRFSASASGSTATLTISGLQAEDEADYYC<br>SEQ ID NO: 192 | FGGGTHLTVLGQPKA<br>SEQ ID NO: 229 |
| L215-79 | SWAQSVLTQPTSVSGSLGQRVTISC<br>SEQ ID NO: 110 | WYRQFPGKAPELLIY<br>SEQ ID NO: 152 | GVPGRFSGSISGNSATLTITGLQAEDEADYHC<br>SEQ ID NO: 193 | FGGGTHLTVLGQPKA<br>SEQ ID NO: 229 |
| L216-79 | SWAQSMLTQPASVSGSLGQKVTISC<br>SEQ ID NO: 112 | WYQQLPGIGPRTVIS<br>SEQ ID NO: 153 | GVPDRFSGSKSGSSATLTISGLQAEDEAEYYC<br>SEQ ID NO: 194 | FGGGTHLTVLGQP<br>SEQ ID NO: 219 |

-continued

| # | Fr$^1$ | Fr$^2$ | Fr$^3$ | Fr$^4$ |
|---|---|---|---|---|
| L217-79 | SWAQSVLTQPASVTGSLGQRVTISC<br>SEQ ID NO: 101 | WFQQFPGTGPRTVIY<br>SEQ ID NO: 154 | GVPDRFSGSRSGSTAILTISGLQAEDEAEYYC<br>SEQ ID NO: 195 | FGGGTHLTVLGQPKA<br>SEQ ID NO: 229 |
| L201-90 | SWAQSVLTQPASVSGSLGQRVTISC<br>SEQ ID NO: 98 | WYQQVPGTRPRTLIY<br>SEQ ID NO: 145 | GVPDRFSGSKSGSTATLTISGLQAEDEADYYC<br>SEQ ID NO: 170 | FGGGTHLTVLSQPKA<br>SEQ ID NO: 230 |
| L217-90 | SWAQSVLTQPASVSGSLGQRVTISC<br>SEQ ID NO: 98 | WYQQVPGTRPRILIY<br>SEQ ID NO: 145 | GVPDRFSGSKSGSTATLTISGLQAEDEADYYC<br>SEQ ID NO: 170 | FGGGTHLTVLSQPKA<br>SEQ ID NO: 230 |
| L242-90 | SWAQSVLTQPASVSGSLGQRVTISC<br>SEQ ID NO: 98 | WYQQVPGTRPRTLIY<br>SEQ ID NO: 145 | GVPDRFSGSKSGSAATLTISGLQAEDEADYYC<br>SEQ ID NO: 196 | FGGGTHLTVLSQPKA<br>SEQ ID NO: 230 |
| L1-706 | SWAQSVXTQPASVSGSLGQRVTTSC<br>SEQ ID NO: 113 | WHQQLPGTGPRTLIY<br>SEQ ID NO: 155 | GVPDRFSGSRSGSTATLTISGLQPEDEADYYC<br>SEQ ID NO: 176 | FGGGTHLTVLGQPKA<br>SEQ ID NO: 229 |
| L1-710 | SWAQSVLTQPASVSGSLGQRITVSC<br>SEQ ID NO: 114 | WYQQLPGRGPRTVIY<br>SEQ ID NO: 126 | GVPDRFSGSRSGTTATLTISGLQAEDEADYYC<br>SEQ ID NO: 175 | FGSGTQLTVLGQPKA<br>SEQ ID NO: 228 |
| L1-714 | SWAQSVLTQPASVSGSLGQRVTISC<br>SEQ ID NO: 98 | WYQQLPETGPRTLIY<br>SEQ ID NO: 156 | GVPDRFSGSRSGSTATLTISGLQADDEADYYC<br>SEQ ID NO: 197 | FGGGTHLTVLGQPKA<br>SEQ ID NO: 229 |
| L1-715 | SWAQSVLTQPASVSGSLGQSVTISC<br>SEQ ID NO: 115 | WYQQVPGTGPRTLIY<br>SEQ ID NO: 157 | GVPERFSGSKSGSTAALTISGLQAEDEADYYC<br>SEQ ID NO: 198 | FGGGTQLTVLGQPKA<br>SEQ ID NO: 217 |
| L1-720 | SWAQSVLTQPASVTGSLGQRVTISC<br>SEQ ID NO: 101 | WFQQLPGTGPRTVIY<br>SEQ ID NO: 141 | GAPDRFSGSRSGSTATLTISGLQAEDEAEYYC<br>SEQ ID NO: 199 | FGGGTHLTVLGQPKA<br>SEQ ID NO: 229 |
| L1-721 | SWAQSMLTQPASVSGSLGQKVTISC<br>SEQ ID NO: 112 | WYQQVPGIGPRTVMY<br>SEQ ID NO: 158 | GVPDRFSSSRSGSSATLTIAGLQAEDEAAYYC<br>SEQ ID NO: 200 | FGGGTHLTVLGQPKA<br>SEQ ID NO: 229 |
| L1-723 | SWAQSVLTQPASVSGPLGQRVTISC<br>SEQ ID NO: 116 | WFQHLPGTRPKSLIY<br>SEQ ID NO: 159 | GVPDRFSGSKSGSTATLTISGLQAEDEAIYYC<br>SEQ ID NO: 201 | FGSGTQLTVLGQPKA<br>SEQ ID NO: 228 |
| L1-731 | SLGQRVTISC<br>SEQ ID NO: 117 | WYQQLPGKAPKLLVD<br>SEQ ID NO: 134 | RVPDRFSGSESGNSATLTITGLQAEDEADYYC<br>SEQ ID NO: 202 | FGSGTQLTVLGQPKA<br>SEQ ID NO: 228 |
| L1-732 | SWAQSVLTQPASVTGSLGQRVTISC<br>SEQ ID NO: 101 | WFQQLPGTGPRTVIY<br>SEQ ID NO: 141 | GVPDRFSGSRSGRTATLTISGLQAEDEAEYYC<br>SEQ ID NO: 203 | FGGGTHLTVLGQPKA<br>SEQ ID NO: 229 |
| L1-733 | SWAQSVLTQPASVTGSLGQRVTISC<br>SEQ ID NO: 101 | WFQQLPGTGPRTVIC<br>SEQ ID NO: 160 | GVPERFSGSRSGSTATLTISGLQAEDEAEYYC<br>SEQ ID NO: 204 | FGGGTHLTVLGQPKA<br>SEQ ID NO: 229 |
| L1-737 | — | WYQQLPGRGPRTVIY<br>SEQ ID NO: 126 | GVPDRFSGSKSGSTATLTISGLQAEDEADYYC<br>SEQ ID NO: 170 | FGGGTHLTVLGQPKA<br>SEQ ID NO: 229 |
| L1-739 | VTISC<br>SEQ ID NO: 118 | WYQLVPGTGPRTLIY<br>SEQ ID NO: 161 | GVPDRFSGSKSGTTAILTISGLQADDEADYFC<br>SEQ ID NO: 205 | FGGGTHLTVLGQPKA<br>SEQ ID NO: 229 |
| L1-742 | SWAQSVLTQPASVSGSLGQRITISC<br>SEQ ID NO: 96 | WYQQLPGRGPRTVIH<br>SEQ ID NO: 162 | GVPDRFSGSKSGSTATLTISGLQADDEADYYC<br>SEQ ID NO: 206 | FGGGAHLTVLGQPKA<br>SEQ ID NO: 231 |
| L1-747 | SWAQAVLNQPASVSGALGQKVTISC<br>SEQ ID NO: 102 | WCQQLPGKAPKLLVD<br>SEQ ID NO: 163 | GIPDRFSGSRSDNSGILTISGLQAEDEADYHC<br>SEQ ID NO: 207 | FGGGTHLTVLGQPKA<br>SEQ ID NO: 229 |
| L1-749 | SWAQSELTQSAAVSGSLGQEVTISC<br>SEQ ID NO: 119 | WYQQFPGTGPRTLIY<br>SEQ ID NO: 164 | GVPARFSGSRSGNTATLTISGLLAEDEADYYC<br>SEQ ID NO: 208 | FGGGTHLTVLGQPKA<br>SEQ ID NO: 229 |
| L1-758 | SWAQSILTQPSSVSGSLGQRVTISC<br>SEQ ID NO: 121 | WYRQLPGEAPKLLLY<br>SEQ ID NO: 165 | GVPDRFSGSNSGFSATLTITGLQADDEADYYC<br>SEQ ID NO: 210 | FGGGTHLTVLGQPKA<br>SEQ ID NO: 229 |
| L1-757 | — | — | GVPDRFSGSRSGSTATLTISGLQAEDEAEYYC<br>SEQ ID NO: 171 | FGGGTHLTVLGQPKA<br>SEQ ID NO: 229 |
| L1-760 | SWAQSVLTQPASVSGSLGQRVTISC<br>SEQ ID NO: 98 | WYQQLPGTGPRTLIY<br>SEQ ID NO: 131 | GVPDRFSGSRSGTTGTLTISGLQAEDEADYYC<br>SEQ ID NO: 211 | FGGGTRLTVLGQPKA<br>SEQ ID NO: 233 |
| or | | | | |
| cnsnss | SWAQSVLTQPASVSGSLGQRVTISC<br>SEQ ID NO: 98 | WYQQLPGTGPRTLIY<br>SEQ ID NO: 131 | GVPDRFSGSRSGSTATLTISGLQAEDEADYYC<br>SEQ ID NO: 183 | FGGGTHLTVLGQPK<br>SEQ ID NO: 212 |

14. Group 1 Light Chain Variable Domain Genus

The chimeric canine group Group 1 light chain variable domain polypeptides according to the invention are compounds comprising the sequence:

$$Fr^1\text{-}CDR^1\text{-}Fr^2\text{-}CDR^2\text{-}Fr^3\text{-}CDR^3\text{-}Fr^4$$

wherein $Fr^1$ is $Z^1\ Z^2\ Z^3\ Z^4\ Z^5\ Z^6\ Z^7\ Z^8\ Z^9\ Z^{10}\ Z^{11}\ Z^{12}\ Z^{13}\ Z^{14}\ Z^{15}\ Z^{16}\ Z^{17}\ Z^{18}\ Z^{19}\ Z^{20}\ Z^{21}\ Z^{22}\ Z^{23}\ Z^{24}\ Z^{25}$ (SEQ ID NO: 234);

$Fr^2$ is $Z^{26}\ Z^{27}\ Z^{28}\ Z^{29}\ Z^{30}\ Z^{31}\ Z^{32}\ Z^{33}\ Z^{34}\ Z^{35}\ Z^{36}\ Z^{37}\ Z^{38}\ Z^{39}\ Z^{40}$ (SEQ ID NO: 235)

$Fr^3$ is $Z^{41}\ Z^{42}\ Z^{43}\ Z^{44}\ Z^{45}\ Z^{46}\ Z^{47}\ Z^{48}\ Z^{49}\ Z^{50}\ Z^{51}\ Z^{11}\ Z^{52}\ Z^{54}\ Z^{55}\ Z^{56}\ Z^{57}\ Z^{58}\ Z^{59}\ Z^{60}\ Z^{61}\ Z^{62}\ Z^{63}\ Z^{64}\ Z^{65}\ Z^{66}\ Z^{67}\ Z^{68}\ Z^{69}\ Z^{70}\ Z^{71}\ Z^{72}$ (SEQ ID NO: 236), and $Fr^4$ is $Z^{73}\ Z^{74}\ Z^{75}\ Z^{76}\ Z^{77}\ Z^{78}\ Z^{79}\ Z^{80}\ Z^{81}\ Z^{82}\ Z^{83}\ Z^{84}\ Z^{85}\ Z^{86}\ Z^{87}$ (SEQ ID NO: 237)

wherein provided that when $Y^a$ for $a \leq 25$ is - -, $Y^b$ for $b<a$ is - -, and when $Y^c$ for $c \geq 94$ is - -, $Y^d$ for $d>c$ is - -.

15. Group 1 Light Chain Variable Domain Subgenus

The chimeric canine group Group 1 light chain variable domain polypeptides according to the invention are compounds comprising the sequence:

$$Fr^1\text{-}CDR^1\text{-}Fr^2\text{-}CDR^2\text{-}Fr^3\text{-}CDR^3\text{-}Fr^4$$

$Z^1$ is A, T, or -, $Z^2$ is D or -, $Z^3$ is S or -, $Z^4$ is Q or -, $Z^5$ is T or -, $Z^6$ is V or -, $Z^7$ is V or -, $Z^8$ is T or -, $Z^9$ is Q or -, $Z^{10}$ is E or -, $Z^{11}$ is P, A, or -, $Z^{12}$ is S, F, or -, $Z^{13}$ is L, V, or -, $Z^{14}$ is S or -, $Z^{15}$ is V or -, $Z^{16}$ is S or -, $Z^{17}$ is P, L, or -, $Z^{18}$ is G or -, $Z^{19}$ is G or -, $Z^{20}$ is T or -, $Z^{21}$ is V, I, or -, $Z^{22}$ is T or -, $Z^{23}$ is L or -, $Z^{24}$ is T or -, $Z^{25}$ is C or -, $Z^{26}$ is W, $Z^{27}$ is Y or S, $Z^{28}$ is Q, $Z^{29}$ is Q or H, $Z^{30}$ is T, $Z^{31}$ is L, Q, or P, $Z^{32}$ G, $Z^{33}$ is R or Q, $Z^{34}$ is A, $Z^{35}$ is P, $Z^{36}$ is R, $Z^{37}$ is T or P, $Z^{38}$ is I, $Z^{39}$ is I or L, $Z^{40}$ is Y or S;

$Z^{41}$ is G, $Z^{42}$ is V, $Z^{43}$ is P, $Z^{44}$ is N, S, D, or R, $Z^{45}$ is R, $Z^{46}$ is F, $Z^{47}$ is S or T, $Z^{48}$ is G or A, $Z^{49}$ is S, $Z^{50}$ is I or V, $Z^{51}$ is S, $Z^{52}$ is G or D, $Z^{53}$ is N, $Z^{54}$ is K or R, $Z^{55}$ is A, $Z^{56}$ is AorT, $Z^{57}$ is L, $Z^{58}$ is T, $Z^{59}$ is I, $Z^{60}$ is T, $Z^{61}$ is G, $Z^{62}$ is A or V, $Z^{63}$ is Q or R, $Z^{64}$ is P, $Z^{65}$ is E, $Z^{66}$ is D, $Z^{67}$ is E, $Z^{68}$ is A, T, or G, $Z^{69}$ is D, $Z^{70}$ is Y, $Z^{71}$ is Y or H, and $Z^{72}$ is C, $Z^{73}$ is F or V, $Z^{74}$ is G, $Z^{75}$ is G or S, $Z^{76}$ is G, $Z^{77}$ is T, $Z^{78}$ is H or Q, $Z^{79}$ is L, $Z^{80}$ is T, $Z^{81}$ is V, $Z^{82}$ is L, $Z^{83}$ is G, $Z^{84}$ is Q, $Z^{85}$ is P, $Z^{86}$ is K, and $Z^{87}$ is A.

wherein
Fr¹ is

| | ADSQTVVTQEPSLSVSPGGTVTLTC |
|---|---|
| — | SEQ ID NO: 238 |

| ITLTC | GTVTLTC |
|---|---|
| SEQ ID NO: 239 | SEQ ID NO: 240 |

| TDSQTVVTQEPSLSVSPGGTVTLTC | ADSQTVVTQEPSLSVSLGGTVTLTC |
|---|---|
| SEQ ID NO: 241 | SEQ ID NO: 242 |

| ADSQTVVTQEASVSVSPGGTVTLTC | or ADSQTVVIQEPFLSVSPGGTVTLTC |
|---|---|
| SEQ ID NO: 243 | SEQ ID NO: 244; |

Fr² is

| WYQQTLGRAPRTIIY | WYQQTQGRAPRTIIY | WSQQTPGQAPRTIIY | WYQQTLGRPPRTIIS |
|---|---|---|---|
| SEQ ID NO: 245 | SEQ ID NO: 246 | SEQ ID NO: 247 | SEQ ID NO: 248 |

| WYQQTLGRPPRPIIY | WSQQTPGQAPRTILY or | | WYQHTQGRAPRTIIY |
|---|---|---|---|
| SEQ ID NO: 249 | SEQ ID NO: 250 | | SEQ ID NO: 251; |

Fr³ is

| GVPNRFSGSISGNKAALTITGAQPEDEADYYC | GVPNRFSGSISGNKAALTIIGVQPEDEADYYC |
|---|---|
| SEQ ID NO: 252 | SEQ ID NO: 253 |

| GVPNRFSGSISDNKAALTITGVQPEDEADYYC | GVPSRFSGSISGNKATLTITGARPEDEADYHC |
|---|---|
| SEQ ID NO: 254 | SEQ ID NO: 255 |

| GVPSRFTGSISGNRAALTITGARPEDEADYYC | GVPDRFSGSISGNKAALTITGAQPEDEGDYYC |
|---|---|
| SEQ ID NO: 256 | SEQ ID NO: 257 |

| GVPNRFTGSISGNKAALTITGAQPEDEADYYC | GVPRRFSASVSGNKATLTITGAQPEDEADYYC |
|---|---|
| SEQ ID NO: 258 | SEQ ID NO: 259 |

| GVPNRFTASISGNKAALTITGAQPEDEADYYC | or |
|---|---|
| SEQ ID NO: 260 | |

GVPNRFSGSISGNKAALTITGAQPEDETDYYC
SEQ ID NO: 261;

Fr⁴ is

| FGGGTHLTVLGQPKA | VGGGTHLTVLGQPKA | FGSGTQLTVLGQPKA | FGGGTHLTVLGQP |
|---|---|---|---|

| FGSGTQLTVLGQ | or | FGGGTHLTVLGQ. |
|---|---|---|

16. Group 1 Light Chain Variable Domain Species

Preferably, the canine Group 1 light chain variable domain according to the invention is a compound comprising the sequence:

$$Fr^1\text{-}CDR^1\text{-}Fr^2\text{-}CDR^2\text{-}Fr^3\text{-}CDR^3\text{-}Fr^4$$

wherein $Fr^1$, $Fr^2$, $Fr^3$, and $Fr^4$ are selected from the following combinations:

| # | Fr¹ | Fr² | Fr³ | Fr⁴ |
|---|---|---|---|---|
| L1-783 SEQ ID NO: 1135 | — SEQ ID NO: 252 | WYQQTQGRAPRTIIY SEQ ID NO: 229 | GVPNRFSGSISGNKAALTITGAQPEDEADYYC | FGGGTHLTVLGQPKA |
| L1-776 | — | WYQQTQGRAPRTIIY SEQ ID NO: 246 | GVPNRFSGSISGNKAALTITGAQPEDEADYYC SEQ ID NO: 252 | VGGGTHLTVLGQPKA SEQ ID NO: 262 |
| L1-785 | ADSQTVVTQEPSLSVSPGGTVTLTC SEQ ID NO: 238 | WYQQTLGRAPRTIIY SEQ ID NO: 245 | GVPNRFSGSISGNKAALTIIGVQPEDEADYYC SEQ ID NO:253 | FGGGTHLTVLGQPKA SEQ ID NO: 229 |
| L1-789 | ITLTC SEQ ID NO: 239 | WYQQTLGRAPRTIIY SEQ ID NO: 245 | GVPNRFSGSISDNKAALTITGVQPEDEADYYC SEQ ID NO:254 | FGSTQLTVLGQPKA SEQ ID NO: 228 |
| λ307 | GTVTLTC SEQ ID NO: 240 | WYQQTQGRAPRTIIY SEQ ID NO: 246 | GVPNRFSGSISGNKAALTITGAQPEDEADYYC SEQ ID NO:252 | FGGGTHLTVLGQP SEQ ID NO: 219 |
| λ322 | ADSQTVVTQEPSLSVSPGGTVTLTC SEQ ID NO: 238 | WYQQTQGRAPRTIIY SEQ ID NO: 246 | GVPNRFSGSISGNKAALTITGAQPEDEADYYC SEQ ID NO:252 | FGSTQLTVLGQ SEQ ID NO: 263 |
| λ305 | TDSQTVVTQEPSLSVSPGGTVTLTC SEQ ID NO: 241 | WYQQTQGRAPRTIIY SEQ ID NO: 246 | GVPSRFSGSISGNKATLTITGARPEDEADYHC SEQ ID NO:255 | FGGGTHLTVLGQ SEQ ID NO: 225 |
| λ303 | ADSQTVVTQEPSLSVSPGGTVTLTC SEQ ID NO: 238 | WYQQTQGRAPRTIIY SEQ ID NO: 246 | GVPNRFSGSISGNKAALTITGAQPEDEADYYC SEQ ID NO:252 | FGGGTHLTVLGQPKA SEQ ID NO: 229 |
| λ125 | ADSQTVVTQEPSLSVSPGGTVTLTC SEQ ID NO: 238 | WYQQTLGRAPRTIIY SEQ ID NO: 245 | GVPNRFSGSISGNKAALTITGAQPEDEADYYC SEQ ID NO:252 | FGSTQLTVLGQPKA SEQ ID NO: 228 |
| λ104 | ADSQTVVTQEPSLSVSLGGTVTLTC SEQ ID NO: 242 | WSQQTPGQAPRTIIY SEQ ID NO: 247 | GVPSRFTGSISGNRAALTITGARPEDEADYYC SEQ ID NO:256 | FGGGTHLTVLGQPKA SEQ ID NO: 229 |
| L220-79 | ADSQTVVTQEASVSVSPGGTVTLTC SEQ ID NO: 243 | WYQQTLGRPPRTIIS SEQ ID NO: 248 | GVPDRFSGSISGNKAALTITGAQPEDEGDYYC SEQ ID NO:257 | FGGGTHLTVLGQ SEQ ID NO: 225 |
| L214-79 | ADSQTVVTQEPSLSVSLGGTVTLTC SEQ ID NO: 242 | WSQQTPGQAPRTIIY SEQ ID NO: 247 | GVPNRFTGSISGNKAALTITGAQPEDEADYYC SEQ ID NO:258 | FGSTQLTVLGQPKA SEQ ID NO: 228 |
| L1-705 | ADSQTVVIQEPFLSVSPGGTVTLTC SEQ ID NO: 244 | WYQQTLGRPPRPIIY SEQ ID NO: 249 | GVPRRFSASVSGNKATLTITGAQPEDEADYYC SEQ ID NO:259 | FGGGTHLTVLGQPKA SEQ ID NO: 229 |
| L1-729 | ADSQTVVTQEPSLSVSLGGTVTLTC SEQ ID NO: 242 | WSQQTPGQAPRTILY SEQ ID NO: 250 | GVPNRFTASISGNKAALTITGAQPEDEADYYC SEQ ID NO:260 | FGGGTHLTVLGQPKA SEQ ID NO: 229 |
| L1-743 | ADSQTVVTQEPSLSVSPGGTVTLTC SEQ ID NO: 238 | WYQHTQGRAPRTIIY SEQ ID NO: 251 | GVPNRFSGSISGNKAALTITGAQPEDEADYYC SEQ ID NO:252 | FGGGTHLTVLGQPKA SEQ ID NO: 229 |
| L1-753 | ADSQTVVTQEPSLSVSPGGTVTLTC SEQ ID NO: 238 | WYQQTQGRAPRTIIY SEQ ID NO: 246 | GVPNRFSGSISGNKAALTITGAQPEDETDYYC SEQ ID NO:261 | FGGGTHLTVLGQPKA SEQ ID NO: 229 |
| L1-759 | ADSQTVVTQEPSLSVSPGGTVTLTC SEQ ID NO: 238 | WYQQTQGRAPRTIIY SEQ ID NO: 246 | GVPNRFSGSISGNKAALTITGAQPEDEADYYC SEQ ID NO:252 | — |
| Cnsnss | ADSQTVVTQEPSLSVSPGGTVTLTC SEQ ID NO: 238 | WYQQTLGRAPRTIIY SEQ ID NO: 245 | GVPNRFSGSISGNKAALTITGAQPEDEADYYC SEQ ID NO:252 | FGGGTHLTVLGQPKA SEQ ID NO: 229 |

17. Group 3 Light Chain Variable Domain Genus

The chimeric canine light chain variable domain polypeptides according to the invention are compounds comprising the sequence:

$Fr^1\text{-}\text{-}CDR^1\text{-}\text{-}Fr^2\text{-}CDR^2\text{-}\text{-}Fr^3\text{-}CDR^3\text{-}\text{-}Fr^4$ wherein $Fr^1$ is $Y'^{1}\ Y'^{2}\ Y'^{3}\ Y'^{4}\ Y'^{5}\ Y'^{6}\ Y'^{7}\ Y'^{8}\ Y'^{9}\ Y'^{10}\ Y'^{11}\ Y'^{12}\ Y'^{13}\ Y'^{14}\ Y'^{15}\ Y'^{16}\ Y'^{17}\ Y'^{18}\ Y'^{19}\ Y'^{20}\ Y'^{21}\ Y'^{22}\ Y'^{23}\ Y'^{24}\ Y'^{25}$ (SEQ ID NO: 264);

$Fr^2$ is $Y'^{26}\ Y'^{27}\ Y'^{28}\ Y'^{29}\ Y'^{30}\ Y'^{31}\ Y'^{32}\ Y'^{33}\ Y'^{34}\ Y'^{35}\ Y'^{36}\ Y'^{37}\ Y'^{38}\ Y'^{39}\ Y'^{40}$ (SEQ ID NO: 265);

$Fr^3$ is $Y'^{41}\ Y'^{42}\ Y'^{43}\ Y'^{44}\ Y'^{45}\ Y'^{46}\ Y'^{47}\ Y'^{48}\ Y'^{49}\ Y'^{50}\ Y'^{51}\ Y'^{52}\ Y'^{53}\ Y'^{54}\ Y'^{55}\ Y'^{56}\ Y'^{57}\ Y'^{58}\ Y'^{59}\ Y'^{60}\ Y'^{61}\ Y'^{62}\ Y'^{63}\ Y'^{64}\ Y'^{65}\ Y'^{66}\ Y'^{67}\ Y'^{68}\ Y'^{69}\ Y'^{70}\ Y'^{71}\ Y'^{72}$ (SEQ ID NO: 266);

$Fr^4$ is $Y'^{73}\ Y'^{74}\ Y'^{75}\ Y'^{76}\ Y'^{77}\ Y'^{78}\ Y'^{79}\ Y'^{80}\ Y'^{81}\ Y'^{82}\ Y'^{83}\ Y'^{84}\ Y'^{85}\ Y'^{86}$ (SEQ ID NO: 267);

provided that when $Y'^{k}$ for $k \leq 22$ is - -, $Y'^{i}$ for $l<k$ is - -, and when $Y'^{m}$ for $n \geq 80$ is - -, $Y'^{m'}$ for $m>n$ is -.

18. Group 3 Light Chain Variable Domain Subgenus

Preferably, the canine λ light chain variable domain according to the invention is a compound comprising the sequence:

$Fr^1\text{-}CDR^1\text{-}Fr^2\text{-}CDR^2\text{-}Fr^3\text{-}CDR^3\text{-}Fr^4$ wherein $Fr^1$ is $Y'^{1}$ is S, P, or -   $Y'^{2}$ is W, A, or -,   $Y'^{3}$ is A or -,   $Y'^{4}$ is Q or -, $Y'^{5}$ is S A, T, or -   $Y'^{6}$ is V, M, or -   $Y'^{7}$ is L or -   $Y'^{8}$ is T or -

$Y'^{9}$ is Q or -,   $Y'^{10}$ is P or -   $Y'^{11}$ is A, P, S, or -   $Y'^{12}$ is S, P, or -

$Y'^{13}$ is V, M, or -   $Y'^{14}$ is S or -   $Y'^{15}$ is G, A, T, or -   $Y'^{16}$ is S, A, T, or -

$Y'^{17}$ is L, P, or -   $Y'^{18}$ is G or -,   $Y'^{19}$ is Q or -,   $Y'^{20}$ is R, T, or -

$Y'^{21}$ is V or -   $Y'^{22}$ is T or -   $Y'^{23}$ is I,   $Y'^{24}$ is S, $Y'^{25}$ is C,   $Y'^{26}$ is W,   $Y'^{27}$ is Y or F,   $Y'^{28}$ is Q or R, $Y'^{29}$ is Q or H,   $Y'^{30}$ is L, F, or V,   $Y'^{31}$ is P or L,   $Y'^{32}$ is G, $Y'^{33}$ is T or K,   $Y'^{34}$ is G, S, or A,   $Y'^{35}$ is P,   $Y'^{36}$ is R, K, or S, $Y'^{37}$ is T, L, or S,   $Y'^{38}$ is L, V, I, or F,   $Y'^{39}$ is I, or A,   $Y'^{40}$ is Y, F, or H, $Y'^{41}$ is G,   $Y'^{42}$ is V or I,   $Y'^{43}$ is P,   $Y'^{44}$ is D, A, V, or E, $Y'^{45}$ is R,   $Y'^{46}$ is F,   $Y'^{47}$ is S,   $Y'^{48}$ is G, or A, $Y'^{49}$ is S or P,   $Y'^{50}$ is R, K, S, or A,   $Y'^{51}$ is S,   $Y'^{52}$ is G, $Y'^{53}$ is S or N,   $Y'^{54}$ is T, or S,   $Y'^{55}$ is A or S,   $Y'^{56}$ is T, S, or A, $Y'^{57}$ is L,   $Y'^{58}$ is T,   $Y'^{59}$ is I,   $Y'^{60}$ is S, T, or A, $Y'^{61}$ is G or V,   $Y'^{62}$ is L or I,   $Y'^{63}$ is Q,   $Y'^{64}$ is A or T, $Y'^{65}$ is E,   $Y'^{66}$ is D,   $Y'^{67}$ is E,   $Y'^{68}$ is A, T, or G, $Y'^{69}$ is D, E, or N,   $Y'^{70}$ is Y,   $Y'^{71}$ is Y or F,   $Y'^{72}$ is C, $Y'^{73}$ is F   $Y'^{74}$ is G, S, or E,   $Y'^{75}$ is G,   $Y'^{76}$ is G, $Y'^{77}$ is T or Q,   $Y'^{78}$ is H,   $Y'^{79}$ is L,   $Y'^{80}$ is T or -, $Y'^{81}$ is V, F, or -,   $Y'^{82}$ is L or -,   $Y'^{83}$ is G or -,   $Y'^{84}$ is Q, H, N, or -, $Y'^{85}$ is P or E, and   $Y'^{86}$ is K or -;

| | | |
|---|---|---|
| SWAQAVLTQPPSVSAALGQRVTISC<br>SEQ ID NO: 268 | SWAQSVLTQPASVSGSLGQRVTISC<br>SEQ ID NO: 98 | SWAQSALTQPSSVSGTLGQTVTISC<br>SEQ ID NO: 269 |
| PWAQSVLTQPASVXGSXGQRVTISC<br>SEQ ID NO: 270 | SWAQSVLTQPASVXGSLGQRVTISC<br>SEQ ID NO: 271 | SWAQAVLTQPPSMSTALGQRVTITC<br>SEQ ID NO: 272 |
| SWAQTVLTQPASVSGSLGQTVTISC<br>SEQ ID NO: 273 | SLGQTVTISC<br>SEQ ID NO: 274 | PVSAAPGQRVTISC<br>SEQ ID NO: 275 |
| GSLGQTVTISC<br>SEQ ID NO: 276 | SWAQAVLTQPASVSGSLGQRVTISC<br>SEQ ID NO: 277 | SWAQSVLTQPASVSGSXGQRVTISC<br>SEQ ID NO: 278 |
| ISC | RVTISC<br>SEQ ID NO: 279 | or |

SWAQSMLTQPASVSGSLGQKVTISC;
SEQ ID NO: 112;

$Fr^2$ is

| | | | |
|---|---|---|---|
| WYQQVPGKSPKIFIY<br>SEQ ID NO: 280 | WYQQFPGTGPRTLIY<br>SEQ ID NO: 164 | WYQQLPGTGPRTLIY<br>SEQ ID NO: 131 | WYQQLPGTSPRTLIY<br>SEQ ID NO:281 |
| WFQHFPGTSPKLLIY<br>SEQ ID NO: 282 | WYQQVPGTSPRTLIY<br>SEQ ID NO: 283 | WYQQLPGTSPKTLIY<br>SEQ ID NO: 284 | WYQQFPGTGPRTIIY<br>SEQ ID NO:285 |
| WYQQLPGKSPKSIIF<br>SEQ ID NO: 286 | WYRQFPGTGPRTVAY<br>SEQ ID NO: 287 | WYQQLPGTGPKTLIY<br>SEQ ID NO: 133 | WYQQLPGKSPKTIIY<br>SEQ ID NO:288 |
| WYQQLPGTSPRTLIH<br>SEQ ID NO: 289 | WYQQFLGTGPRTIIY<br>SEQ ID NO: 290 | WYQQLPGKAPSLLIY<br>SEQ ID NO: 291;or | WYQQLPGKGPRTVIY;<br>SEQ ID NO:292 |

$Fr^3$ is

| | |
|---|---|
| GVPVRFSGSKSGSTATLTITGIQAEDETDYYC<br>SEQ ID NO: 293 | GVPDRFSGSRSGSTATLTISGLQTEDEADYYC<br>SEQ ID NO: 294 |
| GVPDRFSGSRSGNTATLTISGLQAEDEADYYC<br>SEQ ID NO: 295 | GVPDRFSGSRSGSTATLTISGLQAEDEADYYC<br>SEQ ID NO: 183 |
| GIPARFSGSRSGNTASLTISGLQAEDEADYYC<br>SEQ ID NO: 296 | GVPDRFSGSKSGSTATLTXSGLQAEDEADYYC<br>SEQ ID NO: 297 |
| GVPARFSGSKSGNTATLTITGIQAEDEADYYC<br>SEQ ID NO: 298 | GVPDRFSASSSGSTSTLTIAGLQAEDEGDYYC<br>SEQ ID NO: 299 |
| GIPDRFSGSRSGSTATLTISGLQAEDEADYYC<br>SEQ ID NO: 300 | GVPDRFSGSKSGSTATLTISVLQAEDEADYYC<br>SEQ ID NO: 185 |
| GVPDRFSGSSSGSSATLTISGLQAEDEADYYC<br>SEQ ID NO: 301 | GVXDRFSGSRSGSTATLTISGLQAEDEADYYC<br>SEQ ID NO: 302 |
| GVPDRFSGSRSGSTAALTISGLQAEDEADYYC<br>SEQ ID NO: 303 | GVPDRFSGSKSGSTATLTISGLQAEDEADYYC<br>SEQ ID NO: 170 |
| GVPDRFSGSRSGSTATLTISGLQAEDEADYFC<br>SEQ ID NO: 304 | GVPERFSGSKSGSSATLTITGLQAEDEANYYC<br>SEQ ID NO: 305 |

GVPDRFSGSRSGNTATLTTSGLQAEDEADYFC, or GVPDRFSGSASGSSATLTISGLQAEDEAEYYC;
SEQ ID NO: 306                       SEQ ID NO: 307;

Fr⁴ is

| | | | |
|---|---|---|---|
| FGSGTQLTVLGQPK SEQ ID NO: 214 | FGGGTHLTVLGQPK SEQ ID NO: 212 | FGSGTQLTVLGQNE SEQ ID NO: 308 | FGGGTHLTVLGQP SEQ ID NO: 219 |
| FGGGTHLTVLGQHE SEQ ID NO: 309 | FGGGTHL SEQ ID NO: 212 | FGGGTQLTVLGQPKA SEQ ID NO: 217 | FGGGTHLTVLGQPKA SEQ ID NO: 229 |
| FGGGTHLTVLGQ SEQ ID NO: 225 | FGEGTHLTVLGQPKA SEQ ID NO: 310 | FGGGTHLTVFGQPKA, or SEQ ID NO: 311 | FGSGTQLTVLGQPKA. SEQ ID NO: 228. |

19. Group 3 Light Chain Variable Domain Species

Preferably, the canine Group 3 light chain variable domain according to the invention is a compound comprising the sequence:

Fr¹-CDR¹-Fr²-CDR²-Fr³-CDR³-Fr⁴ wherein Fr¹, Fr², Fr³, and Fr⁴ are selected from the following combinations:

| # | Fr¹ | Fr² | Fr³ | Fr⁴ |
|---|---|---|---|---|
| λ124 SEQ ID NO: 268 | SWAQAVLTQPPSVSAALGQRVTISC SEQ ID NO: 280 | WYQQVPGKSPKTFIY SEQ ID NO: 293 | GVPVRFSGSKSGSTATLTITGIQAEDETDYYC SEQ ID NO: 214 | FGSGTQLTVLGQPK |
| λ212 SEQ ID NO: 98 | SWAQSVLTQPASVSGSLGQRVTISC SEQ ID NO: 164 | WYQQFPGTGPRTLIY SEQ ID NO: 294 | GVPDRFSGSRSGSTATLTISGLQTEDEADYYC SEQ ID NO: 212 | FGGGTHLTVLGQPK |
| λ216 SEQ ID NO: 98 | SWAQSVLTQPASVSGSLGQRVTISC SEQ ID NO: 164 | WYQQFPGTGPRTLIY SEQ ID NO: 294 | GVPDRFSGSRSGSTATLTISGLQTEDEADYYC SEQ ID NO: 212 | FGGGTHLTVLGQPK |
| λ218 SEQ ID NO: 98 | SWAQSVLTQPASVSGSLGQRVTISC SEQ ID NO: 131 | WYQQLPGTGPRTLIY SEQ ID NO: 295 | GVPDRFSGSRSGNTATLTISGLQAEDEADYYC SEQ ID NO: 212 | FGGGTHLTVLGQPK |
| λ231 SEQ ID NO: 98 | SWAQSVLTQPASVSGSLGQRVTISC SEQ ID NO: 281 | WYQQLPGTSPRTLIY SEQ ID NO: 183 | GVPDRFSGSRSGSTATLTISGLQAEDEADYYC SEQ ID NO: 214 | FGSGTQLTVLGQPK |
| λ301 SEQ ID NO: 269 | SWAQSALTQPSSVSGTLGQTVTISC SEQ ID NO: 282 | WFQHFPGTSPKLLIY SEQ ID NO: 296 | GIPARFSGSRSGNTASLTISGLQAEDEADYYC SEQ ID NO: 308 | FGSGTQLTVLGQNE |
| λ308 SEQ ID NO: 98 | SWAQSVLTQPASVSGSLGQRVTISC SEQ ID NO: 283 | WYQQVPGTSPRTLIY SEQ ID NO: 183 | GVPDRFSGSRSGSTATLTISGLQAEDEADYYC SEQ ID NO: 219 | FGGGTHLTVLGQP |
| λ311 SEQ ID NO: 270 | PWAQSVLTQPASVXGSXGQRVTISC SEQ ID NO: 284 | WYQQLPGTSPKTLIY SEQ ID NO: 183 | GVPDRFSGSRSGSTATLTISGLQAEDEADYYC SEQ ID NO: 309 | FGGGTHLTVLGQHE |
| λ316 SEQ ID NO: 271 | SWAQSVLTQPASVXGSLGQRVTISC SEQ ID NO: 285 | WYQQFPGTGPRTIIY SEQ ID NO: 297 | GVPDRFSGSKSGSTATLTXSGLQAEDEADYYC SEQ ID NO: 222 | FGGGTHL |
| λ131 SEQ ID NO: 272 | SWAQAVLTQPPSMSTALGQRVTITC SEQ ID NO: 286 | WYQQLPGKSPKSIIF SEQ ID NO: 298 | GVPARFSGSKSGNTATLTITGIQAEDEADYYC SEQ ID NO: 217 | FGGGTQLTVLGQPKA |
| L202-79 SEQ ID NO: 273 | SWAQTVLTQPASVSGSLGQTVTISC SEQ ID NO: 287 | WYRQFPGTGPRTVAY SEQ ID NO: 299 | GVPDRFSASSSGSTSTLTIAGLQAEDEGDYYC SEQ ID NO: 212 | FGGGTHLTVLGQPK |
| L208-79 SEQ ID NO: 274 | SLGQTVTISC SEQ ID NO: 133 | WYQQLPGTGPKTLIY SEQ ID NO: 300 | GIPDRFSGSRSGSTATLTISGLQAEDEADYYC SEQ ID NO: 229 | FGGGTHLTVLGQPKA |
| L211-79 SEQ ID NO: 275 | PVSAAPGQRVTISC SEQ ID NO: 288 | WYQQLPGKSPKTIIY SEQ ID NO: 185 | GVPDRFSGSKSGSTATLTISVLQAEDEADYYC SEQ ID NO: 229 | FGGGTHLTVLGQPKA |
| L212-79 SEQ ID NO: 276 | GSLGQTVTISC SEQ ID NO: 133 | WYQQLPGTGPKTLIY SEQ ID NO: 300 | GIPDRFSGSRSGSTATLTISGLQAEDEADYYC SEQ ID NO: 229 | FGGGTHLTVLGQPKA |
| L218-79 SEQ ID NO: 277 | SWAQAVLTQPASVSGSLGQRVTISC SEQ ID NO: 133 | WYQQLPGTGPKTLIY SEQ ID NO: 301 | GVPDRFSGSSSGSSATLTISGLQAEDEADYYC SEQ ID NO: 225 | FGGGTHLTVLGQ |

| # | Fr¹ | Fr² | Fr³ | Fr⁴ |
|---|-----|-----|-----|-----|
| L1-704 SEQ ID NO: 98 | SWAQSVLTQPASVSGSLGQRVTISC SEQ ID NO: 131 | WYQQLPGTGPRTLIY SEQ ID NO: 183 | GVPDRFSGSRSGSTATLTISGLQAEDEADYYC SEQ ID NO: 229 | FGGGTHLTVLGQPKA |
| L1-711 SEQ ID NO: 98 | SWAQSVLTQPASVSGSLGQRVTISC SEQ ID NO: 281 | WYQQLPGTSPRTLIY SEQ ID NO: 303 | GVPDRFSGSRSGSTAALTISGLQAEDEADYYC SEQ ID NO: 229 | FGGGTHLTVLGQPKA |
| L1-713 SEQ ID NO: 98 | SWAQSVLTQPASVSGSLGQRVTISC SEQ ID NO: 285 | WYQQFPGTGPRTIIY SEQ ID NO: 170 | GVPDRFSGSKSGSTATLTISGLQAEDEADYYC SEQ ID NO: 310 | FGEGTHLTVLGQPKA |
| L1-716 | ISC SEQ ID NO: 131 | WYQQLPGTGPRTLIY SEQ ID NO: 304 | GVPDRFSGSRSGSTATLTISGLQAEDEADYFC SEQ ID NO: 311 | FGGGTHLTVFGQPKA |
| L1-717 SEQ ID NO: 279 | RVTISC SEQ ID NO: 281 | WYQQLPGTSPRTLIY SEQ ID NO: 295 | GVPDRFSGSRSGNTATLTISGLQAEDEADYYC SEQ ID NO: 229 | FGGGTHLTVLGQPKA |
| L1-718 SEQ ID NO: 98 | SWAQSVLTQPASVSGSLGQRVTISC SEQ ID NO: 289 | WYQQLPGTSPRTLIH SEQ ID NO: 183 | GVPDRFSGSRSGSTATLTISGLQAEDEADYYC SEQ ID NO: 229 | FGGGTHLTVLGQPKA |
| L1-727 SEQ ID NO: 98 | SWAQSVLTQPASVSGSLGQRVTISC SEQ ID NO: 290 | WYQQFLGTGPRTIIY SEQ ID NO: 170 | GVPDRFSGSKSGSTATLTISGLQAEDEADYYC SEQ ID NO: 229 | FGGGTHLTVLGQPKA |
| L1-730 SEQ ID NO: 98 | SWAQSVLTQPASVSGSLGQRVTISC SEQ ID NO: 291 | WYQQLPGKAPSLLIY SEQ ID NO: 305 | GVPERFSGSKSGSSATLTITGLQAEDEANYYC SEQ ID NO: 228 | FGSGTQLTVLGQPKA |
| L1-741 SEQ ID NO: 277 | SWAQAVLTQPASVSGSLGQRVTISC SEQ ID NO: 281 | WYQQLPGTSPRTLIY SEQ ID NO: 183 | GVPDRFSGSRSGSTATLTISGLQAEDEADYYC SEQ ID NO: 229 | FGGGTHLTVLGQPKA |
| L1-754 SEQ ID NO: 98 | SWAQSVLTQPASVSGSLGQRVTISC SEQ ID NO: 281 | WYQQLPGTSPRTLIY SEQ ID NO: 183 | GVPDRFSGSRSGSTATLTISGLQAEDEADYYC SEQ ID NO: 229 | FGGGTHLTVLGQPKA |
| L1-748 SEQ ID NO: 98 | SWAQSVLTQPASVSGSLGQRVTISC SEQ ID NO: 284 | WYQQLPGTSPKTLIY SEQ ID NO: 306 | GVPDRFSGSRSGNTATLTTSGLQAEDEADYFC SEQ ID NO: 229 | FGGGTHLTVLGQPKA |
| L1-735 SEQ ID NO: 112 or | SWAQSMLTQPASVSGSLGQKVTISC SEQ ID NO: 292 | WYQQLPGKGPRTVIY SEQ ID NO: 307 | GVPDRFSGSASGSSATLTISGLQAEDEAEYYC SEQ ID NO: 229 | FGGGTHLTVLGQPKA |
| cnsnss | SWAQSVLTQPASVSGSLGQRVTISC SEQ ID NO: 98 | WYQQLPGTGPRTLIY SEQ ID NO: 131 | GVPDRFSGSRSGSTATLTISGLQAEDEADYYC SEQ ID NO: 183 | FGGGTHLTVLGQPK, SEQ ID NO: 212. |

20. Kappa Light Chain Variable Domain Genus

The invention also comprises a kappa light chain variable domain polypeptide of formula:

$$Fr^1\text{-}CDR^1\text{-}Fr^2\text{-}CDR^2\text{-}Fr^3\text{-}CDR^3\text{-}Fr^4$$

wherein $Fr^1$ is $Z^1 \, Z^2 \, Z^3 \, Z^4 \, Z^5 \, Z^6 \, Z^7 \, Z^8 \, Z^9 \, Z^{10} \, Z^{11} \, Z^{12} \, Z^{13} \, Z^{14} \, Z^{15} \, Z^{16} \, Z^{17} \, Z^{18} \, Z^{19} \, Z^{20} \, Z^{21} \, Z^{22} \, Z^{23}$ (SEQ ID NO: 312);

$Fr^2$ is $Z^{24} \, Z^{25} \, Z^{26} \, Z^{27} \, Z^{28} \, Z^{29} \, Z^{30} \, Z^{31} \, Z^{32} \, Z^{33} \, Z^{34} \, Z^{35} \, Z^{36} \, Z^{37} \, Z^{38}$ (SEQ ID NO: 313)

$Fr^3$ is $Z^{39} \, Z^{40} \, Z'41 \, Z^{42} \, Z^{43} \, Z^{44} \, Z^{45} \, Z^{46} \, Z^{47} \, Z^{48} \, Z^{49} \, Z^{50} \, Z^{51} \, Z^{11} \, Z^{52} \, Z^{54} \, Z^{55} \, Z^{56} \, Z^{57} \, Z^{58} \, Z^{59} \, Z^{60} \, Z^{61} \, Z^{62} \, Z^{63} \, Z^{64} \, Z^{65} \, Z^{66} \, Z^{67} \, Z^{68} \, Z^{69} \, Z^{70}$ (SEQ ID NO: 314), and $Fr^4$ is $Z^{71} \, Z^{72} \, Z^{73} \, Z^{74} \, Z^{75} \, Z^{76} \, Z^{77} \, Z^{78} \, Z^{79} \, Z^{80} \, Z^{81} \, Z^{82} \, Z^{83} \, Z^{84} \, Z^{85} \, Z^{86} \, Z^{87} \, Z^{88}$ (SEQ ID NO: 315)

wherein $Z'^1$ is D, E, A or -;

$Z'^2$ is I, L, V or -;

$Z'^3$ is V or -;

$Z'^4$ is M, L, or -;

$Z'^5$ is T or -;

$Z'^6$ is Q, E, or -;

$Z'^7$ is T, A, or -;

$Z'^8$ is P or -;

$Z'^9$ is P, L, R, S, or -;

$Z'^{10}$ is S, P, or -;

$Z'^{11}$ is L or -;

$Z'^{12}$ is S or -;

$Z'^{13}$ is V, A, or -

$Z'^{14}$ is S or -;

$Z'^{15}$ is P or -;

$Z'^{16}$ is G, R, or -;

$Z'^{17}$ is E or -

$Z'^{18}$ is P, T, S, or -;

$Z'^{19}$ is A or -;

$Z'^{20}$ is S, F, or -;

$Z'^{21}$ is I or -, $Z'^{22}$ is S or -;

$Z'^{23}$ is C, Y, or -;

$Z'^{24}$ is W or -;

$Z'^{25}$ is F, Y, S, L, or -;

$Z'^{26}$ is R, L, Q, M, or -;

$Z'^{27}$ is Q, H, or -;

$Z'^{28}$ is K, R, or -;

$Z'^{29}$ is P, S, or -;

$Z'^{30}$ is G or -;

$Z'^{31}$ is Q, H, or -;

$Z'^{32}$ S, A, or -;

$Z'^{33}$ is P or -;

$Z'^{34}$ is Q, E, R, or -;

$Z'^{35}$ is R, G, D, L, T, I, A, or -;

$Z'^{36}$ is L, R, or -;

$Z'^{37}$ is T or -;

$Z'^{38}$ is Y, H, S, W, F, or -;

$Z'^{39}$ is G;

$Z'^{40}$ is V;

$Z'^{41}$ is S or P;

$Z'^{42}$ is D or E, $Z'^{43}$ is R or G, $Z'^{44}$ is F or I;

$Z'^{45}$ is S or A;

$Z'^{46}$ is G;

$Z'^{47}$ is S or R;

$Z'^{48}$ is G;

$Z'^{49}$ is S, $Z'^{50}$ is G or V, $Z'^{51}$ is T or A $Z'^{52}$ is D;

$Z'^{53}$ is F or C;

$Z'^{54}$ is T;

$Z'^{55}$ is L;

$Z'^{56}$ is R, K, T or E;

$Z'^{57}$ is I, $Z'^{58}$ is S, T, or G;

$Z'^{59}$ is R or G;

$Z'^{60}$ is V or A;

$Z'^{61}$ is E, V, or G;

$Z'^{62}$ is A or D;

$Z'^{63}$ is D, N, A, E, or G;

$Z'^{64}$ is D or G;

$Z'^{65}$ is A, T, S, V, or G;

$Z'^{66}$ is G or A;

$Z'^{67}$ is V, L, or I;

$Z'^{68}$ is Y;

$Z'^{69}$ is Y, H, F, or C;

$Z'^{70}$ is C;

$Z'^{71}$ is F, L, or S;

$Z'^{72}$ is S or G;

$Z'^{73}$ is Q, A, K, P, or T;

$Z'^{74}$ is G;

$Z'^{75}$ is T or A;

$Z'^{76}$ is K, N, or H;

$Z'^{77}$ is L or V;

$Z'^{78}$ is E, D, V, or G;

$Z'^{79}$ is I, M, or L;

$Z'^{80}$ is K or R;

$Z'^{81}$ is R;

$Z'^{82}$ is N;

$Z'^{83}$ is D;

$Z'^{84}$ is A;

$Z'^{85}$ is A;

$Z'^{85}$ is Q;

$Z'^{86}$ is P;

$Z'^{87}$ is A; and $Z'^{88}$ is V;

provided that when $Z'^k$ for $k \leq 37$ is - -, $Z'^l$ for $l < k$ is - -.

21. Kappa Light Chain Variable Domain Sub-genus

Preferably, the canine κ light chain variable domain according to the invention is a compound comprising the sequence:

Fr¹-CDR¹-Fr²-CDR²-Fr³-CDR³-Fr⁴ wherein
Fr¹ is

| | | |
|---|---|---|
| DTVLTQTPPSLSVSPGEPASISC | DIVMTQAPPSLSVSPGEPASISC | DLVLTQTPRSLSVSPGETASISC |
| SEQ ID NO: 316 | SEQ ID NO: 317 | SEQ ID NO: 318 |
| DIVMTQTPLSLSVSPGEPASISC | DIVMTQAPPPLSVSPGEPASISC | DIVMTQTPPSLSVSPREPASISC |
| SEQ ID NO: 319 | SEQ ID NO: 320 | SEQ ID NO: 321 |
| ASISC | SLSVSPGEPAFISC | VMTQTPLSLSVSPGEPASISC |
| SEQ ID NO: 322 | SEQ ID NO: 323 | SEQ ID NO: 324 |
| IVMTQTPLSLSVSPGEPASISC | DIVMTQAPPSXSVSPGEPASISC | DVVMTQAPPSLSVSPREPASISC |
| SEQ ID NO: 325 | SEQ ID NO: 326 | SEQ ID NO: 327 |
| DVVMTQAPPSLSVSPGEPASISC | IVMTQTPLSLSVSXXEPASISC | DVVMTQTPPSLSVSPREPASISC |
| SEQ ID NO: 328 | SEQ ID NO: 329 | SEQ ID NO: 330 |
| EIVMTQTPLSLSVSPGETASISY | DIVMTQTPLSLSASPGETASISC | DIVMTEAPPSLSVSPGESASISC |
| SEQ ID NO: 331 | SEQ ID NO: 332 | SEQ ID NO: 333 |
| DIVMTQIPLSLSVSPGEPASISC | DIVMTQTPLSLSVSPGETASISC | DIVMTQTPPSLSVSPGEPASISC |
| SEQ ID NO: 334 | SEQ ID NO: 335 | SEQ ID NO: 336 |
| IIVMTQTPLSLSASPGESASISC | AIVMTQAPPSLSVSPGEPASISC | DIVMTQTPPSLSVSPGETASISC |
| SEQ ID NO: 337 | SEQ ID NO: 338 | SEQ ID NO: 339 |
| —MTQAPPSLSVSPGEPASISC | PSLSVSPREPASISC | TQAPSSLSVSPGEPASISC |
| SEQ ID NO: 340 | SEQ ID NO: 341 | SEQ ID NO: 342 |
| DIVMTQTPPSLSVSPXEPASISC | or —, | |
| SEQ ID NO: 343 | | |

Fr² is

| | | | |
|---|---|---|---|
| WYLQKPGQSPQLLIY | WYRQKPGQSPEDLIY | WFRQKPGQSPQRLIY | WFRQKPGQSPEGLIY |
| SEQ ID NO:344 | SEQ ID NO:345 | SEQ ID NO:346 | SEQ ID NO:347 |
| WFQQKPGQSPEGLIY | WFRQKPGQSPEGLIH | WFRQKPGQSPQRLIS | WFQQKPGQSPQRLIW |
| SEQ ID NO:348 | SEQ ID NO:349 | SEQ ID NO:350 | SEQ ID NO:351 |
| WFRQKPGQSPEDLIY | WFQQKPGQSPQGLIY | WFRHKPGQSPQTLIY | WFQQKPGHSPRGLIY |
| SEQ ID NO:352 | SEQ ID NO:353 | SEQ ID NO:354 | SEQ ID NO:355 |
| WYMQKPGQSPQGRIY | WFRQRPGQSPQRLIY | WLRQKPGQSPEGLIY | WSRQRPGQSPEGLIY |
| SEQ ID NO:356 | SEQ ID NO:357 | SEQ ID NO:358 | SEQ ID NO:359 |
| WYLQKPGQSPQILIY | WFRQKPGQAPQRLIY | WFRQKPGQSPQRLIF | WFQQKPGQSPQRLIY |
| SEQ ID NO:360 | SEQ ID NO:361 | SEQ ID NO:362 | SEQ ID NO:363 |
| WYLQKPGQSPQRLIY | WIRQKPGQSPEGLIY | WFRQRPGQSPEALIY | WFRQKSGQSPQRLIY |
| SEQ ID NO:364 | SEQ ID NO:365 | SEQ ID NO:366 | SEQ ID NO:367 | or Y;

Fr³ is

| | |
|---|---|
| GVSDRFSGSGSGTDFTLRISRVEPNDTGIYYC<br>SEQ ID NO:368 | GVSDRFSGSGSGTDFTLRISRVEADDAGIYYC<br>SEQ ID NO:369 |
| GVPDRFSGSGSGTDFTLRISRVEADDTGLYYC<br>SEQ ID NO:370 | GVSDRFSGSGSGTDFTLTISRVEADDAGVYYC<br>SEQ ID NO:371 |
| GVSDRFSGSGSGTDFTLRISRVEADDAGVYYC<br>SEQ ID NO:372 | GVSDRFSGSGSGTDFTLRISRVEADDAGLYYC<br>SEQ ID NO:373 |
| GVSDRFSGSGSGTDFTLRISRVEADDTGVYYC<br>SEQ ID NO:374 | GVSDRFSGSGSGTDFTLRISRVEADDTGVYYC<br>SEQ ID NO:374 |
| GVPDRFSGSGSGTDFTLRIGRVEADDTGVYYC<br>SEQ ID NO:375 | GVPDRFSGSGSGTDFTLRISRVEADDAGIYYC<br>SEQ ID NO:376 |
| GVPDRFSGSGSGTDCTLTISRVEADDAGVYYC<br>SEQ ID NO:377 | GVSDRESGSGSGTDFTLRISRVEADDAAVYYC<br>SEQ ID NO:378 |
| GVPDRFSGSGSGTDFTLRISRVEADDAGVYYC<br>SEQ ID NO:379 | GVPDRFRGSGSGTDFTLRISRAEADDAGIYYC<br>SEQ ID NO:380 |
| GVSDRFSGSGSGTDFTLRISRVEADDAGVYHC<br>SEQ ID NO:381 | GVPDRFSGSGSGTDFTLRISRVEANDTGVYYC<br>SEQ ID NO:382 |
| GASDRFSGSGSGADFTXRISRVEADDAGVYYC<br>SEQ ID NO:383 | GVPDGFSGSGSGTDFTLRISRVEADDAGVYYC<br>SEQ ID NO:384 |
| GVSDRFSGSGSGTDFTLKISRVEADDTGVYXC<br>SEQ ID NO:385 | GVPDRFSGSGSGTDFTLRISRVEADDSGVYYC<br>SEQ ID NO:386 |
| GVPDRFSGSGSGTDFTLRISRVEADDTGVYYC<br>SEQ ID NO:387 | GVSDRFSGRGSGTDFTLRISRVEAGDAGVYYC<br>SEQ ID NO:388 |
| GVSDRFSGSGSGTDFTLKISRVEADDAGVYFC<br>SEQ ID NO:389 | GVPDRFSGSGSGTDFTLRISRVVADDAGVYYC<br>SEQ ID NO:390 |
| GVPDRFSGSGSGTDFTLRISRVEDEDAGLYYC<br>SEQ ID NO:391 | GVSDRFSGSGSGTDFTLRISRVEADDSGVYYC<br>SEQ ID NO:392 |
| GVPDRFSGSGSGTDFTLRISRVEADDGGVYHC<br>SEQ ID NO:393 | GIPDRFSGSGSGTDFTLRISGVEAADTGVYYC<br>SEQ ID NO:394 |
| GVSDRFSGSGSGTDFTLRISRVEANDTGVYYC<br>SEQ ID NO:395 | GVSDRFSGSGSGTDFTLRISRVEADDXGVYYC<br>SEQ ID NO:396 |
| GVPDRFSGSGSGTDFTLRISRVEADDTGVYFC<br>SEQ ID NO:397 | GVPDRFAGSGSGTDFTLRISRVEADDTGIYYC<br>SEQ ID NO:398 |
| GVPDRFSGSGSGTDCTLTISRVEADGAGVYYC<br>SEQ ID NO:399 | GVPDRFSGSGSGTDCTLTISRVEADDAGVYCC<br>SEQ ID NO:400 |
| GVSERFSGSGSGTDFTLEISRVEADDVGVYYC<br>SEQ ID NO:401 | GVSDRFSGSGSGTDFTLRITRVEADDAGVYYC<br>SEQ ID NO:402 |
| GVSERFSGSGSGTDFTLEISRVGADDVGVYYC<br>SEQ ID NO:403 | GVSDRFSGSGSGTDFTLRISRVEADDTGLYYC<br>SEQ ID NO:404 |
| GVPDRFSGSGSGTDFTLTISRVEADDAGVYYC<br>SEQ ID NO:405 | GVSDRFSGSGSVTDFTLRISRVEADDAGIYYC<br>SEQ ID NO:406 |
| or | GVSERISGSGSGTDFTLRISRVEADDAGIYYC<br>SEQ ID NO:407; |

Fr⁴ is

| | | | |
|---|---|---|---|
| FGAGTKVELKRNDAQPAVY<br>SEQ ID NO:408 | FGKGTHLEIKRNDAQPAVY<br>SEQ ID NO:409 | FSQGTNLEMKRNDAQPAVY<br>SEQ ID NO:410 | FGTGTKVELKRNDAQPAVY<br>SEQ ID NO:411 |
| FSQGTKLEIKRNDAQPAVY<br>SEQ ID NO:412 | FGQGTKVEIKRNDAQPAVY<br>SEQ ID NO:413 | FSQGTPLEIKRNGAQPAVY<br>SEQ ID NO:414 | FGQGTKVDIKRNDAQPAVY<br>SEQ ID NO:415 |
| FGQGTKLEIKRNDAQPAVY<br>SEQ ID NO:416 | FSQGTKLEINRNDAQPAVY<br>SEQ ID NO:417 | FGKGTHLEIKRNDAQPA<br>SEQ ID NO:418 | FSQGXKLEIKRA<br>SEQ ID NO:419 |

-continued

| | | | |
|---|---|---|---|
| FSQGTKLEIKRND<br>SEQ ID NO:420 | FGQGTKLEIKRNDAQPAV<br>SEQ ID NO:421 | FGAGTKLEIKRNDAQPAVY<br>SEQ ID NO:422 | FGQGTKLEIRRNDAQPAVY<br>SEQ ID NO:423 |
| FSQGTKLEIKRNDAQPAV<br>SEQ ID NO:424 | FGAGTKVELKRNDAQPAV<br>SEQ ID NO:425 | FGQGTKVEIKRNDAQPAV<br>SEQ ID NO:426 | LSQGAKLDIKRNDAQPAV<br>SEQ ID NO:427 |
| SSQGTKLEIKRNDAQPAV<br>SEQ ID NO:428 | FGQGTNLEIKRNDAQPAV<br>SEQ ID NO:429 | FGKGTHLEIKRNDAQPAV<br>SEQ ID NO:430 | FSQGTNLEMKRNDAQPAV<br>SEQ ID NO:431 |
| FSQGTRLEIKRNDAQPAV<br>SEQ ID NO:432 | FSQGTNLEIKRNDAQPAV<br>SEQ ID NO:433 | FGPGAKVELKRNDAQPAV<br>SEQ ID NO:434 | FSQGTKLVIKRNDAQPAV<br>SEQ ID NO:435 |
| FGQGTXLEIKRNDAQPAV<br>SEQ ID NO:436 | FSQGTNLGMKRNDAQPAV<br>SEQ ID NO:437 | LSQGTKLEIERNDAQPAV<br>SEQ ID NO:438 | or FSQGTKLEIRRNDAQPAV.<br>SEQ ID NO:439 |

22. Kappa Light Chain Variable Domain Species

Preferably, the canine kappa light chain variable domain according to the invention is a compound comprising the sequence:

$$Fr^1-CDR^1-Fr^2-CDR^2-Fr^3-CDR^3-Fr^4$$

wherein $Fr^1$, $Fr^2$, $Fr^3$, and $Fr^4$ are selected from the following combinations:

| # | $Fr^1$ | $Fr^2$ | $Fr^3$ | $Fr^4$ |
|---|---|---|---|---|
| KAPA129 | DTVLTQTPPSLSVSPGEPASISC<br>SEQ ID NO:316 | WYLQKPGQSPQLLIY<br>SEQ ID NO:344 | GVSDRFSGSGSGTDFTLRISRVEPNDTGIYYC<br>SEQ ID NO:368 | FGAGTKVELKRNDAQPAVY<br>SEQ ID NO:408 |
| KAPA130 | DIVMTQAPPSLSVSPGEPASISC<br>SEQ ID NO:317 | WYRQKPGQSPEDLIY<br>SEQ ID NO:345 | GVSDRFSGSGSGTDFTLRISRVEADDAGIYYC<br>SEQ ID NO:369 | FGKGTHLEIKRNDAQPAVY<br>SEQ ID NO:409 |
| KAPA131 | DLVLTQTPRSLSVSPGETASISC<br>SEQ ID NO:318 | WFRQKPGQSPQRLIY<br>SEQ ID NO:346 | GVPDRFSGSGSGTDFTLRISRVEADDTGLYYC<br>SEQ ID NO:370 | FSQGTNLEMKRNDAQPAVY<br>SEQ ID NO:410 |
| KAPA212 | DIVMTQTPLSLSVSPGEPASISC<br>SEQ ID NO:319 | WFRQKPGQSPEGLIY<br>SEQ ID NO:347 | GVSDRFSGSGSGTDFTLTISRVEADDAGVYYC<br>SEQ ID NO:371 | FGTGTKVELKRNDAQPAVY<br>SEQ ID NO:411 |
| KAPA214 | DLVLTQTPRSLSVSPGETASISC<br>SEQ ID NO:318 | WFRQKPGQSPQRLIY<br>SEQ ID NO:346 | GVPDRFSGSGSGTDFTLRISRVEADDTGLYYC<br>SEQ ID NO:370 | FSQGTNLEMKRNDAQPAVY<br>SEQ ID NO:410 |
| KAPA217 | DIVMTQAPPSLSVSPGEPASISC<br>SEQ ID NO:317 | WFQQKPGQSPEGLIY<br>SEQ ID NO:348 | GVSDRFSGSGSGTDFTLRISRVEADDAGVYYC<br>SEQ ID NO:372 | FSQGTKLEIKRNDAQPAVY<br>SEQ ID NO:412 |
| KAPA218 | DIVMTQAPPPLSVSPGEPASISC<br>SEQ ID NO:320 | WFRQKPGQSPEGLIH<br>SEQ ID NO:349 | GVSDRFSGSGSGTDFTLRISRVEADDAGLYYC<br>SEQ ID NO:373 | FGQGTKVEIKRNDAQPAVY<br>SEQ ID NO:413 |
| K110-79 | DIVMTQTPPSLSVSPREPASISC<br>SEQ ID NO:321 | WYLQKPGQSPQLLIY<br>SEQ ID NO:344 | GVSDRFSGSGSGTDFTLRISRVEADDTGVYYC<br>SEQ ID NO:374 | FGAGTKVELKRNDAQPAVY<br>SEQ ID NO:408 |
| K114-79 | ASISC<br>SEQ ID NO:322 | WFRQKPGQSPQRLIS<br>SEQ ID NO:350 | GVPDRFSGSGSGTDFTLRIGRVEADDTGVYYC<br>SEQ ID NO:375 | FSQGTPLEIKRNGAQPAVY<br>SEQ ID NO:414 |
| K127-75 | — | WFQQKPGQSPQRLIW<br>SEQ ID NO:351 | GVPDRFSGSGSGTDFTLRISRVEADDAGIYYC<br>SEQ ID NO:376 | FGQGTKVDIKRNDAQPAVY<br>SEQ ID NO:415 |
| K203-79 | DIVMTQAPPSLSVSPGEPASISC<br>SEQ ID NO:317 | WFRQKPGQSPEGLIY<br>SEQ ID NO:347 | GVSDRFSGSGSGTDFTLRISRVEADDAGVYYC<br>SEQ ID NO:372 | FSQGTKLEIKRNDAQPAVY<br>SEQ ID NO:412 |
| K208-79 | SLSVSPGEPAFISC<br>SEQ ID NO:323 | WFRQKPGQSPQRLIY<br>SEQ ID NO:346 | GVPDRFSGSGSGTDCTLTISRVEADDAGVYYC<br>SEQ ID NO:377 | FGQGTKLEIKRNDAQPAVY<br>SEQ ID NO:416 |
| K213-79 | VMTQTPLSLSVSPGEPASISC<br>SEQ ID NO:324 | WFRQKPGQSPEDLIY<br>SEQ ID NO:352 | GVPDRFSGSGSGTDFTLRISRVEADDAGIYYC<br>SEQ ID NO:369 | FGKGTHLEIKRNDAQPAVY<br>SEQ ID NO:409 |
| K217-79 | IVMTQTPLSLSVSPGEPASISC<br>SEQ ID NO:325 | WFRQKPGQSPEGLIY<br>SEQ ID NO:347 | GVSDRFSGSGSGTDFTLRISRVEADDAAVYYC<br>SEQ ID NO:378 | FSQGTKLEINRNDAQPAVY<br>SEQ ID NO:417 |
| K219-79 | DIVMTQAPPSXSVSPGEPASISC<br>SEQ ID NO:326 | WYRQKPGQSPEDLIY<br>SEQ ID NO:345 | GVSDRFSGSGSGTDFTLRISRVEADDAAVYYC<br>SEQ ID NO:378 | FSQGTKLEIKRNDAQPAVY<br>SEQ ID NO:412 |
| K1201 | — | WFQQKPGQSPQGLIY<br>SEQ ID NO:353 | GVPDRFSGSGSGTDFTLRISRVEADDAGVYYC<br>SEQ ID NO:379 | FGQGTKLEIKRNDAQPAVY<br>SEQ ID NO:416 |
| K1202 | — | WFQQKPGQSPQGLIY<br>SEQ ID NO:353 | GVPDRFRGSGSGTDFTLRISRAEADDAGIYYC<br>SEQ ID NO:380 | FGKGTHLEIKRNDAQPAVY<br>SEQ ID NO:409 |
| K1204 | DVVMTQAPPSLSVSPREPASISC<br>SEQ ID NO:327 | WFRQKPGQSPQRLIY<br>SEQ ID NO:346 | GVPDRFSGSGSGTDFTLRISRVEADDAGVYYC<br>SEQ ID NO:379 | FGQGTKLEIKRNDAQPAVY<br>SEQ ID NO:416 |

-continued

| # | Fr¹ | Fr² | Fr³ | Fr⁴ |
|---|-----|-----|-----|-----|
| K1206 | DIVMTQTPLSLSVSPGEPASISC<br>SEQ ID NO:319 | WFRQKPGQSPQRLIY<br>SEQ ID NO:346 | GVPDRFSGSGSGTDFTLRISRVEADDAGIYYC<br>SEQ ID NO:376 | FGKGTHLEIKRNDAQPA<br>SEQ ID NO:418 |
| K1208 | DVVMTQAPPSLSVSPREPASISC<br>SEQ ID NO:327 | WFRQKPGQSPEGLIY<br>SEQ ID NO:347 | GVSDRFSGSGSGTDFTLRISRVEADDAGVYHC<br>SEQ ID NO:381 | FSQGTKLEIKRNDAQPAVY<br>SEQ ID NO:412 |
| K1212 | DIVMTQTPLSLSVSPGEPASISC<br>SEQ ID NO:319 | WFRHKPGQSPQTLIY<br>SEQ ID NO:354 | GVPDRFSGSGSGTDFTLRISRVEANDTGVYYC<br>SEQ ID NO:382 | FSQGTKLEIKRNDAQPAVY<br>SEQ ID NO:412 |
| K1213 | DVVMTQAPPSLSVSPGEPASISC<br>SEQ ID NO:328 | WFRQKPGQSPEGLIY<br>SEQ ID NO:347 | GVSDRFSGSGSGTDFTLRISRVEADDAGVYHC<br>SEQ ID NO:381 | FSQGTKLEIKRNDAQPAVY<br>SEQ ID NO:412 |
| K1218 | IVMTQTPLSLSVSXXEPASISC<br>SEQ ID NO:329 | WFRQKPGQSPQRLIY<br>SEQ ID NO:346 | GASDRFSGSGSGADFTXRISRVEADDAGVYYC<br>SEQ ID NO:383 | FSQGXKLEIKRA<br>SEQ ID NO:419 |
| K1219 | - | WFQQKPGHSPRGLIY<br>SEQ ID NO:355 | GVPDRFSGSGSGTDFTLRISRVEADDAGVYYC<br>SEQ ID NO:379 | FGQGTKLEIKRNDAQPAVY<br>SEQ ID NO:416 |
| K1221 | DVVMTQAPPSLSVSPREPASISC<br>SEQ ID NO:327 | WFRQKPGQSPEGLIY<br>SEQ ID NO:347 | GVSDRFSGSGSGTDFTLRISRVEADDAGVYYC<br>SEQ ID NO:372 | FSQGTKLEIKRNDAQPAVY<br>SEQ ID NO:412 |
| K1223 | DVVMTQTPPSLSVSPREPASISC<br>SEQ ID NO:330 | WFRQKPGQSPEGLIY<br>SEQ ID NO:347 | GVSDRFSGSGSGTDFTLRISRVEADDAGVYYC<br>SEQ ID NO:372 | FSQGTKLEIKRND<br>SEQ ID NO:420 |
| K1225 | - | WFQQKPGQSPQGLIY<br>SEQ ID NO:353 | GVPDGFSGSGSGTDFTLRISRVEADDAGVYYC<br>SEQ ID NO:384 | FGQGTKLEIKRNDAQPAV<br>SEQ ID NO:421 |
| K1278 | EIVMTQTPLSLSVSPGETASISY<br>SEQ ID NO:331 | WYMQKPGQSPQGRIY<br>SEQ ID NO:356 | GVSDRFSGSGSGTDFTLKISRVEADDTGVYXC<br>SEQ ID NO:385 | - |
| K1279 | - | WFRQRPGQSPQRLIY<br>SEQ ID NO:357 | GVPDRFSGSGSGTDFTLRISRVEADDSGVYYC<br>SEQ ID NO:386 | FGAGTKLEIKRNDAQPAVY<br>SEQ ID NO:422 |
| K1283 | DIVMTQTPLSLSASPGETASISC<br>SEQ ID NO:332 | WFRQKPGQSPQRLIY<br>SEQ ID NO:346 | GVPDRFSGSGSGTDFTLRISRVEADDTGVYYC<br>SEQ ID NO:387 | FGQGTKLEIRRNDAQPAVY<br>SEQ ID NO:423 |
| K1284 | DIVMTEAPPSLSVSPGESASISC<br>SEQ ID NO:333 | WLRQKPGQSPEGLIY<br>SEQ ID NO:358 | GVSDRFSGRGSGTDFTLRISRVEAGDAGVYYC<br>SEQ ID NO:388 | FSQGTKLEIKRNDAQPAVY<br>SEQ ID NO:412 |
| K1285 | DIVMTQTPLSLSVSPGEPASISC<br>SEQ ID NO:319 | WSRQRPGQSPEGLIY<br>SEQ ID NO:359 | GVSDRFSGSGSGTDFTLKISRVEADDAGVYFC<br>SEQ ID NO:389 | FSQGTKLEIKRNDAQPAV<br>SEQ ID NO:424 |
| K1286 | DIVMTQIPLSLSVSPGEPASISC<br>SEQ ID NO:334 | WFRQKPGQSPQRLIY<br>SEQ ID NO:346 | GVPDRFSGSGSGTDFTLRISRVEADDAGVYYC<br>SEQ ID NO:379 | FGAGTKVELKRNDAQPAV<br>SEQ ID NO:425 |
| K1287 | DIVMTQAPPSLSVSPGEPASISC<br>SEQ ID NO:317 | WFRQKPGQSPEGLIY<br>SEQ ID NO:347 | GVSDRFSGSGSGTDFTLRISRVEADDAGVYYC<br>SEQ ID NO:372 | FGQGTKVEIKRNDAQPAV<br>SEQ ID NO:426 |
| K1288 | DIVMTQTPLSLSVSPGETASISC<br>SEQ ID NO:335 | WFRQKPGQSPQRLIY<br>SEQ ID NO:346 | GVPDRFSGSGSGTDFTLRISRVVADDAGVYYC<br>SEQ ID NO:390 | FGAGTKVELKRNDAQPAV<br>SEQ ID NO:425 |
| K1289 | DIVMTQAPPSLSVSPGEPASISC<br>SEQ ID NO:317 | WFRQKPGQSPEGLIY<br>SEQ ID NO:347 | GVSDRFSGSGSGTDFTLRISRVEADDAGVYYC<br>SEQ ID NO:372 | LSQGAKLDIKRNDAQPAV<br>SEQ ID NO:427 |
| K1243 | IIVMTQTPLSLSASPGESASISC<br>SEQ ID NO:337 | WFRQKPGQSPQRLIY<br>SEQ ID NO:346 | GVPDRFSGSGSGTDFTLRISRVEDEDAGLYYC<br>SEQ ID NO:391 | FGQGTKLEIKRNDAQPAV<br>SEQ ID NO:421 |
| K1244 | - | WYLQKPGQSPQILIY<br>SEQ ID NO:360 | GVSDRFSGSGSGTDFTLRISRVEADDSGVYYC<br>SEQ ID NO:392 | FGAGTKVELKRNDAQPAV<br>SEQ ID NO:425 |
| K1250 | DIVMTQTPLSLSVSPGEPASISC<br>SEQ ID NO:319 | WFRQKPGQAPQRLIY<br>SEQ ID NO:361 | GVPDRFSGSGSGTDFTLRISRVEADDGGVYHC<br>SEQ ID NO:393 | FSQGTKLEIKRNDAQPAV<br>SEQ ID NO:424 |
| K1251 | - | WFRQRPGQSPQRLIY<br>SEQ ID NO:357 | GVPDRFSGSGSGTDFTLRISRVEADDSGVYYC<br>SEQ ID NO:386 | SSQGTKLEIKRNDAQPAV<br>SEQ ID NO:428 |
| K1275 | AIVMTQAPPSLSVSPGEPASISC<br>SEQ ID NO:338 | WFRQKPGQSPQRLIY<br>SEQ ID NO:346 | GVPDRFSGSGSGTDFTLRISRVEADDSGVYYC<br>SEQ ID NO:386 | FGAGTKVELKRNDAQPAV<br>SEQ ID NO:425 |
| K1343 | DIVMTQTPPSLSVSPGETASISC<br>SEQ ID NO:339 | WFRQKPGQSPQRLIY<br>SEQ ID NO:346 | GIPDRFSGSGSGTDFTLRISGVEAADTGVYYC<br>SEQ ID NO:394 | FGQGTNLEIKRNDAQPAV<br>SEQ ID NO:429 |
| K1348 | -MTQAPPSLSVSPGEPASISC<br>SEQ ID NO:340 | WYRQKPGQSPEDLIY<br>SEQ ID NO:345 | GVSDRFSGSGSGTDFTLRISRVEADDAGIYYC<br>SEQ ID NO:369 | FGKGTHLEIKRNDAQPAV<br>SEQ ID NO:430 |
| K1349 | DLVLTQTPRSLSVSPGETASISC<br>SEQ ID NO:339 | WFRQKPGQSPQRLIY<br>SEQ ID NO:346 | GVPDRFSGSGSGTDFTLRISRVEADDTGLYYC<br>SEQ ID NO:394 | FSQGTNLEMKRNDAQPAV |

| # | Fr¹ | Fr² | Fr³ | Fr⁴ |
|---|---|---|---|---|
| | SEQ ID NO:318 | SEQ ID NO:346 | SEQ ID NO:370 | SEQ ID NO:431 |
| K1350 | DLVLTQTPRSLSVSPGETASISC<br>SEQ ID NO:318 | WFRQKPGQSPQRLIY<br>SEQ ID NO:346 | GVPDRFSGSGSGTDFTLRISRVEADDTGLYYC<br>SEQ ID NO:370 | FSQGTNLEMKRNDAQPAV<br>SEQ ID NO:431 |
| K1353 | DIVMTQTPLSLSVSPGEPASISC<br>SEQ ID NO:319 | WYLQKPGQSPQLLIY<br>SEQ ID NO:344 | GVSDRFSGSGSGTDFTLRISRVEANDTGVYYC<br>SEQ ID NO:395 | FGQGTKLEIKRNDAQPAV<br>SEQ ID NO:421 |
| K1354 | —PSLSVSPREPASISC<br>SEQ ID NO:341 | WYLQKPGQSPQLLIY<br>SEQ ID NO:344 | GVSDRFSGSGSGTDFTLRISRVEADDXGVYYC<br>SEQ ID NO:396 | FSQGTRLEIKRNDAQPAV<br>SEQ ID NO:432 |
| K1360 | DLVLTQTPRSLSVSPGETASISC<br>SEQ ID NO:318 | WFRQKPGQSPQRLIY<br>SEQ ID NO:346 | GVPDRFSGSGSGTDFTLRISRVEADDTGLYYC<br>SEQ ID NO:370 | FSQGTNLEMKRNDAQPAV<br>SEQ ID NO:431 |
| K1361 | DLVLTQTPRSLSVSPGETASISC<br>SEQ ID NO:318 | WFRQKPGQSPQRLIY<br>SEQ ID NO:346 | GVPDRFSGSGSGTDFTLRISRVEADDTGLYYC<br>SEQ ID NO:370 | FSQGTNLEMKRNDAQPAV<br>SEQ ID NO:431 |
| K1362 | DIVMTQTPPSLSVSPGEPASISC<br>SEQ ID NO:336 | WYLQKPGQSPQLLIY<br>SEQ ID NO:344 | GVSDRFSGSGSGTDFTLRISRVEANDTGVYYC<br>SEQ ID NO:395 | FGQGTKLEIKRNDAQPAV<br>SEQ ID NO:421 |
| K1363 | DIVMTQTPLSLSVSPGETASISC<br>SEQ ID NO:335 | WFRQKPGQSPQRLIY<br>SEQ ID NO:346 | GVPDRFSGSGSGTDFTLRISRVEADDTGVYFC<br>SEQ ID NO:397 | FSQGTNLEIKRNDAQPAV<br>SEQ ID NO:433 |
| K1366 | DLVLTQTPRSLSVSPGETASISC<br>SEQ ID NO:318 | WFRQKPGQSPQRLIY<br>SEQ ID NO:346 | GVPDRFSGSGSGTDFTLRISRVEADDTGLYYC<br>SEQ ID NO:370 | FSQGTNLEMKRNDAQPAV<br>SEQ ID NO:431 |
| K1370 | DIVMTQTPLSLSVSPGETASISC<br>SEQ ID NO:335 | WFRQKPGQSPQRLIF<br>SEQ ID NO:362 | GVPDRFAGSGSGTDFTLRISRVEADDTGIYYC<br>SEQ ID NO:398 | FGPGAKVELKRNDAQPAV<br>SEQ ID NO:434 |
| K1371 | DIVMTQTPLSLSVSPGEPASISC<br>SEQ ID NO:319 | WFRQKPGQSPQRLIY<br>SEQ ID NO:346 | GVPDRFSGSGSGTDFTLRISRVEADDTGVYYC<br>SEQ ID NO:387 | FSQGTKLVIKRNDAQPAV<br>SEQ ID NO:435 |
| K2420 | DIVMTQTPLSLSVSPGEPASISC<br>SEQ ID NO:319 | WFQQKPGQSPQRLIY<br>SEQ ID NO:363 | GVPDRFSGSGSGTDCTLTISRVEADGAGVYYC<br>SEQ ID NO:399 | FGQGTKLEIKRNDAQPAV<br>SEQ ID NO:421 |
| K2422 | DIVMTQTPPSLSVSPGEPASISC<br>SEQ ID NO:336 | WYLQKPGQSPQRLIY<br>SEQ ID NO:364 | GVPDRFSGSGSGTDFTLRISRVEADDTGLYYC<br>SEQ ID NO:370 | FSQGTNLEMKRNDAQPAV<br>SEQ ID NO:431 |
| K2423 | — | WFQQKPGQSPQRLIY<br>SEQ ID NO:363 | GVPDRFSGSGSGTDCTLTISRVEADDAGVYCC<br>SEQ ID NO:400 | FGQGTXLEIKRNDAQPAV<br>SEQ ID NO:436 |
| K2425 | DIVMTQTPPSLSVSPGEPASISC<br>SEQ ID NO:336 | WYLQKPGQSPQLLIY<br>SEQ ID NO:344 | GVSDRFSGSGSGTDFTLRISRVEANDTGVYYC<br>SEQ ID NO:395 | FGQGTKLEIKRNDAQPAV<br>SEQ ID NO:421 |
| K2426 | DLVLTQTPRSLSVSPGETASISC<br>SEQ ID NO:318 | WFRQKPGQSPQRLIY<br>SEQ ID NO:346 | GVPDRFSGSGSGTDFTLRISRVEADDTGLYYC<br>SEQ ID NO:370 | FSQGTNLGMKRNDAQPAV<br>SEQ ID NO:437 |
| K2427 | DIVMTQAPPSLSVSPGEPASISC<br>SEQ ID NO:317 | WFRQKPGQSPEGLIY<br>SEQ ID NO:347 | GVSERFSGSGSGTDFTLEISRVEADDVGVYYC<br>SEQ ID NO:401 | FSQGTKLEIKRNDAQPAV<br>SEQ ID NO:424 |
| K2430 | DIVMTQTPPSLSVSPGEPASISC<br>SEQ ID NO:336 | WYLQKPGQSPQLLIY<br>SEQ ID NO:344 | GVSDRFSGSGSGTDFTLRISRVEANDTGVYYC<br>SEQ ID NO:395 | FGQGTKLEIKRNDAQPAV<br>SEQ ID NO:421 |
| K2431 | —TQAPSSLSVSPGEPASISC<br>SEQ ID NO:342 | WIRQKPGQSPEGLIY<br>SEQ ID NO:365 | GVSDRFSGSGSGTDFTLRITRVEADDAGVYYC<br>SEQ ID NO:402 | LSQGTKLEIERNDAQPAV<br>SEQ ID NO:438 |
| K2432 | DIVMTQTPPSLSVSPGEPASISC<br>SEQ ID NO:336 | WFRQKPGQSPEGLIY<br>SEQ ID NO:347 | GVSERFSGSGSGTDFTLEISRVGADDVGVYYC<br>SEQ ID NO:403 | FSQGTKLEIKRNDAQPAV<br>SEQ ID NO:424 |
| K2435 | DLVLTQTPRSLSVSPGETASISC<br>SEQ ID NO:318 | WFRQKPGQSPQRLIY<br>SEQ ID NO:346 | GVPDRFSGSGSGTDFTLRISRVEADDTGLYYC<br>SEQ ID NO:370 | FSQGTNLEMKRNDAQPAV<br>SEQ ID NO:431 |
| K2436 | DIVMTQTPPSLSVSPXEPASISC<br>SEQ ID NO:343 | WYLQKPGQSPQLLIY<br>SEQ ID NO:344 | GVSDRFSGSGSGTDFTLRISRVEANDTGVYYC<br>SEQ ID NO:395 | FGQGTKLEIKRNDAQPAV<br>SEQ ID NO:421 |
| K2437 | DIVMTQTPPSLSVSPGEPASISC<br>SEQ ID NO:336 | WYLQKPGQSPQLLIY<br>SEQ ID NO:344 | GVSDRFSGSGSGTDFTLRISRVEADDTGLYYC<br>SEQ ID NO:404 | FSQGTNLEMKRNDAQPAV<br>SEQ ID NO:431 |
| K2438 | DIVMTQTPPSLSVSPGEPASISC<br>SEQ ID NO:336 | WYLQKPGQSPQLLIY<br>SEQ ID NO:344 | GVSDRFSGSGSGTDFTLRISRVEANDTGVYYC<br>SEQ ID NO:395 | FGQGTKLEIKRNDAQPAV<br>SEQ ID NO:421 |
| K2440 | DIVMTQTPPSLSVSPGEPASISC<br>SEQ ID NO:336 | WYLQKPGQSPQLLIY<br>SEQ ID NO:344 | GVSDRFSGSGSGTDFTLRISRVEANDTGVYYC<br>SEQ ID NO:395 | FGQGTKLEIKRNDAQPAV<br>SEQ ID NO:421 |
| K2442 | DLVLTQTPRSLSVSPGETASISC<br>SEQ ID NO:318 | WFRQKPGQSPQRLIY<br>SEQ ID NO:346 | GVPDRFSGSGSGTDFTLTISRVEADDAGVYYC<br>SEQ ID NO:405 | FSQGTKLEIRRNDAQPAV<br>SEQ ID NO:439 |

| # | Fr[1] | Fr[2] | Fr[3] | Fr[4] |
|---|---|---|---|---|
| K2443 | — | WFRQRPGQSPEALIY SEQ ID NO:366 | GVSDRFSGSGSVTDFTLRISRVEADDAGIYYC SEQ ID NO:406 | FGKGTHLEIKRNDAQPAV SEQ ID NO:430 |
| K2444 | — | WFRQKSGQSPQRLIY SEQ ID NO:367 | GVPDRFSGSGSGTDFTLRISRVEADDTGLYYC SEQ ID NO:370 | FSQGTNLEMKRNDAQPAV SEQ ID NO:431 |
| K2446 | — | —Y | GVSERISGSGSGTDFTLRISRVEADDAGIYYC SEQ ID NO:407 | FGQGTKLEIKRNDAQPAV SEQ ID NO:421 |
| K2449 and | — | WFQQKPGQSPQRLIY SEQ ID NO:363 | GVPDRFSGSGSGTDCTLTISRVEADDAGVYYC SEQ ID NO:377 | FGQGTKLEIKRNDAQPAV SEQ ID NO:421 |
| Cnsnss | DIVMTQTPPSLSVSPGEPASISC SEQ ID NO:336 | WFRQKPGQSPQRLIY SEQ ID NO:346 | GVSDRFSGSGSGTDFTLRISRVEADDAGVYYC SEQ ID NO:372 | FSQGTKLEIKRNDAQPAV SEQ ID NO:424. |

23. Other Lambda Light Chain Variable Domains

In another embodiment, the invention comprises the sequence:

Fr[1]-CDR[1]-Fr[2]-CDR[2]-Fr[3]-CDR[3]-Fr[4]

wherein Fr[1], Fr[2], Fr[3], and Fr[4] are framework regions selected from the framework regions of the heavy chain variable sequences displayed in Table $N_\lambda$. The framework sequences of the polypeptides in Table $N_\lambda$ are readily and routinely determinable by those of ordinary skill in the art as those sequences that align with corresponding framework sequences of any of the known human variable domain sequences using any of the many accepted and widely available sequence alignment programs.

Complimentary Determining Regions

As used herein, CDR[1], CDR[2], and CDR[3] are CDR's, which, in one embodiment are canine CDR's, and in another embodiment are non-canine CDR's from the same non-canine antibody. Preferably, two CDR's are from the same non-canine antibody and the third (preferably CDR[1]) is a canine CDR. Preferred amino acids at each position are those that are bolded and underlined. The chimeric canine heavy chain variable domain polypeptides of the invention are not immunologically reactive with canine anti-serum.

In a preferred embodiment, CDR[1] for heavy chains is:

a) $C'^2$ $C'^3$ $C'^4$ $C'^5$ $C'^6$ $C'^7$ $C'^8$ $C'^9$ $C'^{10}$ $C'^{11}$ (SEQ ID NO: 440), wherein $C'^2$ is G, $C'^3$ is F or L, $C'^4$ is T, S, or N, $C'^5$ is F, $C'^6$ is S, G, N, or R, $C'^7$ is S, D, G, N, Y, D, R, H, T, or Y, $C'^8$ is Y, F, N, or C, $C'^9$ is G, D, H, W, S, L, A, or V, $C'^{10}$ is M, and $C'^{11}$ is S, N, G, Y, I, or L;

b) selected from the group consisting of:

| | | | | | |
|---|---|---|---|---|---|
| GFTFSIYGMN SEQ ID NO: 441, | GFTFSDYGMN SEQ ID NO: 442, | GFTFSSYDMS SEQ ID NO: 443, | GFTFSSYSMS SEQ ID NO: 444, | GFTFSDYGMS SEQ ID NO: 445, | GFTFSSYGMS SEQ ID NO: 446, |
| GFNFGSYHMG SEQ ID NO: 447, | GFTFSYYLMS SEQ ID NO: 448, | GFTFRTYGMS SEQ ID NO: 449, | GFTFSGYWMS SEQ ID NO: 450, | GLSFGDFAMN SEQ ID NO: 451, | GFTFSDYYMY SEQ ID NO: 452, |
| GFTFSGCAMI SEQ ID NO: 453, | GFTFSNYDMS SEQ ID NO: 454, | GFTFSAYDML SEQ ID NO: 455, | GFSFSHNDMS SEQ ID NO: 456, | GFTFSRYWMS SEQ ID NO: 457, | GFTFNSYWMS SEQ ID NO: 458, |
| And | GFIFSSFHMS SEQ ID NO: 459; | | | | | c) $C'^1 C'^2 C'^3 C'^4 C'^5 C'^6 C'^7 C'^8 C'^9 C'^{10}$ (SEQ ID NO: 460), wherein $C'^1$ is G, $\quad C'^2$ is Y, $\quad C'^3$ is T or I, $C'^4$ is F, $\quad C'^5$ is T or I, $\quad C'^6$ is D, $C'^7$ is Y or Q, $\quad C'^8$ is Y, $\quad C'^9$ is M, and $C'^{10}$ is H, d) selected from the group consisting of GYTFTDYYMH (SEQ ID NO: 461) and GYIFIDQYMH (SEQ ID NO: 462);

e) $C'^1 C'^2 C'^3 C'^4 C'^5 C'^6 C'^7 C'^8 C'^9 C'^{10}$ (SEQ ID NO: 463), wherein $C'^1$ is G, $\quad C'^2$ is S, $\quad C'^3$ is V, $C'^4$ is T or N, $\quad C'^5$ is D or S, $\quad C'^6$ is I or G, $C'^7$ is Y or H, $\quad C'^8$ is Y, $\quad C'^9$ is W, and $C'^{10}$ is S, f) selected from the group consisting of GSVTDIHYWS (SEQ ID NO: 464) and GSVNSGYYWS (SEQ ID NO: 465), or g) mouse 15A2 antibody $CDR^1$, SGYSFTDYFMN (SEQ ID NO: 466).

In a preferred embodiment, $CDR^2$ for heavy chains is:

a) $C''^1 C''^2 C''^3 C''^4 C''^5 C''^6 C''^7 C''^8 C''^9 C''^{10} C''^{11} C''^{12} C''^{13} C''^{14} C''^{15} C''^{16} C''^{17}$ (SEQ ID NO: 467), wherein $C''^1$ is Y, G, V, Q, D, E, S, T, A, R, or W; $\quad C''^2$ is I; $\quad C''^3$ is S, N, H, W, or R;

$C''^4$ is S, Y, T, N, D, G, R, or D; $\quad C''^5$ is G, D, S, or A; $\quad C''^6$ is G, E, or A;

$C''^7$ is S, D, G, T, R, Y, or E; $\quad C''^8$ is T, S, Y, N, I, or G; $\quad C''^9$ is T, G, R, L F, Y, I, E, or R;

$C''^{10}$ is Y, S, F, —, T, D, or H; $\quad C''^{11}$ is Y, F, or H; $\quad C''^{12}$ is A, T, or S;

$C''^{13}$ is D or G; $\quad C''^{14}$ is A or T; $\quad C''^{15}$ is V;

$C''^{16}$ is K or R; and $\quad C''^{17}$ is G;

b) selected from the group consisting of

```
VINSAGDTG-YAGAVKG    YISTGGGTTSFADAVKG    YISSDGRSTSYTDAVKG    GINSGGSSTYYTDAVKG
SEQ ID NO:468        SEQ ID NO:469        SEQ ID NO:470        SEQ ID NO:471

GINSGGSTTYYTDAVKG    WIRYDGSSTYYADAVKG    YIHNDGGTRTYSDTVKG    EISDSGDYLDYTDAVKG
SEQ ID NO:472        SEQ ID NO:473        SEQ ID NO:474        SEQ ID NO:475

WIWYGGSSTYYADAVKG    SISSSGGTF-YADAVKG    EISGSGTTTHYEDTVRG    TINRSGTTY-YADTVKG
SEQ ID NO:476        SEQ ID NO:477        SEQ ID NO:478        SEQ ID NO:479

RIRGDGTNIYYADAVKG    YINSDGSTTYYADAVKG    AISYDGSSTYYTDAVKG    YINSGGGIIFYADAVKG
SEQ ID NO:480        SEQ ID NO:481        SEQ ID NO:482        SEQ ID NO:483

SIRYDETGTSYTDAVKG    DISDSAYSTYYTDAVKG    QISVGGEIE-YADAVKG    GINGGGTTRFYSDAVRG
SEQ ID NO:484        SEQ ID NO:485        SEQ ID NO:486        SEQ ID NO:487 and                  TISYDGSSTFHTDAVKG
                     SEQ ID NO:488;
``` c) $C''^1 C''^2 C''^3 C''^4 C''^5 C''^6 C''^7 C''^8 C''^9 C''^{10} C''^{11} C''^{12} C''^{13} C''^{14} C''^{15} C''^{16}$ (SEQ ID NO: 489), wherein $C''^1$ is I, $\quad C''^2$ is D, $\quad C''^3$ is P, $C''^4$ is E, $\quad C''^5$ is D, $\quad C''^6$ is G or D, $C''^7$ is T, $\quad C''^8$ is T, $\quad C''^9$ is S or G, $C''^{10}$ is Y, $\quad C''^{11}$ is A, $\quad C''^{12}$ is Q, $C''^{13}$ is K, $\quad C''^{14}$ is F, $\quad C''^{15}$ is Q, and $C''^{16}$ is G, d) selected from the group consisting of IDPEDGTTSYAQKFQG (SEQ ID NO: 490) and IDPEDDTTGYAQKFQG (SEQ ID NO: 491)

e) $C''^1 C''^2 C''^3 C''^4 C''^5 C''^6 C''^7 C''^8 C''^9 C''^{10} C''^{11} C''^{12} C''^{13} C''^{14} C''^{15} C''^{16}$ (SEQ ID NO: 492), wherein $C''^1$ is Y, $\quad C''^2$ is W, $\quad C''^3$ is R or S, $C''^4$ is G, $\quad C''^5$ is G or T, $\quad C''^6$ is T, $C''^7$ is N or H, $\quad C''^8$ is Y or H, $\quad C''^9$ is N, $C''^{10}$ is P, $\quad C''^{11}$ is A or T, $\quad C''^{12}$ is F, $C''^{13}$ is Q, $\quad C''^{14}$ is E or G, $\quad C''^{15}$ is R, and $C''^{16}$ is I, f) selected from the group consisting of YWRGGT-NHNPAFQERI (SEQ ID NO: 493) and YWSGT-THYNPTFQGRI (SEQ ID NO: 494); or g) mouse 15A2 antibody CDR², RINPFNGDPFYNQK-FKG (SEQ ID NO: 495).

In a preferred embodiment, CDR³ for heavy chains is:

a) $C'''^1 C'''^2 C'''^3 C'''^4 C'''^5 C'''^6 C'''^7 C'''^8 C'''^9 C'''^{10} C'''^{11} C'''^{12} C'''^{13} C'''^{14} C'''^{15} C'''^{16} C'''^{17} C'''^{18} C'''^{19} C'''^{20}$ (SEQ ID NO: 496), wherein $C'''^1$ is D, L, Y, T, G, X, E, A, V, W, I, or Q, $C'''^2$ is G, R, I, H, T, P, S, Y, F, D, or W, $C'''^3$ is D, E, Y, V, W, G, S, A, M, I, T, L, P, or R, $C'''^4$ is G, S, I, A, Y, L, T, Q, D, I, N, L, R, $C'''^5$ is T, Y, S, F, L, C, W, X, G, or E, $C'''^6$ is S, T, V, Y, M, H, C, G, F, P, K, W, or —, $C'''^7$ is =, V, E, W, S, T, D, L, G, Y, or K, $C'''^8$ is =, A, G, R, Y, E, D, W, M, or S, $C'''^9$ is =, E, P, V, D, G, Y, W, F, or K, $C'''^{10}$ is =, L, G, W, Y, A, N, S, F, C, D, T, or P, $C'''^{11}$ is =, D, S, F, N, Y, C, A, or R, $C'''^{12}$ is =, Y, F, G, L, D, or P, $C'''^{13}$ is =, F, D, G, N, H, R, or G, $C'''^{14}$ is =, D, V, I, W, or F, $C'''^{15}$ is =, V, D, or G, $C'''^{16}$ is =, H, or F, $C'''^{17}$ is = or D, $C'''^{18}$ is = or Y, $C'''^{19}$ is = or L, and $C'''^{20}$ is = or N;

b) selected from the group consisting of

DREITTVAELD SEQ ID NO: 497,
LIYGYVEGPGSYFD SEQ ID NO: 498,
YHDGSYVRVWFY SEQ ID NO: 499,

TTVATME SEQ ID NO: 500,
GGDSSHWYPYNFD SEQ ID NO: 501,
DPWSSSWYDAFG SEQ ID NO: 502,

XTYGTSSEGNYLG SEQ ID NO: 503,
LSGYYCTDDSCFNVVHDYL LN SEQ ID NO: 504,
GGDLFG SEQ ID NO: 505,

GGDLFG SEQ ID NO: 505,
EYSSSFD SEQ ID NO: 506,
DPATLPTGEFD SEQ ID NO: 507,

DRGQCTVDYCADHID SEQ ID NO: 508,
ASMDTKTFD SEQ ID NO: 509,
DFGDWVL SEQ ID NO: 510,

GDSSXW SEQ ID NO: 511,
VSIISSSWWGRYFD SEQ ID NO: 512,
WDTNG SEQ ID NO: 513,

EYLGE SEQ ID NO: 514,
ITPLGPGDFD SEQ ID NO: 515,
DGGITSYMKTNLD SEQ ID NO: 516,

ARERYCKDDYCFRWGF D SEQ ID NO: 517,
QWRNTWYSFPDPGF D SEQ ID NO: 518;

c) selected from the group consisting of GGSRPFNAFG (SEQ ID NO: 519), KWRYYGSQD (SEQ ID NO: 520), DIWDFD (SEQ ID NO: 521), and YIYGYAAYLD (SEQ ID NO: 522);

d) selected from the group consisting of NSD and LYRS-NYLLD (SEQ ID NO: 523); or e) mouse 15A2 antibody CDR³, FYYGRYYAMDY (SEQ ID NO: 524).

In a preferred embodiment, CDR¹ for light chains is:

a) $C'^1 C'^2 C'^3 C'^4 C'^5 C'^6 C'^7 C'^8 C'^9 C'^{10} C'^{11} C'^{12} C'^{13}$ (SEQ ID NO: 525), wherein $C'^1$ is G or —, $C'^2$ is L or —, $C'^3$ is S, N, P, or —, $C'^4$ is S, P, or —, $C'^5$ is G or —, $C'^6$ is S or —, $C'^7$ is V or —, $C'^8$ is S T, or —, $C'^9$ is T, A, G, P, or —, $C'^{10}$ is S, Q, G, N, or —, $C'^{11}$ is N, H, D, or —, $C'^{12}$ is Y, F, or —, $C'^{13}$ is P or —, and $C'^{13}$ is G, N, A, S, or —, provided that when C'''$^m$ is -- for m>2, C'''$^n$ is -- for n<m;

b) selected from the group consisting of

| | | | |
|---|---|---|---|
| --, | NYPG SEQ ID NO: 526, | GLSSGSVSTSNYPG SEQ ID NO: 527, | GLNSGSVSTSNYPA SEQ ID NO: 528, |
| GLSPGSVSTSNYPN SEQ ID NO: 529, | GLSSGSVSTSNYPA SEQ ID NO: 530, | GLSSGSVTASHFPG SEQ ID NO: 531, | GLSSGSVSGSNYPG SEQ ID NO: 532, |
| GLPSGSVSTQNFPN SEQ ID NO: 533, | GLSSGSVSTGDFPG SEQ ID NO: 534, | GLSSGSVSTSNYPN SEQ ID NO: 535, | GLSSGSVSPSHYPG SEQ ID NO: 536, |
| GLSSGSVSTSNYPS SEQ ID NO: 537, | and | GLSSGSVSTNNYPG SEQ ID NO: 538; | | c) C'$^1$ C'$^2$ C'$^3$ C'$^4$ C'$^5$ C'$^6$ C'$^7$ C'$^8$ C'$^9$ C'$^{10}$ C'$^{11}$ C'$^{12}$ C'$^{13}$ (SEQ ID NO: 539), wherein C'$^1$ is T, S, A, or --,  
C'$^2$ is G, R, or --,  
C'$^3$ is S, T, R, D, A or --,  
C'$^4$ is S, G, E, N, T, P, V, Y, M, or --,  
C'$^5$ is S, N, D, A, Y, or K,  
C'$^6$ is N, D, or Y,  
C'$^7$ is I, V, or L,  
G'$^8$ is G, D, A, or N,  
C'$^9$ is R, Y, G, I, K, S, D, or V,  
C'$^{10}$ is G, R, V, Y, A, S, F, D, or N,  
C'$^{11}$ is Y, N, G, D, F, S, or H, V, or Q,  
C'$^{12}$ is V, A, --,  
or  
C'$^{13}$ is G, H, S, N, A, D, T, or --;

d) selected from the group consisting of

| | | | |
|---|---|---|---|
| TGSGSNIGRGYVG SEQ ID NO: 540, | TGSESNIGRGFVG SEQ ID NO: 541, | TGSSSNVGRGYVG SEQ ID NO: 542, | NIGSVGAT SEQ ID NO: 543, |
| TGSGSNIGGNNVG SEQ ID NO: 544, | TGSSSNIGGYNVG SEQ ID NO: 545, | TGSSSNIGRDYVG SEQ ID NO: 546, | TGSSSNLGRYGVA SEQ ID NO: 547, |
| TGTTSNIGRGFVG SEQ ID NO: 548, | TGSSSNIGSGYVG SEQ ID NO: 549, | TGSSSNIGGYNVN SEQ ID NO: 550, | TGSSSNIGGGYVG SEQ ID NO: 551, |
| SGSTNDIDIFGVS SEQ ID NO: 552, | SGDSSNIGDNFVA SEQ ID NO: 553, | TGSSSNIGKYVVG SEQ ID NO: 554, | TGSSSNIGRGYVG SEQ ID NO: 555, |
| TGSSSNIGRDYVA SEQ ID NO: 556, | SGSTSNIGIVGAS SEQ ID NO: 557, | TGSPSNIGGYDVA SEQ ID NO: 558, | TGSSSNIGGYSVA SEQ ID NO: 559, |
| TGSSSNIGGNYVS SEQ ID NO: 560, | TGSNSNIGRGYVD SEQ ID NO: 561, | TGSNSNIGGNDVA SEQ ID NO: 562, | TGSVSNIGIFDVG SEQ ID NO: 563, |
| TGSGSNIGRDSVG SEQ ID NO: 564, | TGSSSNIGGNQVG SEQ ID NO: 565, | SGSTNDIAIVGAS SEQ ID NO: 566, | TGSSSNIGGNYVG SEQ ID NO: 567, |
| TRSSSNIAGGYVA SEQ ID NO: 568, | TGSSAYIGSGYVG SEQ ID NO: 569, | SGSTKNIGIFGAH SEQ ID NO: 570, | TGSSSNIGGSSVG SEQ ID NO: 571, |
| TGSSSNIGRGFVA SEQ ID NO: 572, | TGAYSNIGTNNVG SEQ ID NO: 573, | TGSGSNIGRGYVA SEQ ID NO: 574, | TGSSINYRYVG SEQ ID NO: 575, |
| SGRTDNIGVAGAA SEQ ID NO: 576, | TGSGSDIGGFG SEQ ID NO: 577, | TGSSSNIGYNVG SEQ ID NO: 578, | TGSSSNVGGGFVG SEQ ID NO: 579, |
| AGTNSDIGTNHVA SEQ ID NO: 580, | SGSTNDIGRFGVN SEQ ID NO: 581, | TGSTANIGSGYVN SEQ ID NO: 582, | TGSSSNIGRNNVG SEQ ID NO: 583, |
| SGSMYNLGVVGAT SEQ ID NO: 584, | TGSNSNIGRGYVG SEQ ID NO: 585, | or | --; | e) C'$^1$ C'$^2$ C'$^3$ C'$^4$ C'$^5$ C'$^6$ C'$^7$ C'$^8$ C'$^9$ C'$^{10}$ C'$^{11}$ C'$^{12}$ C'$^{13}$ C'$^{14}$ (SEQ ID NO: 586), wherein C'$^1$ is T or D,   C'$^2$ is G,   C'$^3$ is S, T, I, N, or R-, C'$^4$ is S, N, T, K, D, or G,   C'$^5$ is S, T, D, or N,   C'$^6$ is N or D-, C'$^7$ is V, I, or L,   C'$^8$ is G or D,   C'$^9$ is Y, N, F, S, D, or G, C'$^{10}$ is G, D, T, or E,   C'$^{11}$ is N, D, Y, or S,   C'$^{12}$ is Y, D, I, S, T, or H, C'$^{13}$ is V, A, or I,   and   C'$^{13}$ is G, Q, H, or A;

or f) selected from the group consisting of

```
TGTNTNIGNGYDVH TGSSSNVGYGDYVG TGSSSNVGYANHVG    TGSSSNVGYGNYVG
SEQ ID NO: 587 SEQ ID NO: 588 SEQ ID NO: 589   SEQ ID NO: 590

DGINSNIDNSNYIE TGSSSDVGYADYVG TGSSSNVGFGNYVG    XGSSSNVGSGSTVG
SEQ ID NO: 591 SEQ ID NO: 592 SEQ ID NO: 593   SEQ ID NO: 594

TGSKTNIGSGYDVQ TGSKDNIGYGNYVG TGSNTNIGSDYDVQ    TGSSSNVGYGDYAG
SEQ ID NO: 595 SEQ ID NO: 596 SEQ ID NO: 597   SEQ ID NO: 598

TGSTSNVGYGNYVG TGSNSNVGYANYVG TGSSSNVGYGDXVG    TGNSSNVGYGNYVG
SEQ ID NO: 599 SEQ ID NO: 600 SEQ ID NO: 601   SEQ ID NO: 602

TGSSSNVGDTSSVG TGSDSNVGYGNYVG TGSSSNVGYGDYVA    TGSTSNLGYSSIVG
SEQ ID NO: 603 SEQ ID NO: 604 SEQ ID NO: 605   SEQ ID NO: 606

TGSTNDIGSENYVH TGSGSNVGYGNYVG TGTSSNVGFGDYVG        TGRSSNIGGGNYVG
SEQ ID NO: 607 SEQ ID NO: 608 SEQ ID NO: 609, and SEQ ID NO: 610
```

In a preferred embodiment, CDR$^2$ for light chains is:
a) C''$^1$ C''$^2$ C''$^3$ C''$^4$ C''$^5$ C''$^6$ C''$^7$ (SEQ ID NO: 611), wherein C''$^1$ is N, R, G, T, S, or H,   C''$^2$ is T or A,   C''$^3$ is N, S, Y, G, or D, C''$^4$ is S, R, N, or T,   C''$^5$ is R,   C''$^6$ is P or L, and   C''$^7$ is S or L;

b) selected from the group consisting of

```
RTSSRP  NTNSRPS GANSRPS NTGSRPS NTYNRLS NTNTRPL
S       SEQ ID  SEQ ID  SEQ ID  SEQ ID  SEQ ID
SEQ ID  NO: 613,NO:614, NO: 615,NO: 616,NO: 617,
NO: 612,

RTNRRPS RTDSRPS TTSSRPS STSSRPS and     HTSSRPS
SEQ ID  SEQ ID  SEQ ID  SEQ ID          SEQ ID
NO: 618,NO: 619,NO:620, NO:621,         NO:622;
``` c) C''$^1$ C''$^2$ C''$^3$ C''$^4$ C''$^5$ C''$^6$ C''$^7$ (SEQ ID NO: 623), wherein d) selected from the group consisting of:

```
GDINRPS GHNHRPS GNNNRPS  SDGHRPS DTYSRLS SRSNRPS
SEQ ID  SEQ ID  SEQ ID   SEQ ID  SEQ ID  SEQ ID
NO: 624,NO: 625,NO: 626, NO: 627,NO: 628,NO: 629,

GNSNRPS SIDNRPS GNGNRPS  SSSNRPS SSTDRPS GDSNRPS
SEQ ID  SEQ ID  SEQ ID   SEQ ID  SEQ ID  SEQ ID
NO: 630,NO: 631,NO: 632, NO: 633,NO: 634,NO: 635,

SDGDRPS GTIYRPS STSYRPS  DDSSRPS DTRSRPS SDGSRPS
SEQ ID  SEQ ID  SEQ ID   SEQ ID  SEQ ID  SEQ ID
NO: 636,NO: 637,NO: 638, NO: 639,NO: 640,NO: 641,
```

C''$^1$ is G, D, S, R, A, T, N, or —,   C''$^2$ is T, D, H, N, R, I, S, F, or K,

C''$^3$ is T, F, H, Y, K, D, S, R, E, or V,   C''$^4$ is N, S, H, D, Y, K, R, F, V, or E,

C''$^5$ is R,   C''$^6$ is P, L, or A, and   C''$^7$ is S or P;

-continued

```
SSTNRPS SNTKRPS ADNYRAS   GTANRPS GKNNRPS STNSRPS
SEQ ID  SEQ ID  SEQ ID    SEQ ID  SEQ ID  SEQ ID
NO: 642,NO: 643,NO: 644,  NO: 645,NO: 646,NO: 647,

GTTNRPS GDNHRPS TFGDRPS   ADDHRPS STTVRPS GDSSRPS
SEQ ID  SEQ ID  SEQ ID    SEQ ID  SEQ ID  SEQ ID
NO: 648,NO: 649,NO: 650,  NO: 651,NO: 652,NO: 653,

STSNRPP NSRERPS GNNYRPS   SISSRPS RSERRPS STDSRPS
SEQ ID  SEQ ID  SEQ ID    SEQ ID  SEQ ID  SEQ ID
NO: 654,NO: 655,NO: 656,  NO: 657,NO: 658,NO: 659,

DTSRRPS DNGKRPS GDNNRPS   GNSKRPS NDGHRPS GDSDRPS
SEQ ID  SEQ ID  SEQ ID    SEQ ID  SEQ ID  SEQ ID
NO: 660,NO: 661,NO: 662,  NO: 663,NO: 664,NO: 665,

STDRRPS GNSDRPS TTNSRPS   TSTNRPS STYSRPS SNGSRPS
SEQ ID  SEQ ID  SEQ ID    SEQ ID  SEQ ID  SEQ ID
NO: 666,NO: 667,NO: 668,  NO: 669,NO: 670,NO: 671,

SSNRPS  or      DTTFRPS   DTSRRPS
SEQ ID          SEQ ID    SEQ ID
NO: 672,        NO: 673,  NO: 660,
``` e) $C''^1$ $C''^2$ $C''^3$ $C''^4$ $C''^5$ $C''^6$ $C''^7$ (SEQ ID NO: 674), wherein $C''^1$ is D, G, R, H, Y, A, or F,   $C''^2$ is S, T, N, D, H, or K,   $C''^3$ is S, G, N, D, R, or T, $C''^4$ is S, R, N, D, A, F, K, Y, or V,   $C''^5$ is R,   $C''^6$ is P, A, or E, and   $C''^7$ is S or A;

or f) selected from the group consisting of

```
GNNNRPS RTGNRPS HSSDRPS DSSSRPS YTNNRPS DTSKRPS
SEQ ID  SEQ ID  SEQ ID  SEQ ID  SEQ ID  SEQ ID
NO: 626,NO: 675,NO: 676,NO: 677,NO: 678,NO: 679,

DSSRRPS YDGSRPS ANDARPS GHGFRPS DTRRRPS AKSNRPS
SEQ ID  SEQ ID  SEQ ID  SEQ ID  SEQ ID  SEQ ID
NO: 680,NO: 681,NO: 682,NO: 683,NO: 684,NO: 685,

GSSYRPS XSXSXPS YSSSRPS FIGSRPS RSSNRAS YNTGRPS
SEQ ID  SEQ ID  SEQ ID  SEQ ID  SEQ ID  SEQ ID
NO: 686,NO: 687,NO: 688,NO: 689,NO: 690,NO: 691,

HSSSRPS YDSSRPS GDDNRES ATSSRPS DTSSRPS DHNVRPA
SEQ ID  SEQ ID  SEQ ID  SEQ ID  SEQ ID  SEQ ID
NO: 692,NO: 693,NO: 694,NO: 695,NO: 696,NO: 697,
                                         and
GNNRRPS
SEQ ID
NO: 698.
```

In a preferred embodiment CDR$^3$ for light chains is:

a) $C'''^1$ $C'''^2$ $C'''^3$ $C'''^4$ $C'''^5$ $C'''^6$ $C'''^7$ $C'''^8$ $C'''^9$ $C'''^{10}$ $C'''^{11}$ $C'''^{12}$ (SEQ ID NO: 699)

$C'''^1$ is S or A,   $C'''^2$ is L, F, or V,   $C'''^3$ is —  or G, $C'''^4$ is Y, F, L, or R,   $C'''^5$ is T, S, or M,   $C'''^6$ is G, D, S, or V, $C'''^7$ is S, G, D, Y, T, R, or I,   $C'''^8$ is Y, Q, V, H, D, P, or S,   $C'''^9$ is —, S, or N, $C'''^{10}$ is T, S, V, I, —, or Y,   $C'''^{11}$ is A, D, V, N, P, Y, —, or G, and   $C'''^{12}$ is V, M, —, or L, b) selected from the group consisting of

| | | | | |
|---|---|---|---|---|
| SVYMGTYTVV SEQ ID NO: 700, | SLRTGYQNTM SEQ ID NO: 701, | SLYMGSYTDM SEQ ID NO: 702, | SLYMGGYSDV SEQ ID NO: 703, | SLYTGSYTAV SEQ ID NO: 704, |
| SFFTDIVVNV SEQ ID NO: 705, | SVYTDDHTPV SEQ ID NO: 706, | SFYTGDYTAV SEQ ID NO: 707, | SLYMVGYTAV SEQ ID NO: 708, | ALGFSGGDYVV SEQ ID NO: 709, |
| SLYMGSYTGL SEQ ID NO: 710, | ALGFSSSSSYV SEQ ID NO: 711, | SLYMDIYTGV SEQ ID NO: 712, | ALGLSGISSIV SEQ ID NO: 713, | SLYTGRPV SEQ ID NO: 714, |
| SLYTGSSTDV, SEQ ID NO: 715, | And | SFYTSSY; SEQ ID NO: 716; | | | c) $C'''^1 \, C'''^2 \, C'''^3 \, C'''^4 \, C'''^5 \, C'''^6 \, C'''^7 \, C'''^8 \, C'''^9 \, C'''^{10} \, C'''^{11} \, C'''^{12}$ (SEQ ID NO: 717), wherein $C'''^1$ is S, Q, or A, $C'''^2$ is S, T, A, G, or —, $C'''^3$ is W, S, L, Y, F, V, or —

$C'''^4$ is D, —, or Q, $C'''^5$ is S, N, Y, P, A, D, T, E, R, H, —, or I, $C'''^6$ is S, N, R, T, G, A, D, — or Y, $C'''^7$ is L, V, R, P, —, or F, $C'''^8$ is S, R, G, K, T, I, N, Q, P, —, or A, $C'''^9$ is G, T, S, V, A, K, D, L, I, E, —, or Y, $C'''^{10}$ is V, Y, T, P, S, —, G, L, Q, A, D, or N, $C'''^{11}$ is S, P, —, Y, A, D, I, or T, and $C'''^{12}$ is V, —, I, or L;

d) selected from the group consisting of

| | | | | |
|---|---|---|---|---|
| SSWDYSLSSTL SEQ ID NO: 718 | SSXDXSLSVVL SEQ ID NO: 719 | SSWDASRSVTV SEQ ID NO: 720 | QSLDSNLGPV SEQ ID NO: 721 | STWDDSLRAYL SEQ ID NO: 722 |
| STWDSSLKAPV SEQ ID NO: 723 | STWDNSLTVPV SEQ ID NO: 724 | STYDTRLGTSV SEQ ID NO: 725 | SSWDNNLIKIL SEQ ID NO: 726 | STYDSTLNAVV SEQ ID NO: 727 |
| SAWDNSLKLPL SEQ ID NO: 728 | SSWDTGLSALV SEQ ID NO: 729 | QSVDSTLGAIV SEQ ID NO: 730 | SSWDDSLXGIV SEQ ID NO: 731 | STYDSSLGGSV SEQ ID NO: 732 |
| SAYDSTLTGTV SEQ ID NO: 733 | STYDSSLSGPL SEQ ID NO: 734 | QSFDPTPPDHYV SEQ ID NO: 735 | SAWDSTLRAGV SEQ ID NO: 736 | STWDSSLKALL SEQ ID NO: 737 |
| QSFDTALGTV SEQ ID NO: 738 | SSWDDGLRALV SEQ ID NO: 739 | SSWDDSLKGHV SEQ ID NO: 740 | STWDENLSVPV SEQ ID NO: 741 | STWDNSVTVL SEQ ID NO: 742 |
| SSWDNDFGHV SEQ ID NO: 743 | QSFDTTLGAYV SEQ ID NO: 744 | SSWDRSLRGQV SEQ ID NO: 745 | SGYDTTVNGVV SEQ ID NO: 746 | SSWDTSLRTI SEQ ID NO: 747 |
| SASDSSLSVV SEQ ID NO: 748 | QSFDTTLGDGDVL SEQ ID NO: 749 | SSWDDSLRISV SEQ ID NO: 750 | SAWDSSLKEAV SEQ ID NO: 751 | STWDDSVTVL SEQ ID NO: 752 |
| SAHDNSVSGVV SEQ ID NO: 753 | SAWDDSLTAYV SEQ ID NO: 754 | STYDITITGGV SEQ ID NO: 755 | SSYDSSFTAD SEQ ID NO: 756 | STWDSSLKAIV SEQ ID NO: 757 |
| SSWDDSLRGHV SEQ ID NO: 758 | STWDNSLTYV SEQ ID NO: 759 | QSFQTTLNIYV SEQ ID NO: 760 | STWDASLRVGV SEQ ID NO: 761 | STWDSSLKAVV SEQ ID NO: 762 |
| STWDDSLSEPV SEQ ID | STYDTRLNDVI SEQ ID | SAWDDRLTEPV SEQ ID | QSVDHTLAAAV SEQ ID | AAYDSSLSIGV SEQ ID |

-continued

| NO: 763 | NO: 764 | NO: 765 | NO: 766 | NO: 767 |
|---|---|---|---|---|
| STWDDYLQIYV | QSLDSTRGYHIV | STWDNSLNTGV | SAYDTSLSSNF | Or SSWDSSLSGVSV |
| SEQ ID | SEQ ID | SEQ ID | SEQ ID | SEQ ID |
| NO: 768 | NO: 769 | NO: 770 | NO: 771 | NO: 772; | e) $C'''^1\ C'''^2\ C'''^3\ C'''^4\ C'''^5\ C'''^6\ C'''^7\ C'''^8\ C'''^9\ C'''^{10}\ C'''^{11}\ C'''^{12}$ (SEQ ID NO: 773)

$C'''^1$ is S, Q, or A, $C'''^2$ is A, T, or V, $C'''^3$ is Y, F, W, or G, $C'''^4$ is D, H, —, or E, $C'''^5$ is S, D, N, R, Y, or T, $C'''^6$ is S, T, N, or G, $C'''^7$ is L, I, V, T, P, or —, $C'''^8$ is S, G, R, K, D, N, A, Q, H, or —, $C'''^9$ is G, T, S, H, A, V, or —, $C'''^{10}$ is G, I, V, R, P, L, Y, S, or —, $C'''^{11}$ is A or —, and $C'''^{12}$ is V or L, f) selected from the group consisting of

| QSYDDNLDGYV | SSFDRSVSAV | SAYDTTLNAV | SSYDSSLSGGV | SAYSGTDTYV |
|---|---|---|---|---|
| SEQ ID NO: 774, | SEQ ID NO: 775, | SEQ ID NO: 776, | SEQ ID NO: 777, | SEQ ID NO: 778, |
| SSYHSSPHGVV | SSYDSEVRVV | SSWDNSQGSV | QSYDDNLAGLV | STYDNSLSVV |
| SEQ ID NO: 779, | SEQ ID NO: 780, | SEQ ID NO: 781, | SEQ ID NO: 782, | SEQ ID NO: 783, |
| ASYDRTIGGGAV | SVGDDSLKAPV | SSYDSSLSGIV | SSYDSSLDGAV | SSYESSLRGVV |
| SEQ ID NO: 784, | SEQ ID NO: 785, | SEQ ID NO: 786, | SEQ ID NO: 787, | SEQ ID NO: 788, |
| SSWDNSLKTRV | SSYDSGLSHIV | SAYDYSLSSGV | SSYDNSLSGGV | SSWDNSLKGIV |
| SEQ ID NO: 789, | SEQ ID NO: 790, | SEQ ID NO: 791, | SEQ ID NO: 792, | SEQ ID NO: 793, |
| QSYDDSLNTYV | SSYDTSLSGGV | SSYDSSLSGAV | SSYDSSLSIV | SSWDDSLRGAL |
| SEQ ID NO: 794, | SEQ ID NO: 795, | SEQ ID NO: 796, | SEQ ID NO: 797, | SEQ ID NO: 798, |
| And | SAYDSSLSGGAV SEQ ID NO: 799. | | | |

The method of choice that is used for frequency tables and CDR identification is by use of the Kabat database on the web. To get frequency tables, the tabulated data can be scored off the kabat data base program from Northwestern University using the "variability" tool under "searching and analysis tools" . . . select "distribution" table, (instead of variability plot, which is the default), a table of the frequency of each amino acid at a given position for each position in the domain it given. See Kabat, E. A., Wu, T. T., Perry, H. M., Gottesman, K. S., Foeller, C., 1991. Sequences of Proteins of Immunological Interests, 5$^{th}$ ed. US Department of Health and Human Service, National Institutes of Health, Bethesda, Md. (NIH Publication No. 91-3242).

Framework Region Variations and Other Homologous Sequences

Polypeptides of the invention also include those having one of the sequences disclosed above modified by replacement of one or more amino acids in one or more of the framework regions with a corresponding amino acid (i.e., at the same position) of a human sequence. Amino acids from human sequences are found in various publicly available databases. See paragraph [0052].

For caninized variable domains and antibodies, Fr$^1$, Fr$^2$, Fr$^3$, and Fr$^4$ framework sequences should be at least 60% homologous to the corresponding framework sequences of the non-canine antibody from which the two or three non-canine CDR's are obtained. More preferably, such sequences are at least 65%, 70%, 75%, 80%, 85%, 90%, 95%, 96%, 97%, 98%, or 99% homologous. The percent homology between sequences can be determined using any art recognized alignment algorithm. Specifically excluded from the scope of the invention are the canine variable domain polypeptide sequences disclosed in:

a) Wasserman and Capra, *Biochem.* 16, 3160 (1977)

```
evklvesggd  lvkpggslrl  scvasgftfs  sngmswvrqd  pgeglqwvad  isssgqtyya davkgrfsis  rdnakntlyl  qmedlrvedt  avyycategd  ieipryfgqg  tivtvss evqlvesggd  lvkpggslrl  scvasgitfs  gydmqwvrqa  pgkglqkvay  fndalsaqgy adavkgrfti  skdnakdsly  lqmnslraed  tavyycapwq  feywgqgtlv  tvss
(SEQ ID NO:800)
``` b) Wasserman and Capra, *Immunochem.* 15, 303 (1978):

```
divmtqtpls  lsvspgepas  iscrssqsnl  dylnwylqka  gqsprllpeq  dsqrasgvpd rfsgsgsgtd  ftlrigrvea  edagiyycmq  rsfypytfgq  gtrlevrr  (SEQ ID NO:801)
``` and c) Tang et al., *Vet. Immunology Immunopathology* 80, 259 (2001).

Homology modeling can be used to identify amino acids in the canine framework regions for back mutation to the sequence from which the non-canine CDR's are obtained, e.g., the 15A2 murine sequence. Back mutation is defined as changing an amino acid in the canine framework region "back" to the amino acid found in the non-canine framework region.

One of ordinary skill in the art can use known methods of creating a three dimensional molecular model of a non-canine antibody having one or more CDRs for use in a caninized antibody to determine appropriate back mutations. For each model, the amino acids within a 3 angstrom shell and a 6 angstrom shell surrounding the CDR's is determined. Amino acids that are found within the 3 and 6 angstrom shells have a strong likelihood of improving affinity for the target antigen. One or more amino acids of the canine antibody framework regions that corresponds to a amino acid within the 6, and preferably 3, angstrom shell are then optionally "back mutated" to the corresponding amino acid of the non-canine antibody.

For manipulation of Brookhaven Protein Data Bank (PDB) files, model building, model refinement, and prediction of specific amino acids for site directed mutagenesis, the molecular modeling/graphics program DEEP VIEW can be used. Guex, N. and Peitsch, M. C. (1997) SWISS-MODEL and the Swiss-PdbViewer: An environment for comparative protein modeling. *Electrophoresis* 18, 2714–2723. In one mode of determining appropriate back mutations by this method, the linear sequences of the non-canine antibody heavy and light chain are compared to existing sequences for which crystal structures exist (e.g., in the Brookhaven Protein Data Bank). Selected sequences are those with known crystal structure having high homology to the different non-canine antibody variable domains. The non-canine antibody heavy and light chains can then be modeled based on the known crystal structures using DEEP VIEW. For each model, the amino acids within a 3 angstrom shell and a 6 angstrom shell surrounding the CDR's is determined. Comparison of the known structures and of the amino acids within these two concentric shells about the CDR's enables identification of key amino acids that may be directly and/or indirectly influence the CDR's.

The canine variable domain polypeptides according to this aspect of the invention can be made by standard techniques known to those of ordinary skill in the art. E.g., Sambrook and Russell, "Molecular Cloning: A Laboratory Manual" (3$^{rd}$ Edition, Cold Spring Harbor Laboratory Press, Cold Spring Harbor, N.Y., 2001). Briefly, the canine variable domain polypeptides can be made via expression of the corresponding nucleic acids encoding the canine variable domain polypeptides. The nucleic acids are described more fully below. The nucleic acids according to the invention can be inserted in appropriate vectors and the canine variable domain polypeptides expressed from these vectors in suitable expression systems.

The invention also comprises a caninized variable region sequence according to any one of paragraphs [0022]–[0043] with one, two, or three CDRs according to any one of paragraphs [0046]–[0051]. The invention further comprises antibodies comprising a caninized variable region sequence according to any one of paragraphs [0022]–[0043] with 0–3 CDRs according to any one of paragraphs [0046]–[0051].

Also encompassed are sequences in which one or more amino acids have been added or deleted from one of the sequences expressly disclosed herein. Sequences differing from one of those expressly disclosed herein by substitution, deletion, and/or addition and having at least 95%, 96%, 97%, 98%, or 99% homology to the sequences expressly disclosed herein are contemplated as encompassed within the invention as well. In particular, the invention also comprises sequences that are or have within them (a) framework sequences that are 95, 96, 97, 98, or 99% homologous with the corresponding framework sequences (Fr$^1$–Fr$^4$) of the polypeptide sequences expressly disclosed herein or (b) framework sequences and CDR$^1$ and CDR$^2$ that are 95, 96, 97, 98, or 99% homologous with the corresponding sequences of the polypeptide sequences expressly disclosed herein.

A sequence that is, for example, 95% homologous with a reference sequence requires that, following alignment of the candidate sequence with the reference sequence, 95% of the amino acids in the sequence are identical to the corresponding amino acids in the reference sequence. Such a homologous sequence will include those differing from a sequence expressly disclosed herein by conservative amino acid substitutions. A conservative amino acid substitution is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

More particularly, a "conservative amino acid substitution" may involve a substitution of a native amino acid residue with a non-native residue such that there is little or no effect on the polarity or charge of the amino acid residue at that position. Furthermore, any native residue in the polypeptide may also be substituted with alanine, as has been previously described for "alanine scanning mutagenesis."

Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Naturally occurring residues may be divided into classes based on common side chain properties:
1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

For example, non-conservative substitutions may involve the exchange of a member of one of these classes for a member from another class.

In making such changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al., 1982, *J. Mol. Biol.* 157:105–31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred. One may also identify epitopes from primary amino acid sequences on the basis of hydrophilicity. These regions are also referred to as "epitopic core regions."

Desired amino acid substitutions (whether conservative or non-conservative) can be determined by those skilled in the art at the time such substitutions are desired. Exemplary amino acid substitutions are set forth in Table I.

| Amino Acid Substitutions | | |
|---|---|---|
| Original Residues | Exemplary Substitutions | Preferred Substitutions |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

In a first variable domain amino acid sequence according to the invention that differs from a second amino acid sequence according to the invention by one or more amino acid substitutions, the amino acid substitution(s) in the second sequence are preferably conservative substitutions. In identifying which amino acid to substitute into a particular position in the first variable domain sequence to arrive at the second sequence, one preferably selects an amino acid that appears in that position in a canine variable domain or a human variable domain having at least 80% (preferably at least 85%, 90%, or 95%) homology with the first sequence. The first sequence and the second sequence according to the invention will be at least 95% homologous.

Guidance concerning how to make phenotypically silent amino acid substitutions is provided in Bowie et al., *Science*, 247:1306–1310 (1990), which teaches that there are two main strategies for studying the tolerance of an amino acid sequence to change.

The first strategy exploits the tolerance of amino acid substitutions by natural selection during the process of evolution. By comparing amino acid sequences in different species, the amino acid positions which have been conserved between species can be identified. These conserved amino acids are likely important for protein function. In contrast, the amino acid positions in which substitutions have been tolerated by natural selection indicate positions which are not critical for protein function. Thus, positions tolerating amino acid substitution can be modified while still maintaining specific binding activity of the polypeptide.

The second strategy uses genetic engineering to introduce amino acid changes at specific positions of a cloned gene to identify regions critical for protein function. For example, site-directed mutagenesis or alanine-scanning mutagenesis (the introduction of single alanine mutations at every residue in the molecule) can be used (Cunningham et al., *Science,* 244:1081–1085 (1989)). The resulting variant molecules can then be tested for specific binding to antibodies of the invention.

According to Bowie et al., these two strategies have revealed that proteins are surprisingly tolerant of amino acid substitutions. The authors further indicate which amino acid changes are likely to be permissive at certain amino acid positions in the protein. For example, the most buried or interior (within the tertiary structure of the protein) amino acid residues require nonpolar side chains, whereas few features of surface or exterior side chains are generally conserved.

Methods of introducing a mutation into amino acids of a protein is well known to those skilled in the art. See, e.g., Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989)). Mutations can also be introduced using commercially available kits such as "QuikChange™ Site-Directed Mutagenesis Kit" (Stratagene). The generation of a functionally active variant of a polypeptide by replacing an amino acid that does not influence the function of a polypeptide can be accomplished by one skilled in the art.

As used herein, percent identity or homology of two amino acid sequences (or of two nucleic acid sequences) is determined using the algorithm of Karlin and Altschul (PNAS USA 87:2264–2268, 1990), modified as in Karlin and Altschul, PNAS USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score=100, wordlength=12. BLAST protein searches are performed with the XBLAST program, score=50, wordlength=3. To obtain gapped alignment for comparison purposes GappedBLAST is utilized as described in Altschul et al. (Nucleic Acids Res. 25:3389–3402, 1997). When utilizing BLAST and GappedBLAST programs the default parameters of the respective programs (e.g., XBLAST and NBLAST) are used to obtain nucleotide sequences homologous to a nucleic acid molecule of the invention.

Preferred Caninized Variable Regions

The following sequences of fully caninized heavy chain variable domains with binding affinity for canine IgE are preferred:

```
(a) H74-1:
    EVQLVQSAAEVKKPGASVKVSCKTSGYSFTDYFMNWVQQAPGAGLDWMGRINPFNGDP-

FYNQKFKGRVTLTADTSTSTAYMELSSLRAEDAAVYYCARFYYGRYYAMDYWGQGTLVTV
    (SEQ ID NO:802)

(b) H74-15:
    EVQLVQSAAEVKKPGASVKVSCKTSGYSFTDYFMNWVQQAPGKGLDWMGRINPFNGDP-

FYNQKFKGRVTLTADTSTSTAYMELSSLRAEDAAVYYCARFYYGRYYAMDYWGQGTLVTV
    (SEQ ID NO:803)

(c) H74-20:
    EVQLVQSAAEVKKPGASVKVSCKTSGYSFTDYFMNWVQQAPGAGLDWMGRINPFNGDP-

FYNQKFKGRVTLTVDTSTSTAYMELSSLRAEDAAVYYCARFYYGRYYAMDYWGQGTLVTV
    (SEQ ID NO:804)

(d) H74-41:
    EVQLVQSAAEVKKPGASVKVSCKTSGYSFTDYFMNWVQQAPGKGLDWMGRINPFNGDP-

FYNQKFKGRVTLTVDTSTSTAYMELSSLRAEDAAVYYCARFYYGRYYAMDYWGQGTLVTV
    (SEQ ID NO:805)

(e) H74-45
    EVQLVQSAAEVKKPGASVKVSCKTSGYSFTDYFMNWVQQAPGAGLDWMGRINPFNGDP-

FYNQKFKGRVTLTVDKSTSTAYMELSSLRAEDAAVYYCARFYYGRYYAMDYWGQGTLVTV
    (SEQ ID NO:806)

(f) H74-55
    EVQLVQSAAEVKKPGASVKVSCKTSGYSFTDYFMNWVQQAPGKGLDWMGRINPFNGDP-
```

-continued
```
FYNQKFKGRVTLTADKSTSTAYMELSSLRSEDAAVYYCARFYYGRYYAMDYWGQGTLVTV
(SEQ ID NO:807).

(g) H74-58
    EVQLVQSAAEVKKPGASVKVSCKTSGYSFTDYFMNWVQQAPGKGLDWMGRINPFNGDP-

FYNQKFKGRVTLTVDTSTSTAYMELRSLRAEDAAVYYCARFYYGRYYAMDYWGQGTLVTV
    (SEQ ID NO:808).
```

The following sequence of fully caninized light chain variable region Tlc with binding affinity for canine IgE is preferred:

```
(a) Tlc:
    TDSQTVVTQEPSLSVSPGGTVTLTCRSSTGAVTTSNYANWVQQTQGRAPRGIIGGPNN-

RAPGVPSRFSGSISGNKATLTITGARPEDEADYFCALWYSNHWVFGGGTHLTVL
    (SEQ ID NO:809)
```

Nucleic Acid Compositions of Matter

In a second aspect, the invention comprises nucleic acids encoding the canine variable domains. In the tables displaying the nucleic acid sequences ($N_{H58}$, $N_{H74}$, $N_{Other\ H}$, $N_{G2}$, $N_{G1}$, $N_{G3}$, $N_\kappa$, and $N_\lambda$), the underlined nucleic acid sequences code for a secretory leader sequence. The nucleic acid sequences in tables $N_{H58}$, $N_{H74}$, $N_{Other\ H}$, $N_{G2}$, $N_{G1}$, $N_{G3}$, $N_\kappa$, and $N_\lambda$ correspond to the polypeptides of the H58, H74, G2, G1, G3, and κ families in paragraphs [0022]–[0044], respectively. The polypeptides encoded by the nucleic acids of tables $N_{H58}$, $N_{H74}$, $N_{Other\ H}$, $N_{G2}$, $N_{G1}$, $N_{G3}$, $N_\kappa$, and $N_\lambda$, with and without the secretory leader sequence, are also an embodiment of the invention. The nucleic acids of the invention include the sequences in tables $N_{H58}$, $N_{H74}$, $N_{Other\ H}$, $N_{G2}$, $N_{G1}$, $N_{G3}$, $N_\kappa$, and $N_\lambda$, with and without the sequence coding the secretory leader. Tables $N_{Other\ H}$ and $N_\lambda$ include the polypeptides encoded by the disclosed nucleic acid sequences. These polypeptides, with or without the secretory leader sequence, are also an embodiment of the invention.

In particular, the nucleic acids of the invention encode a caninized light or heavy chain variable domain polypeptide and comprise framework-encoding sequences from one of the nucleic acids in tables $N_{H58}$, $N_{H74}$, $N_{Other\ H}$, $N_{G2}$, $N_{G1}$, $N_{G3}$, $N_\kappa$, and $N_\lambda$ together with CDR-encoding sequences. The framework-encoding sequences of the nucleic acids in tables $N_{H58}$, $N_{H74}$, $N_{Other\ H}$, $N_{G2}$, $N_{G1}$, $N_{G3}$, $N_\kappa$, and $N_\lambda$ are readily determinable by comparing those nucleic acid sequences with the corresponding polypeptide whose framework sequences are disclosed herein or otherwise determinable. Alternatively, one of ordinary skill in the art can routinely determine the framework encoding regions of the nucleic acid sequences of tables $N_{H58}$, $N_{H74}$, $N_{Other\ H}$, $N_{G2}$, $N_{G1}$, $N_{G3}$, $N_\kappa$, and $N_\lambda$ by comparison with known and characterized human variable domain sequences by sequence alignment using any of the accepted and widely available sequence alignment programs (discussed above). The CDR-encoding sequences will encode appropriate CDRs, such as those in paragraphs [0046]–[0051].

Also part of the invention are the nucleic acids disclosed herein having one or more conservative nucleotide substitutions. A "conservative nucleotide substitution" within a codon does not alter the amino acid encoded by the codon.

1. H58 Heavy Chain Variable Domain

In one embodiment of this aspect of the invention, the nucleic acids comprise those in the Table $N_{H58}$ (infra). These sequences encode $V_H$ polypeptides disclosed in paragraph [0024].

In the broadest embodiment, this aspect of the invention comprises any nucleic acid encoding a variable domain polypeptide disclosed in paragraph [0022] or paragraph [0023]. The sequence of the nucleic acids are routinely determinable from the polypeptides using the genetic code.

2. H74 Heavy Chain Variable Domain

In another embodiment of this aspect of the invention, the nucleic acids comprise those in the Table $N_{H74}$ (infra). These sequences encode the $V_H$ polypeptides disclosed in paragraph [0027].

In another embodiment of this aspect, the invention comprises a nucleic acid encoding a variable domain polypeptide disclosed in paragraph [0025], or, more preferably, in paragraph [0026]. In the broadest embodiment, this aspect of the invention comprises any nucleic acid encoding a variable domain polypeptide disclosed in paragraph [0025] or paragraph [0026]. The sequences of the nucleic acids are routinely determinable using the genetic code.

3. Other Heavy Chain Variable Domains

In another embodiment of this aspect of the invention, the nucleic acids comprise those in Table $N_{Other}$ H (infra).

4. Group 2 Light Chain Variable Domain

In another embodiment of this aspect of the invention, the nucleic acids comprise those in the Table $N_{G2}$ (infra). These sequences encode the Group 2 λ light chain variable domain polypeptides disclosed in paragraph [0034].

In another embodiment of this aspect, the invention comprises a nucleic acid encoding a variable domain polypeptide disclosed in paragraph [0032], or, more preferably, in paragraph [0033]. In the broadest embodiment, this embodiment of the invention comprises any nucleic acid encoding a variable domain polypeptide disclosed in paragraph [0032] or paragraph [0033]. The sequences of the nucleic acids are routinely determinable using the genetic code.

5. Group 1 Light Chain Variable Domain

In another embodiment of this aspect of the invention, the nucleic acids comprise those in the Table $N_{G1}$ (infra). These sequences encode the Group 1 light chain variable domain polypeptides disclosed in paragraph [0037].

In another embodiment of this aspect, the invention comprises a nucleic acid encoding a variable domain polypeptide disclosed in paragraph [0035], or, more preferably, in paragraph [0036]. In the broadest embodiment, this embodiment of the invention comprises any nucleic acid encoding a variable domain polypeptide disclosed in paragraph [0035] or paragraph [0036]. The sequences of the nucleic acids are routinely determinable using the genetic code.

6. Group 3 Light Chain Variable Domain

In another embodiment of this aspect of the invention, the nucleic acids comprise those in the Table $N_{G2}$ (infra). These sequences encode the Group 2 light chain variable domain polypeptides disclosed in paragraph [0040].

In another embodiment of this aspect, the invention comprises a nucleic acid encoding a variable domain polypeptide disclosed in paragraph [0038], or, more preferably, in paragraph [0039]. In the broadest embodiment, this embodiment of the invention comprises any nucleic acid encoding a variable domain polypeptide disclosed in paragraph [0038] or paragraph [0039]. The sequences of the nucleic acids are routinely determinable using the genetic code.

7. Kappa Light Chain Variable Domain

In another embodiment of this aspect of the invention, the nucleic acids comprise those in the Table $N_\kappa$ (infra). These sequences encode the kappa light chain variable domain polypeptides disclosed in paragraph [0043]. The sequences of the nucleic acids are routinely determinable using the genetic code.

In a preferred embodiment, the nucleic acids comprise a sequence from one of Tables $N_{H58}$, $N_{H74}$, $N_{Other\ H}$, $N_{G2}$, $N_{G1}$, $N_{G3}$, $N_\kappa$, or $N_\lambda$ modified as needed to code for the appropriate polypeptide of paragraph [0024], [0027], [0034], [0037], [0040], [0043] [0041], respectively. The modification comprises substituting appropriate codons into a sequence of each of these tables to yield a sequence encoding the subject polypeptide. The codon that is substituted into the sequences of tables is selected from the codons employed in any of the tables and is generally found in sequences within the same table at the same position as the position into which the codon is substituted. Thus, for example, a nucleic acid according to this aspect of the invention encoding a polypeptide that is the same as H3 (in Table $N_{H58}$) except for an A→G amino acid change at position 15 of H3 would comprise the H3 nucleic acid sequence of Table $N_{H58}$ in which the GCG codon (aa's 106–108 of the H3 nucleotide sequence encoding the A at position 15 of the H3 polypeptide) is replaced with GGG, the codon encoding the amino acid G in position 15 of H4 (and which comprises amino acids 106–108 of the H4 nucleotide sequence).

In another preferred embodiment the nucleic acids of the invention are comprised of preferred codons for the host intended to express the nucleic acids. Nakamura et al., *Nucl. Acids Res.* 28, 292 (2000). Preferred codons for numerous species ranging from prokaryotes to mammals are known and documented. E.g., Id. For in vitro applications, bacterial or other preferred codons can be employed.

The nucleic acids of the invention can be made by any suitable technique, many of which are well known to those skilled in the art. E.g., Sambrook and Russell, supra. The nucleic acids of the invention can be synthesized using automated synthesizers and PCR amplified.

Method of Making Canine Variable Domains

In another aspect, the invention comprises a method of making a canine variable domain nucleic acid by isolating it from a canine biological sample. In view of the great homology among mammalian immunoglobulins, our first attempt to isolate canine variable domain nucleic acid sequences employed degenerate primers based on human and mouse variable domain sequences. This approach was taken because no canine variable domain nucleic acid sequences were known to date. We were surprised to discover that employing 5' primers and anchoring the reactions in the canine constant domain sequences at the 3' end, all reactions for light chains failed and heavy chain amplifications were successful at a very low rate (only 1 positive reaction out of 21 possible positive reactions). The tremendous homology among mammalian immunoglobulins made this difficulty unforeseeable. Accordingly, another approach was required, which comprises the method of this aspect of the invention.

In this aspect, the invention comprises a method of making a canine variable domain nucleic acid sequence, which method comprises subjecting a canine biological sample to 5' RACE (Rapid Amplification of cDNA Ends) using a first antisense gene specific primer complementary to a canine constant region sequence and a second gene specific sequence complementary to a sequence within the canine constant region 5' to the sequence to which the first antisense gene specific primer is complementary, wherein the canine biological sample comprises poly(A)+RNA encoding at least one canine immunoglobulin. Preferably the canine biological sample comprises canine peripheral blood lymphocytes. The 5' RACE technique is well known to those skilled in the art and has been the subject of several reviews. E.g., Frohman, M. A. (1990) "PCR Protocols: A Guide to Methods and Applications" (Innis, M. A., Gelfand, D. H., Sninsky, J. J., and White, T. J., eds.) p. 28, Academic Press, San Diego); Loh, E. (1991) Methods 2, 11; and Frohman, M. A., (1993) Rapid Amplification of Complementary DNA Ends for Generation of Full-Length Complementary DNAs: Thermal RACE. *Methods in Enzymology* 218:340–356.

Many canine constant domain sequences are known in the art and can be employed to generate the first and second gene specific primers: Patel et al., *Immunogenetics* 1995; 41(5):282–6; Tang et al. *Vet Immunol Immunopathol Aug.* 10, 2001; 80(3–4):259–70; Wasserman et al., Science 200 (4346), 1159–1161 (1978); U.S. Pat. No. 5,593,851; U.S. Pat. No. 5,852,183; JP 1997169795-A 3 30 Jun. 1997 (Hitachi Chem Co Ltd); JP 1992040894-A 1 12 Feb. 1992 (Chemo Sero Therapeut Res Inst); JP 1991123489-A 1 27 May 1991 (Chemo Sero Therapeut Res Inst); JP 1991083579-A 1 09 Apr. 1991 (Chemo Sero Therapeut Res Inst); Wasserman et al., *Biochemistry* 16 (14), 3160–3168 (1977); McCumber et al., *Mol. Immunol.* 16 (8), 565–570 (1979).

Caninized Antibodies and Methods of Making Them

The present invention provides novel methods for preparing caninized immunoglobulin chains having generally one or more complementarity determining regions (CDR's) from a donor immunoglobulin and a framework region from a canine immunoglobulin. Caninization is accomplished by replacing one or more CDR's of a canine immunoglobulin with a CDR from a non-canine source. According to this aspect of the invention, the non-canine CDR can be substituted for the corresponding CDR in the complete canine immunoglobulin (or binding fragment thereof) directly, or it can be substituted into an immunoglobulin fragment containing the CDR locus (e.g., the variable domain) and the substituted fragment thereafter made into the entire immunoglobulin or binding fragment thereof.

The preferred method comprises first comparing the framework or variable region amino acid sequence of the donor immunoglobulin to corresponding sequences in a collection of canine immunoglobulin chains, and selecting as the canine immunoglobulin one of the more homologous sequences from the collection. The canine immunoglobulin, or acceptor immunoglobulin, sequence is typically selected from a collection of at least 10 to 20 immunoglobulin variable region sequences, and usually will have the highest homology to the donor immunoglobulin sequence of any sequence in the collection. The canine immunoglobulin framework sequence will typically have about 60 to 70% homology or more to the donor immunoglobulin framework sequences. The donor immunoglobulin can be either a heavy chain or light chain, and the canine collection will contain the same kind of chain. A caninized light and heavy chain can be used to form a complete caninized immunoglobulin or antibody, having two light/heavy chain pairs, with or without partial or full-length canine constant regions.

To form the caninized variable region, amino acids in the canine acceptor sequence are replaced by the corresponding amino acids from the CDR of the donor sequence using methods well known to those skilled in the art (e.g., PCR amplification of the variable domain nucleic acid sequence employing primers comprising, in part, the donor CDR coding, as exemplified in Example 5).

In another embodiment of the present invention, either in conjunction with the above comparison step or separately, additional amino acids in the acceptor immunoglobulin chain (preferably the light chain) can be replaced with amino acids from the CDR-donor immunoglobulin chain. More specifically, further optional substitutions of a canine framework amino acid of the acceptor immunoglobulin with the corresponding amino acid from a donor immunoglobulin will be made at positions wherein:
  a. the amino acid in the canine framework region of the acceptor immunoglobulin is rare for that position and the corresponding amino acid in the donor immunoglobulin is common for that position in canine immunoglobulin sequences;
  b. the amino acid is immediately adjacent to one of the CDR's;
  c. the amino acid is predicted to be within about 6 angstroms of the CDR's in a three-dimensional immunoglobulin model and capable of interacting with the antigen or with the CDR's of the donor or caninized immunoglobulin; or
  d. the amino acid in the canine framework region of the acceptor immunoglobulin differs from the corresponding amino acid of the donor immunoglobulin.

Optionally, an amino acid in the acceptor sequence can be replaced with an amino acid typical for canine sequences at that position, if the amino acid in the acceptor immunoglobulin is rare for that position and the corresponding amino acid in the donor immunoglobulin is also rare, relative to other canine sequences.

When combined into an intact antibody, the caninized light and heavy chains of the present invention will be substantially non-immunogenic in canines and retain substantially the same affinity as the donor immunoglobulin to the antigen (such as a protein or other compound containing an epitope). These affinity levels can vary from about $10^8$ $M^{-1}$ or higher, and may be within about 4 fold, preferably within about 2 fold of the donor immunoglobulin. Ideally, the caninized antibodies exhibit affinity levels at least about 60 to 90% of the donor immunoglobulin's original affinity to the antigen.

Once designed, the immunoglobulins of the present invention (including binding fragments) can be produced readily by a variety of recombinant DNA or other techniques. Preferably, polynucleotides encoding the desired amino acid sequences are produced synthetically and by nucleic acid sequences joined, where necessary, using PCR. The polynucleotides can be amplified using PCR or, preferably, inserted into an appropriate cloning vehicle and the encoded polypeptide expressed in a suitable expression system.

Notably, the methods of the present invention maximize the likelihood of producing caninized immunoglobulins with optimum binding characteristics. The caninized immunoglobulins are particularly useful in treating canine disorders susceptible to monoclonal antibody therapy. Thus, in another aspect, the invention comprises methods of treating a canine having an IgE-mediated affliction by administering to the canine an amount of a caninized antibody of the invention (or binding fragment thereof) sufficient to alleviate or eliminate one or more symptoms associated with the affliction.

In addition to complete caninized immunoglobulins, the invention also comprises binding fragments thereof. The use and generation of fragments of antibodies is well known, e.g., Fab fragments [Tijssen, Practice and Theory of Enzyme Immunoassays (Elsevier, Amsterdam, 1985)], Fv fragments [Hochman et al., Biochemistry 12:1130 (1973), scFv fragments (Phage Display: A Laboratory Manual. Carl F. Barbas III, Dennis R. Burton, Jamie K. Scott and Gregg J. Silverman. Cold Spring Harbor Laboratory Press. Cold Spring Harbor, N.Y.).

In another aspect, the invention provides a composition comprising at least one caninized antibody of the invention and a pharmaceutically acceptable carrier.

Caninized antibodies and binding fragments thereof are also useful for in vitro assays for detecting the presence of an antigen in a biological sample.

EXAMPLES

Example 1

Isolation of Canine Variable Domains

Canine lambda and kappa light-chain variable domain cDNA's, as well as IgG$_H$ variable domain cDNA's were synthesized from mRNA isolated from canine peripheral blood lymphocytes (PBL's). Variable domain cDNA's from B-cells that had undergone V-D-J recombination and coded for functional molecules were targeted.

Five to 10 mls of canine blood was collected in Vacutainer CPT™ sodium citrate collection tubes and spun 1,500×g for 20 minutes. After aspiration of the plasma layer, the mononuclear cell layer was collected and washed with PBS. The cell pellet was resuspended into 2 ml of PBS and the polyadenylated mRNA isolated using the Micro-fast Track mRNA isolation kit (Invitrogen) as specified by the manufacturer. After isolation mRNA was stored as a precipitate in ethanol at −80° C.

Variable domains were synthesized from mRNA using a 5'RACE kit (GIBCO Life Technologies, Version 2.0). Briefly, first strand cDNA's were generated from poly(A)+ RNA by SuperScript RT II enzyme (GIBCO Life Technologies) using the antisense gene specific primers (GSP1) complementary to canine constant regions of the lambda, kappa or IgG$_H$ constant regions. For isolation of heavy chain variable domains, GSP1 primers were derived from DNA sequences that are identical in the four different canine IgG constant chains that code for subdomain 1: two are disclosed in U.S. Pat. No. 5,593,861 (DE94 and DB31), and the other two (1e5b and 3k9c) were cloned by applicants. For isolation of light chain variable domains, GSP1 primers were derived from the sequence of the constant regions of the lambda and kappa constant domains as disclosed in the U.S. Pat. No. 5,593,861. The GSP1 primers employed are listed in the following table.

TABLE 1A

GSP1 Primers

| | |
|---|---|
| GSP1 primers for lambda first strand cDNA synthesis | LG014: 5'GTCAGGCTCAGGTAGCTG (SEQ ID NO:810) |
| | LG011: 5'GGCCGCGTACTTGTTGTTG (SEQ ID NO:811) |
| | LG010: 5'GTCGCTGATGAGGCACACC (SEQ ID NO:812) |
| GSP1 primers for Kappa first strand cDNA synthesis | LG018: 5'GCTCTTGTGAGTGATCTCAC (SEQ ID NO:813) |
| | LG017: 5'GTGCTGCTGAGGCTGTAGG (SEQ ID NO:814) |
| | LG016: 5'CCATCCACTTTCCACTTGAC (SEQ ID NO:815) |
| GSP1 primers for IgG$_H$ first strand cDNA synthesis | RK285: 5'GGCTTGTCTACTTTAGTTTTG (SEQ ID NO:816) |
| | RK321: 5'ACTTTAGTGTTGGTGGCCGGGTGG (SEQ ID NO:817) |
| | RK322: 5'ACTTTAGTTTTGCTGGCCGGGTGG (SEQ ID NO:818) |
| | RK323: 5'CTCGCATTCTTTGACCACTGGCTTGTC (SEQ ID NO:819) |
| | RK324: 5'TCTGCATTCATTGAACACTGGCTTGTC (SEQ ID NO:820) |

After first strand syntheses, the RNA was degraded with RNAse Mix and the cDNA was purified with the Glassmax Spin Cartridgy system. The cDNA was then dC-tailed using terminal deoxynucleotide transferase. PCR amplification was performed using the Gibco Abridged Anchor Primer and the appropriate nested GSP2 primer. GSP2 primers were derived for the heavy and light chains from the same sequence used for the GSP1 primers, but modified as described by the 5' RACE protocol. The GSP2 primers employed are listed in the following table.

TABLE 1B

GSP2 Primers

| | |
|---|---|
| Nested GSP2 primers for the amplification of lambda variable regions | LG011: 5'GGCCGCGTACTTGTTGTTG (SEQ ID NO:811) |
| | LG010: 5'GTCGCTGATGAGGCACACC (SEQ ID NO:812) |
| | LG012: 5'GAGCTCCTCAGAGGAG (SEQ ID NO:821) |
| Nested GSP2 primers for the amplification of Kappa variable regions | LG017: 5'GTGCTGCTGAGGCTGTAGG (SEQ ID NO:814) |
| | LG016: 5'CCATCCACTTTCCACTTGAC (SEQ ID NO:815) |
| | LG047: 5'CAGAGGCACTTCCTGTGTGTAACTGG (SEQ ID NO:822) |
| Nested GSP2 primers for the amplification of IgG$_H$ variable regions | RK120: 5'ACCGCTGGTCAAGGAGCCG (SEQ ID NO:823) |
| | RK122: 5'TGGACCACGTTGCAGGTGAAG (SEQ ID NO:824) |
| | RK281: 5'TACAGGCTCGGGGAAGTAG (SEQ ID NO:8205 |
| | RK282: 5'GGGGTCCAGTGGGAAAAC (SEQ ID NO:826) |

TABLE 1B-continued

GSP2 Primers

RK326: 5'GTCTCGCTGGACCACCTGCTGGA
(SEQ ID NO:827)

RK321: 5'ACTTTAGTGTTGGTGGCCGGGTGG
(SEQ ID NO:817)

RK322: 5'ACTTTAGTTTTGCTGGCCGGGTGG
(SEQ ID NO:818)

The amplified cDNA's were then cloned using the PCR 2.1 TOPO TA Cloning kit (Invitrogen) and TOP 10 competent cells (Invitrogen) according the manufacturer's protocol. Plasmid DNA was isolated from single colonies grown in a 5 ml Luria's Broth culture overnight at 37° C. was then isolated using the Qiaspin Mini Isolation kit (QIAGEN) according to the manufacturer's protocol. Automated sequencing of the plasmid inserts was done at the University of Virginia's sequencing facility using an ABI PRISM sequencer model 377 Version 3.3.

DNA sequences were analyzed using the Hitachi DNAsis program. Clones possessing an open reading frame characteristic of a variable domain were selected for compilation of a canine immunoglobulin DNA database. Initial criteria used to evaluate potential heavy chain variable domain clones were the presence of the primer used for 5'RACE at the 3' end of the putative reading frame, the presence of sequences corresponding to the 4 IgG heavy chain constant domain sequences 5' to the sequence of the primer used in 5'RACE, and, after translation of the DNA sequence to the amino acid sequence, the presence the highly conserved cysteines at positions 22 and 96. Criteria used to evaluate potential lambda chain variable domain clones were the presence of the primer used for 5'RACE at the 3'end of the putative reading frame, the presence of sequences corresponding to the kappa chain constant domain 5' to the sequence of the primer used for 5'RACE, and, after translation of the DNA sequence to the amino acid sequence, the presence of the highly conserved cysteines at positions 22 and 90 for lambda chains. Criteria used to evaluate potential kappa chain variable domain clones was the presence of the primer used for 5'RACE at the 3'end of the putative reading frame, the presence of sequences corresponding to the kappa chain constant domain 5' to the sequence of the primer used for 5'RACE, and, after translation of the DNA sequence to the amino acid sequence, the presence of the highly conserved cysteines at positions 23 and 93 for kappa chains.

Sequences with the highest homology to 15A2 were chosen as templates for caninization. Variable domains were first sorted based on the type of constant domains to which they were attached: IgG heavy chains, lambda chains, or kappa chains. Then, using the Hitachi DNAsis protein alignment program, variable domain sequences were grouped into separate genera based on homology and compared to the sequence of the 15A2 heavy chain variable domain or 15A2 light chain variable domain as appropriate. The ranking of regions of homology between mouse 15A2 and the cloned canine variable domain sequences is as follows: first appropriate variable domain family (lambda with lambda, heavy chain variable with heavy chain variable) followed by homology in framework regions 1, 2 and 3, followed by homology in CDR3 of the cloned canine variable domain with the amino acid sequences in CDR3 of the 15A2 heavy or light chain as appropriate.

Example 2

Grafting Variable Domains onto Appropriate Constant Domain

Variable domains that were considered suitable for CDR grafting were fused to the appropriate constant domain (lambda or IgG$_H$) using tailed PCR reactions and tested for expression in a transient COS cell expression system.

Full length clones of canine variable domains include the secretory leader sequence that is proteolytically cleaved from the immunoglobulin during protein synthesis, secretion, and folding. For heavy chain variable domains, an oligonucleotide was synthesized corresponding to the secretory leader sequence of MDWTWRVFFLALLALATGVHS (SEQ ID NO: 828) with a consensus Kozak sequence added to the 5' end (RK278: 5'-GGATCCGCCACCATGAACTTGTGGCTAAACT (SEQ ID NO: 829) for H58 and RK271: 5'-GGATCCGCCACCATGGACTGGACCTGGAGGGTC (SEQ ID NO: 830) for H74). This oligo was paired with RK276 (sequence ACCGAGGGCGCCGTGGTGGA; SEQ ID NO: 831) and the heavy chain variable domain PCR amplified using the pCR2.1 TOPO clone as a DNA template. In a separate PCR reaction, the IgG$_H$ DE94 constant domain (U.S. Pat. No. 5,593,861) was amplified using RK275: 5'-TCCACCACGGCGCCCTCGGT (SEQ ID NO: 832) and RK186 5'-GGGTCTAGAGCCCTTTCATTTACCCGGAGAATG (SEQ ID NO: 833). The products from these reactions were verified by checking their size using agarose gel electrophoresis, followed by gel purification.

After gel purification, approximately 2 ng of each PCR product were combined, mixed with 2 μm of 5' the primer RK271 and 2 μm of the 3' primer RK186, and subjected to PCR amplification to fuse the DNA coding for the variable domain to the DNA coding for the constant domain. The RK275 and RK276 primers create an overlap of the DNA coding sequence corresponding to the variable domain/CH1 domain junction. This overlap allows the fusion of the DNA coding for the variable to the DNA coding for the constant domain during the PCR reaction. After amplification, PCR products were gel purified, phenol-chloroform extracted and EtOH ppt. After re-suspension into TE, the amplified variable domains were then cloned using the pcDNA3.1 TOPO TA Cloning kit (Invitrogen) and transformed into TOP 10 competent cells (Invitrogen) according the manufacturer's protocol. Plasmid DNA was isolated from single colonies grown in a 5 ml Luria's Broth culture overnight at 37° C.

was then isolated using the Qiaspin Mini Isolation kit (QIAGEN) according to the manufacturer's protocol. Clones of functional heavy chains were screened for as described below.

Full length clones of canine immunoglobulins include the secretory leader sequence that is proteolytically cleaved from the mature protein chain, the variable domain, and the constant domains. For the lambda variable domain, an oligonucleotide was synthesized corresponding to the secretory leader sequence with a consensus Kozak sequence added to the 5' end (LG036: 5'-CTACGATCTCT-GAGAGTCC; SEQ ID NO: 834 for Group 2). This oligo was paired with LG012: 5'-GAGCTCCTCAGAGGAG (SEQ ID NO: 821) and the light chain variable domain amplified using PCR. In a separate PCR reaction, the lambda constant domain was amplified using LG035: CCGCCCTC-CTCTGAGGAG (SEQ ID NO: 835) and LG027: 5'-CTAA-GAGCACTCTGCGGG (SEQ ID NO: 836). The products from these reactions were verified by checking their size using agarose gel electrophoresis, followed by gel purification.

Approximately 2 ng of each PCR product were combined, mixed with 2 μm of LG036 and 2 μm of LG027, and PCR amplified as described. PCR products were gel purified, phenol-chloroform extracted and EtOH ppt. After re-suspension into TE, the amplified the full length immunoglobulin chains were then cloned using the pcDNA3.1 TOPO TA Cloning kit (Invitrogen) and TOP 10 competent cells (Invitrogen) according the manufacturer's protocol. Plasmid DNA from single colonies grown in a 5 ml Luria's Broth culture overnight at 37° C. was then isolated using the Qiaspin Mini Isolation kit (QIAGEN) according to the manufacturer's protocol. Clones of functional light chains were screened for as described below.

Example 3

Screening for Functional Variable Domains

DNA clones of functional variable domains were identified using a screen that was dependant on the efficient secretion of an $IgG_H$ chain in a transient COS cell expression system. COS cells were transfected with no DNA (mock transfection), Hx only (1 μg of the Hx expression vector), HxLx (1 μg each of the Hx and Lx expression vectors), or Hx1C9L (1 μg of the Hx expression vector and 1 μg of an expression vector coding for the 1C9 kappa light chain). DNAs and cell culture supernatants were collected at 48 and 72 hours. Tissue culture supernatants were then assayed for IgG by ELISA, as described in Example 4

Without a functional light chain, $IgG_H$ chains are inefficiently secreted from COS cells by T=48 hours post transfection (see FIG. 1). Screening of potential light chain clones was accomplished by co-transfection with an expression clone for the 15A2 chimeric heavy chain. Conversely, screening of potential heavy chain clones was accomplished by co-transfecting with an expression clone for the 15A2 chimeric light chain.

Screening full-length lambda chains involved co-transfecting 10 μl of miniprep DNA with 1 μg of pcDNA3.1::c15A2IgG$_H$. COS cells 75–95% confluent in six well COS-TAR (Corning Inc.) tissue culture plates were used for transfections. DNA was diluted with 230 μl Opti-MEM®I (Gibco BRL) to a final volume of 250 μl. 10 μl of Lipofect AMINE™ 2000 (Gibco-BRL) was diluted with 240 μl of Opti-MEM®I, mixed with the diluted DNA and allowed to incubate at room temperature for 20 minutes to allow the DNA to complex with the Lipofect AMINE™ 2000. During incubation, cells were prepared by removal of growth medium followed by the addition of 500 μl of Opti-MEM®I.

The 0.5 ml DNA/LP2000 complex was added to each well and allowed to incubate 5 hours. An additional 1 ml of growth medium was added to each well (DMEM plus 20% fetal bovine serum, plus L-glu), after which cell culture supernatants were harvested at T=48 hours.

Cell culture supernatants were clarified of cellular debris by centrifugation at 1,000×g for 5 minutes and adjusted to a final concentration of 0.02% sodium azide to prevent bacterial growth. Cell culture supernatants were assayed immediately for $IgG_H$ levels and IgE binding activity or frozen at −20° C. to be assayed at a later time. Control tissue culture wells were prepared by receiving no DNA, pcDNA3.1::c15A2IgG$_H$ only, or pcDNA3.1::c15A2Ig$_H$/ pcDNA3.1c15A2::lambda. Production of $IgG_H$ was assayed for as described below.

Clones scoring positive in this assay were re-transformed into E. coli for large scale DNA isolation using the Qiagen Endotoxin Free Kit (Qiagen Corp., Valencia, Calif.) and sent out for DNA sequencing.

Screening for full-length heavy chain expression clones was done in an identical manner, except 10 μl of miniprep DNA of the potential heavy-chain expression clone was co-transfected with 1 μg of pcDNA3.1:c15A2lambda DNA.

Isolates that encoded for functional variable domains that were of the correct DNA sequence were transfected into COS cells as described above using the ratio of 1 μg light chain to 1 ug of heavy chain. Cell supernatants were collected and scored for $IgG_H$ secretion, IgE binding, and the ability to compete with the recombinant high affinity IgE receptor for soluble IgE.

Example 4

ELISA Assays

To assay for $IgG_H$ expression, ELISA assays were performed 96 well Immulon 4 plates (Thermo Lab Systems, Helsinki, Finland). Throughout this study, four different type of ELISA assays were performed. Determination of $IgG_H$ concentration, IgE binding, IgE mimotope binding, and the neutralization of soluble IgE assay.

To determine $IgG_H$ concentration in cell culture supernatants, 96 well plates were coated with rabbit anti-dog Fc (Jackson Immunologicals, West Grove, Pa.) diluted to 2 μg/ml in sodium carbonate buffer (100 mM, pH 10), with 100 μl applied to each well of the plate. Non-specific binding to the plates was prevented by blocking the plates with 3% bovine serum albumin. A chimeric 15A2 standard was prepared by diluting baculoviral expressed protein to 100, 50, 25, 12.5, 6.25 and 3.13 ng/ml in OptiMEM. Serial dilutions of cell culture supernatants were prepared in Opti-MEM and 100 μl of each dilution was applied to the plate and incubated for 1 hour at room temperature. After incubation plates were washed 5 times with TBS 0.1% Tween 20. For detection of bound antibody, 100 μl of anti-dog Fc Horse Radish Peroxidase (HRP) conjugate (Jackson Immunologicals) diluted 1:5000 in conjugate diluent (IDEXX Labs, Inc., Westbrook, Me.), applied to each well and allowed to incubate for 1 hour at room temperature. After 5 washes with TBS 0.1% Tween 20, the presence of bound rabbit anti-dog HRP conjugate was detected by the addition of TMB substrate (IDEXX Labs, Inc.), allowed to develop for 10 minutes followed by the addition of stop solution (100 μl/well, IDEXX Labs, Inc.). Optical density was read at 650 nm using SOFTmax Pro software to plot a standard curve and analyze data. The activity of IgG expression activity was scored by comparison to the dilution standards of recombinant c15A2, as well as the activity in the transfection controls.

To determine IgE binding activity, 96 Immunolon 4 plates were coated with recombinant canine IgE diluted to 2.5

μg/ml in sodium carbonate buffer (100 mM, pH 9.5), 100 μl applied to each well of the plate. Non-specific binding to the plates was prevented by blocking the plates with 3% bovine serum albumin. Preparation of standards and detection of IgG$_H$ is exactly as described above.

To determine IgE mimotope binding activity, plates were coated with a peptide/KLH conjugate at 2 μg per ml, diluted in sodium carbonate buffer (100 mM, pH 9.5). The peptide mimics the 15A2 epitope found on IgE. Non-specific binding to the plates was prevented by blocking the plates with 3% bovine serum albumin. Preparation of standards and detection of IgG$_H$ is exactly as described above.

The neutralization of soluble IgE assay determines the ability of anti-IgE immunoglobulin molecules to bind and prevent soluble IgE from interacting with the high affinity IgE receptor. The 15A2 immunoglobulin binds to subdomain three of IgE, preventing it from interacting with the high affinity IgE receptor. 96 well Immulon 4 plates are coated with the high affinity IgE receptor diluted to 10 μg per ml in sodium carbonate buffer, with 100 μl applied to each well of the plate. Non-specific binding to the plates was prevented by blocking the plates with 3% bovine serum albumin. IgE was diluted to 100 ng/ml in OptiMEM medium. Serial dilutions of clarified cell culture supernatants were prepared, and mixed 1:1 (final volume 200 μl) with the diluted IgE (final concentration 50 ng). After incubation for 1 hour at room temperature, this mixture was applied to high affinity IgE receptor plate. After incubation for 1 hour, plates were washed 5 times with TBS 0.1% Tween 20. For detection of bound antibody, 100 μl of an anti-IgE monoclonal antibody conjugated to HRP diluted to 2 μg/ml in conjugate diluent (IDEXX Labs, Inc.) was applied to each well and allowed to incubate for 1 hour at room temperature. After 5 washes with TBS 0.1% Tween 20, the presence of bound anti-IgE HRP conjugate was detected by the addition of TMB substrate (IDEXX Labs, Inc.), allowed to develop for 10 minutes followed by the addition of stop solution (100 μl/well, IDEXX Labs, Inc.).

Example 5

CDR Grafting

The complimentary determinant regions (CDR's) of mouse 15A2 were identified using the Kabat numbering system for variable domains as well as homology alignments to other mouse variable domains to which the CDR's had been identified.

CDR grafting was accomplished using the PCR reaction. The protocol for PCR amplification was performed as described, except "tailed" oligos carrying mutations of interest were used to modify the coding sequence of canine variable domains. Once a suitable heavy chain was identified for CDR grafting, synthetic oligo nucleotides were synthesized and used as shown in FIG. 5. The isolated canine variable domains serving as a template for the PCR reactions. The comparison of murine 15A2 to the canine variable domains chosen as graft recipients is in FIGS. 2 and 3. The oligonucleotides used to graft the 15A2 CDR's into the H74 heavy chain and Group 2 light chain are shown in the following tables:

TABLE 2

| CDR Grafting Group 2 | |
|---|---|
| N-terminal primer: | LG036: 5' CTACGATCTCTGAGAGTCC (SEQ ID NO:834) |
| CDR1 primers: | LG029: 5' CGTCACCGCACCCGTGCTGCTGCGACATGTGAGTGTGACTGTCC (SEQ ID NO:837) |
| | LG037: 5' CGCAGCAGCACGGGTGCGGTGACGACGAGCAACTACGCCAA CTGGTATCAGCAGACCCAAGG (SEQ ID NO:838) |
| CDR2 primers: | LG038: 5' CGGCGCTCTGTTGTTAGGGCCGTAGATAATCGTGCGAGG (SEQ ID NO:839) |
| | LG039: 5' GGCCCTAACAACAGAGCGCCGGGCGTCCCTAGTCGCTTCTCTGG (SEQ ID NO:840) |
| CDR3 primers: | LG034: 5' TGGTACAGCAACCATTGGGTGTTCGGCGGAGGCACCCACC (SEQ ID NO:841) |
| | LG040: 5' CACCCAATGGTTGCTGTACCACAACGCACAGTGATAGTCAGCCTC ATCC (SEQ ID NO:842) |
| C-terminal primer: | LG027: 5' CTAAGAGCACTCTGCGGG (SEQ ID NO:836) |

TABLE 3

| H74 Caninization Oligonucleotides | |
|---|---|
| N-terminal primer: | RK271: 5'GGATCCGCCACCATGGACTGGACCTGGAGGGTC (SEQ ID NO:830) |
| CDR1 primers: | RK292: 5'TCATTTACTGACTACTTTATGAACTGGGTAC (SEQ ID NO:843) |

TABLE 3-continued H74 Caninization Oligonucleotides

|  | | |
|---|---|---|
| | RK293: 5'AAAGTAGTCAGTAAATGAGTAACCAGA (SEQ ID NO:844) | |
| CDR2 primers: | RK294: 5'GGTGATCCTTTCTACAACCAGAAGTTCAAGGGCAGAGTC (SEQ ID NO:845) | |
| | RK295: 5'GTTGTAGAAAGGATCACCATTGAAAGGATTAATACGTCCCATCCA (SEQ ID NO:846) | |
| CDR3 primers: | RK308: 5'GTGTACTACTGCGCAAGATTCTAC (SEQ ID NO:847) | |
| | RK309: 5'GTAGAATCTTGCGCAGTAGTACAC (SEQ ID NO:848) | |
| C-terminal primer: | RK186: 5'GGGTCTAGAGCCCTTTCATTTACCCGGAGAATG (SEQ ID NO:833) | |

The final products of these PCR reactions were cloned into pcDNA3.1 TOPO as described. Individual clones were screened for functional secretion of IgG$_H$ chains as described above and positive isolates had their DNA sequenced as described.

Isolates that encoded for functional variable domains and were of the correct DNA sequence were transfected into COS cells as described above. Cell supernatants were collected and scored for IgG$_H$ concentration, IgE binding, and the ability to neutralize soluble IgE and prevent it from interacting with the high affinity IgE receptor. The results manifest IgE binding by the fully caninized molecules are displayed below. Table 4 reports the OD at 650 nm of ELISA assays performed as described. COS cell supernatants are from cells transfected with the shown constructs. Table 5 displays relative concentration levels when compared to expression levels for the 15A2 chimeric antibody. Table 6 displays OD of IgE Binding over relative expression levels. Table 7 displays the ratio IgE binding/expression.

TABLE 4

IgE Binding - Transient COS System

| | Group 2-1 | Lx |
|---|---|---|
| H74-1 | Negative | 1.3 |
| Hx | 0.32 | 3.0 |

TABLE 5

Relative expression levels - IgG concentration assay

| | Group 2-1 | Lx |
|---|---|---|
| H74-1 | 2.4 | 0.1 |
| Hx | 2.7 | 1 |

TABLE 6

OD of IgE Binding over relative expression levels

| | Group 2-1 | Lx |
|---|---|---|
| H74-1 | 2.4/0 | 1.3/.1 |
| Hx | 0.32/2.7 | 3/1 |

TABLE 7

Ratio IgE Binding/Expression

| | Group 2-1 | Lx |
|---|---|---|
| H74-1 | Null | 13 |
| Hx | 0.12 | 3 |

The binding affinity and IgE neutralization by a recombinant molecule in in vivo applications is preferably higher than displayed above. Accordingly, we undertook additional modifications of the caninized immunoglobulin to improve it's binding affinity for IgE.

Example 6

Homology Modeling and Site Directed Mutagenesis

Homology modeling was used to identify potential amino acids from the canine framework regions for back mutations to the 15A2 murine sequence. For manipulation of Brookhaven Protein Data Bank (PDB) files, model building, model refinement, and prediction of specific amino acids for site directed mutagenesis, the molecular modeling/graphics program DEEP VIEW was used. Guex, N. and Peitsch, M. C. (1997) SWISS-MODEL and the Swiss-PdbViewer: An environment for comparative protein modeling. *Electrophoresis* 18, 2714–2723. DEEP VIEW was formerly known as Swiss-PdbViewer.

The linear sequences of murine 15A2 heavy and light chain were found to have high homology to three different variable domains for which crystal structures existed in the Brookhaven Protein Data Bank, designated 1NGQ, 1FBI, and 2VIR. The murine 15A2 heavy and light chains were modeled onto these three separate crystal structures using DEEP VIEW. For each model, the amino acids within a 3 angstrom shell and a 6 angstrom shell surrounding the CDR's was determined. Comparison of the three structures, and of the amino acids within these two concentric shells about the CDR's identified key amino acids that could be in direct and indirect contact supporting the CDR's. Amino acids that were found within the 3 and 6 angstrom shell in all three structures were scored as high for affecting CDR conformation.

FIG. 5 shows the alignment of the Group 2-1 variable domain with the mouse 15A2 light chain variable domain, and H74-1 with the mouse 15A2 heavy chain variable domain. The CDRs are displayed in large, bold, underline typeface, the amino acids that make up the 3 angstrom shell displayed in bold, and amino acids that make up the 6 angstrom shell underlined. Amino acid differences between these domains are indicated with vertical hash marks. Those amino acids which are different within the 3 angstrom and 6 angstrom shells of the CDR's were designated for back mutation. Back mutation is defined as changing an amino acid in the canine framework region "back" to the amino acid found in the mouse framework region. It is believed these amino acids support the CDR's of the antibody, and changing the shell of amino acids supporting the CDR's to sequences found in mouse have the greatest potential in improving affinity for the target antigen.

Figure 6:
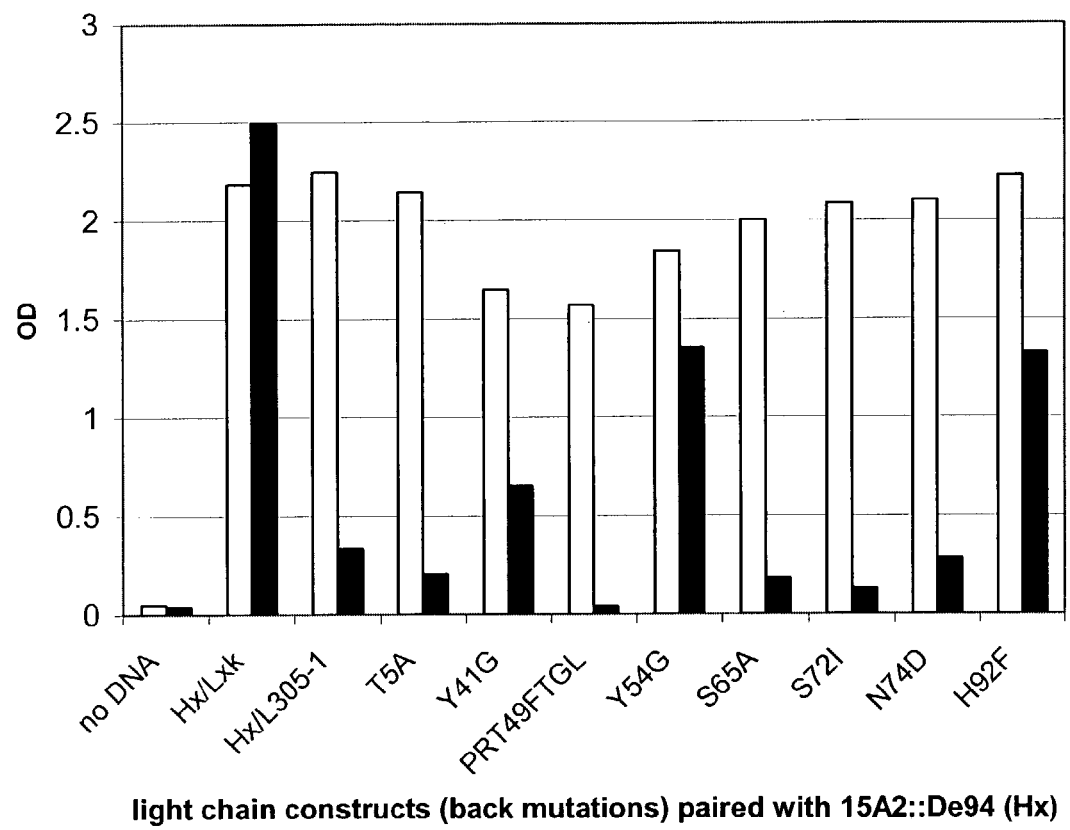
FIG. 6 displays enhanced binding to IgE by caninized light chain variable domains carrying back mutations.

For the light chain: T5A, Y41V, PRTI49FTGC, Y54G, S65A, S72I, N74D and H92F received this designation. Individual Group 2-1 derivatives carrying each back mutation were constructed as described above and coexpressed with the chimeric heavy chain in the transient COS cell expression system as described above. For example, Y51G is the Group 2-1 light chain carrying the additional Y51G mutation, that has been co-transfected with the 15A2 chimeric heavy chain (Hx) into COS cells as described. COS cells are transiently transfected by the indicated DNA's. At T=48 hours, COS cell supernatants are collected and assayed for canine immunoglobulin concentration and IgE binding activity. FIG. 6 shows the OD at 650 nm of Elisa assays that measured canine IgG concentration (anti-dog) or IgE binding activity. In this assay, three Group 2-1 back mutations are found to enhance IgE binding activity of Group 2-1. These are Y41G, Y54G and H92F.

Figure 7:
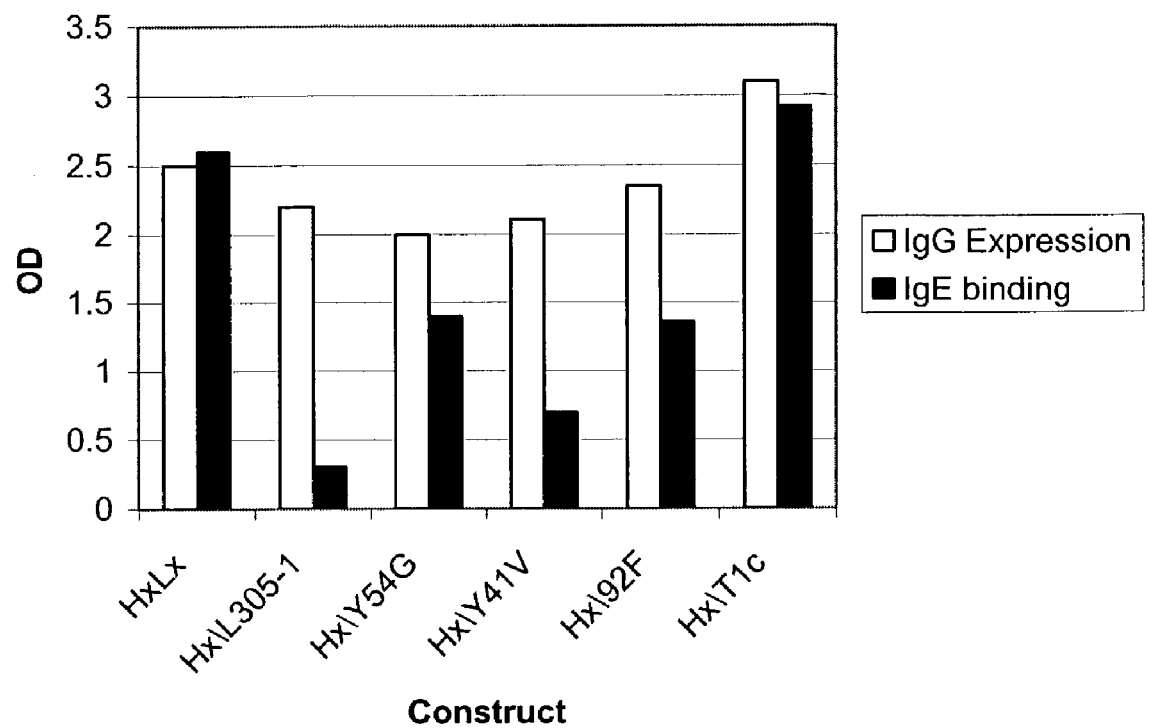
FIG. 7 displays the results of combining individual light chain back mutations into a single molecule and the enhanced binding to IgE.
Figure 8A:
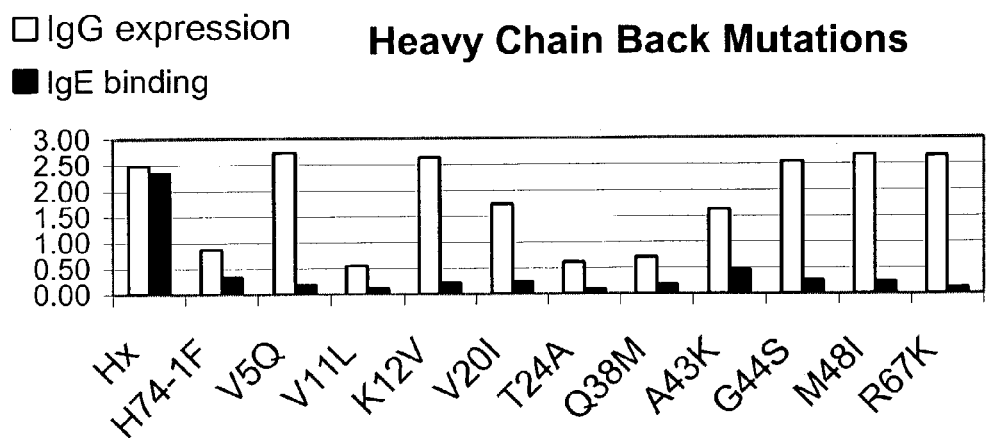
FIGS. 8A and 8B display enhanced binding to IgE by caninized heavy chain variable domains carrying back mutations.
Figure 8B:
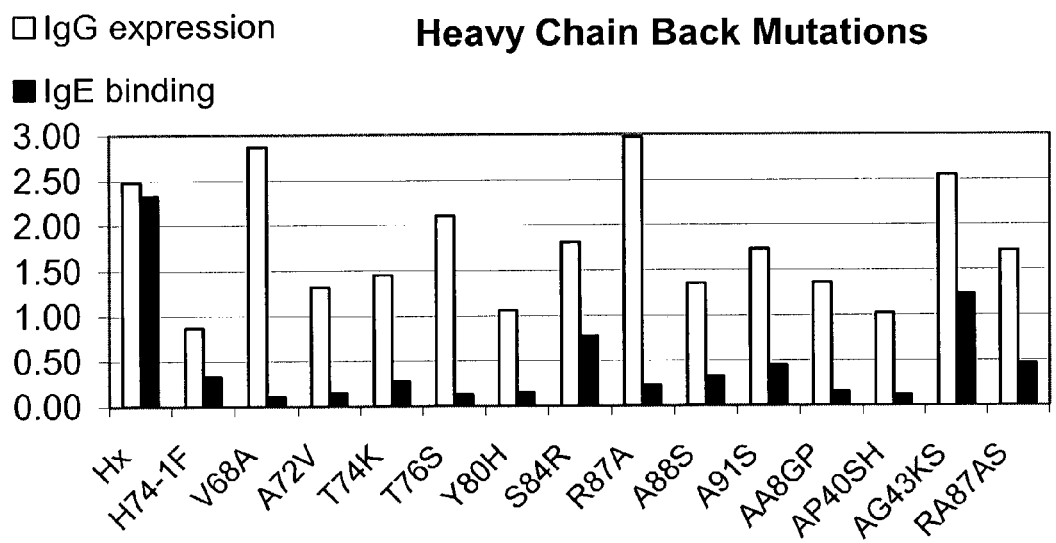
Figure 9:
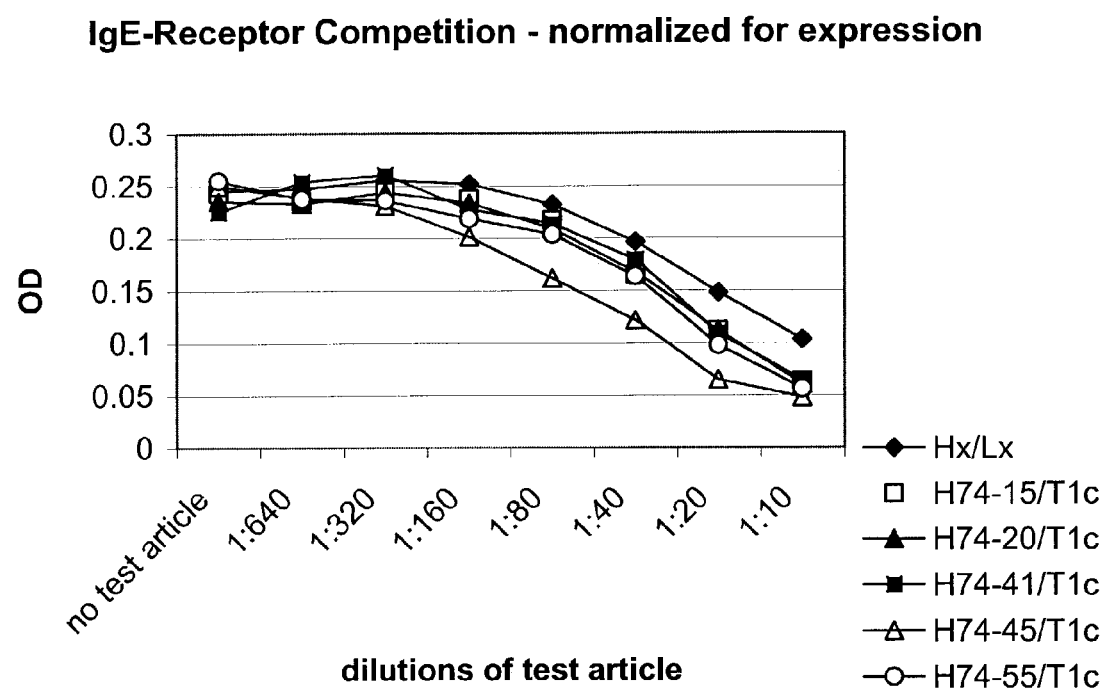
FIG. 9 displays the neutralization of IgE by fully caninized immunoglobulins.

Three back mutations were found to individually enhance the binding of the caninized antibody to IgE. These were Y41V, Y54G and H92F (See FIG. 6). These three backmutations were combined into a single light chain, Group 2-1, and designated T1. (For example, Y54 is the Group 2-1 light chain carrying the additional Y54 mutation that was co-transfected with the 15A2 chimeric heavy chain (Hx) into COS cells as described.) COS cells were transiently transfected by the DNA's indicated in FIG. 7. At T=48 hours, COS cell supernatants were collected and assayed for canine immunoglobulin concentration and IgE binding activity. Shown in FIG. 7 is the OD at 650 nm of Elisa assays that measure canine IgG concentration (anti-dog) or IgE binding activity. The three Group 2-1 back mutations were found to enhance IgE binding synergistically when combined into a single light chain. The enhanced IgE binding is equivalent to the chimeric 15A2, HxLx. One isolate was found to have particularly enhanced binding to IgE. In addition to the three backmutations, this isolate of the light chain was found to have a V7A mutation, and was designated T1c. When T1c co-expressed with the chimeric heavy chain a significant increase in IgE binding and IgE receptor competition was observed in comparison to Group 2-1 (see FIG. 7).

Amino acids that were backmutated for the heavy chain were: V5Q, Q38M, D46E, M48I, R67K, V68A and S84R. Individual H74-1 derivatives carrying each back mutation were constructed as described above and coexpressed with the chimeric light chain using the transient COS cell expression system as described above. One of these backmutations was found to particularly enhance IgE binding and have particularly increased efficiency in neutralizing IgE in the IgE receptor competition assay, S84R (see FIGS. 8A & B, which show the OD at 650 nm of Elisa assays that measure canine IgG concentration or IgE binding activity).

Given the high identity of H74-1 variable domain to the 15A2 variable domain, it was decided to extend back mutations to regions outside of the 3 angstrom and 6 angstrom shells surrounding the CDR's. This included amino acids K12V, V20I, G44S, A72V, T74K, T76S, Y80H, R87A, and A88S. Adjacent amino acids in H74-1 variable domain that differed from the 15A2 heavy chain variable domain were also mutated in pairs. This included AA8GP, AP40SH, AG43KS, RV67KA and RA87AS. When coexpressed with the 15A2 chimeric light chain in the COS cell transient expression system, enhanced IgE binding was found in the cell supernatants from five of these constructs. These were A43K, A72V, T74K, A88S and A91S (see FIGS. 8A & B).

An extensive series of derivatives of H74-1 were created mixing and matching the six back mutations A43K, A72V, T74K, S84R, A88S and A91S. Up to three mutations were combined into a single H74-1 derivative. Six derivatives of H74-1 were found to bind IgE as well as or better than the chimeric antibody (see FIG. 9 and paragraph [0077]).

These antibodies were tested for the ability to neutralize IgE in the competition assay. Constructs indicated in FIG. 9 were transfected as described into COS7L cells growing in serum free medium. For each construct, 30 separate transfections were performed. At T=48 hours cell culture supernatants were harvested (2 ml/transfection), the 30 transfections for each construct pooled, and the material centrifuged to remove cellular debris and filtered through a 0.22 micron filter. Canine immunoglobulin was pruified from cell culture supernatant using protein A chromatography. A 0.25 ml gravity flow column was used, with the cell culture fluid passed through the column three times. After washing with 10 column volumes of PBS, IgG was acid eluted with Pierce ImmunoPure IgG elution buffer. The pH was immediately adjusted to pH 7.0 with $Na_2PO_4$. For each construct, the IgG concentration was determined as described above, and diluted to a concentration of 7.5 ug/ml for comparison to the binding activity of other constructs. A serial dilution of each construct was performed, added to 2 ug/ml of canine IgE conjugated to HRP (100 ul/reaction). After a 1 hour incubation, material was applied to a Elisa plate coated with the canine high affinity IgE receptor. The receptor competition assay was completed as described above. A lower OD indicates less IgE is bound to the high affinity receptor and was thus successfully competed by the recombinant immunoglobulins.

In this assay six different caninized 15A2 derivatives successfully prevented soluble IgE from binding the high affinity receptor. These caninized derivatives bind to IgE as well or better than the parental variable domain from the 15A2 monoclonal antibody. (See FIG. 9.).

Example 7

Therapeutic Administration of Anti-IgE Chimeric Monoclonal Antibody

In order to access the effect of targeting canine IgE in vivo, we created a chimeric anti-IgE monoclonal antibody. The chimeric antibody, c15A2, comprised constant domains from a mouse anti-IgE monoclonal antibody (15A2) and canine anti-IgE variable domains. c15A2 binds to subdomain 3 of IgE, it inhibits binding to high affinity IgE receptor on mast cells and basophils, but does not bind to canine IgE bound by a high affinity IgE receptor. The c15A2 chimeric anti-body was compared to the mouse anti-IgE monoclonal antibody 15A2 for its ability to inhibit binding of IgE to a high affinity receptor and found to be similarly effective.

We next sought to demonstrate the feasibility of an antibody based therapy for allergy in a model system of canine allergy. We sought to determine if we could reduce or eliminate an IgE mediated sensitivity in a live animal. We used ragweed sensitized dogs as our model with the goal to eliminate ragweed sensitivity in these animals after treatment with the chimeric antibody.

We employed the following protocol. We used 8 consecutive doses at approximately 5 day intervals. We determined the pre-experimental free IgE levels 3 days before the first infusion. The first two infusions of the chimeric antibody were given at ten times this level. All of the subsequent doses were given at 5 times the pre-experimental IgE concentration. On a weekly basis serum was taken from the dogs and assays were performed to determine free and total IgE. We also determined on a weekly basis, the amount of free chimeric antibody in these animals and the level of IgE bound to the chimeric antibody as immune complexes. We used flow cytometric analysis to determine the level of high affinity IgE receptor expression on circulating basophils.

We measured free and total serum IgE levels in a control dog over a 6 month period and found the levels to fairly closely parallel each other, generally being in the range of 15–20 µg/ml, but varying as low as about 10 µg/ml to about 35 µg/ml. In a treated dog, the free IgE levels decreased to undetectable levels about 1.5 days after the first infusion of the chimeric anti-IgE antibody, with total serum IgE (representing the IgE bound to the chimeric antibody) displaying a monotonic decrease to undetectable levels at day 15, after three infusions of chimeric antibody. We estimate the level of sensitivity in our assay to be 5 ng/ml of IgE. We did not observe detectable levels of free or total IgE antibody in treated dogs until 150 days, long after the last infusion of chimeric anti-IgE antibody (at 33 days) and long after we determined that the chimeric antibody was cleared from circulation. Even during the period of 150–180 days, the level of IgE was only in the range of 100–200 ng/ml, far below the level in untreated dogs.

An intradermal ragweed sensitivity skin test was performed. After a pre-treatment test, additional tests were conducted at days 36, 40 and 174. In each test there was a titration of ragweed allergen from 1000 protein nitrogen units to 0.1 protein nitrogen units administered and the effects observed. Whereas a control dog showed in increasing sensitivity to ragweed over the course of the experiments, two of three treated dogs displayed no detectable sensitivity at 36 and 40 days and decreased sensitivity (relative to pre-treatment levels). The third treated dog displayed some sensitivity at each of the three post-treatment sensitivity tests, but still below pre-treatment levels. These and other tests showed that the chimeric anti-body c15A2:bound serum IgE;

b) prevented IgE-receptor binding;

c) prevented mast cell degranulation;

d) reduced IgE receptor expression on basophils and mast cells;

e) down-regulated IgE synthesis; and f) eliminated skin test reactivity in ragweed sensitized dogs.

Furthermore, we observed that:

a) free and total serum IgE levels were eliminated in dogs treated with c15a2 anti-IgE antibody for approx 6 mo.;

b) skin test sensitivity to ragweed was eliminated after c15A2 treatment;

c) the capacity to synthesize new IgE was eliminated in treated dogs for up to 6 mo.; and d) IgE receptor expression was down-regulated on circulating basophils.

Example 8

In vivo Use of Caninized Antibodies

The caninized monoclonal antibody 15A2 can be administered to dogs in a variety of formats and cause a reduction in IgE levels.

Elisa Assays to Detect IgE and IgE Complexes Circulating in Serum:

"Free" IgE—Free IgE is defined as IgE in serum that can be bound by the high affinity IgE receptor. This assay uses mouse mAb15A2 on the solid phase. Serial dilutions of canine serum are prepared in conjugate diligent IDEXX #6680 and incubated on the 15A2 plate for 1 hour. After washing the plate, IgE is detected with an α canine HRP conjugate.

IgE Complexes/Total IgE—IgE complexes are defined as IgE in serum, not capable of binding to the high affinity receptor. These IgE molecules may be bound with test article, or some other molecule. This assay uses 14K2 on the solid phase. Serial dilutions of canine serum are prepared in conjugate diligent IDEXX #6680 and incubated on the 14k2 plate for 1 hour. After washing the plate, IgE is detected with an α canine HRP conjugate.

Dose Calculation:

Test article dose calculation incorporates the concentration of IgE and the estimated blood volume of the dog based on the body weight. The formula is used:

$$\mu g/ml\ IgE\ (Free) \times Kg \times 0.06 = mgs\ Free\ IgE\ in\ serum$$

wherein:

µg/ml IgE (Free) is determined by Elisa as described above

Kg=kilogram weight of the dog 0.06=a constant to estimate the volume of blood in a dog For the study disclosed below, 10× of the Free IgE concentration of the caninized 15A2 monoclonal antibody was infused intraveinously in a 30 ml volume over 30 minutes. Prior to administration, the caninized antibody was diluted into PBS with 5% glycerol (vehicle). Placebo dogs received vehicle only, 30 ml volume infused intravenously over 30 minutes. The caninized monoclonal antibody (variant H74-58/Tic) was produced in mammalian cell culture using the NSO expression system. The antibody was affinity purified from tissue culture supernatant using protein A affinity column, followed by adsorption of contaminants by flowing through a mono-Q column. Dogs received a total of 9 doses of the test article weekly, except for dose number 2 that was administered on day 4.

| Dog ID | Wt. (Kg) | Free IgE (µg/ml) | 1X Dose (mg) | 10X Dose (mg) |
|--------|----------|------------------|--------------|---------------|
| CSUAKV | 11       | 1.46             | 1.0          | 9.6           |
| CSVAIJ | 9.1      | 14.58            | 8.0          | 79.6          |
| CSWAKP | 10.6     | 4.9              | Placebo      | Placebo       |
| CSXARA | 11.1     | 1.14             | Placebo      | Placebo       |

There is some variation in the Total IgE concentration in the placebo dogs during the course of the study. In the dogs that received test article, there is an initial increase in serum IgE levels that begins to drop rapidly after 48 hours. By day 25, IgE is undetectable in serum using our assay. The sensitivity of this assay is approximately 5 ng/ml serum.

TABLE N_{H58}

H58 Family Canine V_H Nucleic Acid Sequences

H3 SEQ

<u>ATGGAGTGGG GGCTCAACTT GATTTTCCTT GTCGCTATTT TACAAGGTGT CCAGGGTGAG</u> GTGCAGCTGG
TGGAGTCTGG GGGAGACCTG GTGAAGCCTG CGGGGTCCCT GAGACTGTCC TGTGTGACCT CTGGATTCAC
CTTCAGTATC TACGGCATGA ACTGGGTCCG CCAGGCTCCT GGGAAGGGGC TGCAGTGGGT CGCAGTTATT
AATAGCGCTG GAGACACAGG CTACGCAGGC GCTGTGAAGG GCCGATTCAC CATCTCCAGA GACAACGCCA
AGAACACAGT GTATCTGCAG ATGAACAGCC TGAGAGCCGA GGACACGGCC GTGTATTACT GTGCGAAGGA
TCGGGAAATC ACTACGGTAG CTGAGCTTGA CCACTGGGGC CAGGGAACCC TGGTCACCGT C (SEQ ID NO: 849)
H4 SEQ

<u>ATGAAGTTGT GGTTAAGCTT GGTTTTCCTT GTCGCTTTTT TAAAAGGTGT CCAGACTGAG</u> GTGCAACTGA
TGGAGTCTGG GGGAGACCTG GTGAAGCCTG GGGGATCCCT GAGACTCTCC TGTGTGGCCT CTGGATTCAC
CTTCAGTGAC TATGGCATGA ACTGGGTCCG CCAGGCTCCA GGGAAGGGAC TTCAATGGGT CGCTTACATT
AGCACTGGTG GAGGTACCAC ATCCTTTGCA GATGCTGTGA AGGCCGGTT CACCATCTCC AGAGACAACG
CCAAGAACAC GTTCTATCTT CAGATGAACA GCCTGAGAGC CGAGGACTCG GCCATGTATT ACTGTGCGGC
CTTGATATAT GGATACGTTG AGGGCCCCGG GTCATACTTT GACCTCTGGG GCCCGGGCAC CCTGGTCACC
GTC (SEQ ID NO: 850)
H5 SEQ

<u>ATGAAGTTGG GGCTAAGCTG GGTTTTCCTT GTCGCTATTC TAAAAGGTGT CCAGGGTGAG</u> GTGCAACTGG
TGGAGTCTGG GGGAGACCTG GTGAAGCCTG GGGGGTCCTT GAGACTGTCA TGTGTGGCCT CGGGACTCTC
CTTCGGTGAC TTTGCCATGA ACTGGGTCCG TCAGCCTCCA GGGAAGGGGC CGCAGTGGGT CGCGACTATT
AACAGGAGTG GAACCACATA CTACGCAGAC ACTGTGAAGG GCCGATTCAC CATCTCCAGA GACAGCGCCA
AGAACACGCT ATATCTGCAG TTGAACAGCC TGACAGCCGA GGACACGGCC CGGTATTACT GTGCGGGGGC
CAGTATGGAT ACTAAGACTT TTGACTACTG GGGCCAGGGA ACCCTTGTCA CCGTC (SEQ ID NO: 851)
H7 SEQ

<u>ATGAAGTTCG GGCTAAACTG GGTTTTCCTT GTCGCTATTT TAAAAGGTGT CCAGGGTGAG</u> GTGCAGCTGG
TGGAGTCTGG GGGAGACCTA GTGAGGCCTG GGGGGTCCTT AAGACTCTCC TGTGTGGCCT CTGGATTCAC
CTTCAGTAGC TATGGCATGA GTTGGGTCCG TCAGTCTCCA GGGAAGGGGC TGCAGTGGGT CGCATGGATT
AGGTATGATG GAAGTAGCAC ATACTACGCA GACGCTGTGA AGGGCCGATT CACCATCTCC AGAGACAATG
CCAAGAACAC ACTGTATCTT CAGATGAACA GCCTGAGAGC CGAGGACACG GCCGTGTATT ACTGTGCGAA
GGATCCCTGG AGTAGCAGTT GGTACGATGC TTTTGGTTAT TGGGGCCAGG GCACCCTGGT CACTGTC (SEQ ID NO: 852)
H9 SEQ

<u>ATGGAGTTGT GGCTAAACTG GGTTTTTCTT GTCGCTATTC TACAAGGTGT CCAGGGTGAG</u> GTTCAACTGG
TGGAGTCTGG GGGAGACCTG GTGAAGCCTG GGGGGTCCCT GAGACTCTCC TGTGTAGCCT CTGGATTCAG
CTTCAGTCAC AACGACATGA GTTGGGTCCG CCAGGCTCCT GGGAAGGGTC TGCAGTGGGT CGCATCTATT
AGATATGATG AGACTGGCAC ATCCTACACT GACGCTGTGA AGGCCGATT CACCATCTCC AGAGACAACG
CCAGGAACAC ACTGTATCTG CAGATGAACA GCCTGAGAGC CGAGGACACG GCTGTATATT TCTGTGCGAA
GGAATATTTA GGGGAGTATT GGGGCCCGGG AACCCTGGTC ACCGTC (SEQ ID NO: 853)

TABLE N_{H58}-continued

H58 Family Canine V_H Nucleic Acid Sequences

H51 SEQ

<u>ATGGATATCT GCAGAATTCG CCCTTGGGAA TTCATGGAGT TTGGGCTGAG CTGGCTTTCT CTTGTCGCTA</u>

<u>TTTTACAAGG TGTCCAGGGT</u> GAGGTGCAGC TGGTGGAGTC TGGGGGAGAC CTGGTGAAGC CTGCAGGGTC

CCTGAGACTG TCCTGTGTGG CCTCTGGATT CACCTTCAGT GACTACGGCA TGAGCTGGGT CCGCCAGGCT

CCTGGGAAGG GGCTGCAGTT GGTCGCAGGT ATTAACAGCG GTGGAAGTAC TACATACTAC ACAGACGCAG

TGAAGGGCCG ATTCACCATT TCCAGAGACA ACGCCAAGAA CACAGTGTAT CTGCAGATGA ACAGCCTGAG

AGGCGAAGAC ACGGCCATGT ATTACTGTGC AAAGGGGGGG GACAGTAGTC ACTGGTACCC GTACAATTTT

GACTACTGGG GCCAGGGAAC CCTGGTCACC (SEQ ID NO: 854)
H53 SEQ

<u>ATGGACTTCT GGCTAAGCTG GGTTTTCCTA GTCACTATTT TAAAAGGTGT CCAGTGTGAG</u> GTGCAGCTGG

TGGAGTCTGG GGGAGACCTT GTGAAACCTG AGGGGTCCCT GAGACTCTCC TGTGTGGTCT CTGGCTTCAC

CTTCAGTAGC TACGACATGA GCTGGGTCCG CCAGGCTCCA GGGAAGGGGC TGCAGTGGGT CGCATACATT

AGCAGTGATG GAAGGAGCAC AAGTTACACA GACGCTGTGA AGGGCCGATT CACCATCTCC AGAGACAATG

CCAAGAATAC GCTGTATCTG CAGATGAACA GCCTGAGAAC TGAGGACACA GCCGTGTATT ACTGTGCGAG

GTATCACGAC GGTAGCTACG TACGTGTCTG GTTCTACTAC TGGGGCCAAG GGACCCTGGT CACTGTG (SEQ ID NO: 855)
H55 SEQ

<u>ATGGAGCTTG GCTGAGCTG GCTTTCTCTT GTCGCTATTT TACAAGGTGT CCAGGGTGAG</u> GTGCAGCTGG

TGGAGTCTGG GGGAGACCTG GTGAAGCCTG CAGGGTCCCT GAGACTGTCC TGTGTGGCCT CTGGATTCAC

CTTCAGTAGC TACAGCATGA GCTGGGTCCG CCAGGCTCCT GGGAAGGGGC TGCAGTTGGT CGCAGGTATT

AACAGCGGTG GAAGTAGCAC ATACTACACA GACGCAGTGA AGGGCCGATT CACCATCTCC AGAGACAACG

CCAAGAACAC AGTGTATCTG CAGATGAACA GCCTGAGAGC CGAGGACACG GCCATGTATT ACTGTGCAAA

GGCCGAGCTG ACGTACTACT GTACTGATGA TTACTGTTCC CGAACCTCAA ATTTTGACTA CTGGGGCCAG

GGAACCCTGG TCACCGTC (SEQ ID NO: 856)
H56 SEQ

<u>ATGAACTTGG GGTTAAGCTT GGTTTTCCTT GTCGCTATTT TACAAGGTGT CCAGGGTGAG</u> GTGCAACTGG

TGCAGTCTGG GGGAGACCTA GTAAAGCCTT CGGGGTCCCT GAGACTGTCC TGTGTGGCCT CTGGATTCAT

CTTCAGTAGC TTCCACATGA GTTGGGTCCG CCAGACCCCT GAGAGGGGAC TGGAGTTGGT CGCAGGTATT

AATGGCGGTG GAACCACCAG ATTCTACTCA GACGCTGTGA GGGCCGTTT CATCATTTCC AGAGACCTCG

CCAAGAGTAC AGTCTATCTG CAGATGGACA ACCTGCGAGC CGACGACACG GCCACTTACT ACTGTGCAAG

GGCCCGGGAG AGATACTGTA AAGATGATTA TTGTTTCAGG TGGGGTTTTG ATTCCTGGGG CCGGGGAGCC

CTGGTCACCGTC (SEQ ID NO: 857)
H58 SEQ

<u>ATGAACTTGT GGCTAAACTG GATTTTCCTT GTCGCTATTT TAAAAGGTGT CCAGGGTGAG</u> GTACAACTGG

TGGAGTCTGG GGGAGACCTG GTGAAGCCTG GGGGTCCTT AAGACTCTCC TGTGTGGCCT CTGGATTCAC

CTTCAGTAGT TCCGGCATGA GCTGGGTCCG TCAGTCTCCA GGGAAGGGGC TGCAGTGGGT CGCATGGATT

AAGTCTGATG GAAGTAGTAC ATATTATGTA GACGCTGTGA AGGCCCATT CACCATCGCC AGAGACAACG

CCAAGAACAC CCTGTATCTG CAGATGAACA GCCTGAGAGC CGACGACACG GCCGTGTATT ATTGTGCGAA

TABLE N_{H58}-continued

H58 Family Canine V_H Nucleic Acid Sequences

GCTTTGGGAC AGTTGGGGCG CGTACAATTT TGACTACTGG GGCCAGGGAA CCCTGGTCAC CGTC (SEQ ID NO: 858)
H67 SEQ

<u>ATGGAGTTTG GGCTGACCTG GCTTTCTCTT GTCGCTATTT TACAAGGTGT CCAGGGTGAG</u> GTGCAGCTGG

TGGAGTCTGG GGGAGACCTG GTGAAGCCTG CAGGGTCCCT GAGACTGTCC TGTGTGGCCT CTGGATTCAC

CTTCAGTAGC TACAGCATGA GCTGGGTCCG CCAGGCTCCT GGGAAGGGGC TGCAGTTGGT CGCAGGTATT

AACAGCGGTG GAAGTAGCAC ATACTACACA GACGCAGTGA AGGGCCGATT CACCATCTCC AGAGACAACG

CCAAGAACAC AGTGTATCTG CAGATGAACA GCCTGAGAGC CGAGGACACG GCCATGTATT ACTGTGCCCC

TACTACGGTA GCTACTATGG AGTCCTGGGG CCAGGGAACC CTGGTCACCG TC (SEQ ID NO: 859)
H378 SEQ

<u>ATGGAGTCTG TGCTCTGCTG GGTTTTCCTT GTCGCTATTT TAAAAGGTGT CCAGGGTGAG</u> GTGCAGCTGG

TGGAGTCTGG GGGAGACCTG GTGAAGCCTG GGGGTCCCT GAGACTCTCC TGTGTGACTT CTGGATTCAC

CTTCAGTGGC TGTGCCATGA TCTGGGTCCG CCAGGCTCCA GGGAAGGGGC TGCAGTGGGT CGCATACATT

AACAGTGATG GAAGTACCAC ATACTACGCA GACGCTGTGA AGGGACGATT CACCATCTCC AGAGACAACG

CCAAGAACAC GCTCTATCTG CAGATGAACA GCCTGAGAGC TGANGACACG GCCGTGTATT ACTGTGCGAG

GGGTGATTCT AGTANTTGGG GCTGGGGCCA AGGAACCCTGGTCATCGTC (SEQ ID NO: 860)
H396 SEQ

<u>ATGGAATCTG TGCTCGGATG GATTTTCCTT GCCACTATTT TAAAAGGTGT CCAGGGTGAG</u> GTGCAGTTGG

TGGAGTCTGG GGGAGACCTG GTGAAGCCTG GGGGTCCCT AAGACTCTCC TGTGTGGGCT CTGGATTCAC

CTTCAGTGGT TACTGGATGA GTTGGGTCCG CCAACCTCCA GGGAAGGGGC TACAGTGGAT TGTGGAGATC

AGCGGTAGTG GAACCACCAC ACACTATGAA GACACTGTGA GGGGCCGATT TACCATTTCC AGAGACAATG

CCAAGAACAC GCTGTCTCTG GAGATGAATA GTCTGAGAGA CGAGGACACG GCCATGTATT ATTGTGCAAG

GGATCGGGGG CAATGTACTG TTGATTACTG CGCCGATCAT ATTGACTACT GGGGCCAGGG

AACCCTGGTCATNGTC (SEQ ID NO: 861)
H404 SEQ

<u>ATGGAGTCTG TGCTCTGCTG GGTTTTCCTT GTCGCTATTT TAAAAGGTGT CCAGGGTGAG</u> GTGCAGCTGG

TGGAGTCTGG GGGANACCTG GTGAAGTTTG GGGGGTCCTT GANACTGTCC TGTGTGGCCT CTGGATTCAC

CTTCAGTAGC TACAGCATGA GTTGGGTCCG CCAGGCTCCT GAAAAGGGGC TGCAGTTGGT CGCAGGTATT

AACAGCGGTG GAAGTAGCAC ATACTACACA GACGCTGTGA AGGGCCGATT CACCATCTCC AGAGACAACG

CCAAGAACAC GCTATATCTA CAGTTGAACA GCCTGAGAGT CGAAGACACG GCCGTGTATT ACTGTGCNAG

GCANACCTAT GGTACCTCCT CTGAGGGGAA TTACTTAGGT CTNTGGGGCC AGGGCACCCT

GGTCACCCTGGTCACCGTN (SEQ ID NO: 862)
H442 SEQ

<u>ATGGAATCTG TGCTCGGATG GATTTTCCTT GCCACTATTT TAAAAGGTGT CCAGGGTGAG</u> GTGCAGTTGG

TGGAGTCTGG GGGAGACCTG GTGAAGCCTG GGGGTCCCT GAGACTCTCC TGTGTGGCCT CTGGATTCAC

CTTCAGTTAC TACTTAATGA GCTGGGTCCG CCGGGCTCCA GGGAAGGGGT ACAGTGGAT TGCAGAAATT

TCCGATAGTG GAGATTATCT GGACTATACA GACGCTGTGA AGGGCCGATT CACCATCTCC AGAGACAATG

TABLE N<sub>H58</sub>-continued

H58 Family Canine V<sub>H</sub> Nucleic Acid Sequences

CCAAGAGCAC GCTGTATCTG GAGATGAACA GGCTGAGGCC CGACNACACG GCCATGTATT ACTGTGTTAC

CGGCGGGGAC CTCTTTGGTC ACTGGGGCCA AGGCACCCTG GTCACTGTC (SEQ ID NO: 863)
H445 SEQ

ATGGAGTGGG GGCTCAACTT GATTTTCCTT GTCGCTATTT TACAAGGTGT CCAGGGTGAG GTGCAGCTGG

TGGAGTCTGG GGGAGACCTG GTGAAGCCTG GAGGGTCCCT GAGACTTTCC TGTGTGGCCT CTGGATTCAA

CTTCGGCAGC TACCACATGG GCTGGGTCCG CGAGGCTCCA GGGAAGGGCC TTCAGTGGGT CGCATACATT

CACAATGATG GAGGTACCAG GACCTATTCA GACACTGTGA AGGGCCGATT CACCATCTCC AGAGACAACG

CCGAGAACAC GCTGTATCTT CAGATGAACA GCCTGAGGCC CGAGGACACG GCCGTGTATT ATTGTGCGAG

CCTATCCGGG TATTATTGTA CTGATGATTC CTGTTTCAAC GTTGTACATG ATTACTTAAA CCTCTGGGGC

CAAGGCACCC TGGCAACCGT T (SEQ ID NO: 864)
H574 SEQ

ATGGAGTCTG TGTTCTGCTG GGTTTTCCTT GTCGCTATTT TAAAAGGTGT CCAGGGCGAG GTGCAGCTGG

TGGAGTCTGG GGGAGACCTG GTGAAGCCTG GGGGGTCCCT GAGACTGTCC TGTGTGGCCT CTGGATTCAC

CTTCAGTGAC TACTACATGT ACTGGGTCCG CCAGGCTCCA GGGAAGGGGC TTCAGTACGT CGCACGGATT

AGGGGTGATG GAACTAACAT ATACTACGCA GACGCTGTGA AGGGCCGATT CACCATCTCC AGAGACAATG

CCAAGAACAC GCTGTATCTG CANATGAACA GCCTGAGAGC CGAGGACACG GCTGTGTATT ATTGTGGAAA

GGATTTCGGG GACTGGGTTC TATCCTGGGG CCAGGGAACC CTGGTCACCG TT (SEQ ID NO: 865)
H585 SEQ

ATGAAGTTGG GGCTAAGCTG GGTTTTCCTT GTCGCTATTC TAAAAGGTGT CCAGGGTGAG GTGCAACTGG

TGGAATCTGG GGGAGACCTG GTGAAGCCTG GGGGGTCCCT GAGACTCTCC TGTGTGGGCT CTGGATTCAC

CTTCAATAGT TACTGGATGA GCTGGGTCCG CCAGGCTCCA GGGGAGGGGC TACAATGGAT TGGACAGATA

AGTGTTGGTG GTGAAATAGA GTATGCAGAC GCTGTGAAGG GCCGATTCAC CATCTCCAGA GACAATGCCA

AGAACACGCT GTTTCTGCAG ATGCACAGTC TGAGAGCCGA GGACACGGCC ATATATTACT GTGCAAGAGA

CGGGGGTATT ACCTCATACA TGAAAACGAA TCTTGACTAC TGGGGCCAGG GAAACCTGGT CACCGTC (SEQ ID NO: 866)
H592 SEQ

ATGAAGTTCG GGCTAAACTG GGTTTTCCTT GTCGCTATTT TAAAAGGTGT CCAGGGTGAG GTGCAGCTGG

TGGAGTCTGG GGGAGACCTG GTGAAGCCTG GGGGGTCCCT GAGACTCTCC TGTGTTGGCT CTGGATTCAC

CTTCAGTGCC TATGACATGC TATGGGTCCG TCAGGCTCCA GGGAAGGGGC TGCAGTGGGT CGCATACATT

AACAGCGGTG GAGGGATCAT ATTCTACGCA GACGCTGTGA AGGCCGATT CACCATCTCC AGAGACAACG

CCAAGAACAC ACTCTCTCTG CATATGAACA GCCTGAGAGT CGAGGACACG GCCGTGTATT TCTGTACAAG

ATGGGATACT AACGGACACT GGGGCCAGGG CACCCTGGTC (SEQ ID NO: 867)
H602 SEQ

ATGGAGTTGT GGCTAAACTG GGTTTTTCTT GTCGCTATTC TACAAGGTGT CCAGGGTGAG GTTCAACTGG

TAGAGTCTGG GGGAGACCTG GTGAAGCCTG GGGGGTCCTT AAGACTGTCC TGTGTGGCCT CTGGATTCAC

CTTCAGGACC TATGGCATGA GCTGGGTCCG TCAGTGTCCA GGGAAGGGAC TGCAGTGGGT CACAAGTATC

AGCAGCAGCG CAGGCACGTT CTACGCAGAC GCTGTGAAGG GCCGATTCAC CATCTCCAGA GACAACGCCA

TABLE N$_{H58}$-continued

H58 Family Canine V$_H$ Nucleic Acid Sequences

AGAACACGCT GTATCTGCAG TTGAACAGCC TGAGAGCCGA GGACACGGCC GTGTATTATT GTGCGAAGGA

TCCGGCTACG CTACCTACGG GGGAATTTGA CTACTGGGGC CAGGGCACCC CGGTCACCGTC (SEQ ID NO: 868)

TABLE N$_{H74}$

H392 SEQ

<u>ATGGACTGCA GCTGGAGAAT CTTCTTCCTG CTGGCACTGG CCACAGGTGT GCACTCTGAG</u> GTCCAGCTGG

TGCAGTCTGC AGCTGAGGTT AAAAAGCCAG GGGCATCTGT GAAGGTCTCC TGCAAGACAT CTGGATACAC

CTTCACTGAC TACTATATGC ACTGGGTACA ACAGGCTCCA GGAGCAGGGC TTGATTGGAT GGGATGGATT

GATCCTGAAG ATGGTACCAC AAGTTATGCA CAGAAGTTCC AGGGCAGAGT CACCCTGACG GCAGACACAT

CCACAAGCAC AGCCTACATG GAGCTGAGCA GTCTGAGAGC TGAGGACACA GCTGTGTACT ACTGTGCAAG

CGGAGGGAGT CGGCCCTTCA ATGCTTTTGG TTACTGGGGC CAGGGCACCCTGGTCACTGTT (SEQ ID NO: 869)
H74 SEQ

<u>ATGGACTGG ACCTGGAGGG TCTTCTTCCT GCTGGCACTG GCCACAGGTG TGCACTCTGA</u> GGTCCAGCTG

GTGCAGTCTG CAGCTGAGGT TAAGAAGCCA GGGGCATCTG TGAAGGTCTC CTGCAAGACA TCTGGATACA

CCTTCACTGA CTACTATATG CACTGGGTAC AACAGGCTCC AGGAGCAGGG CTTGATTGGA TGGGATGGAT

TGATCCTGAA GATGGTACCA CAAGTTATGC ACAGAAGTTC CAGGGCAGAG TCACCCTGAC GGCAGACACA

TCCACAAGCA CAGCCTACAT GGAGCTGAGC AGTCTGAGAG CTGAGGACGC AGCTGTGTAC TACTGTGCAA

GCTTATATAT ATATGGATAC GCTGCTTACT TAGACCTCTG GGGCCAGGGC ACCCTGGTCA CCGTC (SEQ ID NO: 870)
H76 SEQ

<u>ATGGACTGGA CCTGGAGGAT CCTCTTCCTG CTGGCACTGG CCACAGGTGT GCACTCTGAG</u> GTCCAGCTGG

TACAGTCTGC AGCTGAGGTT AAGAAGCCAG GGGCATCTGT GAAGGTCTCC TGCAAGACAT CTGGATACAC

CTTCACTGAC TACTATATGC ACTGGGTACA ACAGGCTCCA GGAGCAGGGC TTGATTGGAT GGGATGGATT

GATCCTGAAG ATGATACCAC AGGTTATGCA CAGAAGTTCC AGGGCAGAGT CACCCTGACG GCAGACACAT

CCACAAGCAC AGCCTACATG GAGCTGAGCA GTCTGAGAGC TGAGGACACA GCTGTGTACT ACTGTGCAAG

AAAGTGGAGG TACTACGGTA GCCAAGATTA CTGGGGCCAG GGAACCCTGG TCACCGTC (SEQ ID NO: 871)
H645 SEQ
<u>ATGGACTGCA GCTGGAGAAT CTTCTTCCTG CTGGCACTGG CCACAGGTGT GCACTCTGAG</u> GTCCAGCTGG

TGCAGTCTGC AGCTGAGGTT AAGAAGCCAG GGGCATCTGT GAAGGTCTCC TGCAAGACAT CTGGATACAT

CTTCATTGAC CAGTATATGC ACTGGGTACA GCAGGCTCCA GGAGCAGGGC TTGAATGGAT GGGATGGATT

GATCCTGAGG ATGGTACCAC AAGTTATGCA CAGAAGTTCC AGGGCAGAGT CACCCTGACG GCAGACACAT

CCACAAACAC AGTCTATATG GAGCTGAGCA ATCTGAGAAC TGAGGACACA GCTGTGTACT ACTGTGCAAG

GGATATATGG GATTTTGACT ACTGGGGCCA GGGAACCCTG GTCACCGTC (SEQ ID NO: 872)

TABLE N_other H

Other Canine Heavy Variable Domain Sequences

H6 SEQ

ATGAAGTTGG GGTTAAGCTG GATTTTTCTT GTCGCTATTT TACAAGGTGT CCAGGGTGAG GTGCAGCTGG

TGGAGTCTGG GGGAAACCTG GTGAAGCCGG GGGGGTCCCT GAGACTCTCC TGTGTAGCCT CTGGATTCAC

CTTCAGTAAT TACGACATGA GTTGGGTCCG CCAGGCTCCT GGGAAGGGGC TGCAGTGGGT CGCGACTATT

AGTTATGATG GAAGTAGTAC ATTTCATACT GACGCTGTGA AGGGCCGATT CACCATCTCC AGAGACAACG

CCAGGAACAC AGTGTATCTA CAGCTGAACA GCCTGAGAGC CGAGGACACG GCTGTTTATT ATTGTGGGAA

GCAGTGGAGA AACACCTGGT ATTCTTTTCC CGATCCCGGT TTTGACTATT GGGGTCAGGG AACCCTGGTC

ACCGTC (SEQ ID NO: 873)

MKLGLSWIFL VAILQGVQGE VQLVESGGNL VKPGGSLRLS CVASGFTFSN YDMSWVRQAP GKGLQWVATI

SYDGSSTFHT DAVKGRFTIS RDNARNTVYL QLNSLRAEDT AVYYCGKQWR NTWYSFPDPG FDYWGQGTLV TV (SEQ ID NO: 874)
H27 SEQ

ATGGAGTCTG TGCTCTGCTG GGTTTTCCTT GTCGCTATTT TAAAAGGTGT CCAGGGTGAG GTGCAGCTGG

TGGAATCTGG GGGAGACCTG ATGAAGCCTG GGGGGTCCCT GAGACTCTCC TGTGTGGCCT CTGGATTCAC

TTTCAGTAGC CACTACATGA ACTGGGTCCG CCAGGCTCCA GGGAAGGGGC TGCAGTGGGT CGGATACATT

AACAGTGATG GACATAGCAC GAGCTACGCA GACGCTGTGA AGGGCCGATT CACCATCTCC AGAGACAATG

CCAAGAACAC GCTGTATCTG CAGATGAACA GCCTGAGAAC CGAGGACACC GGCCGTGTAT TACTGTGTGA

AGGGATGGCA GGTAGTACTT ATAGGTGGGG TGGTATGGAC TACTGGGGCC ATGGC (SEQ ID NO: 875)

MEFGFNLIFL XTILKGAQGE VQXVESGGDL MKPGGSLRLS CVASGFTFSS HYMNWVRQAP GKGLQWVGYI

NSDGHSTSYA DAVKGRFTIS RDNAKNTLYL QMNSLRTEDT GRVLLCEGMA GSTYRWGGMD YWGHG (SEQ ID NO: 876)
H52 SEQ

ATGGAGTTCT GGTTCAACTG GATTTTCCTT GTCGSTACTT TAAAAGGTGT CCAGGGTGAG GTGCAACTGG

TGRAGTCTKG GGGAGACATG GTGAAGCCTG GGGGGTCCCT GAGACTYTYC TSTGTGGSCT CTGGATTTAC

CTTCAGTAGT CACTACATGT ATTGGGTCCG CCAGGCTCCA GGGAAGGGGC TTCAGTGGGT CTCACACATT

AACGCAGATG GAGGTACCAC AAGGTATGCG GACGCTGTGA AGGGCCGATT CACCATCTCC AGAGACAACG

CAAAGAATAC GCTGTATCTC CAGATGAACA GCCTGAGAGC CGAGGACACA GCGGTATATT ACTGTACAAA

GGACTCCCAT ACTACGGCTA GTTTTGACTA CTGGGGCCAG GGAACCCTGG TCACC (SEQ ID NO: 877)

MEFWFNWIFL VXTLKGVQGE VQLVXSXGDM VKPGGSLRXX XVXSGFTFSS HYMYWVRQAP GKGLQWVSHI

NADGGTTRYA DAVKGRFTIS RDNAKNTLYL QMNSLRAEDT AVYYCTKDSH TTASFDYWGQ GTLVT (SEQ ID NO: 878)
H60 SEQ

ATGAAGTTCT GGCTCAGCTG GGTTTTTCTT GTCGCTACTT TACAAGGTGT CCAGGGTGAG GTGCAGCTGG

TGGAGTCTGG GGGAGACCTG GTGAAGCCTG GGGGGTCCCT GAGACTCTCC TGTGTTGCCT CCGGATTCAT

CTTCAGTAAC TACGACATGA ACTGGGTCCG CCTGGCTCCT GGGAAGGGGC TGCAGTGGGT CGCAAGTATT

AGCTATGATG GAAGTCGCAC ATACTACACT GACGCTGTGA AGGGCCGATT CACCATCTCC AGAGACAACG

CCACGAACAC AGTGTATCTG CAGATGAATG CCCTGAGAAC CGAGGACACG GCTGTGTATT CCTGTGCGGC

TABLE N<sub>other H</sub>-continued

Other Canine Heavy Variable Domain Sequences

AGATATTTGG ATCCGGGGGG TGGACTACTG GGGCCAGGGA ACCCTGGTCA CC (SEQ ID NO: 879)

<u>MKFWLSWVFL VATLQGVQGE</u> VQLVESGGDL VKPGGSLRLS CVASGFIFSN YDMNWVRLAP GKGLQWVASI

SYDGSRTYYT DAVKGRFTIS RDNATNTVYL QMNGLRTEDT AVYSCAADIW IRGVDYWGQG TLVT (SEQ ID NO: 880)
H100 SEQ

<u>ATGCAGATGC CGTGGTCCCT CCTCTGCCTG CTGGCAGCTC CCCTGGGTGT CCTGTCTGAA</u> CTCACACTCC

AGGAGGCAGG GCCAGGACTG GTGAAGCCCT CAGAGACCCT CTCTCTCACC TGTCTTGTGT CCGGAGGCTC

CGTCAACAGC GGTTATTACT GGAGTTGGAT CCGTCGACGC CCTGGGGGAG AATTGGAATG GATGGGATAC

TGGTCAGGTA CGACCCACTA CAACCCGACA TTCCAGGGAC GCATTTCCAT TACTACTGAT ACGGCCACGA

ACCAATTCTT CCTCCAGCTG ACTTCCGTGA CCACCGAAGA CACGGCCGTT TATTTCTGTA TACGACTCTA

TAGGTCTAAC TACTTTCTTG ACTTTTGGGG TCAGGGAACC CTGGTCACCG TC (SEQ ID NO: 881)

<u>MQMPWSLLCL LAAPLGVLSE</u> LTLQEAGPGL VKPSETLSLT CLVSGGSVNS GYYWSWIRRR PGGELEWMGY

WSGTTHYNPT FQGRISITTD TATNQFFLQL TSVTTEDTAV YFCIRLYRSN YFLDFWGQGT LVTV (SEQ ID NO: 882)
H101 SEQ

<u>ATGCAGATGC CGTGGTCCCT CCTCTGCCTG CTGGCAGCTC CCCTGGGTGT CCTGTCTGAA</u> CTCACACTCC

AGGAGGCAGG GCCAGGACTG GTGAAGCCCT CARAGACCCT CTCTCTCACC TGTCTTGTGT CCGGAGGCTC

CGTCAACAGC GGTTATTACT GGAGTTGGAT CCGTCGACGC CCTGGGGGAG AATTGGAATG GATGGGATAC

TGGTCAGGTA CGACCCACTA CAACCCGACA TTCCAGGGAC GCATTTCCAT TACTACTGAT ACGGCCACGA

ACCAATTCTT CCTCCAGCTG ACTTCCGTGA CCACCGAAGA CACGGCCGTT TATTTCTGTA TACGACTCTA

TAGGTCTAAC TACTTTCTTG ACTTTTGGGG TCAGGGAACC CTGGTCACCG TC (SEQ ID NO: 883)

<u>MQMPWSLLCL LAAPLGVLSE</u> LTLQEAGPGL VKPSXTLSLT CLVSGGSVNS GYYWSWIRRR PGGELEWMGY

WSGTTHYNPT FQGRISITTD TATNQFFLQL TSVTTEDTAV YFCIRLYRSN YFLDFWGQGT LVTV (SEQ ID NO: 884)
H102 SEQ

<u>ATGGAGTTGT GGTTCAACTG GATTTTCCTT GTCGCTATTT TAAAAGGTGT CCAGGGTGAG</u> GTGCAGTTGG

TGGAGTCTGG GGGAGACCTG GTGAAGCCTG GGGGGTCCTT AAGACTCTCC TGTGTGGCCT CTGGATTCAC

CTTCAGTGAT TATGGCATGA ACTGGGTCCG TCACTCTCCA GGGAAGGGGC TGCAGTGGGT CGCATGGATT

TGGTATGGCG GGAGTAGCAC ATACTACGCA GACGCTGTGA AGGGCCGATT CACCATCTCC AGAGACGACG

CCAACAACAC ACTATATCTA CAGATGAACA GCCTGAGAGC CGAGGACACG GCCGTCTATT ACTGTGCGAA

GGAGTATAGT AGTAGCTTTG ACTACTGGGG CCAGGGAACC CTGGTCACCG TCT (SEQ ID NO: 885)

<u>MELWFNWIFL VAILKGVQGE</u> VQLVESGGDL VKPGGSLRLS CVASGFTFSD YGMNWVRHSP GKGLQWVAWI

WYGGSSTYYA DAVKGRFTIS RDDANNTLYL QMNSLRAEDT AVYYCAKEYS SSFDYWGQGT LVTV (SEQ ID NO: 886)
H103 SEQ

<u>ATGGAGTCTG TGCTCTGCTG GGTTTTCCTT GTCGCCATTC TAAATGGTGT CCAGGGTGAG</u> GTGCAGCTGG

AGGAGGCAGG GCCAGGACTG GTGAAGCCCT CAGAGACCCT CTCTCTCACC TGTCTTGTGT CCGGAGGCTC

TABLE N<sub>other H</sub>-continued

Other Canine Heavy Variable Domain Sequences

CGTCAACAGC GGTTATTACT GGAGTTGGAT CCGTCGACGC CTGGGGGAG AATTGGAATG GATGGGATAC

TGGTCAGGTA CGACCCACTA CAACCCGACA TTCCAGGGAC GCATTTCCAT TACTACTGAT ACGGCCACGA

ACCAATTCTT CCTCCAGCTG ACTTCCGTGA CCACCGAAGA CACGGCCGTT TATTTCTGTA TACGACTCTA

TAGGTCTAAC TACCTTCTTG ACTTTTGGGG TCAGGGAACC CTGGTCACCG TC (SEQ ID NO: 887)

MQMPWSLLCL LAAPLGVLSE LTLQEAGPGL VKPSETLSLT CLVSGGSVNS GYYWSWIRRR PGGELEWMGY

WSGTTHYNPT FQGRISITTD TATNQFFLQL TSVTTEDTAV YFCIRLYRSN YLLDFWGQGT LVTV (SEQ ID NO: 888)
H109 SEQ

ATGGACTGCA GCTGGAGAAT CTTCTTCCTG CTGGCACTGG CCACAGGTGT GCACTCTGAG GTCCAGCTGG

AGGAGGCAGG GCCAGGACTG GTGAAGCCCT CAGAGACCCT CTCTCTCACC TGTCTTGTGT CCGGAGGCTC

CGTCAACAGC GGTTATTACT GGAGTTGGAT CCGTCGACGC CTGGGGGAG AATTGGAATG GATGGGATAC

TGGTCAGGTA CGACCCACTA CAACCCGACA TTCCAGGGAC GCATTTCCAT TACTACTGAT ACGGCCACGA

ACCAATTCTT CCTCCAGCTG ACTTCCGTGA CCACCGAAGA CACGGCCGTT TATTTCTGTA TACGACTCTA

TAGGCCTAAC TACTTTCTTG ACTTTTGGGG TCAGGGAACC CTGGTCACCG TC (SEQ ID NO: 889)

MQMPWSLLCL LAAPLGVLSE LTLQEAGPGL VKPSETLSLT CLVSGGSVNS GYYWSWIRRR PGGELEWMGY

WSGTTHYNPT FQGRISITTD TATNQFFLQL TSVTTEDTAV YFCIRLYRPN YFLDFWGQGT LVTV (SEQ ID NO: 890)
H637 SEQ

ATGCAGATGC CGTGGTCCCT CCTCTGCCTG CTGGCAGCTC CCCTGGGTGT CCTGTCTGAA GTCATACTGC

AGGAGTCCGG GCCAGGACTG GTGAAGCCCT CACAGACCCT CTCTCTCACC TGTACGGNGT CCGGAGGCTC

CGTCACCGAC ATTCACTACT GGAGCTGGAT CCGCCAGCGC CTGACAGGG GACTGGAATG GATGGGATAC

TGGAGAGGTG GCACAAATCA CAACCCGGCA TTCCAGGAAC GCATCTCCAT CACTGCTGAC GGGACCAAAA

ACCACCTCTC CCTGCAATTG ACCTCCACGA CCACCGAGGA CACGGCCGTC TATTACTGTA CAAGAAACTC

AGACGTCTGG GGCCAGGGCA CCCTGGTCAC CGTC (SEQ ID NO: 891)

MQMPWSLLCL LAAPLGVLSE VILQESGPGL VKPSQTLSLT CTXSGGSVTD IHYWSWIRQR PDRGLEWMGY

WRGGTNHNPA FQERISITAD GTKNHLSLQL TSTTTEDTAV YYCTRNSDVW GQGTLVTV (SEQ ID NO: 892)
H674 SEQ

ATGGACTGCA GCTGGAGAAT CTTCTTCCTG CTGGCACTCG CCACAGGTGT GCACTCTGAG GTCCAGCTGG

TGCAGTCTGC AGCTGAGGTT AAGAAGCCAG GGGCATCTGT GAAGGTCTCC TGCAAGACAT CTGGATACAT

CTTCATTGAC CAGTATATGC ACTGGGTACA GCAGGCTCCA GGAGCAGGGC TTGAATGGAT GGGATGGATT

GATCCTGAGG ATGGTACCAC AAGTTATGCA CAGAAGTTCC AGGCAGAGT CACCCTGACG GCAGACACAT

TABLE N_other H-continued

Other Canine Heavy Variable Domain Sequences

CCACAAACAC AGTCTATATG GAGCTGAGCA ATCTGAGAAC TGAGGACACA GCTGTGTACT ACTGTGCAAG

GGATATATGG GATTTTGACT ACTGGGGCCA GGGAACCCTG GTCACCGTC (SEQ ID NO: 893)

MDCSWRIFFL LALATGVHSE VQLVQSAAEV KKPGASVKVS CKTSGYIFID QYMHWVQQAP GAGLEWMGWI

DPEDGTTSYA QKFQGRVTLT ADTSTNTVYM ELSNLRTEDT AVYYCARDIW DFDYWGQGTL VTV (SEQ ID NO: 894)

TABLE N_G2

Group 2 Nucleic Acid Sequences

λ101:

TGGTCCCCTC TCCTCCTCAC CATCCTCGCT CACTGCACAG GGTCCTGGGC CCAGTCTCTA CTGACTCAGC

CGGCCTCAGT GTCCGGGTCC CTGGGCCAGA GGGTCACCCT CTCCTGCACT GGAAGCGGCT CCAACATCGG

TAGAGGTTAT GTGGGCTGGT ACCAACACCT CCCGGGGACA GGCCCCAGAA CCCTCATCTA TGGTGATATT

AACCGACCCT CAGGGGTCCC CGATCGGTTC TCTGGCTCCA GGTCAGGCAT ACAGCCACC CTGACCATCT

CTGGGCTCCA GGCTGAGGAT GAGGCTGATT ATTACTGTTC ATCGTGGGAC TACAGTCTCA GTAGTACTTT

GTTCGGCGGA GGCACCCACC TGACCGTCCT CGGTCAGCCC AAGGCC (SEQ ID NO: 895)
λ109:

ATGACCTCCA CCATGGGCTG GTCCCCTCTC CTCCTCACCA TCCTCGCTCA CTGCACAGGG TCCTGGGCCC

AATCTGTTCT GACTCAGCCG GCCTCAGTGT CCGGGTCCCT GGGCCAGACG GTCACCATCT CCTGCACTGG

AAGCGAATCC AACATCGGTA GAGGTTTTGT TGGCTGGTAC CAACAGATCC CGGGAACAGG CCCCAGAACC

GTCATTTACG GTCATAATCA CCGACCCTCA GGGGTCCCCG AACGGTTCTC TGGCCCCAGG TCCGGCATCA

CCTCTACCCT GACCATCTCT GGACTCCGGG CTGAGGATGA GGGTGATTAT TATTGTTCAT CCNNGGACNC

TAGTCTCAGT GTCGTTCTGT TCGGCGGAGG CACCCACCTG ACCGTCCTCG GTCAGCCCAA GGCC (SEQ ID NO: 896)
λ111:

AGTCTGTG CTTGACTCAG CCGGCCTCAG TGTCCGGGTC CCTGGGCCAG AGGGTCACCA TCTCCTGCAC

TGGAAGCAGC TCCAACGTCG GTAGAGGTTA TGTGGGCTGG TACCAACAGT CCCGGGAGC GGGCCCCAGA

ACCCTCATCT ATGGTAATAA TAATCGGCCC TCAGGGGTCC CCGATCGGTT CTCTGGCTCC ACGTCAGGCA

GCACAGCCAC TCTGACCATC TCTGGCCTCC GGGCTGAGGA TGAGGCTGAT TATTACTGCT CATCGTGGGA

CGCCAGTCGC AGTGTTACTG TCTTCGGCGG AGGCACCCAC CTGGCCGTCC TCGGTCAGCC CAAGGCC (SEQ ID NO: 897)
λ120:

CTTGGCCAGA GGGTCACCAT TTCCTGCTCT GGAAGTACGT ACAACATCGG TAGTGTTGGT GCGACCTGGT

ACCAACAGCT CCCAGGGAGG TCCCCTAAAC TTCTCGTCTA TAGTGATGGG CATCGCCCGT CAGGGGTTCC

TGACCGGTTC TCCGGCTCCA AGTCTGACAA CTCTGCCACC CTGACCTTCA CTGGGCTTCA GGCTGAGGAC

GAGGCTGATT ATTATTGTCA GTCTCTTGAT CCAACCTCG GGCCTGTGTT CGGCGGAGGC ACCCACCTGA

CCGTCCTCGG TCAGCCCAAG GCC (SEQ ID NO: 898)
λ127:

TABLE N_{G2}-continued

Group 2 Nucleic Acid Sequences

<u>ATGA</u> <u>CCTCCACCAT</u> <u>GGCCTGGTTC</u> <u>CCTCTCCTCC</u> <u>TGACCCTCCT</u> <u>TGCTCACTAC</u> <u>ACAGGGTCCT</u>
GGGCCCAGTC TGTGCTGACT CAGCCGGCCT CAGTGTCTGG GTCCCTGGGC CAGAGGATCA CCATCTCCTG
CACTGGAAGC GGTTCCAACA TTGGAGGTAA TAATGTGGGT TGGTACCAGC AGCTCCCAGG AAGAGGCCCC
AGAACTGTCA TCTATGATAC TTATAGTCGA CTCTCGGGGG TGCCCGATCG ATTCTCTGGC TCCAAGTCTG
GCAGCACAGC CACCCTGACC ATCTCTGGGC TCCAGGCTGA GGATGAGGCT GATTATTACT GCTCAACGTG
GGATGATAGT CTCCGTGCTT ACTTGTTCGG GTCAGGAACC CAACTGACCG TTCTTGGTCA GCCCAAGGCC (SEQ ID NO: 899)
λ201:

<u>ATGACCTC</u> <u>CACCATGGGC</u> <u>TGGTCCCCTC</u> <u>TCCTCCTTAC</u> <u>CCTCCTCGCT</u> <u>CACTGCACAG</u> <u>GTTCCTGGGC</u>
CCAGTCTGCG CTGACTCAGC CGGCCTCAGT GACTGGGTCC CTGGGCCAGA GGGTCACCAT CTCCTGCACT
GGAAGCAGCT CCAACATCGG TGGATATAAT GTTGGCTGGT TCCAACAGGT CCCGGGAACA GGCCCCAGAA
CCGTCATCTA TAGTCGTAGT AATCGACCCT CGGGGGTCCC GGATCGATTC TCTGGCTCCA GGTCAGGCAG
CACAGCCACC CTGACCATCT CTGGCCTCCA GGCAGAAGAC GAGGCTGAAT ATTACTGCTC AACATGGGAC
AGCAGTCTCA AGCTCCTGT GTTCGGCGGA GGCACCCACC TGACCGTCCT CGGTCAGCCC AAGGCC (SEQ ID NO: 900)
λ203:

<u>ATGACCTC</u> <u>CACCATGGCC</u> <u>TGGTCCTCTT</u> <u>TCCTCCTCAC</u> <u>CCTCCTCGCT</u> <u>CACTTCACAG</u> <u>GTTCCTGGGC</u>
CCAGTCTGTG CTGACTCAAC CAGCCTCAGT GTCCGGGTCT CTGGGCCAGA GGGTCACCAT CTCCTGCACT
GGAAGCAGCT CCAACATTGG TAGAGATTAT GTGGGCTGGT ACCAACAGCT CCCGGGAACA CGCCCCAGAA
CCCTCATCTA TGGTAATAGT AACCGACCCT CGGGGGTCCC CGATCGATTC TCTGGCTCCA AGTCAGGCAG
CACAGCCACC CTGACCATCT CTGGGCTCCA GGCTGAGGAC GAGGCTGATT ATTACTGCTC TACATGGGAC
AACAGTCTCA CTGTTCCTGT GTTCGGCGGA GGCACCCACC TGACCGTCCT CGGTCAGCCC AAGGCC (SEQ ID NO: 901)
λ204:

<u>ATGACCTCCA</u> <u>CCATGGGCTG</u> <u>GTCCCCTCTC</u> <u>CTCCTCACCC</u> <u>TCCTCGCTCA</u> <u>CTGCACAGGT</u> TCCTGGGCCC
AGTCTGTACT GACTCAGCCG GCCTCAGTGT CTGGGTCCCT GGGTCAGAGG GTCACCATCT CCTGCACTGG
AAGCAGCTCC AACCTCGGTA GATATGGTGT TGCCTGGTTC AGCAGCTCC CGGGAAAAGG CCCCAGAACC
GTCATCTATA GTATTGATAA CCGACCCTCA GGGGTCCCTG ATCGATTCTC TGGCTCCAAG TCCCGCAGTA
CAGCCACCCT GACCATCTNT GGGCTCCAGG CTGAGGACGA GGCTGATTAT TTNTGCTCAA CATACGACAC
CAGGCTCGGT ACTAGTGTGT TCGT (SEQ ID NO: 902)
λ207:

<u>AT</u> <u>GACCTCCACC</u> <u>ATGGGCTGGT</u> <u>CCCCTCTCCT</u> <u>CCTCACCATC</u> <u>CTCGCTCACT</u> <u>GCACAGGGTC</u>
CTGGGCCCAA TCTCTACTGA CGCAGCCGGC CTCAGTGTCC GGGTCCCTGG CCAGAGGGT CACCATCTCC
TGCACCGGAA CCACCTCCAA CATTGGTAGA GGTTTTGTGG CTGGTTTCA AGAACTCCCG GAACAGGCC
CCAAAATTCT CATCTATGGC AATGGTAACC GACCCTCAGG GGTCCCCGAT CGATTCTCTG CTCCACGTC
AGGCAACACA GCCACCCTGA CCATCTCTGG GCTCCAGCCT GAGGATGAGA CTGATTATTA CTGTTCATCG
TGGGACAACA ATCTCATAAA AATTTTGTTC GGCGGAGGCA CTCATCTGAC CGTCCTCGGT CAGCCCAAGG
CC (SEQ ID NO: 903)
λ215:

TABLE N<sub>G2</sub>-continued

Group 2 Nucleic Acid Sequences

A TGACCTCCAC CATGGGCTGG TTCCCTNTGC TCCTCACCCT CCTGGCTCAC TGCACAGGTT

CCTGGGCCCA GTCTGTGCTG ACTCAGCCGG CCTCAGTGTC TGGGTCCCTG GCCAGAAGG TCACCATCTC

CTGCACTGGG AGCAGCTCCA ACATAGGTAG TGGTTATGTG GGCTGGTACC AGCAGCTCCC AGGAACAGGC

CCCAGAACCC TCATCTATAG TAGTAGTAAC CGACCTTCGG GGGTCCCCGA TCGATTCTCT GGCTCCACGT

CAGGCAGCAC GGCAACCCTG ACCATCTCTG GCTCCAGGC TGAGGACGAG GCTGATTATT ACTGCTCAAC

ATATGACAGC ACTCTCAATG CTGTTGTGTT CGGCGGAGGC ACCCACCTGA CCGTCCTCGG TCAGCCCAAG

GCC (SEQ ID NO: 904)
λ220:

ATGACCTCC ACCATGGGCT GGTCCCCTCT CCTCCTTACC CTCCTCGCTC ACTGCACAGG TTCCTGGGCC

CAGTCTGTGC TGACTCAGCC GGCCTCAGTG ACTGGGTCCC TGGGCCAGAG GGTCACCATC TCCTGCACTG

GAAGCAGCTC CAACATCGGT GGATATAATG TTAATTGGTT CCAACAGTTC CCGGGAAAAG CCCCAAAAC

CGTCATCTAT AGTAGTACTG ACCGACCCTC GGGGGTCCCG GATCGATTCT CCGGGTCCAG GTCAGGCACC

ACAGCCACCC TGACCATCTC TGGACTCCAG GCTGAGGACG AGGCTGACTA TTATTGCTCA GCATGGGACA

ACAGTCTCAA ACTTCCTCTG TTCGGCGGAG GCACACACCT GACCGTCCTC GGTCAGCCCA AGGCC (SEQ ID NO: 905)
λ225:

ATGGGCTGGT CCCCTCTCCT CCTCACCATC CTCGCTCACT GCACAGGGTC CTGGGCCCAG TCTGTGCTGA

CTCAGCCGGC CTCAGTGTCC GGGTCCCTGG GCCAGAGGGT CACCATCTCC TGCACTGGAA GCAGCTCCAA

CATCGGTGGA GGTTATGTGG GCTGGTACCA ACAACTCCCG GAACAGGCC CCAAAACCCT CATCTATGGT

GATAGTAACC GACCCTCAGG GGTCCCCGAT CGGTTCTCTG GCTCCAGGTC AGGCAGCACA GCCACCCTGA

CCATCTCTGG GCTCCAGCCT GAGGATGAGG CTGATTATTA CTGCTCATCG TGGGACACCG GTCTCAGTGC

TCTTGTGTTC GGCGGAGGCA CCCACCTGAC CGTCCTCAGT CAGCCCAAGG CC (SEQ ID NO: 906)
λ227:

ATG TCCTCCGACA TGGCCTGGTC CCCTCTCCTC TTCACACTCC TCGCTCACTG CACAGGGTCC

TGGGCCCAGG CTGTGCTGAA TCAGCCGGCC TCAGTGTCTG GGGCCCTGGG CCAGAAGGTC ACCATCTCCT

GCTCTGGAAG CACAAATGAC ATTGATATAT TTGGTGTGAG CTGGTACCAA CAGCTCCCAG GAAAGGCCCC

TAAACTCCTC GTGGACAGTG ATGGGGATCG ACCCTCAGGG GTCCCTGACA GATTTTCTGG CTCCAGCTCT

GGCAACTCAG GCACCCTGAC CATCACTGGG CTCCAGGCTG AGGACGAGGC TGATTATTAC TGTCAGTCTG

TTGATTCCAC GCTTGGTGCT ATTGTGTTCG GCGGAGGCAC CCATCTGACC GTCCTCGGTC AGCCCAAGGC

C (SEQ ID NO: 907)
λ228:

ATG ATCTTCACCA TGGCCTGGTC CCCTCTCCTC CTCGGCCTCC TTGCTCACTG CACAGGGTCC

TGGGCCCAGT CTATACTGAC TCAGCCAGCC TCAGTGTCTG GGTCCCTGGG CCAGAAGGTC ACCATCTCCT

GCTCTGGAGA CAGTTCCAAC ATCGGTGATA ATTTTGTGGC CTGGTACCAA CAACTCCCAG GAATAGGCCC

AAAAACCGTC ATCTATGGTA CTATTTACCG ACCTTCAGGG GTCCCCGATC GATTTTCTGG CTCCAAGTCA

GGCAATTCAG CCACCCTGAC CATCTCTGGG CTCCAGCCTG AGGACGAGGC TGAATATTAC TGCTCATCAT

GGGATGATAG TCTCANAGGT ATTGTGTTCG GCGGAGGCAC CCTTCTGACC GTCCTCGGTC AGCCCAAGGC

C

TABLE N<sub>G2</sub>-continued

Group 2 Nucleic Acid Sequences (SEQ ID NO: 908)
λ302:

<u>ATGACCTCCA</u> <u>CCATGGGCTG</u> <u>GTCCCTCTC</u> <u>CTCCTCACCC</u> <u>TCCTCGCTCA</u> <u>CTGCACAGGT</u> TCCTGGGCCC

AGTCTGTGCT GACTCAGCCG GCCTCAATGT CTGGGTCCCT GGGCCAGAAG GTCACCATCT CCTGCACTGG

AAGCAGCTCC AACATCGGTA AATATGTTGT CGGCTGGTTC CAGCAGTTTC CGGGAGAAGG CCCCAGAACC

GTCATCTATA GTACTAGTTA TCGACCCTCA GGGGTCCCTG ATCGATTCTC TGGCTCCAAG TCAGGCAGCA

CAGCCACCCT GACCATCTCT GAACTCCAGG CTGAGGACGA GGCTGATTAT TACTGCTCAA CATACGACAG

CAGTCTCGGT GGTAGTGTGT TCGGCGGAGG CACCCATCAT GAC (SEQ ID NO: 909)
λ306:

<u>ATGA</u> <u>CCTCCACCAT</u> <u>GGGATGGTTC</u> <u>CCTCTGCTCC</u> <u>TCACCCTCCT</u> <u>GGCTCACTGC</u> <u>ACAGGTTCCT</u>

GGGCCCAGTC TGTGCTGACT CAGCCGGCCT CAGTGTCTGG GTCCCTGGGC CAGAGGGTCA CCATCTCCTG

CACTGGAAGC AGCTCCAACA TCGGTAGAGG TTATGTGGGC TGGTACCGGC AGCTCCCAGG AACAGGCCCC

ACAACCCTCA TCTATGATGA TAGTAGCCGA CCCTCGGGGG TCCCTAATCG ATTCTCTGGC TCCAGGTCAG

GCAGCACTGC AACCCTGACC ATCTCGGGCC TCCAGGCTGA CGACGAGGCT GATTATTACT GCTCAGCATA

TGACAGCACT CTCACTGGTA CTGTATTCGG CGGAGGCACC CACCTGACCG TCCTCGGTCA GCCC (SEQ ID NO: 910)
λ310:

<u>A</u> <u>TGACCTCCAC</u> <u>CATGGGATGG</u> <u>TTCCCTCTGC</u> <u>TCCTCACCCT</u> <u>CCTGGCTCAC</u> <u>TGCACAGGTT</u>

CCTGGGCCCA GTCTGTGCTG ACTCAGCCGG CCTCAGTGTC TGGGTCCCTG GCCAGAGGG TCACCATCTC

CTGCACTGGA AGCAGCTCCA ACATCGGTAG AGATTATGTG GCCTGGTACC AACAGTTCCC AGGAACAGGC

CCCAGAATCC TCATCTATGA TACTCGTAGC CGACCCTCGG GGGTCCCTGA TCGATTCTCT GGCTCCAGGT

CAGGCTACAC AGCTGCCCTG ACCATCTCTG GACTCCAGGC TGAGGACGAG GCTGACTATT ACTGCTCAAC

ATATGACAGC AGTCTCAGTG GTCCTCTTTT CGGCGGAGGC ACCCACCTGA CCGTCCTCGG TCAGCCCGAG

GCC (SEQ ID NO: 911)
λ320:

<u>ATGACCTC</u> <u>CAACATGGCN</u> <u>TGGTCCCCTT</u> <u>TCCTCCTCAC</u> <u>ACTCCTTGCT</u> <u>TACTGCACAG</u> <u>GATCCTGGGC</u>

CCAGTCTGCG CTGACTCAGC CGACCTCAGT GTCGGGGTCC CTTGGCCAGA GGGTCTCCAT TTCCTGCTCT

GGAAGCACGA GCAACATCGG TATTGTCGGT GCGAGCTGGT ACCAACAACT CCCAGGAAAG CCCCTAAAC

TCCTCCTGAA CAGTGATGGG AGTCGACCGT CAGGGGTCCC TGACCGGTTT TCCGGCTCCA ACTCTGGCGC

CTCAGCCACC CTGACCATCA CTGGGCTTCA GGCTGAGGAC GAGGCTGATT ATTACTGTCA GTCTTTTGAT

CCCACGCCTC CTGATCATTA CGTGTTCGGC TCAGGAACCC AACTGACCGT CCTTGGTCAG CCC (SEQ ID NO: 912)
λ325:

<u>ATGACCTC</u> <u>CACCATGGGC</u> <u>TGGTCCCCTC</u> <u>TCCTCCTTAC</u> <u>CCTCCTCGCT</u> <u>CACTGCACAG</u> <u>GTTCCTGGGC</u>

CCAGTCTGTA CTGACTCAGC CGGCCTCAGT GAGTGGGTCC TTGGGCCAGA GGGTCACCAT CTCCTGCACT

GGAAGCCCCT CCAACATCGG TGGATATGAT GTTGCCTGGC TCCAGCAGCT CCCGGGAACA GGCCCCAAGA

CCGTCATCTA TAGTAGTACT AACCGACCCT CGGGGGTCCC GGATCGATTC TCCGGCTCCA GGTCAGGCAG

CACAGCCACC CTGACCATCT CTGGGCTCCA GGCTGAGGAC GAGGCTGACT ATTACTGTTC CGCATGGGAC

AGCACTCTCA GAGCTGGTGT GTTCGGCGGA GGCACCCACC TGACCGTCCT CGGTCAGCCC AAGGC

TABLE N<sub>G2</sub>-continued

Group 2 Nucleic Acid Sequences (SEQ ID NO: 913)
λ326:

<u>AT</u> <u>GACCTCCACC</u> <u>ATGGGCTGGT</u> <u>CCCCTCTCCT</u> <u>CCTTACCCTC</u> <u>CTCGCTCACT</u> <u>GCACAAGTTC</u>

CTGGGCCCAG TCTGTGCTGA CTCAGCCGGC CTCAGTGACT GGGTCCCTGG GCCAGAGGGT CACCATCTCC

TGCACTGGAA GCAGCTCCAA CATCGGTGGA TATAGTGTTG CCTGGTTCCA GCACCTCCCG GGAACAGGCC

CCAGAACCGT CATCTATAGT AATACTAAGC GACCCTCGGG GGTCCCGGAT CGATTCTCTG GCTCCAGGTC

AGGCAGCACA GCCACCCTGA CCATCTCTGG GCTCCTGGCT GAGGACGACG CTGATTATTA TTGCTCAACA

TGGGACAGCA GTCTCAAAGC TCTTCTGTTC GGCGGAGGCA CCCATCTGAC CGTCCTCGGT CAG (SEQ ID NO: 914)
λ129:

TCCT GGGCCCACTC TGTCCTGACT CAGCCGGCCT CAGTGTCTGG GTTTCTGGGC CAGAGGGTCA

CCATCTCCTG CACTGGAAGC AGCTCCAACA TTGGTGGAAA TTATGTGAGC TGGCACCAGC AGGTCCCAGA

AACAGGCCCC AGAAACATCA TCTATGCTGA TAACTACCGA GCCTCGGGGG TCCCTGATCA ATTTTCTGGC

TCCAAGTCAG GCAGCACAGC CACCCTGACC ATCTCTGTGC TCCAGGCTGA GGATGAGGCT GATTATTACT

GCCAGTCCTT TGATACCGCT CTTGGTACTG TGTTCGGCGG AGGCACCCAC CTGACCGTCC TCGGTCAGCC

CAGGGCC (SEQ ID NO: 915)
λ130:

<u>ATGACC</u> <u>TCCACCATGG</u> <u>CCTGGTTCCC</u> <u>TCTCCTCCTG</u> <u>ACCCTCCTTG</u> <u>CTCACTACAC</u> <u>AGGG</u>TCCTGG

GCCCAGTCTG TGCTGACTCA GCCGGCCTCA GTGTCCGGGT CCCTGGGCCA GAGGGTCACC GTCTCCTGCA

CTGGAAGCAA CTCCAACATC GGTCGAGGTT ATGTGGACTG GTACCAACAA CTCCCGGGAA GAGGCCCCAC

AACCCTCTTG TATGGTACTG CTAACCGCCC CTCAGGGGTC CCCGATCGGT TCTCTGGCTC CAGGTCAGGA

CGCACAGCCA CCCTGACCAT CTCTGGGCTC CAGGCTGAGG ATGAGGCTGA TTATTACTGC TCATCGTGGG

ACGACGGTCT CAGGGCTCTC GTGTTCGGCT CAGGAACCCA CCTGACCGCC CTTGGTCAGC CCAAGGCC (SEQ ID NO: 916)
λ134:

<u>CTCCTCACCA</u> <u>TCCTCGCTCA</u> <u>CTGCACAGGG</u> TCCTGGGCCC AGTCTCTACT GACTCAGCCA GCCTCAGTGT

CTGGGTCCCT GGGCCAGAAG GTCACCATCT CCTGCACTGG AAGCAACTCC AACATCGGTG GTAATGATGT

GGCCTGGTAT CAACAGCTCC CAGGAATAGG CCCTAGAACC GTCATCTATG GTAAAAATAA CCGACCTTCA

GGAATCTCCG ATCGATTCTC TGGCTCCAAG TCAGGCAATT CAGCCAGTTT GACCATATCT GGGCTCCAGG

CTGAGGACGA GGCTGATTAT TTCTGCTCAT CATGGGATGA TAGTCTCAAA GGTCACGTGT TCGGCTCAGG

AACCCAACTG ACCGTCCTTG GTCAGCCCAA GGCC (SEQ ID NO: 917)
λ213:

<u>ATGAC</u> <u>CTCCACCATG</u> <u>GCCTGGTTCC</u> <u>CTCTCCTCCT</u> <u>GACCCTCCTT</u> <u>GCTCACTACA</u> <u>CAGGG</u>TCCTG

GGCCCAGTCT GTGCTGACTC AGCCGGCCTC AGTGTCTGGG TCCCTGGGCC AGAGGATCAC CATCTCCTGC

ACTGGAAGCG TCTCCAACAT TGGCATTTTT GATGTGGGTT GGTATCAACA ACTCCCAGGA AGAGGCCCCA

GAACTGTCAT CTATTCTACA AACAGTCGCC CCTCGGGGGT GCCCGATCGA TTTTCTGGCT CCAAGTCTGG

CAGCACAGCC ACCCTGACCA TCTCTGGGCT CCAGGCTGAG GATGAGGCTG ATTATTACTG CTCAACGTGG

GATGAGAATC TCAGTGTTCC CGTGTTCGGC GGAGGCACCC ACCTGACCGT CCTCGGTCAG CCCAAGGCC (SEQ ID NO: 918)

TABLE N_{G2}-continued

Group 2 Nucleic Acid Sequences

λ214:

<u>ATGACCT</u> <u>CCACCATGGC</u> <u>CTGGTCCTCT</u> <u>TTCCTCCTCA</u> <u>CCCTCCTCGC</u> <u>TCACTTCACA</u> <u>GGTTCCTGGG</u>

CCCAGTCTGT ACTGACTCAA CCAGCCTCAG TGTCCGGGTC TCTGGGCCAG AGGGTCACCA TCTCGTGCAC

TGGAAGCGGC TCCAACATTG GTAGAGATTC TGTGGGCTGG TACCAACAGG TCCCGGGAAC ACGCCCCAGA

ACCCTCATCT ATGGTACTAC TAACCGACCC TCGGGGTCC CCGATCGATT CTCTGGCTCC AAGTCAGGCA

GCACAGCCAC CCTGACCATC TCTGGCCTCC AGGCTGAGGA CGAGGCTGAT TATTACTGCT CTACATGGGA

CAACAGTGTC ACTGTTCTGT TCGGCGGAGG CACCCATCTG ACCGTCCTCA GTCAGCCCAA GGCC (SEQ ID NO: 919)
λ216a:

<u>ATGATCTTC</u> <u>ACCATGGCCT</u> <u>GGTCCCCTCT</u> <u>CCTCCTCGGC</u> <u>CTCCTTGCTC</u> <u>ACTGCACAGG</u> <u>GTCCTGGGCC</u>

CAGTCTATGC TGACTCAGCC AGCCTCAGTG TCTGGGTCCC TGGGCCAGAC GGTCACCATC TCCTGCACTG

GAAGTAGCTC CAACATCGGT GGTAATCAAG TGGGCTGGTA CCAACAGTTC CAGGAAGAG GCCCTAGAAG

CGTCATCTAT GGTGATAATC ATCGACCCTC AGGGGTCCCC GATCGATTCT CTGTCTCCAA GTCAGGCAGT

TCAGCCACCC TGACCATCTC TGGACTCCAG GCTGAGGACG AGGCTGAATA TTACTGCTCA TCATGGGATA

ATGATTTCGG TCACGTGTTC GGCTCAGGAA CCCAACTGAC CGTCCTTAGT CAGCCCAAGG CC (SEQ ID NO: 920)
L204-79:

<u>ATGACCT</u> <u>CCAACATGGC</u> <u>CTGGTCCCCT</u> <u>CTCCTCCTCA</u> <u>CACTCCTTGC</u> <u>TTACTGCACA</u> <u>GGGTCCTGGG</u>

CCCAGTCTGT GCTGACTCAG CCGACCTCAG TGTCGGGGTC CCTTGGCCAG AGGGTCACCA TCTCCTGCTC

TGGAAGCACG AACGACATCG CTATTGTTGG TGCGAGCTGG TACCAGCAGC TCCCAGGAAA GGCCCCTAAA

CTCCTCGTGT ACACTTTTGG GGATCGGCCG TCAGGGGTCC CTGACCGGTT TTCCGGCTCC AACTCTGGCA

ACTCAGCCAC CCTGACCATC ACTGGGCTTC AGGCTGAGGA CGAGGCTGAT TATTACTGCC AGTCCTTTGA

TACCACGCTT GGTGCTTACG TCTTCGGCTC AGGAACCCAA CTGACCGTCC TTGGTCAGCC CAAGGCC (SEQ ID NO: 921)
L205-79:

<u>ATGATC</u> <u>TTCACCATGG</u> <u>CCTGGTCCCC</u> <u>TCTCCTCCTC</u> <u>GGCCTCCTTG</u> <u>CTCACTGCAC</u> <u>AGGG</u>TCCTGG

GCCCAGTCTA TCCTGACTCA GCCAGCCTCA GTGTCTGGGT CCCTGGGCCA GAAGGTCACC ATCTCCTGCA

CTGGAAGCAG CTCCAATATC GGTGGTAATT ATGTGGGCTG GTACCAAAAT CTCCCAGGAA AAGGCCCTAA

AACCGTCATC TTTGCTGATG ATCACCGACC TTCAGGGGTC CCCGATCGAT TCTCTGGCTC CAGGTCAGGC

AGTTCAGCCA CCCTGACCAT TTCTGGGCTC CAGGCTGAGG ACGAGGCTGA CTATTATTGT TCATCATGGG

ATAGGAGTCT CAGAGGTCAG GTTTTCGGCG GAGGCACCCA CCTGACCGTC CTCGGTCAGC C (SEQ ID NO: 922)
L206-79:

<u>A</u> <u>TGACCTCCAC</u> <u>CATGGGCTGG</u> <u>TTCCCTCTGC</u> <u>TCCTCACCCT</u> <u>CCTGGCTCAC</u> <u>TGCACAGG</u>TT

CCTGGGCCCA GTCTGTGCTG ACTCAGCCGG CCTCAGTGTC TGGGCCCCTG GGCCAGAAGG TCACCATCTC

CTGCACTAGA AGCAGCTCCA ACATTGCTGG TGGTTATGTG GCCTGGTACC AGCAGATCCC AGGAACAGGC

CCCAGAACCC TCATCTATAG TACTACTGTC CGACCTTCGG GGGTCCCCGA TCGATTCTCT GGCTCCAGGT

CAGGCAGCAC AGCAACCCTG ACCATCTCTG GGCTCCAGGC TGAGGACGAG GCTGATTATT ATTGCTCAGG

ATATGACACC ACTGTCAATG GTGTTGTCTT CGGCGGAGGC ACCCATCTGA CCGTCCTCGG TCAGCCCAAG

GCC (SEQ ID NO: 923)

TABLE N<sub>G2</sub>-continued

Group 2 Nucleic Acid Sequences

L207-79:

<u>ATGACCTC</u> <u>CACCATGGGC</u> <u>TGGTCCCCTC</u> <u>TCCTCCTCAC</u> <u>CATCCTCGCT</u> <u>CACTGCACAG</u> <u>GGTCCTGGGC</u>

CCACTCTGTG CTGACTCAGC CGGCCTCAGT GTCCGGGTCC CTGGGCCAGA GGGTCACCAT CTCATGCACT

GGAAGCGGGT CCAACATCGG GAGAGGTTAT GTGGGCTGGT ACCAACAGTA CCCGGGAACA GGCCCCAAAA

CGCTAATCTA TGGTGATAGT AGTCGACCCT CAGGGGTCCC CGATCGGTTC TCTGCCTCCA GGTCAGGCAA

CTCAGCCACC CTGACCATCT CTGGGCTCCA GGCTGAGGAT GAGGCGGATT ATTACTGTTC ATCGTGGGAC

ACCAGTCTCA GAACTATATT CGGCGGAGGC ACCTATCTGA CCGTCGTCGG TCAGCCCAAG GCC (SEQ ID NO: 924)

L210-79:

<u>ATGACC</u> <u>TCCACCATGG</u> <u>GCTGGTTCCC</u> <u>TCTGCTCCTC</u> <u>ACCCTCCTGG</u> <u>CTCACTGCAC</u> <u>AGGT</u>TCCTGG

GCCCAGTCTC TGCTGACTCA GCCGGCCTCA GTGTCTGGGT CCCTGGGACA GAAGGTCACC ATCTCCTGCA

CTGGAAGCAG TGCCTACATT GGTAGTGGCT ATGTGGGCTG GTACCAGCAG GTCCCAGGAA CAGGCCCCAG

AACCCTCATT CATAGTACCA GTAACCGACC CCCGGGGGTC CCCGATCGAT TCTCTGCCTC CGCGTCAGGC

AGCACAGCAA CCCTGACCAT TTCTGGGCTC CAGGCTGAGG ACGAGGCTGA TTATTACTGC TCAGCCTCTG

ACAGCAGTCT CAGTGTTGTG TTCGGCGGAG GCACCCACCT GACCGTCCTC GGTCAGCCCA AGGCC (SEQ ID NO: 925)

L215-79:

<u>ATGGC</u> <u>CTGGTCCCCT</u> <u>CTCCTCCTCA</u> <u>CACTCCTTGC</u> <u>GTACTGCACA</u> <u>GGG</u>TCCTGGG CCCAGTCTGT

ACTGACTCAG CCGACCTCAG TGTCGGGGTC CCTTGGCCAG AGGGTCACCA TTTCCTGCTC TGGAAGCACG

AAGAACATCG GAATTTTTGG TGCGCACTGG TACCAGCAAT CCCGGGAAAG GCCCCTGAAC TCCTCATTT

ATAATAGTAG AGAACGACCG TCAGGGGTCC CTGGCCGGTT TTCCGGCTCC ATCTCTGGCA ACTCAGCCAC

CCTGACCATC ACTGGGCTTC AGGCTGAGGA CGAGGCTGAT TATCACTGCC AGTCTTTTGA TACCACGCTT

GGTGATGGTG ATGTTTTGTT CGGCGGCGGC ACCCACCTGA CCGTCCTCGG TCAGCCCAAG GCC (SEQ ID NO: 926)

L216-79:

AGGATCAGTG ATGATCTTCA CCATGGCCTG GTCCCTCTC CTCCTCGGCC TCCTTGCTCA CTGCACAGGG

TCCTGGGCCC AGTCTATGCT GACTCAGCCA GCCTCAGTGT CTGGGTCCCT GGGCCAGAAG GTCACCATCT

CCTGCACTGG AAGCAGCTCC AACATCGGTG GTAATTATGT GGGCTGGTAC AACAGCTCC AGGAATAGG

CCCTAGAACC GTCATCTCTG GTAATAATTA CCGACCTTCA GGGGTCCCCG ATCGATTCTC TGGCTCCAAG

TCAGGCAGTT CAGCCACCCT GACCATCTCT GGGCTCCAGG CTGAGGACGA GGCTGAGTAT TACTGCTCAT

CATGGGATGA TAGTCTCAGA ATTTCTGTGT TGGCGGAGG CACCCACCTG ACCGTCCTCG GTCAGCCCA (SEQ ID NO: 927)

L217-79:

<u>ATGACCTC</u> <u>CACCATGGGC</u> <u>TGGTCCCCTC</u> <u>TCCTCCTTAC</u> <u>CCTCCTCGCT</u> <u>CACTGCACAG</u> <u>GTTCCTGGGC</u>

CCAGTCTGTC CTGACTCAGC CGGCCTCAGT GACTGGGTCC CTGGGCCAGA GGGTCACCAT CTCCTGCACT

GGAAGCAGCT CCAACATCGG TGGATCTAGT GTTGGTTGGT TCCAGCAGTT CCCGGGAACA GGCCCCAGAA

CCGTCATCTA TAGTATTAGT AGCCGACCCT CGGGGGTCCC GGATCGATTC TCTGGCTCCA GGTCAGGCAG

CACAGCCATC CTGACCATCT CTGGGCTCCA GGCTGAGGAC GAGGCTGAGT ATTACTGCTC AGCATGGGAC

AGCAGTCTCA AGAAGCTGT GTTCGGCGGA GGCACCCACC TGACCGTCCT CGGTCAGCCC AAGGCC (SEQ ID NO: 928)

L201-90:

TABLE N_{G2}-continued

Group 2 Nucleic Acid Sequences

ATGACCT CCACCATGGC CTGGTCCTCT TTCCTCCTCA CCCTCCTCGC TCACTTCACA GGTTCCTGGG

CCCAGTCTGT ACTGACTCAA CCAGCCTCAG TGTCCGGGTC TCTGGGCCAG AGGGTCACCA TCTCGTGCAC

TGGAAGCGGC TCCAACATTG GTAGAGATTC TGTGGGCTGG TACCAACAGG TCCCGGGAAC ACGCCCAGA

ACCCTCATCT ATGGTACTAC TAACCGACCC TCGGGGTCC CCGATCGATT CTCTGGCTCC AAGTCAGGCA

GCACAGCCAC CCTGACCATC TCTGGCCTCC AGGCTGAGGA CGAGGCTGAT TATTACTGCT CTACATGGGA

CAACAGTGTC ACTGTTCTGT TCGGCGGAGG CACCCATCTG ACCGTCCTCA GTCAGCCCAA GGCC (SEQ ID NO: 929)
L217-90:

ATG ACCTCCACCA TGGCCTGGTC CTCTTTCCTC CTCACCCTCC TCGCTCACTT CACAGGTTCC

TGGGCCCAGT CTGTACTGAC TCAACCAGCC TCAGTGTCCG GGTCTCTGGG CCAGAGGGTC ACCATCTCGT

GCACTGGAAG CGGCTCCAAC ATTGGTAGAG ATTCTGTGGG CTGGTACCAA CAGGTCCCGG GAACACGCCC

CAGAACCCTC ATCTATGGTA CTACTAACCG ACCCTCGGGG GTCCCCGATC GATTCTCTGG CTCCAAGTCA

GGCAGCACAG CCACCCTGAC CATCTCTGGC CTCCAGGCTG AGGACGAGGC TGATTATTAC TGCTCTACAT

GGGACGACAG TGTCACTGTT CTGTTCGGCG GAGGCACCCA TCTGACCGTC CTCAGTCAGC CCAAGGCC (SEQ ID NO: 930)
L242-90

ATGACCTCCA CCATGGCTGG TCCTCTTTCC TCCTCACCCT CCTCGCTCAC TTCACAGGTT CCTGGGCCCA

GTCTGTACTG ACTCAACCAG CCTCAGTGTC CGGGTCTCTG GCCAGAGGG TCACCATCTC GTGCACTGGA

AGCGGCTCCA ACATTGGTAG AGATTCTGTG GCTGGTACC AACAGGTCCC GGGAACACGC CCCAGAACCC

TCATCTATGG TACTACTAAC CGACCCTCGG GGTCCCCGA TCGATTCTCT GGCTCCAAGT CAGGCAGCGC

AGCCACCCTG ACCATCTCTG GCCTCCAGGC TGAGGACGAG GCTGATTATT ACTGCTCTAC ATGGGACAAC

AGTGTCACTG TTCTGTTCGG CGGAGGCACC CATCTGACCG TCCTCAGTCA GCCCAAGGCC (SEQ ID NO: 931)
L1-706:

ATGACCTC CACCATGGGA TGGTTCCNTN TGCTCCTCAC CCTCCTGGCT CACTGCACAG GTTCNTGGGC

CCAGTCTGTG NTGACTCAGC CGGCCTCAGT GTCTGGGTCC CTGGGCCAGA GGGTCACCAC CTCCTGCACT

GGAAGCAGCT CCAACATCGG TAGAGGTTTT GTGGCCTGGC ACCAGCAACT CCCAGGAACA GGCCCCAGAA

CACTCATATA TCGTTCTGAG AGGCGGCCCT CGGGGGTCCC TGATCGATTC TCCGGCTCCA GGTCAGGCAG

CACAGCAACC CTGACCATCT CTGGGCTCCA GCCTGAGGAC GAGGCTGATT ATTACTGTTC AGCACATGAC

AACAGTGTCA GTGGTGTTGT GTTCGGCGGA GGCACCCATC TGACCGTCCT CGGTCAGCCC AAGGCC (SEQ ID NO: 932)
L1-710:

ATG ACCTCCACCA TGGCCTGGTT CCCTCTCCTC CTGACCCTCC TTGCTCACTA CACAGGGTCC

TGGGCCCAGT CTGTGCTGAC TCAGCCGGCC TCAGTGTCTG GGTCCCTGGG CCAGAGGATC ACCGTCTCCT

GCACTGGCGC CTACTCCAAC ATTGGAACTA ATAATGTGGG TTGGTACCAA CAACTCCCAG GAAGAGGCCC

CAGAACTGTC ATCTATAGTA CAGATAGTCG ACCCTCGGGG GTGCCCGATC GATTCTCTGG CTCCAGGTCT

GGCACCACTG CCACCCTGAC CATCTCTGGG CTCCAGGCTG AGGATGAGGC TGATTATTAC TGCTCAGCAT

GGGATGATAG TCTCACTGCT TACGTGTTCG GCTCAGGGAC CCAACTGACC GTCCTTGGTC AGCCCAAGGC

C (SEQ ID NO: 933)
L1-714:

TABLE N_{G2}-continued

Group 2 Nucleic Acid Sequences

<u>ATG</u> <u>ACCTCCACCA</u> <u>TGGGATGGTT</u> <u>CCCTCTGCTC</u> <u>CTCACCCTCC</u> <u>TGGCTCACTG</u> <u>CACAGGTTCC</u>
TGGGCCCAGT CTGTGCTGAC TCAGCCGGCC TCAGTGTCTG GGTCCCTGGG CCAGAGGGTC ACCATCTCCT
GCACTGGAAG CGGCTCCAAC ATCGGTCGAG GTTATGTGGC CTGGTACCAA CAGCTCCCAG AAACAGGCCC
CAGAACCCTC ATCTATGATA CTAGTCGTCG ACCCTCGGGG GTCCCTGATC GATTCTCTGG CTCCAGGTCA
GGCAGCACAG CGACCCTGAC CATCTCTGGA CTCCAGGCAG ACGACGAGGC TGATTATTAC TGTTCAACAT
ATGACATCAC TATCACTGGT GGTGTGTTCG GCGGGGCAC CCACCTGACC GTCCTCGGTC AGCCCAAGGC
C (SEQ ID NO: 934)
L1-715:

<u>ATGA</u> <u>CCTTCACCGT</u> <u>GGGATGGTCC</u> <u>CCTCTCCTCC</u> <u>TCACCTTCCT</u> <u>TGCTCACTGC</u> <u>ACAGGGTCTT</u>
GGGCCCAGTC TGTCCTGACT CAGCCGGCCT CAGTGTCCGG GTCTCTGGGC AGAGCGTCA CCATCTCCTG
CACTGGCTCC AGCATCAATT ATAGATACGT TGGCTGGTAC CAGCAGGTCC CGGGAACAGG CCCCAGAACC
CTCATCTATG ATAATGGCAA ACGACCCTCG GGGGTTCCCG AGCGATTCTC TGGCTCCAAG TCAGGCAGCA
CAGCCGCCCT AACCATCTCT GGGCTCCAGG CTGAGGACGA GGCTGATTAT TATTGCTCTT CATATGACAG
CAGTTTCACT GCTGACTTCG GCGGAGGCAC CCAGTTGACC GTCCTCGGTC AGCCCAAGGC C (SEQ ID NO: 935)
L1-720:

<u>ATGGG</u> <u>NTGGTCCCCT</u> <u>CTCCTCCTTA</u> <u>CCCTCCTCGC</u> <u>TCACTGCACA</u> <u>GGTTCCTGGG</u> CCCAGTCTGT
GCTGACTCAG CCGGCCTCAG TGACTGGGTC CCTGGGCCAG AGGGTCACCA TCTCCTGCAC TGGAAGCAGC
TCCAACATCG TGGATATAA TGTTGGCTGG TTCCAGCAGC TCCCGGGAAC AGGCCCCAGA ACCGTCATCT
ATAGTAGTAG TAACCGACCC TCGGGGGCCC CGGATCGATT CTCTGGCTCC AGGTCAGGCA GCACAGCCAC
CCTGACCATC TCTGGGCTCC AGGCTGAGGA CGAGGCTGAG TATTACTGCT CAACATGGGA CAGCAGTCTC
AAAGCTATTG TGTTCGGCGG AGGCACCCAT CTGACCGTCC TCGGTCAGCC CAAGGCC (SEQ ID NO: 936)
L1-721:

<u>AT</u> <u>GATCTTCACC</u> <u>ATGGCTTGGT</u> <u>CCCCTCTCCT</u> <u>CCTCGGCCTC</u> <u>CCTGCTCACT</u> <u>GCACAGGGTC</u>
CTGGGCCCAG TCTATGCTGA CTCAGCCAGC CTCAGTGTCT GGGTCCCTGG GCCAGAAGGT CACCATCTCC
TGCACTGGAA GCAGTTCCAA CATCGGTGGT AATTATGTGG CTGGTACCA ACAGGTCCCA GGAATAGGCC
CTAGAACCGT CATGTATGGT GATAATAACC GACCTTCAGG GGTCCCCGAT CGATTCTCTA GCTCCAGGTC
AGGCAGTTCA GCCACCCTGA CCATCGCTGG CCTCCAGGCG GAGGACGAGG CTGCGTATTA CTGTTCGTCA
TGGGATGATA GTCTCAGAGG TCATGTGTTC GGCGGAGGCA CCCATCTGAC CGTCCTCGGT CAGCCCAAGG
CC (SEQ ID NO: 937)
L1-723:

<u>ATGGCNTGGT</u> <u>CCTCTTTCCT</u> <u>CCTCACCCTC</u> <u>CTCGCTCACT</u> <u>TCACAGGTTC</u> CTGGGCCCAG TCTGTGCTGA
CTCAACCAGC CTCAGTGTCC GGGCTCTGG GCCAGAGGGT CACCATCTCC TGCACTGGAA GCAGCTCCAA
CATTGGTAGA GATTATGTGG CTGGTTCCA ACACCTCCCG GAACACGCC CAAAAGCCT CATCTATGGT
AATAGTAAGC GACCCTCGGG GGTCCCCGAT CGATTCTCTG CTCCAAGTC AGGCAGCACA GCCACCCTGA

TABLE N<sub>G2</sub>-continued

Group 2 Nucleic Acid Sequences

CCATCTCTGG GCTCCAGGCT GAGGACGAGG CTATTTATTA CTGCTCTACA TGGGACAACA GTCTCACTTA

CGTGTTCGGC TCAGGAACCC AACTGACCGT CCTTGGTCAG CCCAAGGCC (SEQ ID NO: 938)
L1-731:

GGGTCACCAT CTCGTGCTCT GGACGTACGG ACAACATCGG TGTCGCTGGT GCGGCTTGGT ACCAACAACT

CCCAGGAAAG GCCCCTAAAC TCCTCGTGGA CAATGATGGC CATCGACCGT CAAGGGTCCC TGACCGGTTT

TCCGGCTCCG AGTCTGGCAA CTCAGCCACT CTGACCATCA CTGGGCTTCA GGCTGAGGAC GAGGCTGATT

ACTACTGCCA GTCCTTTCAA ACCACGCTTA ATATTTACGT GTTCGGCTCA GGGACCCAAC TGACCGTCCT

TGGTCAGCCC AAGGCC (SEQ ID NO: 939)
L1-732:

ATGACCT CCACCATGGG CTGGTCCCCT CTCCTCCTTA CCCTCCTCGC TCACTGCACA GGTTCCTGGG

CCCAGTCTGT GCTGACTCAG CCGGCCTCAG TGACTGGGTC CCTGGGCCAG AGGGTCACCA TCTCCTGCAC

TGGAAGCGGC TCCGACATCG GTGGATTTGG CTGGTTCCAG CAGCTCCCGG GAACAGGCCC CAGAACCGTC

ATCTATGGTG ATAGTGACCG ACCCTCGGGG GTCCCGGATC GATTCTCTGG CTCCAGGTCA GGCAGGACAG

CCACCCTGAC CATCTCTGGG CTCCAGGCTG AGGACGAGGC TGAGTATTAC TGCTCAACAT GGGACGCCAG

TCTCCGGGTT GGTGTGTTCG GCGGAGGCAC CCACCTGACC GTCCTCGGTC AGCCCAAGGC C (SEQ ID NO: 940)
L1-733:

AT GACCTCCACC ATGGGCTGGT CCCCTCTCCT CCTTACCCTC CTCGCTCACT GCACAGGTTC

CTGGGCCCAG TCTGTGCTGA CTCAGCCGGC CTCAGTGACT GGGTCCCTGG GCCAGAGGGT CACCATCTCC

TGCACTGGAA GCAGCTCCAA CATCGGTGGA TATAATGTTG GCTGGTTCCA GCAGCTCCCG GGAACAGGCC

CCAGAACCGT CATCTGTAGT AGTAGTAACC GACCCTCGGG GGTCCCGGAA CGATTCTCTG GCTCCAGGTC

AGGCAGCACA GCCACCCTGA CCATCTCTGG GCTCCAGGCT GAAGACGAGG CTGAGTATTA CTGCTCAACA

TGGGACAGCA GTCTCAAAGC TGTTGTGTTC GGCGGAGGCA CCCACCTGAC CGTCCTCGGT CAGCCCAAGG

CC (SEQ ID NO: 941)
L1-737:

AGCAGCTCCC AGGAAGAGGC CCCAGAACTG TCATCTATAG TACAGATAGG CGACCCTCGG GGGTGCCCGA

TCGATTCTCT GGCTCCAAGT CTGGCAGCAC AGCCACCCTG ACCATCTCTG GCTCCAGGC TGAGGATGAG

GCTGATTATT ACTGCTCAAC GTGGGATGAC AGTCTCAGTG AACCTGTGTT CGGCGGAGGC ACCCACCTGA

CCGTCCTCGG TCAGCCCAAG GCC (SEQ ID NO: 942)
L1-739:

CCTGCACTGG AAGCAGCTCC AACGTCGGTG GAGGTTTTGT GGGCTGGTAC CAACTGGTCC CAGGGACAGG

TCCCAGAACA CTCATCTATG GTAATTCTGA CCGACCCTCG GGGGTCCCTG ATCGGTTCTC TGGCTCCAAG

TCAGGCACCA CAGCCATTCT GACCATCTCT GGACTCCAGG CTGACGACGA GGCTGATTAT TTTTGCTCGA

TABLE N_{G2}-continued

Group 2 Nucleic Acid Sequences

CATACGACAC CAGACTCAAT GATGTTATTT TCGGCGGCGG CACCCACCTG ACCGTCCTCG GTCAGCCCAA

GGCC (SEQ ID NO: 943)
L1-742:

AT <u>GACCTCCACC ATGGCCTGGT TCCCTCTCCT CCTGACCCTC CTTGCTCACT ACACAGGG</u>TC

CTGGGCCCAG TCTGTGCTGA CTCAGCCCGC CTCAGTGTCT GGGTCCCTGG GCCAGAGGAT CACCATCTCT

TGCGCTGGAA CCAACTCCGA CATTGGAACT AATCATGTGG CTTGGTACCA GCAGCTCCCA GGGAGAGGCC

CCAGAACTGT CATCCATACT ACAAATAGTC GGCCCTCGGG GGTGCCCGAT CGATTCTCTG GTTCCAAGTC

TGGCAGCACA GCCACCCTGA CCATCTCTGG GCTCCAGGCT GACGATGAGG CTGATTATTA CTGTTCAGCG

TGGGATGATC GTCTCACTGA GCCTGTATTC GGCGGAGGCG CCCACCTGAC CGTCCTCGGT CAGCCCAAGG

CC (SEQ ID NO: 944)
L1-747:

ATGTCCT CCGACATGGC CTGGTCCCCT CTCCTCTTCA CACTCCTCGC TCACTGCACA GGGTCCTGGG

CCCAGGCTGT ACTGAATCAG CCGGCCTCAG TGTCTGGGGC CCTGGGCCAG AAGGTCACCA TCTCCTGCTC

TGGTAGCACA AATGACATAG GTAGATTTGG TGTCAACTGG TGCCAACAAC TCCCAGGAAA GGCCCCTAAG

CTCCTCGTGG ACAGTGATGG GGACCGACCC TCAGGGATCC CTGACAGATT TCAGGCTCC CGCTCTGACA

ACTCAGGCAT CCTGACCATC AGTGGCCTCC AGGCTGAGGA CGAGGCTGAT TATCACTGTC AGTCTGTTGA

TCACACGCTT GCCGCTGCTG TGTTCGGCGG GGGCACCCAC CTGACCGTCC TCGGTCAGCC CAAGGCC (SEQ ID NO: 945)
L1-749:

<u>ATGA CCTCCACCAT GGGCTGGTTC CCTCTGCTCC TCACCCTCCT GGCTCACTGC ACAGGTTC</u>CT

GGGCCCAGTC TGAACTGACT CAGTCGGCCG CCGTATCTGG GTCCCTGGGC CAGAAGTCA CCATCTCCTG

CACTGGAAGC ACCGCCAACA TTGGAAGTGG TTATGTGAAT TGGTACCAAC AATTCCCAGG ACAGGTCCC

AGAACCCTCA TCTATACTTC TACTAACCGA CCTTCGGGGG TCCCCGCTCG ATTTTCTGGG TCCAGGTCAG

GCAACACAGC GACCCTGACC ATCTCTGGGC TCCTGGCTGA GGACGAGGCT GATTATTATT GCGCTGCATA

TGACAGTAGT CTCAGTATTG GTGTGTTCGG CGGAGGCACC CACCTGACCG TCCTCGGTCA GCCCAAGGCC (SEQ ID NO: 946)
L1-757:

CAGAACCGTC ATCTATATGA GTAGTAACCG ACCCTCGGGG GTCCCGGATC GATTCTCTGG CTCCAGGTCA

GGCAGCACAG CCACCCTGAC CATCTCTGGG CTCCAGGCTG AGGACGAGGC TGAGTATTAT TGCTCAACAT

GGGACAACAG TCTCAATACT GGTGTGTTCG GCGGGGGCAC CCACCTGACC GTCCTCGGTC AGCCCAAGGC

C (SEQ ID NO: 947)
L1-758:

<u>ATG ACCTCCAACA TGGCNTGGTC CCCTCTCCTC CTCCCACTCC TTGCTTACTG CACAGGG</u>TCC

TGGGCCCAGT CTATACTGAC TCAGCCGTCC TCAGTGTCGG GGTCCCTTGG CCAGAGGGTC ACCATCTCCT

GTTCTGGAAG CATGTACAAC CTCGGTGTTG TTGGTGCGAC CTGGTACCGA CAACTCCCAG GGGAGGCCCC

TAAACTCCTC CTATACAGTA ATGGGAGTCG ACCGTCAGGG GTCCCTGACC GGTTTTCCGG CTCCAACTCT

GGCTTCTCTG CCACCCTGAC CATCACTGGG CTTCAGGCTG ACGACGAGGC TGATTATTAC TGCCAGTCCC

TTGATTCCAC GCGTGGTTAT CATATTGTAT TCGGCGGAGG CACCCACCTG ACCGTCCTCG GTCAGCCCAA

TABLE $N_{G2}$-continued

Group 2 Nucleic Acid Sequences

GGCC (SEQ ID NO: 948)
L1-760:

<u>ATGA</u> <u>CCTCCACCAT</u> <u>GGGATGGTTC</u> <u>CCTCTGCTCC</u> <u>TCACCCTCCT</u> <u>GGCTCACTGC</u> <u>ACAGGTTCCT</u>

GGGCCCAGTC TGTGCTGACT CAGCCGGCCT CAGTGTCTGG GTCCCTGGGC CAGAGGGTCA CCATCTCCTG

CACTGGAAGC AACTCCAACA TCGGTAGAGG TTATGTGGGC TGGTACCAGC AGCTCCCAGG AACAGGCCCC

AGAACCCTCA TCTATGATAC TACTTTCCGA CCCTCGGGGG TCCCTGATCG ATTCTCTGGC TCCCGGTCAG

GCACCACAGG AACCCTGACC ATCTCTGGGC TCCAGGCTGA GGACGAGGCT GATTATTACT GCTCAGCATA

TGACACCAGT CTCAGTAGTA ATTTCTTCGG CGGAGGCACC CGCCTGACCG TCCTCGGTCA GCCCAAGGCC (SEQ ID NO: 949)

TABLE $N_{G1}$

Group 1 Light Chain Variable Domain Nucleic Acid Sequences

L1-783:

TGGTACCAGC AGACCCTAGG CCGGGCTCCT CGCACGATTA TCTACAGAAC AAGCAGCCGC CCCTCTGGGG

TCCCTAATCG CTTCTCCGGA TCCATCTCTG GAACAAAGC CGCCCTCACC ATCACAGGAG CCCAGCCTGA

GGACGAGGCT GACTATTACT GTTCCGTGTA TATGGGTACT TACACTGTTG TGTTCGGCGG AGGCACCCAC

CTGACCGTCC TCGGTCAGCC CAAGGCC (SEQ ID NO: 950)
L1-776:

TAATTACCCT GGNTGGTACC AGCAGACCCA AGGCCGGGCT CCTCGCACGA TTATCTACAA CACAAACAGC

CGGCCCTCTG GGGTCCCTAA TCGCTTCTCT GGATCCATCT CTGGAAACAA AGCCGCCCTC ACCATCACAG

GAGCCCAGCC CGAGGATGAG GCTGACTATT ATTGTTCCTT GCGCACGGGT TATCAAAATA CTATGGTCGG

CGGAGGCACC CACCTGACCG TCCTCGGTCA GCCCAAGGCC (SEQ ID NO: 951)
L1-785:

<u>GCTTGGAACG</u> <u>TTGCTTCTTC</u> <u>TTTGTGCTCC</u> <u>TTGCCTATGG</u> <u>CTCAGGA</u>GCA GATTCTCAGA CTGTGGTAAC

CCAGGAGCCA TCACTNTCAG TGTCTCCAGG AGGGACAGTC ACACTCACAT GTGGCCTCAG CTCTGGGTCA

GTCTCCACAA GTAATTACCC TGGCTGGTAC AGCAGACCC TAGGCCGGGC TCCTCGCACG ATTATCTACA

GAACAAGCAG CCGCCCCTCT GGGGTCCCTA ATCGCTTCTC TGGATCCATC TCTGGGAACA AAGCCGCCCT

CACCATCATA GGAGTCCAGC CTGAGGACGA GGCTGACTAT TACTGTTCCT TATATATGGG TAGTTACACT

GATATGTTCG GCGGAGGCAC CCACCTGACC GTCCTCGGTC AGCCCAAGGC C (SEQ ID NO: 952)
L1-789:

GGATCACACT CACATGTGGC CTCAACTCTG GGTCAGTCTC TACAAGTAAT TACCCTGCCT GGTACCAGCA

GACCCTAGGC CGGGCTCCTC GCACGATTAT CTATGGAGCA AACAGCCGCC CCTCTGGGGT CCCTAATCGC

TTCTCTGGAT CCATCTCTGA CAACAAAGCC GCCCTCACCA TCACAGGAGT CCAGCCTGAG GACGAGGCTG

ACTATTACTG TTCCTTGTAT ATGGGTGGTT ATAGTGACGT GTTCGGCTCA GGAACCCAAC TGACCGTCCT

TGGTCAGCCC AAGGCC (SEQ ID NO: 953)
λ104:

TABLE N<sub>G1</sub>-continued

Group 1 Light Chain Variable Domain Nucleic Acid Sequences

<u>ATGGCCTGGA</u> <u>CACTGATTCT</u> <u>CCTTGGACTT</u> <u>CTTGCTTATG</u> <u>GCTCAGGA</u>GC AGATTCTCAG ACTGTGGTGA

CCCAGGAGCC ATCACTCTCA GTGTCTCTGG GAGGGACAGT CACCCTCACA TGTGGCCTCC CCTCCGGGTC

AGTCTCTACA CAAAACTTCC CCAACTGGTC CCAGCAGACC CCAGGGCAGG CTCCTCGCAC GATTATTTAC

AACACAAACA CCCGCCCCTT AGGGGTCCCT AGTCGCTTCA CGGGATCCAT CTCTGGGAAC AGGGCCGCCC

TCACCATCAC AGGAGCCCGG CCTGAGGACG AGGCTGACTA CTATTGTGCT CTGGGCTTCA GTGGTGGTGA

TTATGTCGTG TTCGGCGGAG GCACCCACCT GACCGTCCTC GGTCAGCCCA AGGCC (SEQ ID NO: 954)
λ-753:

<u>ATGGCT</u> <u>TGGACGGTGC</u> <u>TTCTTCTTGT</u> <u>GCTCCTTGCC</u> <u>TATGGCTCAG</u> <u>GA</u>GCAGATTC TCAGACTGTG

GTAACCCAGG AGCCATCACT CTCAGTGTCT CCAGGAGGGA CAGTCACACT CACATGTGGC CTCAGCTCTG

GGTCAGTCTC TACAAATAAT TACCCTGGCT GGTACCAGCA GACCCAAGGC CGGGCTCCTG CACGATTAT

CTACAGCACA AGCAGCCGCC CCTCTGGGGT CCCTAATCGC TTCTCTGGAT CCATCTCTGG AAACAAAGCC

GCCCTCACCA TCACAGGAGC CCAGCCCGAG GATGAAACTG ACTATTACTG TTCCTTATAT ACGGGTAGTT

CCACTGATGT GTTCGGCGGA GGCACCCATC TGACCGTCCT CGGTCAGCCC AAGGCC (SEQ ID NO: 955)
λ303:

<u>ATGGCTTG</u> <u>GACGGTGCTT</u> <u>CTTCTTGTGC</u> <u>TCCTTGCCTA</u> <u>TGGCTCAGGA</u> GCAGATTCTC AGACTGTGGT

AACCCAGGAG CCATCCCTCT CAGTGTCTCC AGGAGGGACA GTCACACTCA CATGTGGCCT CAGCTCTGGG

TCAGTCTCTA CAAGTAATTA CCCTGGCTGG TACCAGCAGA CCCAAGGCCG GGCTCCTCGC ACGATTATCT

ACAACACAAA CAGCCGCCCC TCTGGGGTCC CTAATCGCTT CTCTGGATCC ATCTCTGGAA CAAAGCCGC

CCTCACCATC ACAGGAGCCC AGCCCGAGGA TGAGGCTGAC TATTACTGTT CCTTCTATAC GGGTGATTAC

ACTGCTGTGT TCGGCGGAGG CACCCACCTG ACCGTCCTCG GTCAGCCCAA GGCC (SEQ ID NO: 956)
λ305:

<u>ATGGCTTGG</u> <u>ACGGTGCTTC</u> <u>TTCTTGTGCT</u> <u>CCTTGCCTAT</u> <u>GGCTCAGGAA</u> CAGATTCTCA GACTGTGGTC

ACCCAGGAGC CATCACTCTC AGTGTCTCCA GGAGGGACGG TCACACTCAC ATGTGGCCTC AGCTCTGGGT

CAGTTACTGC GAGTCATTTC CCTGGCTGGT ACCAGCAGAC CCAAGGCCGG GCTCCTCGCA CGATTATCTA

CAACACATAC AACCGCCTTT CTGGGGTCCC TAGTCGCTTC TCTGGATCCA TCTCTGGAAA CAAAGCCACC

CTCACCATCA CAGGGGCCCG GCCCGAGGAT GAGGCTGACT ATCACTGTTC TGTATATACG GATGATCACA

CTCCTGTATT CGGCGGAGGC ACCCACCTGA CCGTCCTCGG TCAGCACGAG GCC (SEQ ID NO: 957)
λ307:

GGGACGGTCA CACTCACATG TGGCCTCAGC CCTGGGTCAG TCTCTACGAG TAATTACCCT AATTGGTACC

AGCAGACCCA AGGCCGGGCT CCCCGCACGA TTATCTACAA CACAGGTAGC CGCCCCTCTG GGGTCCCTAA

TCGCTTCTCT GGATCCATCT CTGGAAACAA AGCCGCCCTC ACCATCACAG GAGCCCAGCC CGAGGATGAG

GCTGACTATT ACTGTTCCTT ATATACGGGT AGTTATACTG CTGTGTTCGG CGGAGGCACC CACCTGACCG

TCCTCGGTCA GCCC (SEQ ID NO: 958)
λ322:

<u>AT</u> <u>GGCTTGGACG</u> <u>GTGCTTCTTC</u> <u>TTGTGCTCCT</u> <u>TGCCTATGGC</u> <u>TCAGGA</u>GCAG ATTCTCAGAC

TGTGGTAACC CAGGAGCCAT CACTCTCAGT GTCTCCAGGA GGGACAGTCA CACTCACATG TGGCCTCAGC

TABLE N_{G1}-continued

Group 1 Light Chain Variable Domain Nucleic Acid Sequences

TCTGGGTCGG TCTCTACGAG TAATTATCCT GCCTGGTACC AGCAGACCCA AGGCCGGGCT CCTCGCACGA

TTATCTACAA CACAAACAGC CGCCCCTCTG GGGTCCCTAA TCGCTTCTCT GGATCCATCT CTGGAAACAA

AGCCGCCCTC ACCATCACAG GAGCCCAGCC CGAGGATGAG GCTGACTATT ATTGTTCCTT TTTTACAGAT

ATTGTCGTTA ACGTGTTCGG CTCAGGAACT CAATTGACCG TCCTTGGTCA GCC (SEQ ID NO: 959)
λ125:

<u>ATGGC</u> <u>TTGGACGTTG</u> <u>CTTCTTCTTG</u> <u>TGCTCCTTGC</u> <u>CTATGGCTCA</u> <u>GGA</u>GCAGATT CTCAGACTGT

GGTAACCCAG GAGCCATCAC TCTCAGTGTC TCCAGGAGGG ACAGTCACAC TCACATGTGG CCTCAGCTCT

GGGTCGGTCT CTGGAAGTAA TTACCCTGGC TGGTACCAGC AGACCCTAGG CCGGGCTCCT CGCACGATTA

TCTACAGAAC AAGCAGCCGC CCCTCTGGGG TCCCTAATCG CTTCTCTGGA TCCATCTCTG GAAACAAAGC

CGCCCTCACC ATCACAGGAG CCCAGCCTGA GGACGAGGCT GACTATTACT GTTCCTTGTA TATGGTCGGT

TACACTGCCG TGTTCGGCTC AGGGACCCAA CTGACCGTCC TTGGTCAGCC CAAGGCC (SEQ ID NO: 960)
L214-79:

<u>ATGG</u> <u>CCTGGACACT</u> <u>GATTCTCCTT</u> <u>GGGCTTCTTG</u> <u>CTTATGGCTC</u> <u>AGGA</u>GCAGAT TCTCAGACTG

TGGTGACCCA GGAGCCATCA CTCTCAGTGT CTCTGGGAGG ACAGTCACC CTCACATGTG GCCTCAGCTC

CGGGTCAGTC TCTACAAGTA ACTACCCAA CTGGTCCCAG CAGACCCCAG GCAGGCTCC TCGCACGATT

ATCTACAACA CAAACAGCCG CCCCTCTGGG GTCCCTAATC GCTTCACTGG ATCCATCTCT GGGAACAAAG

CCGCCCTCAC CATCACAGGA GCCCAGCCTG AGGACGAGGC TGACTACTAC TGTGCTCTGG GATTTAGTAG

TAGTAGTAGT TACGTGTTCG GCTCAGGAAC CCAACTGACC GTCCTTGGTC AGCCCAAGGC C (SEQ ID NO: 961)
L220-79:

<u>AT</u> <u>GGCTTGGACG</u> <u>TTGCTTCTTC</u> <u>TTGTGCTCCT</u> <u>TGCCTATGGC</u> <u>TCAGGA</u>GCAG ATTCTCAGAC

TGTGGTGACC CAGGAGGCAT CAGTCTCGGT GTCTCCAGGA GGGACAGTCA CACTCACATG TGGTCTCAGC

TCTGGGTCAG TCTCTACAGG TGATTTCCCT GGCTGGTACC AGCAGACCCT AGGCCGGCCT CCTCGCACGA

TTATATCCAG AACGAATAGA CGCCCCTCTG GGGTCCCTGA TCGCTTCTCT GGATCCATCT CTGGGAACAA

ACCCGCCCTC ACCATCACAG GAGCCCAGCC TGAGGACGAG GGTGACTATT ATTGTTCCTT ATATATGGGT

TCTTACACTG GTTTGTTCGG CGGAGGCACC CACCTGACCG TCCTCGGTCA GCC (SEQ ID NO: 962)
L1-705:

<u>TTGCTTCCTC</u> <u>TTGTGCTCCT</u> <u>TGCCTATGGC</u> <u>TCAGGA</u>GCCG ATTCTCAGAC TGTGGTCATC CAGGAGCCAT

TCCTCTCAGT GTCTCCAGGA GGGACGGTCA CACTCACATG TGGCCTCAGC TCTGGGTCAG TCTCTCCAAG

TCATTACCCT GGCTGGTACC AGCAGACCCT AGGCCGGCCT CCTCGCCCGA TCATCTACAG AACAGACAGC

CGCCCCTCTG GGGTCCCTCG TCGCTTCTCT GCATCCGTCT CTGGGAACAA AGCCACCCTC ACCATTACAG

GAGCCCAGCC TGAGGACGAG GCTGACTATT ACTGTTCCTT ATATATGGAC ATTTACACTG GTGTGTTCGG

CGGAGGCACC CACCTGACCG TCCTCGGTCA GCCCAAGGCC (SEQ ID NO: 963)
L1-729:

<u>ATG</u> <u>GCTTGGACAC</u> <u>TGATTCTCCT</u> <u>TGGGCTTCTT</u> <u>GCTTATGGCT</u> <u>CAGGA</u>GCAGA TTCTCAGACT

GTGGTGACCC AGGAGCCATC ACTCTCAGTG TCTCTGGGAG GACAGTCAC CCTCACATGT GGCCTCAGCT

CCGGGTCAGT CTCTACAAGT AACTACCCCA GCTGGTCCCA GCAGACCCCA GGGCAGGCTC CTCGCACGAT

TABLE N<sub>G1</sub>-continued

Group 1 Light Chain Variable Domain Nucleic Acid Sequences

TCTCTACAAC ACAAACAGCC GCCCCTCTGG GGTCCCTAAT CGCTTCACTG CATCCATCTC TGGGAACAAA

GCCGCCCTCA CCATCACAGG AGCCCAGCCT GAGGACGAGG CTGACTACTA CTGTGCTCTG GGATTAAGTG

GGATTAGCAG TATTGTGTTC GGCGGAGGCA CCCACCTGAC CGTCCTCGGT CAGCCCAAGG CC (SEQ ID NO: 964)
L1-743:

<u>GACGGTGT</u> <u>TCTTCTTGTG</u> <u>CTCCTTGCCT</u> <u>ATGGCTCAGG</u> AGCAGATTCT CAGACTGTGG TAACCCAGGA

GCCATCACTC TCAGTGTCTC CAGGAGGGAC AGTCACACTC ACATGTGGCC TCAGCTCTGG GTCAGTCTCT

ACAAGTAATT ACCCTGGCTG GTACCAGCAC ACCCAAGGCC GGGCTCCTCG CACGATTATC TACACCACAA

GCAGCCGCCC CTCTGGGGTC CCTAATCGCT TCTCTGGATC CATCTCTGGA AACAAAGCCG CCCTCACCAT

CACAGGAGCC CAGCCCGAGG ATGAGGCTGA CTATTACTGT TCCTTGTATA CGGGTAGGCC TGTGTTCGGC

GGAGGCACCC ACCTGACCGT CCTCGGTCAG CCCAAGGCC (SEQ ID NO: 965)
L1-759:

ATGGC TTGGATGGTG CTTCTTCTTG TGCTCCTTGC CTATGGCTCA GGAGCAGATT CTCAGACTGT

GGTAACCCAG GAGCCATCAC TCTCAGTGTC TCCAGGAGGG ACAGTCACAC TCACATGTGG CCTCAGCTCT

GGGTCAGTCT CTACAAGTAA TTACCCTGGC TGGTACCAGC AGACCCAAGG CCGGGCTCCT CGCACGATTA

TCTACCACAC AAGCAGCCGC CCCTCTGGGG TCCCTAATCG CTTCTCTGGA TCCATCTCTG GAAACAAAGC

CGCCCTCACC ATCACAGGAG CCCAGCCCGA GGATGAGGCT GACTATTACT GTTCCTTTTA TACGAGTAGT

TACATTGCTG CCTGGTCACG CACGAGGGGA GCACCTGACC GTCCTCGGTC AGCCCAAGGC C (SEQ ID NO: 966)

TABLE N<sub>G3</sub>

Group 3 Light Chain Variable Domain Nucleic Acid Sequences

λ212:

<u>ATGACCTCC</u> <u>ACCATGGGCT</u> <u>GGTCCCCTCT</u> <u>CGTCCTCACC</u> <u>CTCTTCGCTC</u> <u>ACTGCGCAGG</u> GTCCTGGGCC

CAGTCTGTGC TGACTCAGCC GGCCTCAGTG TCCGGGTCCC TGGGCCAGAG GGTCACCATC TCCTGCACTG

GAAGCAGTTC CAATGTTGGT TATGGCGATT ATGTGGGCTG GTACCAGCAG TTCCCAGGAA CAGGCCCCAG

AACCCTCATC TATCGTACTG GTAATCGACC CTCGGGGGTC CCTGATCGAT TCTCTGGCTC CAGGTCGGGC

AGCACAGCAA CCCTGACCAT CTCTGGGCTC CAGACTGAGG ATGAAGCCGA TTATTACTGC TCATCCTTTG

ACAGAAGTGT CAGTGCTGTG TTCGGCGGAG GCACCCACCT GACCGTCCTC GGTCAGCCCA AGGCC (SEQ ID NO: 967)
λ216:

AT <u>GACCTCCACC</u> <u>ATGGGCTGGT</u> <u>CCCCTCTCGT</u> <u>CCTCACCCTC</u> <u>TTCGCTCACT</u> <u>GCGCAGGGTC</u>

CTGGGCCCAG TCTGTGCTGA CTCAGCCGGC CTCAGTGTCC GGGTCCCTGG GCCAGAGGGT CACCATCTCC

TGCACTGGAA GCAGTTCCAA TGTTGGTTAT GGCGATTATG TGGGCTGGTA CCAGCAGTTC CAGGAACAG

GCCCCAGAAC CCTCATCTAT CGTACTGGTA ATCGACCCTC GGGGGTCCCT GATCGATTCT CTGGCTCCAG

GTCGGGCAGC ACAGCAACCC TGACCATCTC TGGGCTCCAG ACTGAGGATG AAGCCGATTA TTACTGCTCA

TCCTTTGACA GAAGTGTCAG TGCTGTGTTC GGCGGAGGCA CCCACCTGAC CGTCCTCGGT CAGCCCAAGG

CC

TABLE N_{G3}-continued

Group 3 Light Chain Variable Domain Nucleic Acid Sequences (SEQ ID NO: 968)
λ218:

<u>ATGGG</u> <u>CTGGTCCCCT</u> <u>CTCATCCTCA</u> <u>CCCTCTTCGC</u> <u>TCACTGCGCA</u> <u>GGG</u>TCCTGGG CCCAGTCTGT
GCTGACTCAG CCGGCCTCAG TGTCTGGGTC CCTGGGCCAG AGGGTCACCA TCTCCTGCAC TGGAAGCAGC
TCCAATGTTG GTTATGCCAA TCATGTGGGC TGGTACCAGC AGCTCCCAGG AACAGGCCCC AGAACCCTCA
TCTATCATAG TAGTGACCGA CCTTCGGGGG TCCCCGATCG ATTCTCTGGC TCCAGGTCAG GCAACACAGC
AACCCTGACC ATCTCTGGCC TCCAGGCTGA GGACGAGGCT GATTATTACT GCTCAGCGTA TGACACCACT
CTCAATGCTG TGTTCGGCGG AGGCACACAC CTGACCGTCC TCGGTCAGCC CAAGGCC (SEQ ID NO: 969)
λ231:

<u>ATGAT</u> <u>GACCTCCACC</u> <u>ATGGGCTGGT</u> <u>TCCCTCTCAT</u> <u>CCTCACCCTC</u> <u>CTCGCTCACT</u> <u>GCGCAGGG</u>TC
CTGGGCCCAG TCTGTGCTGA CTCAGCCGGC CTCAGTGTCT GGGTCCCTGG GCCAGAGGGT CACCATCTCC
TGCACTGGAA GCAGCTCCAA TGTTGGTTAT GGCAATTATG TGGGCTGGTA CCAGCAGCTC CCAGGAACAA
GCCCCAGAAC CCTCATCTAT GATAGTAGTA GCCGACCCTC GGGGGTCCCT GATCGATTCT CTGGCTCCAG
GTCAGGCAGC ACAGCAACCC TGACCATCTC TGGGCTCCAG GCTGAGGATG AAGCCGATTA TTACTGCTCA
TCCTATGACA GCAGTCTCAG TGGTGGCGTG TTCGGCTCAG GAACCCAACT GACCGTCCTC GGTCAGCCCA
AGGCC (SEQ ID NO: 970)
λ301:

<u>A</u> <u>TGGCCTGGAC</u> <u>TCTGGTCCTC</u> <u>CTCACCTTTC</u> <u>TCTCTCAGGG</u> <u>CACAGGG</u>TCC TGGGCCCAGT
CTGCCCTGAC TCAACCTTCC TCGGTGTCTG GGACTTTGGG CCAGACTGTC ACCATCTCCT GTGATGGAAT
CAACAGTAAC ATTGACAATA GTAATTATAT CGAATGGTTC CAACATTTCC CAGGCACCTC CCCCAAACTC
CTGATTTACT ATACCAATAA TCGGCCATCA GGAATCCCTG CTCGCTTCTC TGGCTCCAGG TCTGGGAACA
CGGCCTCCTT GACCATCTCT GGGCTCCAGG CTGAAGATGA GGCAGATTAT TACTGTAGCG CATATAGTGG
CACTGATACT TACGTGTTCG GCTCAGGAAC CCAACTGACC GTCCTTGGTC AGAACGAGGC C (SEQ ID NO: 971)
λ308:

<u>ATGATGAC</u> <u>CTCCACCATG</u> <u>GGCTGGTTCC</u> <u>CTCTCATCCT</u> <u>CACCCTCCTC</u> <u>GCTCACTGCG</u> <u>CAGGG</u>TCCTG
GGCCCAGTCT GTGCTGACTC AGCCGGCCTC AGTGTCTGGG TCCCTGGGCC ACAGGGTCAC CATCTCCTGC
ACTGGAAGCA GCTCCGATGT TGGTTATGCC GATTATGTGG GCTGGTACCA GCAGGTCCCA GGAACAAGCC
CCAGAACCCT AATCTATGAT ACTAGTAAGC GACCCTCGGG GGTCCCTGAT CGATTCTCTG GGTCCAGGTC
AGGCAGCACA GCAACCCTGA CCATCTCTGG GCTCCAGGCT GAGGATGAAG CCGATTATTA CTGTTCATCC
TATCACAGCA GTCCTCATGG TGTTGTCTTC GGCGGAGGCA CCCACCTGAC CGTCCTCGGT CAGCC (SEQ ID NO: 972)
λ311:

<u>ATGATGACC</u> <u>TCCACCATGG</u> <u>CTGGTTCCC</u> <u>TCTCATCCTC</u> <u>ACCCTCCTCG</u> <u>CTCACTGCGC</u> <u>AGGG</u>CCCTGG
GCCCAGTCTG TGCTGACTCA GCCGGCCTCA GTGTNTGGGT CCNTGGGCCA GAGGGTCACC ATCTCCTGCA
CTGGAAGCAG CTCCAATGTT GGTTTTGGCA ATTATGTGGG NTGGTACCAG CAGCTCCCAG GAACAAGCCC

TABLE $N_{G3}$-continued

Group 3 Light Chain Variable Domain Nucleic Acid Sequences

```
CAAAACCCTT ATCTATGATA GTAGTAGACG ACCCTCGGGG GTCCCTGATC GATTCTCTGG CTCCAGGTCA

GGCAGCACAG CAACCCTGAC CATCTCTGGG CTCCAGGCTG AGGATGAAGC CGATTATTAC TGCTCATCGT

ATGACAGCGA GGTCAGGGTT GTGTTCGGCG GAGGCACCCA CCTGACCGTC CTCGGTCAGC ACGAGGC
```

(SEQ ID NO: 973)
λ316:

```
           AT GACCTCCACC ATGGCCTGGT CCCCTCTCCT ACTCACCCTC CTTGCTCATT TCACAGGGTC

CTGGGCCCAG TCTGTGCTGA CTCAGCCAGC CTCCGTGTNT GGGTCCCTGG GCCAGAGGGT CACCATTTCN

TGCANTGGGA GCAGCTCCAA CGTTGGTTCT GGCAGTACTG TGGGCTGGTA CCAGCAGTTC CCAGGAACAG

GCCCCAGAAC CATCATCTAT TATGATGGTA GCCGACCCTC GGGGGTCCCC GATCGATTCT CTGGCTCCAA

GTCTGGCAGC ACAGCCACCC TGACCNNCTC TGGGCTCCAG GCTGAGGATG AGGCTGATTA TTACTGCTCA

TCTTGGGACA ACAGTCAAGG TAGTGTGTTC GGCGGAGGCA CCCATCTTGA CCGTCCTCGG GTCAGCCCAA

GGCC
```

(SEQ ID NO: 974)
λ131:

```
        ATGA CCTCCACCAT GGCNTGGTCC CCTCTCCTCC TCACCCTCCT CGCTCATTGC ACAGTGTCCT

GGGCCCAGGC TGTGCTGACT CAGCCACCCT CTATGTCTAC AGCCCTGGGG CAGAGGGTCA CCATAACCTG

CACTGGAAGT AAGACCAACA TCGGCAGTGG TTATGATGTA CAATGGTACC AGCAGCTCCC AGGAAAGTCC

CCTAAAAGTA TCATCTTCGC TAATGACGCT CGACCCTCGG GGGTCCCGGC TCGATTCTCT GGCTCCAAGT

CAGGCAACAC AGCCACCCTG ACCATCACTG GGATCCAGGC TGAGGATGAG GCTGATTATT ACTGCCAGTC

CTATGATGAC AACCTCGCTG GTCTTGTGTT CGGCGGAGGC ACCCAGTTGA CCGTCCTCGG TCAGCCCAAG

GCC
```

(SEQ ID NO: 975)
L202-79:

```
           AT GACCTCCACC ATGGGCTGGT TCCCTCTCCT CCTCACCTTC CTGGCTCACT GCACAGGGTC

CTGGGCCCAG ACTGTATTGA CTCAGCCGGC CTCAGTGTCT GGGTCTCTGG GCCAGACGGT CACCATCTCC

TGCACTGGAA GCAAGGACAA TATTGGTTAT GGCAATTATG TGGGCTGGTA TCGACAATTC CCAGGAACAG

GCCCCAGAAC CGTCGCCTAT GGTCATGGAT TTCGACCCTC GGGGGTTCCT GACCGATTCT CTGCCTCCAG

TTCAGGCAGC ACATCCACAC TGACCATCGC CGGGCTCCAG GCTGAAGATG AAGGTGATTA TTACTGCTCA

ACCTATGACA ACAGTCTCTC TGTTGTGTTC GGCGGAGGCA CCCACCTGAC CGTCCTCGGT CAGCCCAAG
```

(SEQ ID NO: 976)
L208-79:

```
CAGACGGTCA CCATCTCCTG CACTGGAAGC AGCTCCAATG TTGGTTATGG CGATTATGTG GGCTGGTACC

AACAACTCCC AGGGACAGGT CCCAAAACCC TCATCTATGA TACTCGTAGG CGACCCTCGG GGATTCCTGA

TCGATTCTCT GGGTCCAGGT CAGGCAGCAC AGCGACCCTG ACCATCTCTG GACTCCAGGC TGAGGATGAG

GCCGATTATT ACTGTGCATC CTATGACCGT ACTATCGGTG GTGGTGCTGT GTTCGGCGGA GGCACCCACC

TGACCGTCCT CGGTCAGCCC AAGGCC
```

(SEQ ID NO: 977)
L211-79:

```
CCGGGGCAGA GGGTCACCAT CTCCTGCACT GGAAGTAACA CCAACATCGG CAGTGATTAT GATGTTCAAT
```

TABLE N_{G3}-continued

Group 3 Light Chain Variable Domain Nucleic Acid Sequences

GGTACCAGCA ACTCCCAGGA AAGTCCCCTA AAACTATCAT TTACGCTAAG AGCAATCGAC CCTCGGGGT

CCCTGATCGA TTCTCTGGCT CCAAGTCAGG CAGCACAGCC ACCCTGACCA TCTCTGTGCT CCAGGCTGAG

GATGAGGCTG ATTATTACTG CTCAGTGGGG GATGATAGTC TCAAAGCACC TGTGTTCGGC GGAGGCACCC

ACCTGACCGT CCTCGGTCAG CCCAAGGCC (SEQ ID NO: 978)
L212-79:

TCCCTGGGCC AGACGGTCAC CATCTCCTGC ACTGGAAGCA GCTCCAATGT TGGTTATGGC GATTATGCGG

GCTGGTACCA CAACTCCCA GGGACAGGTC CCAAAACCCT CATCTATGAT ACTCGTAGGC GACCCTCGGG

GATTCCTGAT CGATTCTCTG GGTCCAGGTC AGGCAGCACA GCGACCCTGA CCATCTCTGG ACTCCAGGCT

GAGGATGAGG CCGATTATTA CTGTGCATCC TATGACCGTA CTATCGGTGG TGGTGCTGTG TTCGGCGGAG

GCACCCACCT GACCGTCCTC GGTCAGCCCA AGGCC (SEQ ID NO: 979)
L218-79:

ATGACCTC CACCATGGGC TGGTTCCCTC TCCTCCTCAC CTTCCTGGCT CACTGCACAG GGTCCTGGGC

CCAGGCTGTG CTGACTCAGC CGGCCTCAGT GTCTGGGTCC CTGGGCCAGA GGGTCACCAT CTCCTGCACT

GGAAGCACCT CCAATGTTGG TTATGGCAAT TATGTGGGCT GGTACCAGCA GCTCCCAGGA ACAGGCCCCA

AAACCCTCAT CTATGGTAGT AGTTACCGAC CCTCGGGGGT CCCTGATCGA TTCTCTGGCT CCAGTTCAGG

CAGCTCAGCC ACACTGACCA TCTCTGGGCT CCAGGCTGAG GATGAAGCTG ATTATTACTG CTCATCCTAT

GACAGCAGTC TCAGTGGGAT TGTGTTCGGC GGAGGCACCC ATCTGACCGT CCTCGGTCAG C (SEQ ID NO: 980)
L1-704:

A TGACCTCCAC CATGGGCTGG TCCCCTATCA TCCTCACCCT CCTCGCTCAC TGCGCAGGGT

CCTGGGCCCA GTCTGTGCTG ACTCAGCCGG CCTCAGTGTC TGGGTCCCTG GGCCAGAGGG TCACCATCTC

CTGCACTGGA AGCAACTCCA ATGTTGGTTA TGCCAATTAT GTGGGCTGGT ACCAGCAGCT CCCAGGAACA

GGCCCCAGAA CCCTCATCTA TGATAGTAGT AGCCGACCCT CGGGGGTCCC TGATCGATTC TCTGGCTCCA

GGTCAGGCAG CACAGCAACC CTGACCATCT CTGGGCTCCA GGCTGAGGAT GAAGCCGATT ATTACTGCTC

ATCCTATGAC AGCAGTCTCG ATGGTGCTGT GTTCGGCGGA GGCACCCACC TGACCGTCCT CGGTCAGCCC

AAGGCC (SEQ ID NO: 981)
L1-711:

ATGACCTCC ACCATGGGCT GGTTCCCTCT CATCCTCACC CTCTTCGCTC ACTGCGCAGG GTCCTGGGCC

CAGTCTGTGC TGACTCAGCC GGCCTCAGTG TCTGGGTCCC TGGGCCAGAG GGTCACCATC TCCTGCACTG

GAAACAGCTC CAATGTTGGT TATGGCAATT ATGTGGGCTG GTACCAGCAG CTCCCAGGAA CAAGCCCCAG

AACCCTCATC TATTATAGTA GTAGCCGACC CTCGGGAGTC CCGATCGAT TCTCTGGCTC CAGGTCAGGC

AGCACAGCTG CCCTAACCAT CTCTGGGCTC CAGGCTGAGG ATGAAGCCGA TTATTACTGC TCATCCTATG

ACAGCAGTCT CAGTGGTGGT GTATTCGGCG GAGGCACCCA TCTGACCGTC CTCGGTCAGC CCAAGGCC (SEQ ID NO: 982)
L1-713:

TABLE N<sub>G3</sub>-continued

Group 3 Light Chain Variable Domain Nucleic Acid Sequences

<u>ATGA</u> <u>CCTCCACCAT</u> <u>GGCCTGGTCC</u> <u>CCTCTCCTAC</u> <u>TCACCCTCCT</u> <u>TGCTCATTTC</u> <u>ACAGGGTCCT</u>

GGGCCCAGTC TGTGCTGACT CAGCCAGCCT CCGTGTCTGG GTCCCTGGGC CAGAGGGTCA CCATTTCCTG

CACTGGAAGC AGCTCCAACG TTGGTGACAC AAGTAGTGTG GGCTGGTACC AACAGTTCCC AGGAACAGGC

CCCAGAACCA TCATCTATTT TATTGGTAGC CGACCCTCGG GGGTCCCCGA TCGCTTCTCT GGCTCCAAGT

CTGGCAGCAC AGCCACCCTG ACCATCTCTG GCTCCAGGC TGAGGATGAG GCTGATTATT ACTGCTCATC

TTGGGACAAC AGTCTCAAAA CTCGGGTGTT CGGCGAAGGC ACCCATCTGA CCGTCCTCGG TCAGCCCAAG

GCC (SEQ ID NO: 983)
L1-716:

CATCTCCTG CACTGGAAGC AGCTCCAATG TTGGTTATGG CAATTATGTG GGCTGGTACC AACAGCTCCC

AGGAACAGGC CCCAGAACCC TCATCTATCG TAGTAGTAAC CGAGCCTCGG GGGTCCCTGA TCGATTCTCT

GGCTCCAGGT CAGGCAGCAC AGCAACCCTG ACCATCTCTG GCTCCAGGC TGAGGATGAG GCCGATTATT

TCTGCTCATC CTATGACAGC GGTCTCAGTC ATATTGTGTT CGGCGGAGGC ACCCACCTGA CCGTCTTCGG

TCAGCCCAAG GCC (SEQ ID NO: 984)
L1-717:

AGGGTCACCA TCTCCTGCA CTGGAAGCGA CTCCAATGTT GGTTATGGCA ATTATGTGGG CTGGTACCAG

CAGCTCCCAG GAACAAGCCC CAGAACCCTC ATTTATTATA ATACTGGGCG ACCCTCGGGA GTCCCCGATC

GCTTTTCTGG CTCCAGGTCA GGCAATACAG CAACCCTGAC CATCTCTGGG CTCCAGGCTG AGGATGAAGC

CGATTATTAC TGTTCAGCCT ATGACTACAG TCTCAGTTCT GGCGTCTTCG GCGGAGGCAC CCACCTGACC

GTCCTCGGTC AGCCCAAGGC (SEQ ID NO: 985)
L1-718:

<u>ATGACCTCC</u> <u>ACCATGGGCT</u> <u>GGTTCCCTCT</u> <u>CATCCTCACC</u> <u>CTTTTCGCTC</u> <u>ACTGCGCAGG</u> <u>GTCCTGGGCC</u>

CAGTCTGTGC TGACTCAGCC GGCCTCAGTG TCTGGGTCCC TGGGCCAGAG GGTCACCATC TCCTGCACTG

GAAGCAGTTC CAATGTTGGT TATGGCGATT ATGTGGCCTG GTACCAGCAG CTCCCAGGAA CAAGCCCCAG

AACCCTCATC CATCATAGTA GTAGCCGACC CTCGGGAGTC CCCGATCGAT TCTCTGGCTC CAGGTCAGGC

AGCACAGCAA CCCTGACCAT CTCTGGGCTC CAGGCTGAGG ATGAAGCCGA TTATTACTGC TCATCCTATG

ACAACAGTCT CAGTGGTGGC GTGTTCGGCG GAGGCACCCA CCTGACCGTC CTCGGTCAGC CAAGGCC (SEQ ID NO: 986)
L1-727:

<u>ATGA</u> <u>CCTCCACCAT</u> <u>GGCCTGGTCC</u> <u>CCTCTCCTAC</u> <u>TCACCCTCCT</u> <u>TGCTCATTTC</u> <u>ACAGGGTCCT</u>

GGGCCCAGTC TGTGCTGACT CAGCCAGCCT CCGTGTCTGG GTCCCTGGGC CAGAGGGTCA CCATTTCCTG

CACTGGAAGC ACCTCCAACC TTGGTTATAG CAGTATTGTG GGCTGGTACC AGCAGTTCCT AGGAACAGGC

CCCAGAACCA TCATCTATTA TGATAGTAGC CGACCCTCGG GGGTCCCCGA TCGATTCTCT GGCTCCAAGT

CTGGCAGCAC AGCCACCCTG ACCATCTCTG GCTCCAGGC TGAGGATGAG GCTGATTATT ATTGTTCATC

TTGGGACAAC AGTCTCAAAG GTATTGTGTT CGGCGGAGGC ACCCATCTGA CCGTCCTCGG TCAGCCCAAG

GCC (SEQ ID NO:

TABLE N_{G3}-continued

Group 3 Light Chain Variable Domain Nucleic Acid Sequences (SEQ ID NO:
987)
L1-730:

<u>ATGACCTCT</u> <u>ACCATGGCCT</u> <u>GGTTCCCTCT</u> <u>CCTCCTCACC</u> <u>CTCCTCGCTC</u> <u>ACTGCACAGG</u> GTCCTGGGCC

CAGTCTGTGC TGACTCAGCC AGCCTCAGTG TCTGGATCCC TGGGCCAAAG GGTCACCATC TCCTGCACTG

GAAGCACAAA CGACATCGGT AGTGAGAATT ATGTGCACTG GTACCAACAG CTCCCAGGAA AGGCACCCAG

TCTCCTCATC TATGGTGATG ATAACAGAGA ATCTGGGGTC CCTGAACGAT TCTCTGGCTC CAAGTCAGGC

AGCTCAGCCA CTCTGACCAT CACTGGGCTC CAGGCTGAGG ACGAGGCTAA TTATTATTGC CAGTCCTATG

ATGACAGTCT CAATACTTAC GTGTTCGGCT CAGGAACCCA ACTGACCGTC CTTGGTCAGC CCAAGGCC (SEQ ID NO:
988)
L1-735:

<u>ATGATC</u> <u>TTCACCATGG</u> <u>CCTGGTCCCC</u> <u>TCTCCTCCTC</u> <u>GGCCTCCTTG</u> <u>CTCACTGCAC</u> AGGGTCCTGG

GCCCAGTCTA TGCTGACTCA GCCAGCCTCA GTGTCTGGGT CCCTGGGCCA GAAGGTCACC ATCTCCTGCA

CTGGAAGAAG CTCCAACATC GGTGGTAATT ATGTGGGCTG GTACCAACAG CTCCCAGGAA AGGCCCTAG

AACCGTCATC TATGGTAATA ATCGTCGACC TTCAGGGGTC CCCGATCGAT TCTCTGGCTC CGCGTCAGGC

AGTTCAGCCA CCCTGACCAT CTCTGGGCTC CAGGCTGAGG ACGAGGCTGA GTATTACTGC TCATCATGGG

ATGATAGTCT CAGAGGTGCT TTGTTCGGCG GAGGCACCCA CCTGACCGTC CTCGGTCAGC CCAAGGCC (SEQ ID NO:
989)
L1-741:

<u>ATGAT</u> <u>GACCTCCACC</u> <u>ATGGGNTGGT</u> <u>TCCCTCTCAT</u> <u>CCTCACCCTC</u> <u>CTCGCTCACT</u> GCGCAGGGTC

CTGGGCCCAG GCTGTGCTGA CTCAGCCGGC CTCAGTGTCT GGGTCCCTGG GCCAGAGGGT CACCATCTCC

TGCACTGGAA GCGGCTCCAA TGTTGGTTAT GGCAATTATG TGGGCTGGTA CCAGCAGCTC CCAGGAACAA

GCCCCAGAAC CCTCATCTAT GCTACTAGTA GCCGACCCTC GGGGGTCCCT GATCGATTCT CTGGCTCCAG

GTCAGGCAGC ACAGCAACCC TGACCATCTC TGGGCTCCAG GCTGAGGATG AAGCCGATTA TTACTGCTCA

TCCTATGACA CCAGTCTCAG TGGTGGCGTG TTCGGCGGAG GCACCCACCT GACCGTCCTC GGTCAGCCCA

AGGCC (SEQ ID NO:
990)
L1-748:

<u>ATGACCTC</u> <u>CACCATGGGC</u> <u>TGGTTCCCTC</u> <u>TCATCCTCAC</u> <u>CCTCTTCGCT</u> <u>CACTGCGCAG</u> GGTCCTGGGC

CCAGTCTGTG CTGACTCAGC CGGCCTCAGT GTCTGGGTCC CTGGGCCAGA GGGTCACCAT CTCCTGCACT

GGAACCAGTT CCAATGTTGG TTTTGGCGAT TATGTGGGCT GGTACCAGCA GCTCCCAGGA ACGAGCCCCA

AAACCCTCAT CTATGATCAT AATGTCCGAC CCGCGGGGGT CCCCGATCGA TTCTCTGGCT CCAGGTCAGG

CAACACAGCA ACCCTGACCA CCTCTGGGCT CCAGGCTGAG GATGAAGCCG ACTATTTCTG TTCATCCTAT

GACAGTAGTC TCAGTATTGT GTTCGGCGGA GGCACCCATC TGACCGTCCT CGGTCAGCCC AAGGCC (SEQ ID NO:
991)
L1-754:

<u>ATGATGAC</u> <u>CTCCACCATG</u> <u>GGCTGGTTCC</u> <u>CTNTCATCCT</u> <u>CACCCTCCTC</u> <u>GCTCACTGCG</u> CAGGGTCCTG

GGCCCAGTCT GTGCTGACTC AGCCGGCCTC AGTGTCTGGG TCCCTGGGCC AGAGGGTCAC CATCTCCTGC

ACTGGAAGCA GCTCCAATGT TGGTTATGGC AATTATGTGG GCTGGTACCA GCAGCTCCCA GGAACAAGCC

CCAGAACCCT CATCTATGAT ACTAGTAGCC GACCCTCGGG GGTCCCTGAT CGATTCTCTG GCTCCAGGTC

TABLE N_{G3}-continued

Group 3 Light Chain Variable Domain Nucleic Acid Sequences

AGGCAGCACA GCAACCCTGA CCATCTCTGG GCTCCAGGCT GAGGATGAAG CCGATTATTA CTGCTCATCC

TATGACAGCA GTCTCAGTGG TGCTGTGTTC GGCGGAGGCA CCCACCTGAC CGTCCTCGGT CAGCCCAAGG

CC
(SEQ ID NO: 992)

TABLE N_{K}

κ Light Chain Variable Domain Amino Acid Sequences

Kapa 129:

ATGA GGTTCCCTTC TCAGCTCCTG GGCTGCTGA TGCTCTGGAT CCCAGGATCC GGTGGGGATA

CTGTCCTGAC ACAGACCCCA CCGTCCCTGT CTGTCAGCCC TGGAGAGCCG GCCTCCATCC CCTGCAAGGC

CAGTCAGAGC CTCCTGCACA GTAATGGAAA CACCAATTTA TATTGGTACC TGCAAAAGCC AGGCCAGTCT

CCACAACTTC TGATCTACTT GGTTTCCAAC CGCTTCACTG GCGTGTCAGA CAGGTTCAGT GGCAGCGGGT

CAGGGACAGA TTTCACCCTC AGAATCAGCA GGGTGGAGCC TAACGATACT GGAATTTATT ACTGCGGGCA

ACAGTCACAA CTTCCTCCGA CGTTCGGAGC AGGAACCAAG GTGGAGCTCA AACGGAATGA TGCCCAGCCA

GCCGTCTAT (SEQ ID NO: 993)
Kapa130:

CTGGGGCTG CTGATGCTCT GGATCCCAGG ATCCAGTGGG GATATTGTCA TGACACAGGC CCCACCGTCT

CTGTCCGTCA GCCCTGGAGA GCCGGCCTCC ATCTCCTGCA CGGCCAGTCA GAGCCTCCTG CACAGTAATG

GGAACGCCTA TTTAACCTGG TACGACAGA AGCCAGGCCA GTCTCCAGAG GACCTGATCT ATGAGGTGTC

CAACCGCTTC TCTGGCGTGT CAGACAGGTT CAGTGGCAGC GGGTCAGGGA CAGATTTCAC CCTGAGAATC

AGCAGAGTGG AGGCTGACGA TGCTGGAATT TATTACTGCG GGCAGAATCT ACAGTTTCCG ATCACCTTTG

GCAAAGGGAC ACATCTGGAG ATTAAACGGA ATGATGCCCA GCCAGCCGTC TAT (SEQ ID NO: 994)
Kapa 131:

GAGGTTC CCATCTCAGC TCCTGGGGCT GCTGATGCTC TGGATCCCAG GATCCAGTGA GGATCTTGTC

TTGACACAGA CCCCACGGTC CCTGTCTGTC AGCCCTGGAG AGACTGCCTC CATCTCCTGC AAGGCCAGTC

AGAGCCTCCT GTCTCCTGAT GGAAACACAT ACTTGAATTG GTTCCGACAG AAGCCAGGCC AGTCTCCTCA

GCGTTTGATC TATAAGGTCT CCAATAGAGA CATTGGGGTC CCAGACAGGT TCAGTGGCAG CGGGTCAGGG

ACAGATTTCA CCCTGAGAAT CAGCAGAGTG GAGGCTGACG ATACTGGACT TTATTACTGT GGGCAAGTCA

CATATCTTCC CATTACTTTC AGCCAGGGAA CCAACCTGGA GATGAAACGG AATGATGCCC AGCCAGCCGT

CTAT (SEQ ID NO: 995)
Kapa212:

CTCCTGGG GCTGCTGATG CTCTGGATCC CAGGATCCAG TGGGGATATC GTCATGACAC AGACCCCACT

GTCCCTGTCC GTCTCCCCTG GAGAGCCGGC CTCCATCTCC TGCAAGGCCA GTCAGAGTCT CCTGCACAGT

AATGGGAACA CCTATTTGTC TTGGTTCCGA CAGAAGCCAG GCCAGTCTCC AGAGGGCCTG ATCTATGAGG

TGTCCAAGCG CTTCACTGGC GTGTCAGACA GGTTCAGTGG CAGCGGGTCA GGGACAGATT TCACCCTGAC

AATCAGTAGA GTGGAGGCTG ACGATGCTGG AGTTTATTAC TGCGGGCAGG GTCTACAATA TCCTCGGACG

TTCGGAACAG GAACCAAGGT GGAGCTCAAG CGGAATGATG CCCAGCCAGC CGTCTAT

TABLE N<sub>κ</sub>-continued

κ Light Chain Variable Domain Amino Acid Sequences (SEQ ID NO: 996)
Kapa214:

TTCCCATCTC AGCTCCTGGG GCTGCTGATG CTCTGGATCC CAGGATCCAG TGAGGATCTT GTCTTGACAC

AGACCCCACG GTCCCTGTCT GTCAGCCCTG GAGAGACTGC CTCCATCTCC TGCAAGGCCA GTCAGAGCCT

CCTGTCTCCT GATGGAAACA CATACTTGAA TTGGTTCCGA CAGAAGCCAG GCCAGTCTCC TCAGCGTTTG

ATCTATAAGG TCTCCAATAG AGACATTGGG GTCCCAGACA GGTTCAGTGG CAGCGGGTCA GGGACAGATT

TCACCCTGAG AATCAGCAGA GTGGAGGCTG ACGATACTGC ACTTTATTAC TGTGGGCAAG TCACATATCT

TCCCATTACT TTCAGCCAGG GAACCAACCT GGAGATGAAA CGGAATGATG CCCAGCCAGC CGTCTAT (SEQ ID NO: 997)
Kapa216:

ATGAGGT TCCCATCTCA GCTCCTGGGG CTGCTGATGC TCTGGATCCC AGGATCCAGT GAGGATCTTG

TCTTGACACA GACCCCACGG TCCCTGTCTG TCAGCCCTGG AGAGACTGCC TCCATCTCCT GCAAGGCCAG

TCAGAGCCTC CTGTCTCCTG ATGGAAACAC ATACTTGAAT TGGTTCCGAC AGAAGCCAGG CCAGTCTCCT

CAGCGTTTGA TCTATAAGGT CTCCAATAGA GACATTGGGG TCCCAGACAG GTTCAGTGGC AGCGGGTCAG

GGACAGATTT CACCCTGAGA ATCAGCAGAG TGGAGGCTGA CGATACTGGA CTTTATTACT GTGGGCAAGT

CACATATCTT CCCATTACTT TCAGCCAGGG AACCAACCTG GAGATGAAAC GGAATGATGC CCAGCCAGCC

GTCTAT (SEQ ID NO: 998)
Kapa217:

ATGAGGTT CCCTTCTCAG CTCCTGGGGC TGCTGATGCT CTGGATCCCA GGATCCAGTG GGATATTGT

CATGACACAG GCCCCACCGT CTCTGTCCGT CAGCCCTGGA GAGCCGGCCT CCATCTCCTG CAAGGCCAGT

CAGAGCCTCC TGCACAGTAA TGGGGACACC TATTTCTCTT GGTTCCAACA GAAGCCAGGC CAGTCTCCAG

AGGGCCTGAT CTATAAGGTG TCCAATCGCT ACACTGGCGT GTCAGACAGG TTCAGTGGCA GCGGGTCAGG

GACAGATTTC ACCCTGAGAA TCAGCAGAGT GGAGGCTGAC GATGCTGGAG TTTATTACTG CGGGCAGATT

TCACAGTTTC CTTATACTTT CAGCCAGGGA ACCAAGCTGG AGATAAAACG GAATGATGCC CAGCCAGCCG

TCTAT (SEQ ID NO: 999)
Kapa218:

ATGAGGTTC CCTTCTCAGC TCCTGGGGCT GCTGATGCTC TGGATCCCAG GATCCAGTGG GGATATTGTC

ATGACACAGG CCCCACCGCC TCTGTCCGTC AGTCCTGGAG AGCCGGCCTC CATCTCCTGC AAGGCCAGTC

AGACCCTCCT ACACAGTAAT GGGAACACCT ATTTGTATTG GTTCCGACAG AAGCCAGGCC AGTCTCCAGA

GGGCCTGATC CATAAGGTGT CCAACCGCTT CACTGGCGTG TCAGACAGGT TCAGTGGCAG CGGGTCAGGG

ACAGATTTCA CCCTGAGAAT CAGCAGAGTG GAGGCTGACG ATGCTGGACT TTATTACTGC GGGCAAAATT

TACAGTGGCC TCTTACGTTC GGCCAAGGGA CCAAGGTGGA GATCAAACGG AATGATGCCC AGCCAGCCGT

CTAT (SEQ ID NO: 1000)
Kapa110-79:

ATGAGG TTCCCTTCTC AGCTCCTGGG GCTGCTGATG CTCTGGATCC CAGGATCCGG TGGGGATATT

GTCATGACAC AGACGCCACC GTCCCTGTCT GTCAGCCCTA GAGAGCCGGC CTCCATCTCC TGCAGGGCCA

GTCAGAGCCT CCTGCACAGT AACGGGAACA CCTATTTGAG TTGGTACCTG CAAAAGCCAG GCCAGTCTCC

ACAGCTTCTG ATCTACTTGG TTTCCAACCG CTTCACTGGC GTGTCAGACA GGTTCAGTGG CAGCGGGTCA

TABLE N$_\kappa$-continued

κ Light Chain Variable Domain Amino Acid Sequences

GGGACAGATT TCACCCTGAG AATCAGCAGA GTGGAGGCTG ACGATACTGG AGTTTATTAC TGCGGGCAAG

GTACACAGTT TCCTCCGACG TTCGGAGCAG GAACCAAGGT GGAGCTCAAA CGGAATGATG CCCAGCCAGC

CGTCTAT (SEQ ID NO: 1001)
Kapa114-79:

ACTGCCTCCA TCTCCTGCAA GGCCAGTCAG AGTCTCCTGC ACAGTGATGG CTACACGTAT TTGAGTTGGT

TCCGACAGAA GCCAGGCCAG TCTCCACAGC GTTTGATCTC TAAGGTCTCC AACAGAGACA CTGGGGTCCC

AGACAGGTTC AGTGGCAGCG GGTCAGGGAC AGATTTCACC CTGAGAATCG GCAGAGTGGA GGCTGACGAT

ACTGGAGTTT ATTACTGTGG GCAAGTTATA CAAGATCCTT ATACTTTCAG CCAGGGAACC CCGCTGGAGA

TAAAACGGAA TGGTGCCCAG CCAGCCGTCT AT (SEQ ID NO: 1002)
Kapa127-79:

TGCAAGGCCC AGTCAGAGTC TCTTGCACAG TAATGGGAAC ACCTATTTGT GTTGGTTCCA ACAGAAGCCA

GGCCAGTCTC CACAGCGTTT GATCTGGCGG GTCTCCAACA GAGACCCTGG GGTCCCAGAC AGGTTCAGTG

GCAGCGGGTC AGGGACAGAT TTTACCCTGA GAATCAGCAG AGTGGAGGCT GATGATGCTG AATTTATTA

CTGCGGACAA GGTACACAAT ATCCTTTTAC GTTCGGCCAA GGGACCAAGG TGGACATTAA ACGGAATGAT

GCCCAGCCAG CCGTCTAT (SEQ ID NO: 1003)
Kapa203-79:

ATGAG GTTCCCTTCT CAGCTCCTGG GGCTGCTGAT GCTCTGGATC CCAGGATCCA GTGGGGATAT

TGTCATGACA CAGGCCCCAC CGTCTCTGTC CGTCAGCCCT GGAGAGCCGG CCTCCATCTC CTGCAAGGCC

AGTCAGAGCT CCTGCACAG TGATGGGAAC ACCTATTTGT ATTGGTTCCG ACAGAAGCCA GGCCAGTCTC

CAGAGGGCCT GATCTATAAG GTGTCCAACC GCTTCACTGG CGTGTCAGAC AGGTTCAGTG GCAGCGGGTC

AGGGACAGAT TTCACCCTGA GAATCAGCAG AGTGGAGGCT GACGATGCTG GAGTTTATTA CTGCGGGCAG

AATTTACATT TTCCTTATAC TTTCAGCCAG GGAACCAAGC TGGAGATAAA ACGGAATGAT GCCCAGCCAG

CCGTCTAT (SEQ ID NO: 1004)
Kapa208-79:

TCCGTCAGCC CTGGAGAGCC GGCCTTCATC TCCTGCAAGG CCAGTCAGAG CCTCCTGCAC AGTAATGGGT

ACAGCTTGTT GTATTGGTTC CGACAGAAGC CAGGCCAGTC TCCTCAGCGT TTGATCTATA AGGTCTCCAA

TAGAGACATT GGGGTCCCAG ACAGGTTCAG TGGCAGCGGG TCAGGGACAG ATTGCACCCT GACAATTAGC

AGAGTGGAGG CTGATGATGC TGGAGTTTAT TACTGCGGGC AAGGTATACA AGATCCGTTC ACTTTTGGCC

AAGGGACCAA ACTGGAGATC AAACGGAATG ATTCCCAGCC AGCCGTCTAT (SEQ ID NO: 1005)
Kapa213-79:

ATGACACA GACCCCACTG TCCCTGTCCG TCAGCCCTGG AGAGCCGGCC TCCATCTCCT GCAAGGCCAG

TCAGAGCCTC CTGCACAGTA ATGGGTACAG CTTGTTGTAT TGGTTCCGAC AGAAGCCAGG CCAGTCTCCA

GAGGACCTGA TCTATGAGGT GTCCAACCGC TTCTCTGGCG TGTCAGACAG GTTCAGTGGC AGCGGGTCAG

GGACAGATTT CACCCTGAGA ATCAGCAGAG TGGAGGCTGA CGATGCTGGA ATTTATTACT GCGGGCAGAA

TCTACAGTTT CCGATCACCT TTGGCAAAGG GACACATCTG GAGATTAAAC GGAATGATGC CCAGCCAGCC

GTCTAT

TABLE N<sub>κ</sub>-continued

κ Light Chain Variable Domain Amino Acid Sequences (SEQ ID NO: 1006)
Kapa217-79:

GTCATGACA CAGACCCCAC TGTCCCTGTC CGTCAGCCCT GGAGAGCCGG CCTCCATCTC CTGCAAGGCC

AGTCAGAGCC TCCTGCACAG TAATGGGAAC ACCTATTTTA ATTGGTTCCG ACAGAAGCCA GGCCAGTCTC

CAGAGGGCCT GATCTATCAG GTGTCCAACC GCTTCACTGG CGTGTCAGAC AGGTTCAGTG GCAGCGGGTC

AGGGACAGAT TTCACCCTGA GAATCAGCAG AGTGGAGGCT GACGATGCTG CAGTTTATTA CTGCGGGCAA

GATACACACT TTCCTTATAC TTTCAGCCAG GGAACCAAGC TGGAGATAAA TCGGAATGAT GCCCAGCCAG

CCGTCTAT (SEQ ID NO: 1007)
Kapa219-79:

GATATTGTCATGACACAGGCCCCACCGTCTN TGTCCGTCAG CCCTGGAGAG CCGGCCTCCA TCTCCTGCAC

GGCCGGTCAG AGCCTCCTGC ACAGTAATGG GAACACCTAT TTAACNTGGT ACCGACAGAA GCCAGGCCAG

TCTCCAGAGG ACCTGATCTA TGAGGTGTCC AACCGCTTCT CTGGNGTGTC AGACAGGTTC AGTGGCAGCG

GGTCAGGGAC AGATTTCACC CTGAGAATCA GCAGAGTGGA GGCTGACGAT GCTGCAGTTT ATTACTGCGG

GCAAGATACA CACTTTCCTT ATACTTTCAG CCAGGGAACC AAGCTGGAAA TAAAACGGAA TGATGCCCAG

CCAGCCGTCT AT (SEQ ID NO: 1008)
Kapa1201:

CTCCATCTCC TGCACAGTAC CGGGAACACC TATTTGAATT GGTTCCAACA GAAGCCAGGC CAGTCTCCAC

AGGGCCTGAT CTATAAGGTC TCCAACAGAG ACCCTGGGGT CCCAGACAGG TTCAGTGGCA GCGGGTCAGG

GACAGATTTC ACCCTGAGAA TCAGCAGAGT GGAGGCTGAC GATGCTGGAG TTTATTACTG CATGCAAGGT

GTACAAACTC CGTTCACTTT TGGCCAAGGG ACCAAACTGG AGATCAAACG GAATGATGCC CAGCCAGCCG

TCTAT (SEQ ID NO: 1009)
Kapa1202:

CTCCATCT CCTGCACAGT ACCGGGAACA CCTATTTGAA TTGGTTCCAA CAGAAGCCAG GCCAGTCTCC

ACAGGGCCTG ATCTATAAGG TCTCCAACAG AGACCCTGGG GTCCCAGACA GGTTCAGAGG CAGCGGGTCA

GGGACAGATT TCACCCTGAG AATCAGCAGA GCGGAGGCTG ATGATGCTGG AATTTATTAC TGCGGGCAAG

GTACACAAGA TCCTCCCACC TTTGGCAAAG GGACACATCT GGAGATTAAA CGGAATGATG CCCAGCCAGC

CGTCTAT (SEQ ID NO: 1010)
Kapa1204:

<u>AT GAGGTTCCCT TCTCAGCTCC TGGGGCTGCT GATGCTCTGG ATCCCAGGAT CCAGTGGGGA</u>

TGTTGTCATG ACACAGGCCC CACCGTCTCT GTCCGTCAGC CCTAGAGAGC CGGCCTCCAT CTCCTGCAAG

GCCAGTCAGA GCCTCCTGTA TAGTAATGGG AACACCTATT TGTATTGGTT CCGCCAGAAG CCAGGCCAGT

CTCCACAGCG TTTGATCTAT AAGGTCTCCA ATAGAGACCC TGGGGTCCCA GACAGGTTCA GTGGCAGCGG

GTCAGGGACA GATTTCACCC TGAGAATCAG CAGAGTGGAG GCTGACGATG CTGGAGTTTA TTACTGCATG

CAAGGTGTAC AAACTCCGTT CACTTTTGGC CAGGGAACCA AGCTGGAGAT AAAACGGAAT GATGCCCAGC

CAGCCGTCTA T (SEQ ID NO: 1011)
Kapa1206:

TABLE N<sub>κ</sub>-continued

κ Light Chain Variable Domain Amino Acid Sequences

ATGAGGTTC CCTTCTCAGC TCCTGGGGCT GCTGATGCTC TGGATCCCAG GATCCAGTGG GGATATTGTC

ATGACACAGA CCCCACTGTC CCTGTCCGTC AGCCCTGGAG AGCCGGCCTC CATCTCCTGC AAGGCCAGTC

AGAGCCTCCT GTATAGTAAT GGGAACACCT ATTTGTATTG GTTCCGCCAG AAGCCAGGCC AGTCTCCACA

GCGTTTGATC TATAAGGTCT CCAATAGAGA CCCTGGGGTC CCAGACAGGT TCAGTGGCAG CGGGTCAGGG

ACAGATTTCA CCCTGAGAAT CAGCAGAGTG GAGGCTGATG ATGCTGGAAT TTATTACTGC GGGCAAGGTA

CACAAGATCC TCCCACCTTT GGCAAAGGGA CACATCTGGA GATTAAACGG AATGATGCCC AGCCAGCCG (SEQ ID NO: 1012)
Kapa1207:

ATGAGGT TCCCTTCTCA GCTCCTGGGG CTGCTGATGC TCTGGATCCC AGGATCCAGT GGGGATGTTG

TCATGACACA GACCCCACCG TCTCTGTCCG TCAGCCCTAG AGAGCCGGCC TCCATCTCCT GCAAGGCCAG

TCAGAGCCTC CTGAACAGTA ATGGGCACAC CTATTTGTAT TGGTTCCGAC AGAAACCCGG CCAGTCTCCA

GAGGGCCTGA TCTATAAGGT GTCCAACCGC TTCACTGGCG TGTCAGACAG ATTCAGTGGC AGCGGGTCAG

GGACAGATTT CACCCTGAGA ATCAGCAGAG TGGAGGCTGA CGATGCTGGA GTTTATTACT GCGGGCAAGG

TATACAGGTT CCTTATACTT TCAGCCAGGG AACCAAGCTG GAGATAAAAC GGAATGATGC CCAGCCAGCC

GTCTAT (SEQ ID NO: 1013)
Kapa1208:

ATGAGGT TCCCTTCTCA GCTCCTGGGG CTGCTGATGC TCTGGATCCC AGGATCCAGT GGGGATGTTG

TCATGACACA GGCCCCACCG TCTCTGTCCG TCAGCCCTAG AGAGCCGGCC TCCATCTCCT GCAAGGCCAG

TCAGAGCCTC CTGAACAGTA ATGGGCACAC CTATTTGTAT TGGTTCCGAC AGAAACCCGG CCAGTCTCCA

GAGGGCCTGA TCTATAAGGT GTCCAACCGC TTCACTGGCG TGTCAGACAG ATTCAGTGGC AGCGGGTCAG

GGACAGATTT CACCCTGAGA ATCAGCAGAG TGGAGGCTGA CGATGCTGGA GTTTATCACT GCGGGCAAGG

TATACAGGTT CCTTATACTT TCAGCCAGGG AACCAAGCTG GAGATAAAAC GGAATGATGC CCAGCCAGCC

GTCTAT (SEQ ID NO: 1014)
Kapa1212:

ATGAGG TTCCCTTCTC AGCTCCTGGG GCTGCTGATG CTCTGGATCC CAGGATCCAG TGGGGATATA

GTCATGACAC AGACCCCACT GTCCCTGTCC GTCAGCCCTG GAGAGCCGGC CTCCATCTCC TGCAAGGCCA

GTCAGAGTCT CCTGCGCAGT AACGGGAACA CCTATTTGTT TTGGTTTCGA CACAAGCCAG GCCAGTCTCC

ACAGACTTTG ATCTATGAGG TCTCCAACAG AGACCCTGGG GTCCCAGACA GGTTCAGTGG CAGCGGGTCA

GGGACAGACT TCACTCTGAG AATCAGCAGA GTGGAGGCTA ACGATACTGG AGTTTATTAC TGCGGACAAG

GTACACAGTT CCTTATACT TTCAGCCAGG GAACCAAGCT GGAGATAAAA CGGAATGATG CCCAGCCAGC

CGTCTAT (SEQ ID NO: 1015)
Kapa1213:

ATGAGGTTCC CTTCTCAGCT CCTGGGGCTG CTGATGCTCT GGATCCCAGG ATCCAGTGGG GATGTTGTCA

TGACACAGGC CCCACCGTCT CTGTCCGTCA GCCCTGGAGA GCCGGCCTCC ATCTCCTGCA AGGCCAGTCA

GAGCCTCCTG AACAGTAATG GCACACCTA TTTGTATTGG TTCCGACAGA AACCCGGCCA GTCTCCAGAG

GGCCTGATCT ATAAGGTGTC CAACCGCTTC ACTGGCGTGT CAGACAGATT CAGTGGCAGC GGGTCAGGGA

CAGATTTCAC CCTGAGAATC AGCAGAGTGG AGGCTGACGA TGCTGGAGTT TATCACTGCG GCAAGGTAT

ACAGGTTCCT TATACTTTCA GCCAGGGAAC CAAGCTGGAG ATAAAACGGA ATGATGCCCA GCCAGCCGTC

TABLE N$_\kappa$-continued

κ Light Chain Variable Domain Amino Acid Sequences

TAT (SEQ ID NO: 1016)
Kapa1217:

<u>A TGAGGTTCCC TTCTCAGCTC CTGGGGCTGC TGATGCTCTG GATCCCAGGA TCCAGTGGGG</u>

ATGTTGTCAT GACACAGGCC CCACCGTCTC TGTCCGTCAG CCCTAGAGAG CCGGCCTCCA TCTCCTGCAA

GGCCAGTCAG AGCCTCCTGA ACAGTAATGG GCACACCTAT TTGTATTGGT TCCGACAGAA ACCCGGCCAG

TCTCCAGAGG GCCTGATCTA TAAGGTGTCC AACCGCTTCA CTGGCGTGTC AGACAGATTC AGTGGCAGCG

GGTCAGGGAC AGATTTCACC CTGAGGATCA GCAGAGTGGA GGCTGACGAT GCTGGAGTTT ATTACTGCGG

GCAAGGTATA CAGGTTCCTT ATACTTTCAG CCAGGGAACC AAGCTGGAGA TAAAACGGAA TGATGCCCA (SEQ ID NO: 1017)
Kapa1218:

<u>ATGAGG TTCCNTTCTC AGCTCCTGGG GCTGCTGATG CTCTGGATCC CAGGATCCAN TNGG</u>NATATT

GTCATGACAC AGACCCCACT GTCCCTGTCC GTCAGCCNTG NAGAGCCGGC CTCCATCTCC TGCAAGGCCA

GTCAGAGCCT CCTGTATAGT AATGGGAACA CCTATTTGTA TTGGTTCCGC CAGAAGCCAG GCCAGTCTCC

TCAGCGTTTG ATCTATAAGG TGTCCAACCG CTTCACAGGC GCGTCAGACA GATTCAGTGG CAGCGGGTCA

GGGGCAGATT TCACCNTGAG AATCAGCAGA GTGGAGGCTG ACGATGCTGG AGTTTATTAC TGCGGGCAAG

GTATACAGGT TCCTTATACT TTCAGCCAGG GA (SEQ ID NO: 1018)
Kapa1219:

<u>ATGAGGTTCC CTTCTCAGTT CCTGGGGCTG CTGATGCTNT GGATCCCAGG ATCCAGTGGG</u> GATATTGTCA

TGACACAGAC CCCACTGTCC CTGTCCGTCA GCCCTGGAGA GACGGCCTCC ATCTCCTGCA GAGAACCGGG

AACACCTATT TGAATTGGTT CCAACAGAAG CCAGGCCACT CTCCACGGGG CCTGATCTAT AAGGTCTCCA

ACAGAGACCC TGGGGTCCCA GACAGGTTCA GTGGCAGCGG GTCAGGGACA GATTTCACCC TGAGAATCAG

CAGAGTGGAG GCTGACGATG CTGGAGTTTA TTACTGCATG CAAGGTGTAC AAACTCCGTT CACTTTTGGC

CAAGGGACCA AACTGGAGAT CAAACGGAAT GATGCCCAGC CAGCCGTCTA T (SEQ ID NO: 1019)
Kapa1220:

<u>ATG AGGTTCCCTT CTCAGCTCCT GGGGCTGCTG ATGCTCTGGA TCCCAGGATC CAGTGGGGAT</u>

GTTGTCATGA CACAGGCCCC ACCGTCTCTG TCCGTCAGCC CTAGAGAGCC GGCCTCCATC TCCTGCAAGG

CCAGTCAGAG CCTCCTGAAC AGTAATGGGC ACACCTATTT GTATTGGTTC GACAGAAAC CCGGCCAGTC

TCCAGAGGGC CTGATCTATA AGGTGTCCAA CCGCTTCACT GGCGTGTCAG ACAGATTCAG TGGCAGCGGG

TCAGGGACAG ATTTCACCCT GAGAATCAGC AGAGTGGAGG CTGACGATGC TGGAGTTTAT TACTGCGGGC

AAGGTATACA GGTTCCTTAT ACTTTCAGCC AGGGAACCAA GCTGGAGATA AAACGGAATG ATGCCCAGCC

AGCCGTCTAT (SEQ ID NO: 1020)
Kapa1221:

<u>ATGAGGTT CCCTTCTCAG CCCCTGGGGC TGCTGATGCT CTGGATCCCA GGATCCAGTG GGATGTTGT</u>

CATGACACAG GCCCCACCGT CTCTGTCCGT CAGCCCTAGA GAGCCGGCCT CCATCTCCTG CAAGGCCAGT

CAGAGCCTCC TGAACAGTAA TGGGCACACC TATTTCTATT GGTTCCGACA GAAACCCGGC CAGTCTCCAG

AGGGCCTGAT CTATAAGGTG TCCAACCGCT TCACTGGCGT GTCAGACAGA TTCAGTGGCA GCGGGTCAGG

GACAGATTTC ACCCTGAGAA TCAGCAGAGT GGAGGCTGAC GATGCTGGAG TTTATTACTG CGGGCAAGGT

TABLE N$_\kappa$-continued

κ Light Chain Variable Domain Amino Acid Sequences

ATACAGGTTC CTTATACTTT CAGCCAGGGA ACCAAGCTGG AGATAAAACG GAATGATGCC CAGCCAGCCG

TCTAT (SEQ ID NO: 1021)
Kapa1223:

AT GAGGTTCCCT TCTCAGCTCC TGGGGCTGCT GATGCTCTGG ATCCCAGGAT CCAGTGGGGA

TGTTGTCATG ACACAGACCC CACCGTCTCT GTCCGTCAGC CCTAGAGAGC CGGCCTCCAT CTCCTGCAAG

GCCAGTCAGA GCCTCCTGAA CAGTAATGGG CACACCTATT TGTATTGGTT CCGACAGAAA CCCGGCCAGT

CTCCAGAGGG CCTGATCTAT AAGGTGTCCA ACCGCTTCAC TGGCGTGTCA GACAGATTCA GTGGCAGCGG

GTCAGGGACA GATTTCACCC TGAGAATCAG CAGAGTGGAG GCTGACGATG CTGGAGTTTA TTACTGCGGG

CAAGGTATAC AGGTTCCTTA TACTTTCAGC CAGGGAACCA AGCTGGAGAT AAAACGGAAT GATGCCCAGC

CAGCCGTC (SEQ ID NO: 1022)
Kapa1225:

ATGAG GTTCCCTTCT CAGTTCCTGG GGCTGCTGAT GCTCTGGATC CCAGGATCCA GTGGGGATAT

TGTCATGACA CAGACCCCAC TGTCCCTGTC CGTCAGCCCT GGAGAGACGG CCTCCATCTC CTGCACAGTA

CCGGGAACAC CTATTTGAAT TGGTTCCAAC AGAAGCCAGG CCAGTCTCCA CAGGGCCTGA TCTATAAGGT

CTCCAACAGA GACCCTGGGG TCCCAGACGG GTTCAGTGGC AGCGGGTCAG GGACAGATTT CACCCTGAGA

ATCAGCAGAG TGGAGGCTGA CGATGCTGGA GTTTATTACT GCATGCAAGG TGTACAAACT CCGTTCACTT

TTGGCCAAGG GACCAAACTG GAGATCAAAC GGAATGATGC CCAGCCAGCC GTCTA (SEQ ID NO: 1023)
Kapa1278:

ATGA GGTTCCCTTC TCAGCTCCTG GGGCTGCTGA TGCTCTGGAT CCCAGGGTCC AGTGGGGAGA

TCGTCATGAC ACAGACCCCA CTGTCCCTGT CCGTCAGTCC TGGAGAGACG GCCTCCATCT CCTACAGGGC

CAAGCAGAGC CTCCTGTATA GTGATGGGAA CACCTATTTG GATTGGTACA TGCAGAAGCC AGGCCAGTCT

CCCCAGGGCC GGATCTATTT GGTGTCCAAT CACTTCACAG GCGTGTCAGA CAGGTTCAGT GGCAGCGGGT

CAGGGACAGA TTTCACCCTG AAGATCAGCA GAGTGGAGGC TGACGATACT GGAGTTTATT NCTGCGGGCA

AGGTACACAC TCTCCTCCAC TTTCAGCCAG GGAACCAAGC TGGAGATA (SEQ ID NO: 1024)
Kapa1279:

GCCAGTCAGA GCCTCCTCCA CAGTAACGGG ATCACCTATT TGTTTTGGTT TCGACAGAGG CCAGGCCAGT

CTCCACAGCG TCTGATCTAT AAGGCCTCCA ACAGAGACCC TGGGGTCCCA GACAGGTTCA GTGGCAGCGG

GTCAGGGACA GACTTCACCC TGAGAATCAG CAGAGTGGAG GCTGACGATA TGGAGTTTA TTACTGCGGG

CAAGGTCTAC AGGTTCCGTG GACGTTCGGA GCAGGAACCA AGCTGGAGAT AAAACGGAAT GATGCCCAGC

CAGCCGTCTA T (SEQ ID NO: 1025)
Kapa1283:

ATGA GGTTCCCATC TCAGCTCCTG GGGCTGCTGA TGCTCTGGAT CCCAGGATCC AGTGGGGATA

TTGTCATGAC ACAGACCCCA CTGTCCCTGT CTGCCAGCCC TGGAGAGACT GCCTCCATCT CCTGCAAGGC

CAGACAGAGC CTCCTGCACA GTTATGGAAA CACGTATTTG AATTGGTTCC ACAGAAGCC AGGTCAGTCT

CCACAGCGTT TGATCTATAA GGTCTCCAAC AGAGACACTG GGGTCCCGGA CAGGTTCAGT GGCAGCGGGT

CAGGGACAGA TTTCACCCTG AGAATCAGCA GAGTGGAGGC TGACGATACT GGGGTTTATT ACTGCGGGCA

TABLE N<sub>κ</sub>-continued

κ Light Chain Variable Domain Amino Acid Sequences

AGGTATACAG TTTCCTCGCA CTTTTGGCCA AGGGACCAAA CTGGAGATCA GACGGAATGA TGCCCAGCCA

GCCGTCTAT (SEQ ID NO: 1026)
Kapa1284:

ATG AGGTTCCCTT CTCAGCTCCT GGGGCTGCTG ATGCTCTGGA TCCCAGGATC CAGCGGAGAT

ATTGTCATGA CAGAGGCCCC ACCGTCTCTG TCCGTCAGCC CTGGAGAGTC GGCCTCCATC TCCTGCAAGG

CCAGTCAGAG CCTCCTGCAC AGTAATGGGA ACACCTATTT GTTCTGGCTC CGACAGAAGC CAGGCCAGTC

TCCAGAGGGC CTGATCTATA AGGTGTCCAA CCGCTTCACT GGCGTGTCAG ACAGGTTCAG TGGCAGAGGG

TCAGGGACAG ATTTCACCCT GCGAATCAGC AGAGTGGAGG CTGCGATGC TGGAGTTTAT TACTGCGGGC

AAAATTTACA GTTTCCTTAT ACTTTCAGCC AGGGAACCAA GCTGGAGATA AACGGAATG ATGCCCAGCC

AGCCGTCTAT (SEQ ID NO: 1027)
Kapa1285:

ATGA GGTTCCCTTC TCAGCTCCTG GGCTGCTGA TGCTCTGGAT CCCAGGATCC AGTGGGGATA

TCGTCATGAC ACAGACCCCA CTGTCCCTGT CCGTCAGCCC TGGAGAGCCG GCCTCCATTT CCTGCAAGGC

CAGTCAGAGC CTCCTGCACA GTAACGGGAA CACCTATTTG TATTGGTCTC GACAGAGGCC AGGCCAGTCT

CCGGAGGGCC TGATCTATAA GGTGTCCAAC CGCTTCATTG GCGTGTCAGA CAGGTTCAGT GGCAGCGGGT

CAGGGACAGA TTTCACCCTG AAAATCAGCA GAGTGGAGGC TGACGATGCT GGAGTTTATT TCTGCGGGCA

AAATTTACAG TTTCCTTTTA CTTTCAGCCA GGGAACCAAG CTGGAGATAA ACGGAATGA TGCCCAGCCA

GCCGTCT (SEQ ID NO: 1028)
Kapa1286:

ATGAGGTTCC CTTCTCAGCT CCTGGGGCTG CTGATGCTCT GGATCCCAGG ATCCAGTGGG GATATCGTCA

TGACACAGAT CCCACTGTCC CTCTCCGTCA GTCCTGGAGA GCCGGCCTCC ATCTCCTGCA AGGCCAGTCA

GAGCCTCCTG CACAGTAACG GTGTCACCTA TTTGTTTTGG TTTCGACAGA AGCCAGGCCA GTCTCCACAG

CGTTTGATCT ATAGGGTCTC AGGAGAGAC CCTGGGGTCC AGACAGGTT CAGTGGCAGC GGGTCAGGGA

CAGATTTCAC CCTGAGAATC AGCAGAGTGG AGGCTGATGA TGCTGGAGTT TATTACTGCG GGCAAGCTTT

ACAAACTCGT CGGACGTTCG GAGCAGGAAC CAAGGTGGAG CTCAAACGGA ATGATGCCCA GCCAGCCGTC

TA (SEQ ID NO: 1029)
Kapa1287:

ATGAGG TTCCCTTCTC AGCTCCTGGG GCTGCTGATG CTCTGGATCC AGGATCCAGT GGGGATATTG

TCATGACACA GGCCCCACCG TCTCTGTCCG TCAGCCCTGG AGAGCCGGCC TCCATCTCCT GCAGGGCCAG

TCAGAGCCTC CCGCACAGTG ATGGGAACAC CTATTTGTAC TGGTTCCGCC AGAAGCCAGG CCAGTCTCCA

GAGGGCCTGA TCTATAAGGT GTCCAACCGC TTCACTGGCG TGTCAGACAG GTTCAGTGGC AGCGGGTCAG

GGACAGATTT CACCCTGAGA ATCAGCAGAG TGGAGGCTGA CGATGCTGGA GTTTATTACT GCGGGCAAAA

TTTACAGTTT CCTCTTACGT TCGGCCAAGG GACCAAGGTG GAGATCAAAC GGAATGATGC CCAGCCAGCC

GTCT (SEQ ID NO: 1030)
Kapa1288:

ATGAGGT TCCCTTCTCA GCTCCTGGGG CTGCTGATGC TCTGGATCCC AGGATCCAGT GGGGATATTG

TABLE N_κ-continued

κ Light Chain Variable Domain Amino Acid Sequences

TCATGACACA GACTCCACTG TCCCTGTCTG TCAGCCCTGG AGAGACTGCC TCCATCTCCT GTAAGGCCAG

TCAGAGCCTC CTGTACAGTG ATGGAAACTC GATTTTGAAT TGGTTCCGAC AGAAGCCAGG CCAGTCTCCA

CAGCGTTTGA TCTATAAGGT CTCCAACAGA GACCCTGGGG TCCCAGACAG GTTCAGTGGC AGCGGGTCAG

GGACAGATTT CACCCTGAGA ATCAGTAGAG TGGTGGCTGA TGATGCTGGA GTTTATTACT GCGGGCAAGC

TATACAAGAT CCGTGGACGT TCGGAGCAGG AACCAAGGTG GAGCTCAAAC GGAATGACGC CCAGCCAGCC

GTCTA (SEQ ID NO: 1031)
Kapa1289:

ATGAGG TTCCCTTCTC AGCTCCTGGG GCTGCTGATG CTCTGGATCC CAGGATCCAG TGGGGATATT

GTCATGACAC AGGCCCCACC GTCTCTGTCC GTCAGCCCTG GAGAGCCGGC CTCCATCTCC TGCAAGGCCA

GTCAGAGCCT CCTGTACAGT AATGGGAATA CCTATTTGTA TTGGTTCCGA CAGAAGCCAG GCCAGTCTCC

AGAGGGCCTG ATCTATAAGG TGTCCAACCG CTTCACTGGC GTGTCAGACA GGTTCAGTGG CAGCGGGTCA

GGGACAGATT TCACCCTGAG AATCAGCAGA GTGGAGGCTG ACGATGCTGG AGTTTATTAC TGCGGGCAAG

GTATACAGTT TCCTATTACT CTCAGCCAGG GAGCCAAGCT GGACATAAAA CGGAATGATG CCCAGCCAGC

CGTCTAT (SEQ ID NO: 1139)
Kapa1243:

A TGAGGTTCCC ATCTCAGCTC CTGGGGCTGC TGATGCTCTG GATCCCAGGA TCCAGTGGGA

TTATTGTCAT GACACAGACC CCACTGTCCC TGTCTGCCAG CCCTGGAGAG TCTGCCTCCA TCTCCTGCAA

GGCCAGTCAG AGCCTCCTGC ACAGTACTGG AAACACGTAT TTGAATTGGT TCCGACAGAA GCCAGGCCAG

TCTCCACAGC GTTTGATCTA TAGGGTCTCC AACAGAGACA CGGGGGTCCC AGACAGGTTC AGTGGCAGCG

GGTCAGGGAC AGATTTCACC CTGAGAATCA GCAGAGTGGA GGATGAGGAT GCTGGACTTT ATTACTGCGG

GCAAGGTATA CAATATCCGT TCACTTTTGG CCAAGGGACC AAACTGGAGA TCAAACGGAA TGATGCCCAG

CCAGCCGTCT AT (SEQ ID NO: 1032)
Kapa1244:

CAGAGCCTCC TGCACAGTAA CGGAAACACC TATTTGAATT GGTACCTGCA AAAGCCAGGC CAGTCTCCTC

AGATTCTGAT CTACTTGGCT TCCCACCGCA GCAATGGCGT GTCAGACAGG TTCAGTGGCA GCGGGTCAGG

GACAGACTTC ACCCTGAGAA TCAGCAGAGT GGAGGCTGAC GATAGTGGAG TTTATTACTG CGGGCAAGGT

CTACAGGTTC CGTGGACGTT CGGAGCAGGA ACCAAGGTGG AGCTCAAACG GAATGATGCC CAGCCAGCCG

TCTAT (SEQ ID NO: 1033)
Kapa1249:

CAAGATCCTC ATACTTTCAG CCAGGGAACC AAGCTGGGGA TAAAACGGAA TGATGCCCAG CCAGCCGTCT

ATTTGTTCCA ACCATCTCCA GACCAGTTAC ACACAGGAAG TGCCTCTGTT GTGTGTTTGC TGAATAGCT (SEQ ID NO: 1034)
Kapa1250:

CTGCTGAT GCTCTGGATC CCAGGATCCA GTGGGGATAT TGTCATGACA CAGACCCCAC TGTCCCTGTC

CGTCAGCCCT GGAGAGCCGG CCTCCATCTC CTGCAAGGCC AGTCAGAGCC TCCTGCACAG TGACGGGAAC

ACCTACTTGT ATTGGTTCCG ACAGAAGCCA GGCCAGGCTC CACAGCGCCT GATCTACGTG GGTATCAAGA

GAGACGCTGG GGTCCCAGAC AGGTTCAGTG CAGCGGGTC AGGGACAGAC TTCACCCTGA GAATCAGCAG

TABLE N_κ-continued

κ Light Chain Variable Domain Amino Acid Sequences

AGTGGAGGCT GATGATGGTG GAGTTTATCA CTGCGGGCAA GGTACACAGC TTCCTTATAC TTTCAGCCAG

GGAACCAAGC TGGAGATAAA ACGGAATGAT GCCCAGCCAG CCGTCTAT (SEQ ID NO: 1035)
Kapa1251:

CAGAGCCTCC TCCACAGTAA CGGGATCACC TATTTGTTTT GGTTTCGACA GAGGCCAGGC CAGTCTCCAC

AGCGTCTGAT CTATAAGGCC TCCAACAGAG ACCCTGGGGT CCCAGACAGG TTCAGTGGCA GCGGGTCAGG

GACAGACTTC ACCCTGAGAA TCAGCAGAGT GGAGGCTGAC GATAGTGGAG TTTATTACTG CGGGCAAAAC

ATAGGGTTTC CTAATACTTC CAGCCAGGGA ACCAAGCTGG AGATAAAACG GAATGATGCC CAGCCAGCCG

TCTAT (SEQ ID NO: 1036)
Kapa1275:

ATGAGGTTC CCTTCTCAGC TCCTGGGGCT GCTGATGCTC TGGATCCCAG GATCCAGTGG GGCCATTGTC

ATGACACAGG CCCCACCGTC TCTGTCCGTC AGCCCTGGAG AGCCGGCCTC CATCTCCTGC AAGGCCAGTC

AGAGCCTCCT GCACGGTGAT GGGACCACCT ATTTGTTTTG GTTCCGACAG AAGCCAGGCC AGTCTCCACA

GCGTTTGATC TATAAGGCCT CCAACAGAGA CCCTGGGGTC CCAGACAGGT TCAGTGGCAG CGGGTCAGGG

ACAGACTTCA CCCTGAGAAT CAGCAGAGTG GAGGCTGACG ATAGTGGAGT TTATTACTGC GGGCAAGGTC

TACAGGTTCC GCGGACGTTC GGAGCAGGAA CCAAGGTGGA GCTCAAACGG AATGATGCCC AGCCAGCCGT

CTAT (SEQ ID NO: 1037)
Kapa1343:

GGGCTGCTG ATGCTCTGGA TCCCAGGATC CAGTGGGGAT ATTGTCATGA CACAGACGCC ACCGTCCCTG

TCTGTCAGCC CTGGGGAGAC TGCCTCCATC TCCTGCAAGG CCAGTCAGAG CCTCCTGTTC AGTAACGGGA

AAACCTATTT GTTTTGGTTT CGACAGAAGC CAGGCCAGTC TCCACAACGT TGATCTATC AGGTCTCCAA

TAGAGACCCT GGTATCCCAG ACAGGTTCAG TGGCAGCGGG TCAGGACAG ATTTCACCCT GAGAATCAGC

GGAGTGGAGG CTGCCGATAC TGGAGTTTAT TACTGCGTGC AAGGTATACA GTTTCCTTAT ACTTTCGGCC

AGGGAACCAA CCTGGAGATA AAACGGAATG ATGCCCAGCC AGCCGTCTAT (SEQ ID NO: 1038)
Kapa1346:

ATGGA AGCCCCAGCT CGCCTTCTCT GCCTTCTGTT ACTCTGGCTC CCAGATATCA CCGGAGAAAT

CCTACTGACA CAGTCTCCAG ACTCCCTCTC CTTGTCTCAG GAGACAGAAG TCACCATCAC CTGCCGGGCC

AGTCAGTATG TTAGCAGGGA CTTAGCCTGG TATCAACAAA AACCTGGGCA GGCCCCCAAA CTCCTCATCT

ATGGTGCCTC CAATAAGGCC ACTGGTGTCC CATCCCGTTT CAGTCGCAGT GGGTCTGGGA CAGACTTTAG

CCTCACAATC AGCAGCCTGG AGCCCGAAGA TGTTGCAGTT TATTTCTGTC AACAGTATCA TACGGGTCCG

CTAACGTTCG GCCAAGGGAC CAAGGTGGAG ATCCAGCGGA ATGATGCCCA GCCAGCCGTC TAT (SEQ ID NO: 1039)
Kapa1347:

ATGGA AGCCCCAGCT CGCCTTCTCT GCCTTCTGTT ACTCTGGCTC CCAGATATCA CCGGAGAAAT

CCTACTGACA CAGTCTCCAG ACTCCCTCTC CTTGTCTCAG GAGACAGAAG TCACCATCAC CTGCCGGGCC

AGTCAGTATG TTAGCAGGGA CTTAGCCTGG TATCAACAAA AACCTGGGCA GGCCCCCAAA CTCCTCATCT

ATGGTGCCTC CAATAAGGCC ACTGGTGTCC CATCCCGTTT CAGTCGCAGT GGGTCTGGGA CAGACTTTAG

CCTCATAATC AGCAGCCTGG AGCCCGAAGA TGTTGCAGTT TATTTCTGTC AACAGTATCA TACGGGTCCG

TABLE N$_\kappa$-continued

κ Light Chain Variable Domain Amino Acid Sequences

CTAACGTTCG GCCAAGGGAC AAGGTGGAG ATCCAGCGGA ATGATGCCCA GCCAGCCGTC TAT (SEQ ID NO: 1040)
Kapa1348:

<u>CCTGGGGCTG CTGATGTCTG GATCCCAGGA TCCAGTGGGG</u> ATATTGTCAT GACACAGGCC CCACCGTCTC

TGTCCGTCAG CCCTGGAGAG CCGGCCTCCA TCTCCTGCAC GGCCAGTCAG AGCCTCCTGC ACAGTAATGG

GAACACCTAT TTAACCTGGT ACCGACAGAA GCCAGGCCAG TCTCCAGAGG ACCTGATCTA TGAGGTGTCC

AACCGCTTCT CTGGCGTGTC AGACAGGTTC AGTGGCAGCG GGTCAGGGAC AGATTTCACC CTGAGAATCA

GCAGAGTGGA GGCTGACGAT GCTGGAATTT ATTACTGCGG GCAGAATCTA CAGTTTCCGA TCACCTTTGG

CAAAGGGACA CATCTGGAGA TTAAACGGAA TGATGCCCAG CCAGCCGTCT AT (SEQ ID NO: 1041)
Kapa1349:

<u>GGATCCCAG GATCCAAGTG AG</u>GATCTTGT CTTGACACAG ACCCCACGGT CCCTGTCTGT CAGCCCTGGA

GAGACTGCCT CCATCTCCTG CAAGGCCAGT CAGAGCCTCC TGTCTCCTGA TGGAAACACA TACTTGAATT

GGTTCCGACA GAAGCCAGGC CAGTCTCCTC AGCGTTTGAT CTATAAGGTC TCCAATAGAG ACATTGGGGT

CCCAGACAGG TTCAGTGGCA GCGGGTCAGG GACAGATTTC ACCCTGAGAA TCAGCAGAGT GGAGGCTGAC

GATACTGGAC TTTATTACTG TGGGCAAGTC ACACATCTTC CCATTACTTT CAGCCAGGGA ACCAACCTGG

AGATGAAACG GAATGATGCC CAGCCAGCNG TCTAT (SEQ ID NO: 1042)
Kapa1350:

<u>ATGAGGTT CCCTTCTCAG CTCCTGGGGC TGCTGATGCT CTGGATCCCA GGATCCAGTG AG</u>GATCTTGT

CTTGACACAG ACCCCACGGT CCCTGTCTGT CAGCCCTGGA GAGACTGCCT CCATCTCCTG CAAGGCCAGT

CAGAGCCTCC TGCACAGTAA CGGGAACACC TATTTGTTTT GGTTTCGACA GAAGCCAGGC CAGTCTCCAC

AGCGTTTGAT CTATAAGGTC TCCAATAGAG ACATTGGGGT CCCAGACAGG TTCAGTGGCA GCGGGTCAGG

GACAGATTTC ACCCTGAGAA TCAGCACAGT GGAGGCTGAC GATACTGGAC TTTATTACTG TGGGCAAGTC

ACATATCTTC CCATTACTTT CAGCCAAGGA ACCAACCTGG AGATGAAACG GAATGATGCC CAGCCAGCCG

TCTAT (SEQ ID NO: 1043)
Kapa1353:

<u>ATG AGGTTCCCTT CTCAGCTCCT GGGGCTGCTG ATGCTCTGGA TCCCAGGATC CAGTGGGGAT</u>

ATCGTCATGA CACAGACCCC ACTGTCCCTG TCCGTCAGCC CTGGAGAGCC GGCCTCCATC TCCTGCAAGG

CCAGTCAGAG CCTCCTGCAC AGTAATGAA ACACCAATTT ATATTGGTAC CTGCAAAAGC CAGGCCAGTC

TCCACAACTT CTGATCTACT TGGTTTCCAA CCGCTTCACT GGCGTGTCAG ACAGGTTCAG TGGCAGCGGG

TCAGGGACAC ATTTCACCCT GAGAATCAGC AGAGTGGAGG CTAACGATAC TGGAGTTTAT TACTGCGGAC

AAGGTATATA TTTTCCGTTC GCTTTTGGCC AAGGGACCAA ACTGGAGATC AAACGGAATG ATGCCCAGCC

AGCCGTCTAT (SEQ ID NO: 1044)
Kapa1354:

CCACCGTCC CTGTCTGTCA GCCCTAGAGA GCCGGCCTCC ATCTCCTGCA GGGCCAGTCA GAGCCTCCTG

CACAGTAACG GGAACACCTA TTTGAATTGG TACCTGCAAA AGCCAGGCCA GTCTCCACAG CTTCTGATCT

ACTTGGTTTC CAACCGCTTC ACTGGCGTGT CAGACAGGTT CAGTGGCAGC GGGTCAGGGA CAGATTTCAC

CCTGAGAATC AGCAGAGTGG AGGCTGACGA TANTGGAGTC TATTACTGCG GGCAAGGTAC ACAGGTTCCT

TABLE N<sub>κ</sub>-continued

κ Light Chain Variable Domain Amino Acid Sequences

TATACTTTCA GCCAGGGAAC CAGGCTGGAG ATAAAAAGGA ATGATGCCCA GCCAGCCGTC TAT (SEQ ID NO: 1045)
Kapa1356:

<u>ATGAGGT TCCCATCTCA GCTCCTGGGG CTGCTGATGC TCTGGATCCC AGGATCCAGT GAGGATCTTG</u>

TCTTGACACA GACCCCACGG TCCCTGTCTG TCAGCCCTGG AGAGACTGCC TCCATCTCCT GCAAGGCCAG

TCAGAGCCTC CTGTCTCCTG ATGGAAACAC ATACTTGAAT TGGTTCCGAC AGAAGCCAGG CCAGTCTCCT

CAGCGTTTGA TCTATAAGGT CTCCAATAGA GACATTGGGG TCCCAGACAG GTTCAGTGGC AGCGGGTCAG

GGACAGATTT CACCCTGAGA ATCAGCAGAG TGGAGGCTGA CGATACTGGA CTTTATTACT GTGGGCAAGT

CACATATCTT CCCATTACTT TCAGCCAGGG AACCAACCTG AGATGAAAC GGAATGATGC CCAGCCAGCC

GTCTAT (SEQ ID NO: 1046)
Kapa1360:

<u>ATGAGGTTC CCATCTCAGC TCCTGGGGCT GNTGATGCTC TGGATCCCAG GATCCAGTGA GGATCTTGTC</u>

TTGACACAGA CCCCACGGTC CCTGTCTGTC AGCCCTGGAG AGACTGCCTC CATCTCCTGC AAGGCCAGTC

AGAGCCTCCT GTCTCCTGAT GGAAACACAT ACTTGAATTG GTTCCGACAG AAGCCAGGCC AGTCTCCTCA

GCGTTTGATC TATAAGGTCT CCAATAGAGA CATTGGGGTC CCAGACAGGT TCAGTGGCAG CGGGTCAGGG

ACAGATTTCA CCCTGAGAAT CAGCAGAGTG GAGGCTGACG ATACTGGACT TTATTACTGT GGGCAAGTCA

CACATCTTCC CATTACTTTC AGCCAGGGAA CCAACCTGGA GATGAAACGG AATGATGCCC AGCCAGCCGT

CTAT (SEQ ID NO: 1047)
Kapa1361:

<u>TGGATCCCAG GATCCAGTGA G</u>GATCTTGTC TTGACACAGA CCCCACGGTC CCTGTCTGTC AGCCCTGGAG

AGACTGCCTC CATCTCCTGC AAGGCCAGTC AGAGCCTCCT GTCTCCTGAT GGAAACACAT ACTTGAATTG

GTTCCGACAG AAGCCAGGCC AGTCTCCTCA GCGTTTGATC TATAAGGTCT CCAATAGAGA CATTGGGGTC

CCAGACAGGT TCAGTGGCAG CGGGTCAGGG ACAGATTTCA CCCTGAGAAT CAGCAGAGTG GAGGCTGACG

ATACTGGACT TTATTACTGT GGGCAAGTCA CATATCTTCC CATTACTTTC AGCCAGGGAA CCAACCTGGA

GATGAAACGG AATGATGCCC AGCCAGCCGT CTAT (SEQ ID NO: 1048)
Kapa1362:

<u>ATGAGG TTCCCTTCTC AGCTCCTGGG GCTGCTGATG CTCTGGATCC AGGATCCAG TGGGGATATT</u>

GTCATGACAC AGACCCCACC GTCCCTGTCT GTCAGCCCTG GAGAGCCGGC CTCCATCTCC TGCAAGGCCA

GTCAGAGCCT CCTGTACCCT AATGGAAATA CCTATTTGTA TTGGTATTTG CAAAAGCCAG GCCAGTCTCC

ACAGCTTCTG ATCTACTTGG TTTCCAATCG CTTCACTGGC GTGTCAGACA GGTTCAGTGG CAGCGGGTCA

GGGACAGATT TCACCCTGCG AATTAGCAGA GTGGAGGCTA CGATACTGG AGTTTATTAC TGCGGACAAG

GTACATATTT TCCGTTCGCT TTTGGCCAAG GGACCAAACT GGAGATCAAA CGGAATGATG CCCAGCCAGC

CGTCTAT (SEQ ID NO: 1049)
Kapa1363:

<u>TCTCAGCTC CTGGGGCTGC TGATGCTCTG GATCCCAGGA TCCAGTGGGG</u> ATATTGTCAT GACACAGACC

CCACTGTCCC TGTCTGTCAG CCCTGGAGAG ACTGCCTCCA TCTCCTGCAA GGCCAGTCAG AGCCTCCTCT

ACAGTAATGG AAACACGTAT TTGAGTTGGT TCCGACAGAA GCCAGGCCAG TCTCCACAGC GTTTGATCTA

TABLE N<sub>κ</sub>-continued

κ Light Chain Variable Domain Amino Acid Sequences

TAAGGTCTCC AACAGAGACC CTGGGGTCCC AGACAGATTC AGTGGCAGCG GGTCAGGGAC AGACTTCACC

CTGAGAATCA GCAGAGTGGA GGCTGACGAT ACTGGAGTTT ATTTTTGCGG CCAAGGTATA CACTCTCCTT

TTACTTTCAG CCAGGGAACC AACCTGGAGA TAAAACGGAA TGATGCCCAG CCAGCCGTCT AT (SEQ ID NO: 1050)
Kapa1366:

A TGAGGTTCCC ATCTCAGCTC CTGGGGCTGC TGATGCTCTG GATCCCAGGA TCCAGTGAGG

ATCTTGTCTT GACACAGACC CCACGGTCCC TGTCTGTCAG CCCTGGAGAG ACTGCCTCCA TCTCCTGCAA

GGCCAGTCAG AGCCTCCTGT CTCCTGATGG AAACACATAC TTGAATTGGT TCCGACAGAA GCCAGGCCAG

TCTCCTCAGC GTTTGATCTA TAAGGTCTCC AATAGAGACA TTGGGGTCCC AGACAGGTTC AGTGGCAGCG

GGTCAGGGAC AGATTTCACC CTGAGAATCA GCAGAGTGGA GGCTGACGAT ACTGGACTTT ATTACTGTGG

GCAAGTCACA TATCTTCCCA TTACTTTCAG CCAGGGAACC AACCTGGAGA TGAAACGGAA TGATGCCCAG

CCAGCCGTCT AT (SEQ ID NO: 1051)
Kapa1370:

ATGAGGT TCCCTTCTCA GCTCCTGGGG CTGCTGATGC TCTGGATCCC AGGATCCAGT GGGGATATCG

TCATGACACA GACCCCACTG TCCCTGTCTG TCAGCCCTGG AGAGACTGCC TCCATCTCCT GCAAGGCCGG

TCAGAGCCTC CTCTACAGTA ATGGAAACAC GTATTTGAGT TGGTTCCGAC AGAAGCCAGG CCAGTCTCCA

CAGCGTTTGA TCTTTGAGGT CTCCAACAGA GACACTGGGG TCCCGGACAG GTTCGCTGGC AGCGGGTCAG

GGACAGATTT CACCCTGAGA ATCAGCAGAG TGGAGGCTGA CGATACTGGA ATTTATTACT GCGGGCAAGG

TATACAGTTT CCTCGGACGT TCGGACCAGG AGCCAAGGTG AACTCAAAC GGAATGATGC CCAGCCAGCC

GTCTAT (SEQ ID NO: 1052)
Kapa1371:

CTCAGCTCCT GGGGGCTGCT TGATGTCTGG ATCCCAGGAT CCAGTGGGGA TATCGTCATG ACACAGACCC

CACTGTCCCT GTCCGTCAGC CCTGGAGAGC CGGCCTCCAT CTCCTGCAAG GCCAGTCAGA GCCTCCTGCA

CAGTAACGGG AACACCTATT TGTTTTGGTT TCGACAGAAG CCAGGCCAGT CTCCACAGCT TTTGATCTAT

AAGGTCTCCA ACAGAGACCC TGGGGTCCCA GACAGGTTCA GTGGCAGCGG GTCAGGGACA GATTTCACCC

TGAGAATCAG CAGAGTGGAG GCTGACGATA CTGGAGTTTA CTACTGCGGG CAAGGTATAC AGTTTCCTCA

TACTTTCAGC CAGGGAACCA AGCTGGTGAT AAAACGGAAT GATGCCCAGC CAGCCGTCTA T (SEQ ID NO: 1053)
Kapa2420:

TTCCCTGGA TCCAGTGGGG ATATCGTCAT GACGCAGACC CCACTGTCCC TGTCTGTCAG CCCTGGAGAG

CCGGCCTCCA TCTCCTGCAG GGCCAGTCAG AGCCTCCTGC ACAGTAATGG AAACACCTAT TTCGCTTGGT

TCCAACAGAA GCCAGGCCAG TCTCCACAGC GTTTGATCTA TCACGTCTCC AAGAGAGACC CTGGGGTTCC

AGACAGGTTC AGTGGCAGCG GGTCAGGGAC AGATTGCACC CTGACAATTA GCAGAGTGGA GGCTGATGGT

GCTGGAGTTT ATTACTGCGG GCAAGGTATA CAAGATCCGT TCACTTTTGG CCAAGGGACC AAACTGGAGA

TCAAACGGAA TGATGCCCAG CCAGCCGTCT AT (SEQ ID NO: 1054)
Kapa2422:

ATGA GGTTCCCTTC TCAGCTCCTG GGGCTGCTGA TGCTCTGGAT CCCAGGATCC GGTGGGGATA

TTGTCATGAC ACAGACCCCA CCGTCCCTGT CTGTCAGCCC TGGAGAGCCG GCCTCCATCT CCTGCAAGGC

TABLE N_κ-continued

κ Light Chain Variable Domain Amino Acid Sequences

CAGTCAGAGC CTCCTGTACC CTAATGGAAA TACCTATTTG TATTGGTATT TGCAAAAGCC AGGCCAGTCT

CCTCAGCGTT TGATCTATAA GGTCTCCAAT AGAGACATTG GGTCCCAGA CAGGTTCAGT GGCAGCGGGT

CAGGGACAGA TTTCACCCTG AGAATCAGCA GAGTGGAGGC TGACGATACT GGACTTTATT ACTGTGGGCA

AGTCACATAT CTTCCCATTA CTTTCAGCCA GGGAACCAAC CTGGAGATGA AACGGAATGA TGCCCAGCCA

GCCGTCTAT (SEQ ID NO: 1055)
Kapa2423:

GCTCCTGGGG CTGCTGATGC TCTGGATCCC AGGATCCGGT GGGGATATTG TCATGACACA GACCCCACCG

TCCCTGTCTG TCAGCCCTGG AGAGCCGGCC TCCATCTCCT GCAAGCCAGT CAGAGCCTCC TGCACAGTAA

TGGGAACACC TATTTCGCTT GGTTCCAACA GAAGCCAGGC CAGTCTCCAC AGCGTTTGAT CTATCACGTC

TCCAAGAGAC ACCCTGGGGT TCCAGACAGG TTCAGTGGCA GCGGGTCAGG ACAGATTGC ACCCTGACAA

TTAGCAGAGT GGAGGCTGAT GATGCTGGAG TTTATTGCTG CGGGCAAGGT ATACAAGATC CGTTCACTTT

TGGCCAAGGG ACCNAACTGG AGATCAAACG GAATGATGCC CAGCCAGCCG TCTAT (SEQ ID NO: 1056)
Kapa2425:

<u>ATGAGG TTCCCTTCTC AGCTCCTGGG GCTGCTGATG CTCTGGATCC CAGGATCCGG TGGGGATATT</u>

GTCATGACAC AGACCCCACC GTCCCTGTCT GTCAGCCCTG GAGAGCCGGC CTCCATCTCC TGCAAGGCCA

GTCAGAGCCT CCTGTACCCT AATGGAAATA CCTATTTGTA TTGGTATTTG CAAAAGCCAG GCCAGTCTCC

ACAGCTTCTG ATCTACTTGG TTTCCAATCG CTTCACTGGC GTGTCAGACA GGTTCAGTGG CAGCGGGTCA

GGGACAGATT TCACCCTGCG AATTAGCAGA GTGGAGGCTA CGATACTGG AGTTTATTAC TGCGGACAAG

GTTCATATTT TCCGTTCGCT TTTGGCCAAG GGACCAAACT GGAGATCAAA CGGAATGATG CCCAGCTAGC

CGTCTAT (SEQ ID NO: 1057)
Kapa2426:

<u>ATGAGG TTCCCATCTC AGCTCCTGGG GCTGCTGATG CTCTGGATCC CAGGATCCAG TGAGGATCTT</u>

GTCTTGACAC AGACCCCACG GTCCCTGTCT GTCAGCCCTG GAGAGACTGC CTCCATCTCC TGCAAGGCCA

GTCAGAGCCT CCTGTCTCCT GATGGAAACA CATACTTGAA TTGGTTCCGA CAGAAGCCAG GCCAGTCTCC

TCAGCGTTTG ATCTATAAGG TCTCCAATAG AGACATTGGG GTCCCAGACA GGTTCAGTGG CAGCGGGTCA

GGGACAGATT TCACCCTGAG AATCAGCAGA GTGGAGGCTG ACGATACTGG ACTTTATTAC TGTGGGCAAG

TCACATATCT TCCCATTACT TTCAGCCAGG GAACCAACCT GGGGATGAAA CGGAATGATG CCCAGCCAGC

CGTCTAT (SEQ ID NO: 1058)
Kapa2427:

<u>ATGAG GTTCCCTTCT CAGCTCCTGG GGCTGCTGAT GCTCTGGATC CCAGGATCCA GTGGGGATAT</u>

TGTCATGACA CAGGCCCCAC CGTCTCTGTC CGTCAGCCCT GGAGAGCCGG CCTCCATCTC CTGCAAGGCC

AGTCAGAGCC TCCTGTACAG TAATGGGAAC ACGCATTTGT ATTGGTTCCG ACACAAGCCA GGCCAGTCTC

CAGAGGGCCT GATCTATAGG GTGTCCAAGC GCTTCACTGG CGTGTCAGAA GGTTCAGTG CAGCGGGTC

AGGGACAGAT TCACCCTGG AAATCAGCAG AGTGGAGGCT GACGATGTTG GAGTTTATTA CTGCGGGCAA

AATTTACAGC CTCCTTATAC TTTCAGCCAG GAACCAAGC TGGAAATAAA ACGGAATGAT GCCCAGCCAG

CCGTCTAT

TABLE N<sub>κ</sub>-continued

κ Light Chain Variable Domain Amino Acid Sequences (SEQ ID NO: 1059)
Kapa2430:

ATGAG GTTCCCTTCT CAGCTCCTGG GGCTGCTGAT GCTCTGGATC CCAGGATCCG GTGGGATAT

TGTCATGACA CAGACCCCAC CGTCCCTGTC TGTCAGCCCT GGAGAGCCGG CCTCCATCTC CTGCAAGGCC

AGTCAGAGCC TCCTGTACCC TAATGGAAAT ACCTATTTGT ATTGGTATTT GCAAAAGCCA GGCCAGTCTC

CACAGCTTCT GATCTACTTG GTTTCCAATC GCTTCACTGG CGTGTCAGAC AGGTTCAGTG GCAGCGGGTC

AGGGACAGAT TTCACCCTGC GAATTAGCAG AGTGGAGGCT AACGATACTG GAGTTTATTA CTGCGGACAA

GGTACATATT TTCCGTTCGC TTTTGGCCAA GGGACCAAAC TGGAGATCAA ACGGAATGAT GCCCAGCCAG

CCGTCTAT (SEQ ID NO: 1060)
Kapa2431:

TCGTCTCTG TCCCTCAGTC CTGGAGAGCC GGCCTCCATC TCCTGTAAGG CCAGTCAGAG CCTCCTGTCT

AGTAATGGGA ACACCTATTT ATATTGGATC CGACAGAAGC CAGGCCAGTC TCCAGAGGGC CTGATCTACA

AGGTGTCCAA CCGCTTCACT GGCGTGTCAG ACAGGTTCAG TGGCAGCGGA TCAGGAACAG ATTTCACCCT

GAGAATCACC AGAGTGGAGG CTGACGATGC TGGAGTTTAT TACTGCGGGC AGAATTTCCG GTTTCCTTAT

ACTCTCAGCC AGGGAACCAA ACTGGAGATA GAACGGAATG ATGCCCAGCC AGCCGTCTAT (SEQ ID NO: 1061)
Kapa2432:

ATG AGGTTCCCTT CTCAGCTCCT GGGGCTGCTG ATGCTCTGGA TCCCAGGATC CGGTGGGGAT

ATTGTCATGA CACAGACCCC ACCGTCCCTG TCTGTCAGCC CTGGAGAGCC GGCCTCCATC TCCTGCAAGG

CCAGTCAGAG CCTCCTGTAC AGTAATGGGA ACACGCATTT GTATTGGTTC CGACAGAAGC CAGGCCAGTC

TCCAGAGGGC CTGATCTATA GGGTGTCCAA GCGCTTCACT GGCGTGTCAG AAAGGTTCAG TGGCAGCGGG

TCAGGGACAG ATTTCACCCT GGAAATCAGC AGAGTGGGGG CTGACGATGT GGAGTTTAT TACTGCGGGC

AAAATTTACA GCCTCCTTAT ACTTTCAGCC AGGGAACCAA GCTGGAAATA AAACGGAATG ATGCCCAGCC

AGCCGTCTAT (SEQ ID NO: 1062)
Kapa2435:

ATGAGGT TCCCATCTCA GCTCCTGGGG CTGCTGATGC TCTGGATCCC AGGATCCAGT GAGGATCTTG

TCTTGACACA GACCCCACGG TCCCTGTCTG TCAGCCCTGG AGAGACTGCC TCCATCTCCT GCAAGGCCAG

TCAGAGCCTC CTGTCTCCTG ATGGAAACAC ATACTTGAAT TGGTTCCGAC AGAAGCCAGG CCAGTCTCCT

CAGCGTTTGA TCTATAAGGT CTCCAATAGA GACATTGGGG TCCCAGACAG GTTCAGTGGC AGCGGGTCAG

GGACAGATTT CACCCTGAGA ATCAGCAGAG TGGAGGCTGA CGATACTGGA CTTTATTACT GTGGGCAAGT

CACATATCTT CCCATTACTT TCAGCCAGGG AACCAACCTG GACATGAAAC GGAATGATGC CCAGCCAGCC

GTCTAT (SEQ ID NO: 1063)
Kapa2436:

AT GAGGTTCCCT TCTCAGCTCC TGGGGCTGCT GATGCTCTGG ATCCCAGGAT CCGGTGGGGA

TATTGTCATG ACACAGACCC CACCGTCCCT GTCTGTCAGC CCTGNAGAGC CGGCCTCCAT CTCCTGCAAG

GCCAGTCAGA GCCCCCTGTA CCCTAATGGA AATACCTATT TGTATTGGTA TTTGCAAAAG CCAGGCCAGT

CTCCACAGCT TCTGATCTAC TTGGTTTCCA ATCGCTTCAC TGGCGTGTCA GACAGGTTCA GTGGCAGCGG

GTCAGGGACA GATTTCACCC TGCGAATTAG CAGAGTGGAG GCTAACGATA CTGGAGTTTA TTACTGCGGA

TABLE N<sub>κ</sub>-continued

κ Light Chain Variable Domain Amino Acid Sequences

CAAGGTACAT ATTTTCCGTT CGCTTTTGGC CAAGGGACCA AACTGGAGAT CAAACGGAAT GATGCCCAGC

CAGCCGTCTA T (SEQ ID NO: 1064)
Kapa2437:

ATGAGG TTCCCTTCTC AGCTCCTGGG GCTGCTGATG CTCTGGATCC CAGGATCCGG TGGGGATATT

GTCATGACAC AGACCCCACC GTCCCTGTCT GTCAGCCCTG GAGAGCCGGC CTCCATCTCC TGCAAGGCCA

GTCAGAGCCT CCTGTACCCT AATGGAAATA CCTATTTGTA TTGGTATTTG CAAAAGCCAG GCCAGTCTCC

ACAGCTTCTG ATCTACTTGG TTTCCAATCG CTTCACTGGC GTGTCAGACA GGTTCAGTGG CAGCGGGTCA

GGGACAGATT TCACCCTGAG AATCAGCAGA GTGGAGGCTG ACGATACTGG ACTTTATTAC TGTGGGCAAG

TCACATATCT TCCCATTACT TTCAGCCAGG GAACCAACCT GGAGATGAAA CGGAATGATG CCCAGCCAGC

CGTCTAT (SEQ ID NO: 1065)
Kapa2438:

ATGAG GTTCCCTTCT CAGCTCCTGG GGCTGCTGAT GCTCTGGATC CCAGGATCCG GTGGGGATAT

TGTCATGACA CAGACCCCAC CGTCCCTGTC TGTCAGCCCT GGAGAGCCGG CCTCCATCTC CTGCAAGGCC

AGTCAGAGCC TCCTGTACCC TAATGGAAAT ACCTATTTGT ATTGGTATTT GCAAAAGCCA GGCCAGTCTC

CACAGCTTCT GATCTACTTG GTTTCCAATC GCTTCACTGG CGTGTCAGAC AGGTTCAGTG GCAGCGGGTC

AGGGACAGAT TTCACCCTGC GAATTAGCAG AGTGGAGGCT AACGATACTG AGTTTATTAC TGCGGGCAA

GGTATACAAG ATCCGTTCAC TTTTGGCCAA GGGACCAAAC TGGAGATCAA ACGGAATGAT GCCCAGCCAG

CCGTCTAT (SEQ ID NO: 1066)
Kapa2440:

ATGA GGTTCCCTTC TCAGCTCCTG GGGCTGCTGA TGCTCTGGAT CCCAGGATCC GGTGGGGATA

TTGTCATGAC ACAGACCCCA CCGTCCCTGT CTGTCAGCCC TGGAGAGCCG GCCTCCATCT CCTGCAAGGC

CAGTCAGAGC CTCCTGTACC CTAATGGAAA TACCTATTTG TATTGGTATT TGCAAAAGCC AGGCCAGTCT

CCACAGCTTC TGATCTACTT GGTTTCCAAT CGCTTCACTG GCGTGTCAGA CAGGTTCAGT GGCAGCGGGT

CAGGGACAGA TTTCACCCTG CGAATTAGCA GAGTGGAGGC TAACGATACT GGAGTTTATT ACTGCGGACA

AGGTACATAT TTTCCGTTCG CTTTTGGCCA AGGGACCAAA CTGGAGATCA AACGGAATGA TGCCCAGCCA

GCCGTCTAT (SEQ ID NO: 1067)
Kapa2442:

ATGAGG TTCCCATCTC AGCTCCTGGG GCTGCTGATG CTCTGGATCC CAGGATCCAG TGAGGATCTT

GTCTTGACAC AGACCCCACG GTCCCTGTCT GTCAGCCCTG GAGAGACTGC CTCCATCTCC TGCAAGGCCA

GTCAGAGCCT CCTGTCTCCT GATGGAAACA CATACTTGAA TTGGTTCCGA CAGAAGCCAG GCCAGTCTCC

TCAGCGTTTG ATCTATAAGG CTCCAATAG AGACATTGGG GTCCCAGACA GGTTCAGTGG CAGCGGGTCA

GGGACAGATT TCACCCTGAC AATCAGCAGA GTGGAGGCTG ACGATGCTGG AGTTTATTAC TGTGGCCAAG

TTCTACAGGA TCCTTATACT TTCAGCCAGG GAACCAAGCT GGAGATAAGA CGGAATGATG CCCAGCCAGC

CGTCTAT (SEQ ID NO: 1068)
Kapa2443:

GGGAACAC CTATTTGTAT TGGTTCCGAC AGAGGCCAGG CCAGTCTCCG AGGCCCTGA TCTATAGGGT

TABLE N_κ-continued

κ Light Chain Variable Domain Amino Acid Sequences

GTCCAGCCGC TTCCCTGGCG TGTCAGACAG GTTCAGTGGC AGCGGGTCAG TGACAGATTT CACCCTGAGA

ATCAGCAGAG TGGAGGCTGA CGATGCTGGA ATTTATTACT GCGGGCAGAA TCTACAGTTT CCGATCACCT

TTGGCAAAGG GACACATCTG GAGATTAAAC GGAATGATGC CCAGCCAGCC GTCTAT (SEQ ID NO: 1069)
Kapa2444:

AGCCTCCT GCACAGTAAC GGGAACACCT ATTTGTCTTG GTTTCGACAG AAGTCAGGCC AGTCTCCACA

ACGTTTGATC TATAGGGTCT CCAACAGAGA CCCTGGGGTC CCAGACAGGT TCAGTGGCAG CGGGTCAGGG

ACAGATTTCA CCCTGAGAAT CAGCAGAGTG GAGGCTGACG ATACTGGACT TTATTACTGT GGGCAAGTCA

CATATCTTCC CATTACTTTC AGCCAGGGAA CCAACCTGGA GATGAAACGG AATGATGCCC AGCCAGCCGT

CTAT (SEQ ID NO: 1070)
Kapa2446:

AAGGTGTCC AACCGCTTCA GTGGCGTGTC AGAAAGGATC AGTGGCAGCG GGTCAGGGAC AGATTTCACC

CTGAGAATCA GCAGAGTGGA GGCTGACGAT GCTGGGATTT ATTACTGCGG GCAAACTACA CACTTTCCTT

ATACTTTCGG CCAGGGAACC AAGCTGGAAA TAAAACGGAA TGATGCCCAG CCAGCCGTCT AT (SEQ ID NO: 1071)
Kapa2449:

AGCCTCCTGC ACAGTAATGG GAACACCTAT TTCGCTTGGT TCCAACAGAA GCCAGGCCAG TCTCCACAGC

GTTTGATCTA TCACGTCTCC AAGAGAGACC CTGGGGTTCC AGACAGGTTC AGTGGCAGCG GGTCAGGAAC

AGATTGCACC CTGACAATTA GCAGAGTGGA GGCTGATGAT GCTGGAGTTT ATTACTGCGG GCAAGGTATA

CAAGATCCGT TCACTTTTGG CCAAGGGACC AAACTGGAGA TCAAACGGAA TGATGCCCAG CCAGCCGTCT

AT
(SEQ ID NO: 1072)

TABLE N_λ

Other Canine Lambda Variable Sequences

λ103:

ATGACCT CCAACATGGC CTGGTCCCCT CTCCTCCTCA CACTCCTTCC TTACTACACA GGGTCCTGGG

CCCAGTCTGT GCTGACTCAG CCGACCTCAG TGTCGGGGTC CCCTGGCCAG AGGGTCACCA TCTCCTGCTC

TGGAAGCACG GACAACATCG GTCTTGTTGG TGCGAGTTGG TACCAACAAC TCCCAGGAAG GCCCCTAAAC

TCCTCCTGT ATAGTGATGG GGATCGACCG TCAGGGGTCC CTGACCGGTT TTCCGGCTCC AGGTCTGGCA

ACTCAGCCAC CCTGGCCATC ACTGGGCTTC AGGCTGAGGA CGAGGCTGAC TATTACTGCC AGTCCTTTGA

TTCCACGCTT GATGGTTTCG TGTTCGGCTC AGGAACCCAA CTGACCGTCC TTGGTCAGCC CAAGGCG (SEQ ID NO: 1073)

MTSNMAWSPL LLTLLPYYTG SWAQSVLTQP TSVSGSPGQR VTISCSGSTD NIGLVGASWY QQLPGRAPKL

LLYSDGDRPS GVPDRFSGSR SGNSATLAIT GLQAEDEADY YCQSFDSTLD GFVFGSGTQL TVLGQPKA (SEQ ID NO: 1074)
λ112:

ATGGACTGG GTCCCCTTTT ACCTCCTGCC CTTCATTTTC TCTACAGGTT CTGTGCTCC TCCTGTGCTG

ACCCAGCCTC CAAGTGCATC TGCCTCCCTG GAAGCCTCGG TCAAGCTCAC CTGCACTCTG AGCAGTGAGC

ACAGCAGTTA CTTTATTTAC TGGTATCAAC AACAACAACC AGAGAAGGCC CCTCGGTATC TGATGAGGGT

TABLE N_λ-continued
Other Canine Lambda Variable Sequences

TAACAGTGAT GGAAGCCACA GCAGAGGGGA CGGGATCCCC AGTCGCTTCT CAGGCTCCAG CTCTGGGGCT

GACCGCTATT TAACCATCTC CAACATCCAG TCTGAGGATG AGGCAGATTA TTACTGTTTT ACACCTGATG

ATAGCAATAG TGTGTTCGGC GGAGGCACCC ATCTGACCGT CCTCGGTCAG CCCAAGGCC (SEQ ID NO: 1075)

<u>MDWVPFYLLP FIFSTGF</u>CAP PVLTQPPSAS ASLEASVKLT CTLSSEHSSY FIYWYQQQQP EKAPRYLMRV

NSDGSHSRGD GIPSRFSGSS SGADRYLTIS NIQSEDEADY YCFTPDDSNS VFGGGTHLTV LGQPKA (SEQ ID NO: 1076)
λ121:

<u>ATGACCTCC</u> <u>ACCATGGCCT</u> <u>GGTCCCCTCT</u> <u>CCTCCTCACC</u> <u>CTCCTCGCTC</u> <u>ATTGCACAGT</u> GTCCTGGGCC

CAGGCTGTGC TGACTCAGCC ACCCTCTGTG TCTGCAGCCC TGGGGCAGAG GGTCACCATC TCCTGCACTG

GAACTAACAC CAACATCGGC AATGGTTATG ATGTACATTG GTACCAGCAG GTCCCAGGAA AGTCCCCTAA

AACCTTCATC TATGGTAATA ACAATCGACC CTCGGGGGTC CCGGTTCGAT TCTCTGGCTC CAAGTCAGGC

AGCACAGCCA CCCTGACCAT CACTGGGATC CAGGCTGAGG ATGAGACTGA TTATTACTGC CAGTCCTATG

ATGACAACCT CGATGGTTAC GTGTTCGGCT CGGGAACCCA ACTGACCGTC CTTGGTCAGC CCAAGGCC (SEQ ID NO: 1077)

<u>MTSTMAWSPL LLTLLAHCTV</u> SWAQAVLTQP PSVSAALGQR VTISCTGTNT NIGNGYDVHW YQQVPGKSPK

TFIYGNNNRP SGVPVRFSGS KSGSTATLTI TGIQAEDETD YYCQSYDDNL DGYVFGSGTQ LTVLGQPKA (SEQ ID NO: 1078)
λ202:

<u>ATG</u> <u>GACTGGGTCC</u> <u>CCTTTTACCT</u> <u>CCTGCCCTTC</u> <u>ATTTTCTCTA</u> <u>CAGG</u>TTTCTG TGCTCCTCCT

GTGCTGACCC AGACTCCAAG TGCATCTGCC TCCCTGGAAG ACTCGGTCAA GCTCACCTGC ACTTTGAGCA

GGGAGCACAG CACTTACTAT ATTACCTGGT ATCAACAACA CAACCAGGG AAGGCCCCTC GGTATCTGAT

GAAGGTTAAC AGTGATGGAA GCCACAGCAG GGGAGACGGG ATCCCCAGTC GCTTCTCAGG CTCCAGCTCT

GGGGCTGACC GCTATTTAAC CATCTCCAAC ATCCAGTCTG AGGATGAGGC AGATTATTAC TGTTTTACAC

CCGCTAATAG CAATAGTGTG TTCGGCGGAG GCACCCATCT GACCGTCCTC GGTCAGCCCA AGGCC (SEQ ID NO: 1079)

<u>MDWVPFYLLP FIFSTGF</u>CAP PVLTQTPSAS ASLEDSVKLT CTLSREHSTY YITWYQQQQP GKAPRYLMKV

NSDGSHSRGD GIPSRFSGSS SGADRYLTIS NIQSEDEADY YCFTPANSNS VFGGGTHLTV LGQPKA (SEQ ID NO: 1080)
λ323:

TCCTGGGCCC AGTCTGTGCT GACTCAGCCG GCCTCTGTGT CTGGGTCCCT GGGCCAGAGG GTCGCCATCT

CCTGCACTGG AAGCAGCTCC AATGTTGGTT TTGGCCCTTA TTTGGGCTGG TACCAACAGG TCCCAGGAGC

AGGCCCCAGA ACCCTCATGT ATCGTATTAG TCGCCGCCCC TCGGGGGTCC CTGATCGATT CTCTGGCTCC

AGGTCAGGCA ACACAGCAAC CCTGACCATC TCTGGCCTCC AGCCTGATGA TGAGGGCGAT TATTACTGCT

CATCCTATGA CACCAGTCTC AGTGCGATTG TGTTCGGCGG AGGCACCCAC CTGACCGTTG TC (SEQ ID NO: 1081)

SWAQSVLTQP ASVSGSLGQR VAISCTGSSS NVGFGPYLGW YQQVPGAGPR TLMYRISRRP SGVPDRFSGS

RSGNTATLTI SGLQPDDEGD YYCSSYDTSL SAIVFGGGTH LTVV (SEQ ID NO: 1082)
λ115:

TABLE N$_\lambda$-continued

Other Canine Lambda Variable Sequences

ATGACCTCCA CCATGGGCTG GTTCCCTCTC CTCCTCACCA TCCTCGCTCA CTGCACAGGG TCCTGGGCCC

AGTCTGTGCT GAGTCAGCCG GCCTCAGTGT CCGGGTCCCT GGGCCAGAGG GTCACCATCT CCTGCACTGG

AAGCAGCTCC AACATCGGTA GAGGTTATGT GGGCTGGTAC AACAGCTCC CGGGAACAGG CCCCANAACC

CTCATCTTTG GTCCTAATAA GCGACCCTCA GGGGTCCCCG ATCGCTTCTC TGGCTCCAGG TCGGACAGCA

CAGGCACCCT GACCATCTCT GGGCTCCAGG CTGAGGATGA GGGTGATTAT TACTGCTCAT CGTGGGACAC

CACTCTCAGT GCTTACGTGT TCGGCTCAGG GACCCAACTG ACCGTTCTTG GTCAGCCCAA GGCC (SEQ ID NO: 1083)

MTSTMGWFPL LLTILAHCTG SWAQSVLSQP ASVSGSLGQR VTISCTGSSS NIGRGYVGWY QQLPGTGPXT

LIFGPNKRPS GVPDRFSGSR SDSTGTLTIS GLQAEDEGDY YCSSWDTTLS AYVFGSGTQL TVLGQPKA (SEQ ID NO: 1084)
λ116:

ACCATCCTCG CTCACTGCAC AGGGTCCTGG GCCCAGTNTC TACTGACTCA GCCGGCCTCA GTGTCCGGGT

CCCTGGGCCA GAGGGTCACC CTNTCCTGCA CTGGAAGCGG CTCCAACATC GGTAGAGGTT ATGTGGGCTG

GTACCAACAC CTCCCGGGGA CAGGCCCCAG AACCCTCATC TATGGTGATA TTAACCGACC CTCAGGGGTC

CCCGATCGGT TCTCTGGCTC CAGGTCAGGC ATCACAGCCA CCCTGACCAT CTCTGGGCTC CAGGCTGAGG

ATGAGGCTGA TTATTACTGN TCATCGTGGG ACTACAGTCT CAGTANTACT TTGTTCGGCG GAGGCACCCA

CCTGACCGTN CTCGGTCAGC CCAAGGCC (SEQ ID NO: 1085)

TILAHCTGSW AQXLLTQPAS VSGSLGQRVT LSCTGSGSNI GRGYVGWYQH LPGTGPRTLI YGDINRPSGV

PDRFSGSRSG ITATLTISGL QAEDEADYYX SSWDYSLSXT LFGGGTHLTV LGQPKA (SEQ ID NO: 1086)
λ205:

GCTGATTAT TACTGTTCAG CATATGACAG CAATCTCAGT GGTGTCCTGT TCGGCTCAGG AACCCAACTG

ACCGTCCTTG GTCAGCCCAA GGCC (SEQ ID NO: 1087)

ADYYCSAYDS NLSGVLFGSG TQLTVLGQPK A (SEQ ID NO: 1088)
λ222:

AT GGCCTGGTCC CCTCTCCTCC TCACACTCCT TCCTTACTGC ACAGGGTCCT GGGGGNAGTC

TATACTGACT CAGCCGACCT CACTGTCGGG GTCCCCTGGC CAAAGGGTCA CCATTTCCTG CTCTGGAGGC

ACGAGCAACG TCGTCATTGT CGGTGCGAGT TGGTACCAAC AGGTCCCAGG AAAGGCCCCT AAACTTCTCG

TTTACAGTAA TGGGGATCGA CCGTCAGGGG TCCCTGACCG GTTTTCCGGC TCCAAGTCTG GCAACTCAGC

CACCCTGACC ATCACTGGAC TTCAGGCTGA GGACAGAGGC TGATTATTACT GCCAGTCCTT TGATACCACG

CTTCATGTTC ATCTGTTCGG CGGAGGCACC TATCTGACCG TCCTCGGTCA GCCCAAGGCC (SEQ ID NO: 1089)

MAWSPLLLTL LPYCTGSWGX SILTQPTSLS GSPGQRVTIS CSGGTSNVVI VGASWYQQVP GKAPKLLVYS

NGDRPSGVPD RFSGSKSGNS ATLTITGLQA EDEADYYCQS FDTTLHVHLF GGGTYLTVLG QPKA (SEQ ID NO: 1090)
λ232:

ATGACCTCCA CCATGGGCTG GTCCCCTCTC CTCCTTACCC TCCTCGCTCA CTGCACAGGN TCCTGGGCCC

AGTCTGTGCT GACTCAGCCG GCCTCAGTGA CTGGGTCCCT GGGCCAGAGG GTCACCATCT CCTGCACTGG

TABLE N<sub>λ</sub>-continued
Other Canine Lambda Variable Sequences

AAGCAGCTCC AACATCGGTG GATATAATGT TGGCTGGTTC CAGCAGCTCC CGGGAATAGG CCCCAGAACC

GTCATCTATA GTAGTAGTAA GCGACCCTCG GGGGTCCCGG ATCGATTCTC TGGCTCCAGG TCAGGCAGCA

CAGCCACCCT GACCATCTCT GGGCTCCAGG CTGAGGACGA GGCTGAGTAT TACTGCTCAA CATGGGACAC

CAGTCTCAAA GGTATTGTGT TCGGCGGAGG CACCCATCTG ACCGTCCTCG GTCAAGCCCA (SEQ ID NO: 1091)

MTSTMGWSPL LLTLLAHCTG SWAQSVLTQP ASVTGSLGQR VTISCTGSSS NIGGYNVGWF QQLPGIGPRT

VIYSSSKRPS GVPDRFSGSR SGSTATLTIS GLQAEDEAEY YCSTWDTSLK GIVFGGGTHL TVLGQA (SEQ ID NO: 1092)
λ312:

ATGGCCTG GACTCTGGTC CTCCTCACCT TTCTCTCTCA GGGCACAGGG TCCTGGGCCC AGTCCGCCCT

GACTCAACCT TCCTCGGTGT CTGGGACTTT GGGCCANACT GTCACCATCT CCTGTGATGG GAACAACAAT

AACATTGGCA ATAGTGATTA TATCGAATGG TACCAGCAGT TCCCAGGCAC CTCCCCCAAA CTCCTGATTT

ACTATGTCAA TAGGCGGCCA TCAGGGATCC CTACTCGCTT CTCTGCCTCC AAGTCTGGGA ACACGGCCTC

CTTGACCATC TCTGGGCTCC AGGCTGAAGA TGAGGCTGAT TATTACTGCA ACTCTTATAT TGGCGATGAG

GCTATGTTCG GCGGAGGCAC TCACCTGACC GTCCTCGGTC AGCCCAAGGC C (SEQ ID NO: 1093)

MAWTLVLLTF LSQGTGSWAQ SALTQPSSVS GTLGXTVTIS CDGNNNNIGN SDYIEWYQQF PGTSPKLLIY

YVNRRPSGIP TRFSASKSGN TASLTISGLQ AEDEADYYCN SYIGDEAMFG GGTHLTVLGQ PKA (SEQ ID NO: 1094)
λ217:

ATGACCT CCACCATGGC CTGGTCCCCT CTCCTCCTCA CCCTCCTCGC TCATTGCACA GTGTCCTGGG

CCCAGGCTGT GCTGACTCAG TCACCCTCTG TGTCTGCAGC CCTGGGGCAG AGGGTCTCCA TCTCCTGCAC

TGGAAGTGAC ACCAACATCG GCGGTTATGA TGTACAATGG TACCAGCAGG TCCCAGGAGA GTCCCCTAAA

ACTATCATCC GTGCTAATAC CAATCGACCC TCGGGGGTCC CGGTTCGATT CTCTGGCTCC AGGTCAGGCA

CCACAGCCAC CCTGACCATC ACTGGTATCC AGGCTGAGGA TGAGGCTGAT TATTACTGTC AGTCCTATGA

TGACAAGTCC GATGCTCTTG TGTTCGGCGG AGGCACCCAT CTGACCGTCC TCGGTCAGCC CAAGGCC GG (SEQ ID NO: 1095)

MTSTMAWSPL LLTLLAHCTV SWAQAVLTQS PSVSAALGQR VSISCTGSDT NIGGYDVQWY QQVPGESPKT

IIRANTNRPS GVPVRFSGSR SGTTATLTIT GIQAEDEADY YCQSYDDKSD ALVFGGGTHL TVLGQPKA (SEQ ID NO: 1096)
L201-79:

ATG GCTTNGACGT TGCTTCTTCT TGTGCTCCTT GCCTATGGCT CAGGGGCAGA TTCTCAGACT

GTCGTGATCC AGGACCCATC AGTCTCGGTG TCTCCAGGAG GGACAGTCAC ACTCACATGT GGCCTCAACT

GTGGGTCACT CTCTACAAAT AATTTCCCTG GCTGGTACCA GCAGACCCTA GGCCGGGCTC CTCGCACGAT

TATCTTCAAA ACAAATAGCC GCCCCTCTGG GGTCCCTGAT CGCTTCTNTG GAGCCTTNTC TGACAACAAA

GCTGTCCTTA CCATCACAGG AGTCCAGCCT GAGGACGAGG NTGACTATCA CTGTTCCTTC NATTTGGGTA

GTTATACTAT ATTCGGCGGA GGCACCCACT TGACCGTCCT C (SEQ ID NO: 1097)

MAXTLLLLVL LAYGSGADSQ TVVIQDPSVS VSPGGTVTLT CGLNCGSLST NNFPGWYQQT LGRAPRTIIF

KTNSRPSGVP DRFXGAXSDN KAVLTITGVQ PEDXDYHCS FXLGSYTIFG GGTHLTVL

TABLE N$_\lambda$-continued

Other Canine Lambda Variable Sequences (SEQ ID NO: 1098)
L213-79:

CAGACGGT CACCATCTCC TGCACTGGAA GCAGCTCCAA TGTTGGTTAT GGCGATTATG CGGGCTGGTA

CCAACAACTC CCAGGGACAG GTCCCAAAAC CCTCATCTAT GATACTCGTA GGCGACCCTC GGGGATTCCT

GATCGATTCT CTGGGTCCAG GTCAGGCAGC ACAGCGACCC TGACCATCTC TGGACTCCAG GCTGAGGATG

AGGCCGATTA TTACTGTGCA TCCTATGACC GTACTATCGG TGGTGGTGCT GTGTTCGGCG AGGCACCCA

CCTGACCGTC CTCGGTCAGC CCAAGGCC (SEQ ID NO: 1099)

QTVTISCTGS SSNVGYGDYA GWYQQLPGTG PKTLIYDTRR RPSGIPDRFS GSRSGSTATL TISGLQAEDE

ADYYCASYDR TIGGGAVFGG GTHLTVLGQP KA (SEQ ID NO: 1100)
L1-708:

GCCTCCTATG TGCTGTCTCA GCCGCCATCA GCGACTGTGA CCCTGAGGCA GACGGCCCGC CTCACCTGTG

GGGGAGACAG CATTGGAAGT AAAAGTGCTC AATGGTACCA GCAGAAGCCG GGCCAGCCCC CCGTGCTCAT

TATCTATGGT GATAGCAGCA GGCCGTCAGG GATCCCTGAG CGATTCTCTG GCGCCAACTC GGGGAACACG

GCCACCCTGA CCATCAGCGG GGCCCTGGCC GAGGACGAGG CTGACTATTA CTGCCAGGTG TGGGACCGCA

GTGCTTACGT GTTCGGCTCA GGAACCCAAC TGACCGTCCT TGGTCAGCCC AAGGCC (SEQ ID NO: 1101)

ASYVLSQPPS ATVTLRQTAR LTCGGDSIGS KSAQWYQQKP GQPPVLIIYG DSSRPSGIPE RFSGANSGNT

ATLTISGALA EDEADYYCQV WDRSAYVFGS GTQLTVLGQP KA (SEQ ID NO: 1102)
L1-712:

TGGTACCAG CAGTTCACAG GAACAGGCCC CAGAACCCTC ATCTATGATA CTAGTAGCCG ACCCTCGGGG

GTCCCTGATC GAATCTCTGG CTCCAGGTCA GGCAGCACAG CAACACTGAC CATTTCTGGG CTCCAGGCTG

AGGACGAGGC TGATTATTAC TGCTCAGCAT ATCACAACAG TCTCATTGCT GGTATGTTCG CGGAGGCAC

CCACCTGACC GTCCTCGGTC AGCCCAAGGC C (SEQ ID NO: 1103)

WYQQFTGTGP RTLIYDTSSR PSGVPDRISG SRSGSTATLT ISGLQAEDEA DYYCSAYDNS LIAGMFGGGT

HLTVLGQPKA (SEQ ID NO: 1104)
L1-719:

GCGGTTTC TCAGACTGTG CTAACCCAGG AGCCATCACT CTCAGTGTCT CCAGGAGGGA CAGTCACACT

CACATGTGGC CTCAGTTCTG GGTCAGTCTC TACAAGTAAT TACCCTGGCT GGTACCAGCA GACCCTGGGC

CGGGCTCCTC GCACGATTAT CTACAGAACA AGCAGCCGCC CCTCTGGGGT CCCTGATCGC TTCTCTGGAT

CCATCTCTGG GAACACAGCC GCCCTCACCA TCACAGGAGC CCAGCCTGAG GACGAGGCTG ACTATTACTG

TTCCTTCTAT ATGGGTGATT ACACTACTCT GTTCGGCGGA GGCACCCACC TGACCGTCCT CGGTCAGCCC

AAGGCC (SEQ ID NO: 1105)

AVSQTVLTQE PSLSVSPGGT VTLTCGLSSG SVSTSNYPGW YQQTLGPAPR TIIYRTSSRP SGVPDRFSGS

ISGNTAALTI TGAQPEDEAD YYCSFYMGDY TTLFGGGTHL TVLGQPKA

TABLE N<sub>λ</sub>-continued

Other Canine Lambda Variable Sequences (SEQ ID NO: 1106)
L1-722:

<u>A</u> <u>TGGCCTGGAC</u> <u>CCATCTCCTG</u> <u>CTCCCCGTGC</u> <u>TCACTCTCTG</u> <u>CACAGGCTCC</u> GTGGCCTCCA

GTGTGGTGAC TCAGCCTCCC TCGGTATCAG TGTCTCTGGG ACAGACAGCA ACCATCTCCT GCTCTGGAGA

GAGTCTGAGT AAATATTATG CACAATGGTT CCAGCAGAAG GCAGGCCAAG CCCCTGTGTT GGTCATATAT

AAGGACACTG ACCGGCCCTC TGGGATCCCT GACCGATTCT CTGGCTCCAG TTCAGGGAAC ACACACACCC

TGACCATCAG CGGGGCTCGG GCCGAGGACG AGGCTGACTA TTACTGCGAG TCAGCAGTCA GTACTGATAC

TGCTGTGTTC GGCGGAGGCA CCCACCTGAC CGTCCTCGGT CAGCCCAAGG CC (SEQ ID NO: 1107)

<u>MAWTHLLLPV</u> <u>LTLCTG</u>SVAS SVVTQPPSVS VSLGQTATIS CSGESLSKYY AQWFQQKAGQ APVLVIYKDT

ERPSGIPDRF SGSSSGNTHT LTISGARAED EADYYCESAV STDTAVFGGG THLTVLGQPK A (SEQ ID NO: 1108)
L1-724:

CTCCCTGCA GCCTCGGTCA ACCTCACCTG CACTTTGAGC AGTGAACACA TCAGTTACTT TATTATTTGG

TATCAACAAC AACACCCAGG GAGGGCCCCT CGATATCTGA TGAAGATTAA CTTTGATGGG GAGCACACCA

GGGGAGACGG GATCCCTAGT CGCTTCTCAG GCTCCAGCTC TGGGTCTGAC CGCTATTTAA CCATCTCCAA

CATCCAGTCT GAGGATGAGG CAGATTATTT CTGTTTTACA CCCGCTAGTA CCAACAGTGT TTTCGGCGGA

GGCACCCATC TGACCGTCCT CGGTCAGCCC AAGGCC (SEQ ID NO: 1109)

LPAASVNLTC TLSSEHISYF IIWYQQQHPG RAPRYLMKIN FDGEHTRGDG IPSRPSGSSS GSDRYLTISN

IQSEDEADYF CFTPASTNSV FGGGTHLTVL GQPKA (SEQ ID NO: 1110)
L1-725:

<u>ATGGCCTGGA</u> <u>CCCATCTCCT</u> <u>GCTCCCCGTG</u> <u>CTCACTCTCT</u> <u>GCACAGGCTC</u> CGTGGCCTCC AGTGTGCTGA

CTCAGCCTCC CTCGGTATCA GTGTCTCTGG ACAGACAGC AACCATCTCC TGCTCTGGAG AGAGTCTGAG

TAAATATTAT GCACAATGGT TCCAGCAGAA GGCAGGCCAA GCCCCTGTGT TGGTCATATA TAAGGACACT

GAGCGGCCCT CTGGGATCCC TGACCGATTC TCCGGCTCCA GTTCAGGGAA CACACACACC CTGACCATCA

GCGGGGCTCG GCCGAGGAC GAGGCTGACT ATTACTGCGA GTCAGCAGTC AGTACTGATA CTGTTGTGTT

CGGCGGAGGC ACCCACCTGA CCGTCCTCGG TCAGCCCAAG GCC (SEQ ID NO: 1111)

<u>MAWTHLLLPV</u> <u>LTLCTG</u>SVAS SVLTQPPSVS VSLGQTATIS CSGESLSKYY AQWFQQKAGQ APVLVIYKDT

ERPSGIPDRF SGSSSGNTHT LTISGARAED EADYYCESAV STDTVVFGGG THLTVLGQPK A (SEQ ID NO: 1112)
L1-728:

<u>TCTC</u> <u>TACAG</u>GTTTC TGTGCTCCTC CTGTTCTGAC CCAGACTCCA AGTGCTTCTG CCTCCCTGGA

AGCCTCGGTC AAGCTCACCT GCACTTTGAG CGGTGATCAC AGCAGTCACT ATATTTCCTG GTATCAACAA

CATCAACCAG GGAAGGCCCC TCGGTATCTG ATGAAGGTTA ACAGTGATGG AAGCCACAGC AGGGGAGACG

GGATCCCTAG TCGCTTCTCA GGCTCCAGCT CTGGGGCTGA CCGCTATTTA AGCATCTCCA ACATCCAGTC

TGACGATGAG GCAGATTATT ATTGTTTTAT AGCCACTGGT GACAATAGTG TATTCGGCGG AGGCACCCAT

CTGACCGTCC TCGGTCAGCC CAAGGCC (SEQ ID NO: 1113)

TABLE N<sub>λ</sub>-continued

Other Canine Lambda Variable Sequences

<u>STGF</u>CAPPVL TQTPSASASL EASVKLTCTL SGDHSSHYIS WYQQHQPGKA PRYLMKVNSD GSHSRGDGIP

SRFSGSSSGA DRYLSISNIQ SDDEADYYCF IATGDNSVFG GGTHLTVLGQ PKA (SEQ ID NO: 1114)
L1-744:

<u>A</u> <u>TGGACTGGGT</u> <u>CCCCTTTTAC</u> <u>CTCCTGCCCT</u> <u>TCATTTTCTC</u> <u>TACAGGTTTC</u> TGTGCTCCTC

CTGTGCTGAC CCAGACTCCA AGTGCATCTG CCTCCCTGGA AGCCTCGGTC AAGCTCACCT GCACTTTGAG

CAGTGAGCAC AGCAGTTACT ATATTACCTG GTATCAACAA CAACAACCAG GGAAGGCCCC TCGGTATCTG

ATGAAGGTTA ACAGTGATGG AAGCCACAGC AGGGGAGACG GGATCCCTAG TCGCTTCTCA GGCTCCAGCT

CTGGGGCTGA CCGCTATTTA ACCATCTCCA ACATCCAGTC TGAGGATGAG GCAGATTATT ACTGTTTTAC

ACCCGCTACT GGCATTAGTG TCTTCGGCGG AGGCACCCAT CTGACCGTCC TCGGTCAGCC CAAGGCC (SEQ ID NO: 1115)

<u>MDWVPFYLLP FIFSTG</u>FCAP PVLTQTPSAS ASLEASVKLT CTLSSEHSSY YITWYQQQP GKAPRYLMKV

NSDGSHSRGD GIPSRFSGSS SGADRYLTIS NIQSEDEADY YCFTPATGIS VFGGGTHLTV LGQPKA (SEQ ID NO: 1116)
L1-745:

AGCAACTCC AACATCGGTA GAGGTTATGT GGGCTGGTAC CAACAGCTCC CGGGAACAGG CCCCAGGACC

CTCTTCTATG GAACTGGGAA CCGACCCTCA GGGGTCCCCG ATCGGTTCTC TGGCTCCAGG TCAGGCAGCA

CAGCCACCCT GACCATCTCT GGGCTCCAGG CTGAGGATGA GGCTGATTAT TACTGCTCAT CGTGGGACAC

CAGTCTCAGT ATTTACGTGT TCGCCTCAGG AACCCAACTG ACCGTCCTTG GTCAGCCCAA GGCC (SEQ ID NO: 1117)

SNSNIGRGYV GWYQQLPGTG PRTLFYGTGN RPSGVPDRFS GSRSGSTATL TISGLQAEDE ADYYCSSWDT

SLSIYVFASG TQLTVLGQPK A (SEQ ID NO: 1118)
L1-750:

<u>ATGGACTG</u> <u>GGTTCCCTTT</u> <u>TACATCCTGC</u> <u>CCTTCATTTT</u> <u>CTCTACAGGT</u> CTCTGTGCAT TGCCCGTGCT

GACCCAGCCT ACAAGTGCAT CTGCCCCCCT GGAAGAGTCG GTCAAGCTGA CCTGCACTTT GAGCAGTGAG

CACAGCAATT ACATTGTTCA TTGGTATCAA CAACAACCAG GGAAGGCCCC TCGGTATCTG ATGTATGTCA

GGAGTGATGG AGGCTACAAA AGGGGGGACG GGATCCCCAG TCGCTTCTCA GGCTCCAGCT CTGGGGCTGA

CCGCTATTTA ACCATCTCCA ACATCAAGTC TGAAGATGAG GATGACTATT ATTACTGTGG TGCAGACTAT

ACAATCAGTG GCCAATATGG TAACGTGTTC GGCTCAGGAA CCCGACTGAC CGTCCTTGGT CAGCCCAAGG

CC (SEQ ID NO: 1119)

<u>MDWVPFYILP FIFSTG</u>LCAL PVLTQPTSAS APLEESVKLT CTLSSEHSNY IVHWYQQQPG KAPRYLMYVR

SDGGYKRGDG IPSRFSGSSS GADRYLTISN IKSEDEDDYY YCGADYTISG QYGNVFGSGT RLTVLGQPKA (SEQ ID NO: 1120)
L1-751:

<u>ATGGACTG</u> <u>GGTCCCCTTT</u> <u>TACCTCCTGC</u> <u>CCTTCATTTT</u> <u>CTCTACAGGT</u> TTCTGTGCTC CTCCTGTGCT

GACCCAGACT CCAAGTGCAT CTGCCTCCCT GGAAGCCTCG GTCAAGCTCA CCTGCACTTT GAGCAGTGAG

CACAGCAGTT ACTATATTAC CTGGTATCAA CAACAACAAC CAGGGAAGGC CCCTCGGTAT CTGATGAGGG

TTAACAGCGA TGGAAGCCAC AGCAGGGGAG ACGGGATCCC TAGTCGCTTC TCAGGCTCCA GCTCTGGGGC

TABLE N<sub>λ</sub>-continued

Other Canine Lambda Variable Sequences

TGACCGCTAT TTAACCATCT CCAACATCCA GTCTGAGGAT GAGGCAGATT ATTACTGTTT TACACCCTCT

AGTATAAGTG TGTTCGGCGG AGGCACCCAT CTGACCGTCC TCGGTCAGCC CAAGGCC (SEQ ID NO: 1121)

MDWVPFYLLP FIFSTGFCAP PVLTQTPSAS ASLEASVKLT CTLSSEHSSY YITWYQQQP GKAPRYLMRV

NSDGSHSRGD GIPSRFSGSS SGADRYLTIS NIQSEDEADY YCFTPSSISV FGGGTHLTVL GQPKA (SEQ ID NO: 1122)
L1-755:

TGTGGGTTGG TACCAACAAC TCCCAGAAGA GGCCCCAGAA CTGTCATCTA TAGTACAAGT AGTCGACCCT

CGGGGGTGCC CGATCGATTC TCTGGCTCCA AGTCTGGCAG CACAGCCACC CTGACCATCT CTGGGCTCCA

GGCTGAGGAT GAGGCTGATT ATTACTGCTC GACGTGGGAT GATAGTCTCA GTGGTTACGT TTTCGGCTCA

GGAACCCAAT TGCAATTGAC CGTCCTTGGT CAGCCCAAGG CC (SEQ ID NO: 1123)

CGLVPTTPRR GPRTVIYSTS SRPSGVPDRF SGSKSGSTAT LTISGLQAED EADYYCSTWD DSLSGYVFGS

GTQLQLTVLG QPKA (SEQ ID NO: 1124)
L1-761:

ATGGA CTGGGTCCCC TTTTACCTCC TGCCCTTCAT TTTCTCTACA GGTTTCTGTG CTCCTCCTGT

GCTGACCCAG ACTCCAAGTG CATCTGCCTC CCTGGAAGCC TCGGTCAAGC TCACCTGCAC TTTGAGCAGT

GAACACAGCA GTTACTATAT TACCTGGTAT CAACAACAAC AACCAGGGAA GGCCCCTCGG TATCTGATGA

CGGTTAACAG TGATGGAAGC CACAGCAGGG GAGACGGGAT CCCTAGTCGC TTCTCAGGCT CCAGCTCTGG

GGCTGACCGC TATTTAACCA TCTCCAACAT CCAGTCTGAG GATGAGGCAG ATTATTACTG TTTTGCACCC

GCTAACAATG CTGTATTCGG CGGAGGCACC CACCTGACCG TCCTCGGTCA GCCCAAGGCC (SEQ ID NO: 1125)

MDWVPFYLLP FIFSTGFCAP PVLTQTPSAS ASLEASVKLT CTLSSEHSSY YITWYQQQP GKAPRYLMTV

NSDGSHSRGD GIPSRFSGSS SGADRYLTIS NIQSEDEADY YCFAPANNAV FGGGTHLTVL GQPKA (SEQ ID NO: 1126)
λ108:

CTCCTCAC CATCCTCGCT CACTGCACAG GGTCCTGGGC CCAGTCTCTA CTGACTCAGC CGGCCTCAGT

GTCCGGGTCC CTGGGCCAGA GGGTCACCCT CTCCTGCACT GGAAGCGGCT CCAACATCGG TAGAGGTTAT

GTGGGCTGGT ACCAACACCT CCCGGGGACA GGCCCCAGAA CCCTCATCTA TGGTGATATT AACCGACCCT

CAGGGGTCCC CGATCGGTTC TCTGGCTCCA GGTCAGGCAT CACAGCCACC CTGACCATCT CTGGGCTCCA

GGCTGAGGAT GAGGCTGATT ATTACTGTTC ATCGTGGGAC TACAGTCTCA GTAGTACTTT GTTCGGCGGA

GGCACCCACC TGACCGTCCT CGGTCAGCCC AAGGCC (SEQ ID NO: 1127)

LLTILAHCTG SWAQSLLTQP ASVSGSLGQR VTLSCTGSGS NIGRGYVGWY QHLPGTGPRT LIYGDINRPS

GVPDRFSGSR SGITATLTIS GLQAEDEADY YCSSWDYSLS STLFGGGTHL TVLGQPKA (SEQ ID NO: 1128)
λ118:

ATGACCTCC ACCATGGCCT GGTTCCCTCT CCTCCTGACC CTCCTTGCTC ACTACACAGG GTCCTGGGCC

CAGTCTGTAC TGACTCAGCC GGCCTCAGTG TCTGGGTCCC TGGGCAGAG GATCACCATC TCCTGCACTG

GAAGCGGTTC CAACATTGGA GGTAATAATG TGGGTTGGTA CCAGCAGCTC CCAGGAAGAG GCCCCAGAAC

TABLE N$_\lambda$-continued
Other Canine Lambda Variable Sequences

```
TGTCATCTAT GATACTTATA GTCGACTCTC GGGGGTGCCC GATCGATTCT CTGGCTCCAA GTCTGGCAGC
ACAGCCACCC TGACCATCTC TGGGCTCCAG GCTGAGGATG AGGCTGATTA TTACTGCTCA ACGTGGGATG
ATAGTCTCCG TGCTTACTTG TTCGGGTCAG GAACCCAACT GACCGTTCTT GGTCAGCCCA AGGCC
```
(SEQ ID NO: 1129)

MTSTMAWFPL LLTLLAHYTG SWAQSVLTQP ASVSGSLGQR ITISCTGSGS NIGGNNVGWY QQLPGRGPRT
VIYDTYSRLS GVPDRFSGSK SGSTATLTIS GLQAEDEADY YCSTWDDSLR AYLFGSGTQL TVLGQPKA (SEQ ID NO: 1130)
λ119:

```
    ATGAC CTCCACCATG GCCTGGTTCC CTCTCCTCCT GACCCTCCTT GCTCACTACA CAGGGTCCTG
GGCCCAGTCT GTGCTGACTC AGCCGGCCTC AGTGTCTGGG TCCCTGGGCC AGAGGATCAC CATCTCCTGC
ACTGGAAGCG GTTCCAACAT GGAGGTAAT AATGTGGGTT GGTACCAGCA GCTCCCAGGA AGAGGCCCCA
GAACTGTCAT CTATGATACT TATAGTCGAC TCTCGGGGGT GCCCGATCGA TTCTCTGGCT CCAAGTCTGG
CAGCACAGCA ACCCTGACCA TCTCTGGGCT CCAGGCTGAG GATGAGGCTG ATTATTACTG CTCAACGTGG
GATGATAGTC TCCGTGCTTA CTTGTTCGGG TCAGGAACCC AACTGACCGT TCTTGGTCAG CCCAAGGCC
```
(SEQ ID NO: 1131)

MTSTMAWFPL LLTLLAHYTG SWAQSVLTQP ASVSGSLGQR ITISCTGSGS NIGGNNVGWY QQLPGRGPRT
VIYDTYSRLS GVPDRFSGSK SGSTATLTIS GLQAEDEADY YCSTWDDSLR AYLFGSGTQL TVLGQPKA (SEQ ID NO: 1132)
λ317:

```
    ATGACCT CCAACATGGC CTGGTCCCCT CTCCTCCTCA CACTCCTTGC TTACTGCACA GGATCCTGGG
CCCAGTCTGC GCTGACTCAG CCGACCTCAG TGTCGGGGTC CCTTGGCCAG AGGGTCTCCA TTTCCTGCTC
TGGAAGCACG AGCAACATCG GTATTGTCGG TGCGAGCTGG TACCAACAAC TCCCAGGAAA GGCCCCTAAA
CTCCTCCTGA ACAGTGATGG GAGTCGACCG TCAGGGTCC CTGACCGGTT TTCCGGCTCC AACTCTGGCG
CCTCAGCCAC CCTGACCATC ACTGGGCTTC AGGCTGAGGA CGAGGCTGAT TATTACTGTC AGTCTTTTGA
TCCCACGCCT CCTGATCATT ACGTGTTCGG CTCAGGAACC CAACTGACCG
```
(SEQ ID NO: 1133)

MTSNMAWSPL LLTLLAYCTG SWAQSALTQP TSVSGSLGQR VSISCSGSTS NIGIVGASWY QQLPGKAPKL
LLNSDGSRPS GVPDRFSGSN SGASATLTIT GLQAEDEADY YCQSFDPTPP DHYVFGSGTQ LT
(SEQ ID NO: 1134)

---

The invention claimed is:

1. A method of treating a canine having an IgE-mediated affliction comprising administering to the canine an amount of a composition sufficient to alleviate or eliminate one or more symptoms associated with the affliction, wherein the composition comprises a pharmaceutically acceptable carrier and a canine antibody wherein the antibody binds IgE and comprises a light chain variable domain and a heavy chain variable domain, wherein the light chain variable domain comprises the sequence:

TDSQTVATQEPSLSVSPGGTVTLT-CRSSTGAVTTSNYANWVQQTQGRAPRTI-IGGPNNRAPGVPSRFSGSISGN KATLTITGAR-PEDEADYFCALWYSNHWVFGGGTHLTVL (SEQ ID NO: 809).

2. The method of treating a canine having an IgE-mediated affliction according to claim 1, wherein the antibody binds IgE and wherein the heavy chain variable domain comprises a heavy chain variable domain polypeptide comprising the sequence:

$Fr^1$-$CDR^1$-$Fr^2$-$CDR^2$-$Fr^3$-$CDR^3$-$Fr^4$ wherein $Fr^1$ is $X'^1$ $X'^2$ $X'^3$ $X'^4$ $X'^5$ $X'^6$ $X'^7$ $X'^8$ $X'^9$ $X'^{10}$ $X'^{11}$ $X'^{12}$ $X'^{13}$ $X'^{14}$ $X'^{15}$ $X'^{16}$ $X'^{17}$ $X'^{18}$ $X'^{19}$ $X'^{20}$ $X'^{21}$ $X'^{22}$ $X'^{23}$ $X'^{24}$ $X'^{25}$ (SEQ ID NO: 69);

$Fr^2$ is $X'^{26}$ $X'^{27}$ $X'^{28}$ $X'^{29}$ $X'^{30}$ $X'^{31}$ $X'^{32}$ $X'^{33}$ $X'^{34}$ $X'^{35}$ $X'^{36}$ $X'^{37}$ $X'^{38}$ $X'^{39}$ $X'^{40}$ (SEQ ID NO: 70)

$Fr^3$ is $X'^{41}$ $X'^{42}$ $X'^{43}$ $X'^{44}$ $X'^{45}$ $X'^{46}$ $X'^{47}$ $X'^{48}$ $X'^{49}$ $X'^{50}$ $X'^{51}$ $X'^{52}$ $X'^{53}$ $X'^{54}$ $X'^{55}$ $X'^{56}$ $X'^{57}$ $X'^{58}$ $X'^{59}$ $X'^{60}$ $X'^{61}$ $X'^{62}$ $X'^{63}$ $X'^{64}$ $X'^{65}$ $X'^{66}$ $X'^{67}$ $X'^{68}$ $X'^{69}$ $X'^{70}$ $X'^{71}$ $X'^{72}$ (SEQ ID NO: 71), and $Fr^4$ is $X'^{73}$ $X'^{74}$ $X'^{75}$ $X'^{76}$ $X'^{77}$ $X'^{78}$ $X'^{79}$ $X'^{80}$ $X'^{81}$ $X'^{82}$ (SEQ ID NO: 72), $X'^1$ is E, $X'^2$ is V, $X'^3$ is Q or H; $X'^4$ is L, $X'^5$ is V;

$X'^6$ is Q; $X'^7$ is S, $X'^8$ is A, $X'^9$ is A, $X'^{10}$ is W;

$X'^{11}$ is V, $X'^{12}$ is K, $X'^{13}$ is K, $X'^{14}$ is P, $X'^{15}$ is G, $X'^{16}$ is A, $X'^{17}$ is S, $X'^{18}$ is V, $X'^{19}$ is K, $X'^{20}$ is V

$X'^{21}$ is S, $X'^{22}$ is C, $X'^{23}$ is K, $X'^{24}$ is T, $X'^{25}$ is S, $X'^{26}$ is W, $X'^{27}$ is V, $X'^{28}$ is Q, $X'^{29}$ is Q, $X'^{30}$ is A, $X'^{31}$ is P; $X'^{32}$ is G, $X'^{33}$ is A, $X'^{34}$ is G, $X'^{35}$ is L, $X'^{36}$ is D or E; $X'^{37}$ is W, $X'^{38}$ is M, $X'^{39}$ is G, $X'^{40}$ is W, $X'^{41}$ is R, $X'^{42}$ is V, $X'^{43}$ is T, $X'^{44}$ is L, $X'^{45}$ is T, $X'^{46}$ is A, $X'^{47}$ is D, $X'^{48}$ is T, $X'^{49}$ is S, $X'^{50}$ is T, $X'^{51}$ is S or N, $X'^{52}$ is T, $X'^{53}$ is Q or V, $X'^{54}$ is Y, $X'^{55}$ is M, $X'^{56}$ is E, $X'^{57}$ is L, $X'^{58}$ is S, $X'^{59}$ is S or N, $X'^{60}$ is L, $X'^{61}$ is R, $X'^{62}$ is A or T, $X'^{63}$ is E, $X'^{63}$ is D, $X'^{64}$ is T of A, $X'^{65}$ is $X'^{66}$ is $X'^{67}$ is Y, $X'^{68}$ is $X'^{70}$ is

-continued

| | | | |
|---|---|---|---|
|A,|V,|Y,|C,|
|X'⁷¹ is A,|X'⁷² is R or S,|X'⁷³ is Y or L,|X'⁷⁴ is W;|X'⁷⁵ is G,|
|X'⁷⁶ is Q,|X'⁷⁷ is G,|X'⁷⁸ is T,|X'⁷⁹ is L,|X'⁸⁰ is V,|
|X'⁸¹ is T, and|X'⁸² is V.|

3. The method of treating a canine having an IgE-mediated affliction according to claim 2, wherein the antibody binds IgE and wherein the heavy chain variable domain comprises a heavy chain variable domain polypeptide selected from the group consisting of:

a) H74-1:
EVQLVQSAAEVKKPGASVKVSCKTSGYSFTDYFMNWVQQAPGAGLDWMGR

INPFNGDPFYNQKFKGRVTLTADTSTSTAYMELSSLRAEDAAVYYCARFY

YGRYYAMDYWGQGTLVTV (SEQ ID NO:802);

h) H74-15:
EVQLVQSAAEVKKPGASVKVSCKTSGYSFTDYFMNWVQQAPGKGLDWMGR

INPFNGDPFYNQKFKGRVTLTADTSTSTAYMELSSLRAEDAAVYYCARFY

YGRYYAMDYWGQGTLVTV (SEQ ID NO:803);

i) H74-20:
EVQLVQSAAEVKKPGASVKVSCKTSGYSFTDYFMNWVQQAPGAGLDWMGR

INPFNGDPFYNQKFKGRVTLTVDTSTSTAYMELSSLRAEDAAVYYCARFY

YGRYYAMDYWGQGTLVTV (SEQ ID NO:804);

j) H74-41:
EVQLVQSAAEVKKPGASVKVSCKTSGYSFTDYFMNWVQQAPGKGLDWMGR

INPFNGDPFYNQKFKGRVTLTVDTSTSTAYMELSSLRAEDAAVYYCARFY

YGRYYAMDYWGQGTLVTV (SEQ ID NO:805);

k) H74-45
EVQLVQSAAEVKKPGASVKVSCKTSGYSFTDYFMNWVQQAPGAGLDWMGR

INPFNGDPFYNQKFKGRVTLTVDKSTSTAYMELSSLRAEDAAVYYCARFY

YGRYYAMDYWGQGTLVTV (SEQ ID NO:806);

l) H74-55
EVQLVQSAAEVKKPGASVKVSCKTSGYSFTDYFMNWVQQAPGKGLDWMGR

INPFNGDPFYNQKFKGRVTLTADKSTSTAYMELSSLRSEDAAVYYCARFY

YGRYYAMDYWGQGTLVTV (SEQ ID NO:807); and m) H74-58
EVQLVQSAAEVKKPGASVKVSCKTSGYSFTDYFMNWVQQAPGKGLDWMGR

INPFNGDPFYNQKFKGRVTLTVDTSTSTAYMELRSLRAEDAAVYYCARFY

YGRYYAMDYWGQGTLVTV (SEQ ID NO:808).

* * * * *